United States Patent
Achab et al.

(10) Patent No.: US 12,215,116 B2
(45) Date of Patent: Feb. 4, 2025

(54) ARGINASE INHIBITORS AND METHODS OF USE

(71) Applicant: Merck Sharp & Dohme LLC, Rahway, NJ (US)

(72) Inventors: Abdelghani Abe Achab, Melrose, MA (US); Matthew L. Childers, Medfield, MA (US); Jared N. Cumming, Winchester, MA (US); Christian Fischer, Natick, MA (US); Symon Gathiaka, Waltham, MA (US); Hakan Gunaydin, Somerville, MA (US); Charles A. Lesburg, Newton, MA (US); Derun Li, West Roxbury, MA (US); Min Lu, Brookline, MA (US); Anandan Palani, Needham, MA (US); Rachel L. Palte, Melrose, MA (US); Qinglin Pu, Needham, MA (US); David L. Sloman, Brookline, MA (US); Sung-Sau So, Verona, NJ (US); Chunrui Sun, Westfield, NJ (US); Hongjun Zhang, Boston, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 985 days.

(21) Appl. No.: 16/977,253

(22) PCT Filed: Mar. 8, 2019

(86) PCT No.: PCT/US2019/021247
§ 371 (c)(1),
(2) Date: Sep. 1, 2020

(87) PCT Pub. No.: WO2019/177873
PCT Pub. Date: Sep. 19, 2019

(65) Prior Publication Data
US 2021/0040127 A1    Feb. 11, 2021

Related U.S. Application Data

(60) Provisional application No. 62/642,098, filed on Mar. 13, 2018.

(51) Int. Cl.
*C07F 5/02* (2006.01)
*C07K 16/28* (2006.01)

(52) U.S. Cl.
CPC .......... *C07F 5/025* (2013.01); *C07K 16/2818* (2013.01)

(58) Field of Classification Search
CPC .................................................... C07F 5/025
See application file for complete search history.

(56) References Cited

U.S. PATENT DOCUMENTS

| | | | |
|---|---|---|---|
| 8,894,970 B2 | 11/2014 | Tomczuk et al. | |
| 9,233,985 B2 | 1/2016 | Van Zandt et al. | |
| 9,592,221 B2 | 3/2017 | Ebright et al. | |
| 2009/0209492 A1* | 8/2009 | Bachovchin | A61P 3/06 514/64 |
| 2014/0371175 A1 | 12/2014 | Van Zandt et al. | |
| 2017/0121352 A1 | 5/2017 | Sjogren et al. | |
| 2017/0319536 A1 | 11/2017 | Blaszczyk et al. | |

FOREIGN PATENT DOCUMENTS

| | | | | |
|---|---|---|---|---|
| WO | WO-2011133653 A1 * | 10/2011 | ........... | A61K 31/155 |
| WO | WO-2012058065 A1 * | 5/2012 | ............ | A61K 31/69 |
| WO | 2016108707 A1 | 7/2016 | | |
| WO | 2017075363 A1 | 5/2017 | | |
| WO | 2017189386 A1 | 11/2017 | | |
| WO | 2017191130 A2 | 11/2017 | | |
| WO | 2018089490 A1 | 5/2018 | | |
| WO | 2019173188 A1 | 9/2019 | | |
| WO | 2019245890 A1 | 12/2019 | | |
| WO | WO-2020131598 A1 * | 6/2020 | ............. | A61P 35/00 |

OTHER PUBLICATIONS

Database Reaxys [Online] Jan. 1, 2017 (Jan. 1, 2017), Genesis Biotechnology Group LLC; Calithera Biosciences Inc: "Compositions and Methods for Inhibiting Arginase Activity", XP093021867, 5 pages.
Database Reaxys [Online] Jan. 1, 2017 (Jan. 1, 2017), Molekure Spolka Akcijna: "Arginase Inhibitors and Their Therapeutic Applications", XP093021868, 3 pages, Database accession No. XRN = 44489543.
Kabalka, George W. et al., Hydroboration of Alkene-Containing Hydantoins, Organic Process Research & Development, 2006, 1059-1061, 10.
Development of OAT-1746: A Novel Arginase 1 and 2 Inhibitor for Cancer Immunotherapy, ESMO 2017 Poster, 2017, 1-1.
Papadopoulos et al., CX-1158-101: A First-in-Human Phase 1 Study of CB-1158, a Small Molecule Inhibitor of Arginase, as Monotherapy and in Combination with an anti-PD-1 Checkpoint Inhibitor in Patients with Solid Tumors, ASCO Annual Meeting '17, 2017, 1-22.

(Continued)

*Primary Examiner* — Matthew P Coughlin
(74) *Attorney, Agent, or Firm* — Su Kyung Suh; Anna L. Cocuzzo

(57) ABSTRACT

Described herein are compounds of Formula I or a pharmaceutically acceptable salt thereof. The compounds of Formula I act as arginase inhibitors and can be useful in preventing, treating or acting as a remedial agent for arginase-related diseases.

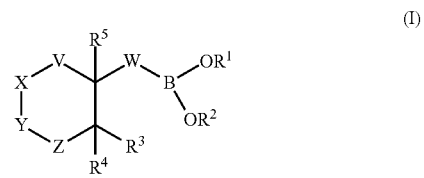

(I)

46 Claims, No Drawings

(56) References Cited

OTHER PUBLICATIONS

Public presentation by Calithera: https://www.calithera.com/wp-content/uploads/2017/06/CB-1158-101-ASCO-2017-FINAL.pdf (22 pages).
Public presentation by OncoArendi: ESMO 2017 poster (1 page).

* cited by examiner

ARGINASE INHIBITORS AND METHODS OF USE

CROSS-REFERENCE TO RELATED APPLICATIONS

This application is a U.S. National Phase application under 35 U.S.C. § 371 of PCT Application No. PCT/US2019/021247, filed Mar. 8, 2019, which published as WO2019/177873 A1 on Sep. 19, 2019 and claims priority under 35 U.S.C. § 365 (b) from U.S. provisional patent application No. 62/642,098, filed Mar. 13, 2018.

TECHNICAL FIELD

The present invention is directed to arginase inhibitors. Specifically, the arginase inhibitors described herein can be useful in preventing, treating or acting as a remedial agent for arginase-related diseases.

BACKGROUND

Arginase is an enzyme that metabolizes L-arginine to L-ornithine and urea. There are two types of arginase, and they are both products of distinct genes that are regulated independently and located on different chromosomes. Arginase I is a cytosolic protein (34.7 kDa) and is dominant in the liver, but also expressed extrahepatically. Arginase II is a mitochondrial protein and is expressed in kidney, small intestine, brain, monocytes and macrophages.

In addition to its fundamental role in the hepatic urea cycle, arginase also influences the immune systems in humans and mice. Arginase participates in many inflammatory disorders by decreasing the synthesis of nitric oxide and inducing fibrosis and tissue regeneration. L-Arginine deficiency, which is modulated by myeloid cell arginase, suppresses T-cell immune response. This mechanism plays a fundamental role in inflammation-associated immunosuppression.

Arginase expression and L-arginine depletion is also a known immune-suppressive pathway of the mammalian immune system. The depletion of arginine in the tumor microenvironment renders cytotoxic T-cells unable to proliferate and therefore unable to effectively mount an anti-tumor attack. Similarly, M2 macrophages and polymorphonuclear cells (PMNs) express high levels of arginase and may contribute to the local suppression of immune responses. Restoration of arginine levels in the tumor microenvironment via arginase inhibition would be expected to allow T-cell activation and proliferation to occur and result in T-cell mediated anti-tumor responses.

Small-molecule arginase inhibitors are currently described as promising therapeutics for the treatment of several diseases, including allergic asthma, inflammatory bowel disease, ulcerative colitis, cardiovascular diseases (atherosclerosis and hypertension), diseases associated with pathogens (e.g., *Helicobacter pylori*, *Trypanosoma cruzi*, *Leishmania*, *Mycobacterium tuberculosis* and *Salmonella*), cancer and induced or spontaneous immune disorders. Development of potent and specific inhibitors of arginase would be useful for the treatment of diseases where depletion of L-arginine from the microenvironment and/or induction of arginase pathway is involved in the evasion of anti-tumor immunity, especially for immuno-oncology indications.

SUMMARY

A compound of Formula I:

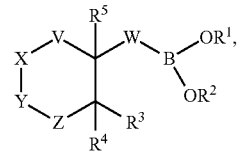

wherein V, W, X, Y, Z, $R^1$, $R^2$, $R^3$, $R^4$ and $R^5$ are described below.

The compounds described herein are arginase inhibitors, which can be useful in the prevention, treatment or amelioration of diseases where depletion of L-arginine from the microenvironment and/or induction of arginase pathway is involved in the evasion of anti-tumor immunity, especially for immuno-oncology indications.

DETAILED DESCRIPTION

Compounds

Described herein are compounds of Formula I:

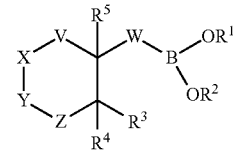

or a pharmaceutically acceptable salt thereof, wherein:

W is selected from the group consisting of straight or branched $(C_2\text{-}C_5)$alkylene, wherein one or more —$CH_2$— groups in W are optionally and independently replaced with a moiety selected from the group consisting of O, S or NH;

V is selected from the group consisting of a bond, O, S, $CR^6R^7$ or $NR^8$;

X is selected from the group consisting of a bond, O, S, $CR^9R^{10}$ or $NR^{11}$;

Y is selected from the group consisting of a bond, O, S, $CR^{12}R^{13}$ or $NR^{14}$;

Z is selected from the group consisting of a bond, O, S, $CR^{15}R^{16}$ or $NR^{17}$;

$R^1$ is selected from the group consisting of hydrogen, $C_3$-$C_6$cycloalkyl or $C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^2$ is selected from the group consisting of hydrogen, $C_3$-$C_6$cycloalkyl or $C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^3$ is hydrogen, halogen, $C_3$-$C_6$cycloalkyl, $C_1$-$C_6$alkyl, halo$C_1$-$C_6$alkyl, $C_1$-$C_6$alkylOH, —COOH, $N(R^{18})(R^{19})$, $C_1$-$C_6$alkylN$(R^{18})(R^{19})$, $C_1$-$C_6$alkylheteroaryl, heteroaryl, $C_1$-$C_6$alkoxy or —COO$C_1$-$C_6$alkyl;

$R^4$ is hydrogen, halogen, $C_3$-$C_6$cycloalkyl, $C_1$-$C_6$alkyl, halo$C_1$-$C_6$alkyl, $C_1$-$C_6$alkylOH, —COOH, $N(R^{18})(R^{19})$, $C_1$-$C_6$alkylN$(R^{18})(R^{19})$, $C_1$-$C_6$alkylheteroaryl, heteroaryl, $C_1$-$C_6$alkoxy and —COO$C_1$-$C_6$alkyl;

$R^5$ is selected from the group consisting of hydrogen, halogen, CN, OH, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, $C_1$-$C_6$alkylheteroaryl, CON($R^{18}$)($R^{19}$), N($R^{18}$)($R^{19}$) or $C_1$-$C_6$alkylN($R^{18}$)($R^{19}$);

$R^6$ is selected from the group consisting of hydrogen, halogen, OH, $C_1$-$C_6$alkylOH, $C_3$-$C_6$cycloalkyl, $C_1$-$C_6$alkyl, halo$C_1$-$C_6$alkyl, COOH, N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^7$ is selected from the group consisting of hydrogen, halogen, OH, $C_1$-$C_6$alkylOH, $C_3$-$C_6$cycloalkyl, $C_1$-$C_6$alkyl, halo$C_1$-$C_6$alkyl, COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^8$ is selected from the group consisting of hydrogen, $C_3$-$C_6$cycloalkyl, $C_1$-$C_6$alkyl, $C_1$-$C_6$alkylheteroaryl, or $C_1$-$C_6$alkylN($R^{18}$)($R^{19}$);

$R^9$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^{10}$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^{11}$ is selected from the group consisting of hydrogen, $C_3$-$C_6$cycloalkyl, $C_1$-$C_6$alkyl, $C_1$-$C_6$alkylheteroaryl, or $C_1$-$C_6$alkylN($R^{18}$)($R^{19}$);

$R^{12}$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, —COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^{13}$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, —COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^{14}$ is selected from the group consisting of hydrogen, $C_3$-$C_6$cycloalkyl, $C_1$-$C_6$alkyl, —$C_1$-$C_6$alkylheteroaryl, or $C_1$-$C_6$alkylN($R^{18}$)($R^{19}$);

$R^{15}$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, —COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^{16}$ is selected from the group consisting of hydrogen, halogen, OH, $C_1$-$C_6$alkylOH, $C_3$-$C_6$cycloalkyl, $C_1$-$C_6$alkyl, halo$C_1$-$C_6$alkyl, COOH, N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^{17}$ is selected from the group consisting of hydrogen, $C_3$-$C_6$cycloalkyl, $C_1$-$C_6$alkyl, —$C_1$-$C_6$alkylheteroaryl, and $C_1$-$C_6$alkylN($R^{18}$)($R^{19}$);

$R^{18}$ is selected from the group consisting of hydrogen, $C_3$-$C_6$cycloalkyl, halo$C_1$-$C_6$alkyl, $C_1$-$C_6$alkyl, $C_1$-$C_6$alkylNH$_2$, COheterocycle, and CO$C_1$-$C_6$alkyl, wherein the CO$C_1$-$C_6$alkyl can be optionally substituted with one or two substituents selected from the group consisting of N($R^{19}$)($R^{19}$), OH, cycloalkyl, or a 3-7 membered nitrogen containing ring or when $R^{18}$ is taken with $R^{19}$ forms a 3-7 membered nitrogen containing ring; and $R^{19}$ is selected from the group consisting of hydrogen, $C_3$-$C_6$cycloalkyl, halo$C_1$-$C_6$alkyl and $C_1$-$C_6$alkyl, or when $R^{19}$ is taken with $R^{18}$ forms a 3-7 membered nitrogen containing ring.

Also described herein are compounds of Formula I:

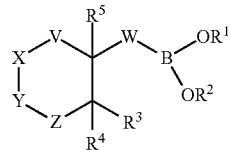

I or a pharmaceutically acceptable salt thereof, wherein:

W is selected from the group consisting of straight or branched ($C_2$-$C_5$)alkylene, wherein one or more —CH$_2$— groups in W are optionally and independently replaced with a moiety selected from the group consisting of O, S or NH;

V is selected from the group consisting of a bond, O, S, CR$^6$R$^7$ or NR$^8$;

X is selected from the group consisting of a bond, O, S, CR$^9$R$^{10}$ or NR$^{11}$;

Y is selected from the group consisting of a bond, O, S, CR$^{12}$R$^{13}$ or NR$^{14}$;

Z is selected from the group consisting of a bond, O, S, CR$^{15}$R$^{16}$ or NR$^{17}$;

$R^1$ is selected from the group consisting of hydrogen, $C_3$-$C_6$cycloalkyl or $C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^2$ is selected from the group consisting of hydrogen, $C_3$-$C_6$cycloalkyl or $C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^3$ is hydrogen, halogen, $C_3$-$C_6$cycloalkyl, $C_1$-$C_6$alkyl, —$C_1$-$C_6$alkylOH, —COOH, —$C_1$-$C_6$alkylheteroaryl, heteroaryl, —$C_1$-$C_6$alkylN($R^{18}$)($R^{19}$), $C_1$-$C_6$alkoxy or —COO$C_1$-$C_6$alkyl;

$R^4$ is hydrogen, halogen, $C_3$-$C_6$cycloalkyl, $C_1$-$C_6$alkyl, $C_1$-$C_6$alkylOH, —COOH, —$C_1$-$C_6$alkylheteroaryl, heteroaryl, —$C_1$-$C_6$alkylN($R^{18}$)($R^{19}$), $C_1$-$C_6$alkoxy and —COO$C_1$-$C_6$alkyl;

$R^5$ is selected from the group consisting of hydrogen, —OH, $C_3$-$C_6$cycloalkyl, —$C_1$-$C_6$alkylheteroaryl, or —$C_1$-$C_6$alkylN($R^{18}$)($R^{19}$);

$R^6$ is selected from the group consisting of hydrogen, halogen, —OH, —$C_1$-$C_6$alkylOH, $C_3$-$C_6$cycloalkyl, —COOH, —N($R^{18}$)($R^{19}$), —$C_1$-$C_6$alkylheteroaryl, —$C_1$-$C_6$alkylN($R^{18}$)($R^{19}$), $C_1$-$C_6$alkoxy or —COO$C_1$-$C_6$alkyl;

$R^7$ is selected from the group consisting of hydrogen, halogen, —OH, —$C_1$-$C_6$alkylOH, $C_3$-$C_6$cycloalkyl, —COOH, —N($R^{18}$)($R^{19}$), —$C_1$-$C_6$alkylheteroaryl, —$C_1$-$C_6$alkylN($R^{18}$)($R^{19}$), $C_1$-$C_6$alkoxy or —COO$C_1$-$C_6$alkyl;

$R^8$ is selected from the group consisting of hydrogen, $C_3$-$C_6$cycloalkyl, $C_1$-$C_6$alkyl, —$C_1$-$C_6$alkylheteroaryl, or —$C_1$-$C_6$alkylN($R^{18}$)($R^{19}$);

$R^9$ is selected from the group consisting of hydrogen, halogen, —OH, —$C_1$-$C_6$alkylOH, $C_3$-$C_6$cycloalkyl, —COOH, —N($R^{18}$)($R^{19}$), —$C_1$-$C_6$alkylheteroaryl, —$C_1$-$C_6$alkylN($R^{18}$)($R^{19}$), $C_1$-$C_6$alkoxy or —COO$C_1$-$C_6$alkyl;

$R^{10}$ is selected from the group consisting of hydrogen, halogen, —OH, —$C_1$-$C_6$alkylOH, $C_3$-$C_6$cycloalkyl, —COOH, —N($R^{18}$)($R^{19}$), —$C_1$-$C_6$alkylheteroaryl, —$C_1$-$C_6$alkylN($R^{18}$)($R^{19}$), $C_1$-$C_6$alkoxy or —COO$C_1$-$C_6$alkyl;

$R^{11}$ is selected from the group consisting of hydrogen, $C_3$-$C_6$cycloalkyl, $C_1$-$C_6$alkyl, —$C_1$-$C_6$alkylheteroaryl, or —$C_1$-$C_6$alkylN($R^{18}$)($R^{19}$);

$R^{12}$ is selected from the group consisting of hydrogen, halogen, —OH, —$C_1$-$C_6$alkylOH, $C_3$-$C_6$cycloalkyl, —COOH, —N($R^{18}$)($R^{19}$), —$C_1$-$C_6$alkylheteroaryl, —$C_1$-$C_6$alkylN($R^{18}$)($R^{19}$), $C_1$-$C_6$alkoxy or —COO$C_1$-$C_6$alkyl;

$R^{13}$ is selected from the group consisting of hydrogen, halogen, —OH, —$C_1$-$C_6$alkylOH, $C_3$-$C_6$cycloalkyl, —COOH, —N($R^{18}$)($R^{19}$), —$C_1$-$C_6$alkylheteroaryl, —$C_1$-$C_6$alkylN($R^{18}$)($R^{19}$), $C_1$-$C_6$alkoxy or —COO$C_1$-$C_6$alkyl;

$R^{14}$ is selected from the group consisting of hydrogen, $C_3$-$C_6$cycloalkyl, $C_1$-$C_6$alkyl, —$C_1$-$C_6$alkylheteroaryl, or —$C_1$-$C_6$alkylN($R^{18}$)($R^{19}$);

$R^{15}$ is selected from the group consisting of hydrogen, halogen, —OH, —$C_1$-$C_6$alkylOH, $C_3$-$C_6$cycloalkyl, —COOH, —N($R^{18}$)($R^{19}$), —$C_1$-$C_6$alkylheteroaryl, —$C_1$-$C_6$alkylN($R^{18}$)($R^{19}$), $C_1$-$C_6$alkoxy or —COO$C_1$-$C_6$alkyl;

$R^{16}$ is selected from the group consisting of hydrogen, halogen, —OH, —$C_1$-$C_6$alkylOH, $C_3$-$C_6$cycloalkyl, $C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), $C_1$-$C_6$alkoxy or —COO$C_1$-$C_6$alkyl;

$R^{17}$ is selected from the group consisting of hydrogen, $C_3$-$C_6$cycloalkyl, $C_1$-$C_6$alkyl, —$C_1$-$C_6$alkylheteroaryl, and —$C_1$-$C_6$alkylN($R^{18}$)($R^{19}$);

$R^{18}$ is selected from the group consisting of hydrogen, $C_3$-$C_6$cycloalkyl, $C_1$-$C_6$alkyl, an amino acid and CO$C_1$-$C_6$alkyl, wherein the CO$C_1$-$C_6$alkyl can be optionally substituted with N($R^{19}$)($R^{19}$), or when $R^{18}$ is taken with $R^{19}$ forms a 3-7 membered nitrogen containing ring; and $R^{19}$ is selected from the group consisting of hydrogen, $C_3$-$C_6$cycloalkyl and $C_1$-$C_6$alkyl, or when $R^{19}$ is taken with $R^{18}$ forms a 3-7 membered nitrogen containing ring.

Also described herein are compounds of Formula II, III, IV, V and VI:

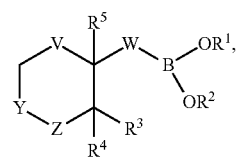

II

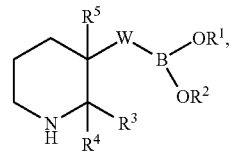

III

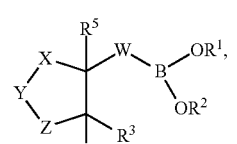

IV

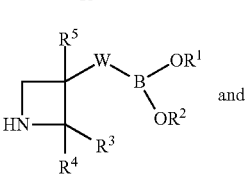

V

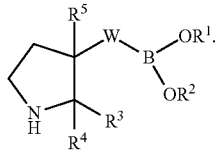

VI

With regard to the compounds described herein, W is selected from the group consisting of straight or branched ($C_2$-$C_5$)alkylene, wherein one or more $CH_2$— groups in W are optionally and independently replaced with a moiety selected from the group consisting of O, S or NH. In certain embodiments, W is ethelenyl, propylenyl, butylenyl or pentylenyl. In certain embodiments W is propylenyl. In other embodiments, one or more —$CH_2$— groups in W are optionally and independently replaced with a moiety selected from the group consisting of O, S or NH. In certain embodiments, W is In certain embodiments, W is ($C_2$-$C_5$) alkylene or O—$C_1$-$C_4$alkylene

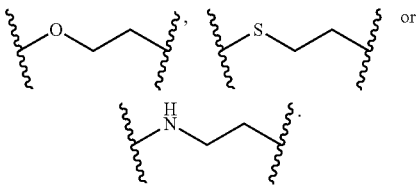

With regard to the compounds described herein, V is selected from the group consisting of a bond, O, S, $CR^6R^7$ or $NR^8$. In certain embodiments, V is a bond. In certain embodiments, V is O. In certain embodiments, V is S. In other embodiments, V is $CR^6R^7$. In still other embodiments, V is $NR^8$. In certain embodiments, V is —$CH_2$—. In other embodiments, V is $CH(CH_3)$. In yet other embodiments, V is —NH—. In one embodiment, V is a bond or $CR^6R^7$. In another embodiment, V is a bond or $CH_2$.

With regard to the compounds described herein, X is selected from the group consisting of a bond, O, S, $CR^9R^{10}$ or $NR^{11}$. In certain embodiments, X is a bond. In certain embodiments, X is O. In certain embodiments, X is S. In other embodiments, X is $CR^9R^{10}$. In still other embodiments, X is $NR^{11}$. In certain embodiments, X is —$CH_2$. In other embodiments, X is —CH(OH). In yet other embodiments, X is —NH. In one embodiment, X is a bond or $CR^6R^7$. In another embodiment, X is a bond, CH(OH), $CH(CO_2H)$ or $CH_2$.

With regard to the compounds described herein, Y is selected from the group consisting of a bond, O, S, $CR^{12}R^{13}$ or $NR^{14}$. In certain embodiments, Y is selected from the group consisting of, O, S, $CR^{12}R^{13}$ and $NR^{14}$. In certain embodiments, Y is a bond. In certain embodiments, Y is O. In certain embodiments, Y is S. In other embodiments, Y is $CR^{12}R^{13}$. In still other embodiments, Y is $NR^{14}$. In one embodiment, Y is $CR^{12}R^{13}$ or $NR^{14}$. In certain embodiments, Y is —$CH_2$. In other embodiments, Y is —$CH(CH_3)$. In yet other embodiments, Y is —NH. In another embodiment, Y is $CH(CH_3)$, NH or $CH_2$.

With regard to the compounds described herein, Z is selected from the group consisting of a bond, O, S, $CR^{15}R^{16}$ or $NR^{11}$. In certain embodiments, Z is selected from the group consisting of O, S, $CR^{15}R^{16}$ or $NR^{11}$. In certain embodiments, Z is a bond. In certain embodiments, Z is O.

In certain embodiments, Z is S. In other embodiments, Z is $CR^{15}R^{16}$. In still other embodiments, Z is $NR^{11}$. In one embodiment, Z is $CR^{12}R^{13}$ or $NR^{14}$. In certain embodiments, Z is —$CH_2$. In other embodiments, Z is $CH(CH_3)$. In yet other embodiments, Z is —NH. In certain embodiments, Z is —$CH_2$ or NH. In one embodiment, Z is $CH_2$, $CH(CO_2H)$, $C(CO_2H)$, NH, $NCH_2CH_2$piperidinyl or $CH_2CH_2$piperidinyl)

In certain embodiments of the compounds described herein, at least two of the substituents selected for V, X, Y and Z are $CR^6R^7$, $CR^9R^{10}$, $CR^{12}R^{13}$ or $CR^{15}R^{16}$ respectively. In other embodiments, V, X, Y and Z are not simultaneously a bond. In other embodiments, only one of V, X, Y and Z are O, S or $NR^8$, $NR^{14}$ or $NR^{17}$ respectively. In other embodiments, only two of V, X, Y and Z are O, S or $NR^8$, $NR^{14}$ or $NR^{17}$ respectively.

With regard to the compounds described herein, $R^1$ is selected from the group consisting of hydrogen, $C_3$-$C_6$cycloalkyl or $C_1$-$C_6$alkyl, or when taken with $R^2$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH. In certain embodiments, $R^1$ is hydrogen. In certain embodiments, $R^1$ is $C_3$-$C_6$cycloalkyl. Suitable cycloalkyl groups include, but are not limited to, cyclopropyl, cyclobutyl, cyclopentyl, cyclohexyl. In certain embodiments, $R^1$ is $C_1$-$C_6$alkyl. Examples of suitable $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, when $R^1$ and $R^2$ taken together form a $C_3$-$C_8$cycloalkyl, wherein the $C_3$-$C_8$cycloalkyl is optionally substituted with one to four substituents selected from the group consisting of halogen, $C_1$-$C_6$alkyl or OH. In certain embodiments, the $C_3$-$C_8$cycloalkyl is a six or seven-membered carbon ring. In certain embodiments, the $C_3$-$C_8$cycloalkyl is a six or seven-membered, saturated carbon ring. In certain embodiments, the $C_3$-$C_8$cycloalkyl is a bridged ring. In certain embodiments, the $C_3$-$C_8$cycloalkyl is substituted with one substituent selected from the group consisting of halogen, $C_1$-$C_6$alkyl or —OH. In certain embodiments, the $C_3$-$C_8$cycloalkyl is substituted with two substituents selected from the group consisting of halogen, $C_1$-$C_6$alkyl or —OH. In certain embodiments, the $C_3$-$C_8$cycloalkyl is substituted with three substituents selected from the group consisting of halogen, $C_1$-$C_6$alkyl or —OH. In certain embodiments, the $C_3$-$C_8$cycloalkyl is substituted with four substituents selected from the group consisting of halogen, $C_1$-$C_6$alkyl or —OH. In certain embodiments, the $C_3$-$C_8$cycloalkyl is substituted with three substituents, wherein all the substituents are $C_1$-$C_6$alkyl groups. In certain embodiments, the $C_3$-$C_8$cycloalkyl is substituted with three substituents, wherein all the substituents are methyl. In certain embodiments, the $C_3$-$C_8$cycloalkyl is substituted with four substituents, wherein all the substituents are $C_1$-$C_6$alkyl groups. In certain embodiments, the $C_3$-$C_8$cycloalkyl is substituted with four substituents, wherein all the substituents are methyl.

In certain embodiments, $R^1$ and $R^2$, when taken together form a $C_3$-$C_8$cycloalkyl selected from the group consisting of:

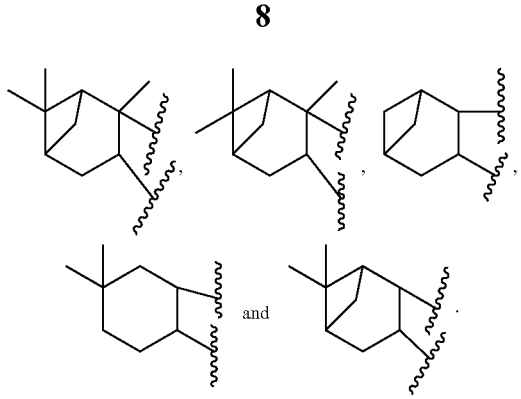

In certain embodiments, $R^1$ and $R^2$ when taken together form the following $C_3$-$C_8$cycloalkyl

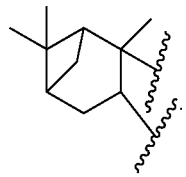 [SMILES: *C1CC2CC(C1(*)C)C2(C)C]

With regard to the compounds described herein, $R^2$ is hydrogen, $C_3$-$C_6$cycloalkyl or $C_1$-$C_6$alkyl, or when taken with $R^1$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH. In certain embodiments, $R^2$ is hydrogen. In certain embodiments, $R^2$ is $C_3$-$C_6$cycloalkyl. Suitable cycloalkyl groups include, but are not limited to, cyclopropyl, cyclobutyl, cyclopentyl, cyclohexyl. In certain embodiments, $R^2$ is $C_1$-$C_6$alkyl. Examples of suitable $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^2$ when taken with R forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH. In certain embodiments, the $C_3$-$C_8$cycloalkyl is a six or seven carbon ring. In certain embodiments, the $C_3$-$C_8$cycloalkyl is a six or seven-membered saturated carbon ring. In certain embodiments, the $C_3$-$C_8$cycloalkyl is a bridged ring. In certain embodiments, the $C_3$-$C_8$cycloalkyl is substituted with one substituent selected from the group consisting of halogen, $C_1$-$C_6$alkyl or —OH. In certain embodiments, the $C_3$-$C_8$cycloalkyl is substituted with two substituents selected from the group consisting of halogen, $C_1$-$C_6$alkyl or —OH. In certain embodiments, the $C_3$-$C_8$cycloalkyl is substituted with three substituents selected from the group consisting of halogen, $C_1$-$C_6$alkyl or —OH. In certain embodiments, the $C_3$-$C_8$cycloalkyl is substituted with four substituents selected from the group consisting of halogen, $C_1$-$C_6$alkyl or —OH. In certain embodiments, the $C_3$-$C_8$cycloalkyl is substituted with three substituents, wherein all the substituents are $C_1$-$C_6$alkyl groups. In certain embodiments, the $C_3$-$C_8$cycloalkyl is substituted with three substituents, wherein all the substituents are methyl. In certain embodiments, the $C_3$-$C_8$cycloalkyl is substituted with four substituents, wherein all the substituents are $C_1$-$C_6$alkyl groups. In certain embodiments, the $C_3$-$C_5$cycloalkyl is substituted with four substituents, wherein all the substituents are methyl.

In certain embodiments, $R^1$ and $R^2$, when taken together form a $C_3$-$C_8$cycloalkyl selected from the group consisting of:

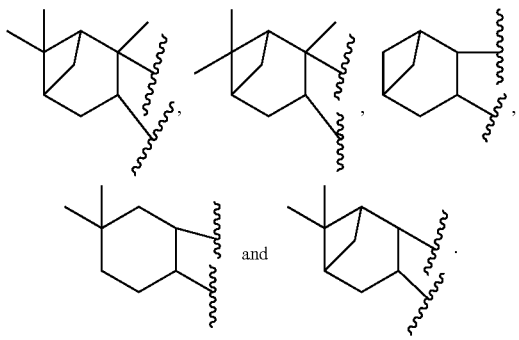

In certain embodiments, $R^1$ and $R^2$ when taken together form the following $C_3$-$C_8$cycloalkyl

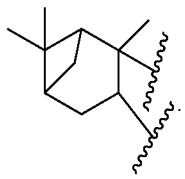 [SMILES: *C1CC2CC(C1(*)C)C2(C)C]

In certain embodiments, $R^1$ and $R^2$ are both hydrogen. In certain embodiments, R and $R^2$ are each hydrogen or taken together form a pinane.

With regard to the compounds described herein, $R^3$ is hydrogen, halogen, $C_3$-$C_6$cycloalkyl, $C_1$-$C_6$alkyl, halo$C_1$-$C_6$alkyl, $C_1$-$C_6$alkylOH, —COOH, $N(R^{18})(R^{19})$, $C_1$-$C_6$alkylN($R^{18}$)($R^{19}$), $C_1$-$C_6$alkylheteroaryl, heteroaryl, $C_1$-$C_6$alkoxy or —COOC$_1$-$C_6$alkyl. In certain embodiments, $R^3$ is hydrogen, halogen, $C_3$-$C_6$cycloalkyl, $C_1$-$C_6$alkyl, $C_1$-$C_6$alkylOH, —COOH, —$C_1$-$C_6$alkylheteroaryl, heteroaryl, —$C_1$-$C_6$alkyN($R^{18}$)($R^{19}$), $C_1$-$C_6$alkoxy or —COOC$_1$-$C_6$alkyl.

In certain embodiments described herein, $R^3$ is hydrogen. In certain embodiments described herein, $R^3$ is halogen. Examples of suitable halogens include, but are not limited to, chlorine, bromine, fluorine and iodine. In certain embodiments, $R^3$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^3$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments described herein, $R^3$ is halo$C_1$-$C_6$alkyl. Suitable examples of halo alkyls include, but are not limited to, fluoromethyl, difluoromethyl, trifluoromethyl, 2-fluoroethyl, 1,2-difluoroethyl and 2,2-difluoroethyl.

In certain embodiments, $R^3$ is $C_1$-$C_6$alkylOH. Examples of suitable alcohols, include, but are not limited to, methanol, ethanol, propanol, butanol and iso-butanol. In certain embodiments, $R^3$ is —COOH. In certain embodiments, $R^3$ is —$C_1$-$C_6$alkyN($R^{18}$)($R^{19}$). Examples of suitable —$C_1$-$C_6$alkylN($R^{18}$)($R^{19}$) groups include, but are not limited to, —CH$_2$NH$_2$, —CH$_2$NH(CH$_3$), —CH$_2$N(CH$_3$)$_2$, —CH$_2$CH$_2$N(CH$_3$)$_2$, —CH$_2$piperidinyl and —CH$_2$CH$_2$piperidinyl. In certain embodiments, $R^3$ is

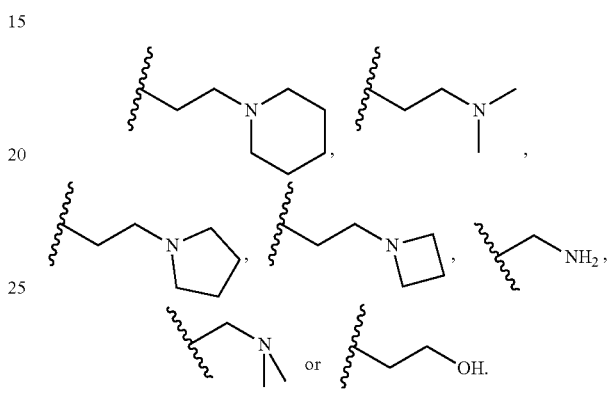

In certain embodiments, R is $C_1$-$C_6$alkoxy. Examples of suitable alkoxys, include but are not limited to, methoxy, ethoxy, butoxy and propoxy. In certain embodiments, $R^3$ is —COOC$_1$-$C_6$alkyl. Examples of suitable —COOC$_1$-$C_6$alkyl groups include, but are not limited to, methoxycarbonyl, ethoxycarbonyl and butoxycarbonyl.

In certain embodiments, $R^3$ is —$C_1$-$C_6$alkylheteroaryl. In certain embodiments, $R^3$ is a heteroaryl. In certain embodiments, the heteroaryl is a nitrogen containing heteroaryl. In certain embodiments the heteroaryl is an oxygen containing heteroaryl. In certain embodiments the heteroaryl is a sulfur containing heteroaryl. Suitable heteroaryls include, but are not limited to, pyrrolyl, isoxazolyl, isothiazolyl, pyrazolyl, pyridyl (pyridinyl), oxazolyl, oxadiazolyl (in particular, 1,3, 4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl. In certain embodiments, the heteroaryl is pyridine. In certain embodiments, $R^3$ is a tetrazolyl.

In one embodiment, $R^3$ is H, CO$_2$H, CH$_2$OH or CH$_2$CH$_2$piperidinyl.

With regard to the compounds described herein, $R^4$ is hydrogen, halogen, $C_3$-$C_6$cycloalkyl, $C_1$-$C_6$alkyl, halo$C_1$-$C_6$alkyl, $C_1$-$C_6$alkylOH, —COOH, $N(R^{18})(R^{19})$, $C_1$-$C_6$alkylN($R^{18}$)($R^{19}$), $C_1$-$C_6$alkylheteroaryl, heteroaryl, $C_1$-$C_6$alkoxy and —COOC$_1$-$C_6$alkyl. In certain embodiments, $R^4$ is hydrogen, halogen, $C_3$-$C_6$cycloalkyl, $C_1$-$C_6$alkyl, $C_1$-$C_6$alkylOH, COOH, $C_1$-$C_6$alkylheteroaryl, heteroaryl, $C_1$-$C_6$alkylN($R^{18}$)($R^{19}$), $C_1$-$C_6$alkoxy and COOC$_1$-$C_6$alkyl.

In certain embodiments described herein, $R^4$ is hydrogen. In certain embodiments described herein, $R^4$ is halogen. Examples of suitable halogens include, but are not limited to, chlorine, fluorine, bromine and iodine. In certain embodiments, $R^4$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^4$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments described herein, $R^4$ is halo$C_1$-$C_6$alkyl. Suitable examples of halo alkyls include, but are not limited to, fluoromethyl, difluoromethyl, trifluoromethyl, 2-fluoroethyl, 1,2-difluoroethyl and 2,2-difluoroethyl.

In certain embodiments, $R^4$ is —$C_1$-$C_6$alkylOH. Examples of suitable alcohols, include, but are not limited to, methanol, ethanol, propanol, butanol and iso-butanol. In certain embodiments, $R^4$ is COOH. In certain embodiments, $R^4$ is —$C_1$-$C_6$alkylN($R^{18}$)($R^{19}$). Examples of suitable $C_1$-$C_6$alkylN($R^{18}$)($R^{19}$) groups include, but are not limited to, —$CH_2NH_2$, —$CH_2NH(CH_3)$, $CH_2N(CH_3)_2$, —$CH_2CH_2N(CH_3)_2$, —$CH_2$piperidinyl and —$CH_2CH_2$piperidinyl.

In certain embodiments, $R^4$ is $C_1$-$C_6$alkoxy. Examples of suitable alkoxys, include but are not limited to, methoxy, ethoxy, butoxy and propoxy. In certain embodiments, $R^4$ is —COO$C_1$-$C_6$alkyl. Examples of —COO$C_1$-$C_6$alkyl groups include, but are not limited to, methoxycarbonyl, ethoxycarbonyl and butoxycarbonyl.

In certain embodiments, $R^4$ is —$C_1$-$C_6$alkylheteroaryl. In certain embodiments, $R^4$ is heteroaryl. In certain embodiments, the heteroaryl is a nitrogen containing heteroaryl. In certain embodiments the heteroaryl is an oxygen containing heteroaryl. In certain embodiments the heteroaryl is a sulfur containing heteroaryl. Suitable heteroaryl groups include, but are not limited to, pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl. In certain embodiments, the heteroaryl is pyridine. In certain embodiments, the heteroaryl is tetrazolyl.

In one embodiment, $R^4$ is H, $CO_2H$, $CH_2OH$ or $CH_2CH_2$piperidinyl. In one embodiment, $R^4$ is H or $CO_2H$.

In certain embodiments, $R^3$ and $R^4$ are both hydrogen. In other embodiments, at least one of $R^3$ and $R^4$ is $CO_2H$. In another embodiment, one of $R^3$ and $R^4$ is $CO_2H$ and the other is H, or $CH_2CH_2$piperidinyl.

In certain embodiments, $R^3$ is not hydrogen. In certain embodiments, $R^4$ is not hydrogen. In certain embodiments, neither $R^3$ nor $R^4$ are hydrogen.

With regard to the compounds described herein, $R^5$ is selected from the group consisting of hydrogen, halogen, CN, OH, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, $C_1$-$C_6$alkylheteroaryl, CON($R^{18}$)($R^{19}$), N($R^{18}$)($R^{19}$) or $C_1$-$C_6$alkylN($R^{18}$)($R^{19}$). In certain embodiments, $R^5$ is selected from the group consisting of hydrogen, —OH, $C_3$-$C_6$cycloalkyl, $C_1$-$C_6$alkyl, —$C_1$-$C_6$alkylOH, —$C_1$-$C_6$alkylheteroaryl, or —$C_1$-$C_6$alkylN($R^{18}$)($R^{19}$).

In certain embodiments described herein, $R^5$ is halogen. Examples of suitable halogens include, but are not limited to, chlorine, bromine, fluorine and iodine. In certain embodiments, $R^5$ is —OH. In certain embodiments, $R^5$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^5$ is $C_1$-$C_6$alkyl. Examples of suitable $C_1$-$C_6$alkyl groups can include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments described herein, $R^5$ is halo$C_1$-$C_6$alkyl. Suitable examples of halo alkyls include, but are not limited to, fluoromethyl, difluoromethyl, trifluoromethyl, 2-fluoroethyl, 1,2-difluoroethyl and 2,2-difluoroethyl.

In certain embodiments, $R^5$ is $C_1$-$C_6$alkylOH. Examples of suitable alcohols, include, but are not limited to, methanol, ethanol, propanol, butanol and iso-butanol. In certain embodiments, $R^5$ is —COOH. In certain embodiments, $R^5$ is $C_1$-$C_6$alkyN($R^{18}$)($R^{19}$). Examples of suitable —$C_1$-$C_6$alkylN($R^{18}$)($R^{19}$) groups include, but are not limited to, —$CH_2NH_2$, —$CH_2NH(CH_3)$, —$CH_2N(CH_3)_2$, —$CH_2CH_2N(CH_3)_2$, —$CH_2$piperidinyl and $CH_2CH_2$piperidinyl.

In certain embodiments, $R^5$ is $C_1$-$C_6$alkoxy. Examples of suitable alkoxys include, but are not limited to, methoxy, ethoxy, butoxy and propoxy. In certain embodiments, $R^5$ is —COO$C_1$-$C_6$alkyl. Examples of suitable COO$C_1$-$C_6$alkyl groups include, but are not limited to, methoxycarbonyl, ethoxycarbonyl and butoxycarbonyl.

In certain embodiments, $R^5$ is $C_1$-$C_6$alkylheteroaryl. In certain embodiments, the heteroaryl is a nitrogen containing heteroaryl. In certain embodiments the heteroaryl is an oxygen containing heteroaryl. In certain embodiments the heteroaryl is a sulfur containing heteroaryl. Suitable heteroaryls include, but are not limited to, pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl. In certain embodiments, the heteroaryl is pyridine.

In one embodiment, $R^5$ is hydrogen, methyl, fluoro, $CH_2(NH_2)$, $N(CH_3)_2$, CN, $CH_2NH(CH_3)$, $CONH_2$, $CH_2COOH$ or $CH_2OH$.

With regard to the compounds described herein, $R^6$ is selected from the group consisting of hydrogen, halogen, OH, $C_1$-$C_6$alkylOH, $C_3$-$C_6$cycloalkyl, $C_1$-$C_6$alkyl, halo$C_1$-

$C_6$alkyl, COOH, $N(R^{18})(R^{19})$, $C_1$-$C_6$alkylheteroaryl, $C_1$-$C_6$alkyN$(R^{18})(R^{19})$, $C_1$-$C_6$alkoxy or COO$C_1$-$C_6$alkyl. In certain embodiments, $R^6$ is hydrogen, halogen, —OH, $C_1$-$C_6$alkylOH, $C_3$-$C_6$cycloalkyl, $C_1$-$C_6$alkyl, —COOH, —N$(R^{18})(R^{19})$, —$C_1$-$C_6$alkylheteroaryl, —$C_1$-$C_6$alkyN $(R^{18})(R^{19})$, $C_1$-$C_6$alkoxy or —COO$C_1$-$C_6$alkyl. In certain embodiments described herein, $R^6$ is hydrogen. In certain embodiments described herein, $R^6$ is halogen. Examples of suitable halogens include, but are not limited to, chlorine, bromine, fluorine and iodine. In certain embodiments described herein, $R^6$ is —OH. In certain embodiments, $R^6$ is —$C_1$-$C_6$alkylOH. Examples of suitable alcohols, include, but are not limited to, methanol, ethanol, propanol, butanol and iso-butanol.

In certain embodiments, $R^6$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^6$ is $C_1$-$C_6$alkyl. Examples of suitable $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments described herein, $R^6$ is halo$C_1$-$C_6$alkyl. Suitable examples of halo alkyls include, but are not limited to, fluoromethyl, difluoromethyl, trifluoromethyl, 2-fluoroethyl, 1,2-difluoroethyl and 2,2-difluoroethyl.

In certain embodiments, $R^6$ is —COOH. In certain embodiments, $R^6$ is —$C_1$-$C_6$alkylN$(R^{18})(R^{19})$. Examples of suitable —$C_1$-$C_6$alkyN$(R^{18})(R^{19})$ groups include, but are not limited to, —$CH_2NH_2$, —$CH_2NH(CH_3)$, —$CH_2N(CH_3)_2$, —$CH_2CH_2N(CH_3)_2$, —$CH_2$piperidinyl and —$CH_2CH_2$piperidinyl. In certain embodiments, $R^6$ is —N$(R^{18})(R^{19})$. Examples of suitable —N$(R^{18})(R^{19})$ groups include, but are not limited to, —$NH_2$, —$NH(CH_3)$ and —$N(CH_3)_2$.

In certain embodiments, $R^6$ is $C_1$-$C_6$alkoxy. Examples of suitable alkoxys, include but are not limited to, methoxy, ethoxy, butoxy and propoxy. In certain embodiments, $R^6$ is —COO$C_1$-$C_6$alkyl. Examples of suitable —COO$C_1$-$C_6$alkyl groups include, but are not limited to, methoxycarbonyl, ethoxycarbonyl and butoxycarbonyl.

In certain embodiments, $R^6$ is —$C_1$-$C_6$alkylheteroaryl. In certain embodiments, the heteroaryl is a nitrogen containing heteroaryl. In certain embodiments the heteroaryl is an oxygen containing heteroaryl. In certain embodiments the heteroaryl is a sulfur containing heteroaryl. Suitable heteroaryls include, but are not limited to, pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl. In certain embodiments, the heteroaryl is pyridine.

With regard to the compounds described herein, $R^7$ is selected from the group consisting of hydrogen, halogen, OH, $C_1$-$C_6$alkylOH, $C_3$-$C_6$cycloalkyl, $C_1$-$C_6$alkyl, halo$C_1$-$C_6$alkyl, COOH, —N$(R^{18})(R^{19})$, $C_1$-$C_6$alkylheteroaryl, $C_1$-$C_6$alkyN$(R^{18})(R^{19})$, $C_1$-$C_6$alkoxy or COO$C_1$-$C_6$alkyl. In certain embodiments, $R^7$ is hydrogen, halogen, —OH, $C_1$-$C_6$alkylOH, $C_3$-$C_6$cycloalkyl, $C_1$-$C_6$alkyl, —COOH, —N$(R^{18})(R^{19})$, —$C_1$-$C_6$alkylheteroaryl, —$C_1$-$C_6$alkyN $(R^{18})(R^{19})$, $C_1$-$C_6$alkoxy or —COO$C_1$-$C_6$alkyl.

In certain embodiments described herein, $R^7$ is hydrogen. In certain embodiments described herein, $R^7$ is halogen. Examples of suitable halogens include, but are not limited to, chlorine, bromine, fluorine and iodine. In certain embodiments described herein, $R^7$ is —OH. In certain embodiments, $R^7$ is —$C_1$-$C_6$alkylOH. Examples of suitable alcohols, include, but are not limited to, methanol, ethanol, propanol, butanol and iso-butanol.

In certain embodiments, $R^7$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^7$ is $C_1$-$C_6$alkyl. Examples of suitable $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments described herein, $R^7$ is halo$C_1$-$C_6$alkyl. Suitable examples of halo alkyls include, but are not limited to, fluoromethyl, difluoromethyl, trifluoromethyl, 2-fluoroethyl, 1,2-difluoroethyl and 2,2-difluoroethyl.

In certain embodiments, $R^7$ is —COOH. In certain embodiments, $R^7$ is —$C_1$-$C_6$alkylN$(R^{18})(R^{19})$. Examples of suitable —$C_1$-$C_6$alkyN$(R^{18})(R^{19})$ groups include, but are not limited to, —$CH_2NH_2$, —$CH_2NH(CH_3)$, —$CH_2N(CH_3)_2$, —$CH_2CH_2N(CH_3)_2$, —$CH_2$piperidinyl and —$CH_2CH_2$piperidinyl. In certain embodiments, $R^7$ is —N$(R^{18})(R^{19})$. Examples of suitable —N$(R^{18})(R^{19})$ groups include, but are not limited to, —$NH_2$, —$NH(CH_3)$ and —$N(CH_3)_2$.

In certain embodiments, $R^7$ is $C_1$-$C_6$alkoxy. Examples of suitable alkoxys, include but are not limited to, methoxy, ethoxy, butoxy and propoxy. In certain embodiments, $R^7$ is COO$C_1$-$C_6$alkyl. Examples of suitable —COO$C_1$-$C_6$alkyl groups include, but are not limited to, methoxycarbonyl, ethoxycarbonyl and butoxycarbonyl.

In certain embodiments, $R^7$ is —$C_1$-$C_6$alkylheteroaryl. In certain embodiments, the heteroaryl is a nitrogen containing heteroaryl. In certain embodiments the heteroaryl is an oxygen containing heteroaryl. In certain embodiments, the heteroaryl is a sulfur containing heteroaryl. Suitable heteroaryls include, but are not limited to, pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl. In certain embodiments, the heteroaryl is pyridine.

In certain embodiments, $R^6$ is not —COOH. In certain embodiments, $R^6$ is not —NH$_2$. In certain embodiments, $R^7$ is not —COOH. In certain embodiments, $R^7$ is not —NH$_2$. In certain embodiments, neither $R^6$ nor $R^7$ are not —COOH. In certain embodiments, neither $R^6$ nor $R^7$ are not —NH$_2$.

With regard to the compounds described herein, $R^8$ is selected from the group consisting of hydrogen, $C_3$-$C_6$cycloalkyl, $C_1$-$C_6$alkyl, —$C_1$-$C_6$alkylheteroaryl, or —$C_1$-$C_6$alkylN($R^{18}$)($R^{19}$). In certain embodiments, $R^8$ is hydrogen. In certain embodiments, $R^8$ is $C_3$-$C_6$cycloalkyl. Suitable cycloalkyl groups include, but are not limited to, cyclopropyl, cyclobutyl, cyclopentyl, cyclohexyl. In certain embodiments, $R^8$ is $C_1$-$C_6$alkyl. Examples of suitable $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^8$ is —$C_1$-$C_6$alkylN($R^{18}$)($R^{19}$). Examples of suitable —$C_1$-$C_6$alkylN($R^{18}$)($R^{19}$) groups include, but are not limited to, —CH$_2$NH$_2$, —CH$_2$NH(CH$_3$), —CH$_2$N(CH$_3$)$_2$, —CH$_2$CH$_2$N(CH$_3$)$_2$, —CH$_2$piperidinyl and —CH$_2$CH$_2$piperidinyl.

In certain embodiments, $R^8$ is —$C_1$-$C_6$alkylheteroaryl. In certain embodiments, the heteroaryl is a nitrogen containing heteroaryl. In certain embodiments the heteroaryl is an oxygen containing heteroaryl. In certain embodiments the heteroaryl is a sulfur containing heteroaryl. Suitable heteroaryls include, but are not limited to, pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl. In certain embodiments, the heteroaryl is pyridine.

With regard to the compounds described herein, $R^9$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, COOH, —N($R^{18}$)($R^{19}$), $C_1$-$C_6$alkylheteroaryl, $C_1$-$C_6$alkyN($R^{18}$)($R^{19}$), $C_1$-$C_6$alkoxy or COOC$_1$-$C_6$alkyl. In certain embodiments, $R^9$ is hydrogen, halogen, —OH, —$C_1$-$C_6$alkylOH, $C_3$-$C_6$cycloalkyl, $C_1$-$C_6$alkyl, —COOH, —N($R^{18}$)($R^{19}$), —$C_1$-$C_6$alkylheteroaryl, —$C_1$-$C_6$alkyN($R^{18}$)($R^{19}$), $C_1$-$C_6$alkoxy or —COOC$_1$-$C_6$alkyl.

In certain embodiments described herein, $R^9$ is hydrogen. In certain embodiments described herein, $R^9$ is halogen. Examples of suitable halogens include, but are not limited to, chlorine, bromine, fluorine and iodine. In certain embodiments described herein, $R^9$ is —OH. In certain embodiments, $R^9$ is —$C_1$-$C_6$alkylOH. Examples of suitable alcohols, include, but are not limited to, methanol, ethanol, propanol, butanol and iso-butanol.

In certain embodiments, $R^9$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^9$ is $C_1$-$C_6$alkyl. Examples of suitable $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments described herein, $R^9$ is halo$C_1$-$C_6$alkyl. Suitable examples of halo alkyls include, but are not limited to, fluoromethyl, difluoromethyl, trifluoromethyl, 2-fluoroethyl, 1,2-difluoroethyl and 2,2-difluoroethyl.

In certain embodiments, $R^9$ is —COOH. In certain embodiments, $R^9$ is —$C_1$-$C_6$alkylN($R^{18}$)($R^{19}$). Examples of suitable —$C_1$-$C_6$alkylN($R^{18}$)($R^{19}$) groups include, but are not limited to, —CH$_2$NH$_2$, —CH$_2$NH(CH$_3$), —CH$_2$N(CH$_3$)$_2$, —CH$_2$CH$_2$N(CH$_3$)$_2$, —CH$_2$piperidinyl and —CH$_2$CH$_2$piperidinyl. In certain embodiments, $R^9$ is —N($R^{18}$)($R^{19}$). Examples of suitable N($R^{18}$)($R^{19}$) groups include, but are not limited to, —NH$_2$, —NH(CH$_3$) and —N(CH$_3$)$_2$.

In certain embodiments, $R^9$ is $C_1$-$C_6$alkoxy. Examples of suitable alkoxys, include but are not limited to, methoxy, ethoxy, butoxy and propoxy. In certain embodiments, $R^9$ is —COOC$_1$-$C_6$alkyl. Examples of suitable —COOC$_1$-$C_6$alkyl groups include, but are not limited to, methoxycarbonyl, ethoxycarbonyl and butoxycarbonyl.

In certain embodiments, $R^9$ is —$C_1$-$C_6$alkylheteroaryl. In certain embodiments, the heteroaryl is a nitrogen containing heteroaryl. In certain embodiments the heteroaryl is an oxygen containing heteroaryl. In certain embodiments the heteroaryl is a sulfur containing heteroaryl. Suitable heteroaryls include, but are not limited to, pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl. In certain embodiments, the heteroaryl is pyridine.

In one embodiment $R^9$ is selected from H or CO$_2$H.

With regard to the compounds described herein, $R^{10}$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, COOH, —N($R^{18}$)($R^{19}$), $C_1$-$C_6$alkylheteroaryl, $C_1$-$C_6$alkyN($R^{18}$)($R^{19}$), $C_1$-$C_6$alkoxy or COOC$_1$-$C_6$alkyl. In certain embodiments, $R^{10}$ is hydrogen, halogen, —OH, $C_3$-$C_6$cycloalkyl, $C_1$-$C_6$alkyl, —COOH, —$C_1$-$C_6$alkylheteroaryl, —$C_1$-$C_6$alkyN($R^{18}$)($R^{19}$), $C_1$-$C_6$alkoxy and —COOC$_1$-$C_6$alkyl.

In certain embodiments described herein, $R^{10}$ is hydrogen. In certain embodiments described herein, $R^{10}$ is halogen. Examples of suitable halogens include, but are not limited to, chlorine, bromine, fluorine and iodine. In certain embodiments described herein, $R^{10}$ is —OH. In certain embodiments, $R^{10}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{10}$ is $C_1$-$C_6$alkyl. Examples of suitable $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments described herein, $R^{10}$ is halo$C_1$-$C_6$alkyl. Suitable examples of halo alkyls include, but are not limited to, fluoromethyl, difluoromethyl, trifluoromethyl, 2-fluoroethyl, 1,2-difluoroethyl and 2,2-difluoroethyl.

In certain embodiments, $R^{10}$ is —COOH. In certain embodiments, $R^{10}$ is —$C_1$-$C_6$alkylN($R^{18}$)($R^{19}$). Examples of suitable —$C_1$-$C_6$alkyN($R^{18}$)($R^{19}$) groups include, but are not limited to, —$CH_2NH_2$, —$CH_2NH(CH_3)$, —$CH_2N(CH_3)_2$, —$CH_2CH_2N(CH_3)_2$, —$CH_2$piperidinyl and —$CH_2CH_2$piperidinyl.

In certain embodiments, $R^{10}$ is $C_1$-$C_6$alkoxy. Examples of suitable alkoxys, include but are not limited to, methoxy, ethoxy, butoxy and propoxy. In certain embodiments, $R^{10}$ is —COO$C_1$-$C_6$alkyl. Examples of suitable —COO$C_1$-$C_6$alkyl groups include, but are not limited to, methoxycarbonyl, ethoxycarbonyl and butoxycarbonyl.

In certain embodiments, $R^{10}$ is —$C_1$-$C_6$alkylheteroaryl. In certain embodiments, the heteroaryl is a nitrogen containing heteroaryl. In certain embodiments the heteroaryl is an oxygen containing heteroaryl. In certain embodiments the heteroaryl is a sulfur containing heteroaryl. Suitable heteroaryls include, but are not limited to, pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl. In certain embodiments, the heteroaryl is pyridine.

With regard to the compounds described herein, $R^{11}$ is selected from the group consisting of hydrogen, $C_3$-$C_6$cycloalkyl, $C_1$-$C_6$alkyl, —$C_1$-$C_6$alkylheteroaryl, or —$C_1$-$C_6$alkylN($R^{18}$)($R^{19}$). In certain embodiments described herein, $R^{11}$ is hydrogen. In certain embodiments, $R^{11}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{11}$ is $C_1$-$C_6$alkyl. Examples of suitable $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{11}$ is —$C_1$-$C_6$alkylN($R^{18}$)($R^{19}$). Examples of suitable —$C_1$-$C_6$alkyN($R^{18}$)($R^{19}$) groups include, but are not limited to, —$CH_2NH_2$, —$CH_2NH(CH_3)$, —$CH_2N(CH_3)_2$, —$CH_2CH_2N(CH_3)_2$, —$CH_2$piperidinyl and —$CH_2CH_2$piperidinyl.

In certain embodiments, $R^{11}$ is —$C_1$-$C_6$alkylheteroaryl. In certain embodiments, the heteroaryl is a nitrogen containing heteroaryl. In certain embodiments the heteroaryl is an oxygen containing heteroaryl. In certain embodiments the heteroaryl is a sulfur containing heteroaryl. Suitable heteroaryls include, but are not limited to, pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl. In certain embodiments, the heteroaryl is pyridine.

With regard to the compounds described herein, $R^{12}$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, —COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl. In certain embodiments, $R^{12}$ is hydrogen, halogen, —OH, —$C_1$-$C_6$alkylOH, $C_3$-$C_6$cycloalkyl, $C_1$-$C_6$alkyl, —COOH, —N($R^{18}$)($R^{19}$), —$C_1$-$C_6$alkylheteroaryl, —$C_1$-$C_6$alkyN($R^{18}$)($R^{19}$), $C_1$-$C_6$alkoxy or —COO$C_1$-$C_6$alkyl.

In certain embodiments, $R^{12}$ is hydrogen, halogen, —OH, —$C_1$-$C_6$alkylOH, $C_3$-$C_6$cycloalkyl, $C_1$-$C_6$alkyl, —COOH, —N($R^{18}$)($R^{19}$), —$C_1$-$C_6$alkylheteroaryl, $C_1$-$C_6$alkoxy or —COO$C_1$-$C_6$alkyl. In certain embodiments described herein, $R^{12}$ is hydrogen. In certain embodiments described herein, $R^1$ is halogen. Examples of suitable halogens include, but are not limited to, chlorine, bromine, fluorine and iodine. In certain embodiments described herein, $R^1$ is —OH. In certain embodiments, $R^{12}$ is —$C_1$-$C_6$alkylOH. Examples of suitable alcohols, include, but are not limited to, methanol, ethanol, propanol, butanol and iso-butanol.

In certain embodiments, $R^1$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{12}$ is $C_1$-$C_6$alkyl. Examples of suitable $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments described herein, $R^{12}$ is halo$C_1$-$C_6$alkyl. Suitable examples of halo alkyls include, but are not limited to, fluoromethyl, difluoromethyl, trifluoromethyl, 2-fluoroethyl, 1,2-difluoroethyl and 2,2-difluoroethyl.

In certain embodiments, $R^1$ is —COOH. In certain embodiments, $R^1$ is —$C_1$-$C_6$alkylN($R^{18}$)($R^{19}$). Examples of suitable —$C_1$-$C_6$alkylN($R^{18}$)($R^{19}$) groups include, but are not limited to, —$CH_2NH_2$, —$CH_2NH(CH_3)$, —$CH_2N(CH_3)_2$, —$CH_2CH_2N(CH_3)_2$, —$CH_2$piperidinyl and —$CH_2CH_2$piperidinyl. In certain embodiments, $R^{12}$ is —N($R^{18}$)($R^{19}$). Examples of suitable N($R^{18}$)($R^{19}$) groups include, but are not limited to, —$NH_2$, —$NH(CH_3)$ and —$N(CH_3)_2$.

In certain embodiments, $R^1$ is $C_1$-$C_6$alkoxy. Examples of suitable alkoxys, include but are not limited to, methoxy, ethoxy, butoxy and propoxy. In certain embodiments, $R^1$ is —COOC$_1$-C$_6$alkyl. Examples of suitable —COOC$_1$-C$_6$alkyl groups include, but are not limited to, methoxycarbonyl, ethoxycarbonyl and butoxycarbonyl.

In certain embodiments, R$^1$ is —C$_1$-C$_6$alkylheteroaryl. In certain embodiments, the heteroaryl is a nitrogen containing heteroaryl. In certain embodiments the heteroaryl is an oxygen containing heteroaryl. In certain embodiments the heteroaryl is a sulfur containing heteroaryl. Suitable heteroaryls include, but are not limited to, pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl. In certain embodiments, the heteroaryl is pyridine.

In one embodiment R$^1$ is H or CH$_3$.

With regard to the compounds described herein, R$^{13}$ is selected from the group consisting of hydrogen, halogen, OH, —C$_1$-C$_6$alkylOH, C$_3$-C$_6$cycloalkyl, C$_1$-C$_6$alkyl, haloC$_1$-C$_6$alkyl, —COOH, —N(R$^{18}$)(R$^{19}$), C$_1$-C$_6$alkylheteroaryl, C$_1$-C$_6$alkylN(R$^{18}$)(R$^{19}$), C$_1$-C$_6$alkoxy or COOC$_1$-C$_6$alkyl. In certain embodiments, R$^{13}$ is hydrogen, halogen, —OH, —C$_1$-C$_6$alkylOH, C$_3$-C$_6$cycloalkyl, C$_1$-C$_6$alkyl, —COOH, —N(R$^{18}$)(R$^{19}$), —C$_1$-C$_6$alkylheteroaryl, —C$_1$-C$_6$alkyN(R$^{18}$)(R$^{19}$), C$_1$-C$_6$alkoxy or —COOC$_1$-C$_6$alkyl. In certain embodiments, R$^{13}$ is hydrogen, halogen, —OH, —C$_1$-C$_6$alkylOH, C$_3$-C$_6$cycloalkyl, C$_1$-C$_6$alkyl, —COOH, —N(R$^{18}$)(R$^{19}$), —C$_1$-C$_6$alkylheteroaryl, C$_1$-C$_6$alkoxy or —COOC$_1$-C$_6$alkyl.

In certain embodiments described herein, R$^{13}$ is hydrogen. In certain embodiments described herein, R$^{13}$ is halogen. Examples of suitable halogens include, but are not limited to, chlorine, bromine, fluorine and iodine. In certain embodiments described herein, R$^{13}$ is —OH. In certain embodiments, R$^{13}$ is —C$_1$-C$_6$alkylOH. Examples of suitable alcohols, include, but are not limited to, methanol, ethanol, propanol, butanol and iso-butanol.

In certain embodiments, R$^{13}$ is C$_3$-C$_6$cycloalkyl. Suitable cycloalkyl groups include, but are not limited to, cyclopropyl, cyclobutyl, cyclopentyl, cyclohexyl. In certain embodiments described herein, R$^{13}$ is C$_1$-C$_6$alkyl. Examples of suitable C$_1$-C$_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments described herein, R$^{13}$ is haloC$_1$-C$_6$alkyl. Suitable examples of halo alkyls include, but are not limited to, fluoromethyl, difluoromethyl, trifluoromethyl, 2-fluoroethyl, 1,2-difluoroethyl and 2,2-difluoroethyl. In certain embodiments described herein, R$^{13}$ is haloC$_1$-C$_6$alkyl. Suitable examples of halo alkyls include, but are not limited to, fluoromethyl, difluoromethyl, trifluoromethyl, 2-fluoroethyl, 1,2-difluoroethyl and 2,2-difluoroethyl.

In certain embodiments, R$^{13}$ is —COOH. In certain embodiments, R$^{13}$ is —C$_1$-C$_6$alkylN(R$^{18}$)(R$^{19}$). Examples of suitable —C$_1$-C$_6$alkylN(R$^{18}$)(R$^{19}$) groups include, but are not limited to, —CH$_2$NH$_2$, —CH$_2$NH(CH$_3$), —CH$_2$N(CH$_3$)$_2$, —CH$_2$CH$_2$N(CH$_3$)$_2$, —CH$_2$piperidinyl and —CH$_2$CH$_2$piperidinyl. In certain embodiments, R$^{13}$ is —N(R$^{18}$)(R$^{19}$). Examples of suitable —N(R$^{18}$)(R$^{19}$) groups include, but are not limited to, —NH$_2$, —NH(CH$_3$) and —N(CH$_3$)$_2$.

In certain embodiments, R$^{13}$ is C$_1$-C$_6$alkoxy. Examples of suitable alkoxys, include but are not limited to, methoxy, ethoxy, butoxy and propoxy. In certain embodiments, R$^{13}$ is —COOC$_1$-C$_6$alkyl. Examples of suitable —COOC$_1$-C$_6$alkyl groups include, but are not limited to, methoxycarbonyl, ethoxycarbonyl and butoxycarbonyl.

In certain embodiments, R$^{13}$ is —C$_1$-C$_6$alkylheteroaryl. In certain embodiments, the heteroaryl is a nitrogen containing heteroaryl. In certain embodiments the heteroaryl is an oxygen containing heteroaryl. In certain embodiments the heteroaryl is a sulfur containing heteroaryl. Suitable heteroaryls include, but are not limited to, pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl. In certain embodiments, the heteroaryl is pyridine.

In one embodiment, R$^{13}$ is H or CH$_3$.

With regard to the compounds described herein, R$^{14}$ is hydrogen, C$_3$-C$_6$cycloalkyl, C$_1$-C$_6$alkyl, —C$_1$-C$_6$alkylheteroaryl, or —C$_1$-C$_6$alkylN(R$^{18}$)(R$^{19}$). In certain embodiments described herein, R$^{14}$ is hydrogen. In certain embodiments, R$^{14}$ is C$_3$-C$_6$cycloalkyl. Suitable cycloalkyl groups include, but are not limited to, cyclopropyl, cyclobutyl, cyclopentyl, cyclohexyl. In certain embodiments described herein, R$^{14}$ is C$_1$-C$_6$alkyl. Examples of suitable C$_1$-C$_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, R$^{14}$ is —C$_1$-C$_6$alkylN(R$^{18}$)(R$^{19}$). Examples of suitable —C$_1$-C$_6$alkylN(R$^{18}$)(R$^{19}$) groups include, but are not limited to, —CH$_2$NH$_2$, —CH$_2$NH(CH$_3$), —CH$_2$N(CH$_3$)$_2$, —CH$_2$CH$_2$N(CH$_3$)$_2$, —CH$_2$piperidinyl and —CH$_2$CH$_2$piperidinyl.

In certain embodiments, R$^1$ is —C$_1$-C$_6$alkylheteroaryl. In certain embodiments, the heteroaryl is a nitrogen containing heteroaryl. In certain embodiments the heteroaryl is an oxygen containing heteroaryl. In certain embodiments the heteroaryl is a sulfur containing heteroaryl. Suitable heteroaryls include, but are not limited to, pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl. In certain embodiments, the heteroaryl is pyridine.

With regard to the compounds described herein, $R^{15}$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, —COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl. In certain embodiments, $R^{15}$ is hydrogen, halogen, —OH, —$C_1$-$C_6$alkylOH, $C_3$-$C_6$cycloalkyl, $C_1$-$C_6$alkyl, —COOH, —N($R^{18}$)($R^{19}$), —$C_1$-$C_6$alkylheteroaryl, —$C_1$-$C_6$alkyN($R^{18}$)($R^{19}$), $C_1$-$C_6$alkoxy or —COO$C_1$-$C_6$alkyl.

In certain embodiments described herein, $R^{15}$ is hydrogen. In certain embodiments described herein, $R^{15}$ is halogen. Examples of suitable halogens include, but are not limited to, chlorine, bromine, fluorine and iodine. In certain embodiments described herein, $R^{15}$ is —OH. In certain embodiments, $R^{15}$ is —$C_1$-$C_6$alkylOH. Examples of suitable alcohols, include, but are not limited to, methanol, ethanol, propanol, butanol and iso-butanol.

In certain embodiments, $R^{15}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{15}$ is $C_1$-$C_6$alkyl. Examples of suitable $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments described herein, $R^{15}$ is halo$C_1$-$C_6$alkyl. Suitable examples of halo alkyls include, but are not limited to, fluoromethyl, difluoromethyl, trifluoromethyl, 2-fluoroethyl, 1,2-difluoroethyl and 2,2-difluoroethyl.

In certain embodiments, $R^{15}$ is —COOH. In certain embodiments, $R^{15}$ is —$C_1$-$C_6$alkylN($R^{18}$)($R^{19}$). Examples of suitable —$C_1$-$C_6$alkylN($R^{18}$)($R^{19}$) groups include, but are not limited to, —$CH_2NH_2$, —$CH_2NH(CH_3)$, —$CH_2N(CH_3)_2$, —$CH_2CH_2N(CH_3)_2$, —$CH_2$piperidinyl and —$CH_2CH_2$piperidinyl. In certain embodiments, $R^{15}$ is —N($R^{18}$)($R^{19}$). Examples of suitable —N($R^{18}$)($R^{19}$) groups include, but are not limited to, —$NH_2$, —NH($CH_3$) and —N($CH_3$)$_2$.

In certain embodiments, $R^{15}$ is $C_1$-$C_6$alkoxy. Examples of suitable alkoxys, include but are not limited to, methoxy, ethoxy, butoxy and propoxy. In certain embodiments, $R^{15}$ is —COO$C_1$-$C_6$alkyl. Examples of suitable —COO$C_1$-$C_6$alkyl groups include, but are not limited to, methoxycarbonyl, ethoxycarbonyl and butoxycarbonyl.

In certain embodiments, $R^{15}$ is —$C_1$-$C_6$alkylheteroaryl. In certain embodiments, the heteroaryl is a nitrogen containing heteroaryl. In certain embodiments the heteroaryl is an oxygen containing heteroaryl. In certain embodiments the heteroaryl is a sulfur containing heteroaryl. Suitable heteroaryls include, but are not limited to, pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl. In certain embodiments, the heteroaryl is pyridine.

In one embodiment $R^{15}$ is H, $CO_2H$ or $CH_2$piperidinyl.

With regard to the compounds described herein, $R^{16}$ is selected from the group consisting of hydrogen, halogen, OH, $C_1$-$C_6$alkylOH, $C_3$-$C_6$cycloalkyl, $C_1$-$C_6$alkyl, halo$C_1$-$C_6$alkyl, COOH, N($R^{18}$)($R^{19}$), $C_1$-$C_6$alkylheteroaryl, $C_1$-$C_6$alkyN($R^{18}$)($R^{19}$), $C_1$-$C_6$alkoxy or COO$C_1$-$C_6$alkyl. In certain embodiments, $R^{16}$ is hydrogen, halogen, —OH, —$C_1$-$C_6$alkylOH, $C_3$-$C_6$cycloalkyl, $C_1$-$C_6$alkyl, —COOH, —N($R^{18}$)($R^{19}$), —$C_1$-$C_6$alkylheteroaryl, —$C_1$-$C_6$alkyN ($R^{18}$)($R^{19}$), $C_1$-$C_6$alkoxy or —COO$C_1$-$C_6$alkyl. In certain embodiments described herein, $R^{16}$ is hydrogen. In certain embodiments described herein, $R^{16}$ is halogen. Examples of suitable halogens include, but are not limited to, chlorine, bromine, fluorine and iodine. In certain embodiments described herein, $R^{16}$ is —OH. In certain embodiments, $R^{16}$ is —$C_1$-$C_6$alkylOH. Examples of suitable alcohols, include, but are not limited to, methanol, ethanol, propanol, butanol and iso-butanol.

In certain embodiments, $R^{16}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{16}$ is $C_1$-$C_6$alkyl. Examples of suitable $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments described herein, $R^{16}$ is halo$C_1$-$C_6$alkyl. Suitable examples of halo alkyls include, but are not limited to, fluoromethyl, difluoromethyl, trifluoromethyl, 2-fluoroethyl, 1,2-difluoroethyl and 2,2-difluoroethyl.

In certain embodiments, $R^{16}$ is —COOH. In certain embodiments, $R^{16}$ is —$C_1$-$C_6$alkylN($R^{18}$)($R^{19}$). Examples of suitable —$C_1$-$C_6$alkyN($R^{18}$)($R^{19}$) groups include, but are not limited to, —$CH_2NH_2$, —$CH_2NH(CH_3)$, —$CH_2N(CH_3)_2$, —$CH_2CH_2N(CH_3)_2$, —$CH_2$piperidinyl and —$CH_2CH_2$piperidinyl. In certain embodiments, $R^{16}$ is —N($R^{18}$)($R^{19}$). Examples of suitable —N($R^{18}$)($R^{19}$) groups include, but are not limited to, —$NH_2$, —NH($CH_3$) and —N($CH_3$)$_2$.

In certain embodiments, $R^{16}$ is $C_1$-$C_6$alkoxy. Examples of suitable alkoxys, include but are not limited to, methoxy, ethoxy, butoxy and propoxy. In certain embodiments, $R^{16}$ is —COO$C_1$-$C_6$alkyl. Examples of suitable —COO$C_1$-$C_6$alkyl groups include, but are not limited, methoxycarbonyl, ethoxycarbonyl and butoxycarbonyl.

In certain embodiments, $R^{16}$ is —$C_1$-$C_6$alkylheteroaryl. In certain embodiments, the heteroaryl is a nitrogen containing heteroaryl. In certain embodiments the heteroaryl is an oxygen containing heteroaryl. In certain embodiments the heteroaryl is a sulfur containing heteroaryl. Suitable heteroaryls include, but are not limited to, pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl. In certain embodiments, the heteroaryl is pyridine.

In one embodiment $R^{16}$ is H, $CO_2H$ or $CH_2$piperidinyl.

With regard to the compounds described herein, $R^{17}$ is selected from the group consisting of hydrogen, $C_3$-$C_6$cycloalkyl, $C_1$-$C_6$alkyl, —$C_1$-$C_6$alkylheteroaryl and —$C_1$-$C_6$alkyN($R^{18}$)($R^{19}$). In certain embodiments described herein, $R^{17}$ is hydrogen. In certain embodiments, $R^{17}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{17}$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^1$ is —$C_1$-$C_6$alkylN($R^{18}$)($R^{19}$). Examples of suitable —$C_1$-$C_6$alkylN($R^{18}$)($R^{19}$) groups include, but are not limited to, —$CH_2NH_2$, —$CH_2NH(CH_3)$, —$CH_2N(CH_3)_2$, —$CH_2CH_2N(CH_3)_2$, —$CH_2$piperidinyl and —$CH_2CH_2$piperidinyl.

In certain embodiments, $R^{17}$ is —$C_1$-$C_6$alkylheteroaryl. In certain embodiments, the heteroaryl is a nitrogen containing heteroaryl. In certain embodiments the heteroaryl is an oxygen containing heteroaryl. In certain embodiments the heteroaryl is a sulfur containing heteroaryl. Suitable heteroaryls include, but are not limited to, pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl and dibenzofuranyl. In certain embodiments, the heteroaryl is pyridine.

In one embodiment $R^{17}$ is H, $CO_2H$ or $CH_2$piperidinyl.

With regard to the compounds described herein, $R^{18}$ is selected from the group consisting of hydrogen, $C_3$-$C_6$cycloalkyl, halo$C_1$-$C_6$alkyl, $C_1$-$C_6$alkyl, $C_1$-$C_6$alkylNH$_2$, COheterocycle, and COC$_1$-$C_6$alkyl, wherein the COC$_1$-$C_6$alkyl can be optionally substituted with one or two substituents selected from the group consisting of N($R^{19}$)($R^{19}$), OH, cycloalkyl, or a 3-7 membered nitrogen containing ring or when $R^{18}$ is taken with $R^{19}$ forms a 3-7 membered nitrogen containing ring. In certain embodiments, $R^{18}$ is hydrogen, $C_3$-$C_6$cycloalkyl, $C_1$-$C_6$alkyl, an amino acid and COC$_1$-$C_6$alkyl, wherein the COC$_1$-$C_6$alkyl can be optionally substituted with N($R^{19}$)($R^{19}$), or $R^{18}$ when taken with $R^{19}$ forms a 3-7 membered nitrogen containing ring.

In certain embodiments, $R^6$ and $R^7$, $R^9$ and $R^{10}$, $R^{12}$ and $R^{13}$ or $R^1$ and $R^{16}$ cannot be COOH and N($R^{18}$)($R^{19}$) or N($R^{18}$)($R^{19}$) and COOH. In certain embodiments, $R^6$ and $R^7$, $R^9$ and $R^{10}$, $R^1$ and $R^{13}$ or $R^5$ and $R^{16}$ cannot be COOH and NH$_2$ or NH$_2$ and COOH.

In certain embodiments, $R^{18}$ is hydrogen. In certain embodiments, $R^{18}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{18}$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments described herein, $R^{18}$ is halo$C_1$-$C_6$alkyl. Suitable examples of halo alkyls include, but are not limited to, fluoromethyl, difluoromethyl, trifluoromethyl, 2-fluoroethyl, 1,2-difluoroethyl and 2,2-difluoroethyl.

In certain embodiments, $R^{18}$ is $C_1$-$C_6$alkylNH$_2$. Suitable examples of $C_1$-$C_6$alkylNH$_2$s include, but are not limited to, CH$_2$NH$_2$, CH$_2$CH$_2$NH$_2$ and CH$_2$CH$_2$CH$_2$NH$_2$. In certain embodiments, $R^{18}$ is COC$_1$-$C_6$alkyl. In certain embodiments, when $R^{18}$ is COC$_1$-$C_6$alkyl, the COC$_1$-$C_6$alkyl can be optionally substituted with one or two substituents selected from the group consisting of N($R^{19}$)($R^{19}$), OH, cycloalkyl, or a 3-7 membered nitrogen containing ring. In certain embodiments, when $R^{18}$ is COC$_1$-$C_6$alkyl, COC$_1$-$C_6$alkyl can be substituted with one substituent selected from the group consisting of N($R^{19}$)($R^{19}$), OH, cycloalkyl, or a 3-7 membered nitrogen containing ring. In certain embodiments, when $R^{18}$ is COC$_1$-$C_6$alkyl, the COC$_1$-$C_6$alkyl is substituted with two substituents selected from the group consisting of N($R^{19}$)($R^{19}$), OH, cycloalkyl, or a 3-7 membered nitrogen containing ring. In certain embodiments, when $R^{18}$ is COC$_1$-$C_6$alkyl, the —COC$_1$-$C_6$alkyl can be optionally substituted with —N($R^{19}$)($R^{19}$).

In certain embodiments, $R^{18}$ is COheterocycle. In certain embodiments, $R^{18}$ is COheterocycle, wherein the heterocycle is a 3-7 membered nitrogen-containing ring. Examples of 3-7 membered nitrogen containing ring include, but are not limited to, aziridinyl, azirinyl, azetidinyl, azete, pyrrolidinyl, pyrrolyl, piperidinyl and pyridinyl. Examples of 3-7 membered nitrogen containing ring include, but are not limited to, azetidinyl, pyrrolidinyl and piperidinyl.

In certain embodiments, $R^{18}$ is hydrogen, methyl,

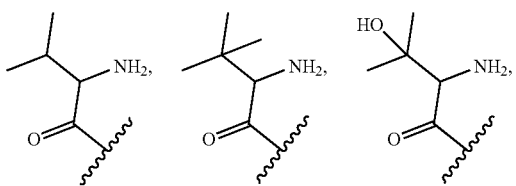

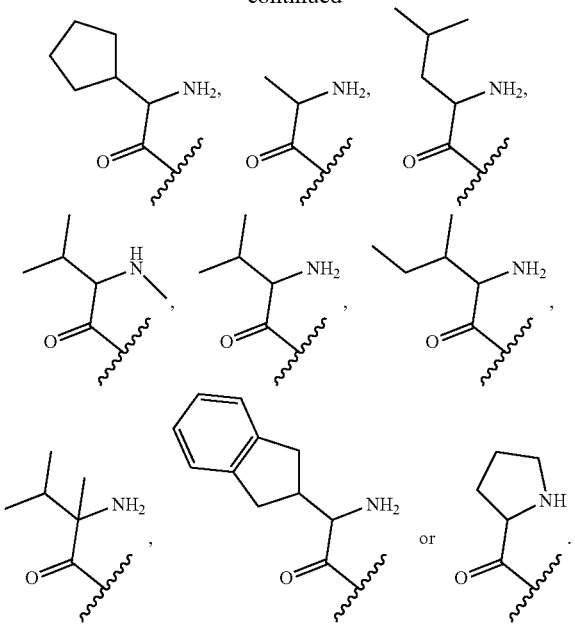

In certain embodiments, $R^{18}$ is an amino acid. In certain embodiments, $R^{18}$ is a proteinogenic amino acid. Suitable proteinogenic amino acids include, but are not limited to, alanine, arginine, asparagine, aspartic acid, cysteine, glutamic acid, glutamine, glycine, histidine, isoleucine, leucine, lysine, methionine, phenylalanine, proline, pyrrolysine, selenocysteine, serine, threonine, tryptophan, tyrosine and valine In certain embodiments, $R^{18}$ is

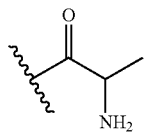

In certain embodiments, $R^{18}$ is taken with $R^{19}$ and forms a 3-7 membered nitrogen containing ring. Examples of 3-7 membered nitrogen containing ring include, but are not limited to, aziridinyl, azirinyl, azetidinyl, azete, pyrrolidinyl, pyrrolyl, piperidinyl and pyridinyl. Examples of 3-7 membered nitrogen containing ring include, but are not limited to, azetidinyl, pyrrolidinyl and piperidinyl.

With regard to the compounds described herein, $R^{19}$ is selected from the group consisting of hydrogen, $C_3$-$C_6$cycloalkyl, halo$C_1$-$C_6$alkyl and $C_1$-$C_6$alkyl, or when $R^{19}$ is taken with $R^{18}$ forms a 3-7 membered nitrogen containing ring. In certain embodiments, $R^{19}$ is hydrogen, $C_3$-$C_6$cycloalkyl or $C_1$-$C_6$alkyl, or $R^{19}$ when taken with $R^{18}$ forms a 3-7 membered nitrogen containing ring.

In certain embodiments, $R^{19}$ is hydrogen. In certain embodiments, $R^{19}$ is $C_3$-$C_6$cycloalkyl. Suitable cycloalkyl groups include, but are not limited to, cyclopropyl, cyclobutyl, cyclopentyl, cyclohexyl. In certain embodiments described herein, $R^{19}$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments described herein, $R^{19}$ is halo$C_1$-$C_6$alkyl. Suitable examples of halo alkyls include, but are not limited to, fluoromethyl, difluoromethyl, trifluoromethyl, 2-fluoroethyl, 1,2-difluoroethyl and 2,2-difluoroethyl. In certain embodiments, $R^{19}$ is hydrogen or methyl.

In certain embodiments, $R^{19}$ is taken with $R^{18}$ and forms a 3-7 membered nitrogen containing ring. Examples of 3-7 membered nitrogen containing ring include, but are not limited to, aziridinyl, azirinyl, azetidinyl, azete, pyrrolidinyl, pyrrolyl, piperidinyl and pyridinyl.

Also described herein are compounds of Formula II:

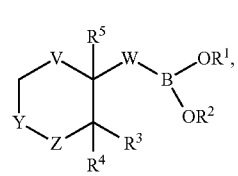

II or a pharmaceutically acceptable salt thereof, wherein:

W is a straight or branched ($C_2$-$C_5$)alkylene, wherein one or more —$CH_2$— groups in W are optionally and independently replaced with a O, S or NH moiety;

V is a bond, O, S, $CR^6R^7$ or $NR^8$;

Y is O, S, $CR^{12}R^{13}$ or $NR^{14}$;

Z is O, S, $CR^{15}R^{16}$ or $NR^{17}$;

$R^1$ is hydrogen or —$C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^2$ is hydrogen or $C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^3$ is hydrogen, halogen, $C_1$-$C_6$alkyl, —$C_1$-$C_6$alkylOH, —COOH, —$C_1$-$C_6$alkyN($R^{18}$)($R^{19}$), $C_1$-$C_6$alkoxy or —COO$C_1$-$C_6$alkyl;

$R^4$ is hydrogen, halogen, $C_1$-$C_6$alkyl, $C_1$-$C_6$alkylOH, —COOH, —$C_1$-$C_6$alkyN($R^{18}$)($R^{19}$), $C_1$-$C_6$alkoxy or —COO$C_1$-$C_6$alkyl;

$R^5$ is hydrogen, —OH, $C_1$-$C_6$alkyl, —$C_1$-$C_6$alkylOH or —$C_1$-$C_6$alkyN($R^{18}$)($R^{19}$);

$R^6$ is hydrogen, halogen, —OH, —$C_1$-$C_6$alkylOH, $C_1$-$C_6$alkyl, —COOH, —N($R^{18}$)($R^{19}$), —$C_1$-$C_6$alkylN($R^{18}$)($R^{19}$), $C_1$-$C_6$alkoxy or —COO$C_1$-$C_6$alkyl;

$R^7$ is hydrogen, halogen, —OH, —$C_1$-$C_6$alkylOH, $C_1$-$C_6$alkyl, —COOH, —N($R^{18}$)($R^{19}$), —$C_1$-$C_6$alkylN($R^{18}$)($R^{19}$), $C_1$-$C_6$alkoxy or —COO$C_1$-$C_6$alkyl;

$R^8$ is hydrogen, $C_1$-$C_6$alkyl or —$C_1$-$C_6$alkyN($R^{18}$)($R^{19}$);

$R^{12}$ is hydrogen, halogen, —OH, —$C_1$-$C_6$alkylOH, $C_1$-$C_6$alkyl, —COOH, —N($R^{18}$)($R^{19}$), —$C_1$-$C_6$alkylN($R^{18}$)($R^{19}$), $C_1$-$C_6$alkoxy or —COO$C_1$-$C_6$alkyl;

$R^{13}$ is hydrogen, halogen, —OH, —$C_1$-$C_6$alkylOH, $C_1$-$C_6$alkyl, —COOH, —N($R^{18}$)($R^{19}$), —$C_1$-$C_6$alkylN($R^{18}$)($R^{19}$), $C_1$-$C_6$alkoxy or —COO$C_1$-$C_6$alkyl;

$R^{14}$ is hydrogen, $C_1$-$C_6$alkyl or —$C_1$-$C_6$alkyN($R^{18}$)($R^{19}$);

$R^{15}$ is hydrogen, halogen, —OH, —$C_1$-$C_6$alkylOH, $C_1$-$C_6$alkyl, —COOH, —N($R^{18}$)($R^{19}$), —$C_1$-$C_6$alkylN($R^{18}$)($R^{19}$), $C_1$-$C_6$alkoxy or —COO$C_1$-$C_6$alkyl;

$R^{16}$ is hydrogen, halogen, —OH, —$C_1$-$C_6$alkylOH, $C_1$-$C_6$alkyl, —COOH, —N($R^{18}$)($R^{19}$), —$C_1$-$C_6$alkylN($R^{18}$)($R^{19}$), $C_1$-$C_6$alkoxy or —COO$C_1$-$C_6$alkyl;

$R^{17}$ is hydrogen, $C_1$-$C_6$alkyl or —$C_1$-$C_6$alkyN($R^{18}$)($R^{19}$);

$R^{18}$ is hydrogen, $C_1$-$C_6$alkyl, COheterocycle or CO$C_1$-$C_6$alkyl, wherein the CO$C_1$-$C_6$alkyl can be optionally substituted with N($R^{19}$)($R^{19}$), or when $R^{18}$ is taken with $R^{19}$ forms a 3-7 membered nitrogen containing ring; and $R^{19}$ is hydrogen and $C_1$-$C_6$alkyl, or when $R^{19}$ is taken with $R^{18}$ forms a 3-7 membered nitrogen containing ring.

Also described herein are compounds of Formula III or a pharmaceutically acceptable salt thereof, wherein:

W is a straight or branched ($C_3$-$C_5$)alkylene, wherein one or more —$CH_2$— groups in W are optionally and independently replaced with a O, S or NH moiety;

$R^1$ is hydrogen or —$C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, $C_1$-$C_6$alkyl and —OH;

$R^2$ is hydrogen or $C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, $C_1$-$C_6$alkyl and —OH;

$R^3$ is hydrogen, halogen, $C_1$-$C_6$alkyl, —$C_1$-$C_6$alkylOH, —COOH, —$C_1$-$C_6$alkyN($R^{18}$)($R^{19}$), $C_1$-$C_6$alkoxy or —COO$C_1$-$C_6$alkyl;

$R^4$ is hydrogen, halogen, $C_1$-$C_6$alkyl, $C_1$-$C_6$alkylOH, —COOH, —$C_1$-$C_6$alkyN($R^{18}$)($R^{19}$), $C_1$-$C_6$alkoxy or —COO$C_1$-$C_6$alkyl;

$R^5$ is hydrogen, —OH, $C_1$-$C_6$alkyl, —$C_1$-$C_6$alkylOH or —$C_1$-$C_6$alkyN($R^{18}$)($R^{19}$);

$R^{18}$ is hydrogen, $C_1$-$C_6$alkyl, $C_1$-$C_6$alkyl, COheterocycle or CO$C_1$-$C_6$alkyl, wherein the CO$C_1$-$C_6$alkyl can be optionally substituted with N($R^{19}$)($R^{19}$), or when $R^{18}$ is taken with $R^{19}$ forms a 3-7 membered nitrogen containing ring; and $R^{19}$ is hydrogen or $C_1$-$C_6$alkyl, or when $R^{19}$ is taken with $R^{18}$ forms a 3-7 membered nitrogen containing ring.

Also described herein are compounds of Formula IV:

or a pharmaceutically acceptable salt thereof, wherein:

W is a straight or branched ($C_2$-$C_5$)alkylene, wherein one or more —$CH_2$— groups in W are optionally and independently replaced with a O, S or NH moiety;

X is a O, S, CR$^9$R$^{10}$ or NR$^{11}$;
Y is O, S, CR$^{12}$R$^{13}$ or NR$^{14}$;
Z is a O, S, CR$^{15}$R$^{16}$ or NR$^{17}$;

$R^1$ is hydrogen or —$C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, $C_1$-$C_6$alkyl and —OH;

$R^2$ is hydrogen or $C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, $C_1$-$C_6$alkyl and —OH;

$R^3$ is hydrogen, halogen, $C_1$-$C_6$alkyl, —$C_1$-$C_6$alkylOH, —COOH, —$C_1$-$C_6$alkyN($R^{18}$)($R^{19}$), $C_1$-$C_6$alkoxy or —COO$C_1$-$C_6$alkyl;

$R^4$ is hydrogen, halogen, $C_1$-$C_6$alkyl, $C_1$-$C_6$alkylOH, —COOH, —$C_1$-$C_6$alkyN($R^{18}$)($R^{19}$), $C_1$-$C_6$alkoxy or —COO$C_1$-$C_6$alkyl;

$R^5$ is hydrogen, —OH, $C_1$-$C_6$alkyl, —$C_1$-$C_6$alkylOH or —$C_1$-$C_6$alkyN($R^{18}$)($R^{19}$);

$R^9$ is hydrogen, halogen, —OH, —$C_1$-$C_6$alkylOH, $C_1$-$C_6$alkyl, —COOH, —N($R^{18}$)($R^{19}$), —$C_1$-$C_6$alkylN($R^{18}$)($R^{19}$), $C_1$-$C_6$alkoxy or —COO$C_1$-$C_6$alkyl;

$R^{10}$ is hydrogen, halogen, —OH, —$C_1$-$C_6$alkylOH, $C_1$-$C_6$alkyl, —COOH, —N($R^{18}$)($R^{19}$), —$C_1$-$C_6$alkylN($R^{18}$)($R^{19}$), $C_1$-$C_6$alkoxy or —COO$C_1$-$C_6$alkyl;

$R^{11}$ is hydrogen, $C_1$-$C_6$alkyl or —$C_1$-$C_6$alkyN($R^{18}$)($R^{19}$);

$R^{12}$ is hydrogen, halogen, —OH, —$C_1$-$C_6$alkylOH, $C_1$-$C_6$alkyl, —COOH, —N($R^{18}$)($R^{19}$), —$C_1$-$C_6$alkylN($R^{18}$)($R^{19}$), $C_1$-$C_6$alkoxy or —COO$C_1$-$C_6$alkyl;

$R^{13}$ is hydrogen, halogen, —OH, —$C_1$-$C_6$alkylOH, $C_1$-$C_6$alkyl, —COOH, —N($R^{18}$)($R^{19}$), —$C_1$-$C_6$alkylN($R^{18}$)($R^{19}$), $C_1$-$C_6$alkoxy or —COO$C_1$-$C_6$alkyl;

$R^{14}$ is hydrogen, $C_1$-$C_6$alkyl or —$C_1$-$C_6$alkyN($R^{18}$)($R^{19}$);

$R^{15}$ is hydrogen, halogen, —OH, —$C_1$-$C_6$alkylOH, $C_1$-$C_6$alkyl, —COOH, —N($R^{18}$)($R^{19}$), —$C_1$-$C_6$alkylN($R^{18}$)($R^{19}$), $C_1$-$C_6$alkoxy or —COO$C_1$-$C_6$alkyl;

$R^{16}$ is hydrogen, halogen, —OH, —$C_1$-$C_6$alkylOH, $C_1$-$C_6$alkyl, —COOH, —N($R^{18}$)($R^{19}$), —$C_1$-$C_6$alkylN($R^{18}$)($R^{19}$), $C_1$-$C_6$alkoxy or —COO$C_1$-$C_6$alkyl;

$R^{17}$ is hydrogen, $C_1$-$C_6$alkyl or —$C_1$-$C_6$alkyN($R^{18}$)($R^{19}$);

$R^{18}$ is hydrogen, $C_1$-$C_6$alkyl, COheterocycle, or CO$C_1$-$C_6$alkyl, wherein the CO$C_1$-$C_6$alkyl can be optionally substituted with N($R^{19}$)($R^{19}$), or when $R^{18}$ is taken with $R^{19}$ forms a 3-7 membered nitrogen containing ring; and $R^{19}$ is hydrogen or $C_1$-$C_6$alkyl, or when $R^{19}$ is taken with $R^{18}$ forms a 3-7 membered nitrogen containing ring.

Also described herein are compounds of Formula V:

or a pharmaceutically acceptable salt thereof, wherein:

W is a straight or branched ($C_3$-$C_5$)alkylene, wherein one or more —$CH_2$— groups in W are optionally and independently replaced with a O, S or NH moiety;

$R^1$ is hydrogen or —$C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, $C_1$-$C_6$alkyl and —OH;

$R^2$ is hydrogen or $C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, $C_1$-$C_6$alkyl and —OH;

$R^3$ is hydrogen, halogen, $C_1$-$C_6$alkyl, —$C_1$-$C_6$alkylOH, —COOH, —$C_1$-$C_6$alkyN($R^{18}$)($R^{19}$), $C_1$-$C_6$alkoxy or —COO$C_1$-$C_6$alkyl;

$R^4$ is hydrogen, halogen, $C_1$-$C_6$alkyl, $C_1$-$C_6$alkylOH, —COOH, —$C_1$-$C_6$alkyN($R^{18}$)($R^{19}$), $C_1$-$C_6$alkoxy and —COO$C_1$-$C_6$alkyl;

$R^5$ is hydrogen, —OH, $C_1$-$C_6$alkyl, —$C_1$-$C_6$alkylOH or —$C_1$-$C_6$alkyN($R^{18}$)($R^{19}$); $R^{18}$ is hydrogen, $C_1$-$C_6$alkyl, COheterocycle, or COC$_1$-C$_6$alkyl, wherein the COC$_1$-C$_6$alkyl can be optionally substituted with N($R^{19}$)($R^{19}$), or when $R^{18}$ is taken with $R^{19}$ forms a 3-7 membered nitrogen containing ring; and $R^{19}$ is hydrogen and $C_1$-$C_6$alkyl, or when $R^{19}$ is taken with $R^{18}$ forms a 3-7 membered nitrogen containing ring.

Also described herein are compounds having Formula VI:

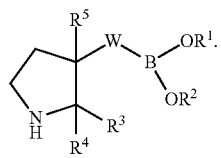

VI or a pharmaceutically acceptable salt thereof, wherein:

W is a straight or branched ($C_3$-$C_5$)alkylene, wherein one or more —CH$_2$— groups in W are optionally and independently replaced with a O, S or NH moiety;

$R^1$ is hydrogen or —$C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, $C_1$-$C_6$alkyl and —OH;

$R^2$ is hydrogen or $C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, $C_1$-$C_6$alkyl and —OH;

$R^3$ is hydrogen, halogen, $C_1$-$C_6$alkyl, —$C_1$-$C_6$alkylOH, —COOH, —$C_1$-$C_6$alkyN($R^{18}$)($R^{19}$), $C_1$-$C_6$alkoxy or —COO$C_1$-$C_6$alkyl;

$R^4$ is hydrogen, halogen, $C_1$-$C_6$alkyl, $C_1$-$C_6$alkylH, —COOH, —$C_1$-$C_6$alkyN($R^{18}$)($R^{19}$), $C_1$-$C_6$alkoxy and —COO$C_1$-$C_6$alkyl;

$R^5$ is hydrogen, —OH, $C_1$-$C_6$alkyl, —$C_1$-$C_6$alkylOH or —$C_1$-$C_6$alkyN($R^{18}$)($R^{19}$); $R^{18}$ is hydrogen, $C_1$-$C_6$alkyl, COheterocycle or COC$_1$-C$_6$alkyl, wherein the COC$_1$-C$_6$alkyl can be optionally substituted with N($R^{19}$)($R^{19}$), or when $R^{18}$ is taken with $R^{19}$ forms a 3-7 membered nitrogen containing ring; and $R^{19}$ is hydrogen or $C_1$-$C_6$alkyl, or when $R^{19}$ is taken with $R^{18}$ forms a 3-7 membered nitrogen containing ring.

Also described herein are compounds having Formula II:

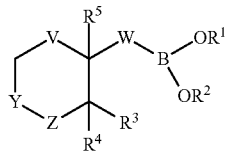

II or a pharmaceutically acceptable salt thereof, wherein:

W is selected from the group consisting of straight or branched ($C_2$-$C_5$)alkylene, wherein one or more —CH$_2$— groups in W are optionally and independently replaced with a moiety selected from the group consisting of O, S or NH;

V is selected from the group consisting of a bond, O, S, CR$^6$R$^7$ or NR$^8$;

Y is selected from the group consisting of a bond, O, S, CR$^{12}$R$^{13}$ or NR$^{14}$;

Z is selected from the group consisting of a bond, O, S, CR$^{15}$R$^{16}$ or NR$^{17}$;

$R^1$ is selected from the group consisting of hydrogen, $C_3$-$C_6$cycloalkyl or $C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^2$ is selected from the group consisting of hydrogen, $C_3$-$C_6$cycloalkyl or $C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^3$ is hydrogen, halogen, $C_3$-$C_6$cycloalkyl, $C_1$-$C_6$alkyl, halo$C_1$-$C_6$alkyl, $C_1$-$C_6$alkylOH, —COOH, N($R^{18}$)($R^{19}$), $C_1$-$C_6$alkylN($R^{18}$)($R^{19}$), $C_1$-$C_6$alkylheteroaryl, heteroaryl, $C_1$-$C_6$alkoxy or —COO$C_1$-$C_6$alkyl;

$R^4$ is hydrogen, halogen, $C_3$-$C_6$cycloalkyl, $C_1$-$C_6$alkyl, halo$C_1$-$C_6$alkyl, $C_1$-$C_6$alkylOH, —COOH, N($R^{18}$)($R^{19}$), $C_1$-$C_6$alkylN($R^{18}$)($R^{19}$), $C_1$-$C_6$alkylheteroaryl, heteroaryl, $C_1$-$C_6$alkoxy and —COO$C_1$-$C_6$alkyl;

$R^5$ is selected from the group consisting of hydrogen, halogen, CN, OH, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, $C_1$-$C_6$alkylheteroaryl, CON($R^{18}$)($R^{19}$), N($R^{18}$)($R^{19}$) or $C_1$-$C_6$alkylN($R^{18}$)($R^{19}$);

$R^6$ is selected from the group consisting of hydrogen, halogen, OH, $C_1$-$C_6$alkylOH, $C_3$-$C_6$cycloalkyl, $C_1$-$C_6$alkyl, halo$C_1$-$C_6$alkyl, COOH, N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^7$ is selected from the group consisting of hydrogen, halogen, OH, $C_1$-$C_6$alkylOH, $C_3$-$C_6$cycloalkyl, $C_1$-$C_6$alkyl, halo$C_1$-$C_6$alkyl, COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^8$ is selected from the group consisting of hydrogen, $C_3$-$C_6$cycloalkyl, $C_1$-$C_6$alkyl, $C_1$-$C_6$alkylheteroaryl, or $C_1$-$C_6$alkylN($R^{18}$)($R^{19}$);

$R^9$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^{10}$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^{11}$ is selected from the group consisting of hydrogen, $C_3$-$C_6$cycloalkyl, $C_1$-$C_6$alkyl, $C_1$-$C_6$alkylheteroaryl, or $C_1$-$C_6$alkylN($R^{18}$)($R^{19}$);

$R^{12}$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, —COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^{13}$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, —COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^{14}$ is selected from the group consisting of hydrogen, $C_3$-$C_6$cycloalkyl, $C_1$-$C_6$alkyl, —$C_1$-$C_6$alkylheteroaryl, or $C_1$-$C_6$alkylN($R^{18}$)($R^{19}$);

$R^{15}$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, —COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^{16}$ is selected from the group consisting of hydrogen, halogen, OH, $C_1$-$C_6$alkylOH, $C_3$-$C_6$cycloalkyl, $C_1$-$C_6$alkyl, halo$C_1$-$C_6$alkyl, COOH, N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^{17}$ is selected from the group consisting of hydrogen, $C_3$-$C_6$cycloalkyl, $C_1$-$C_6$alkyl, —$C_1$-$C_6$alkylheteroaryl, and $C_1$-$C_6$alkylN($R^{18}$)($R^{19}$);

$R^{18}$ is selected from the group consisting of hydrogen, $C_3$-$C_6$cycloalkyl, halo$C_1$-$C_6$alkyl, $C_1$-$C_6$alkyl, $C_1$-$C_6$alkylNH$_2$, COheterocycle and CO$C_1$-$C_6$alkyl, wherein the CO$C_1$-$C_6$alkyl can be optionally substituted with one or two substituents selected from the group consisting of N($R^{19}$)($R^{19}$), OH, cycloalkyl, or a 3-7 membered nitrogen containing ring or when $R^1$ is taken with $R^{19}$ forms a 3-7 membered nitrogen containing ring; and $R^{19}$ is selected from the group consisting of hydrogen, $C_3$-$C_6$cycloalkyl, halo$C_1$-$C_6$alkyl and $C_1$-$C_6$alkyl, or when $R^{19}$ is taken with $R^{18}$ forms a 3-7 membered nitrogen containing ring.

Also described herein are compounds having Formula The compound of claim 1, having Formula III

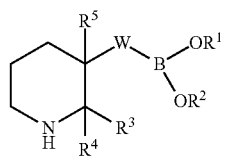

III or a pharmaceutically acceptable salt thereof, wherein:

W is selected from the group consisting of straight or branched ($C_2$-$C_5$)alkylene, wherein one or more —$CH_2$— groups in W are optionally and independently replaced with a moiety selected from the group consisting of O, S or NH;

$R^1$ is selected from the group consisting of hydrogen, $C_3$-$C_6$cycloalkyl or $C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^2$ is selected from the group consisting of hydrogen, $C_3$-$C_6$cycloalkyl or $C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^3$ is hydrogen, halogen, $C_3$-$C_6$cycloalkyl, $C_1$-$C_6$alkyl, halo$C_1$-$C_6$alkyl, $C_1$-$C_6$alkylOH, —COOH, N($R^{18}$)($R^{19}$), $C_1$-$C_6$alkylN($R^{18}$)($R^{19}$), $C_1$-$C_6$alkylheteroaryl, heteroaryl, $C_1$-$C_6$alkoxy or —COO$C_1$-$C_6$alkyl;

$R^4$ is hydrogen, halogen, $C_3$-$C_6$cycloalkyl, $C_1$-$C_6$alkyl, halo$C_1$-$C_6$alkyl, $C_1$-$C_6$alkylOH, —COOH, N($R^{18}$)($R^{19}$), $C_1$-$C_6$alkylN($R^{18}$)($R^{19}$), $C_1$-$C_6$alkylheteroaryl, heteroaryl, $C_1$-$C_6$alkoxy and —COO$C_1$-$C_6$alkyl;

$R^5$ is selected from the group consisting of hydrogen, halogen, CN, OH, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, $C_1$-$C_6$alkylheteroaryl, CON($R^{18}$)($R^{19}$), N($R^{18}$)($R^{19}$) or $C_1$-$C_6$alkylN($R^{18}$)($R^{19}$);

$R^{18}$ is selected from the group consisting of hydrogen, $C_3$-$C_6$cycloalkyl, halo$C_1$-$C_6$alkyl, $C_1$-$C_6$alkyl, $C_1$-$C_6$alkylNH$_2$, COheterocycle and CO$C_1$-$C_6$alkyl, wherein the CO$C_1$-$C_6$alkyl can be optionally substituted with one or two substituents selected from the group consisting of N($R^{19}$)($R^{19}$), OH, cycloalkyl, or a 3-7 membered nitrogen containing ring or when $R^{18}$ is taken with $R^{19}$ forms a 3-7 membered nitrogen containing ring; and $R^{19}$ is selected from the group consisting of hydrogen, $C_3$-$C_6$cycloalkyl, halo$C_1$-$C_6$alkyl and $C_1$-$C_6$alkyl, or when $R^{19}$ is taken with $R^{18}$ forms a 3-7 membered nitrogen containing ring.

Also described herein are compounds having Formula IV:

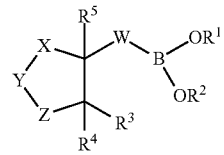

IV or a pharmaceutically acceptable salt thereof, wherein:

W is selected from the group consisting of straight or branched ($C_2$-$C_5$)alkylene, wherein one or more —$CH_2$— groups in W are optionally and independently replaced with a moiety selected from the group consisting of O, S or NH;

Y is selected from the group consisting of a bond, O, S, $CR^{12}R^{13}$ or $NR^{14}$;

X is selected from the group consisting of a bond, O, S, $CR^9R^{10}$ or $NR^{11}$;

Z is selected from the group consisting of a bond, O, S, $CR^{15}R^{16}$ or $NR^{17}$;

$R^1$ is selected from the group consisting of hydrogen, $C_3$-$C_8$cycloalkyl or $C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^2$ is selected from the group consisting of hydrogen, $C_3$-$C_8$cycloalkyl or $C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^3$ is hydrogen, halogen, $C_3$-$C_8$cycloalkyl, $C_1$-$C_6$alkyl, halo$C_1$-$C_6$alkyl, $C_1$-$C_6$alkylOH, —COOH, N($R^{18}$)($R^{19}$), $C_1$-$C_6$alkylN($R^{18}$)($R^{19}$), $C_1$-$C_6$alkylheteroaryl, heteroaryl, $C_1$-$C_6$alkoxy or —COO$C_1$-$C_6$alkyl;

$R^4$ is hydrogen, halogen, $C_3$-$C_8$cycloalkyl, $C_1$-$C_6$alkyl, halo$C_1$-$C_6$alkyl, $C_1$-$C_6$alkylOH, —COOH, N($R^{18}$)($R^{19}$), $C_1$-$C_6$alkylN($R^{18}$)($R^{19}$), $C_1$-$C_6$alkylheteroaryl, heteroaryl, $C_1$-$C_6$alkoxy and —COO$C_1$-$C_6$alkyl;

$R^5$ is selected from the group consisting of hydrogen, halogen, CN, OH, $C_1$-$C_6$alkylCOOH, COOH, $C_3$-$C_8$cycloalkyl, $C_1$-$C_6$alkyl, halo$C_1$-$C_6$alkyl, $C_1$-$C_6$alkylOH, $C_1$-$C_6$alkylheteroaryl, CON($R^{18}$)($R^{19}$), N($R^{18}$)($R^{19}$) or $C_1$-$C_6$alkylN($R^{18}$)($R^{19}$);

$R^9$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^{10}$ is selected from the group consisting of hydrogen, halogen, OH, —$C_1$-$C_6$alkylOH, $C_3$-$C_6$cycloalkyl, $C_1$-$C_6$alkyl, halo$C_1$-$C_6$alkyl, COOH, —N($R^{18}$)($R^{19}$), $C_1$-$C_6$alkylheteroaryl, $C_1$-$C_6$alkylN($R^{18}$)($R^{19}$), $C_1$-$C_6$alkoxy or COO$C_1$-$C_6$alkyl;

$R^{11}$ is selected from the group consisting of hydrogen, $C_3-C_8$cycloalkyl, $C_1-C_6$alkyl, $C_1-C_6$alkylheteroaryl, or $C_1-C_6$alkylN$(R^{18})(R^{19})$;

$R^{12}$ is selected from the group consisting of hydrogen, halogen, OH, —$C_1-C_6$alkylOH, $C_3-C_6$cycloalkyl, $C_1-C_6$alkyl, haloC$_1$-C$_6$alkyl, —COOH, —N$(R^{18})(R^{19})$, $C_1-C_6$alkylheteroaryl, $C_1-C_6$alkylN$(R^{18})(R^{19})$, $C_1-C_6$alkoxy or COOC$_1$-C$_6$alkyl;

$R^{13}$ is selected from the group consisting of hydrogen, halogen, OH, —$C_1-C_6$alkylOH, $C_3-C_6$cycloalkyl, $C_1-C_6$alkyl, haloC$_1$-C$_6$alkyl, —COOH, —N$(R^{18})(R^{19})$, $C_1-C_6$alkylheteroaryl, $C_1-C_6$alkylN$(R^{18})(R^{19})$, $C_1-C_6$alkoxy or COOC$_1$-C$_6$alkyl;

$R^{14}$ is selected from the group consisting of hydrogen, $C_3-C_8$cycloalkyl, $C_1-C_6$alkyl, —$C_1-C_6$alkylheteroaryl, or $C_1-C_6$alkyN$(R^{18})(R^{19})$;

$R^{15}$ is selected from the group consisting of hydrogen, halogen, OH, —$C_1-C_6$alkylOH, $C_3-C_6$cycloalkyl, $C_1-C_6$alkyl, haloC$_1$-C$_6$alkyl, —COOH, —N$(R^{18})(R^{19})$, $C_1-C_6$alkylheteroaryl, $C_1-C_6$alkylN$(R^{18})(R^{19})$, $C_1-C_6$alkoxy or COOC$_1$-C$_6$alkyl;

$R^{16}$ is selected from the group consisting of hydrogen, halogen, OH, $C_1-C_6$alkylOH, $C_3-C_6$cycloalkyl, $C_1-C_6$alkyl, haloC$_1$-C$_6$alkyl, COOH, N$(R^{18})(R^{19})$, $C_1-C_6$alkylheteroaryl, $C_1-C_6$alkylN$(R^{18})(R^{19})$, $C_1-C_6$alkoxy or COOC$_1$-C$_6$alkyl;

$R^{17}$ is selected from the group consisting of hydrogen, $C_3-C_6$cycloalkyl, $C_1-C_6$alkyl, —$C_1-C_6$alkylheteroaryl, and $C_1-C_6$alkyN$(R^{18})(R^{19})$;

$R^{18}$ is selected from the group consisting of hydrogen, $C_3-C_6$cycloalkyl, haloC$_1$-C$_6$alkyl, $C_1-C_6$alkyl, $C_1-C_6$alkylNH$_2$, COheterocycle and COC$_1$-C$_6$alkyl, wherein the COC$_1$-C$_6$alkyl can be optionally substituted with one or two substituents selected from the group consisting of N$(R^{19})(R^{19})$, OH, cycloalkyl, or a 3-7 membered nitrogen containing ring or when $R^{18}$ is taken with $R^{19}$ forms a 3-7 membered nitrogen containing ring; and $R^{19}$ is selected from the group consisting of hydrogen, $C_3-C_6$cycloalkyl, haloC$_1$-C$_6$alkyl and $C_1-C_6$alkyl, or when $R^{19}$ is taken with $R^{18}$ forms a 3-7 membered nitrogen containing ring.

Also described herein are compounds having Formula V:

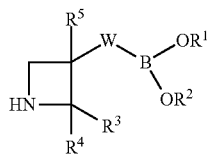

V or a pharmaceutically acceptable salt thereof, wherein:

W is selected from the group consisting of straight or branched $(C_2-C_5)$alkylene, wherein one or more —CH$_2$— groups in W are optionally and independently replaced with a moiety selected from the group consisting of O, S or NH;

$R^1$ is selected from the group consisting of hydrogen, $C_3-C_6$cycloalkyl or $C_1-C_6$alkyl or, taken with $R^2$ forms a $C_3-C_8$cycloalkyl, wherein the $C_3-C_8$cycloalkyl is optionally substituted with one to four substituents selected from the group consisting of halogen, $C_1-C_6$alkyl or —OH;

$R^2$ is selected from the group consisting of hydrogen, $C_3-C_6$cycloalkyl or $C_1-C_6$alkyl or, taken with $R^1$ forms a $C_3-C_8$cycloalkyl, wherein the $C_3-C_8$cycloalkyl is optionally substituted with one to four substituents selected from the group consisting of halogen, $C_1-C_6$alkyl or —OH;

$R^3$ is hydrogen, halogen, $C_3-C_6$cycloalkyl, $C_1-C_6$alkyl, haloC$_1$-C$_6$alkyl, $C_1-C_6$alkylOH, —COOH, N$(R^{18})(R^{19})$, $C_1-C_6$alkylN$(R^{18})(R^{19})$, $C_1-C_6$alkylheteroaryl, heteroaryl, $C_1-C_6$alkoxy or —COOC$_1$-C$_6$alkyl;

$R^4$ is hydrogen, halogen, $C_3-C_6$cycloalkyl, $C_1-C_6$alkyl, haloC$_1$-C$_6$alkyl, $C_1-C_6$alkylOH, —COOH, N$(R^{18})(R^{19})$, $C_1-C_6$alkylN$(R^{18})(R^{19})$, $C_1-C_6$alkylheteroaryl, heteroaryl, $C_1-C_6$alkoxy and —COOC$_1$-C$_6$alkyl;

$R^5$ is selected from the group consisting of hydrogen, halogen, CN, OH, $C_1-C_6$alkylCOOH, COOH, $C_3-C_6$cycloalkyl, $C_1-C_6$alkyl, haloC$_1$-C$_6$alkyl, $C_1-C_6$alkylOH, $C_1-C_6$alkylheteroaryl, CON$(R^{18})(R^{19})$, N$(R^{18})(R^{19})$ or $C_1-C_6$alkylN$(R^{18})(R^{19})$;

$R^{18}$ is selected from the group consisting of hydrogen, $C_3-C_6$cycloalkyl, haloC$_1$-C$_6$alkyl, $C_1-C_6$alkyl, $C_1-C_6$alkylNH$_2$, COheterocycle and COC$_1$-C$_6$alkyl, wherein the COC$_1$-C$_6$alkyl can be optionally substituted with one or two substituents selected from the group consisting of N$(R^{19})(R^{19})$, OH, cycloalkyl, or a 3-7 membered nitrogen containing ring or when $R^{18}$ is taken with $R^{19}$ forms a 3-7 membered nitrogen containing ring; and $R^{19}$ is selected from the group consisting of hydrogen, $C_3-C_6$cycloalkyl, haloC$_1$-C$_6$alkyl and $C_1-C_6$alkyl, or when $R^{19}$ is taken with $R^{18}$ forms a 3-7 membered nitrogen containing ring.

Also described herein are compounds having Formula VI

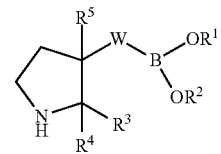

VI or a pharmaceutically acceptable salt thereof, wherein:

W is selected from the group consisting of straight or branched $(C_2-C_5)$alkylene, wherein one or more —CH$_2$— groups in W are optionally and independently replaced with a moiety selected from the group consisting of O, S or NH;

$R^1$ is selected from the group consisting of hydrogen, $C_3-C_6$cycloalkyl or $C_1-C_6$alkyl or, taken with $R^2$ forms a $C_3-C_8$cycloalkyl, wherein the $C_3-C_8$cycloalkyl is optionally substituted with one to four substituents selected from the group consisting of halogen, $C_1-C_6$alkyl or —OH;

$R^2$ is selected from the group consisting of hydrogen, $C_3-C_6$cycloalkyl or $C_1-C_6$alkyl or, taken with $R^1$ forms a $C_3-C_8$cycloalkyl, wherein the $C_3-C_8$cycloalkyl is optionally substituted with one to four substituents selected from the group consisting of halogen, $C_1-C_6$alkyl or —OH;

$R^3$ is hydrogen, halogen, $C_3-C_6$cycloalkyl, $C_1-C_6$alkyl, haloC$_1$-C$_6$alkyl, $C_1-C_6$alkylOH, —COOH, N$(R^{18})(R^{19})$, $C_1-C_6$alkylN$(R^{18})(R^{19})$, $C_1-C_6$alkylheteroaryl, heteroaryl, $C_1-C_6$alkoxy or —COOC$_1$-C$_6$alkyl;

$R^4$ is hydrogen, halogen, $C_3-C_6$cycloalkyl, $C_1-C_6$alkyl, haloC$_1$-C$_6$alkyl, $C_1-C_6$alkylOH, —COOH, N$(R^{18})(R^{19})$, $C_1-C_6$alkylN$(R^{18})(R^{19})$, $C_1-C_6$alkylheteroaryl, heteroaryl, $C_1-C_6$alkoxy and —COOC$_1$-C$_6$alkyl;

$R^5$ is selected from the group consisting of hydrogen, halogen, CN, OH, $C_1-C_6$alkylCOOH, COOH, $C_3-C_6$cycloalkyl, $C_1-C_6$alkyl, haloC$_1$-C$_6$alkyl, $C_1-C_6$alkylOH, $C_1-C_6$alkylheteroaryl, CON$(R^{18})(R^{19})$, N$(R^{18})(R^{19})$ or $C_1-C_6$alkylN$(R^{18})(R^{19})$;

$R^{18}$ is selected from the group consisting of hydrogen, $C_3-C_6$cycloalkyl, haloC$_1$-C$_6$alkyl, $C_1-C_6$alkyl, $C_1-C_6$alkylNH$_2$, COheterocycle and COC$_1$-C$_6$alkyl, wherein the $COC_1$-$C_6$alkyl can be optionally substituted with one or two substituents selected from the group consisting of $N(R^{19})(R^{19})$, OH, cycloalkyl, or a 3-7 membered nitrogen containing ring or when $R^{18}$ is taken with $R^{19}$ forms a 3-7 membered nitrogen containing ring; and $R^{19}$ is selected from the group consisting of hydrogen, $C_3$-$C_6$cycloalkyl, halo$C_1$-$C_6$alkyl and $C_1$-$C_6$alkyl, or when $R^{19}$ is taken with $R^{18}$ forms a 3-7 membered nitrogen containing ring.

Also described herein are compounds having Formula VI

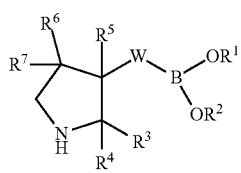

VII or a pharmaceutically acceptable salt thereof, wherein:

W is selected from the group consisting of straight or branched $(C_2$-$C_5)$alkylene, wherein one or more —$CH_2$— groups in W are optionally and independently replaced with a moiety selected from the group consisting of O, S or NH;

$R^1$ is selected from the group consisting of hydrogen, $C_3$-$C_6$cycloalkyl or $C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^2$ is selected from the group consisting of hydrogen, $C_3$-$C_6$cycloalkyl or $C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^3$ is hydrogen, halogen, $C_3$-$C_6$cycloalkyl, $C_1$-$C_6$alkyl, halo$C_1$-$C_6$alkyl, $C_1$-$C_6$alkylOH, —COOH, $N(R^{18})(R^{19})$, $C_1$-$C_6$alkylN$(R^{18})(R^{19})$, $C_1$-$C_6$alkylheteroaryl, heteroaryl, $C_1$-$C_6$alkoxy or —COO$C_1$-$C_6$alkyl;

$R^4$ is hydrogen, halogen, $C_3$-$C_6$cycloalkyl, $C_1$-$C_6$alkyl, halo$C_1$-$C_6$alkyl, $C_1$-$C_6$alkylOH, —COOH, $N(R^{18})(R^{19})$, $C_1$-$C_6$alkylN$(R^{18})(R^{19})$, $C_1$-$C_6$alkylheteroaryl, heteroaryl, $C_1$-$C_6$alkoxy and —COO$C_1$-$C_6$alkyl;

$R^5$ is selected from the group consisting of hydrogen, halogen, CN, OH, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, $C_1$-$C_6$alkylheteroaryl, CON$(R^{18})(R^{19})$, $N(R^{18})(R^{19})$ or $C_1$-$C_6$alkylN$(R^{18})(R^{19})$;

$R^6$ is selected from the group consisting of hydrogen, halogen, —OH, —$C_1$-$C_6$alkylOH, $C_3$-$C_6$cycloalkyl, $C_1$-$C_6$alkyl, —COOH, —$N(R^{18})(R^{19})$, —$C_1$-$C_6$alkylheteroaryl, —$C_1$-$C_6$alkyN$(R^{18})(R^{19})$, $C_1$-$C_6$alkoxy or —COO$C_1$-$C_6$alkyl;

$R^7$ is selected from the group consisting of hydrogen, halogen, —OH, —$C_1$-$C_6$alkylOH, $C_3$-$C_6$cycloalkyl, $C_1$-$C_6$alkyl, —COOH, —$N(R^{18})(R^{19})$, —$C_1$-$C_6$alkylheteroaryl, —$C_1$-$C_6$alkyN$(R^{18})(R^{19})$, $C_1$-$C_6$alkoxy or —COO$C_1$-$C_6$alkyl;

$R^{18}$ is selected from the group consisting of hydrogen, $C_3$-$C_6$cycloalkyl, halo$C_1$-$C_6$alkyl, $C_1$-$C_6$alkyl, $C_1$-$C_6$alkylNH$_2$, COheterocycle and COC$_1$-$C_6$alkyl, wherein the COC$_1$-$C_6$alkyl can be optionally substituted with one or two substituents selected from the group consisting of $N(R^{19})(R^{19})$, OH, cycloalkyl, or a 3-7 membered nitrogen containing ring or when $R^{18}$ is taken with $R^{19}$ forms a 3-7 membered nitrogen containing ring; and $R^{19}$ is selected from the group consisting of hydrogen, $C_3$-$C_6$cycloalkyl, halo$C_1$-$C_6$alkyl and $C_1$-$C_6$alkyl, or when $R^{19}$ is taken with $R^{18}$ forms a 3-7 membered nitrogen containing ring.

The compound of claim 1, having Formula VIII:

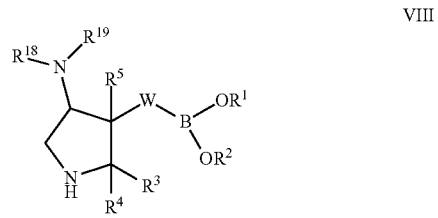

VIII or a pharmaceutically acceptable salt thereof, wherein:

W is selected from the group consisting of straight or branched $(C_2$-$C_5)$alkylene, wherein one or more —$CH_2$— groups in W are optionally and independently replaced with a moiety selected from the group consisting of O, S or NH;

$R^1$ is selected from the group consisting of hydrogen, $C_3$-$C_6$cycloalkyl or $C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^2$ is selected from the group consisting of hydrogen, $C_3$-$C_6$cycloalkyl or $C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, $C_1$-$C_6$alkyl or —OH;

$R^3$ is hydrogen, halogen, $C_3$-$C_6$cycloalkyl, $C_1$-$C_6$alkyl, halo$C_1$-$C_6$alkyl, $C_1$-$C_6$alkylOH, —COOH, $N(R^{18})(R^{19})$, $C_1$-$C_6$alkylN$(R^{18})(R^{19})$, $C_1$-$C_6$alkylheteroaryl, heteroaryl, $C_1$-$C_6$alkoxy or —COO$C_1$-$C_6$alkyl;

$R^4$ is hydrogen, halogen, $C_3$-$C_6$cycloalkyl, $C_1$-$C_6$alkyl, halo$C_1$-$C_6$alkyl, $C_1$-$C_6$alkylOH, —COOH, $N(R^{18})(R^{19})$, $C_1$-$C_6$alkylN$(R^{18})(R^{19})$, $C_1$-$C_6$alkylheteroaryl, heteroaryl, $C_1$-$C_6$alkoxy and —COO$C_1$-$C_6$alkyl;

$R^5$ is selected from the group consisting of hydrogen, halogen, CN, OH, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, $C_1$-$C_6$alkylheteroaryl, CON$(R^{18})(R^{19})$, $N(R^{18})(R^{19})$ or $C_1$-$C_6$alkylN$(R^{18})(R^{19})$;

$R^{18}$ is selected from the group consisting of hydrogen, $C_3$-$C_6$cycloalkyl, halo$C_1$-$C_6$alkyl, $C_1$-$C_6$alkyl, $C_1$-$C_6$alkylNH$_2$, COheterocycle and COC$_1$-$C_6$alkyl, wherein the COC$_1$-$C_6$alkyl can be optionally substituted with one or two substituents selected from the group consisting of $N(R^{19})(R^{19})$, OH, cycloalkyl, or a 3-7 membered nitrogen containing ring or when $R^{18}$ is taken with $R^{19}$ forms a 3-7 membered nitrogen containing ring; and $R^{19}$ is selected from the group consisting of hydrogen, $C_3$-$C_6$cycloalkyl, halo$C_1$-$C_6$alkyl and $C_1$-$C_6$alkyl, or when $R^{19}$ is taken with $R^{18}$ forms a 3-7 membered nitrogen containing ring.

In certain embodiments, the compounds described herein include:

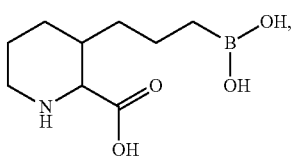

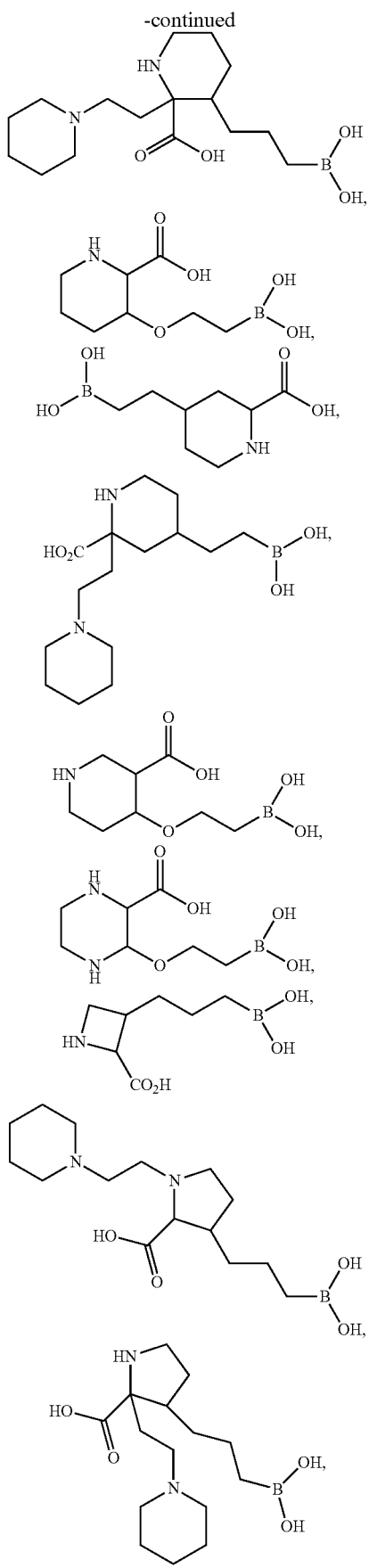
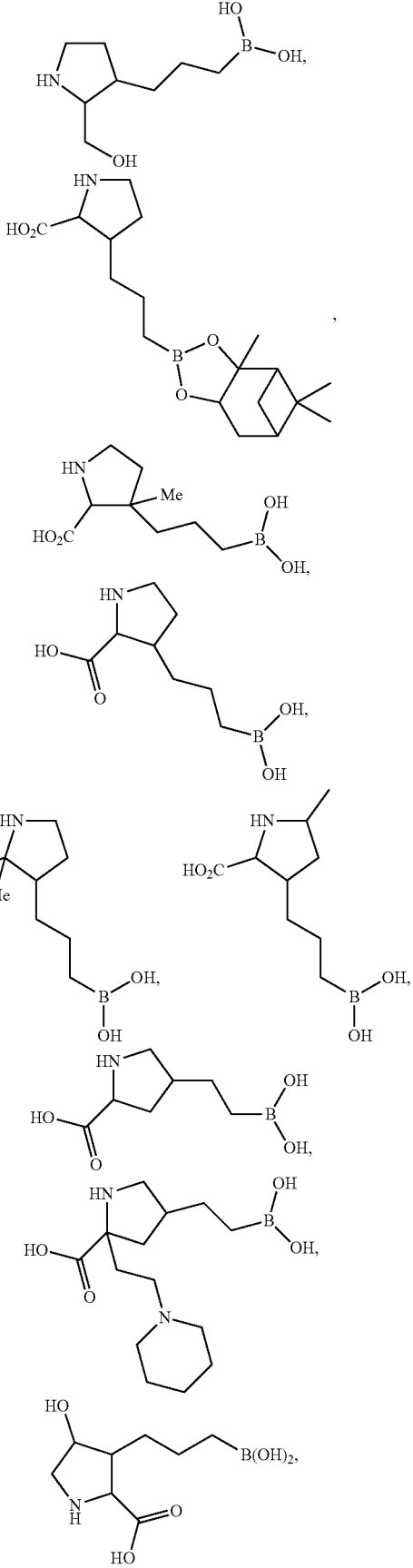

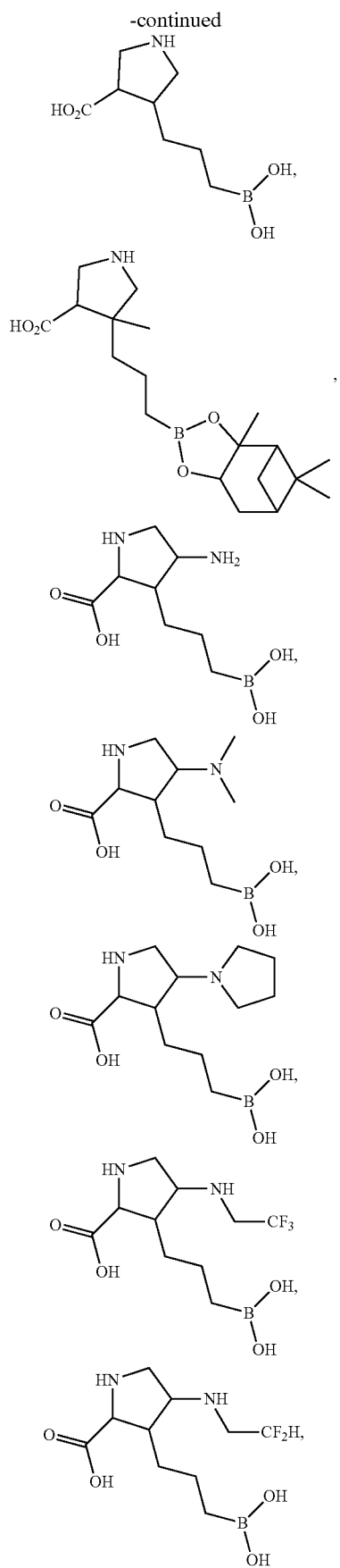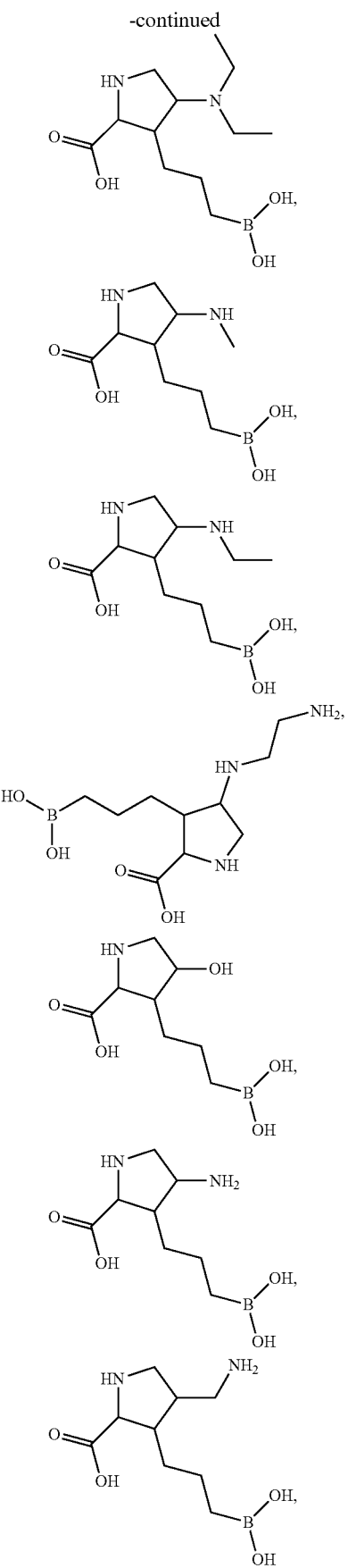

-continued
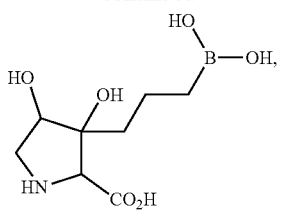
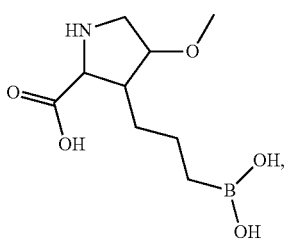
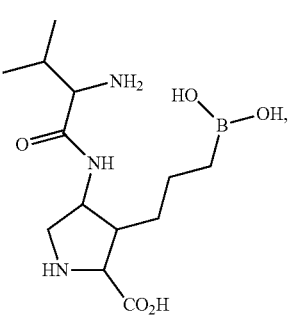
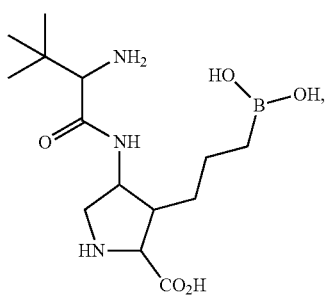
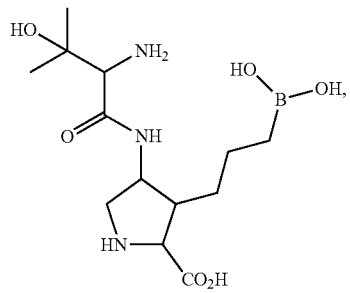
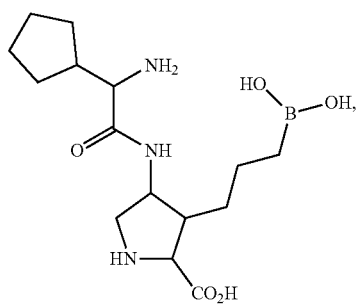
-continued
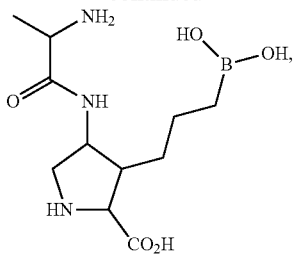
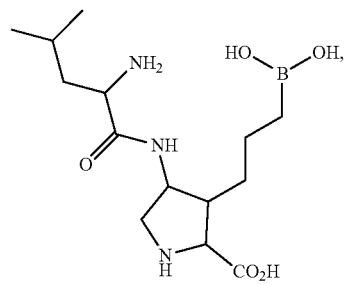
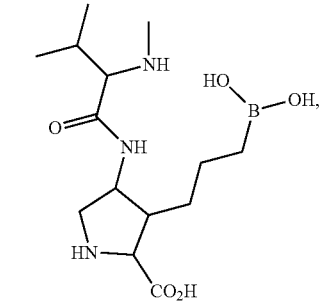
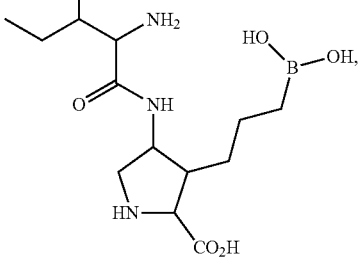
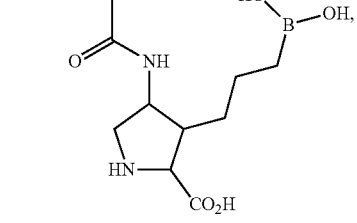

-continued
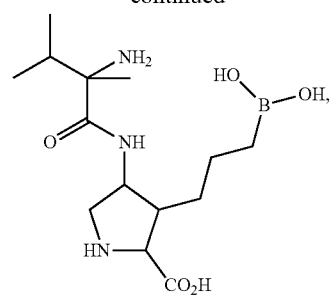
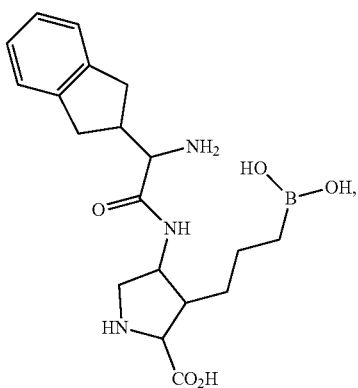
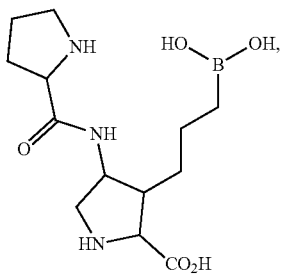
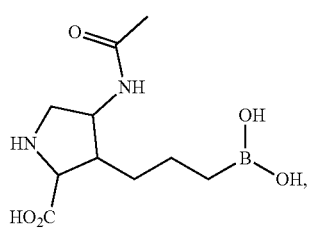
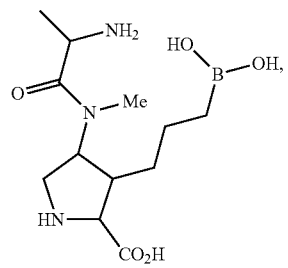
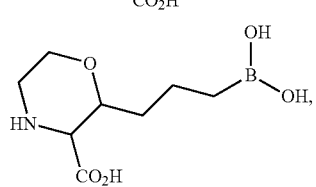
-continued
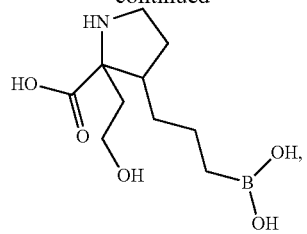
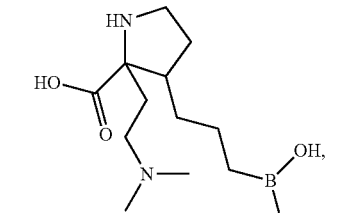
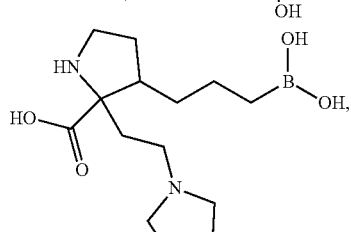
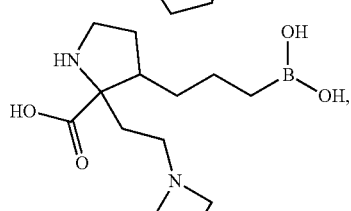
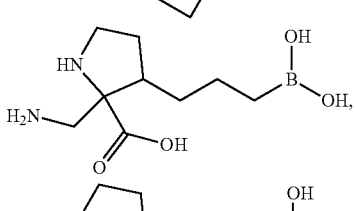
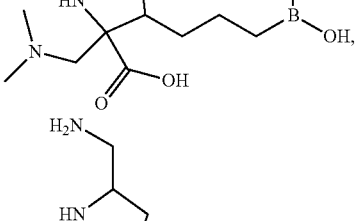
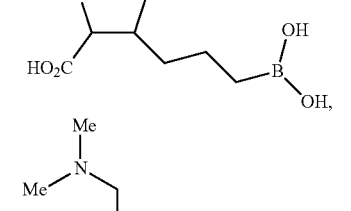
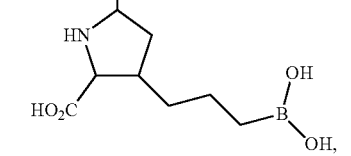

-continued
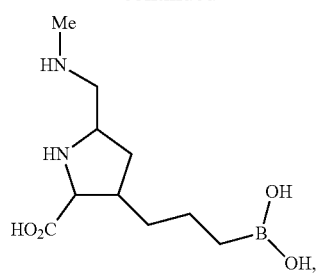
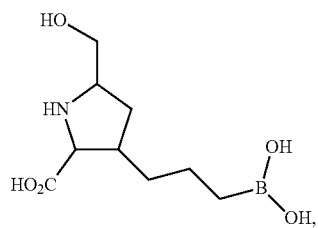
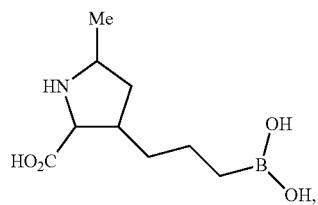
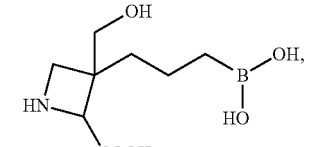
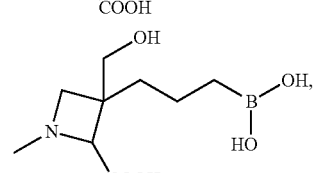
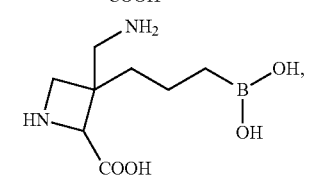
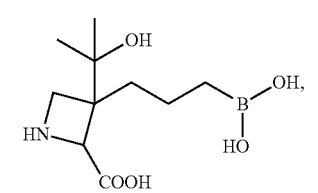

-continued
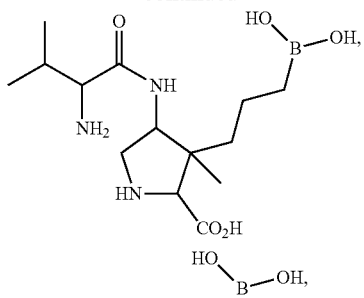
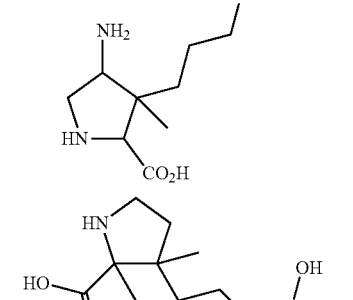
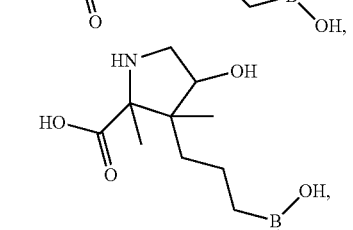
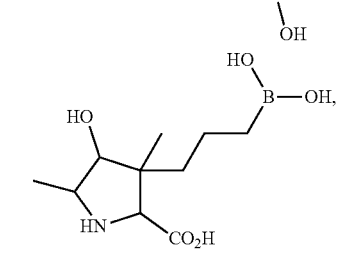
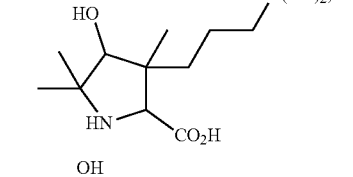
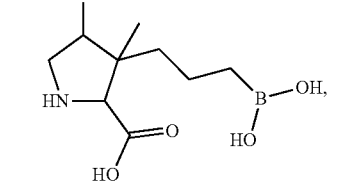
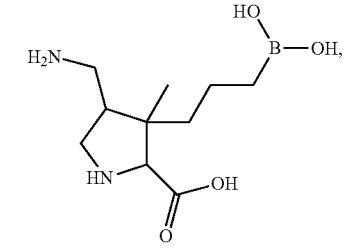

-continued
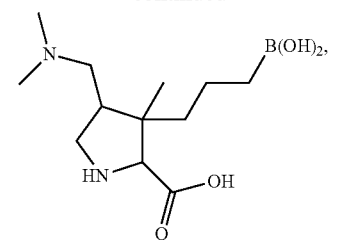
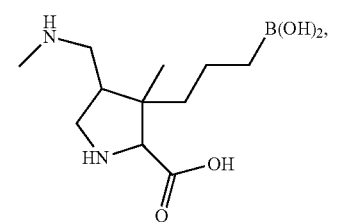
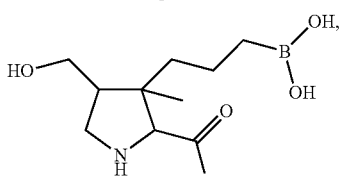
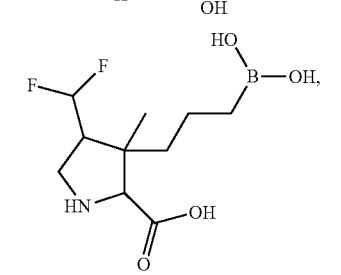
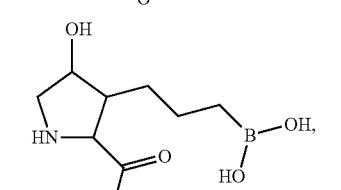
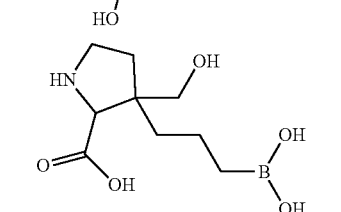
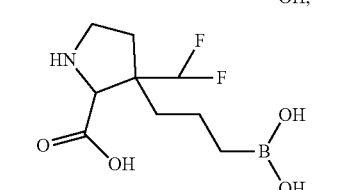
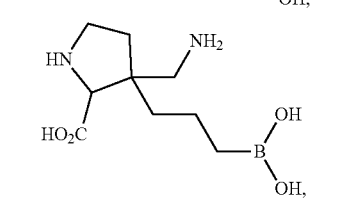
-continued
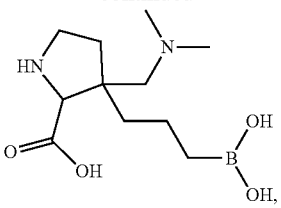
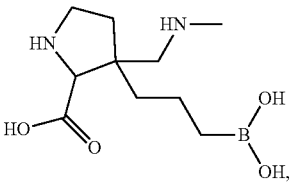
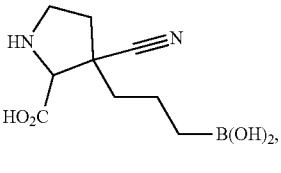
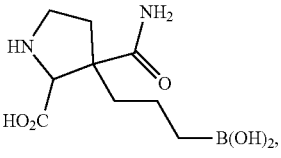
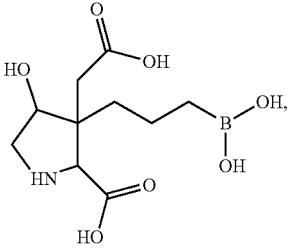
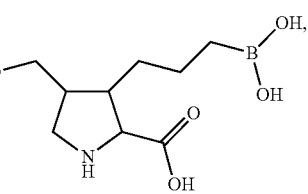
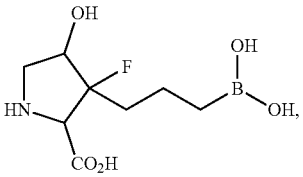
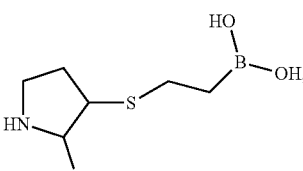

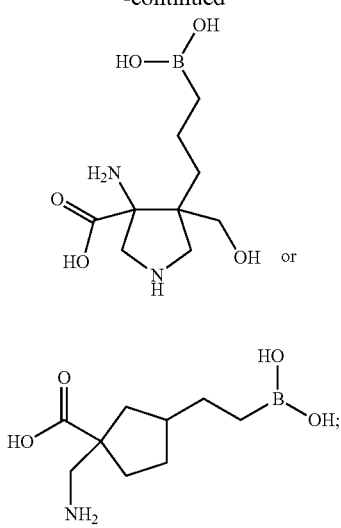
or pharmaceutically acceptable salts thereof.
In certain embodiments, the compounds described herein include:
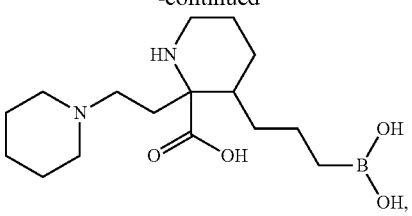
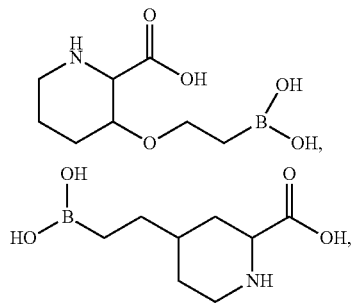
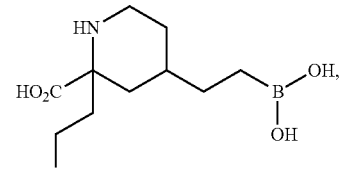
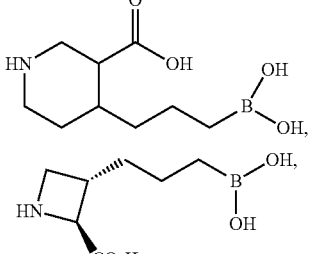
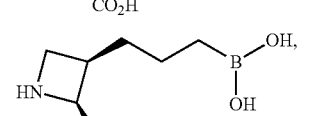
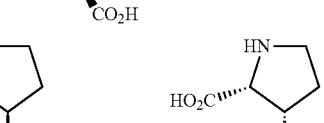

51
-continued
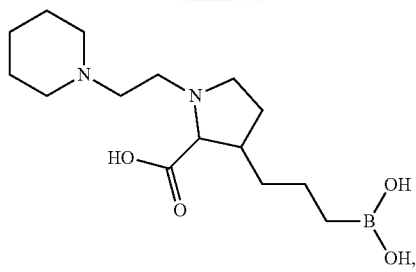
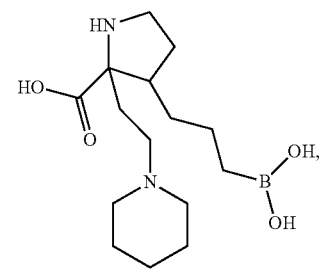
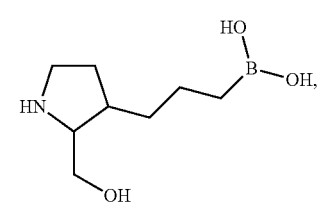
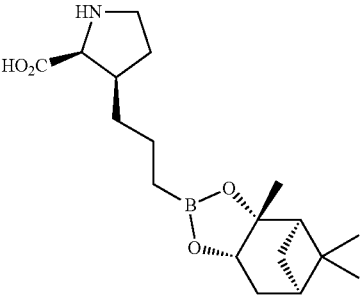
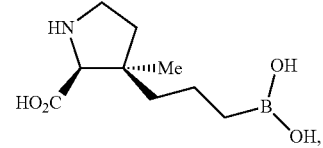
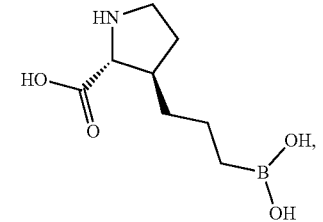
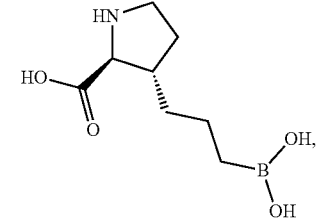
52
-continued
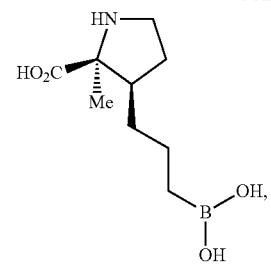
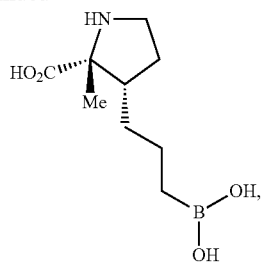
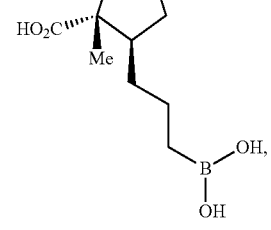
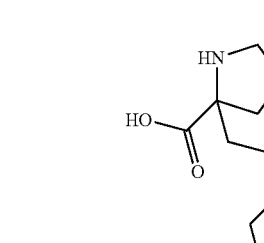
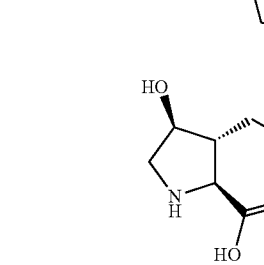
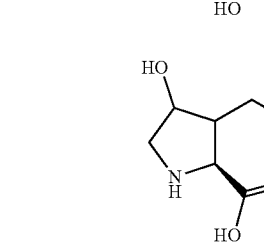
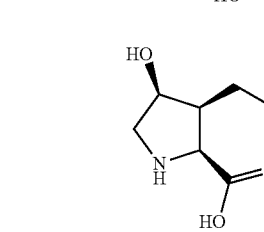
or -continued

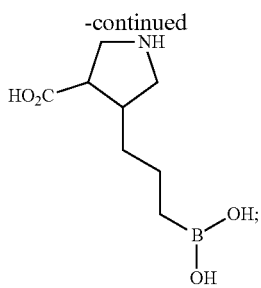

or a pharmaceutically acceptable salt thereof.

Definitions

The term "alkylene," by itself or as part of another substituent means a divalent straight, branched or cyclic chain hydrocarbon radical having the stated number of carbon atoms. For example, —($C_1$-$C_5$) alkylene, would include, e.g., —$CH_2$—, —$CH_2CH_2$—, —$CH_2CH_2CH_2$—, —$CH_2CH_2CH_2CH_2$—, —$CH_2CH(CH_3)CH_2$— or —$CH_2CH_2CH_2CH_2CH_2$—.

The term "halogen" includes a fluorine, a chlorine, a bromine or an iodine radical.

The term "$C_1$-$C_6$alkyl" encompasses straight alkyl having a carbon number of 1 to 6 and branched alkyl having a carbon number of 3 to 6. Specific examples thereof include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, and the like.

The term "halo$C_1$-$C_6$alkyl" refers to a $C_1$-$C_6$alkyl with the hydrogen atoms thereof being partially or completely substituted with halogen, examples thereof including fluoromethyl, difluoromethyl, trifluoromethyl, 2-fluoroethyl, 1,2-difluoroethyl, 2,2-difluoroethyl and the like.

The term "$C_1$-$C_6$alkoxy" refers to an alkyl group having 1 to 6 carbons linked to oxygen. Examples include methoxy, ethoxy, butoxy, isopropoxy and propoxy.

The term "—COO$C_1$-$C_6$alkyl" refers to a —COOH group wherein the —OH is replaced with an alkoxy group as defined above. Examples include methoxycarbonyl, ethoxycarbonyl, isopropylcarbonyl and butoxycarbonyl.

The term "$C_3$-$C_8$cycloalkyl" encompasses bridged, saturated, unsaturated or aromatic cycloalkyl groups having 3 to 8 carbons. "Cycloalkyl" also includes aromatic or "aryl" rings and non-aromatic rings as well as monocyclic, non-aromatic rings fused to an aryl group in which the point of attachment is on the non-aromatic portion. Examples of cycloalkyl include phenyl, naphthyl, cyclopropyl, cyclobutyl, cyclopentyl, cyclohexyl, cycloheptyl, tetrahydronaphthyl, decahydronaphthyl, indanyl and the like.

The term "heterocycle" means mono- or bicyclic or bridged saturated rings containing at least one heteroatom selected from N, S and O, each of said ring having from 3 to 10 atoms in which the point of attachment may be carbon, N, S or O. Examples also include tetrahydropyranyl, tetrahydrofuranyl, pyrrolidinyl, piperidinyl, piperazinyl, dioxanyl, imidazolidinyl, morpholinyl, and the like.

The term "nitrogen-containing heterocycle" means mono- or bicyclic or bridged saturated rings containing at least one nitrogen, each of said ring having from 5 to 11 atoms in which the point of attachment may be carbon or nitrogen.

"Heteroaryl" means an aromatic or partially aromatic heterocycle that contains at least one ring heteroatom selected from O, S and N. "Heteroaryl" thus includes heteroaryls fused to other kinds of rings, such as aryls, cycloalkyl groups and heterocycles that are not aromatic.

Examples of heteroaryl groups include pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), oxo-dihydro-diazole, oxadiazolone, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For cycloheteroalkyl and heteroaryl groups, rings and ring systems containing from 3-15 atoms are included, forming 1-3 rings.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidinyl, glucamine, glucosamine, histidine, hydrabamine, isopropylamine, lysine, methylglucamine, morpholine, piperazine, piperidinyl, polyamine resins, procaine, purines, theobromine, triethylamine, trimethylamine, tripropylamine, tromethamine, and the like.

The term "patient" refers to a mammalian patient, preferably a human patient, receiving or about to receive medical treatment.

The compounds of the present invention may contain one or more asymmetric centers and can thus occur as racemates, racemic mixtures, single enantiomers, diastereomeric mixtures, and individual diastereomers. The present invention is meant to comprehend all such isomeric forms of these compounds.

Some of the compounds described herein contain olefinic double bonds, and unless specified otherwise, are meant to include both E and Z geometric isomers.

Some of the compounds described herein contain substituted cycloalkanes having cis- and trans-isomers, and unless specified otherwise, are meant to include both cis- and trans-geometric isomers.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated.

The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In certain embodiments, wherein $R^3$ is COOH, the compounds herein can have the following stereochemistry.

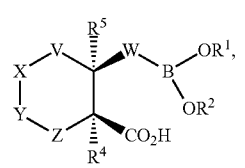

Ia

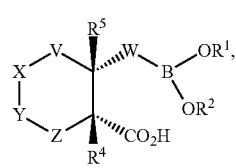

Ib

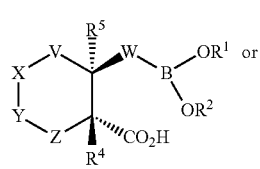

Ic

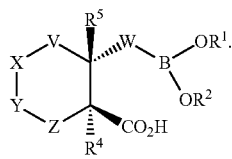

Id

It will be understood that the present invention encompasses compounds described herein is meant to include the pharmaceutically acceptable salts, and also salts that are not pharmaceutically acceptable when they are used as precursors to the free compounds or their pharmaceutically acceptable salts or in other synthetic manipulations.

Solvates, and in particular, the hydrates of the compounds of the structural formulas described herein are included in the present invention as well.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

The compounds of the present invention may also exist in open-chain or cyclized forms.

In some cases one or more of the cyclized forms may result in loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the invention.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples.

Isotopically-enriched compounds can be prepared without undue experimentation by conventional techniques well known to those skilled in the art or by processes analogous to those described in the Schemes and Examples herein using appropriate isotopically-enriched reagents and/or Intermediates.

Methods of Treatment

Also encompassed by the present invention are methods of treating arginase-related diseases. The compounds described herein can be effective in preventing or treating various arginase-related diseases, such as gastrointestinal diseases, pulmonary inflammatory diseases, sexual arousal disorders, cardiovascular disorders, diseases caused by pathogenic microorganisms, immunological disorders, cancer, pre-term labor, Reynaud's disease, psoriasis, rheumatoid arthritis, and Peyronie's Disease, among others.

An increase in arginase activity has been associated with the pathophysiology of a number of conditions including impairment in non-adrenergic and non-cholinergic (NANC) nerve-mediated relaxation of gastrointestinal smooth muscle. An arginase inhibitor can be used to alleviate such impairment by administering the inhibitor to a mammal experiencing such impairment or a mammal which is anticipated to experience such impairment (e.g., a human afflicted with a gastrointestinal motility disorder).

Accordingly, the compounds of the invention may be useful in the treatment or prevention of gastrointestinal motility disorders, which is based on the observation that arginase is present in opossum internal anal sphincter muscle and the known arginase inhibitor, (S)-2-amino-6-boronohexanoic acid (ABH), has been shown to relax this muscle. See, e.g., Baggio et al., J. Pharm. Exp. Ther. 290, 1409-16 (1999).

The compounds of the invention may also be useful in the treatment or prevention of inflammatory bowel disease (IBD, e.g., Crohn's disease and ulcerative colitis). In fact, IBD has been shown to be characterized by increased arginase activity and endothelial dysfunction. See, e.g., Horowitz et al., Am. J. Physiol. Gastrointest. Liver Physiol. 292, G1323-36 (2007).

Likewise, the compounds of the invention may be useful in the treatment or prevention of gastric ulcers, because the bacterium that causes stomach ulcers, *Helicobacter pylori*, exhibits increased arginase activity upon colonization in order to evade the human immune response. See, e.g., Gobert et al., Proc. Natl. Acad. Sci. (USA) 98, 13844-49 (2001).

The compounds of the invention may be useful in the treatment or prevention of asthma based on the observation that arginase is upregulated in the asthmatic airway. See, e.g., Zimmermann and Rothenberg, Eur. J. Pharmacol. 533, 253-62 (2006). Furthermore, nebulizer treatment of guinea pigs with ABH in an allergic asthma model prevents airway hyperresponsiveness. See, e.g., Maarsingh, "Arginase: A Novel Key Enzyme in the Pathophysiology of Allergic Asthma," Ph. D. dissertation, Chapter 9, University of Groningen, Netherlands (2006); Maarsingh et al., Am. J. Respir. Crit. Care Med. 178, 565-73 (2008). The asthma phenotype is characterized by airway constriction, airway smooth muscle hyperplasia, and the chronic accumulation of fibrotic tissue; an arginase inhibitor can relax airway smooth muscle and attenuate cellular hyperplasia and fibrosis.

Additionally, the compounds of the invention may be useful in the treatment or prevention of chemically-induced lung fibrosis because arginase I and II are induced in bleomycin-induced lung fibrosis in order to provide more L-ornithine for collagen biosynthesis.

See, e.g., Endo et al., Am. J. Physiol. Lung Cell Mol. Physiol. 285, L313-21 (2003).

The compounds of the invention may also be useful in the treatment or prevention of idiopathic pulmonary fibrosis, based on the observation that virus-induced upregulation of arginase I is observed in an animal model. See, e.g., Mora et al., Am. J. Respir. Cell Mol. Biol. 35, 466-73 (2006).

Furthermore, the compounds of the invention may be useful in the treatment or prevention of cystic fibrosis. Increased sputum arginase activity contributes to nitric oxide deficiency in cystic fibrosis lung disease; arginase activity also contributes to fibrosis. See, e.g., Graseman et al., Am. J. Respir. Crit. Care Med. 172, 1523-28 (2005).

Erectile dysfunction afflicts one-half of the male population over the age of forty. This malady often results from defects in the complex cascade of enzyme-catalyzed reactions governing blood flow into and out of the corpus cavernosum, a chamber of muscular, spongy tissue that becomes engorged with blood in the erect penis. Defects that compromise cavernosal blood flow often occur as secondary complications related to other health conditions, such as heart disease, hypertension, diabetes, use of certain medications, and the like.

In an important embodiment, the invention relates to use of an arginase inhibitor described herein for enhancing penile erectile function in a mammal (preferably a male human) or for alleviating erectile dysfunction in a mammal. Nitric oxide is an important regulator of erectile function and mediates NANC neurotransmission in penile corpus cavernosum smooth muscle, leading to rapid relaxation, which in turn leads to erection. Nitric oxide synthase, which catalyzes oxidation of L-arginine to form L-citrulline and nitric oxide, is for this reason a key enzyme in penile smooth muscle physiology. Arginase catalyzes hydrolysis of L-arginine to form L-ornithine and urea. Arginase regulates nitric oxide synthase activity by affecting the amount of L-arginine available for oxidation catalyzed by nitric oxide synthase activity. Thus, inhibition of arginase activity can enhance nitric oxide synthase activity, thereby enhancing nitric oxide-dependent smooth muscle relaxation in the corpus cavernosum and enhancing penile erection.

Arginase is present in rabbit and human penile corpus cavernosum and ABH enhances the nitric oxide-dependent relaxation of this tissue. See, e.g., Cox et al., Nature Struct. Biol. 6, 1043-47 (1999). The arginase inhibitor, ABH, enhances the erectile response in live male rabbits.

See, e.g., Cama et al., Biochemistry 42, 8445-51 (2003). Arginase II is upregulated in the corpus cavernosum of the diabetic man, resulting in reduced nitric oxide biosynthesis which, in turn, leads to erectile dysfunction; administration of ABH in ex vivo experiments restores nitric oxide biosynthesis. See, e.g., Bivalacqua et al., Biochem. Biophys. Res. Commun. 283, 923-27 (2001).

Arginase I is upregulated in the penis of aged mice and impairs erectile function. See, e.g., Bivalacqua et al., Am. J. Physiol. Heart Circ. Physiol. 292, H1340-51 (2007).

The compounds of the invention may also be useful in the treatment or prevention of female sexual arousal disorder. The arginase inhibitor, ABH, enhances the engorgement response in the genitalia of live female rabbits. See, e.g., Cama et al., Biochemistry 42, 8445-51 (2003).

The compounds of the invention may be useful in the treatment or prevention of endothelial vascular dysfunction in atherosclerosis, hypertension, hypercholesterolemia, and diabetes. Arginase modulates NOS activity by regulation of L-arginine availability, and the deleterious effects of arginase can be blocked by an arginase inhibitor. See, e.g., Berkowitz et al., Circulation 108, 2000-06 (2003); Yang and Ming, Clin. Med. Res. 4, 53-65 (2006). Increased arginase activity in diabetes contributes to vascular endothelial dysfunction by decreasing L-arginine availability to nitric oxide synthase. See, e.g., Romero et al., Circ. Res. 102, 95-102 (2008). Arginase inhibition attenuates hypertension in spontaneously hypertensive rats. See, e.g., Demougeot et al., J. Hypertens. 23, 971-78 (2005). Other relevant conditions include ischemia-reperfusion injury, peripheral vascular disease (PVD), peripheral arterial disease (PAD), and subarachnoid hemorrhage. Arginase has been identified as a new drug target for the treatment of atherosclerosis. See, e.g., Yang and Ming, Curr. Hypertension Rep. 8, 54-59 (2006).

The compounds of the invention may be useful in the treatment or prevention of pulmonary arterial hypertension. Elevated arginase activity contributes to vascular endothelial dysfunction by compromising L-arginine availability to nitric oxide synthase. See, e.g., Morris et al., Adv. Pulmonary Hypertension 5, 31-36 (2007).

The compounds of the invention may be useful in the treatment or prevention of African sleeping sickness, Chagas' disease, leishmaniasis, malaria, and other diseases caused by pathogenic microorganisms. Polyamine biosynthetic enzymes are essential for growth and survival of protozoa. See, e.g., Heby et al., Biochem. Soc. Trans. 31, 415-19 (2003). Arginase is essential for viability. See, e.g., Roberts et al., J. Biol. Chem. 279, 23668-78 (2004). Therefore, inhibitors of protozoan arginases can kill the protozoa.

The compounds of the invention may be useful in the treatment or prevention of multiple sclerosis, and possibly other autoimmune diseases, based upon the observation that arginase I is upregulated in an animal model of multiple sclerosis (experimental autoimmune encephalomyelitis) and administration of the arginase inhibitor ABH improves the disease score of animals. See, e.g., Xu et al., Immunology 110, 141-48 (2003).

Tumor-induced tolerance impairs the therapeutic efficacy of immunotherapy; one mechanism leading to T-cell tolerance is the generation of myeloid-derived suppressor cells (MDSCs), which produce arginase, thereby depleting the tumor microenvironment of L-arginine, which impairs T-cell signal transduction and function. Notably, arginase activity is a mechanism of immune system evasion that is also shared by certain bacteria, e.g., *Helicobacter pylori*.

MDSCs are regarded as "cancer's bulwark against immune attack." See, e.g., Marx, Science 319, 154-56 (2008).

Accordingly, arginase is upregulated in the following types of cancers, which may be treated with an arginase inhibitor described herein: Renal cell carcinoma (see, e.g., Zea et al., Cancer Res. 65, 3044-48 (2005); Ochoa et al., Clin. Cancer Res. 13, 721s-26s (2007)); prostate cancer (see, e.g., Bronte et al., J. Exp. Med. 201, 1257-68 (2005) (arginase inhibition with N-hydroxy-L-arginine facilitates tumor immunotherapy); colorectal cancer (see, e.g., Leu and Wang, Cancer 70, 733-36 (1992); Bronte and Zanovello, Nature Rev. Immunol. 5, 641-54 (2005)); breast cancer (see, e.g., Singh et al., Cancer Res. 60, 3305-12 (2000); Bronte and Zanovello, Nature Rev. Immunol. 5, 641-54 (2005)(the arginase inhibitor, N-hydroxy-L-arginine, inhibits cell proliferation and induces apoptosis)); skin cancer (squamous cell and basal cell cancers)(see, e.g., Gokmen et al., J. Lab. Clin. Med. 137, 340-44 (2001); Bronte and Zanovello, Nature Rev. Immunol. 5, 641-54 (2005)); lung cancer (see, e.g., Rodriguez et al., J. Exp. Med. 202, 931-39 (2005); Bronte and Zanovello, Nature Rev. Immunol. 5, 641-54 (2005)); ovarian cancer (see, e.g., Melichar et al., J. Translational Med. 1, 1-5 (2003)(doi:10.11861479-5876-1-5)); and gastric cancer (see, e.g., Wu et al., Life Sci. 51, 1355-61 (1992)); among others.

Enhancement of uterine smooth muscle relaxation with an arginase inhibitor may be useful in the management of pre-term labor.

Reynaud's disease is a disease of the microvasculature. Because subcutaneous administration of the arginase inhibitor (S)-(2-Boronoethyl)-L-cysteine (BEC, which is an analogue of ABH) in humans is vasodilatory and enhances circulation, an arginase inhibitor may be useful in treating Reynaud's disease. See, e.g., Holowatz et al., J. Physiol. 574, 573-81 (2006).

Arginase I is highly overexpressed in the hyperproliferative psoriatic epidermis in human skin, and therefore arginase inhibitors may be useful in the treatment of psoriasis. See, e.g., Bruch-Gerharz et al., Am. J. Pathology 162, 203-11 (2003).

Arginase II is upregulated in synovial fluid from human patients, and therefore arginase inhibitors may be useful in the treatment of arthritis. See, e.g., Huang et al., Kaohsiung J. Med. Sci. 17, 358-63 (2001); Corraliza and Moncada, J. Rheumatol. 29, 2261-65 (2002).

The compounds of the invention may be useful in the treatment or prevention of Peyronie's disease. Arginase II is upregulated in the rat penis in an animal model for this disease. See, e.g., Bivalacqua et al., J. Andrology 22, 497-506 (2001). While this disorder can contribute to erectile dysfunction, it is principally an inflammatory condition in which fibrotic tissue builds up in the penis.

The composition of the invention can be used to treat a disorder in a mammal, wherein the disorder is associated with expression of an abnormally high level of arginase activity in a tissue of the mammal. Because nitric oxide synthase activity is regulated in a reciprocal fashion with respect to arginase activity in mammals, more particularly humans, the compounds and compositions of the invention can be used to treat a disorder in a mammal, wherein the disorder is associated with expression of an abnormally low level of nitric oxide synthase activity in a tissue of the mammal. Since the reciprocal interaction of arginase and nitric oxide synthase has implications for the function of smooth muscle, the use of the compounds described herein for the regulation of smooth muscle activity in an animal is also contemplated in the invention. Of course, a compound of the invention or a composition comprising the compound of the invention which comprises an arginase inhibitor described herein can also be used to inhibit arginase in a mammal having normal levels of arginase and nitric oxide synthase activity, particularly where the physiology which is desired to be effected is one which is affected by arginase or nitric oxide synthase activity, or where a disorder which is not caused by aberrant arginase or nitric oxide synthase activity levels can nonetheless be alleviated or inhibited by inhibiting arginase activity (e.g., certain forms of erectile dysfunction).

The invention also includes a method of enhancing smooth muscle relaxation comprising contacting the smooth muscle with an arginase inhibitor. The smooth muscle is preferably within the body of an animal. The type of smooth muscle to be relaxed includes, but is not limited to, gastrointestinal smooth muscle, anal sphincter smooth muscle, esophageal sphincter muscle, sphincter of Oddi, arterial smooth muscle, heart smooth muscle, pulmonary smooth muscle, kidney smooth muscle, uterine smooth muscle, vaginal smooth muscle, cervical smooth muscle, placental smooth muscle, and ocular smooth muscle. When the smooth muscle is gastrointestinal smooth muscle, the type of gastrointestinal smooth muscle includes, but is not limited to, the internal anal sphincter muscle.

When the smooth muscle is within the body of the animal, the invention includes a method of alleviating (e.g., reducing the incidence or severity) or inhibiting (e.g., reducing the likelihood of developing, or preventing) an arginase-related disorder in an animal. In a preferred embodiment, the animal is a human.

To alleviate an arginase-related disorder in a mammal, an arginase inhibitor described herein is administered to a mammal afflicted with the disorder. The inhibitor is preferably administered in combination with one or more pharmaceutically acceptable carriers, as described in further detail herein. The inhibitor (preferably in combination with a carrier) can also be administered to a mammal afflicted with a disorder characterized by aberrant nitric oxide synthase activity, or to one which exhibits normal (i.e. non-diseased) levels of arginase and nitric oxide synthase activities, but in which inhibition of arginase activity is desired. The invention also contemplates use of an arginase inhibitor in an in vitro arginase inhibition/smooth muscle relaxation functional assay, for the purpose of identifying compounds which affect smooth muscle function.

Accordingly, in certain embodiments, the invention is directed to methods of inhibiting arginase in a mammal, comprising the step of administering to said mammal an effective amount of a compound of the formulas described herein or a pharmaceutically acceptable salt thereof.

Accordingly, in certain embodiments, the invention is directed to methods of treating an arginase-related disorder in a mammal, comprising the step of administering to said mammal an effective amount of a compound of any of the formulas described herein or a pharmaceutically acceptable salt thereof. In certain preferred embodiments, the arginase-related disorder is a disorder associated with an abnormally low level of nitric oxide synthase activity in a tissue of the human, a disorder associated with an abnormally high level of arginase activity in a tissue of the human, or combinations thereof, including heart disease, systemic hypertension, pulmonary hypertension, erectile dysfunction, autoimmune encephalomyelitis, chronic renal failure, gastrointestinal motility disorders, gastric cancers, reduced hepatic blood flow, insufficient hepatic blood flow, cerebral vasospasm, or a combination thereof.

In still other certain embodiments, the invention is directed to methods of relaxing smooth muscle in a mammal, comprising the step of administering to said mammal an effective amount of a compound of the formulas described herein or a pharmaceutically acceptable salt thereof. In certain preferred embodiments, the smooth muscle which is relaxed according to this method is at least one selected from the group consisting of a gastrointestinal smooth muscle, anal sphincter smooth muscle, esophageal sphincter muscle, corpus cavemosum, sphincter of Oddi, arterial smooth muscle, heart smooth muscle, pulmonary smooth muscle, kidney smooth muscle, uterine smooth muscle, vaginal smooth muscle, cervical smooth muscle, placental smooth muscle, and ocular smooth muscle.

In certain embodiments, the invention is directed to methods of treating a disease or condition associated with upregulation of arginase in a mammal, comprising the step of administering to said mammal an effective amount of a compound of the formulas described herein or a pharmaceutically acceptable salt thereof, wherein said disease or condition is a gastrointestinal disease, a pulmonary inflammatory disease, a sexual arousal disorder, a cardiovascular disorder, a hemolytic disorder, an autoimmune disease, wound healing, a cancer, pre-term labor, psoriasis, or a combination thereof.

In certain embodiments, the invention is directed to methods of treating a disease or condition caused by parasitic protozoa, a disease caused by bacteria, or a combination thereof.

Inhibiting arginase impacts cancer in two ways. The first way is relief from immune-suppression that leads to tolerance of the tumor, and the second way is by restricting the production of ornithine and subsequent polyamines, which have a role in proliferation.

In certain preferred embodiments, the gastrointestinal disease is a gastrointestinal motility disorder, inflammatory bowel disease, Crohn's disease, ulcerative colitis, gastric ulcer, adenotonsilar disease or a combination thereof.

In certain preferred embodiments, the pulmonary inflammatory disease is asthma, chemically-induced lung fibrosis, idiopathic pulmonary fibrosis, cystic fibrosis, chronic obstructive pulmonary disease (COPD) or a combination thereof.

In certain preferred embodiments, the sexual arousal disorder is male erectile dysfunction, Peyronie's Disease, or a female sexual arousal disorder.

In certain preferred embodiments, the cardiovascular disorder is endothelial vascular dysfunction in atherosclerosis, hypertension, ischemia reperfusion injury, peripheral vascular disease, peripheral arterial disease, subarachnoid hemorrhage, hypercholesterolemia, diabetes, or a combination thereof, diabetic cardiovascular disease, pulmonary arterial hypertension, Reynaud's disease, or a combination thereof.

In certain preferred embodiments, the hemolytic disorder is paroxysmal nocturnal hemoglobinuria (PNH), sickle-cell disease, thalassemias, hereditary spherocytosis and stomatocytosis, microangiopathic hemolytic anemias, pyruvate kinase deficiency, ABO mismatch transfusion reaction, paroxysmal cold hemoglobinuria, severe idiopathic autoimmune hemolytic anemia, infection-induced anemia, malaria, cardiopulmonary bypass, mechanical heart valve-induced anemia, chemical induced anemia, or a combination thereof.

In certain preferred embodiments, the autoimmune disease is encephalomyelitis, multiple sclerosis, anti-phospholipid syndrome 1, autoimmune hemolytic anaemia, chronic inflammatory demyelinating polyradiculoneuropathy, dermatitis herpetiformis ("Celiac Disease"), dermatomyositis, myasthenia gravis, pemphigus, rheumatoid arthritis, stiff-person syndrome, type 1 diabetes, ankylosing spondylitis, or a combination thereof.

In certain preferred embodiments, the condition is wound healing.

In certain preferred embodiments, the disease caused by parasitic protozoa is African sleeping sickness, Chagas' disease, leishmaniasis, malaria, or a combination thereof.

In certain preferred embodiments, the cancer is renal cell carcinoma, prostate cancer, colorectal cancer, breast cancer, skin cancer, lung cancer, ovarian cancer, gastric cancer, or a combination thereof. In certain embodiments, the skin cancer is a squamous cell cancer, basal cell cancer, or a combination thereof.

In certain preferred embodiments, the condition is pre-term labor.

In certain preferred embodiments, the condition is Reynaud's disease.

In certain embodiments, the invention is directed to methods of providing relief from immune suppression in a mammal, comprising the step of administering to said mammal an effective amount of a compound of the formulas described herein or a pharmaceutically acceptable salt thereof, wherein said mammal is suffering from a disease or condition selected from the group consisting of a chronic infectious disease, a bacterial infection, a parasitic infection, trauma, leprosy, tuberculosis, liver transplantation, a cancer, and combinations thereof.

In certain embodiments, the invention is directed to methods of inhibiting the production of ornithine or other related metabolites (e.g. agmatine, putrescine, spermine, spermidine, citruline, proline, glutamate, etc.) in a mammal suffering from at least one tumor, comprising the step of administering to said mammal an effective amount of a compound of the formulas described herein or a pharmaceutically acceptable salt thereof.

Pharmaceutical Compositions Compounds described herein may be administered orally or parenterally. As formulated into a dosage form suitable for administration, the compounds described herein can be used as a pharmaceutical composition for the prevention, treatment, or remedy of the above diseases.

In clinical use of the compounds described herein, usually, the compound is formulated into various preparations together with pharmaceutically acceptable additives according to the dosage form, and may then be administered. By "pharmaceutically acceptable" it is meant the additive, carrier, diluent or excipient must be compatible with the other ingredients of the formulation and not deleterious to the recipient thereof. As such, various additives ordinarily used in the field of pharmaceutical preparations are usable. Specific examples thereof include gelatin, lactose, sucrose, titanium oxide, starch, crystalline cellulose, hydroxypropyl methylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, hydroxypropyl cyclodextrin, and the like.

Preparations to be formed with those additives include, for example, solid preparations such as tablets, capsules, granules, powders, suppositories; and liquid preparations such as syrups, elixirs, injections. These may be formulated according to conventional methods known in the field of pharmaceutical preparations. The liquid preparations may also be in such a form that may be dissolved or suspended in water or in any other suitable medium in their use.

Especially for injections, if desired, the preparations may be dissolved or suspended in physiological saline or glucose liquid, and a buffer or a preservative may be optionally added thereto.

The pharmaceutical compositions may contain the compound of the invention in an amount of from 1 to 99.9% by weight, preferably from 1 to 60% by weight of the composition.

The compositions may further contain any other therapeutically-effective compounds.

In case where the compounds of the invention are used for prevention or treatment for the above-mentioned diseases, the dose and the dosing frequency may be varied, depending on the sex, the age, the body weight and the disease condition of the patient and on the type and the range of the intended remedial effect. In general, when orally administered, the dose may be from 0.001 to 50 mg/kg of body weight/day, and it may be administered at a time or in several times. In specific embodiments, the dose is from about 0.01 to about 25 mg/kg/day, in particular embodiments, from about 0.05 to about 10 mg/kg/day. For oral administration, the compositions are preferably provided in the form of tablets or capsules containing from 0.01 mg to 1,000 mg.

In specific embodiments, the dose is 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850 or 1,000 milligrams of a compound described herein. This dosage regimen may be adjusted to provide the optimal therapeutic response.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds described herein or the other drugs may have utility, where the combination of the drugs together are safer or more effective than either drug alone. Such other drug(s) may be administered in an amount commonly used therefore, contemporaneously or sequentially with a compound described herein or a pharmaceutically acceptable salt thereof. When a compound described herein is used contemporaneously with one or more other drugs, the pharmaceutical composition may in specific embodiments contain such other drugs and the compound described herein or its pharmaceutically acceptable salt in unit dosage form. However, the combination therapy may also include therapies in which the compound described herein or its pharmaceutically acceptable salt and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound described herein or a pharmaceutically acceptable salt thereof.

Examples of other active ingredients that may be administered in combination with a compound of any of the Formulas described herein or a pharmaceutically acceptable salt thereof and either administered separately or in the same pharmaceutical composition, include, but are not limited to pain relieving agents, anti-angiogenic agents, anti-neoplastic agents, anti-diabetic agents, anti-infective agents, or gastrointestinal agents, or combinations thereof.

Suitable compounds that may be used in combination with a compound according to the present invention include without limitation sildenafil, vardenafil, tadalafil and alprostadil, epoprostenol, iloprost, bosentan, amlodipine, diltiazem, nifedipine, ambrisentan and warfarin, fluticasone, budesonide, mometasone, flunisolide, beclomethasone, montelukast, zafirlukast, zileuton, salmeterol, formoterol, theophylline, albuterol, levalbuterol, pirbuterol, ipratropium, prednisone, methylprednisolone, omalizumab, corticosteroid and cromolyn, atorvastatin, lovastatin, simvastatin, pravastatin, fluvastatin, rosuvastatin, gemfibrozil, fenofibrate, nicotinic acid and clopidogrel.

Additionally, a compound of any of the Formulas disclosed herein may be used in combination with one or more other active agents, including but not limited to, other anti-cancer agents that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indoi-6-yl)-2-[(4-pyridinyimethyj)amino]-3-pyfidinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUB EX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP 005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L, and useful in the treatment method, medicaments and uses of the present invention, are described in WO2013/019906, WO2010/077634 A1 and U.S. Pat. No. 8,383,796. Specific anti-human PD-L1 mAbs useful as the PD-L1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

The invention further relates to a method of treating cancer in a human patient comprising administration of a compound of the invention (i.e., a compound of Formula I) and a PD-1 antagonist to the patient. The compound of the invention and the PD-1 antagonist may be administered concurrently or sequentially.

In particular embodiments, the PD-1 antagonist is an anti-PD-1 antibody, or antigen binding fragment thereof. In alternative embodiments, the PD-1 antagonist is an anti-PD-L1 antibody, or antigen binding fragment thereof. In some embodiments, the PD-1 antagonist is pembrolizumab (KEYTRUDA™, Merck & Co., Inc., Kenilworth, NJ, USA), nivolumab (OPDIVO™, Bristol-Myers Squibb Company, Princeton, NJ, USA), cemiplimab (LIBTAYO™ Regeneron Pharmaceuticals, Inc., Tarrytown, NY, USA), atezolizumab (TECENTRIQ™ Genentech, San Francisco, CA, USA), durvalumab (IMFINZI™, AstraZeneca Pharmaceuticals LP, Wilmington, DE), or avelumab (BAVENCIO™, Merck KGaA, Darmstadt, Germany). In some embodiments, the PD-1 antagonist is pembrolizumab. In particular sub-embodiments, the method comprises administering 200 mg of pembrolizumab to the patient about every three weeks.

In other sub-embodiments, the method comprises administering 400 mg of pembrolizumab to the patient about every six weeks.

In further sub-embodiments, the method comprises administering 2 mg/kg of pembrolizumab to the patient about every three weeks. In particular sub-embodiments, the patient is a pediatric patient.

In some embodiments, the PD-1 antagonist is nivolumab. In particular sub-embodiments, the method comprises administering 240 mg of nivolumab to the patient about every two weeks. In other sub-embodiments, the method comprises administering 480 mg of nivolumab to the patient about every four weeks.

In some embodiments, the PD-1 antagonist is cemiplimab. In particular sub-embodiments, the method comprises administering 350 mg of cemiplimab to the patient about every 3 weeks. In some embodiments, the PD-1 antagonist is atezolizumab. In particular sub-embodiments, the method comprises administering 1200 mg of atezolizumab to the patient about every three weeks. In some embodiments, the PD-1 antagonist is durvalumab. In particular sub-embodiments, the method comprises administering 10 mg/kg of durvalumab to the patient about every two weeks. In some embodiments, the PD-1 antagonist is avelumab. In particular sub-embodiments, the method comprises administering 800 mg of avelumab to the patient about every two weeks.

Examples of cytotoxic agents include, but are not limited to, arsenic trioxide (sold under the tradename TRISENOX), asparaginase (also known as L-asparaginase, and Erwinia L-asparaginase, sold under the tradenames ELSPAR and KIDROLASE)

When a compound of the present invention is used contemporaneously with one or more other drugs a specific embodiment hereof pertains to, a pharmaceutical composition containing such other drugs in addition to the compound of the present invention. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, in particular embodiments from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

EXAMPLES

The meanings of the abbreviations in Examples are shown below.
ACN=MeCN=CH$_3$CN=acetonitrile
AIBN=azobisisobutyronitrile
Boc=tert-butoxycarbonyl
Cbz=carboxybenzyl
Cbz-OSu=N-(Benzyloxycarbonyloxy)succinimide
CELITE=diatomaceous earth
Conc.=concentrated
Cs$_2$CO$_3$=cesium carbonate
DAST=diethylaminosulfur trifluoride
DBU=1,8-Diazabicyclo[5.4.0]undec-7-ene
DCE=1,2-Dichloroethene
DCM=dichloromethane
DIBALH=diisobutylaluminum hydride
DIEA=N, N-Diisopropylethylamine
DMP=Dimethyl phthalate
DMAP=4-dimethylaminopyridine
DMF=N,N-Dimethylformamide
DPPE=1,2-Bis(diphenylphosphino)ethane
Et$_2$O=diethyl ether
EtOAc=ethyl acetate
EtOH=ethanol
h=hours
HATU=1-[Bis(dimethylamino)methylene]-1H-1,2,3-triazolo[4,5-b]pyridinium 3-oxid hexafluorophosphate HCl=hydrochloric acid
HBr=hydrobromic acid
HFBA=heptafluorobutyric acid
HOAc=acetic acid
IPA=isopropyl alcohol
[Ir(cod)Cl]$_2$=1,5-Cyclooctadiene-iridium(I) chloride
K$_2$CO$_3$=potassium carbonate
KHMDS=potassium bis(trimethylsilyl)amide
KOTMS=potassium trimethylsilanolate
K$_3$PO$_4$=Tripotassium phosphate
LCMS=Liquid chromatography-mass spectrometry
LHMDS=LiHMDS=lithium bis(trimethylsilyl)amide
LiOH=lithium hydroxide
min=minutes
Me=methyl
MeI=methyl iodide
MeOH=methanol
NaBH$_4$=sodium borohydride
NaBH(OAc)$_3$=sodium triacetoxyborohydride
NaH=sodium hydride
Na$_2$SO$_3$=sodium sulfite
Na$_2$SO$_4$=sodium sulfate
NH$_4$Cl=Ammonium chloride
NH$_4$OH=Ammonium hydroxide
PdCl$_2$(dppf)-CH$_2$Cl$_2$=[1,1'-Bis(diphenylphosphino)ferrocene]dichloropalladium(II)
RP-HPLC=reverse phase high performance liquid chromatography
SFC=Supercritical Fluid Chromatography
TEA=triethylamine
TFA=trifluoroacetic acid
THF=tetrahydrofuran
TMS=Trimethylsilyl
CDCl$_3$=heavy chloroform
CD$_3$OD=heavy methanol
1 Standard atmosphere [atm]=101325 pascal [Pa]=14.6959488 psi The meanings of the abbreviations in the nuclear magnetic resonance spectra are shown below:
s=singlet, d=doublet, dd=double doublet, dt=double triplet, ddd=double double doublet, Sept=septet, t=triplet, m=multiplet, br=broad, brs=broad singlet, q=quartet J=coupling constant and Hz=hertz.

Compounds of this invention can be prepared using the intermediates and processes outlined below. The various starting materials used are commercially available or are readily made by persons skilled in the art.

Example 1: 3-[3-(dihydroxyboranyl)propyl]piperidinyl-2-carboxylic acid

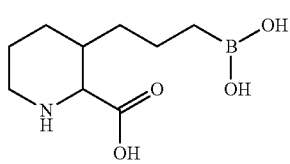 [SMILES: O=C(O)C1NCCCC1CCCB(O)O]

Step 1: tert-butyl 3-bromopicolinate

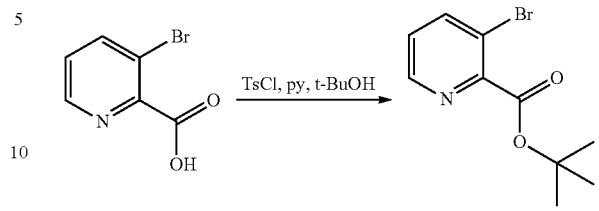

4-methylbenzene-1-sulfonyl chloride (13 g, 67 mmol) was added portion wise to a solution of 3-bromopicolinic acid (5.4 g, 27 mmol) and pyridine (11 mL, 134 mmol) in tert-butanol (t-BuOH)(60 mL) at 0° C., and the reaction mixture was stirred at 10° C. for 12 h. The mixture was quenched with saturated aqueous Na$_2$CO$_3$, and then concentrated in vacuo. The crude mixture was extracted with ethyl acetate, and the combined organic phase was dried over anhydrous Na$_2$SO$_4$, filtered and concentrated under reduced pressure. The residue was purified by silica gel column chromatography (EtOAc in hexanes) to afford tert-butyl 3-bromopicolinate. LCMS (C$_{10}$H$_{13}$BrNO$_2$$^+$)(ES, m/z): 258 [M+H]$^+$.

Step 2: tert-butyl 3-allypicolinate

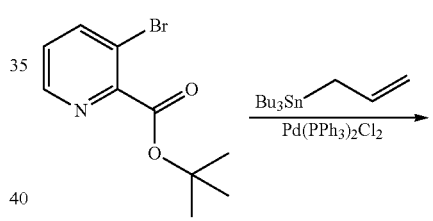

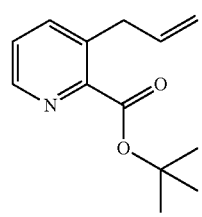

A mixture of bis(triphenylphosphine)palladium(II) chloride (219 mg, 0.33 mmol), tert-butyl 3-bromopicolinate (850 mg, 3.3 mmol) and allyltributylstannane (923 mg, 2.8 mmol) in DMF (15 mL) was heated to 150° C. in a sealed tube under nitrogen for 2 h. The reaction mixture was diluted with saturated aqueous potassium fluoride and EtOAc, and the organic phase was dried over anhydrous Na$_2$SO$_4$, filtered and concentrated under reduced pressure. The residue was purified by silica gel column chromatography (EtOAc in hexanes) to afford tert-butyl 3-allylpicolinate. $^1$H NMR (400 MHz, CDCl$_3$) δ 8.53 (d, J=3.5 Hz, 1H), 7.59 (d, J=7.5 Hz, 1H), 7.31 (dd, J=4.8, 7.9 Hz, 1H), 6.01-5.92 (m, 1H), 5.18-4.96 (m, 2H), 3.55-3.59 (m, 2H), 1.60 (s, 9H).

Step 3: tert-butyl 3-(3-(4,4,5,5-tetramethyl-1,3,2-dioxaborolan-2-yl)propyl)picolinate

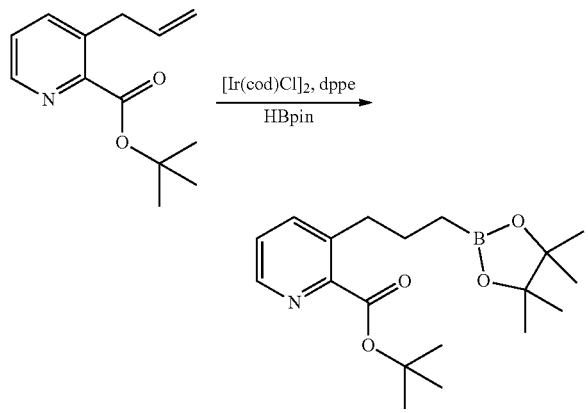

A solution of 4,4,5,5-tetramethyl-1,3,2-dioxaborolane (13 g, 105 mmol), chloro(1,5-cyclooctadiene)Iridium(I) dimer (705 mg, 1.0 mmol) and 1,2-bis(diphenylphosphino)ethane (836 mg, 2.1 mmol) in anhydrous DCM (150 mL) was bubbled with a stream of nitrogen for 3 min, and the resulting mixture was stirred at 10° C. for 20 min. Tert-butyl 3-allylpicolinate (4.6 g, 21 mmol) was added to the reaction mixture which was stirred at 10° C. for 16 h under nitrogen, and was directly purified by silica gel column chromatography (EtOAc in hexanes) to give tert-butyl 3-(3-(4,4,5,5-tetramethyl-1,3,2-dioxaborolan-2-yl)propyl)picolinate. LCMS ($C_{19}H_{31}BNO_4^+$) (ES, m/z): 348 [M+H]$^+$.

Step 4: tert-butyl 3-(3-(4,4,5,5-tetramethyl-1,3,2-dioxaborolan-2-yl)propyl)piperidinyl-2-carboxylate

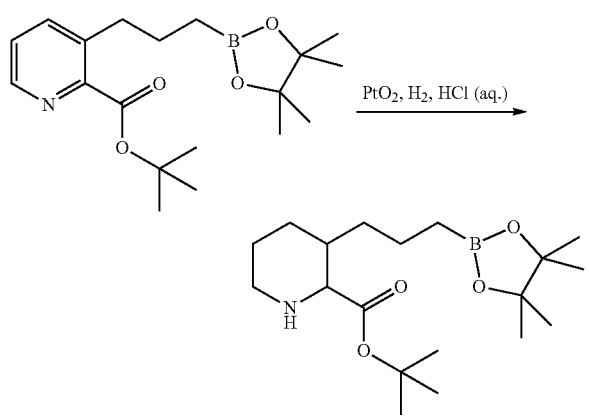

Platinum dioxide (13 mg, 0.058 mmol) was added to a solution of tert-butyl 3-(3-(4,4,5,5-tetramethyl-1,3,2-dioxaborolan-2-yl)propyl)picolinate (200 mg, 0.58 mmol) in EtOH (3.0 mL) and 2N HCl in water (2.0 mL, 4.0 mmol) at 10° C., and the reaction mixture was degassed and backfilled with H$_2$ three times, and then stirred under 50 psi of H$_2$ at 50° C. for 16 h. The mixture was neutralized with concentrated aqueous NH$_4$OH to pH ~7, then filtered and concentrated under reduced pressure to give crude tert-butyl 3-(3-(4,4,5,5-tetramethyl-1,3,2-dioxaborolan-2-yl)propyl) piperidinyl-2-carboxylate which was used in the next step without purification. LCMS ($C_{19}H_{37}BNO_4^+$)(ES, m/z): 354 [M+H]$^+$.

Step 5: di-tert-butyl 3-(3-(4,4,5,5-tetramethyl-1,3,2-dioxaborolan-2-yl)propyl)piperidinyl-1,2-dicarboxylate

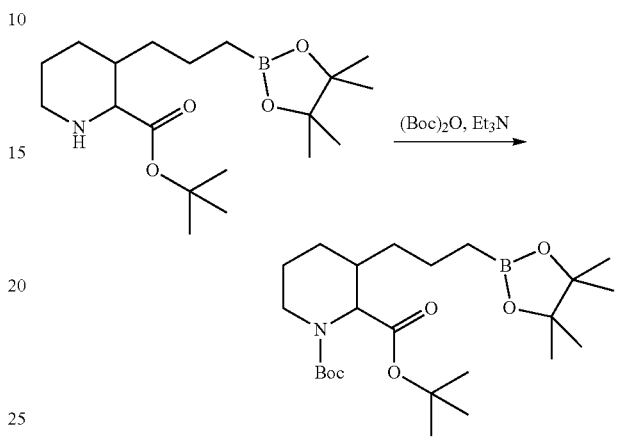

Di-tert-butyl dicarbonate (285 mg, 1.3 mmol) was added to a solution of triethylamine (0.11 mL, 0.76 mmol) and tert-butyl 3-(3-(4,4,5,5-tetramethyl-1,3,2-dioxaborolan-2-yl)propyl)piperidinyl-2-carboxylate (90 mg, 0.26 mmol) in DCM (5.0 mL) at 10° C. The reaction mixture was stirred at 15° C. for 1 h then purified directly by silica gel preparative thin layer chromatography (EtOAc in hexanes) to give di-tert-butyl 3-(3-(4,4,5,5-tetramethyl-1,3,2-dioxaborolan-2-yl)propyl)piperidinyl-1,2-dicarboxylate. LCMS ($C_{24}H_{45}BNO_6^+$)(ES, m/z): 454 [M+H]$^+$.

Step 6: 3-[3-(dihydroxyboranyl)propyl]piperidinyl-2-carboxylic acid

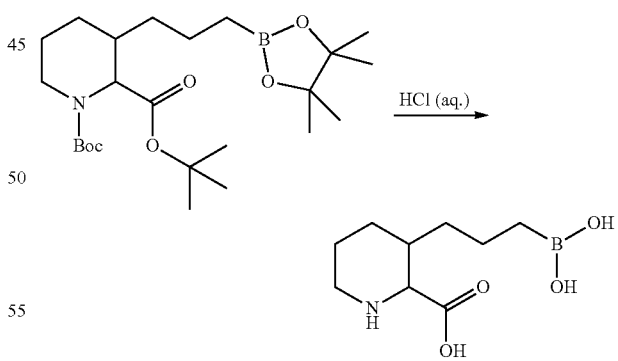

A mixture of di-tert-butyl 3-(3-(4,4,5,5-tetramethyl-1,3,2-dioxaborolan-2-yl)propyl)piperidinyl-1,2-dicarboxylate (100 mg, 0.22 mmol) in 12 N HCl in water (0.5 mL, 6.0 mmol) was stirred at 80° C. for 4 h. The mixture was concentrated under reduced pressure to give 3-[3-(dihydroxyboranyl)propyl]piperidinyl-2-carboxylic acid as an HCl salt. LCMS ($C_9H_{17}BNO_3^+$)(ES, m/z): 198 [M−H$_2$O+H]$^+$. $^1$H NMR (400 MHz, D$_2$O) δ 3.93 (d, J=3.5 Hz, 1H), 3.24 (d, J=12.7 Hz, 1H), 2.90-2.74 (m, 1H), 2.30-2.13 (m, 1H), 1.74 (d, J=11.8 Hz, 1H), 1.64-1.44 (m, 3H), 1.33 (t, J=9.9 Hz, 2H), 1.30-1.10 (m, 1H), 0.99-0.95 (m, 1H), 0.72-0.46 (m, 2H).

Example 1A: (2R,3S)-3-[3-(dihydroxyboranyl)propyl]piperidinyl-2-carboxylic acid

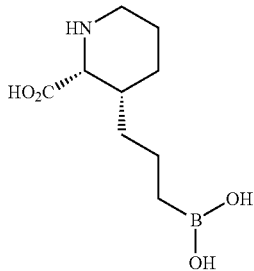

Step 1: methyl 3-allylpicolinate

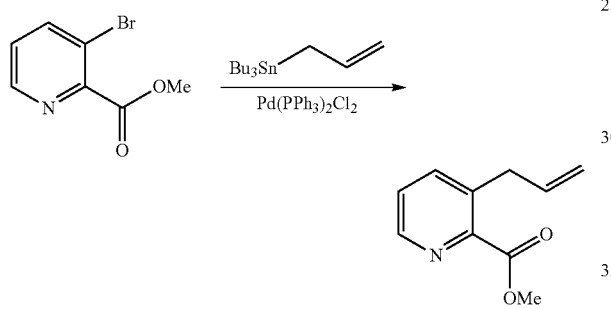

Allyltributylstannane (31 g, 94 mmol) was added to a mixture of methyl 3-bromopicolinate (18 g, 82 mmol) and dichlorobis(triphenylphosphine)palladium(II)(5.5 g, 8.2 mmol) in DMF (4.0 mL) under nitrogen. The mixture was degassed and backfilled with nitrogen three times. The solution was heated to 120° C. for 2 h and saturated aqueous potassium fluoride (100 mL) was added and stirred for 1 h. The reaction mixture was filtered through CELITE and concentrated under reduced pressure. EtOAc and water were added and the organic phase was separated and dried over anhydrous Na$_2$SO$_4$, filtered and concentrated under reduced pressure. The resulting residue was purified by silica gel column chromatography (EtOAc in hexanes) to give methyl 3-allylpicolinate. LCMS (C$_{10}$H$_{12}$NO$_2{}^+$)(ES, m/z): 178 [M+H]$^+$.

Step 2: methyl 3-(3-(4,4,5,5-tetramethyl-1,3,2-dioxaborolan-2-yl)propyl)picolinate

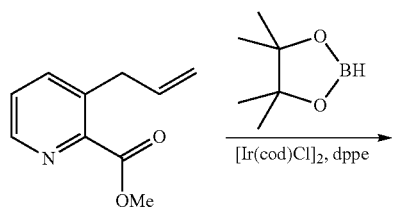

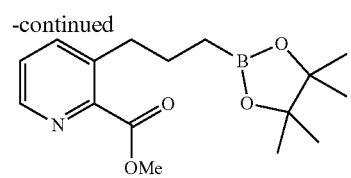

A solution of 4,4,5,5-tetramethyl-1,3,2-dioxaborolane (54.0 mL, 372 mmol), chloro(1,5-cyclooctadiene)iridium (I) dimer (2.5 g, 3.7 mmol) and 1,2-bis(diphenylphosphino)ethane (2.1 g, 5.2 mmol) in anhydrous DCM (500 mL) was bubbled with a stream of nitrogen for 3 min. The mixture was stirred at 12° C. for 20 min, and then treated with methyl 3-allylpicolinate (13 g, 75 mmol). The resulting mixture was stirred at 12° C. for 16 h under nitrogen and was directly purified by silica gel column chromatography (EtOAc in hexanes) to give methyl 3-(3-(4,4,5,5-tetramethyl-1,3,2-dioxaborolan-2-yl)propyl)picolinate. LCMS (C$_{16}$H$_{25}$BNO$_4{}^+$) (ES, m/z): 306 [M+H]$^+$.

Step 3: methyl 3-(3-(4,4,5,5-tetramethyl-1,3,2-dioxaborolan-2-yl)propyl)piperidinyl-2-carboxylate

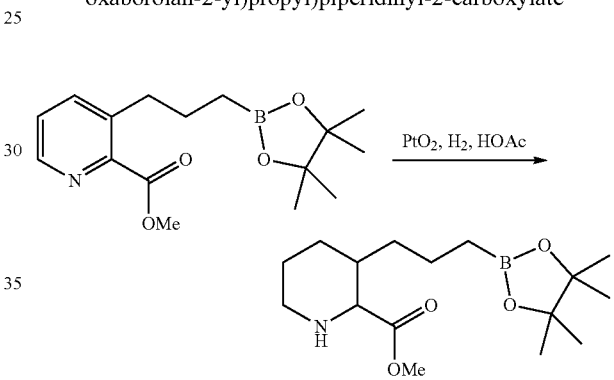

Platinum (IV) oxide (0.45 g, 2.0 mmol) was added to a solution of methyl 3-(3-(4,4,5,5-tetramethyl-1,3,2-dioxaborolan-2-yl)propyl)picolinate (6.1 g, 4.0 mmol) in EtOH (10 mL) and HOAc (20 mL) at 10° C. The solution was degassed with hydrogen three times, and was stirred under 4.5 MPa of hydrogen at 50° C. for 48 h. The mixture was concentrated under reduced pressure and the resulting residue was dissolved in EtOAc, and neutralized to pH 7 by TEA, and the resulting mixture was filtered and concentrated under reduced pressure to give crude methyl 3-(3-(4,4,5,5-tetramethyl-1,3,2-dioxaborolan-2-yl)propyl)piperidinyl-2-carboxylate which was used in the next step without purification. LCMS (C$_{16}$H$_{31}$BNO$_4{}^+$)(ES, m/z): 312 [M+H]$^+$.

Step 4: 1-benzyl 2-methyl 3-(3-(4,4,5,5-tetramethyl-1,3,2-dioxaborolan-2-yl)propyl)piperidinyl-1,2-dicarboxylate

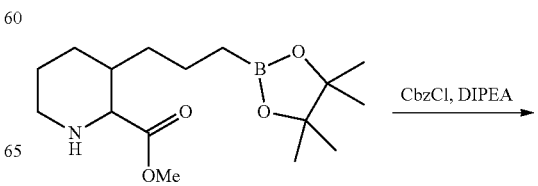

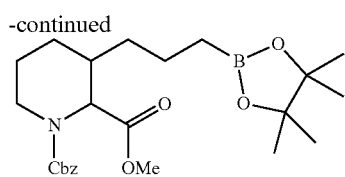

Ethyldiisopropylamine (5.3 mL, 32 mmol) was added to a solution of methyl 3-(3-(4,4,5,5-tetramethyl-1,3,2-dioxaborolan-2-yl)propyl)piperidinyl-2-carboxylate (5.0 g, 16 mmol) in DCM (30 mL) followed by dropwise addition of benzyl chloroformate (2.487 mL, 17.67 mmol) under nitrogen atmosphere at 0° C. The mixture was stirred at 20° C. for 16 h then concentrated under reduced pressure. The resulting residue was purified by silica gel column chromatography (EtOAc in hexanes) to give 1-benzyl 2-methyl 3-(3-(4,4,5,5-tetramethyl-1,3,2-dioxaborolan-2-yl)propyl)piperidinyl-1,2-dicarboxylate. LCMS ($C_{24}H_{37}BNO_6^+$)(ES, m/z): 446 [M+H]$^+$.

Step 5: 1-benzyl 2-methyl 3-(3-(4,4,5,5-tetramethyl-1,3,2-dioxaborolan-2-yl)propyl)piperidinyl-1,2-dicarboxylate

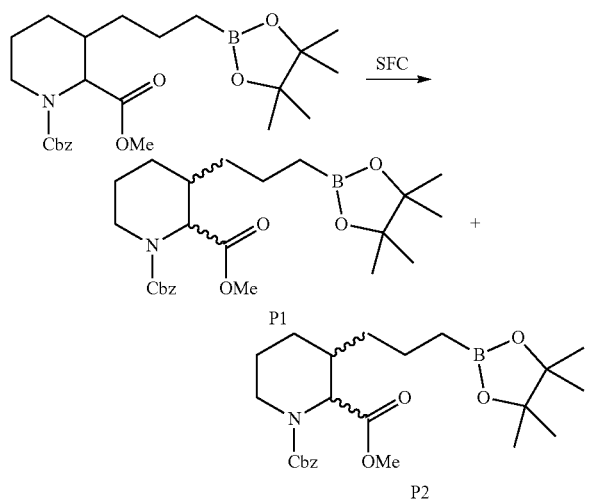

1-benzyl 2-methyl 3-(3-(4,4,5,5-tetramethyl-1,3,2-dioxaborolan-2-yl)propyl)piperidinyl-1,2-dicarboxylate (1.5 g, 3.4 mmol) was resolved by Chiral-SFC [Column: OD (250 mm*50 mm, 10 μm), Mobile phase: A: CO$_2$, B: IPA (0.1% NH$_3$.H$_2$O), Gradient: 15% of B in 3.5 min, and hold 15% for 1 min, Flow Rate (mL/min) 180, Column temperature: 40° C.] to give 1-benzyl 2-methyl 3-(3-(4,4,5,5-tetramethyl-1,3, 2-dioxaborolan-2-yl)propyl)piperidinyl-1,2-dicarboxylate (P1, t$_r$=2.736 min) as the first eluting peak, and 1-benzyl 2-methyl 3-(3-(4,4,5,5-tetramethyl-1,3,2-dioxaborolan-2-yl) propyl)piperidinyl-1,2-dicarboxylate (P2, t$_r$=2.985 min) as the second eluting peak. P1 LCMS ($C_{24}H_{37}BNO_6^+$)(ES, m/z): 446 [M+H]$^+$. $^1$H NMR (400 MHz, CDCl$_3$) δ 7.41-7.28 (m, 5H), 5.27-5.05 (m, 2H), 4.94-4.70 (m, 1H), 4.09-3.91 (m, 1H), 3.76-3.56 (m, 3H), 3.42-3.15 (m, 1H), 1.70-1.62 (m, 3H), 1.48 (m, 4H), 1.40-1.30 (m, 1H), 1.23 (br s, 13H), 0.81 0.72 (m, 2H). P2 LCMS ($C_{24}H_{37}BNO_6^+$)(ES, m/z): 446 [M+H]$^+$. $^1$H NMR (400 MHz, CDCl$_3$) δ 7.42-7.28 (m, 5H), 5.26-5.03 (m, 2H), 4.94-4.72 (m, 1H), 4.09-3.93 (m, 1H), 3.71-3.60 (m, 3H), 3.40-3.15 (m, 1H), 1.79-1.64 (m, 3H), 1.48 (m, 4H), 1.40-1.29 (m, 1H), 1.23 (br s, 13H), 0.83 0.70 (m, 2H).

Step 6: (2R,3S)-3-[3-(dihydroxyboranyl)propyl] piperidinyl-2-carboxylic acid

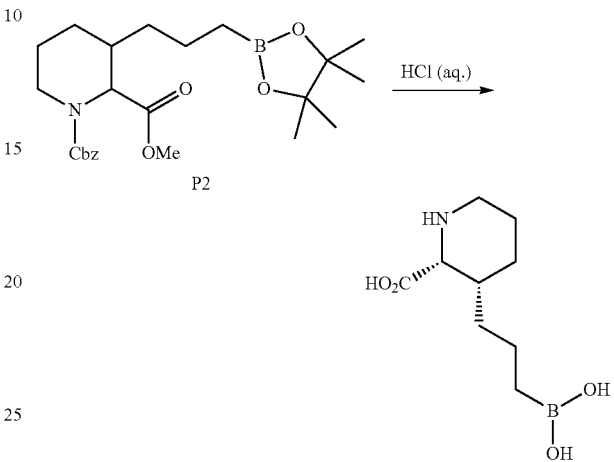

Example 1A

12 N HCl in water (2.5 mL) was added to a stirred suspension of 1-benzyl 2-methyl 3-(3-(4,4,5,5-tetramethyl-1,3,2-dioxaborolan-2-yl)propyl)piperidinyl-1,2-dicarboxylate (P2, 425 mg, 0.95 mmol) in water (2.5 mL) in one portion at room temperature. The reaction mixture was heated to 80° C. with stirring overnight, and then cooled to room temperature. The mixture was diluted with water, filtered through a 0.2 μm filter and lyophilized to afford (2R,3S)-3-[3-(dihydroxyboranyl)propyl]piperidinyl-2-carboxylic acid as an HCl salt. LCMS ($C_9H_{17}BNO_3^+$) (ES, m/z): 198 [M–H$_2$O+H]$^+$. $^1$H NMR (500 MHz, D$_2$O) δ 4.07 (d, J=3.8 Hz, 1H), 3.41 (d, J=12.5 Hz, 1H), 2.99 (td, J=12.5, 3.8 Hz, 1H), 2.41-2.33 (m, 1H), 1.91 (d, J=12.5 Hz, 1H), 1.81-1.60 (m, 3H), 1.58-1.42 (m, 2H), 1.39-1.26 (m, 1H), 1.21-1.10 (m, 1H), 0.86-0.68 (m, 2H).

Example 1B: (2S,3R)-3-[3-(dihydroxyboranyl)propyl]piperidinyl-2-carboxylic acid

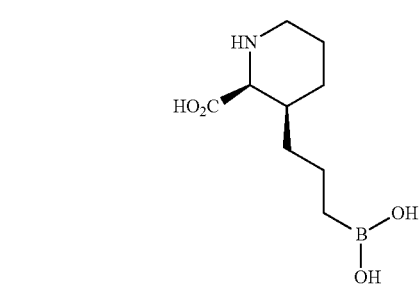

Example 1B was made from P1 from the previous example using the same procedure. LCMS ($C_9H_{17}BNO_3^+$) (ES, m/z): 198 [M–H$_2$O+H]$^+$.

Example 1C: (2R,3R)-3-[3-(dihydroxyborany)propyl]piperidinyl-2-carboxylic acid

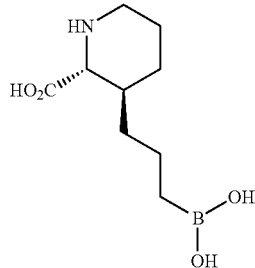 [SMILES: O=C(O)[C@@H]1NCCC[C@H]1CCCB(O)O]

Step 1: 1-benzyl 2-methyl 3-(3-(4,4,5,5-tetramethyl-1,3,2-dioxaborolan-2-yl)propyl)piperidinyl-1,2-dicarboxylate

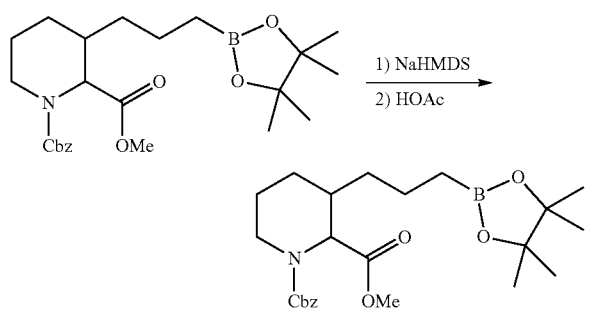

Sodium bis(trimethylsilyl)amide (2.5 mL, 2.5 mmol, 1.0 M in THF) was added dropwise to a solution of 1-benzyl 2-methyl 3-(3-(4,4,5,5-tetramethyl-1,3,2-dioxaborolan-2-yl)propyl)piperidinyl-1,2-dicarboxylate (500 mg, 1.1 mmol, 2,3-cis isomer) in dry THE (3 mL) at −40° C. under nitrogen. The reaction mixture was stirred for 30 min at −40° C. then warmed to 0° C. and stirred for 1 h. The mixture was quenched with acetic acid (0.3 mL) at −40° C., dried over $Na_2SO_4$, filtered and evaporated to dryness under reduced pressure. The resulting residue was purified by silica gel column chromatography (EtOAc in hexanes) to give 1-benzyl 2-methyl 3-(3-(4,4,5,5-tetramethyl-1,3,2-dioxaborolan-2-yl)propyl)piperidinyl-1,2-dicarboxylate. LCMS ($C_{24}H_{37}BNO_6^+$)(ES, m/z): 446 [M+H]$^+$.

Step 2: 1-benzyl 2-methyl 3-(3-(4,4,5,5-tetramethyl-1,3,2-dioxaborolan-2-yl)propyl)piperidinyl-1,2-dicarboxylate (2,3-trans) Q1 and Q2

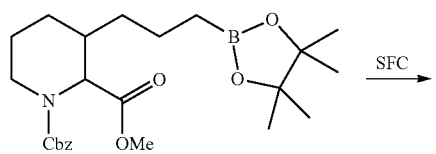

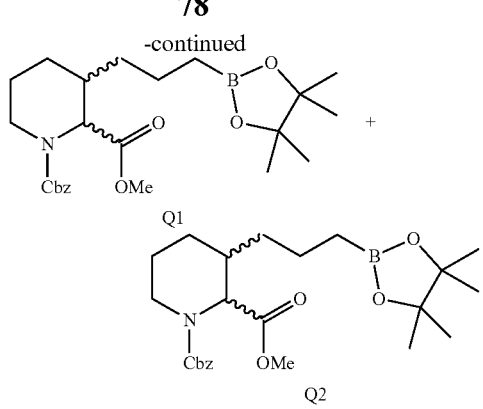

1-Benzyl 2-methyl 3-(3-(4,4,5,5-tetramethyl-1,3,2-dioxaborolan-2-yl)propyl)piperidinyl-1,2-dicarboxylate (450 mg, 1.0 mmol, 2,3-trans isomer) was resolved by Chiral-SFC [Column: Lux Cellulose-2 250 mm*30 mm, 10 μm, Mobile phase: A: $CO_2$, B: IPA (0.1% $NH_3.H_2O$), Gradient: 20% of B in 4.2 min and hold 20% for 1 min, Flow Rate (mL/min) 60, Column temperature: 40° C.] to give 1-benzyl 2-methyl 3-(3-(4,4,5,5-tetramethyl-1,3,2-dioxaborolan-2-yl)propyl) piperidinyl-1,2-dicarboxylate (Q1, $t_r$=1.958 min) as the first eluting peak, and 1-benzyl 2-methyl 3-(3-(4,4,5,5-tetramethyl-1,3,2-dioxaborolan-2-yl)propyl)piperidinyl-1,2-dicarboxylate (Q2, $t_r$=2.855 min) as the second eluting peak. Q1 LCMS ($C_{24}H_{37}BNO_6^+$)(ES, m/z): 446 [M+H]$^+$. $^1$H NMR (400 MHz, CDCl$_3$) δ 7.41-7.27 (m, 5H), 5.14 (m, 2H), 4.83-4.65 (m, 1H), 4.19-3.95 (m, 1H), 3.70 (m, 3H), 3.16-2.87 (m, 1H), 2.27 (m, 1H), 1.71-1.62 (m, 1H), 1.56 (m, 1H), 1.50-1.36 (m, 6H), 1.27-1.19 (m, 12H), 0.77 (m, 2H). Q2 LCMS ($C_{24}H_{37}BNO_6^+$) (ES, m/z): 446 [M+H]$^+$. $^1$H NMR (400 MHz, CDCl$_3$) δ 7.46-7.28 (m, 5H), 5.14 (m, 2H), 4.80-4.58 (m, 1H), 4.22-3.95 (m, 1H), 3.70 (m, 3H), 3.22-2.83 (m, 1H), 2.45-2.16 (m, 1H), 1.77-1.62 (m, 1H), 1.58-1.53 (m, 1H), 1.50-1.37 (m, 6H), 1.23 (s, 12H), 0.78 (m, 2H).

Step 3: (2R,3R)-3-[3-(dihydroxyboranyl)propyl]piperidinyl-2-carboxylic acid

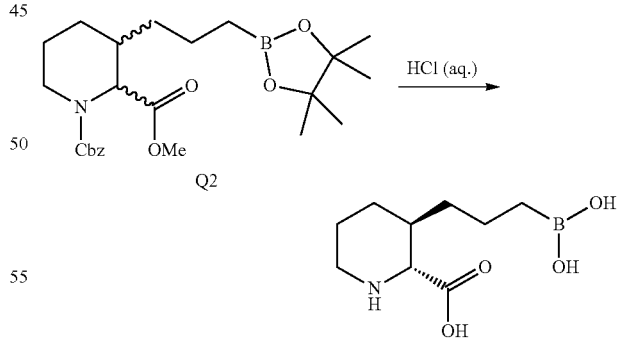

Example 1C

A solution of 1-benzyl 2-methyl 3-(3-(4,4,5,5-tetramethyl-1,3,2-dioxaborolan-2-yl)propyl)piperidinyl-1,2-dicarboxylate (120 mg, 0.27 mmol) in 12 N HCl in water (8.0 mL) was stirred at 90° C. for 3 h. The mixture was washed with EtOAc, and the aqueous phase was concentrated under reduced pressure to give the (2R,3R)-3-[3-(dihydroxyboranyl)propyl]piperidinyl-2-carboxylic acid as an HCl salt.

LCMS ($C_9H_{19}BNO_4^+$) (ES, m/z): 216 [M+H]$^+$. $^1$H NMR (400 MHz, CD$_3$OD) δ 3.59-3.54 (m, 1H), 3.35-3.32 (m, 1H), 3.04-2.97 (m, 1H), 2.03-1.99 (m, 1H), 1.92-1.89 (m, 1H), 1.82-1.76 (m, 2H), 1.66-1.49 (m, 2H), 1.42-1.27 (m, 1H), 1.39-1.27 (m, 2H), 0.77-0.69 (m, 2H).

Example 1D: (2S,3S)-3-[3-(dihydroxyboranyl)propyl]piperidinyl-2-carboxylic acid

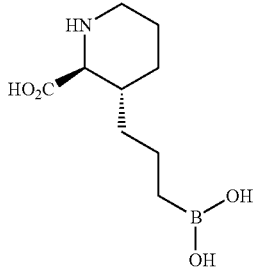

Example 1D was made from Q1 using the same procedure. LCMS ($C_9H_{19}BNO_4^+$)(ES, m/z): 216 [M+H]$^+$. Additionally, Example 1 was also made from 1-benzyl 2-methyl 3-(3-(4,4,5,5-tetramethyl-1,3,2-dioxaborolan-2-yl)propyl)piperidinyl-1,2-dicarboxylate using the same procedure.

Example 2: 3-[3-(dihydroxyboranyl)propyl]-2-[2-(piperidin-1-yl)ethyl]piperidinyl-2-carboxylic acid

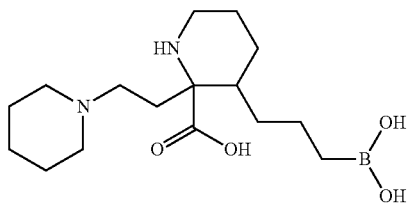 [SMILES: O=C(O)C1(CCN2CCCCC2)NCCCC1CCCB(O)O]

Step 1: 1-(tert-butyl) 2-methyl 3-(3-(4,4,5,5-tetramethyl-1,3,2-dioxaborolan-2-yl)propyl)piperidinyl-1,2-dicarboxylate

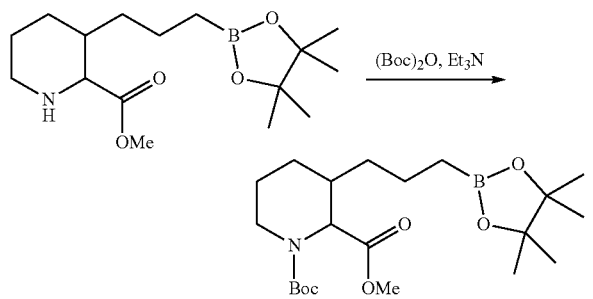

Di-tert-butyl dicarbonate (2.62 g, 12 mmol) and triethylamine (1.65 mL, 12 mmol) were added to a solution of methyl 3-(3-(4,4,5,5-tetramethyl-1,3,2-dioxaborolan-2-yl)propyl)piperidinyl-2-carboxylate (5.3 g, 17 mmol) in DCM (20 mL). The mixture was stirred at 15° C. for 1 h then directly purified by silica gel column chromatography (EtOAc in hexanes) to give 1-(tert-butyl) 2-methyl 3-(3-(4,4,5,5-tetramethyl-1,3,2-dioxaborolan-2-yl)propyl)piperidinyl-1,2-dicarboxylate. LCMS ($C_{21}H_{39}BNO_6^+$)(ES, m/z): 412 [M+H]$^+$.

Step 2: 1-(tert-butyl) 2-methyl 2-allyl-3-(3-(4,4,5,5-tetramethyl-1,3,2-dioxaborolan-2-yl)propyl)piperidinyl-1,2-dicarboxylate

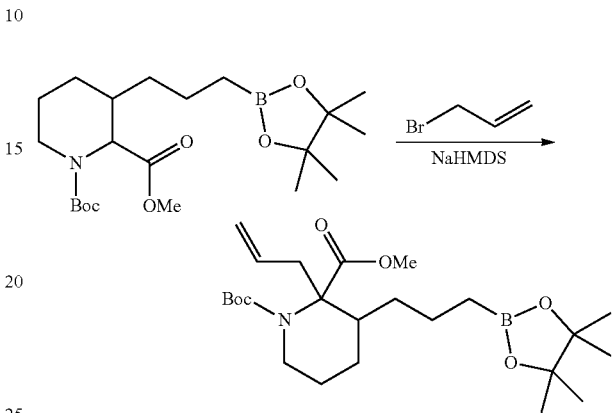

Sodium bis(trimethylsilyl)amide (1.0 M in THF, 3.2 mL, 3.2 mmol) was added dropwise over 2 min to the stirred solution of 1-tert-butyl 2-methyl 3-(3-(4,4,5,5-tetramethyl-1,3,2-dioxaborolan-2-yl)propyl)piperidinyl-1,2-dicarboxylate (600 mg, 1.5 mmol) in THF (6.0 mL) at −78° C. The reaction mixture was allowed to warm to −30° C. and stirred for 0.5 h. The solution was warmed to 0° C. and stirred for 2 h, followed by dropwise addition of 3-bromoprop-1-ene (1.9 mL, 22 mmol) at −40° C. After stirring for an additional 1 h at −40° C., the reaction mixture was slowly warmed to 50° C. and stirred for 12 h. The mixture was quenched by acetic acid (0.4 mL), and concentrated under reduced pressure. The resulting residue was directly purified by silica gel column chromatography (EtOAc in hexanes) to give the 1-tert-butyl 2-methyl 2-allyl-3-(3-(4,4,5,5-tetramethyl-1,3,2-dioxaborolan-2-yl)propyl)piperidinyl-1,2-dicarboxylate. LCMS ($C_{24}H_{43}BNO_7^+$)(ES, m/z): 452 [M+H]$^+$.

Step 3: 1-(tert-butyl) 2-methyl 2-(2-oxoethyl)-3-(3-(4,4,5,5-tetramethyl-1,3,2-dioxaborolan-2-yl)propyl)piperidinyl-1,2-dicarboxylate

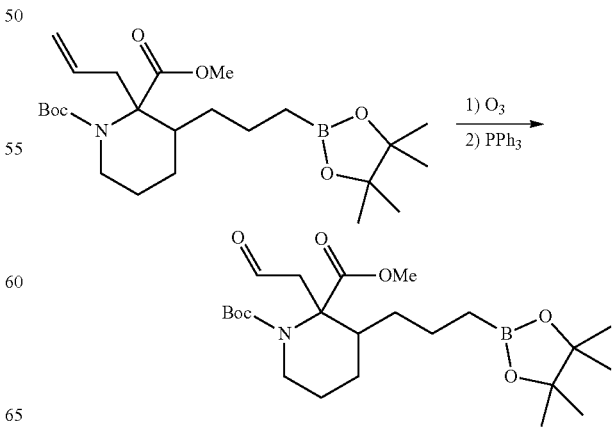

A solution of 1-tert-butyl 2-methyl 2-allyl-3-(3-(4,4,5,5-tetramethyl-1,3,2-dioxaborolan-2-yl)propyl)piperidinyl-1,2-dicarboxylate (445 mg, 0.99 mmol) in DCM (20 mL) was bubbled with ozone at −78° C. until the solution turned blue, and then bubbled with oxygen until solution became colorless. Triphenylphosphine (776 mg, 3.0 mmol) was added and the mixture was stirred at 10° C. for 1.5 h. The mixture was directly purified by silica gel column chromatography (EtOAc in hexanes) to give 1-tert-butyl 2-methyl 2-(2-oxoethyl)-3-(3-(4,4,5,5-tetramethyl-1,3,2-dioxaborolan-2-yl)propyl)piperidinyl-1,2-dicarboxylate. LCMS ($C_{23}H_{41}BNO_7^+$)(ES, m/z): 454 [M+H]$^+$.

Step 4: 1-(tert-butyl) 2-methyl 2-(2-(piperidin-1-yl)ethyl)-3-(3-(4,4,5,5-tetramethyl-1,3,2-dioxaborolan-2-yl)propyl)piperidinyl-1,2-dicarboxylate

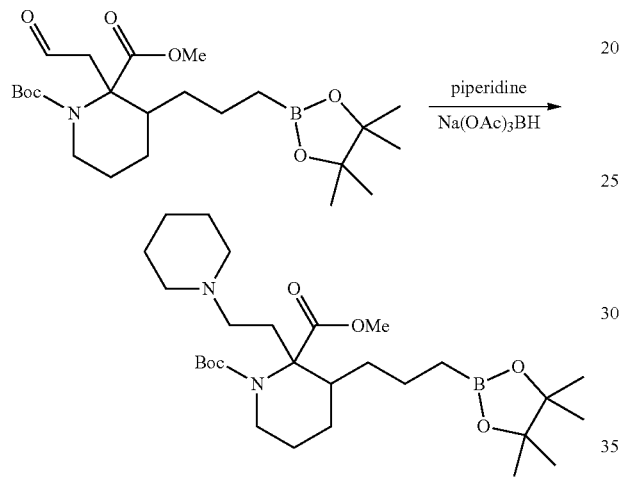

Sodium triacetoxyborohydride (348 mg, 1.6 mmol) was added to a solution of 1-tert-butyl 2-methyl 2-(2-oxoethyl)-3-(3-(4,4,5,5-tetramethyl-1,3,2-dioxaborolan-2-yl)propyl) piperidinyl-1,2-dicarboxylate (298 mg, 0.66 mmol) and piperidinyl (224 mg, 2.6 mmol) in 1,2-dichloroethane (5.0 mL). The reaction mixture was stirred at 15° C. for 12 h under nitrogen then quenched with water and diluted with DCM. The organic layer was dried over anhydrous $Na_2SO_4$, filtered and concentrated under reduced pressure. The resulting residue was purified by RP-HPLC [C18 column, water (10 mM $NH_4HCO_3$)—$CH_3CN$] to give 1-tert-butyl 2-methyl 2-(2-(piperidin-1-yl)ethyl)-3-(3-(4,4,5,5-tetramethyl-1,3,2-dioxaborolan-2-yl)propyl)piperidinyl-1,2-dicarboxylate. LCMS ($C_{28}H_{52}BN_2O_6^+$)(ES, m/z): 523 [M+H]$^+$.

Step 5: 3-[3-(dihydroxyboranyl)propyl]-2-[2-(piperidin-1-yl)ethyl]piperidinyl-2-carboxylic acid

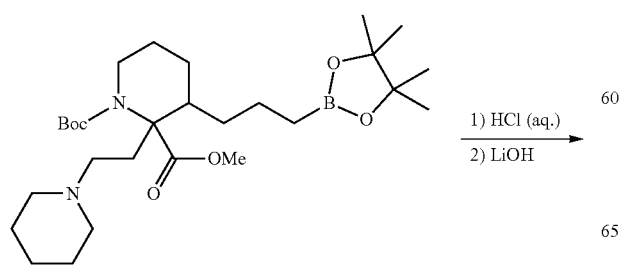

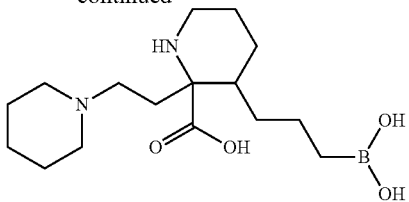

Example 2

1-(tert-butyl) 2-methyl 2-(2-(piperidin-1-yl)ethyl)-3-(3-(4,4,5,5-tetramethyl-1,3,2-dioxaborolan-2-yl)propyl)piperidinyl-1,2-dicarboxylate (40 mg, 0.077 mmol) was dissolved in 12 N HCl in water (8.0 mL). The reaction mixture was stirred at 120° C. for 4 h then concentrated under reduced pressure. The resulting residue was dissolved in water (1.0 mL) and MeOH (5.0 mL), followed by addition of lithium hydroxide (9.2 mg, 0.38 mmol) at 10° C. under nitrogen. The mixture was stirred at 50° C. for 14 h, then concentrated under reduced pressure. The resulting residue was purified by RP-HPLC [C18 column, water (0.1% TFA)-$CH_3CN$] to give 3-[3-(dihydroxyboranyl)propyl]-2-[2-(piperidin-1-yl)ethyl]piperidinyl-2-carboxylic acid as a TFA salt. LCMS ($C_{16}H_{30}BN_2O_3^+$)(ES, m/z): 309 [M−H$_2$O+H]$^+$. $^1$H NMR (400 MHz, CD$_3$OD) δ 3.57-3.52 (m, 2H), 3.22-3.15 (m, 2H), 3.14-3.06 (m, 1H), 3.03-2.82 (m, 2H), 2.56-2.42 (m, 2H), 2.01-1.89 (m, 3H), 1.89-1.67 (m, 8H), 1.62-1.48 (m, 3H), 1.37-1.26 (m, 2H), 0.87-0.72 (m, 2H).

Example 3: 3-[2-(dihydroxyboranyl)ethoxy]piperidinyl-2-carboxylic acid

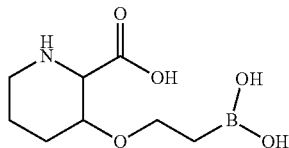 [SMILES: O=C(O)C1NCCCC1OCCB(O)O]

Step 1: methyl 3-(2-((tert-butyldimethylsilyl)oxy)ethoxy)picolinate

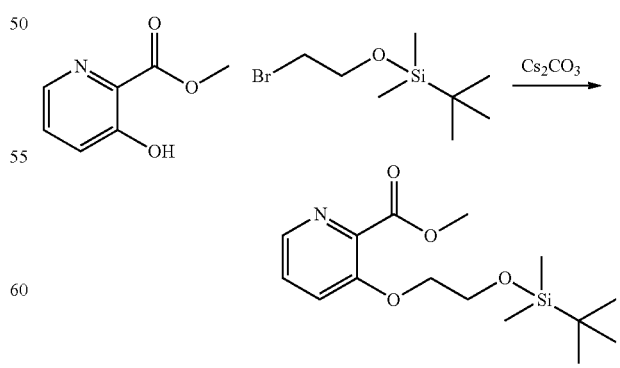

$Cs_2CO_3$ (16 g, 49 mmol) was added to a mixture of methyl 3-hydroxypicolinate (3.0 g, 20 mmol), (2-bromoethoxy)(tert-butyl)dimethylsilane (7.0 g, 29 mmol) in DMF (40 mL), and the reaction mixture was stirred at 50° C. for 6 h under nitrogen. The mixture was quenched with saturated aqueous NH₄Cl and extracted with EtOAc, and the combined organic phase was dried over anhydrous Na₂SO₄, filtered and concentrated in vacuo. The residue was purified by silica gel column chromatography (EtOAc in hexanes) to give methyl 3-(2-((tert-butyldimethylsilyl)oxy)ethoxy)picolinate. LCMS ($C_{15}H_{26}NO_4Si^+$)(ES, m/z): 312 [M+H]⁺.

Step 2: methyl 3-(2-hydroxyethoxy)piperidinyl-2-carboxylate

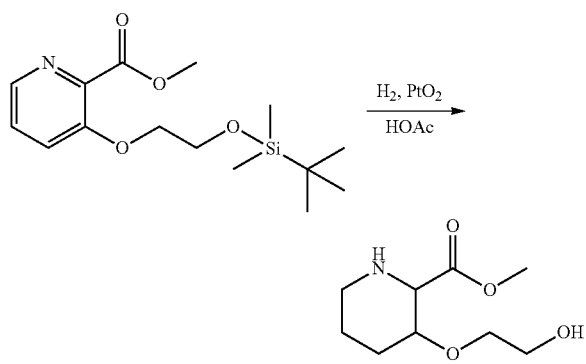

Acetic acid (30 mL, 21 mmol) and platinum(IV) oxide (1.5 g, 6.6 mmol) were added to a solution of methyl 3-(2-((tert-butyldimethylsilyl)oxy)ethoxy)picolinate (6.6 g, 21 mmol) in MeOH (20 mL) under nitrogen atmosphere, and the reaction mixture was degassed and backfilled with hydrogen (three times), then stirred under hydrogen (40 atm) at 50° C. for 72 h. The mixture was filtered and filtrate was concentrated under reduced pressure to give crude methyl 3-(2-hydroxyethoxy)piperidinyl-2-carboxylate, which was used in next step without further purification. ¹H NMR (400 MHz, CDCl₃) δ 4.14-3.99 (m, 1H), 3.77-3.82 (m, 3H), 3.59-3.73 (m, 5H), 2.90-2.87 (br s, 2H), 1.64-1.82 (m, 2H), 1.41-1.57 (m, 2H).

Step 3: 1-benzyl 2-methyl 3-(2-hydroxyethoxy)piperidinyl-1,2-dicarboxylate

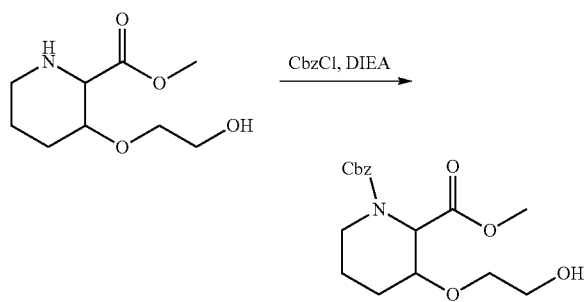

Ethyldiisopropylamine (13 mL, 74 mmol) was added to a solution of methyl 3-(2-hydroxyethoxy)piperidinyl-2-carboxylate (5.0 g, 25 mmol) in DCM (70 mL), followed by dropwise addition of benzyl chloroformate (4.2 mL, 30 mmol) under nitrogen atmosphere at 0° C., and the reaction mixture was stirred at 25° C. for 12 h. The mixture was diluted with water and extracted with DCM, and the combined organic layer was washed with brine, dried over anhydrous Na₂SO₄, filtered and concentrated in vacuo. The residue was purified by silica gel column chromatography (EtOAc in hexanes) to give 1-benzyl 2-methyl 3-(2-hydroxyethoxy)piperidinyl-1,2-dicarboxylate. LCMS ($C_7H_{24}NO_6^+$)(ES, m/z): 338 [M+H]⁺.

Step 4: 1-benzyl 2-methyl 3-(2-bromoethoxy)piperidinyl-1,2-dicarboxylate

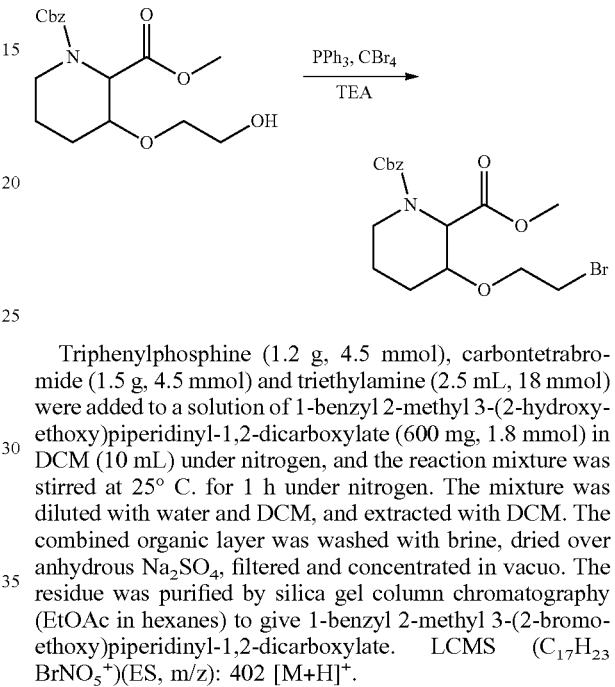

Triphenylphosphine (1.2 g, 4.5 mmol), carbontetrabromide (1.5 g, 4.5 mmol) and triethylamine (2.5 mL, 18 mmol) were added to a solution of 1-benzyl 2-methyl 3-(2-hydroxyethoxy)piperidinyl-1,2-dicarboxylate (600 mg, 1.8 mmol) in DCM (10 mL) under nitrogen, and the reaction mixture was stirred at 25° C. for 1 h under nitrogen. The mixture was diluted with water and DCM, and extracted with DCM. The combined organic layer was washed with brine, dried over anhydrous Na₂SO₄, filtered and concentrated in vacuo. The residue was purified by silica gel column chromatography (EtOAc in hexanes) to give 1-benzyl 2-methyl 3-(2-bromoethoxy)piperidinyl-1,2-dicarboxylate. LCMS ($C_{17}H_{23}BrNO_5^+$)(ES, m/z): 402 [M+H]⁺.

Step 5: 1-benzyl 2-methyl 3-(2-(4,4,5,5-tetramethyl-1,3,2-dioxaborolan-2-yl)ethoxy)piperidinyl-1,2-dicarboxylate

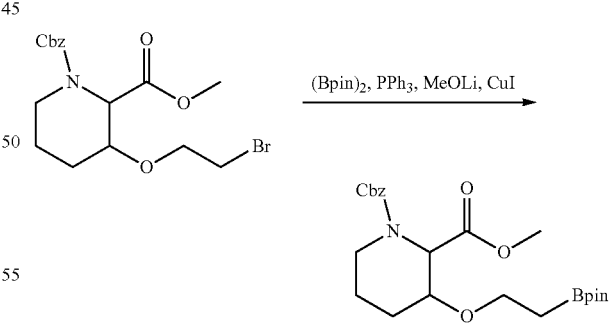

Lithium methanolate (110 mg, 2.9 mmol), copper(I) iodide (55 mg, 0.29 mmol) and triphenylphosphine (76 mg, 0.29 mmol) were added to a solution of 1-benzyl 2-methyl 3-(2-bromoethoxy)piperidinyl-1,2-dicarboxylate (580 mg, 1.4 mmol), and 4,4,4',4',5,5,5',5'-octamethyl-2,2'-bi(1,3,2-dioxaborolane)(736 mg, 2.9 mmol) in DMF (8.0 mL) at 25° C. under nitrogen, and the reaction mixture was stirred at 25° C. for 12 h under nitrogen. The mixture was quenched with water and extracted with EtOAc, and the combined organic layer was washed with brine, dried over anhydrous Na$_2$SO$_4$, filtered and concentrated in vacuo. The residue was purified by RP-HPLC [C18 column, water (0.10% TFA)-CH$_3$CN] to give 1-benzyl 2-methyl 3-(2-(4,4,5,5-tetramethyl-1,3,2-dioxaborolan-2-yl)ethoxy)piperidinyl-1,2-dicarboxylate. LCMS (C$_{23}$H$_{35}$BNO$_7^+$)(ES, m/z): 448 [M+H]$^+$.

Step 6: 3-[2-(dihydroxyboranyl)ethoxy]piperidinyl-2-carboxylic acid

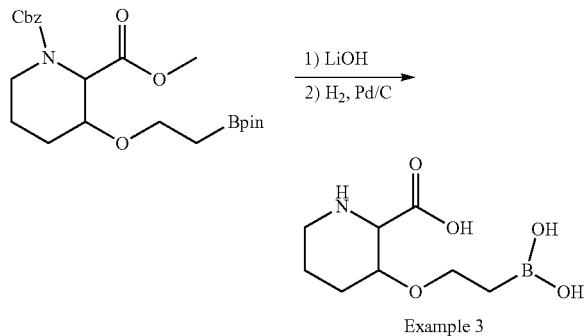

Example 3

Lithium hydroxide monohydrate (28 mg, 0.67 mmol) was added to a mixture of 1-benzyl 2-methyl 3-(2-(4,4,5,5-tetramethyl-1,3,2-dioxaborolan-2-yl)ethoxy)piperidinyl-1,2-dicarboxylate (100 mg, 0.22 mmol) in water (3.0 mL) and THF (3.0 mL) at 25° C., and the reaction mixture was stirred at 25° C. for 1 h. Then 10% palladium on carbon (15 mg, 0.014 mmol) was added, and the resulting mixture was degassed and backfilled with hydrogen (three times), and stirred under hydrogen (15 psi) at 25° C. for 2 h. The mixture was filtered and the filtrate was concentrated under reduced pressure. The residue was purified by RP-HPLC [C18 column, water (0.1% TFA)-CH$_3$CN] to give 3-[2-(dihydroxyboranyl)ethoxy]piperidinyl-2-carboxylic acid as a TFA salt. LCMS (CH$_{17}$BNO$_5^+$)(ES, m/z): 218 [M+H]$^+$. $^1$H NMR (400 MHz, D$_2$O) δ 4.15 (br s, 1H), 4.01-3.86 (m, 1H), 3.77-3.60 (m, 1H), 3.54-3.40 (m, 1H), 3.35 (br d, J=12.1 Hz, 1H), 3.00-2.88 (m, 1H), 2.15 (br d, J=12.8 Hz, 1H), 1.92-1.72 (m, 1H), 1.70-1.45 (m, 2H), 1.09-0.95 (m, 2H).

Example 4: 4-[2-(dihydroxyboranyl)ethyl]piperidinyl-2-carboxylic acid

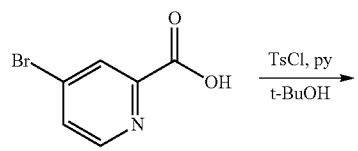

Step 1: tert-butyl 4-bromopicolinate

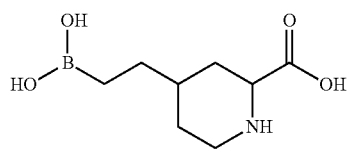 [SMILES: O=C(O)C1CC(CCB(O)O)CCN1]

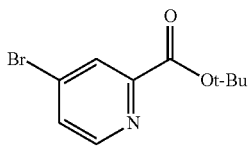

4-methylbenzene-1-sulfonyl chloride (11 g, 59 mmol) was added portion wise to a solution of 4-bromopicolinic acid (5.0 g, 25 mmol) and pyridine (10 mL, 124 mmol) in t-BuOH (tert-butyl alcohol)(50 mL) at 0° C. The reaction mixture was stirred at 0° C. for 16 h. The mixture was quenched with saturated aqueous NaHCO$_3$ and extracted with ethyl acetate. The combined organic phase was dried over anhydrous Na$_2$SO$_4$, filtered and concentrated under reduced pressure. The resulting residue was purified by silica gel column chromatography (EtOAc in hexanes) to afford tert-butyl 4-bromopicolinate. $^1$H NMR (400 MHz, CDCl$_3$) δ 8.55 (d, J=5.3 Hz, 1H), 8.19 (d, J=2.2 Hz, 1H), 7.61 (dd, J=2.0, 5.0 Hz, 1H), 1.64 (s, 9H).

Step 2: tert-butyl 4-vinylpicolinate

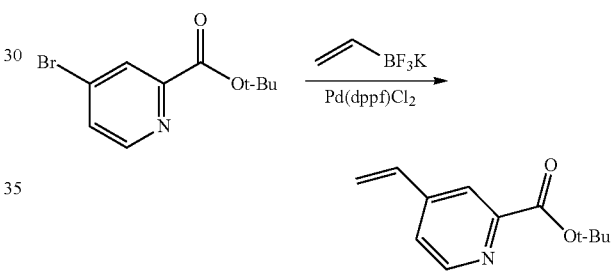

Potassium vinyltrifluoroborate (3.4 g, 25 mmol), [1,1'-Bis(diphenylphosphino)ferrocene]palladium(II)(0.92 g, 1.3 mmol) and K$_2$CO$_3$ (3.5 g, 25 mmol) were added to a solution of tert-butyl 4-bromopicolinate (3.3 g, 13 mmol) in 1,4-dioxane (40 mL) and water (8.0 mL). The resulting reaction mixture was stirred at 100° C. for 3 h under nitrogen. The mixture was diluted with water and extracted EtOAc. The combined organic layer was washed with brine, dried over anhydrous Na$_2$SO$_4$, filtered and concentrated under reduced pressure. The residue was purified by silica gel column chromatography (EtOAc in hexanes) to give tert-butyl 4-vinylpicolinate. LCMS (C$_{12}$H$_{16}$NO$_2^+$)(ES, m/z): 206 [M+H]$^+$.

Step 3: tert-butyl 4-(2-(4,4,5,5-tetramethyl-1,3,2-dioxaborolan-2-yl)ethyl)picolinate

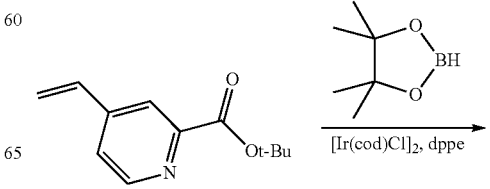

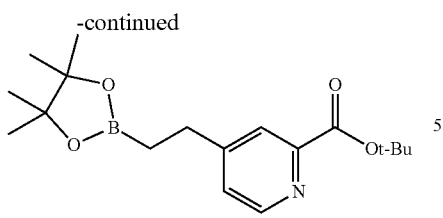

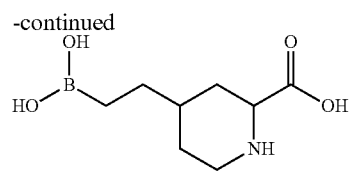

Example 4

A solution of 4,4,5,5-tetramethyl-1,3,2-dioxaborolane (7.4 mL, 51 mmol), chloro(1,5-cyclooctadiene)iridium(I) dimer (0.34 g, 0.51 mmol) and 1,2-bis(diphenylphosphino) ethane (0.29 g, 0.72 mmol) in anhydrous DCM (40 mL) was bubbled with a stream of nitrogen for 3 minutes. The resulting mixture was stirred at 12° C. for 20 minutes, followed by addition of tert-butyl 4-vinylpicolinate (2.1 g, 10 mmol). The reaction mixture was stirred at 12° C. for 16 h under nitrogen, then quenched with water and extracted with DCM. The combined organic layer was dried over anhydrous Na$_2$SO$_4$, filtered and concentrated under reduced pressure. The resulting residue was purified by silica gel column chromatography (EtOAc in hexanes) to give the tert-butyl 4-(2-(4,4,5,5-tetramethyl-1,3,2-dioxaborolan-2-yl)ethyl)picolinate. LCMS (C$_{18}$H$_{29}$BNO$_4{}^+$)(ES, m/z): 334 [M+H]$^+$.

A mixture of (2-(2-(tert-butoxycarbonyl)piperidin-4-yl)ethyl)boronic acid (40 mg, 0.16 mmol) and 1N HCl in water (1.0 mL, 1.0 mmol) was stirred at 100° C. for 12 h. The mixture was concentrated under reduced pressure to give 4-[2-(dihydroxyboranyl)ethyl]piperidinyl-2-carboxylic acid as an HCl salt. LCMS (C$_8$H$_{17}$BNO$_4{}^+$)(ES, m/z): 202 [M+H]$^+$. $^1$H NMR (400 MHz, CD$_3$OD) δ 3.92 (br d, J=12.3 Hz, 1H), 3.42 (br d, J=10.1 Hz, 1H), 3.06-2.95 (m, 1H), 2.37 (br d, J=13.6 Hz, 1H), 1.96 (br d, J=13.2 Hz, 1H), 1.63 (br s, 1H), 1.43-1.20 (m, 4H), 0.83 (br s, 2H).

Example 5: 4-[2-(dihydroxyboranyl)ethyl]-2-[2-(piperidin-1-yl)ethyl]piperidinyl-2-carboxylic acid Step 4 (2-(2-(tert-butoxycarbonyl)piperidin-4-v/ethyl)boronic acid

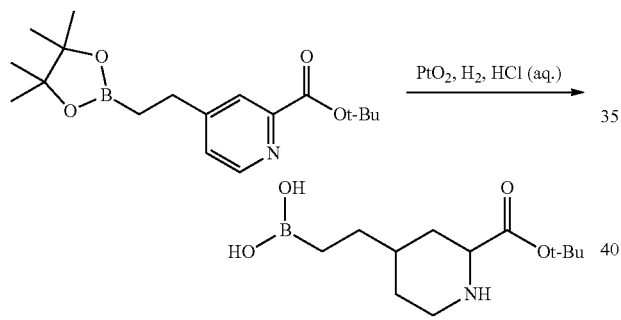

Platinum(IV) oxide (4.1 mg, 0.018 mmol) was added to a solution of tert-butyl 4-(2-(4,4,5,5-tetramethyl-1,3,2-dioxaborolan-2-yl)ethyl)picolinate (60 mg, 0.18 mmol) in EtOH (3.0 mL) and 2N HCl in water (2.0 mL, 4.0 mmol) at 10° C. The reaction mixture was degassed with hydrogen three times then stirred under 50 psi of hydrogen at 50° C. for 16 h. The mixture was filtered and concentrated under reduced pressure to give the crude (2-(2-(tert-butoxycarbonyl)piperidin-4-yl)ethyl)boronic acid which was used in the next step without purification. LCMS (C$_{12}$H$_{25}$BNO$_4{}^+$)(ES, m/z): 258 [M+H]$^+$.

Step 5: 4-[2-(dihydroxyboranyl)ethyl]piperidinyl-2-carboxylic acid

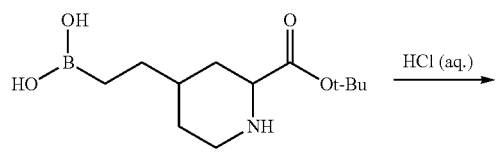

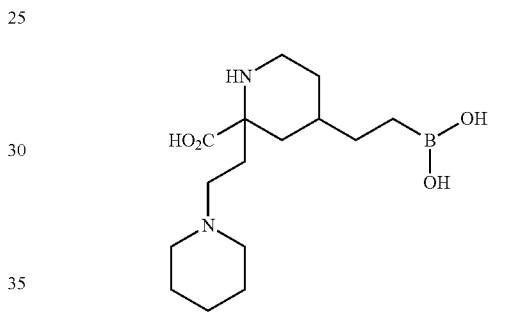

Step 1: di-tert-butyl 4-(2-(4,4,5,5-tetramethyl-1,3,2-dioxaborolan-2-yl)ethyl)piperidinyl-1,2-dicarboxylate

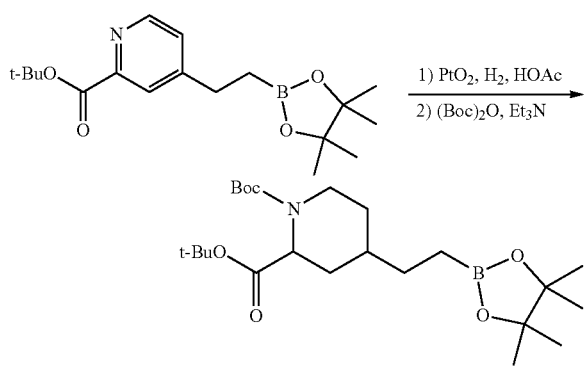

Platinum (IV) oxide (0.82 g, 3.6 mmol) was added to a solution of tert-butyl 4-(2-(4,4,5,5-tetramethyl-1,3,2-dioxaborolan-2-yl)ethyl)picolinate (3.0 g, 9.0 mmol) in EtOH (10 mL) and acetic acid (20 mL) at 10° C. The reaction mixture was degassed with hydrogen three times and stirred under 4.5 MPa of hydrogen at 50° C. for 48 h. The mixture was concentrated under reduced pressure. The resulting residue was dissolved in EtOAc and neutralized to pH 7 by triethylamine, then filtered and concentrated under reduced pressure. The crude residue was dissolved in DCM (20 mL), followed by addition of di-tert-butyl dicarbonate (3.924 g, 18 mmol) and triethylamine (3.8 mL, 27 mmol), and the reaction mixture was stirred at 15° C. for 1 h. The mixture was directly purified by silica gel column chromatography (EtOAc in hexanes) to give di-tert-butyl 4-(2-(4,4,5,5-tetramethyl-1,3,2-dioxaborolan-2-yl)ethyl)piperidinyl-1,2-dicarboxylate. LCMS ($C_{23}H_{43}BNO_6^+$)(ES, m/z): 440 [M+H]$^+$.

Step 2: di-tert-butyl 2-allyl-4-(2-(4,4,5,5-tetramethyl-1,3,2-dioxaborolan-2-yl)ethyl)piperidinyl-1,2-dicarboxylate

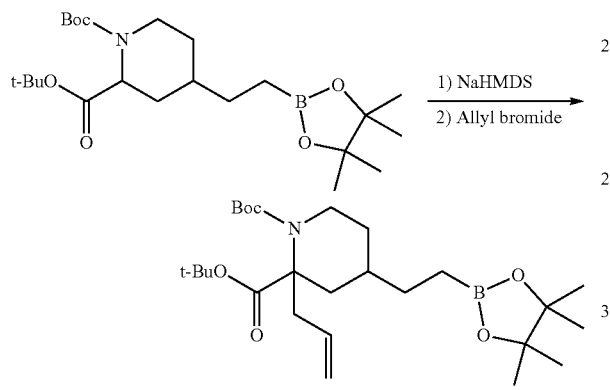

Sodium bis(trimethylsilyl)amide (1.0 M in THF, 1.4 mL, 1.4 mmol) was added dropwise to a stirred solution of di-tert-butyl 4-(2-(4,4,5,5-tetramethyl-1,3,2-dioxaborolan-2-yl)ethyl)piperidinyl-1,2-dicarboxylate (300 mg, 0.68 mmol) in THF (3.0 mL) over 2 min at −30° C. under nitrogen. The resulting mixture was stirred for 1 h at 0° C., followed by dropwise addition of 3-bromoprop-1-ene (0.89 mL, 10 mmol) at −40° C. The reaction mixture was stirred for an additional 1 h at −40° C., then slowly warmed to 20° C. and stirred for 2 h, followed by another 16 h at 50° C. The mixture was quenched with acetic acid (0.2 mL) and concentrated under reduced pressure. The resulting residue was purified by silica gel column chromatography (EtOAc in hexanes) to give di-tert-butyl 2-allyl-4-(2-(4,4,5,5-tetramethyl-1,3,2-dioxaborolan-2-yl)ethyl)piperidinyl-1,2-dicarboxylate. LCMS ($C_{26}H_{47}BNO_6^+$)(ES, m/z): 480 [M+H]$^+$.

Step 3: di-tert-butyl 2-(2-oxoethyl)-4-(2-(4,4,5,5-tetramethyl-1,3,2-dioxaborolan-2-yl)ethyl)piperidinyl-1,2-dicarboxylate

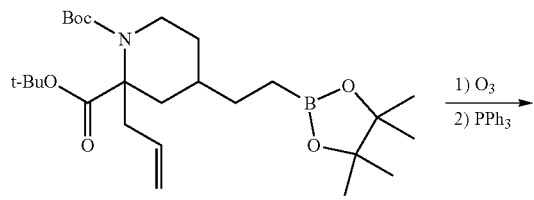

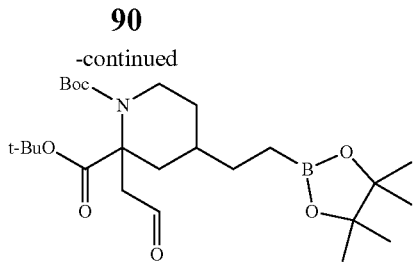

A mixture of di-tert-butyl 2-allyl-4-(2-(4,4,5,5-tetramethyl-1,3,2-dioxaborolan-2-yl)ethyl)piperidinyl-1,2-dicarboxylate (105 mg, 0.22 mmol) in dry DCM (10 mL) was bubbled with O$_3$ at −78° C. until the solution became blue, and then bubbled with O$_2$ until solution became colorless, followed by addition of triphenylphosphine (115 mg, 0.44 mmol). The resulting mixture was stirred at 15° C. for 5 h. The mixture was directly purified by silica gel column chromatography (EtOAc in hexanes) to give di-tert-butyl 2-(2-oxoethyl)-4-(2-(4,4,5,5-tetramethyl-1,3,2-dioxaborolan-2-yl)ethyl)piperidinyl-1,2-dicarboxylate. LCMS ($C_{25}H_{44}BNO_7Na^+$)(ES, m/z): 504 [M+Na]$^+$.

Step 4: di-tert-butyl 2-(2-(piperidin-1-yl)ethyl)-4-(2-(4,4,5,5-tetramethyl-1,3,2-dioxaborolan-2-yl)ethyl)piperidinyl-1,2-dicarboxylate

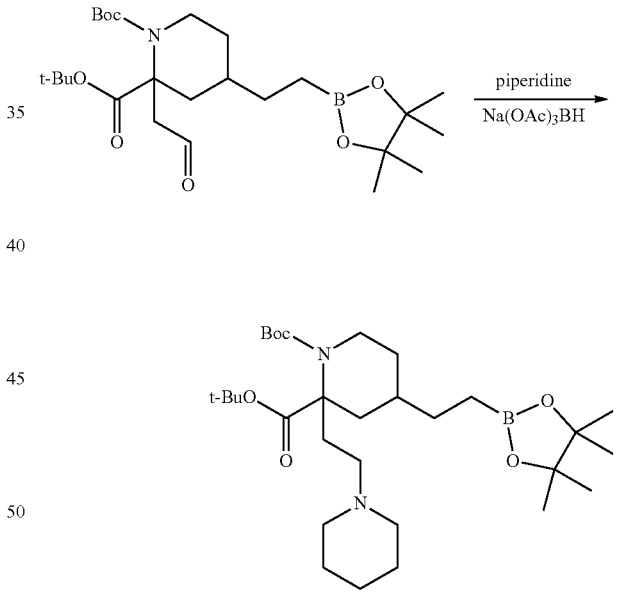

Sodium triacetoxyborohydride (137 mg, 0.65 mmol) was added to a solution of 1-tert-butyl 2-methyl 2-(2-oxoethyl)-4-(2-(4,4,5,5-tetramethyl-1,3,2-dioxaborolan-2-yl)ethyl)piperidinyl-1,2-dicarboxylate (95 mg, 0.22 mmol) and piperidine (55 mg, 0.65 mmol) in 1,2-dichloroethane (2.0 mL), and the reaction mixture was stirred at 15° C. for 12 h under nitrogen. The mixture was directly purified by RP-HPLC [C18 column, water (10 mM NH$_4$HCO$_3$)—CH$_3$CN] to give 1-tert-butyl 2-methyl 2-(2-(piperidin-1-yl)ethyl)-4-(2-(4,4,5,5-tetramethyl-1,3,2-dioxaborolan-2-yl)ethyl)piperidinyl-1,2-dicarboxylate. LCMS ($C_{30}H_{56}BN_2O_6^+$)(ES, m/z): 551 [M+H]$^+$.

Step 5: 4-[2(dihydroxyboranyl)ethyl]-2-[2-(piperidin-1-yl)ethyl]piperidinyl-2-carboxylic acid

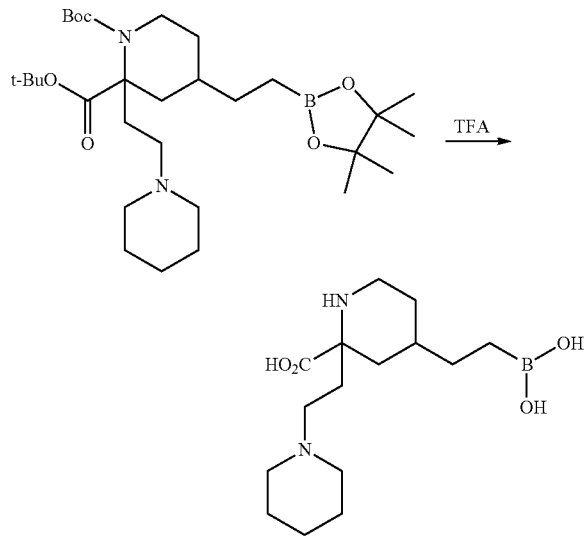

Example 5

Di-tert-butyl 2-(2-(piperidin-1-yl)ethyl)-4-(2-(4,4,5,5-tetramethyl-1,3,2-dioxaborolan-2-yl)ethyl)piperidinyl-1,2-dicarboxylate (65 mg, 0.12 mmol) was dissolved in TFA (5.0 mL) and water (1.0 mL), and the reaction mixture was stirred at 90° C. for 4 h. The mixture was concentrated under reduced pressure and the resulting residue was purified by RP-HPLC [C18 column, water (0.1% TFA)-CH$_3$CN] to give 4-[2-(dihydroxyboranyl)ethyl]-2-[2-(piperidin-1-yl)ethyl]piperidinyl-2-carboxylic acid as a TFA salt. LCMS (C$_{15}$H$_{30}$BN$_2$O$_4$$^+$)(ES, m/z): 313 [M+H]$^+$. $^1$H NMR (400 MHz, CD$_3$OD) δ 3.54 (m, 2H), 3.42-3.33 (m, 1H), 3.28-3.07 (m, 3H), 2.94 (br s, 2H), 2.49-2.44 (m, 1H), 2.35-2.14 (m, 2H), 1.93-1.75 (m, 7H), 1.56-1.42 (m, 2H), 1.41-1.35 (m, 2H), 1.1.31-1.27 (m, 1H), 0.80 (br s, 2H).

Example 6: 4-[3-(dihydroxyboranyl)propyl]piperidinyl-3-carboxylic acid

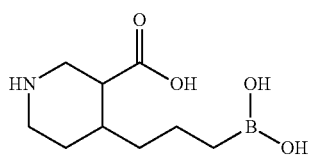 [SMILES: O=C(O)C1CNCCC1CCCB(O)O]

Step 1: methyl 4-allylnicotinate

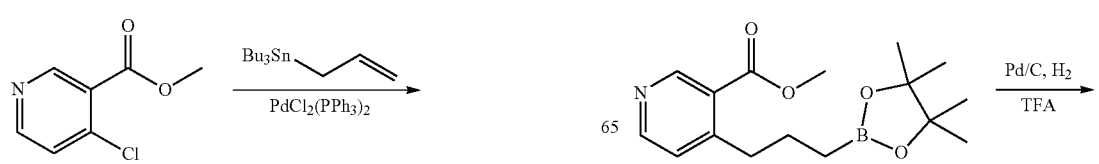

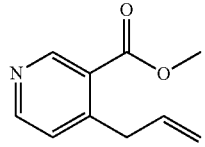

Allyltributylstannane (17 mL, 53 mmol) and dichlorobis(triphenylphosphine)palladium (II)(1.6 g, 2.3 mmol) were added to a mixture of methyl 4-chloronicotinate (3.9 g, 23 mmol) in DMF (30 mL) under nitrogen, the reaction mixture was degassed three times under nitrogen, and stirred at 130° C. for 10 h under nitrogen. The mixture was quenched with saturated aqueous potassium fluoride, filtered and concentrated in vacuo. The crude mixture was diluted with EtOAc and brine, and the separated organic phase was dried over Na$_2$SO$_4$, filtered and concentrated in vacuo. The residue was purified by silica gel column chromatography (EtOAc in hexanes) to give methyl 4-allylnicotinate. LCMS (C$_{10}$H$_{12}$NO$_2$$^+$)(ES, m/z): 178 [M+H]$^+$.

Step 2: methyl 4-(3-(4,4,5,5-tetramethyl-1,3,2-dioxaborolan-2-yl)propyl)nicotinate

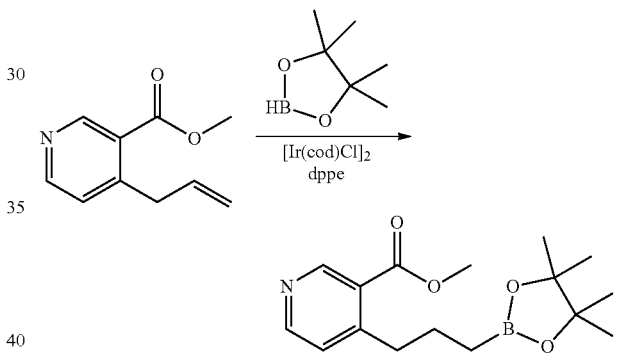

1,2-Bis(diphenylphosphino)ethane (427 mg, 1.1 mmol), chloro(1,5-cyclooctadiene)iridium(I) dimer (360 mg, 0.54 mmol) and 4,4,5,5-tetramethyl-1,3,2-dioxaborolane (3.1 mL, 21 mmol) was added to a mixture of methyl 4-allylnicotinate (1.9 g, 11 mmol) in DCM (50 mL) under nitrogen, the reaction mixture was degassed three times under nitrogen, and stirred at 15° C. for 15 h under nitrogen. The mixture was quenched with water and extracted with DCM. The combined organic phase was concentrated under reduced pressure and the residue was purified by silica gel column chromatography (EtOAc in hexanes) to give methyl 4-(3-(4,4,5,5-tetramethyl-1,3,2-dioxaborolan-2-yl)propyl)nicotinate. LCMS (C$_{16}$H$_{25}$BNO$_4$$^+$) (ES, m/z): 306 [M+H]$^+$.

Step 3: (3-(3-(methoxycarbonyl)piperidin-4-yl)propyl)boronic acid

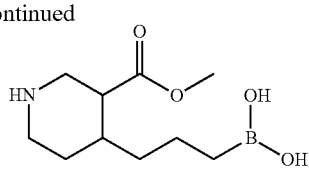

2,2,2-trifluoroacetic acid (41 mg, 0.36 mmol) and 10% palladium on carbon (20 mg, 0.019 mmol) were added to a solution of methyl 4-(3-(4,4,5,5-tetramethyl-1,3,2-dioxaborolan-2-yl)propyl)nicotinate (100 mg, 0.33 mmol) in MeOH (5.0 mL) under nitrogen atmosphere, and the resulting mixture was degassed and backfilled with hydrogen (three times), and stirred under hydrogen (Pressure: 50 psi) at 50° C. for 16 h. The mixture was filtered, the filtrate was concentrated, and the residue was purified by RP-HPLC [C18 column, water (0.1% TFA)-CH$_3$CN] to give (3-(3-(methoxycarbonyl)piperidin-4-yl)propyl)boronic acid. LC-MS (C$_{10}$H$_{21}$BNO$_4$$^+$)(ES, m/z): 230 [M+H]$^+$.

Step 4: 4-[3-(dihydroxyboranyl)propyl]piperidinyl-3-carboxylic acid

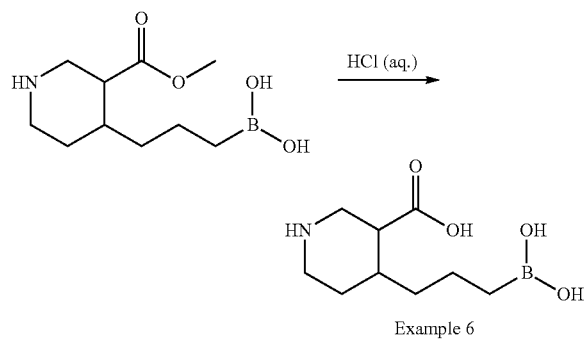

Example 6

A mixture of (3-(3-(methoxycarbonyl)piperidin-4-yl)propyl)boronic acid (60 mg, 0.26 mmol) in 12 N HCl in water (2.0 mL, 24 mmol) was stirred at 100° C. for 16 h, and concentrated under reduced pressure. The residue was purified by RP-HPLC [C18 column, water (0.1% TFA)-CH$_3$CN] to give 4-[3-(dihydroxyboranyl)propyl]piperidinyl-3-carboxylic acid as a TFA salt. LCMS (C$_9$H$_{19}$BNO$_4$$^+$)(ES, m/z): 216 [M+H]$^+$. $^1$H NMR (400 MHz, D$_2$O) δ 3.45 (br dd, J=4.7, 13.3 Hz, 1H), 3.35-3.25 (m, 1H), 3.14 (dd, J=3.5, 13.5 Hz, 1H), 3.07-2.98 (m, 1H), 2.98-2.93 (m, 1H), 2.09-1.97 (m, 1H), 1.88-1.77 (m, 1H), 1.76-1.63 (m, 1H), 1.48-1.37 (m, 2H), 1.35-1.23 (m, 2H), 0.73 (br t, J=7.5 Hz, 2H).

Example 7: 3-[3-(dihydroxyboranyl)propyl]piperazine-2-carboxylic acid

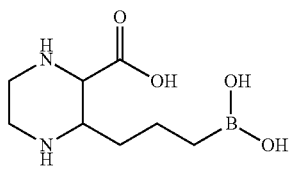 [SMILES: O=C(O)C1NCCNC1CCCB(O)O]

Step 1: methyl 3-allylpyrazine-2-carboxylate

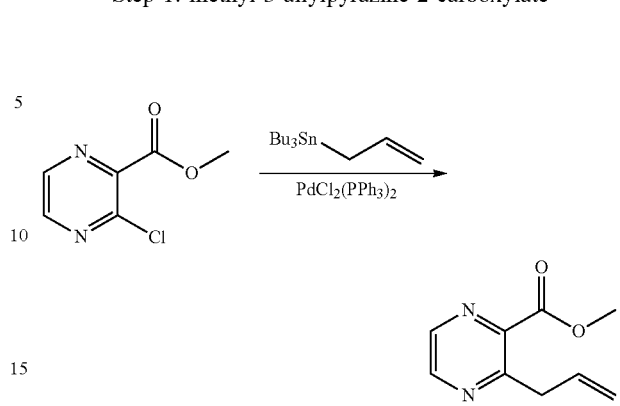

A mixture of methyl 3-chloropyrazine-2-carboxylate (1.0 g, 5.8 mmol), allyltributylstannane (7.4 g, 22 mmol) and bis(triphenylphosphine)palladium(II) dichloride (0.41 g, 0.58 mmol) in DMF (15 mL) was degassed and backfilled with nitrogen (three times), and the reaction mixture was heated to 110° C. for 1.5 h. The mixture was quenched with saturated aqueous potassium fluoride, and filtered. The filtrate was extracted with EtOAc, and the combined organic layer was dried over Na$_2$SO$_4$, filtered and concentrated. The residue was purified by silica gel column chromatography (EtOAc in hexanes) to give methyl 3-allylpyrazine-2-carboxylate. LCMS (C$_9$H$_{11}$N$_2$O$_2$$^+$)(ES, m/z): 179 [M+H]$^+$.

Step 2: methyl 3-(3-(4,4,5,5-tetramethyl-1,3,2-dioxaborolan-2-yl)propyl)pyrazine-2-carboxylate

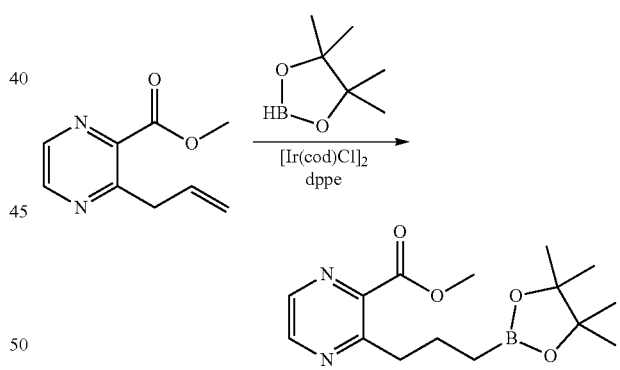

1,2-Bis(diphenylphosphino)ethane (143 mg, 0.36 mmol), chloro(1,5-cyclooctadiene)iridium(I) dimer (121 mg, 0.18 mmol) and 4,4,5,5-tetramethyl-1,3,2-dioxaborolane (919 mg, 7.2 mmol) were added to a mixture of methyl 3-allylpyrazine-2-carboxylate (640 mg, 3.6 mmol) in DCM (25 mL) under nitrogen, and the reaction mixture was degassed and backfilled with nitrogen three times, and stirred at 15° C. for 15 h under nitrogen. The mixture was filtered and concentrated, and the residue was purified by RP-HPLC [C18 column, water (10 mM NH$_4$HCO$_3$)—CH$_3$CN] to give methyl 3-(3-(4,4,5,5-tetramethyl-1,3,2-dioxaborolan-2-yl) propyl)pyrazine-2-carboxylate [contained (3-(3-(methoxycarbonyl)pyrazin-2-yl)propyl)boronic acid] as a yellow solid. LCMS (C$_{15}$H$_{24}$BN$_2$O$_4$$^+$)(ES, m/z): 307 [M+H]$^+$.

Step 3: (3-(3-(methoxycarbonyl)piperazin-2-yl)propyl)boronic acid

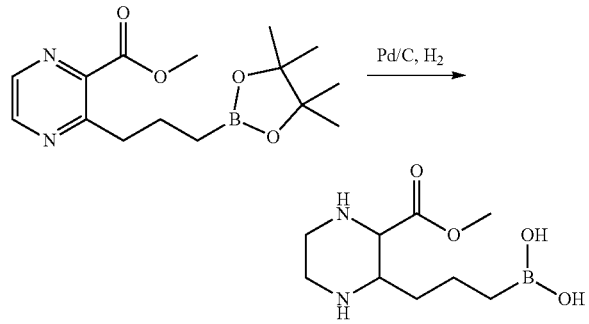

10% palladium on carbon (20 mg, 0.019 mmol) was added to a solution of methyl 3-(3-(4,4,5,5-tetramethyl-1,3,2-dioxaborolan-2-yl)propyl)pyrazine-2-carboxylate (85 mg, 0.28 mmol) in MeOH (10 mL) under nitrogen atmosphere, and the reaction mixture was degassed and backfilled with hydrogen (three times), and stirred under hydrogen (Pressure: 50 psi) at 50° C. for 16 h. The mixture was filtered and the filtrate was concentrated, and the residue was purified by RP-HPLC [C18 column, water (0.1% TFA)-CH$_3$CN] to give (3-(3-(methoxycarbonyl)piperazin-2-yl)propyl)boronic acid. LCMS (C$_9$H$_{20}$BN$_2$O$_4{}^+$)(ES, m/z): 231 [M+H]$^+$.

Step 4: 3-[3-(dihydroxyboranyl)propyl]piperazine-2-carboxylic acid

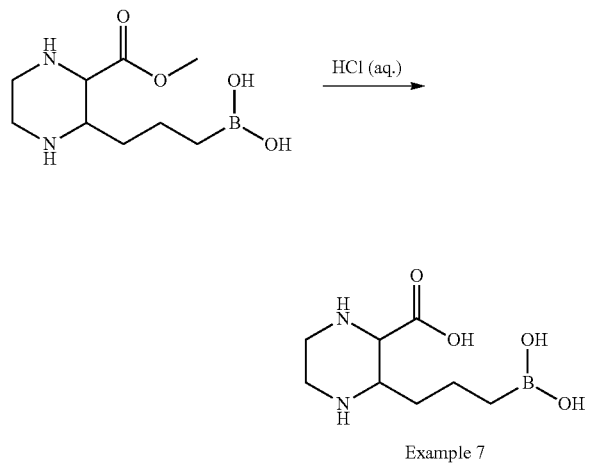

A mixture of (3-(3-(methoxycarbonyl)piperazin-2-yl)propyl)boronic acid (35 mg, 0.15 mmol) and 12 N HCl in water (2.0 mL, 24 mmol) was stirred at 100° C. for 15 h, and concentrated to give 3-[3-(dihydroxyboranyl)propyl]piperazine-2-carboxylic acid as an HCl salt. LCMS (C$_8$H$_{18}$BN$_2$O$_4{}^+$)(ES, m/z): 217 [M+H]$^+$. $^1$H NMR (400 MHz, D$_2$O) δ 4.11 (d, J=4.0 Hz, 1H), 3.91-3.81 (m, 1H), 3.62-3.49 (m, 1H), 3.39-3.33 (m, 2H), 3.32-3.24 (m, 1H), 1.75-1.63 (m, 1H), 1.62-1.49 (m, 1H), 1.46-1.25 (m, 2H), 0.71-0.55 (m, 2H)

Example 8A: (2S,3S)-3-[3-(dihydroxyboranyl)propyl]azetidine-2-carboxylic acid

Step 1: (S)-4-methoxy-4-oxo-2-((9-phenyl-9H-fluoren-9-yl)amino)butanoic acid

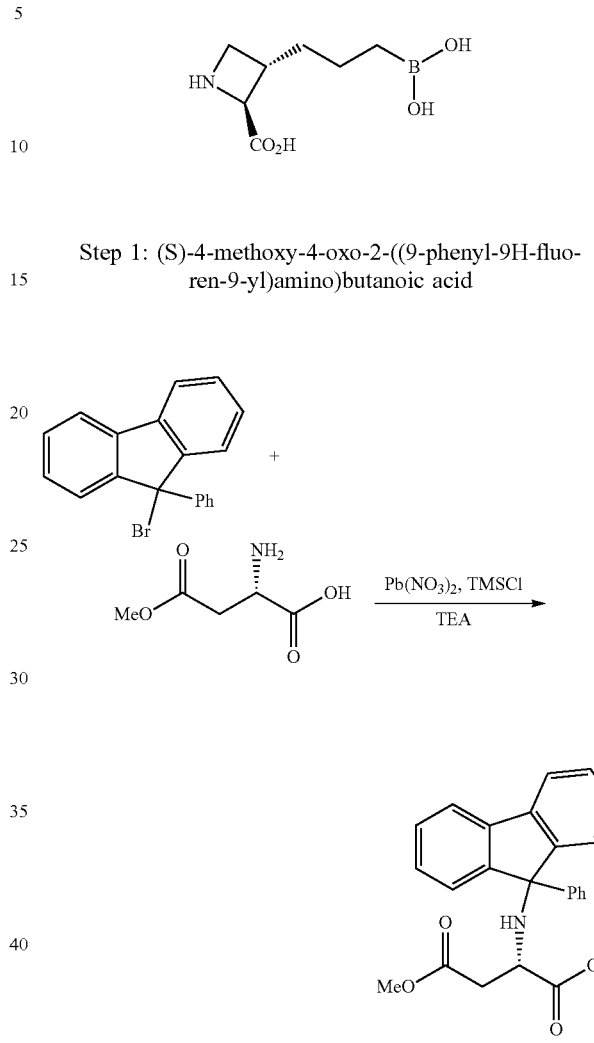

TMS-Cl (3.2 mL, 25 mmol) was added to a stirred suspension of (S)-2-amino-4-methoxy-4-oxobutanoic acid (3.3 g, 22 mmol) in chloroform (100 mL) at 20° C., followed by addition of TEA (6.6 mL, 47 mmol) after 2 h, then addition of Pb(NO$_3$)$_2$ (4.4 g, 15 mmol) and 9-bromo-9-phenyl-9H-fluorene (9.4 g, 29 mmol) in chloroform (50 mL) after another 15 min. The reaction mixture was stirred vigorously for 72 h, then quenched with MeOH and stirred for another 15 min. The mixture was filtered and concentrated under reduced pressure. The crude mixture was diluted with 5% aqueous citric acid and EtOAc, and extracted with EtOAc. The combined organic phase was washed with brine, dried over anhydrous Na$_2$SO$_4$, filtered and concentrated. The residue was purified by silica gel column chromatography (EtOAc in hexanes) to give (S)-4-methoxy-4-oxo-2-((9-phenyl-9H-fluoren-9-yl)amino)butanoic acid. LCMS (C$_{26}$H$_{24}$N$_2$O$_4$Na$^+$)(ES, m/z): 451 [M+MeCN+Na]$^+$. $^1$H NMR (400 MHz, CDCl$_3$) δ 7.73 (dd, J=7.5, 18.9 Hz, 2H), 7.54-7.14 (m, 11H), 3.70-3.56 (m, 3H), 2.87 (t, J=4.2 Hz, 1H), 2.77 (dd, J=3.7, 17.3 Hz, 1H), 1.95 (dd, J=4.8, 17.1 Hz, 1H).

Step 2: (S)-1-tert-butyl 4-methyl 2-((9-phenyl-9H-fluoren-9-yl)aminosuccinate

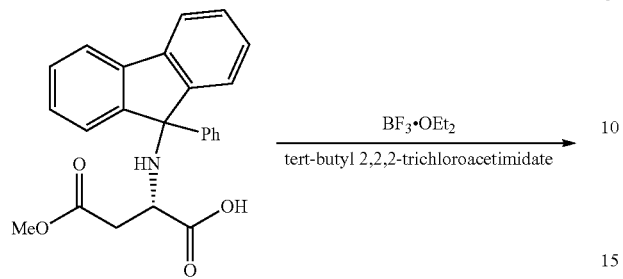

Boron trifluoride etherate (98 µL, 0.77 mmol) was added to the stirred solution of (S)-4-methoxy-4-oxo-2-((9-phenyl-9H-fluoren-9-yl)amino)butanoic acid (1.5 g, 3.9 mmol), tert-butyl 2,2,2-trichloroacetimidate (1.7 g, 7.7 mmol) in THF (50 mL) at 0° C., and the reaction mixture was stirred at 20° C. for 15 h. The mixture was quenched with saturated aqueous NaHCO$_3$ and extracted with EtOAc, and the combined organic phase was washed with brine, dried over anhydrous Na$_2$SO$_4$, filtered and concentrated under reduced pressure. The residue was purified by silica gel column chromatography (EtOAc in hexanes) to give (S)-1-tert-butyl 4-methyl 2-((9-phenyl-9H-fluoren-9-yl)amino)succinate. LCMS (C$_{28}$H$_{30}$NO$_4^+$)(ES, m/z): 444 [M+H]$^+$.

Step 3: (3S)-4-tert-butyl 1-methyl 2-allyl-3-((9-phenyl-9H-fluoren-9-yl)amino)succinate

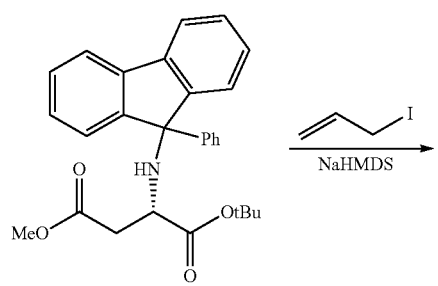

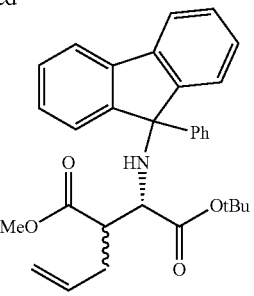

Sodium bis(trimethylsilyl)amide (1.0 M in THF, 2.2 mL, 2.2 mmol) was added to the stirred solution of (S)-1-tert-butyl 4-methyl 2-((9-phenyl-9H-fluoren-9-yl)amino)succinate (800 mg, 1.8 mmol) in THF (20 mL) under nitrogen at −78° C., and the resulting mixture was stirred for 0.5 h at −78° C., followed by addition of 3-iodoprop-1-ene (909 mg, 5.4 mmol). The reaction mixture was stirred at −78° C. for 1 h, then quenched with saturated aqueous NH$_4$Cl, and extracted with EtOAc. The combined organic phase was washed with brine, dried over anhydrous Na$_2$SO$_4$, filtered and concentrated under reduced pressure. The residue was purified by silica gel preparative thin layer chromatography (EtOAc in hexanes) to give (3S)-4-tert-butyl 1-methyl 2-allyl-3-((9-phenyl-9H-fluoren-9-yl)amino)succinate as a mixture of isomers. LCMS (C$_{31}$H$_{34}$NO$_4^+$)(ES, m/z): 484 [M+H]$^+$.

Step 4: (2S)-tert-butyl 3-(hydroxymethyl)-2-((9-phenyl-9H-fluoren-9-ylamino)hex-5-enoate

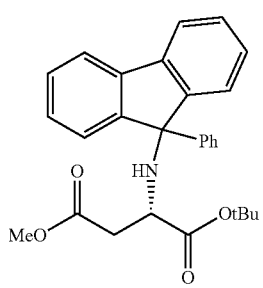

DIBAL-H (1.0 M in toluene, 5.4 mL, 5.4 mmol) was added to the stirred solution of (3S)-4-tert-butyl 1-methyl 2-allyl-3-((9-phenyl-9H-fluoren-9-yl)amino)succinate (650 mg, 1.3 mmol) in DCM (30 mL) under nitrogen at −78° C. over 5 min, and the reaction mixture was stirred at −78° C. for 1 h. The mixture was quenched with MeOH (0.5 mL) in DCM (10 mL) at −78° C., then diluted with water, and extracted with DCM. The combined organic phase was washed with brine, dried over anhydrous Na$_2$SO$_4$, filtered and concentrated under reduced pressure. The residue was purified by silica gel preparative thin layer chromatography (EtOAc in hexanes) to give (2S)-tert-butyl 3-(hydroxymethyl)-2-((9-phenyl-9H-fluoren-9-yl)amino)hex-5-enoate as a mixture of isomers. LCMS (C$_{30}$H$_{34}$NO$_3^+$)(ES, m/z): 456 [M+H]$^+$.

Step 5: (2S,3S)-tert-butyl 3-allyl-1-(9-phenyl-9H-fluoren-9-yl)azetidine-2-carboxylate and (2S,3R)-tert-butyl 3-allyl-1-(9-phenyl-9H-fluoren-9-yl)azetidine-2-carboxylate

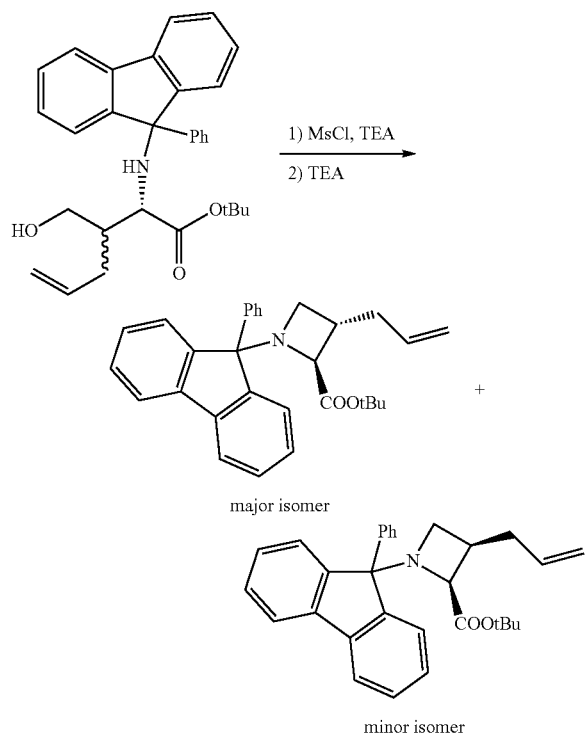

major isomer minor isomer

TEA (1.1 mL, 8.2 mmol) and methanesulfonyl chloride (0.43 mL, 5.5 mmol) were added to the stirred solution of (2S)-tert-butyl 3-(hydroxymethyl)-2-((9-phenyl-9H-fluoren-9-yl)amino)hex-5-enoate (250 mg, 0.55 mmol) in DCM (10 mL) at 0° C. and the reaction mixture was stirred for 1 h at the same temperature. The mixture was quenched with water (10 mL) and neutralized with 12 N HCl in water to pH=5. The organic phase was washed with brine, dried over anhydrous Na$_2$SO$_4$, filtered and concentrated under reduced pressure. The crude mixture was dissolved in DMF (5.0 mL), followed by addition of TEA (0.77 mL, 5.5 mmol), and the resulting mixture was stirred at 80° C. for 15 h. The mixture was quenched with water and extracted with EtOAc, and the combined organic phase was washed with brine, dried over anhydrous Na$_2$SO$_4$, filtered and concentrated under reduced pressure. The residue was purified by silica gel preparative thin layer chromatography (EtOAc in hexanes) to give (2S,3S)-tert-butyl 3-allyl-1-(9-phenyl-9H-fluoren-9-yl)azetidine-2-carboxylate (major isomer), and (2S,3R)-tert-butyl 3-allyl-1-(9-phenyl-9H-fluoren-9-yl)azetidine-2-carboxylate (minor isomer). Stereochemistry was confirmed by 2D NMR. Major Isomer LCMS (C$_3$H$_{32}$NO$_2^+$) (ES, m/z): 438 [M+H]$^+$. $^1$H NMR (400 MHz, CDCl$_3$) δ 7.76 (d, J=7.5 Hz, 1H), 7.64 (d, J=7.9 Hz, 1H), 7.56 (dd, J=1.3, 7.9 Hz, 2H), 7.49-7.35 (m, 3H), 7.35-7.27 (m, 2H), 7.26-7.14 (m, 4H), 5.59-5.42 (m, 1H), 4.84 (dd, J=2.0, 13.8 Hz, 2H), 3.56-3.46 (m, 1H), 3.05 (d, J=7.0 Hz, 1H), 2.94 (t, J=7.5 Hz, 1H), 2.53-2.46 (m, 1H), 1.95-1.88 (m, 2H), 1.19 (s, 9H). Minor Isomer LCMS (C$_{30}$H$_{32}$NO$_2^+$)(ES, m/z): 438 [M+H]$^+$. $^1$H NMR (400 MHz, CDCl$_3$) δ 7.76 (d, J=7.5 Hz, 1H), 7.59 (d, J=7.5 Hz, 1H), 7.54 (d, J=1.8 Hz, 1H), 7.55-7.51 (m, 1H), 7.48-7.40 (m, 2H), 7.37 (d, J=7.5 Hz, 1H), 7.34-7.32 (m, 1H), 7.28-7.19 (m, 4H), 7.17-7.09 (m, 1H), 5.71-5.59 (m, 1H), 5.02-4.92 (m, 2H), 3.47 (t, J=8.1 Hz, 1H), 3.35 (d, J=9.2 Hz, 1H), 3.22 (dd, J=3.9, 7.5 Hz, 1H), 2.55-2.44 (m, 1H), 2.41-2.30 (m, 1H), 2.26-2.17 (m, 1H), 1.20 (s, 9H).

Step 6:2S,3S)-tert-butyl 3-allyl-(9-phenyl-9H-fluoren-9-yl)azetidine-2-carboxylate

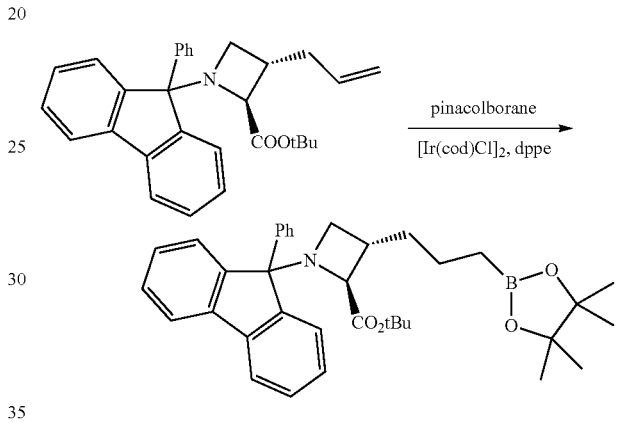

A mixture of (2S,3S)-tert-butyl 3-allyl-1-(9-phenyl-9H-fluoren-9-yl)azetidine-2-carboxylate (400 mg, 0.91 mmol), chloro(1,5-cyclooctadiene)iridium(I) dimer (31 mg, 0.046 mmol), and 1,2-bis(diphenylphosphino)ethane (26 mg, 0.064 mmol) in DCM (20 mL) was degassed and backfilled with nitrogen (three times), followed by addition of 4,4,5,5-tetramethyl-1,3,2-dioxaborolane (585 mg, 4.6 mmol), and the resulting mixture was stirred at 20° C. for 15 h under nitrogen. The mixture was quenched with water and extracted with DCM. The combined organic phase was washed with brine, dried over anhydrous Na$_2$SO$_4$, filtered and concentrated under reduced pressure. The residue was purified by silica gel column chromatography (EtOAc in hexanes) to give (2S,3S)-tert-butyl 1-(9-phenyl-9H-fluoren-9-yl)-3-(3-(4,4,5,5-tetramethyl-1,3,2-dioxaborolan-2-yl) propyl)azetidine-2-carboxylate. LCMS (C$_{36}$H$_{45}$BNO$_4^+$) (ES, m/z): 566 [M+H]$^+$.

Step 7: (2S,3S)-tert-butyl 3-(3-(4,4,5,5-tetramethyl-1,3,2-dioxaborolan-2-yl)propyl)azetidine-2-carboxylate

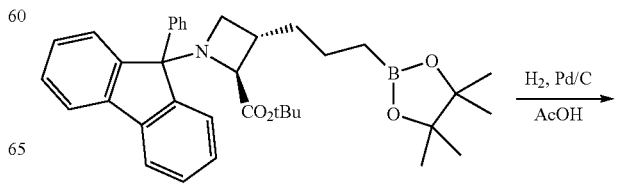

-continued

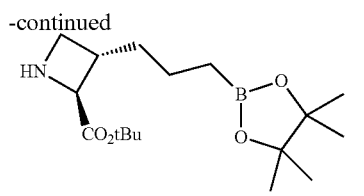

Acetic acid (186 mg, 3.1 mmol) and 10% Pd/C (66 mg, 0.062 mmol) was added to a solution of (2S,3S)-tert-butyl 1-(9-phenyl-9H-fluoren-9-yl)-3-(3-(4,4,5,5-tetramethyl-1,3,2-dioxaborolan-2-yl)propyl)azetidine-2-carboxylate (350 mg, 0.62 mmol) in MeOH (20 mL) under nitrogen atmosphere, and the resulting mixture was degassed and backfilled with hydrogen (three times), and stirred under hydrogen (Pressure: 1 atm) at 20° C. for 3 h. The mixture was filtered and the filtrate was concentrated under reduced pressure to give crude (2S,3S)-tert-butyl 3-(3-(4,4,5,5-tetramethyl-1,3,2-dioxaborolan-2-yl)propyl)azetidine-2-carboxylate which was used in next step without further purification. LCMS ($C_{17}H_{33}BNO_4^+$)(ES, m/z): 326 [M+H]$^+$.

Step 8: (2S,3S)-3-[3-(dihydroxyboranyl)propyl]azetidine-2-carboxylic acid

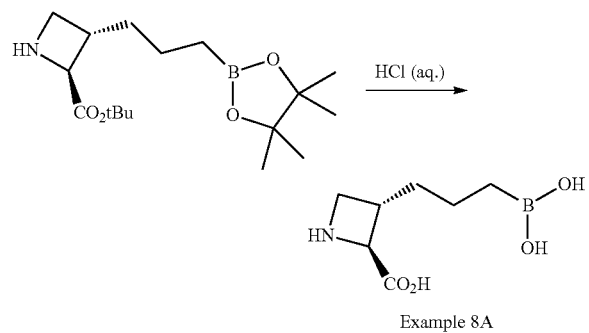

Example 8A

A mixture of (2S,3S)-tert-butyl 3-(3-(4,4,5,5-tetramethyl-1,3,2-dioxaborolan-2-yl)propyl)azetidine-2-carboxylate (100 mg, 0.31 mmol) and 12 N HCl in water (2.5 mL, 30 mmol) was stirred at 0° C. for 2 h, and solvent was evaporated in nitrogen stream at 0° C. The residue was purified by RP-HPLC [C18 column, water (0.1% TFA)-CH$_3$CN] to give (2S,3S)-3-[3-(dihydroxyboranyl)propyl]azetidine-2-carboxylic acid as a TFA salt. LCMS ($C_7H_{15}BNO_4^+$) (ES, m/z): 188 [M+H]$^+$. $^1$H NMR (400 MHz, CD$_3$OD) δ 4.70 (d, J=7.9 Hz, 1H), 3.97 (t, J=9.4 Hz, 1H), 3.74 (dd, J=8.3, 10.1 Hz, 1H), 2.98 (sxt, J=8.0 Hz, 1H), 1.84-1.63 (m, 2H), 1.57-1.29 (m, 2H), 0.80 (br s, 2H).

Example 8B: (2S,3R)-3-[3-(dihydroxyboranyl)propyl]azetidine-2-carboxylic acid

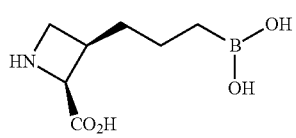 [SMILES: O=C(O)[C@H]1NC[C@H]1CCCB(O)O]

Step 1: (2S,3R)-tert-butyl 1-(9-phenyl-9H-fluoren-9-yl)-3-(3-(4,4,5,5-tetramethyl-1,3,2-dioxaborolan-2-yl)propyl)azetidine-2-carboxylate

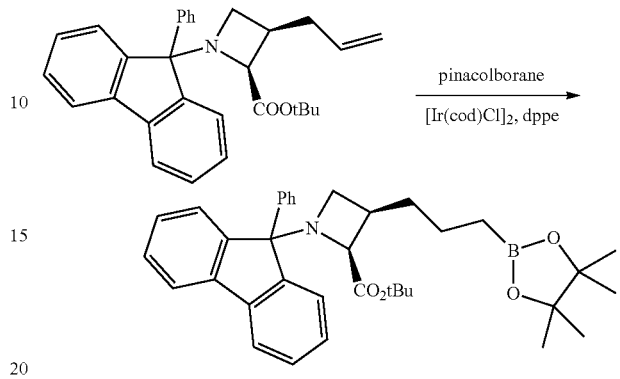

A mixture of (2S,3R)-tert-butyl 3-allyl-1-(9-phenyl-9H-fluoren-9-yl)azetidine-2-carboxylate (300 mg, 0.55 mmol), 4,4,5,5-tetramethyl-1,3,2-dioxaborolane (351 mg, 2.7 mmol), 1,2-bis(diphenylphosphino)ethane (22 mg, 0.055 mmol), and chloro(1,5-cyclooctadiene)iridium(I) dimer (18 mg, 0.027 mmol) in DCM (10 mL) was degassed and backfilled with nitrogen (three times), and stirred at 20° C. for 15 h. The mixture was quenched with water and extracted with DCM, and the combined organic phase was washed with brine, dried over anhydrous Na$_2$SO$_4$, filtered and concentrated under reduced pressure. The residue was purified by silica gel column chromatography (EtOAc in hexanes) to give (2S,3R)-tert-butyl 1-(9-phenyl-9H-fluoren-9-yl)-3-(3-(4,4,5,5-tetramethyl-1,3,2-dioxaborolan-2-yl)propyl)azetidine-2-carboxylate. LCMS ($C_{36}H_{45}BNO_4^+$)(ES, m/z): 566 [M+H]$^+$.

Step 2: (3-((2S,3R)-2-(tert-butoxycarbonyl)-1-(9-phenyl-9H-fluoren-9-yl)azetidin-3-yl)propyl)boronic acid

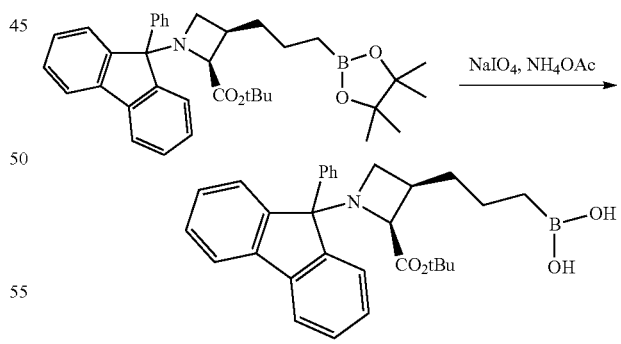

Ammonium acetate (327 mg, 4.2 mmol) and sodium periodate (454 mg, 2.1 mmol) were added to the stirred suspension of (2S,3R)-tert-butyl 1-(9-phenyl-9H-fluoren-9-yl)-3-(3-(4,4,5,5-tetramethyl-1,3,2-dioxaborolan-2-yl)propyl)azetidine-2-carboxylate (120 mg, 0.21 mmol) in THF (5.0 mL) and water (2.5 mL) at 0° C., and the reaction mixture was stirred at 30° C. for 15 h. The mixture was quenched with water and extracted with EtOAc, and the combined organic phase was washed with brine, dried over anhydrous Na$_2$SO$_4$, filtered and concentrated under reduced pressure to give crude (3-((2S,3R)-2-(tert-butoxycarbonyl)-1-(9-phenyl-9H-fluoren-9-yl)azetidin-3-yl)propyl)boronic acid, which was used in the next step without further purification. LCMS (C$_{30}$H$_{35}$BNO$_4{}^+$)(ES, m/z): 484 [M+H]$^+$.

Step 3: (2S,3R)-3-(3-boronopropyl)-1-(9-phenyl-9H-fluoren-9-yl)azetidine-2-carboxylic acid

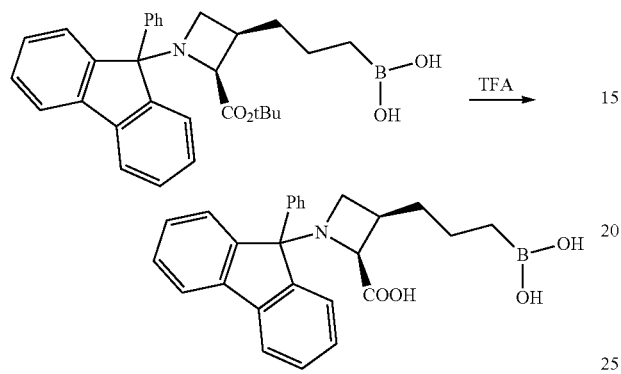

TFA (2.0 mL, 26 mmol) was added to the stirred solution of (3-((2S,3R)-2-(tert-butoxycarbonyl)-1-(9-phenyl-9H-fluoren-9-yl)azetidin-3-yl)propyl)boronic acid (110 mg, 0.23 mmol) in DCM (2.0 mL) and the reaction mixture was stirred at 20° C. for 15 h. The mixture was concentrated under reduced pressure, and the residue was purified by RP-HPLC [C18 column, water (0.1% TFA)-CH$_3$CN] to give (2S,3R)-3-(3-boronopropyl)-1-(9-phenyl-9H-fluoren-9-yl) azetidine-2-carboxylic acid. LCMS (C$_{26}$H$_{27}$BNO$_4{}^+$)(ES, m/z): 428 [M+H]$^+$.

Step 4: (2S,3R)-3-[3-(dihydroxyboranyl)propyl] azetidine-2-carboxylic acid

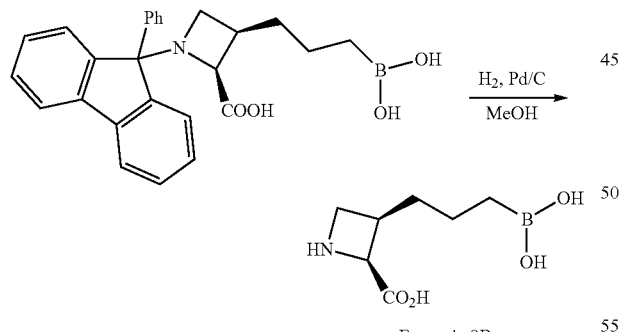

Example 8B

10% palladium on carbon (69 mg, 0.064 mmol) was added to the stirred solution of (2S,3R)-3-(3-boronopropyl)-1-(9-phenyl-9H-fluoren-9-yl)azetidine-2-carboxylic acid (55 mg, 0.13 mmol) in MeOH (2.0 mL) under nitrogen atmosphere, and the reaction mixture was degassed and backfilled with hydrogen (three times), and then stirred under hydrogen (Pressure: 1 atm) at 20° C. for 4 h. The mixture was filtered and the filtrate was concentrated under reduced pressure, and the crude mixture was diluted with DCM and extracted with water. The combined aqueous layer was evaporated in nitrogen stream, and the residue was purified by RP-HPLC [C18 column, water (10 mM NH$_4$HCO$_3$)—CH$_3$CN] to give (2S,3R)-3-[3-(dihydroxyboranyl)propyl]azetidine-2-carboxylic acid. LCMS (C$_7$H$_{13}$BNO$_3{}^+$)(ES, m/z): 170 [M−H$_2$O+H]$^+$. $^1$H NMR (400 MHz, D$_2$O) δ 4.60 (d, J=9.7 Hz, 1H), 3.97 (dd, J=8.8, 10.4 Hz, 1H), 3.48 (dd, J=6.7, 10.5 Hz, 1H), 3.00-2.74 (m, 1H), 1.56-1.39 (m, 1H), 1.36-1.24 (m, 1H), 1.22-1.03 (m, 2H), 0.63-0.41 (m, 2H).

Example 9A: (3R)-3-[3-(dihydroxyboranyl)propyl]-L-proline

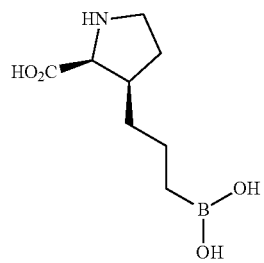 [SMILES: O=C(O)[C@H]1NCC[C@H]1CCCB(O)O]

Step 1: 1-tert-butyl 2-methyl 3-bromo-1H-pyrrole-1,2-dicarboxylate

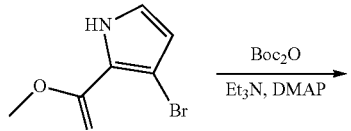

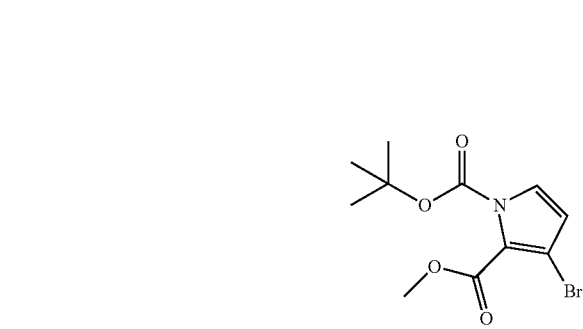

N,N-dimethylpyridin-4-amine (1.5 g, 12 mmol) was added to a solution of methyl 3-bromo-1H-pyrrole-2-carboxylate (5.0 g, 25 mmol), di-tert-butyl dicarbonate (8.0 g, 37 mmol) and triethylamine (14 mL, 98 mmol) in DCM (60 mL), and the reaction mixture was stirred at 25° C. for 2 h. The mixture was diluted with water and extracted with DCM, and the combined organic phase was washed with brine, dried over anhydrous Na$_2$SO$_4$, filtered, and concentrated under reduced pressure. The residue was purified by silica gel column chromatography (EtOAc in hexanes) to give 1-tert-butyl 2-methyl 3-bromo-1H-pyrrole-1,2-dicarboxylate. LCMS (C$_7$H$_7$BrNO$_4{}^+$)(ES, m/z): 248 [M−C$_4$H$_8$+H]$^+$.

Step 2: 1-tert-butyl 2-methyl 3-allyl-1H-pyrrole-1,2-dicarboxylate

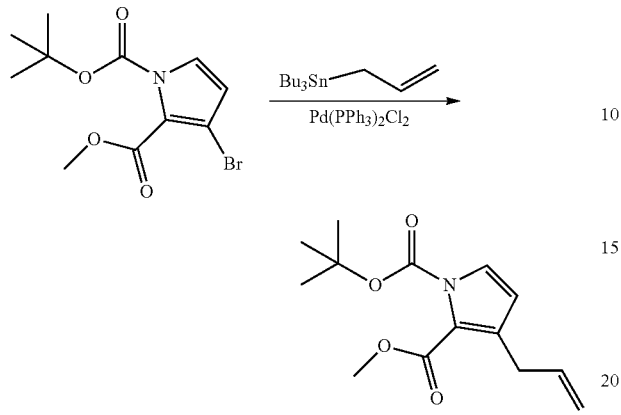

Bis(triphenylphosphine)-palladium (II) dichloride (0.99 g, 1.5 mmol) was added to a mixture of 1-tert-butyl 2-methyl 3-bromo-1H-pyrrole-1,2-dicarboxylate (3.0 g, 9.9 mmol), and allyltributylstannane (7.5 mL, 24 mmol) in DMF (65 mL), and the reaction mixture was stirred at 100° C. for 3 h under nitrogen. The mixture was quenched with 5% aqueous potassium fluoride, and stirred at 20° C. for 1 h, then extracted with EtOAc. The combined organic phase was dried over anhydrous Na$_2$SO$_4$, filtered and concentrated in vacuo. The residue was purified by silica gel column chromatography (EtOAc in hexanes) to give 1-tert-butyl 2-methyl 3-allyl-1H-pyrrole-1,2-dicarboxylate. LCMS (C$_{10}$H$_{12}$NO$_4$$^+$)(ES, m/z): 210 [M-C$_4$H$_8$+H]$^+$.

Step 3: 1-tert-butyl 2-methyl 3-(3-(4,4,5,5-tetramethyl-1,3,2-dioxaborolan-2-yl)propyl)-1H-pyrrole-1,2-dicarboxylate

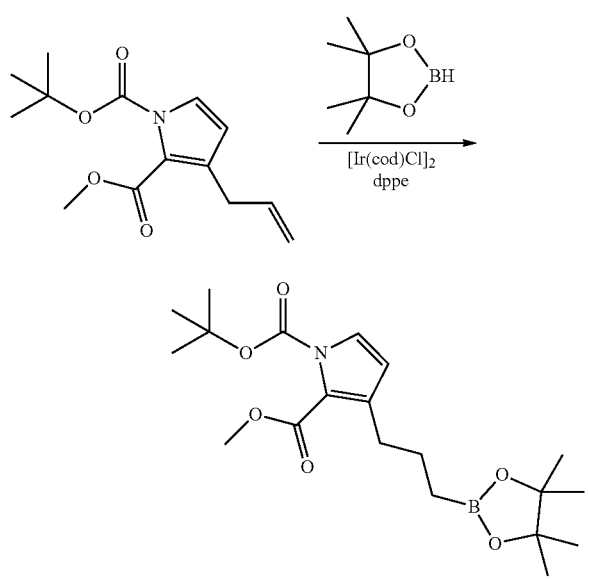

1-Tert-butyl 2-methyl 3-allyl-1H-pyrrole-1,2-dicarboxylate (2.2 g, 8.3 mmol) was added to a solution of 4,4,5,5-tetramethyl-1,3,2-dioxaborolane (3.6 mL, 25 mmol), chloro(1,5-cyclooctadiene)iridium (I) dimer (0.39 g, 0.58 mmol), and bis(diphenylphosphino)ethane (0.32 g, 0.83 mmol) in dry DCM (50 mL), and the reaction mixture was stirred at 20° C. for 13 h under nitrogen. The mixture was quenched with water and extracted with DCM, and the combined organic phase was dried over anhydrous Na$_2$SO$_4$, filtered and concentrated in vacuo. The residue was purified by silica gel column chromatography (EtOAc in hexanes) to give 1-tert-butyl 2-methyl 3-(3-(4,4,5,5-tetramethyl-1,3,2-dioxaborolan-2-yl)propyl)-1H-pyrrole-1,2-dicarboxylate. LCMS (C$_{16}$H$_{25}$BNO$_6$$^+$)(ES, m/z): 338 [M-C$_4$H$_8$+H]$^+$.

Step 4: 1-tert-butyl 2-methyl 3-(3-(4,4,5,5-tetramethyl-1,3,2-dioxaborolan-2-yl)propyl)pyrrolidine-1,2-dicarboxylate

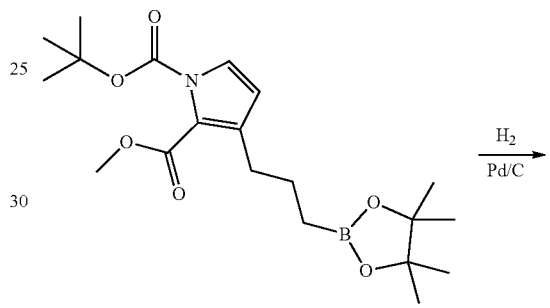

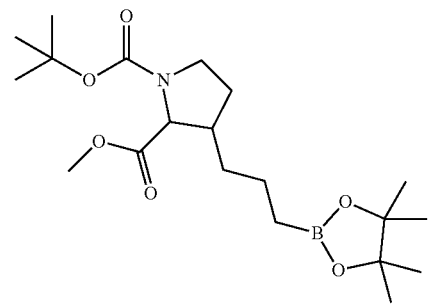

10% palladium on carbon (0.50 g, 0.21 mmol) was added to a solution of 1-tert-butyl 2-methyl 3-(3-(4,4,5,5-tetramethyl-1,3,2-dioxaborolan-2-yl)propyl)-1H-pyrrole-1,2-dicarboxylate (2.2 g, 5.6 mmol) in MeOH (35 mL) under nitrogen atmosphere, and the reaction mixture was degassed and backfilled with hydrogen (three times), and stirred under hydrogen (45-50 psi) at 45° C. for 12 h. The mixture was filtered and the filtrate was concentrated under reduced pressure, and the residue was purified by silica gel column chromatography (EtOAc in hexanes) to give 1-tert-butyl 2-methyl 3-(3-(4,4,5,5-tetramethyl-1,3,2-dioxaborolan-2-yl)propyl)pyrrolidine-1,2-dicarboxylate. LCMS (C$_{15}$H$_{29}$BNO$_4$$^+$)(ES, m/z): 298 [M-CO$_2$C$_4$H$_8$+H]$^+$.

Step 5: 3-(3-(4,4,5,5-tetramethyl-1,3,2-dioxaborolan-2-yl)propyl)pyrrolidine-2-carboxylate

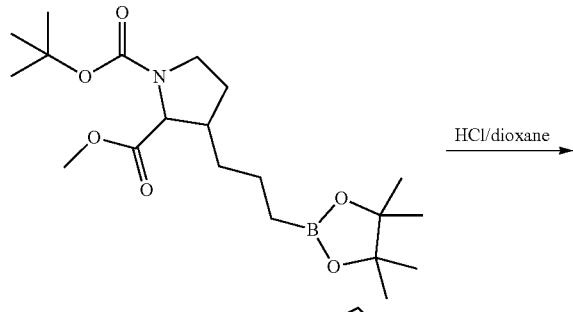

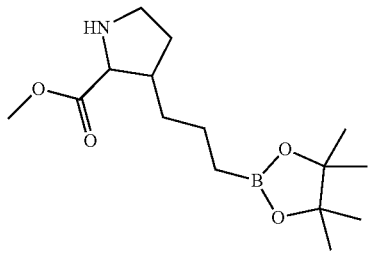

HCl in dioxane (4.0 M, 30 mL, 120 mmol) was added to a solution of 1-tert-butyl 2-methyl 3-(3-(4,4,5,5-tetramethyl-1,3,2-dioxaborolan-2-yl)propyl)pyrrolidine-1,2-dicarboxylate (3.2 g, 8.1 mmol) in DCM (30 mL) under nitrogen at 20° C., and the reaction mixture was stirred for 1 h at 20° C. The mixture was concentrated under reduced pressure to give methyl 3-(3-(4,4,5,5-tetramethyl-1,3,2-dioxaborolan-2-yl)propyl)pyrrolidine-2-carboxylate, which was used in next step without further purification. $^1$H NMR (400 MHz, CDCl$_3$) δ 4.39 (br s, 1H), 3.83 (s, 3H), 3.60-3.67 (m, 1H), 3.47 (br s, 1H), 2.59 (br s, 1H), 2.19 (br s, 1H), 1.75-1.83 (m, 1H), 1.62 (br s, 2H), 1.46 (br d, J=7.45 Hz, 2H), 1.23 (s, 12H), 0.78 (br s, 2H).

Step 6: 1-benzyl 2-methyl 3-(3-(4,4,5,5-tetramethyl-1,3,2-dioxaborolan-2-yl)propyl)pyrrolidine-1,2-dicarboxylate

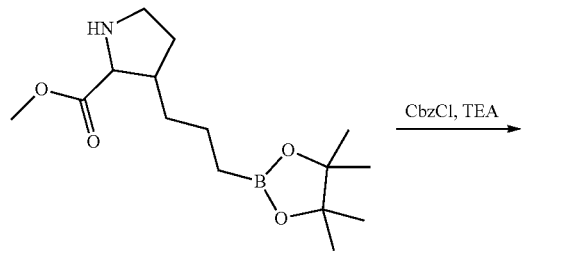

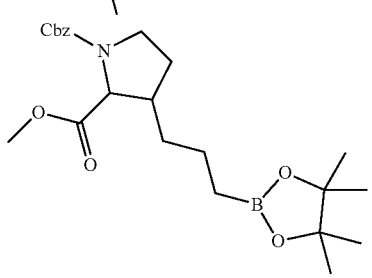

Benzyl chloroformate (1.5 mL, 10 mmol) was added to a stirred solution of methyl 3-(3-(4,4,5,5-tetramethyl-1,3,2-dioxaborolan-2-yl)propyl)pyrrolidine-2-carboxylate (2.4 g, 9.4 mmol) and triethylamine (3.9 mL, 28 mmol) in dry DCM (5 mL) at 0° C., and the reaction mixture was stirred for 3 h at 20° C. The mixture was quenched with saturated aqueous NH$_4$Cl and extracted with DCM, and the combined organic phase was washed with brine, dried over Na$_2$SO$_4$, filtered and concentrated. The residue was purified by silica gel column chromatography (EtOAc in hexanes) to give 1-benzyl 2-methyl 3-(3-(4,4,5,5-tetramethyl-1,3,2-dioxaborolan-2-yl)propyl)pyrrolidine-1,2-dicarboxylate. LCMS (C$_{23}$H$_{35}$BNO$_6^+$)(ES, m/z): 432 [M+H]$^+$.

Step 7: 1-benzyl 2-methyl 3-(3-(4,4,5,5-tetramethyl-1,3,2-dioxaborolan-2-yl)propyl)pyrrolidine-1,2-dicarboxylate R-1 and R-2

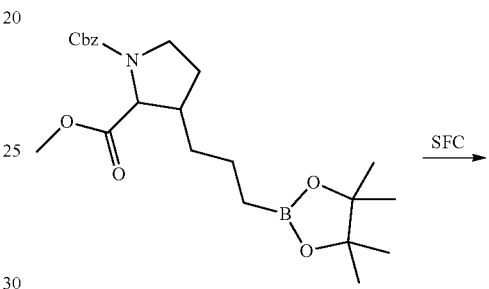

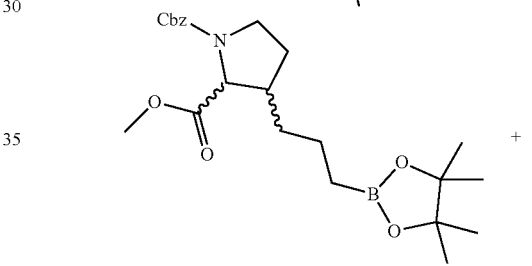

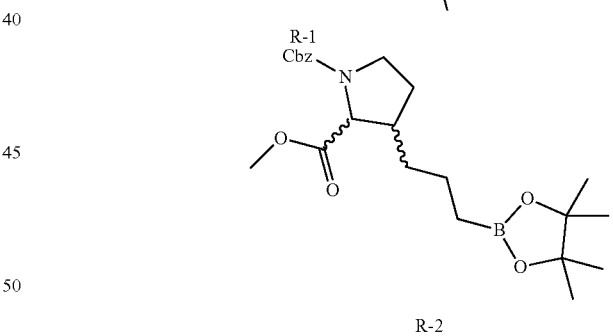

1-benzyl 2-methyl 3-(3-(4,4,5,5-tetramethyl-1,3,2-dioxaborolan-2-yl)propyl)pyrrolidine-1,2-dicarboxylate (3.3 g, 7.6 mmol) was resolved by chiral-SFC [Column: AD (250 mm*50 mm, 10 μm), Mobile phase: A: CO$_2$, B: EtOH (0.1% NH$_3$.H$_2$O), Gradient: 25% of B in 3.5 min and hold 25% for 1 min, Flow Rate (mL/min) 200, Column temperature: 40° C.] to give 1-benzyl 2-methyl 3-(3-(4,4,5,5-tetramethyl-1,3,2-dioxaborolan-2-yl)propyl)pyrrolidine-1,2-dicarboxylate (R-1, t$_r$=2.355 min) as the first eluting peak, and 1-benzyl 2-methyl 3-(3-(4,4,5,5-tetramethyl-1,3,2-dioxaborolan-2-yl)propyl)pyrrolidine-1,2-dicarboxylate (R-2, t$_r$=2.869 min) as the second eluting peak. R-1 LCMS (C$_{23}$H$_{35}$BNO$_6^+$)(ES, m/z): 432 [M+H]$^+$. $^1$H NMR (400 MHz, CDCl$_3$) δ 7.39-7.25 (m, 5H), 5.20-4.99 (m, 2H), 4.34 (dd, J=8.4, 15.7 Hz, 1H), 3.73-3.56 (m, 3H), 3.41-3.30 (m, 1H), 2.41-2.28 (m, 1H), 2.07-1.96 (m, 1H), 1.87-1.62 (m, 2H), 1.54-1.39 (m, 3H), 1.23 (d, J=1.5 Hz, 12H), 1.16-1.05 (m, 1H), 0.83-0.73 (m, 2H). R-2 LCMS ($C_{23}H_{35}BNO_6^+$)(ES, m/z): 432 [M+H]$^+$. $^1$H NMR (400 MHz, CDCl$_3$) δ 7.38-7.25 (m, 5H), 5.22-4.96 (m, 2H), 4.34 (dd, J=8.4, 15.7 Hz, 1H), 3.72-3.56 (m, 3H), 3.35 (dq, J=7.0, 10.2 Hz, 1H), 2.42-2.27 (m, 1H), 2.03-1.97 (m, 1H), 1.81-1.61 (m, 2H), 1.51-1.41 (m, 3H), 1.23 (d, J=1.5 Hz, 12H), 1.17-1.06 (m, 1H), 0.82-0.71 (m, 2H).

Step 8: (3R)-3-[3-(dihydroxyboranyl)propyl]-L-proline

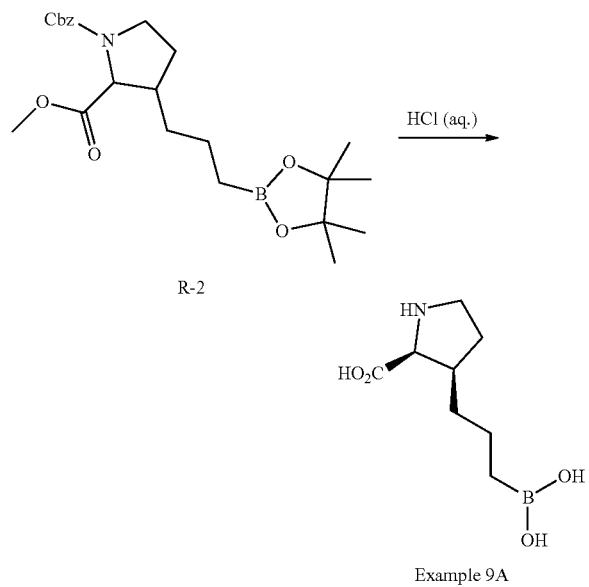

12 N HCl in water (3.0 mL) was added to the stirred suspension of 1-benzyl 2-methyl 3-(3-(4,4,5,5-tetramethyl-1,3,2-dioxaborolan-2-yl)propyl)piperidinyl-1,2-dicarboxylate (R-2, 578 mg, 1.3 mmol) in water (3.0 mL) at room temperature, and the reaction mixture was stirred at 80° C. overnight. The mixture was diluted with water, filtered through a 0.20 µm filter and lyophilized to afford (3R)-3-[3-(dihydroxyboranyl)propyl]-L-proline as an HCl salt. LCMS ($C_8H_{15}BNO_3^+$)(ES, m/z): 184 [M–H$_2$O+H]$^+$. $^1$H NMR (500 MHz, D$_2$O) δ 4.30 (d, J=7.9 Hz, 1H), 3.54-3.45 (m, 1H), 3.30 (dt, J=12, 7.9 Hz, 1H), 2.64-2.54 (m, 1H), 2.18 (dq, J=13, 6.7 Hz, 1H), 1.79 (dq, J=13, 7.8 Hz, 1H), 1.50-1.33 (m, 3H), 1.25-1.16 (m, 1H), 0.82-0.68 (m, 2H).

Example 9B: (3S)-3-[3-(dihydroxyboranyl)propyl]-L-proline

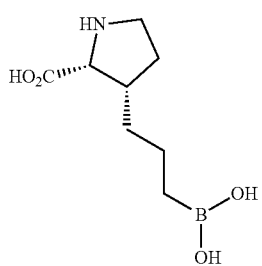 [SMILES: O=C(O)C1NCCC1CCCB(O)O]

Example 9B was made from R-1 using the same procedure as Example 9A. 184 [M–H$_2$O+H]$^+$ Example 9: 3-[3-(dihydroxyboranyl)propyl]-L-proline

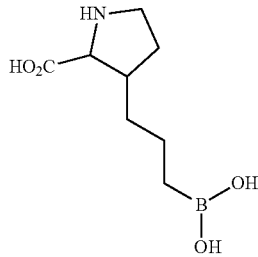

Example 9 was made from 1-benzyl 2-methyl 3-(3-(4,4,5,5-tetramethyl-1,3,2-dioxaborolan-2-yl)propyl)pyrrolidine-1,2-dicarboxylate using the same procedure as Example 9A. 184 [M–H$_2$O+H]$^+$ Step 9: (3R)-3-[3-(dihydroxyboranyl)propyl]-L-proline (Free Base)

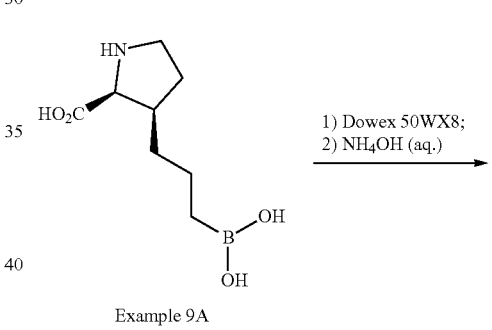

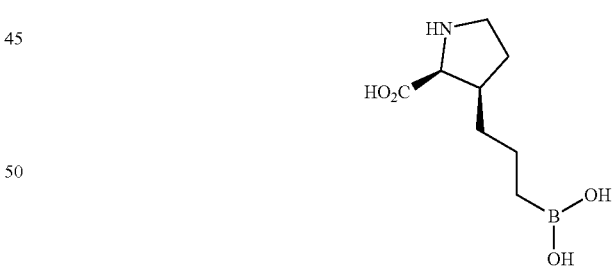

(3R)-3-[3-(dihydroxyboranyl)propyl]-L-proline (HCl salt, 70 mg) was purified on 2.2 g of Dowex 50WX8 acidic resin (washed with water until pH neutral, then eluted with 2N aqueous ammonium hydroxide) to afford (3R)-3-[3-(dihydroxyboranyl)propyl]-L-proline as a free base. LCMS ($C_8H_{15}BNO_3^+$)(ES, m/z): 184 [M–H$_2$O+H]$^+$. $^1$H NMR (500 MHz, D$_2$O) δ 4.05 (d, J 7.9 Hz, 1H), 3.48 (dt, J=12, 6.7 Hz, 1H), 3.26 (dt, J=12, 7.9 Hz, 1H), 2.59-2.46 (m, 1H), 2.15 (dq, J=13, 6.7 Hz, 1H), 1.79 (dq, J=13, 7.8 Hz, 1H), 1.54-1.31 (m, 3H), 1.24-1.12 (m, 1H), 0.85-0.68 (m, 2H).

Example 10: 3-(3-boronopropyl)-1-(2-(piperidin-1-yl)ethyl)pyrrolidine-2-carboxylic acid

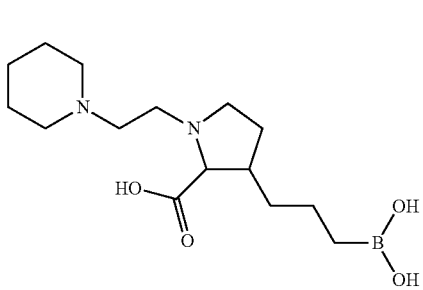 [SMILES: O=C(O)C1C(CCCB(O)O)CCN1CCN1CCCCC1]

Step 1: methyl 1-(2-(piperidin-1-yl) ethyl)-3-(3-(4,4,5,5-tetramethyl-1,3,2-dioxaborolan-2-yl)propyl)pyrrolidine-2-carboxylate

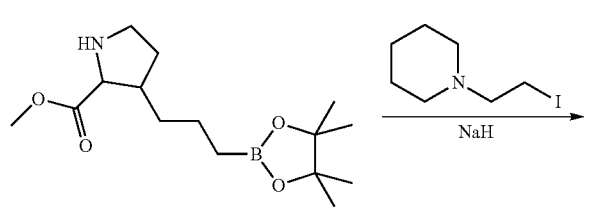

Sodium hydride (24 mg, 0.61 mmol, 60% in mineral oil) was added to a solution of methyl 3-(3-(4,4,5,5-tetramethyl-1,3,2-dioxaborolan-2-yl)propyl)pyrrolidine-2-carboxylate (120 mg, 0.40 mmol) in DMF (5.0 mL) under nitrogen at 0° C., and the resulting mixture was stirred for 0.5 h at 0° C., followed by addition of 1-(2-iodoethyl)piperidinyl (145 mg, 0.61 mmol) in DMF (1.0 mL). The reaction mixture was stirred for another 3.5 h at 15° C., then diluted with water and extracted with DCM. The combined organic phase was washed with brine, dried over anhydrous $Na_2SO_4$, filtered, and concentrated under reduced pressure. The residue was purified by RP-HPLC [C18 column, water (10 mM $NH_4HCO_3$)—$CH_3CN$] to give methyl 1-(2-(piperidin-1-yl) ethyl)-3-(3-(4,4,5,5-tetramethyl-1,3,2-dioxaborolan-2-yl)propyl)pyrrolidine-2-carboxylate. LCMS ($C_{22}H_{42}BN_2O_4^+$) (ES, m/z): 409 [M+H]$^+$.

Step 2: 3-(3-boronopropyl)-1-(2-(piperidin-1-yl)ethyl)pyrrolidine-2-carboxylic acid

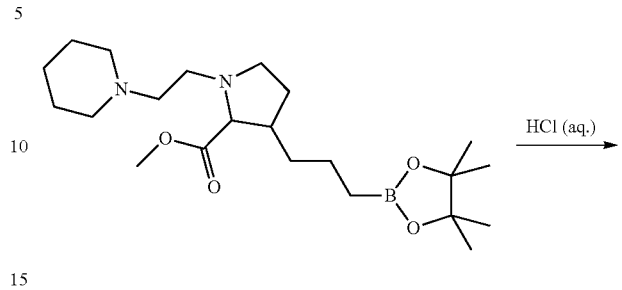

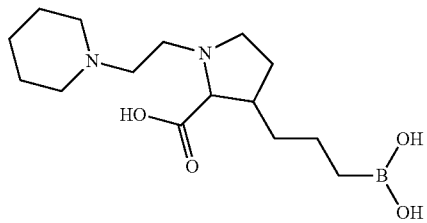

Example 10

A mixture of methyl 1-(2-(piperidin-1-yl)ethyl)-3-(3-(4,4,5,5-tetramethyl-1,3,2-dioxaborolan-2-yl)propyl)pyrrolidine-2-carboxylate (50 mg, 0.12 mmol) in 12 N HCl in water (2.0 mL, 24 mmol) was stirred at 100° C. for 12 h. The mixture was concentrated under reduced pressure to give 3-(3-boronopropyl)-1-(2-(piperidin-1-yl) ethyl) pyrrolidine-2-carboxylic acid as an HCl salt. LCMS ($C_{15}H_{28}BN_2O_3^+$) (ES, m/z): 295 [M–$H_2O$+H]$^+$. $^1$H NMR (400 MHz, $D_2O$) δ 4.14 (d, J=8.8 Hz, 1H), 3.58-3.74 (m, 2H), 3.51 (td, J=6.8, 13.6 Hz, 1H), 3.33-3.43 (m, 4H), 3.08-3.21 (m, 1H), 2.77-2.93 (m, 2H), 2.55-2.68 (m, 1H), 2.14-2.27 (m, 1H), 1.82-1.76 (m, 2H), 1.61-1.71 (m, 2H), 1.48-1.60 (m, 2H), 1.24-1.37 (m, 3H), 1.14-1.24 (m, 1H), 0.97-1.11 (m, 1H), 0.52-0.67 (m, 2H).

Example 11: 3-(3-boronopropyl)-1-(2-(piperidin-1-yl)ethyl)pyrrolidine-2-carboxylic acid

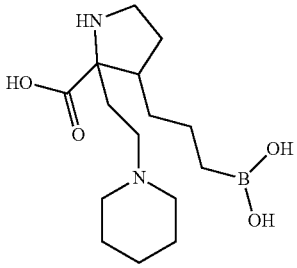 [SMILES: O=C(O)C1(CCN2CCCCC2)NCCC1CCCB(O)O]

Step 1: 1-tert-butyl 2-methyl 2-(2-oxoethyl)-3-(3-(4,4,5,5-tetramethyl-1,3,2-dioxaborolan-2-yl)propyl)pyrrolidine-1,2-dicarboxylate

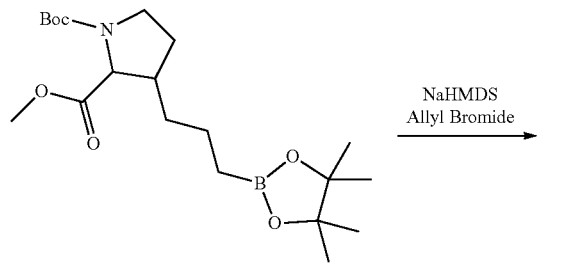

Sodium bis(trimethylsilyl)amide (3.8 mL, 3.8 mmol, 1.0 M in THF) was added to a solution of 1-tert-butyl 2-methyl 3-(3-(4,4,5,5-tetramethyl-1,3,2-dioxaborolan-2-yl)propyl)pyrrolidine-1,2-dicarboxylate (600 mg, 1.5 mmol) in THF (10 mL) at −40° C. under nitrogen, and the resulting mixture was stirred at −40° C. for 0.5 h, and then at 0° C. for another 1 h. 3-Bromoprop-1-ene (0.65 mL, 7.6 mmol) was added at −40° C., and the reaction mixture was stirred at −40° C. for 1 h, then at 15° C. for another 12 h. The mixture was poured into water and extracted with EtOAc, and the combined organic phase was washed with brine, dried over anhydrous Na$_2$SO$_4$, filtered and concentrated. The residue was purified by silica gel column chromatography (EtOAc in hexanes) to give 1-tert-butyl 2-methyl 2-allyl-3-(3-(4,4,5,5-tetramethyl-1,3,2-dioxaborolan-2-yl)propyl)pyrrolidine-1,2-dicarboxylate. LCMS (C$_{23}$H$_{41}$BNO$_6$$^+$)(ES, m/z): 438 [M+H]$^+$.

Step 2: 1-tert-butyl 2-methyl 2-allyl-3-(3-(4,4,5,5-tetramethyl-1,3,2-dioxaborolan-2-yl)propyl)pyrrolidine-1,2-dicarboxylate

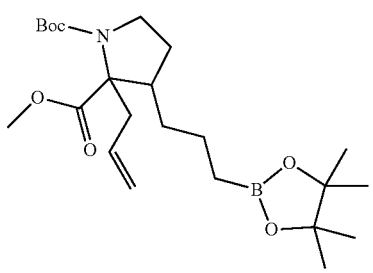

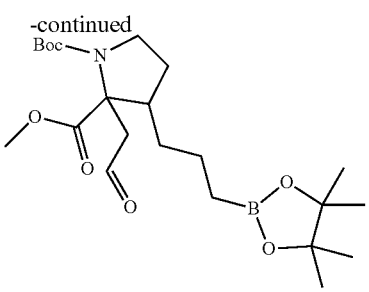

A solution of 1-tert-butyl 2-methyl 2-allyl-3-(3-(4,4,5,5-tetramethyl-1,3,2-dioxaborolan-2-yl)propyl)pyrrolidine-1,2-dicarboxylate (200 mg, 0.46 mmol) in DCM (20 mL) was bubbled with a stream of ozone at −78° C. for 30 min to give a blue solution. The reaction mixture was then bubbled with oxygen for 5 min, followed by addition of triphenylphosphine (240 mg, 0.92 mmol) at 0° C. under nitrogen, and then stirred at 15° C. for 16 h. The mixture was concentrated in vacuum, and the residue was purified by silica gel column chromatography (EtOAc in hexanes) to give 1-tert-butyl 2-methyl 2-(2-oxoethyl)-3-(3-(4,4,5,5-tetramethyl-1,3,2-dioxaborolan-2-yl)propyl)pyrrolidine-1,2-dicarboxylate, which was used for next step directly. LCMS (C$_{22}$H$_{39}$BNO$_7$$^+$)(ES, m/z): 440 [M+H]$^+$.

Step 3: 1-tert-butyl 2-methyl 2-allyl-3-(3-(4,4,5,5-tetramethyl-1,3,2-dioxaborolan-2-yl)propyl)pyrrolidine-1,2-dicarboxylate

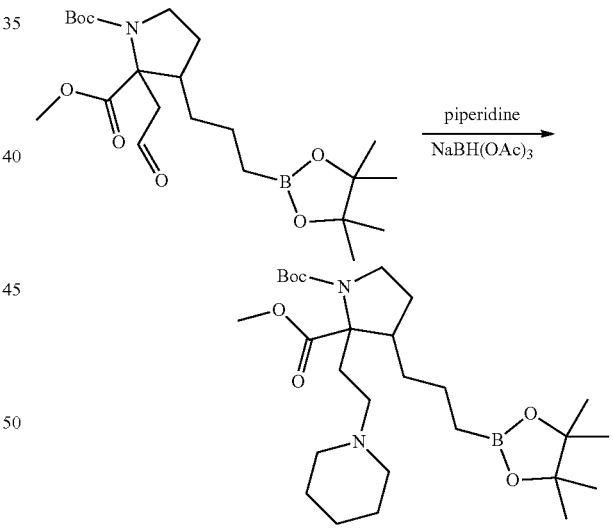

Sodium triacetoxyborohydride (86 mg, 0.41 mmol) was added to a solution of 1-tert-butyl 2-methyl 2-(2-oxoethyl)-3-(3-(4,4,5,5-tetramethyl-1,3,2-dioxaborolan-2-yl)propyl)pyrrolidine-1,2-dicarboxylate (90 mg, 0.21 mmol) and piperidinyl (52 mg, 0.62 mmol) in 1,2-dichloroethane (5.0 mL), and the reaction mixture was stirred at 20° C. for 14 h under nitrogen. The mixture was quenched with water, and extracted with DCM. The combined organic phase was washed with brine, dried over anhydrous Na$_2$SO$_4$, filtered and concentrated. The residue was purified by RP-HPLC [C18 column, water (0.1% TFA)-CH$_3$CN] to give 1-tert-butyl 2-methyl 2-(2-(piperidin-1-yl)ethyl)-3-(3-(4,4,5,5-te-

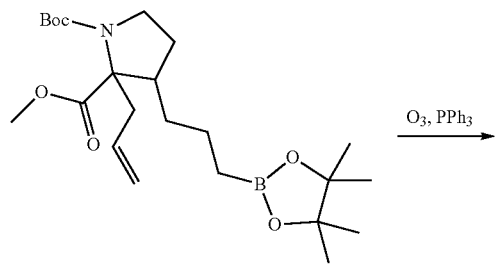

tramethyl-1,3,2-dioxaborolan-2-yl)propyl)pyrrolidine-1,2-dicarboxylate. LCMS ($C_{27}H_{50}BN_2O_6^+$)(ES, m/z): 509 [M+H]$^+$.

Step 4: 3-(3-boronopropyl)-2-(2-(piperidin-1-yl)ethyl)pyrrolidine-2-carboxylic acid

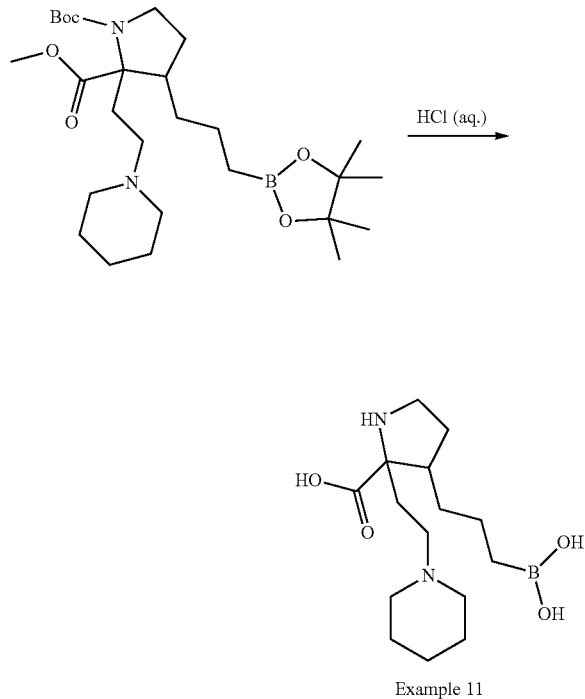

Example 11

A mixture of 1-tert-butyl 2-methyl 2-(2-(piperidin-1-yl)ethyl)-3-(3-(4,4,5,5-tetramethyl-1,3,2-dioxaborolan-2-yl)propyl)pyrrolidine-1,2-dicarboxylate (50 mg, 0.098 mmol) in 12 N HCl in water (1.0 mL) was stirred at 100° C. for 12 h. The mixture was concentrated to give 3-(3-boronopropyl)-2-(2-(piperidin-1-yl)ethyl)pyrrolidine-2-carboxylic acid as an HCl salt. LCMS ($C_{15}H_{30}BN_2O_4^+$)(ES, m/z): 313 [M+H]$^+$. $^1$H NMR (400 MHz, D$_2$O) δ 3.50-3.26 (m, 3H), 3.18 (br d, J=8.3 Hz, 1H), 3.11-2.93 (m, 2H), 2.77 (br d, J=11.0 Hz, 2H), 2.41 (br t, J=11.4 Hz, 1H), 2.25-1.99 (m, 3H), 1.75 (br d, J=14.5 Hz, 2H), 1.65-1.44 (m, 4H), 1.44-1.10 (m, 4H), 1.01 (br d, J=10.1 Hz, 1H), 0.60 (br d, J=7.0 Hz, 2H).

Example 12: {3-[2-(hydroxymethyl)pyrrolidin-3-yl]propyl}boronic acid

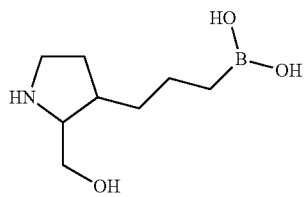 [SMILES: OCC1NCCC1CCCB(O)O]

Step 1: benzyl 2-(hydroxymethyl)-3-[3-(4,4,5,5-tetramethyl-1,3,2-dioxaborolan-2-yl)propyl]pyrrolidine-1-carboxylate

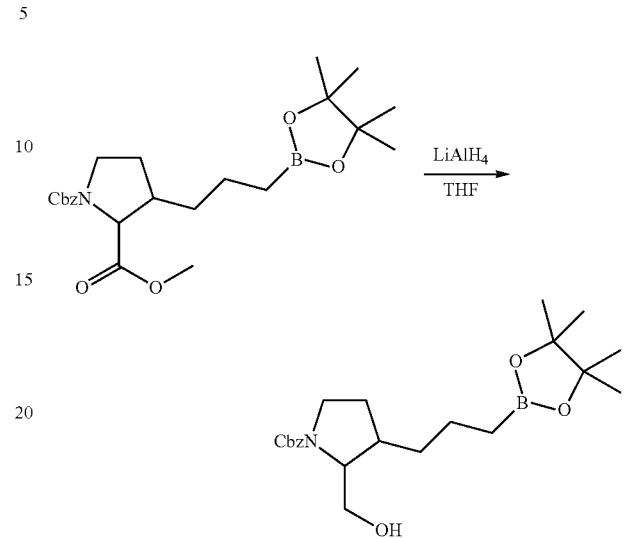

A mixture of 1-benzyl 2-methyl 3-(3-(4,4,5,5-tetramethyl-1,3,2-dioxaborolan-2-yl)propyl)pyrrolidine-1,2-dicarboxylate (40 mg, 0.093 mmol) and lithium aluminum hydride (11 mg, 0.28 mmol) in THF (8.0 mL) was stirred at 0° C. for 1 h, and the reaction mixture was quenched with water, followed by addition of Na$_2$SO$_4$, and stirred for 0.5 h at 25° C. The mixture was filtered and the filtrate was concentrated under reduced pressure. The residue was purified by RP-HPLC [C18 column, water (0.10% TFA)-CH$_3$CN] to give benzyl 2-(hydroxymethyl)-3-[3-(4,4,5,5-tetramethyl-1,3,2-dioxaborolan-2-yl)propyl]pyrrolidine-1-carboxylate. LCMS ($C_{22}H_{35}BNO_5^+$)(ES, m/z): 404 [M+H]$^+$.

Step 2: {3-[2-(hydroxymethyl)pyrrolidin-3-yl]propyl}boronic acid

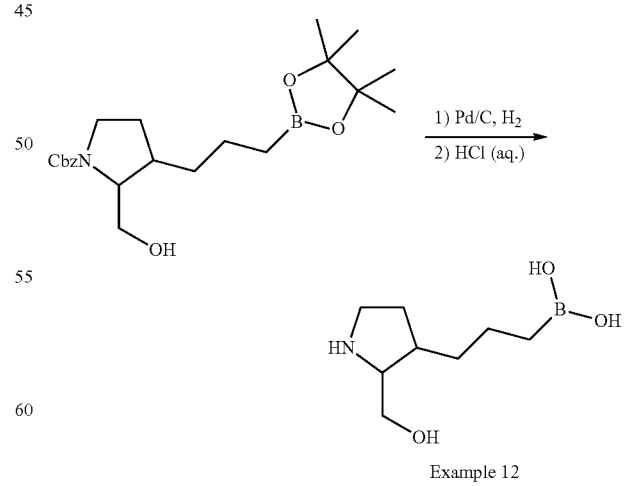

Example 12

10% palladium on carbon (66 mg, 0.062 mmol) was added to a solution of benzyl 2-(hydroxymethyl)-3-[3-(4,4,5,5-tetramethyl-1,3,2-dioxaborolan-2-yl)propyl]pyrrolidine-1-carboxylate (25 mg, 0.062 mmol) in THF (3.0 mL) under nitrogen atmosphere, and the reaction mixture was degassed and backfilled with hydrogen (three times). The resulting mixture was stirred under hydrogen (Pressure: 15 psi) at 25° C. for 12 h, then filtered and the filtrate was concentrated under reduced pressure. The crude mixture was dissolved in 6 N HCl in water (3.0 mL) and stirred for 0.5 h at room temperature, and the mixture was concentrated under reduce pressure. The residue was purified by RP-HPLC [C18 column, water (0.1% TFA)-CH$_3$CN] to give (3-((2S,3R)-2-(hydroxymethyl)pyrrolidin-3-yl)propyl)boronic acid as a TFA salt. LCMS (C$_8$H$_{19}$BNO$_3{}^+$)(ES, m/z): 188 [M+H]$^+$. $^1$H NMR (400 MHz, D$_2$O) δ 3.78-3.68 (m, 1H), 3.67-3.43 (m, 2H), 3.33-3.22 (m, 1H), 3.13 (td, J=8.4, 11.9 Hz, 1H), 2.30-2.17 (m, 1H), 2.13-1.98 (m, 1H), 1.69-1.50 (m, 1H), 1.39-1.07 (m, 4H), 0.71-0.54 (m, 2H).

Example 13: (3R)-3-{3-[(3aR,4R,6R,7aS)-3a,5,5-trimethylhexahydro-4,6-methano-1,3,2-benzodioxaborol-2-yl]propyl}-L-proline

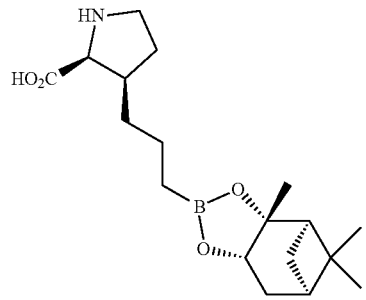 [SMILES: CC1(C)[C@H]2C[C@@H]3OB(CCC[C@@H]4CCN[C@@H]4C(=O)O)O[C@]3(C)[C@@H]1C2]

Step 1: (3R)-3-{3-[(3aR,4R,6R,7aS)-3a,5,5-trimethylhexahydro-4,6-methano-1,3,2-benzodioxaborol-2-yl]propyl}-L-proline

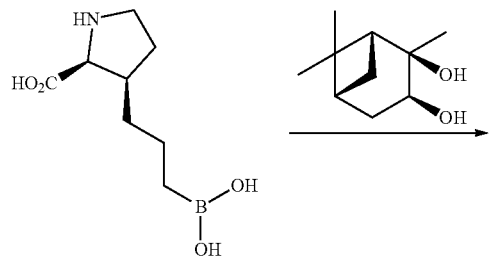

Example 9A

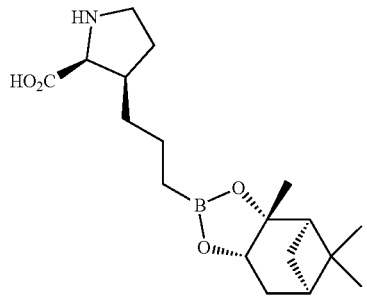

Example 13

(1R,2R,3S,5R)-(−)-2,3-pinanediol (50 mg, 0.30 mmol) was added to the stirred suspension of (3R)-3-[3-(dihydroxyboranyl)propyl]-L-proline (HCl salt, 35 mg, 0.15 mmol) in CH$_3$CN (1.7 mL) in one portion at room temperature. The reaction mixture was heated to 85° C. with stirring overnight, and then cooled to room temperature. The mixture was concentrated under reduced pressure, and the residue was triturated three times with a mixture of methyl tert-butyl ether and hexanes (1/20 V/V) to afford (3R)-3-{3-[(3aR,4R,6R,7aS)-3a,5,5-trimethylhexahydro-4,6-methano-1,3,2-benzodioxaborol-2-yl]propyl}-L-proline as an HCl salt. LCMS (C$_1$H$_{31}$BNO$_4$)(ES, m/z): 336 [M+H]$^+$. $^1$H NMR (500 MHz, DMSO-d6) δ 4.28 (dd, J=8.5, 3.0 Hz, 1H), 4.19 (d, J=7.9 Hz, 1H), 3.18-3.11 (m, 1H), 2.46-2.39 (m, 1H), 2.34-2.24 (m, 1H), 2.21-2.14 (m, 1H), 2.12-2.04 (m, 1H), 1.95 (t, J=5.5 Hz, 1H), 1.86 (br, 1H), 1.72-1.59 (m, 2H), 1.47-1.32 (m, 2H), 1.30 (s, 3H), 1.25 (s, 3H), 1.21-1.12 (m, 1H), 0.98 (d, J=11.0 Hz, 1H), 0.81 (s, 3H), 0.78-0.66 (m, 2H).

Example 14: (3R)-3-[3-(dihydroxyboranyl)propyl]-3-methyl-L-proline

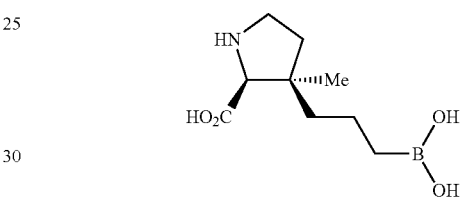

Step 1: 1-tert-butyl 2-methyl (2S)-3-methyl-4-oxo-3-(prop-2-en-1-yl)pyrrolidine-1,2-dicarboxylate

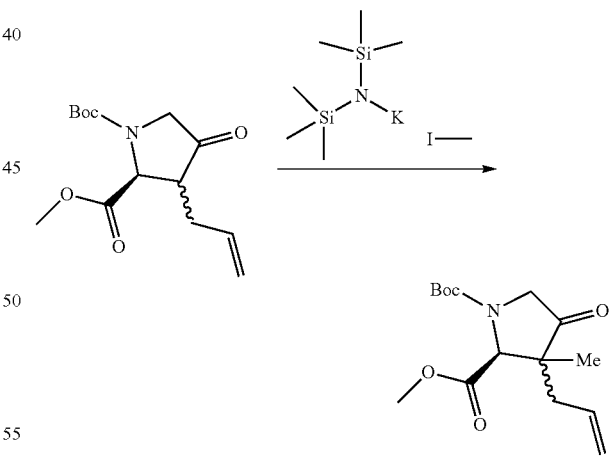

Potassium bis(trimethylsilyl)amide (0.5 M in Toluene, 15 mL, 7.5 mmol) was added dropwise to the stirred solution of 1-tert-butyl 2-methyl (2S)-4-oxo-3-(prop-2-en-1-yl)pyrrolidine-1,2-dicarboxylate (2.1 g, 7.5 mmol) in THF (23 mL) at −78° C., and the reaction mixture was stirred for 1 h at −78° C., followed by addition of iodomethane (0.47 mL, 7.5 mmol) at −78° C., and the resulting mixture was allowed to warm to room temperature and stirred overnight. The mixture was quenched with saturate aqueous NH$_4$Cl, and extracted with DCM.

The combined organic layer was dried over Na₂SO₄, filtered, and concentrated under reduced pressure. The residue was purified by silica gel column chromatography (EtOAc in hexanes) to afford 1-tert-butyl 2-methyl (2S)-3-methyl-4-oxo-3-(prop-2-en-1-yl)pyrrolidine-1,2-dicarboxylate as a mixture of diastereomers. LC-MS ($C_{10}H_{16}NO_3^+$) (ES, m/z): 198 [M-$CO_2C_4H_8$+H]⁺.

Step 2: 1-tert-butyl 2-methyl (2S,3S,4S)-4-hydroxy-3-methyl-3-(prop-2-en-1-yl)pyrrolidine-1,2-dicarboxylate

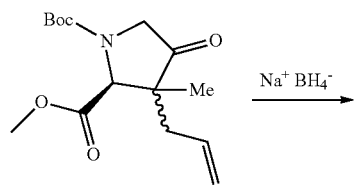

Sodium borohydride (0.23 g, 6.1 mmol) was added in two portions to the stirred solution of 1-tert-butyl 2-methyl (2S)-3-methyl-4-oxo-3-(prop-2-en-1-yl)pyrrolidine-1,2-dicarboxylate (1.2 g, 4.0 mmol) in MeOH (12 mL) within 10 min at 0° C., and the reaction mixture was allowed to warm to room temperature and stirred overnight. The mixture was quenched with saturated aqueous NH₄Cl, and extracted with EtOAc. The combined organic layer was dried over Na₂SO₄, filtered, and concentrated under reduced pressure. The residue was purified by silica gel column chromatography (EtOAc in hexanes) to afford 1-tert-butyl 2-methyl (2S,3S,4S)-4-hydroxy-3-methyl-3-(prop-2-en-1-yl)pyrrolidine-1,2-dicarboxylate as the first eluting peak (existed as two rotamers) followed by an inseparable mixture of isomers. LC-MS ($C_{10}H_{18}NO_3^+$)(ES, m/z): 200 [M-$CO_2C_4H_8$+H]⁺. ¹H NMR (600 MHz, DMSO-d₆): δ 5.82-5.72 (m, 1H), 5.08-4.99 (m, 2H), 4.92 (dd, J=12.6, 4.5 Hz, 1H), 3.83 (s, 0.37H), 3.81 (s, 0.63H), 3.76-3.71 (m, 1H), 3.62 (s, 1.90H), 3.60 (s, 1.10H), 3.60-3.53 (m, 1H), 3.33-3.30 (m, 1H), 2.27-2.20 (m, 1H), 2.05-1.96 (m, 1H), 1.39 (s, 3.30H), 1.31 (s, 5.70H), 0.97 (s, 1.90H), 0.95 (s, 1.10H). LC-MS ($C_{10}H_{18}NO_3^+$) (ES, m/z): 200 [M-$CO_2C_4H_8$+H]⁺.

Step 3: 1-tert-butyl 2-methyl (2S,3S,4S)-3-methyl-4-{[(4-methylphenoxy)carbonothioyl]oxy}-3-(prop-2-en-1-yl)pyrrolidine-1,2-dicarboxylate

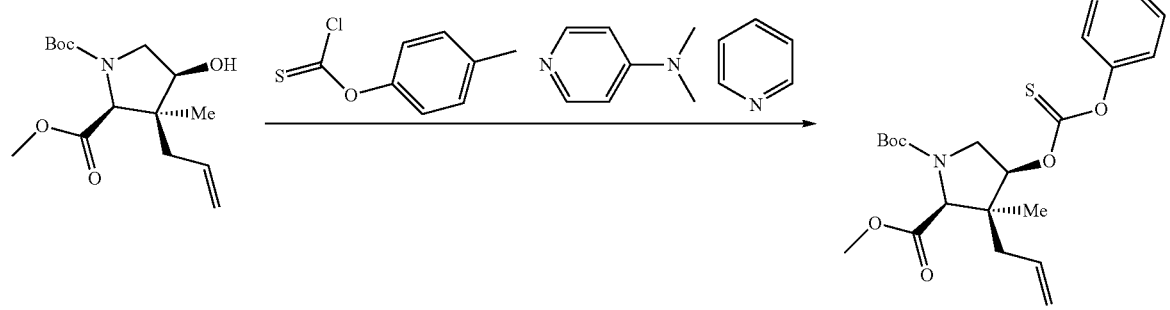

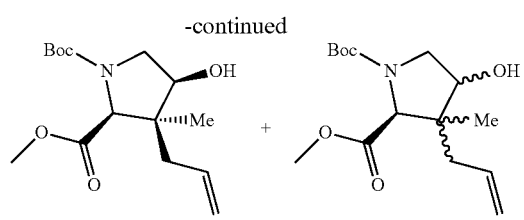

Pyridine (927 μL, 11 mmol) was added to the stirred solution of 1-tert-butyl 2-methyl (2S,3S,4S)-4-hydroxy-3-methyl-3-(prop-2-en-1-yl)pyrrolidine-1,2-dicarboxylate (686 mg, 2.3 mmol) and 4-dimethylaminopyridine (28 mg, 0.23 mmol) in DCM (6.0 mL), followed by dropwise addition of p-tolyl chlorothionoformate (873 μL, 5.7 mmol) at 0° C., and the reaction mixture was allowed to warm to room temperature and stirred overnight. The resulting mixture was cooled to 0° C., and pyridine (927 μL, 11 mmol) was added in one portion, followed by dropwise addition of p-tolyl chlorothionoformate (873 μL, 5.7 mmol). The reaction mixture was allowed to warm to room temperature and stirred for another 8 h. The mixture was quenched with saturated aqueous NaHCO₃, and extracted with DCM. The combined organic layer was dried over Na₂SO₄, filtered, and concentrated under reduced pressure. The residue was purified by silica gel column chromatography (EtOAc in hexanes) to afford 1-tert-butyl 2-methyl (2S,3S,4S)-3-methyl-4-{[(4-methylphenoxy)carbonothioyl]oxy}-3-(prop-2-en-1-yl)pyrrolidine-1,2-dicarboxylate. LC-MS ($C_{23}H_{31}NNaO_6S^+$)(ES, m/z): 472 [M+Na]⁺.

Step 4. 1-tert-butyl 2-methyl (2S,3R)-3-methyl-3-(prop-2-en-1-yl)pyrrolidine-1,2-dicarboxylate

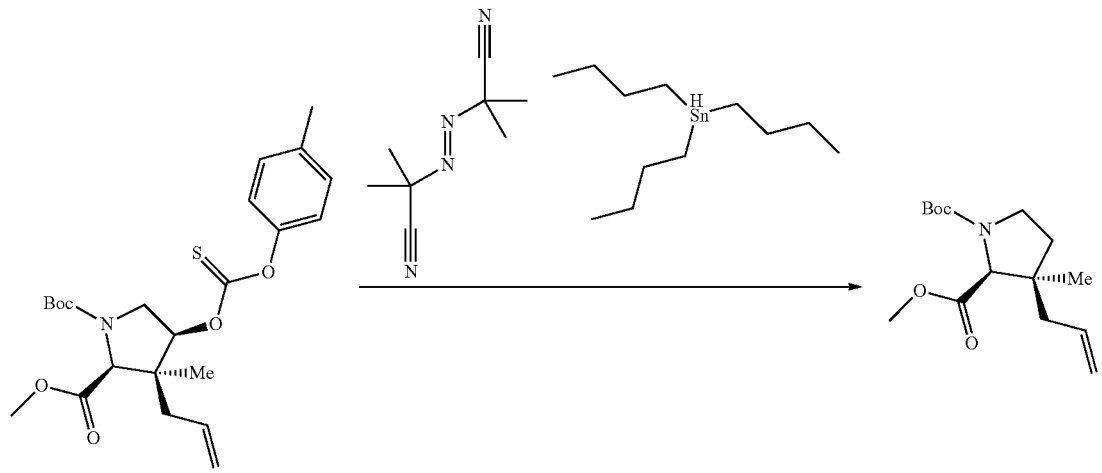

Tri-n-butyltin hydride (0.60 mL, 2.2 mmol) was added to the stirred solution of 1-tert-butyl 2-methyl (2S,3S,4S)-3-methyl-4-{[(4-methylphenoxy)carbonothioyl]oxy}-3-(prop-2-en-1-yl)pyrrolidine-1,2-dicarboxylate (452 mg, 1.0 mmol) and 2,2'-azobis(2-methylpropionitrile)(17 mg, 0.10 mmol) in toluene (7.0 mL) under nitrogen atmosphere at room temperature, and the reaction mixture was heated to 110° C. and stirred for 2.5 h, then cooled to room temperature and purified by silica gel column chromatography (EtOAc in hexanes) to afford 1-tert-butyl 2-methyl (2S,3R)-3-methyl-3-(prop-2-en-1-yl)pyrrolidine-1,2-dicarboxylate. LC-MS ($C_{10}H_{18}NO_2^+$)(ES, m/z): 184 [M-$CO_2C_4H_8$+H]$^+$.

Step 5: 1-tert-butyl 2-methyl (2S,3R)-3-methyl-3-[3-(4,4,5,5-tetramethyl-1,3,2-dioxaborolan-2-yl)propyl]pyrrolidine-1,2-dicarboxylate A pre-formed solution of bis(1,5-cyclooctadiene)diiridium(I) dichloride (22 mg, 0.032 mmol), 1,2-bis(diphenylphosphino)ethane (26 mg, 0.064 mmol), and pinacolborane (500 μL, 3.1 mmol) in DCM (2.5 mL) was added to the stirred solution of 1-tert-butyl 2-methyl (2S,3R)-3-methyl-3-(prop-2-en-1-yl)pyrrolidine-1,2-dicarboxylate (182 mg, 0.64 mmol) in DCM (2.5 mL) under nitrogen atmosphere at room temperature, and the reaction mixture was stirred at room temperature for 24 h, and then concentrated under reduced pressure. The residue was purified by silica gel column chromatography (EtOAc in hexanes) to afford 1-tert-butyl 2-methyl (2S,3R)-3-methyl-3-[3-(4,4,5,5-tetramethyl-1,3,2-dioxaborolan-2-yl)propyl]pyrrolidine-1,2-dicarboxylate. LC-MS ($C_{16}H_{31}BNO_4^+$)(ES, m/z): 312 [M-$CO_2C_4H_8$+H]$^+$.

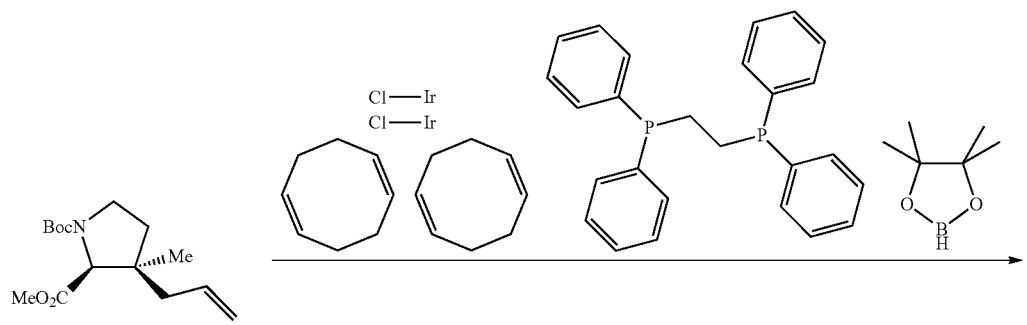

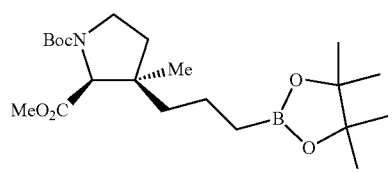

Step 6: (3R)-3-[3-(dihydroxyboranyl)propyl]-3-methyl-L-proline

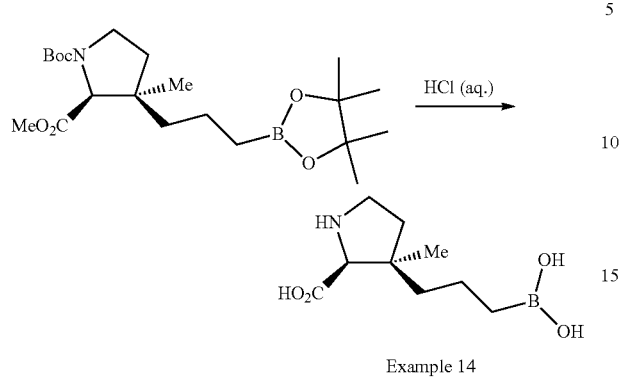

Example 14

12 N HCl in water (1.3 mL) was added to the stirred suspension of 1-tert-butyl 2-methyl (2S,3R)-3-methyl-3-[3-(4,4,5,5-tetramethyl-1,3,2-dioxaborolan-2-yl)propyl]pyrrolidine-1,2-dicarboxylate (256 mg, 0.62 mmol) in water (1.3 mL) at room temperature, and the reaction mixture was heated to 90° C. with stirring overnight, then cooled to room temperature. The mixture was diluted with water, filtered through a 0.25 μm filter and lyophilized to afford (3R)-3-[3-(dihydroxyboranyl)propyl]-3-methyl-L-proline as an HCl salt. LCMS ($C_9H_{17}BNO_3^+$)(ES, m/z): 198 [M–$H_2O$+H]$^+$. $^1$H NMR (500 MHz, $D_2O$) δ 3.91 (s, 1H), 3.50-3.38 (m, 2H), 2.14 (ddd, J=12.9, 7.3, 5.1 Hz, 1H), 1.87 (dt, J=13.4, 8.9 Hz, 1H), 1.54-1.28 (m, 4H), 1.28 (s, 3H), 0.79 (t, J=7.5 Hz, 2H).

Step 7: (3R)-3-[3-(dihydroxyboranyl)propyl]-3-methyl-L-proline (free base)

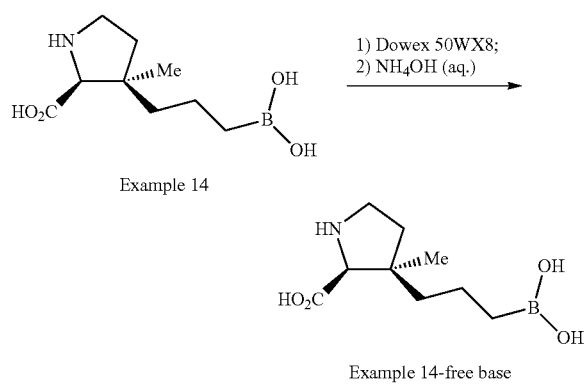

(3R)-3-[3-(dihydroxyboranyl)propyl]-3-methyl-L-proline (crude HCl salt, 15 g) was purified on 600 g of Dowex 50WX8 acidic resin (washed with water until pH neutral, then eluted with 8N aqueous ammonium hydroxide) to afford (3R)-3-[3-(dihydroxyboranyl)propyl]-3-methyl-L-proline as a free base. LCMS ($C_8H_{15}BNO_3^+$)(ES, m/z): 198 [M–$H_2O$+H]$^+$. $^1$H NMR (400 MHz, $D_2O$) δ 3.63 (s, 1H), 3.42-3.22 (m, 2H), 2.07-2.03 (m, 1H), 1.79-1.41 (m, 1H), 1.31-1.20 (m, 7H), 0.76-0.71 (m, 2H).

Example 15A: (3R)-3-[3-(dihydroxyboranyl)propyl]-D-proline

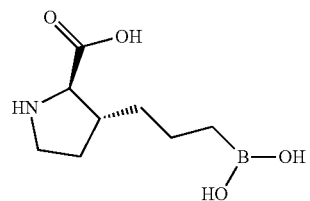 [SMILES: O=C(O)[C@@H]1NCC[C@H]1CCCB(O)O]

Step 1: (2R,3R)-1-benzyl 2-methyl 3-allylpyrrolidine-1,2-dicarboxylate

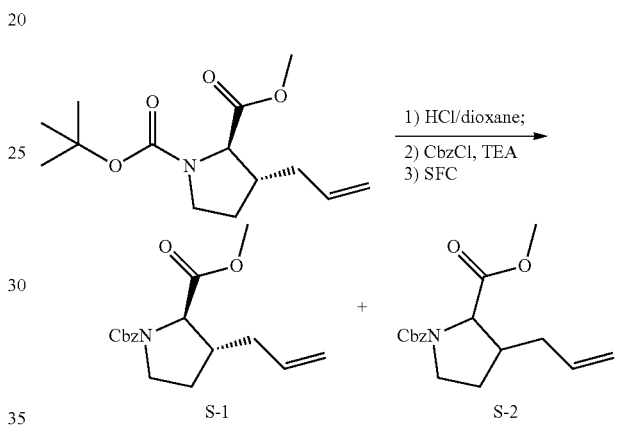

HCl in dioxane (4.0 M, 5.0 mL, 20 mmol) was added to (2R,3R)-1-tert-butyl 2-methyl 3-allylpyrrolidine-1,2-dicarboxylate (540 mg, 2.0 mmol) and the reaction mixture was stirred for 1 h at 0° C., then for another 12 h at 25° C. The mixture was concentrated under reduced pressure, and the residue was dissolved in DCM (8.0 mL), followed by addition of benzyl chloroformate (0.46 mL, 3.3 mmol) and triethylamine (1.4 mL, 9.7 mmol) at 0° C. The resulting mixture was stirred at 25° C. for 12 h, then quenched with saturated aqueous NaHCO$_3$, and extracted with DCM. The combined organic layer was washed with brine, dried over anhydrous Na$_2$SO$_4$, filtered and concentrated. The residue was purified by silica gel column chromatography (EtOAc in hexanes) to give crude product, which was further purified by RP-HPLC [C18 column, water (0.1% TFA)-CH$_3$CN] and chiral SFC [Column: DAICEL CHIRALPAK AD-H (250 mm*30 mm, 5 μm), Mobile phase: A: CO$_2$, B: EtOH (0.1% NH$_3$.H$_2$O), Gradient: 15% of B in 7.2 min and hold 15% for 1 min, Flow Rate (mL/min) 50, Column temperature: 40° C.] to give (2R,3R)-1-benzyl 2-methyl 3-allylpyrrolidine-1,2-dicarboxylate (S-1, t$_r$=2.26 min) as the first eluting peak and 1-benzyl 2-methyl 3-allylpyrrolidine-1,2-dicarboxylate (S-2, t$_r$=2.82 min) as the second eluting peak. S-1 LCMS ($C_{17}H_{22}NO_4^+$)(ES, m/z): 304 [M+H]$^+$. $^1$H NMR (400 MHz, CDCl$_3$) δ 7.39-7.27 (m, 5H), 5.85-5.66 (m, 1H), 5.22-5.14 (m, 1H), 5.14-4.99 (m, 3H), 4.13-4.00 (m, 1H), 3.75 (s, 1H), 3.67-3.53 (m, 4H), 2.39-2.25 (m, 2H), 2.18-1.97 (m, 2H), 1.65 (tt, J=6.8, 13.7 Hz, 1H). S-2 LCMS ($C_{17}H_{22}NO_4^+$)(ES, m/z): 304 [M+H]$^+$.

Step 2: (2R,3R)-1-benzyl 2-methyl 3-(3-(4,4,5,5-tetramethyl-1,3,2-dioxaborolan-2-yl)propyl)pyrrolidine-1,2-dicarboxylate

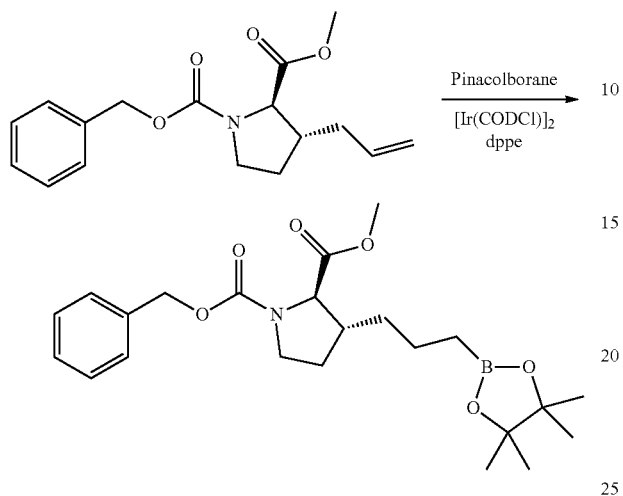

A solution of 4,4,5,5-tetramethyl-1,3,2-dioxaborolane (0.14 mL, 0.99 mmol), chloro(1,5-cyclooctadiene)iridium(I) dimer (11 mg, 0.016 mmol) and 1,2-bis(diphenylphosphino)ethane (13 mg, 0.033 mmol) in anhydrous DCM (3.0 mL) was bubbled with a stream of nitrogen for 3 min, and stirred at 25° C. for 20 min, followed by addition of (2R,3R)-1-benzyl 2-methyl 3-allylpyrrolidine-1,2-dicarboxylate (100 mg, 0.33 mmol) in DCM (3.0 mL). The reaction mixture was stirred at 25° C. for 12 h under nitrogen, and concentrated in vacuo. The residue was purified by silica gel column chromatography (EtOAc in hexanes) to give (2R,3R)-1-benzyl 2-methyl 3-(3-(4,4,5,5-tetramethyl-1,3,2-dioxaborolan-2-yl)propyl)pyrrolidine-1,2-dicarboxylate. LCMS ($C_{23}H_{35}BNO_6^+$)(ES, m/z): 432 [M+H]$^+$.

Step 3: (3R)-3-[3-(dihydroxyboranyl)propyl]-D-proline

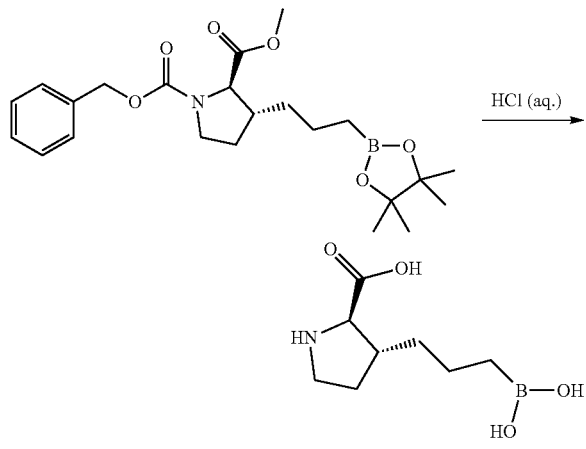

Example 15A

A mixture of (2R,3R)-1-benzyl 2-methyl 3-(3-(4,4,5,5-tetramethyl-1,3,2-dioxaborolan-2-yl)propyl)pyrrolidine-1,2-dicarboxylate (130 mg, 0.30 mmol) in 12 N HCl in water (3.0 mL, 36 mmol) was stirred at 100° C. for 13 h. The mixture was washed with DCM, and the aqueous layer was concentrated in vacuum to give (3R)-3-[3-(dihydroxyboranyl)propyl]-D-proline as an HCl salt. LCMS ($C_8H_{17}BNO_4^+$) (ES, m/z): 202 [M+H]$^+$. $^1$H NMR (400 MHz, D$_2$O) δ 3.89 (d, J=7.5 Hz, 1H), 3.43-3.35 (m, 1H), 3.34-3.25 (m, 1H), 2.47-2.34 (m, 1H), 2.26-2.14 (m, 1H), 1.74-1.60 (m, 2H), 1.49-1.30 (m, 3H), 0.81-0.65 (m, 2H).

Example 15B: (3S)-3-[3-(dihydroxyboranyl)propyl]-L-proline

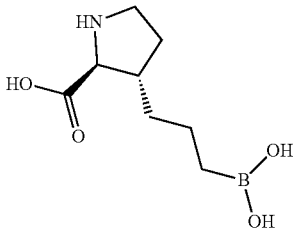 [SMILES: O=C(O)[C@H]1NCC[C@@H]1CCCB(O)O]

Step 1: 1-benzyl 2-methyl 3-allylpyrrolidine-1,2-dicarboxylate

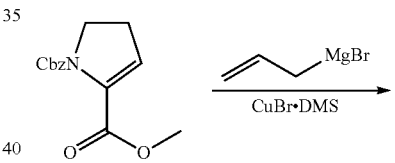

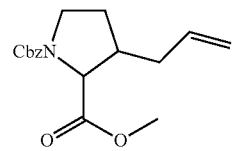

Allylmagnesium bromide (1.0 M in Et$_2$O, 11 mL, 11 mmol) was added to a solution of Copper(I) bromide-dimethyl sulfide (787 mg, 3.8 mmol) in diethyl ether (20 mL) at −35° C., and the resulting mixture was stirred for 1 h at −35° C. A solution of 1-benzyl 2-methyl 4,5-dihydro-1H-pyrrole-1,2-dicarboxylate (2.0 g, 7.7 mmol) in Et$_2$O (50 mL) was added over 30 min, and the reaction mixture was stirred for 30 min at −35° C. and then for another 30 min at 0° C. The mixture was quenched with saturated aqueous NH$_4$Cl and extracted with EtOAc, and the combined organic phase was washed with brine, dried over anhydrous Na$_2$SO$_4$, filtered and concentrated under reduced pressure. The residue was purified by RP-HPLC [C18 column, water (0.1% TFA)-CH$_3$CN] to give 1-benzyl 2-methyl 3-allylpyrrolidine-1,2-dicarboxylate. LCMS ($C_{17}H_{22}NO_4^+$)(ES, m/z): 304 [M+H]$^+$.

Step 2: 1-benzyl 2-methyl 3-allylpyrrolidine-1,2-dicarboxylate

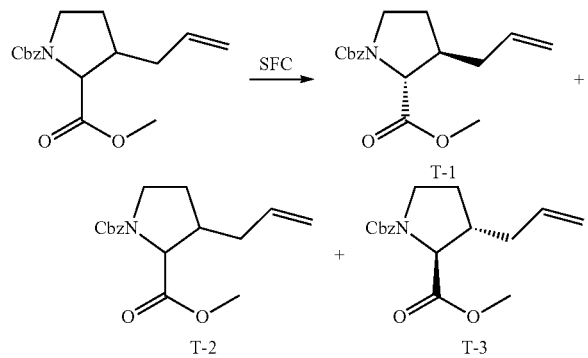

The 1-benzyl 2-methyl 3-allylpyrrolidine-1,2-dicarboxylate (150 mg, 0.49 mmol) was resolved by chiral-SFC [Column: DAICEL CHIRALPAK AD-H (250 mm*30 mm, 5 μm), Mobile phase: A: $CO_2$, B: MeOH (0.1% $NH_3.H_2O$), Gradient: 10% of B in 11.5 min and hold 10% for 1 min, Flow Rate (mL/min) 50, Column temperature: 40° C.] to give (2R,3R)-1-benzyl 2-methyl 3-allylpyrrolidine-1,2-dicarboxylate (T-1, $t_r$=2.112 min) as the first eluting peak, and 1-benzyl 2-methyl 3-allylpyrrolidine-1,2-dicarboxylate (T-2, $t_r$=2.412 min) as the second eluting peak, and (2S,3S)-1-benzyl 2-methyl 3-allylpyrrolidine-1,2-dicarboxylate (2-T-3, $t_r$=2.706 min) as the third eluting peak. $^1$H NMR showed that T-1 and T-2 were rotamers. T-1 LCMS $(C_{17}H_{22}NO_4^+)$(ES, m/z): 304 [M+H]$^+$. $^1$H NMR (400 MHz, $CDCl_3$) δ 7.39-7.24 (m, 5H), 5.82-5.67 (m, 1H), 5.20-4.96 (m, 4H), 4.00 (d, J=4.4 Hz, 1H), 3.73 (s, 1H), 3.63-3.51 (m, 3H), 2.36-2.24 (m, 2H), 2.17-2.03 (m, 2H), 1.68-1.58 (m, 1H). T-2 LCMS $(C_{17}H_{22}NO_4^+)$(ES, m/z): 304 [M+H]$^+$. T-3 LCMS $(C_{17}H_{22}NO_4^+)$(ES, m/z): 304 [M+H]$^+$. $^1$H NMR (400 MHz, $CDCl_3$) δ 7.40-7.24 (m, 5H), 5.83-5.66 (m, 1H), 5.22-4.97 (m, 4H), 4.13-3.98 (m, 1H), 3.75 (s, 1H), 3.67-3.53 (m, 4H), 2.40-2.24 (m, 2H), 2.19-2.00 (m, 2H), 1.70-1.57 (m, 1H).

Step 3: 1-benzyl 2-methyl (2S,3S)-3-(3-(4,4,5,5-tetramethyl-1,3,2-dioxaborolan-2-yl)propyl)pyrrolidine-1,2-dicarboxylate

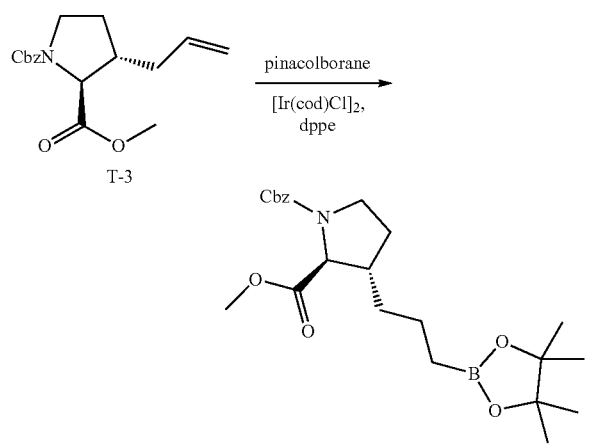

4,4,5,5-Tetramethyl-1,3,2-dioxaborolane (0.029 mL, 0.20 mmol) was added to a solution of bis(1,5-cyclooctadiene)diiridium(I) dichloride (4.4 mg, 6.6 μmol) and 1,2-bis(diphenylphosphino)ethane (5.3 mg, 0.013 mmol) in anhydrous DCM (5.0 mL) under nitrogen and the mixture was stirred for 10 min, followed by addition of 1-benzyl 2-methyl (2S,3S)-3-allylpyrrolidine-1,2-dicarboxylate (T-3, 45 mg, 0.10 mmol). The reaction mixture was stirred at 30° C. for 14 h under nitrogen. The mixture was concentrated under reduced pressure, and the residue was purified by RP-HPLC [C18 column, water (0.1% TFA)-$CH_3CN$] to give (2S,3S)-1-benzyl 2-methyl 3-(3-(4,4,5,5-tetramethyl-1,3,2-dioxaborolan-2-yl)propyl)pyrrolidine-1,2-dicarboxylate. LCMS $(C_{17}H_{25}BNO_6^+)$(ES, m/z): 350 [M-$C_6H_{10}$+H]$^+$.

Step 4: (3S)$_3$-[3-(dihydroxyboranyl)propyl]-L-proline

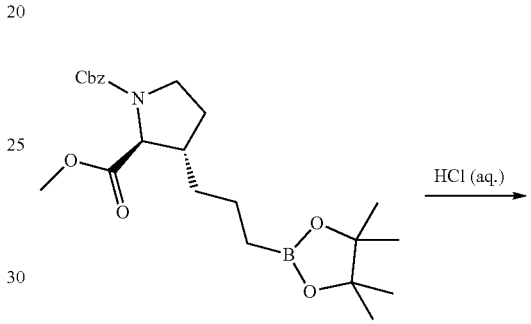

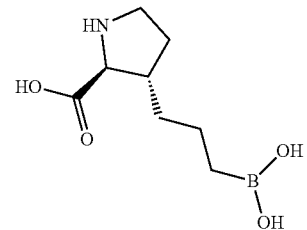

Example 15B

A mixture of (2S,3S)-1-benzyl 2-methyl 3-(3-(4,4,5,5-tetramethyl-1,3,2-dioxaborolan-2-yl)propyl)pyrrolidine-1,2-dicarboxylate (40 mg, 0.093 mmol) in 12 N HCl in water (3.0 mL, 36 mmol) was stirred at 100° C. for 16 h, and the mixture was diluted with water and washed with DCM. The combined aqueous phase was concentrated under reduced pressure to give (3S)-3-[3-(dihydroxyboranyl)propyl]-L-proline as an HCl salt. LCMS $(C_8H_{17}BNO_4^+)$(ES, m/z): 202 [M+H]$^+$. $^1$H NMR (400 MHz, $D_2O$) δ 3.76 (d, J=7.5 Hz, 1H), 3.34-3.14 (m, 2H), 2.35-2.21 (m, 1H), 2.15-2.02 (m, 1H), 1.63-1.50 (m, 2H), 1.39-1.20 (m, 3H), 0.68-0.55 (m, 2H).

Example 16A: (3R)-3-[3-(dihydroxyboranyl)propyl]-2-methyl-L-proline

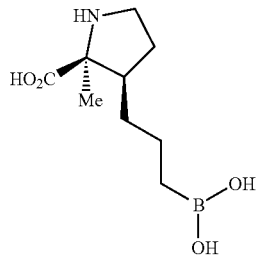 [SMILES: C[C@]1(C(=O)O)NCC[C@H]1CCCB(O)O]

Step 1: 1-tert-butyl 2-methyl 3-allyl-2-methylpyrrolidine-1,2-dicarboxylate

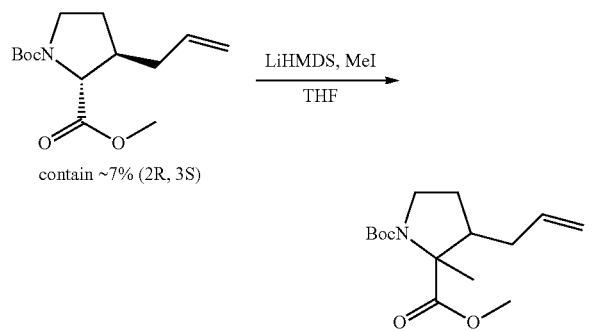

contain ~7% (2R, 3S)

To a solution of 1-(tert-butyl) 2-methyl (2R,3R)-3-allylpyrrolidine-1,2-dicarboxylate (700 mg, 2.6 mmol, contained ~7% 2R,3S isomer) in THF (6.0 mL) was added lithium bis(trimethylsilyl)amide (3.9 mL, 3.9 mmol, 1.0 M in THF) at −35° C. over 5 min under nitrogen. After stirring for 30 min at −35° ° C., the cooling bath was removed and the reaction mixture was stirred for 15 min. After cooling to −35° C., iodomethane (3.6 mL, 57 mmol) was added, and the reaction mixture was stirred for another 20 min at −35° C., then slowly warmed to 25° C. and stirred for 30 min. The mixture was quenched with saturated aqueous NH₄Cl and extracted with EtOAc. The combined organic phase was washed with brine, dried over anhydrous Na₂SO₄, filtered and concentrated under reduced pressure. The residue was purified by RP-HPLC [C18 column, water (0.10% TFA)-CN₃CN] to give 1-tert-butyl 2-methyl 3-allyl-2-methylpyrrolidine-1,2-dicarboxylate (mixture of isomers). LC-MS ($C_{15}H_{26}NO_4^+$)(ES, m/z): 284 [M+H]⁺.

Step 2: methyl 3-allyl-2-methylpyrrolidine-2-carboxylate

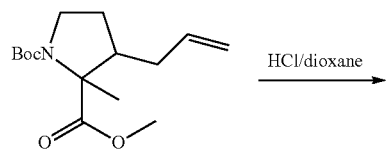

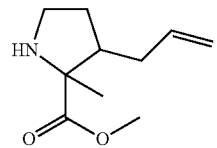

A solution of 1-tert-butyl 2-methyl 3-allyl-2-methylpyrrolidine-1,2-dicarboxylate (400 mg, 1.4 mmol) in HCl in dioxane (4.0 M, 2.0 mL, 8.0 mmol) was stirred at 25° C. for 4 h. The reaction mixture was concentrated under reduced pressure to give crude methyl 3-allyl-2-methylpyrrolidine-2-carboxylate (mixture of isomers), which was used in the next step without further purification. LC-MS ($C_{10}H_{18}NO_2^+$)(ES, m/z): 184 [M+H]⁺.

Step 3: 1-benzyl 2-methyl-3-allyl-2-methylpyrrolidine-1,2-dicarboxylate

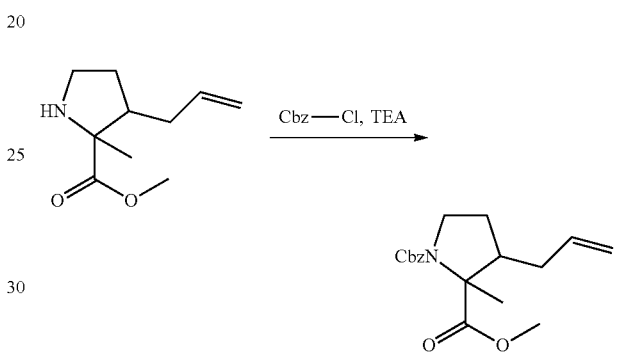

A solution of methyl 3-allyl-2-methylpyrrolidine-2-carboxylate (250 mg, 1.4 mmol) and TEA (0.57 mL, 4.1 mmol) in dry DCM (10 mL) was stirred at 0° C. Benzyl chloroformate (349 mg, 2.0 mmol) was added, and the reaction was stirred for 3 h at 25° C. The reaction mixture was washed with water and brine, dried over Na₂SO₄, and concentrated. The residue was purified by silica gel column chromatography (EtOAc in hexanes) to give 1-benzyl 2-methyl 3-allyl-2-methylpyrrolidine-1,2-dicarboxylate. LC-MS ($C_{18}H_{24}NO_4^+$)(ES, m/z): 318 [M+H]⁺.

Step 4: (2S,3R)-1-benzyl 2-methyl 3-allyl-2-methylpyrrolidine-1,2-dicarboxylate, (2R,3S)-1-benzyl 2-methyl 3-allyl-2-methylpyrrolidine-1,2-dicarboxylate, and (2R,3R)-1-benzyl 2-methyl 3-allyl-2-methylpyrrolidine-1,2-dicarboxylate

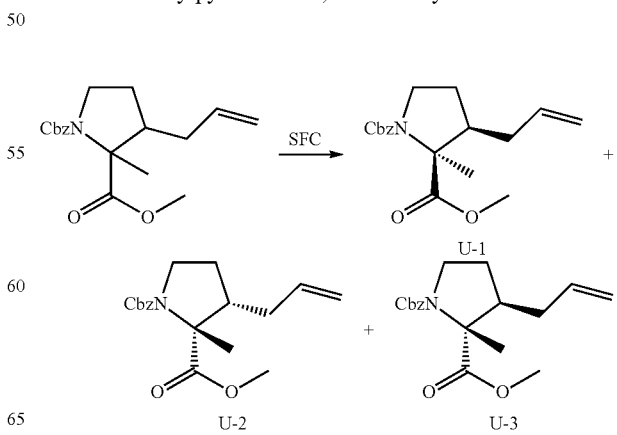

1-Benzyl 2-methyl 3-allyl-2-methylpyrrolidine-1,2-dicarboxylate (170 mg, 0.54 mmol) was resolved by chiral-SFC [Column: DAICEL CHIRALPAK IC (250 mm*30 mm, 5 μm), Mobile phase: A: $CO_2$, B: IPA (0.1% $NH_3.H_2O$), Gradient: 25% of B in 5.4 min and hold 25% for 1 min, Flow Rate (mL/min) 50, Column temperature: 40° C.] to give U-1 (2S,3R)-1-benzyl 2-methyl 3-allyl-2-methylpyrrolidine-1,2-dicarboxylate ($t_r$=3.577 min) as the first eluting peak, U-2 (2R,3S)-1-benzyl 2-methyl 3-allyl-2-methylpyrrolidine-1,2-dicarboxylate ($t_r$=4.195 min) as the second eluting peak, and U-3 (2R,3R)-1-benzyl 2-methyl 3-allyl-2-methylpyrrolidine-1,2-dicarboxylate ($t_r$=4.560 min) as the third eluting peak. The stereochemistry of U-1 and U-3 were confirmed by NMR, U-1 and U-2 have identical $^1H$ NMR spectrum. U-1 LC-MS ($C_{18}H_{24}NO_4^+$)(ES, m/z): 318 $[M+H]^+$. $^1H$ NMR (400 MHz, $CDCl_3$) δ 7.38-7.26 (m, 5H), 5.72 (ddt, J=7.6, 9.4, 16.7 Hz, 1H), 5.23-4.98 (m, 4H), 3.93-3.76 (m, 1H), 3.72-3.42 (m, 3H), 3.36 (ddt, J=4.3, 6.3, 10.7 Hz, 1H), 2.40-2.18 (m, 1H), 2.13-1.98 (m, 1H), 1.92 (td, J=6.0, 12.2 Hz, 1H), 1.77-1.66 (m, 2H), 1.65-1.56 (m, 3H). U-2 LC-MS ($C_{18}H_{24}NO_4^+$)(ES, m/z): 318 $[M+H]^+$. $^1H$ NMR (400 MHz, $CDCl_3$) δ 7.34-7.21 (m, 5H), 5.76-5.57 (m, 1H), 5.18-4.90 (m, 4H), 3.87-3.68 (m, 1H), 3.66-3.38 (m, 3H), 3.30 (ddt, J=4.3, 6.3, 10.8 Hz, 1H), 2.32-2.12 (m, 1H), 2.08-1.95 (m, 1H), 1.85 (td, J=6.0, 12.2 Hz, 1H), 1.71-1.60 (m, 2H), 1.59-1.50 (m, 3H). U-3 LC-MS ($C_{18}H_{24}NO_4^+$)(ES, m/z): 318 $[M+H]^+$. $^1H$ NMR (400 MHz, $CDCl_3$) δ 7.37-7.27 (m, 5H), 5.76-5.60 (m, 1H), 5.08-4.98 (m, 4H), 3.73-3.70 (m, 2H), 3.70-3.58 (m, 1H), 3.51-3.41 (m, 1H), 3.40 (br s, 1H), 2.46-2.32 (m, 1H), 2.29-2.14 (m, 1H), 2.08-1.93 (m, 2H), 1.68-1.53 (m, 1H), 1.43-1.34 (m, 3H).

Step 5: 1-benzyl 2-methyl (2S,3R)-2-methyl-3-(3-(4,4,5,5-tetramethyl-1,3,2-dioxaborolan-2-yl)propyl)pyrrolidine-1,2-dicarboxylate

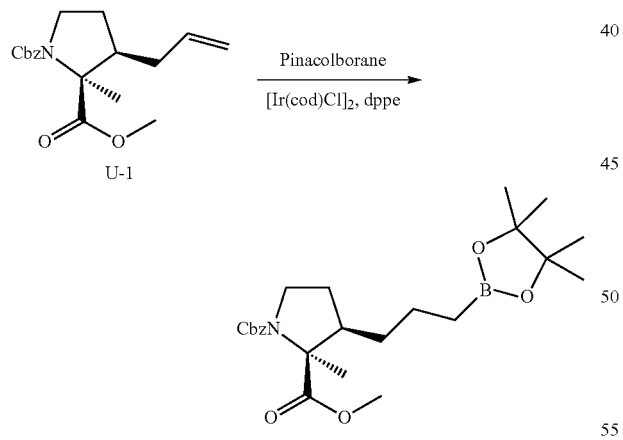

4,4,5,5-Tetramethyl-1,3,2-dioxaborolane (0.041 mL, 0.28 mmol) was added to a solution of bis(1,5-cyclooctadiene)diiridium(I) dichloride (6.4 mg, 9.5 μmol) and bis(diphenylphosphino)ethane (7.5 mg, 0.019 mmol) in anhydrous DCM (5 mL) under nitrogen for 10 min, followed by addition of (2S,3R)-1-benzyl 2-methyl 3-allyl-2-methylpyrrolidine-1,2-dicarboxylate (U-1, 60 mg, 0.19 mmol), and the reaction mixture was stirred at 30° C. for 3 h under nitrogen. The mixture was concentrated under reduced pressure, and the residue was purified by RP-HPLC [C18 column, water (0.1% TFA)-$CH_3CN$] to give 1-benzyl 2-methyl (2S,3R)-2-methyl-3-(3-(4,4,5,5-tetramethyl-1,3,2-dioxaborolan-2-yl)propyl)pyrrolidine-1,2-dicarboxylate. LC-MS ($C_{24}H_{37}BNO_6^+$)(ES, m/z): 446 $[M+H]^+$. $^1H$ NMR (400 MHz, $CDCl_3$) δ 7.38-7.24 (m, 5H), 5.21-4.98 (m, 3H), 3.91-3.74 (m, 1H), 3.69-3.39 (m, 3H), 3.34 (tdd, J=2.9, 10.8, 13.9 Hz, 1H), 2.08-1.87 (m, 2H), 1.71-1.63 (m, 1H), 1.62-1.51 (m, 4H), 1.50-1.42 (m, 1H), 1.41-1.29 (m, 1H), 1.22 (d, J=3.1 Hz, 12H), 0.83-0.63 (m, 2H).

Step 6: (2S,3R)-3-(3-boronopropyl)-2-methylpyrrolidine-2-carboxylic acid

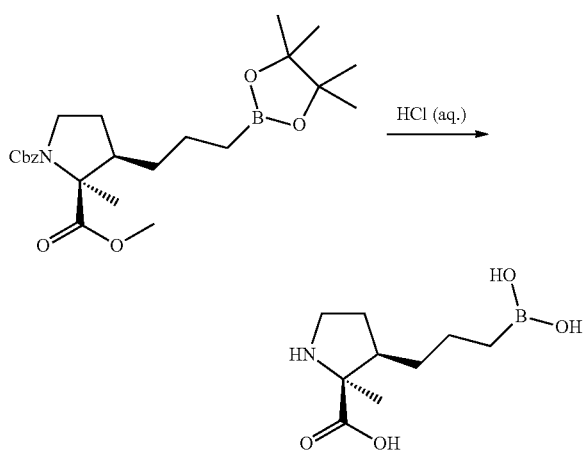

Example 16A

A mixture of 1-benzyl 2-methyl (2S,3R)-2-methyl-3-(3-(4,4,5,5-tetramethyl-1,3,2-dioxaborolan-2-yl)propyl)pyrrolidine-1,2-dicarboxylate (75 mg, 0.17 mmol) in 12 N HCl in water (1.0 mL, 0.17 mmol) was stirred at 100° C. for 16 h. The mixture was diluted with water and washed with DCM. The aqueous phase was concentrated under reduced pressure to give (2S,3R)-3-(3-boronopropyl)-2-methylpyrrolidine-2-carboxylic acid as an HCl salt. LC-MS ($C_9H_{17}BNO_3^+$)(ES, m/z): 198 $[M-H_2O+H]^+$. $^1H$ NMR (400 MHz, $D_2O$) δ 3.44-3.31 (m, 1H), 3.24-3.11 (m, 1H), 2.23-2.10 (m, 1H), 2.07-1.97 (m, 1H), 1.57 (qd, J=9.4, 13.1 Hz, 1H), 1.45 (s, 3H), 1.42-1.27 (m, 2H), 1.24-1.14 (m, 1H), 1.07-0.94 (m, 1H), 0.71-0.51 (m, 2H).

Example 16B: (3S)-3-[3-(dihydroxyboranyl)propyl]-2-methyl-D-proline

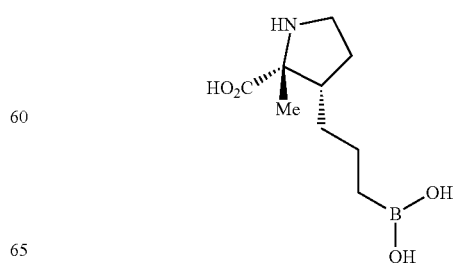

Example 16B was made from (2R,3S)-1-benzyl 2-methyl 3-allyl-2-methylpyrrolidine-1,2-dicarboxylate (U-2), and using the same procedure as Example 16A. 198 [M−H$_2$O+H]$^+$ Example 16C: (3R)-3-[3-(dihydroxyboranyl)propyl]-2-methyl-D-proline

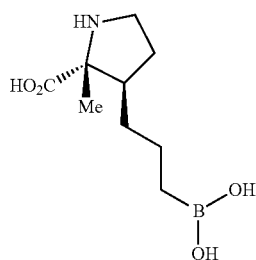 [SMILES: C[C@@]1(C(=O)O)NCC[C@H]1CCCB(O)O]

Example 16C was made from (2R,3R)-1-benzyl 2-methyl 3-allyl-2-methylpyrrolidine-1,2-dicarboxylate (U-3) using the same procedure as Example 16A. 198 [M−H$_2$O+H]$^+$ Example 17: 3-[3-(dihydroxyboranyl)propyl]-5-methylproline

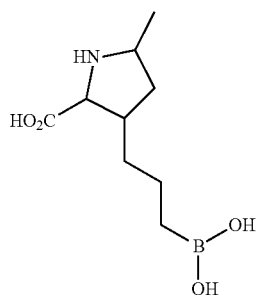

Step 1: 1-tert-butyl 2-ethyl 5-methyl-1H-pyrrole-1,2-dicarboxylate

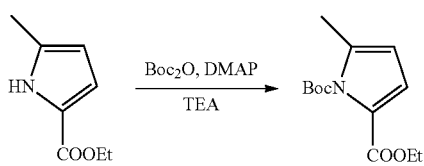

A mixture of ethyl 5-methyl-1H-pyrrole-2-carboxylate (4.0 g, 26 mmol), Boc$_2$O (8.5 g, 39 mmol), DMAP (1.6 g, 13 mmol) and TEA (11 mL, 78 mmol) in DCM (80 mL) was stirred at 30° C. for 2 h. The reaction mixture was quenched with water and extracted with DCM. The combined organic phase was dried over anhydrous Na$_2$SO$_4$, filtered and concentrated under reduced pressure. The residue was purified by silica gel column chromatography (EtOAc in hexanes) to give 1-tert-butyl 2-ethyl 5-methyl-1H-pyrrole-1,2-dicarboxylate1. LC-MS (C$_9$H$_{12}$NO$_4^+$)(ES, m/z): 198 [M−C$_4$H$_8$+H]$^+$.

Step 2: 1-tert-butyl 2-ethyl 5-methylpyrrolidine-1,2-dicarboxylate

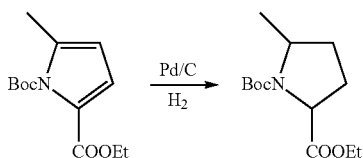 [SMILES: CCOC(=O)c1ccc(C)n1C(=O)OC(C)(C)C ; "H2" ; "Pd/C" ; CCOC(=O)C1CCC(C)N1C(=O)OC(C)(C)C]

10% palladium on carbon (0.70 g, 0.66 mmol) was added to a solution of 1-tert-butyl 2-ethyl 5-methyl-1H-pyrrole-1,2-dicarboxylate (3.2 g, 12 mmol) in MeOH (100 mL) under nitrogen atmosphere. The mixture was degassed and back filled with hydrogen (three times). The resulting mixture was stirred under hydrogen (Pressure: 50 psi) at 50° C. for 24 h. The reaction mixture was filtered, and the filtrate was concentrated under reduced pressure to give 1-tert-butyl 2-ethyl 5-methylpyrrolidine-1,2-dicarboxylate, which was used in the next step without further purification. $^1$H NMR (400 MHz, CDCl$_3$) δ 4.39-4.08 (m, 3H), 4.06-3.83 (m, 1H), 2.17 (br d, J=6.0 Hz, 1H), 2.08-1.87 (m, 2H), 1.65 (br s, 1H), 1.48-1.38 (m, 9H), 1.32-1.22 (m, 6H).

Step 3: 1-tert-butyl 2-ethyl 3-bromo-5-methyl-1H-pyrrole-1,2-dicarboxylate

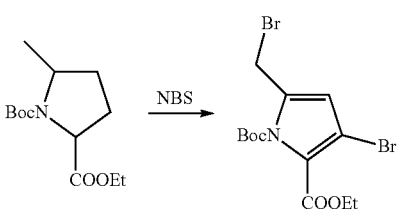

A mixture of 1-tert-butyl 2-ethyl 5-methylpyrrolidine-1,2-dicarboxylate (1.0 g, 3.9 mmol) and N-bromo succinimide (2.4 g, 14 mmol) in carbon tetrachloride (500 mL) was stirred at 85° C. for 1 h. The mixture was filtered and the filtrate was concentrated under reduced pressure, and the residue was purified by silica gel column chromatography (EtOAc in hexanes) to give 1-tert-butyl 2-ethyl 3-bromo-5-(bromomethyl)-1H-pyrrole-1,2-dicarboxylate. $^1$H NMR (400 MHz, CDCl$_3$) δ 6.31 (s, 1H), 4.64 (s, 2H), 4.36 (q, J=7.1 Hz, 2H), 1.59 (s, 9H), 1.42-1.35 (m, 3H).

Step 4: 1-tert-butyl 2-ethyl 3-bromo-5-methyl-1H-pyrrole-1,2-dicarboxylate

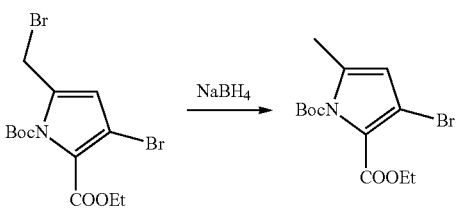

A mixture of 1-tert-butyl 2-ethyl 3-bromo-5-(bromomethyl)-1H-pyrrole-1,2-dicarboxylate (1.9 g, 4.6 mmol) and NaBH₄ (0.87 g, 23 mmol) in ethanol (20 mL) was stirred at 25° C. for 30 min. Acetone (5 mL) was added at 0° C. to quench the reaction. The solvent was removed under reduce pressure, and water was added to the reaction. The reaction mixture was extracted with EtOAc and the combined organic phase was washed with brine, dried over anhydrous Na₂SO₄, filtered and concentrated under reduced pressure. The residue was purified by silica gel column chromatography (EtOAc in hexanes) to give 1-tert-butyl 2-ethyl 3-bromo-5-methyl-1H-pyrrole-1,2-dicarboxylate. LC-MS (C₉H₁₁BrNO₄⁺)(ES, m/z): 278 [M-C₄H₈+H]⁺.

Step 5: 1-tert-butyl 2-ethyl 3-allyl-5-methyl-H-pyrrole-1,2-dicarboxylate

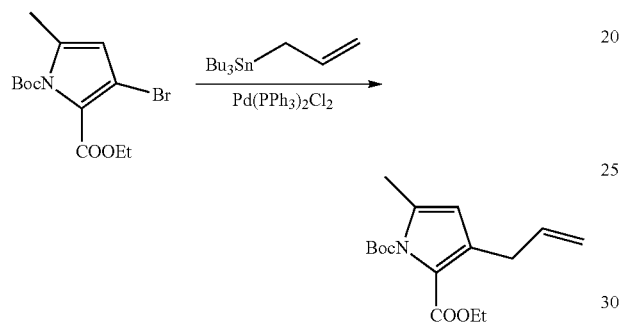

Bis-(triphenylphosphino)-palladium(II) chloride (0.28 g, 0.42 mmol) was added to a mixture of 1-tert-butyl 2-ethyl 3-bromo-5-methyl-1H-pyrrole-1,2-dicarboxylate (1.4 g, 4.2 mmol), allyltributylstannane (2.6 mL, 8.4 mmol) in DMF (40 mL) and the reaction mixture was stirred at 100° C. for 3 h under nitrogen. The mixture was quenched with potassium fluoride aqueous solution (1.5 g in 100 mL of water), then stirred at 0° C. for 1.5 h, and filtered. EtOAc (20 mL) was added to the filtrate and the mixture was stirred for 10 min, then extracted with EtOAc, and the combined organic phase was dried over anhydrous Na₂SO₄, filtered and concentrated in vacuum. The residue was purified by silica gel column chromatography (EtOAc in hexanes) to give 1-tert-butyl 2-ethyl 3-allyl-5-methyl-1H-pyrrole-1,2-dicarboxylate. LC-MS (C₁₂H₁₆NO₄⁺)(ES, m/z): 238 [M-C₄H₈+H]⁺.

Step 6: 1-tert-butyl 2-ethyl 5-methyl-3-(3-(4,4,5,5-tetramethyl-1,3,2-dioxaborolan-2-yl)propyl)-1H-pyrrole-1,2-dicarboxylate

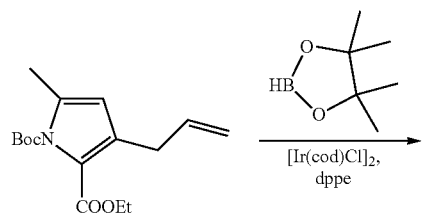

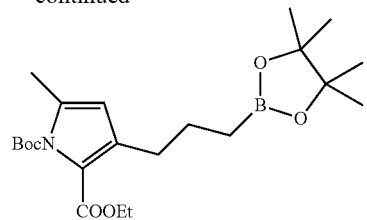

4,4,5,5-Tetramethyl-1,3,2-dioxaborolane (0.89 mL, 6.1 mmol) was added to a solution of bis(1,5-cyclooctadiene)diiridium(I) dichloride (0.14 g, 0.21 mmol) and 1,2-bis(diphenylphosphino)ethane (0.16 g, 0.41 mmol) in DCM (15 mL) and the reaction mixture was bubbled with a stream of nitrogen for 5 min, followed by addition of 1-tert-butyl 2-ethyl 3-allyl-5-methyl-1H-pyrrole-1,2-dicarboxylate (1.2 g, 4.1 mmol), and the resulting mixture was stirred at 30° C. for 12 h under nitrogen. The reaction mixture was concentrated under reduced pressure, and the residue was purified by silica gel column chromatography (EtOAc in hexanes) to give 1-tert-butyl 2-ethyl 5-methyl-3-(3-(4,4,5,5-tetramethyl-1,3,2-dioxaborolan-2-yl)propyl)-1H-pyrrole-1,2-dicarboxylate. LC-MS (C₂₂H₃₇BNO₆⁺)(ES, m/z): 422 [M+H]⁺.

Step 7: 5-methyl-3-(3-(4,4,5,5-tetramethyl-1,3,2-dioxaborolan-2-yl)propyl)pyrrolidine-2-carboxylate

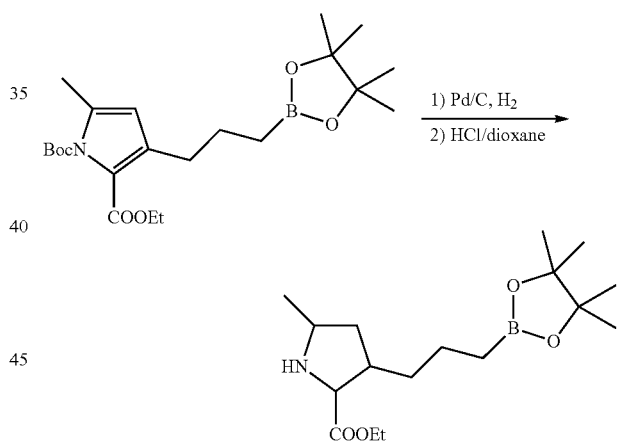

10% palladium on carbon (300 mg, 0.28 mmol) was added to a solution of 1-tert-butyl 2-ethyl 5-methyl-3-(3-(4,4,5,5-tetramethyl-1,3,2-dioxaborolan-2-yl)propyl)-1H-pyrrole-1,2-dicarboxylate (850 mg, 2.0 mmol) in MeOH (50 mL) under nitrogen atmosphere. The reaction mixture was degassed and back filled with hydrogen (three times), and stirred under hydrogen (Pressure: 50 psi) at 50° C. for 18 h. The mixture was filtered, and the filtrate was concentrated under reduced pressure. The residue was dissolved in DCM (3.0 mL), followed by addition of HCl in dioxane (4.0 M, 3.0 mL, 12 mmol), and the resulting mixture was stirred at 25° C. for 1 h. The mixture was concentrated under reduced pressure to give crude ethyl 5-methyl-3-(3-(4,4,5,5-tetramethyl-1,3,2-dioxaborolan-2-yl)propyl)pyrrolidine-2-carboxylate, which was used in next step without further purification. LC-MS (C₁₇H₃₃BNO₄⁺)(ES, m/z): 326 [M+H]⁺.

Step 8: 1-benzyl 2-ethyl 5-methyl-3-(3-(4,4,5,5-tetramethyl-1,3,2-dioxaborolan-2-yl)propyl)pyrrolidine-1,2-dicarboxylate

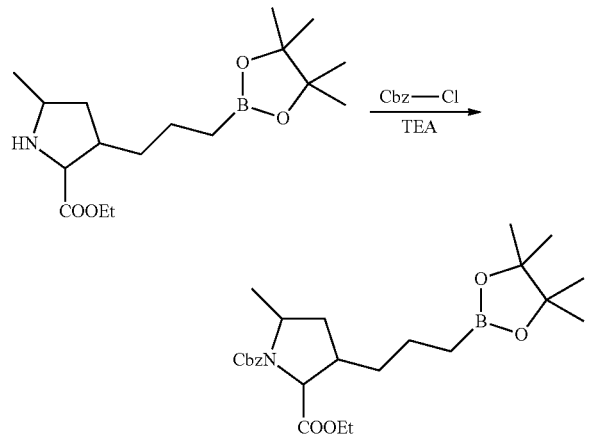

A solution of ethyl 5-methyl-3-(3-(4,4,5,5-tetramethyl-1,3,2-dioxaborolan-2-yl)propyl)pyrrolidine-2-carboxylate (560 mg, 1.7 mmol) and TEA (0.72 mL, 5.2 mmol) in dry DCM (10 mL) was stirred at 0° C. Benzyl chloroformate (0.31 mL, 2.6 mmol) was added. The reaction mixture was stirred for 2.5 h at 25° C., and washed with water (20 mL) and brine (10 mL), dried over $Na_2SO_4$, filtered, and concentrated. The residue was purified by silica gel column chromatography (EtOAc in hexanes) to give 1-benzyl 2-ethyl 5-methyl-3-(3-(4,4,5,5-tetramethyl-1,3,2-dioxaborolan-2-yl)propyl)pyrrolidine-1,2-dicarboxylate. LC-MS ($C_{25}H_{39}BNO_6^+$)(ES, m/z): 460 [M+H]$^+$.

Step 9: 1-benzyl 2-ethyl 5-methyl-3-(3-(4,4,5,5-tetramethyl-1,3,2-dioxaborolan-2-yl)propyl)pyrrolidine-1,2-dicarboxylate

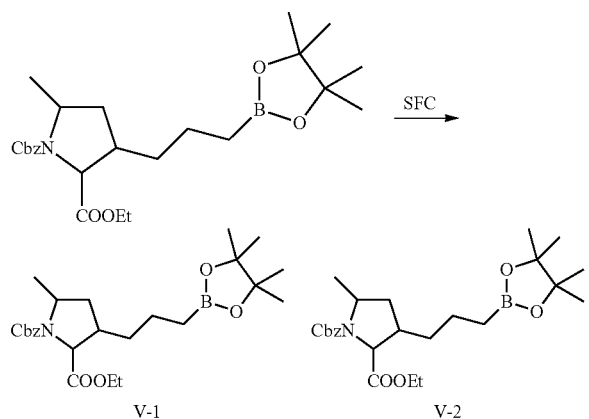

Benzyl 2-ethyl 5-methyl-3-(3-(4,4,5,5-tetramethyl-1,3,2-dioxaborolan-2-yl)propyl)pyrrolidine-1,2-dicarboxylate (650 mg, 1.4 mmol) was resolved by chiral-SFC [Column: Lux Cellulose-2 250 mm*30 mm, 10 μm, Mobile phase: A: $CO_2$, B: MeOH (0.1% $NH_3.H_2O$), Gradient: 15% of B in 6.1 min and hold 15% for 1 min, Flow Rate (mL/min) 60, Column temperature: 40° C.] to give 1-benzyl 2-ethyl 5-methyl-3-(3-(4,4,5,5-tetramethyl-1,3,2-dioxaborolan-2-yl)propyl)pyrrolidine-1,2-dicarboxylate (V-1, $t_r$=1.786 and 1.989 min, two rotamers) and 1-benzyl 2-ethyl 5-methyl-3-(3-(4,4,5,5-tetramethyl-1,3,2-dioxaborolan-2-yl)propyl)pyrrolidine-1,2-dicarboxylate (V-2, $t_r$=2.253 and 2.551 min, two rotamers). V-1 LC-MS ($C_{25}H_{39}BNO_6^+$)(ES, m/z): 460 [M+H]$^+$. $^1$H NMR (400 MHz, CDCl$_3$) δ 7.44-7.26 (m, 5H), 5.13 (d, J=1.1 Hz, 1H), 5.09 (d, J=3.5 Hz, 1H), 4.52-4.35 (m, 1H), 4.25-4.06 (m, 2H), 3.94-3.77 (m, 1H), 2.35-2.13 (m, 2H), 1.58 (br s, 2H), 1.63-1.53 (m, 1H), 1.49-1.38 (m, 6H), 1.33-1.25 (m, 2H), 1.25-1.19 (m, 12H), 1.17-1.06 (m, 1H), 0.84-0.66 (m, 2H). V-2 LC-MS ($C_{25}H_{39}BNO_6^+$)(ES, m/z): 460 [M+H]$^+$. $^1$H NMR (400 MHz, CDCl$_3$) δ 7.40-7.27 (m, 5H), 5.13 (br s, 1H), 5.09 (d, J=3.8 Hz, 1H), 4.52-4.35 (m, 1H), 4.28-4.06 (m, 2H), 3.95-3.77 (m, 1H), 3.51-3.45 (m, 1H), 2.32-2.14 (m, 2H), 1.62 (br s, 1H), 1.48-1.38 (m, 6H), 1.31-1.24 (m, 2H), 1.22 (s, 12H), 1.16-1.10 (m, 1H), 0.85-0.66 (m, 2H).

Step 10: 3-[3-(dihydroxyboranyl)propyl]-5-methylproline

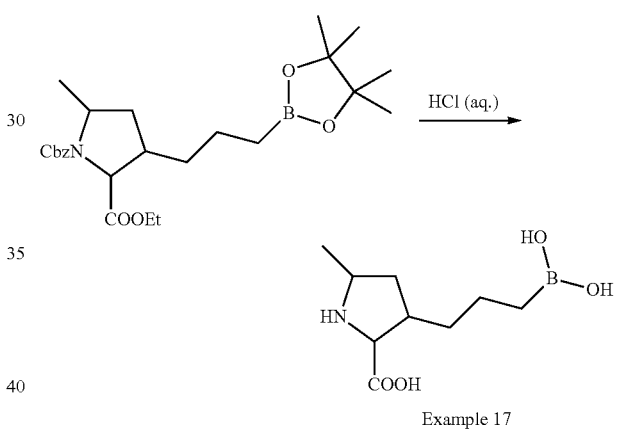

Example 17

A mixture of 1-benzyl 2-ethyl 5-methyl-3-(3-(4,4,5,5-tetramethyl-1,3,2-dioxaborolan-2-yl)propyl)pyrrolidine-1,2-dicarboxylate (80 mg, 0.17 mmol) and 12 N HCl in water (3.0 mL, 36 mmol) was stirred at 100° C. for 16 h. The mixture was washed with DCM, and the aqueous layer was concentrated under reduced pressure to give 3-[3-(dihydroxyboranyl)propyl]-5-methylproline as an HCl salt. LC-MS ($C_9H_{17}BNO_3^+$)(ES, m/z): 198 [M–$H_2O$+H]$^+$. $^1$H NMR (400 MHz, $D_2O$) δ 4.19 (d, J=9.0 Hz, 1H), 3.66-3.50 (m, 1H), 2.59-2.41 (m, 1H), 2.24 (td, J=6.6, 13.2 Hz, 1H), 1.45-1.17 (m, 7H), 1.14-0.98 (m, 1H), 0.71-0.50 (m, 2H).

Example 18: 4-[2-(dihydroxyboranyl)ethyl]proline

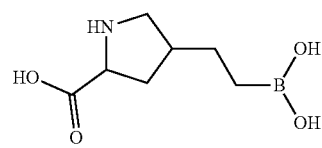 [SMILES: O=C(O)C1CC(CCB(O)O)CN1]

Step 1: 1-tert-butyl 2-methyl 4-bromo-1H-pyrrole-1,2-dicarboxylate

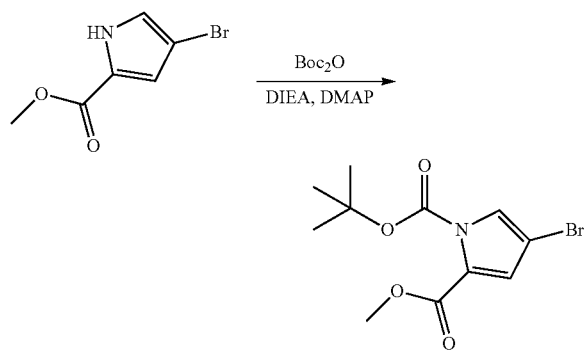

N,N-dimethylpyridin-4-amine (0.30 g, 2.5 mmol) was added to a solution of methyl 4-bromo-1H-pyrrole-2-carboxylate (1.0 g, 4.9 mmol), di-tert-butyl dicarbonate (1.4 g, 6.4 mmol) and triethylamine (2.0 mL, 15 mmol) in DCM (20 mL), and the reaction mixture was stirred at 25° C. for 12 h. The mixture was diluted with water and extracted with DCM. The combined organic phase was washed with brine, dried over anhydrous Na$_2$SO$_4$, filtered, and concentrated under reduced pressure. The residue was purified by silica gel column chromatography (EtOAc in hexanes) to give 1-tert-butyl 2-methyl 4-bromo-1H-pyrrole-1,2-dicarboxylate. LCMS (C$_7$H$_7$BrNO$_4$$^+$)(ES, m/z): 248 [M-C$_4$H$_8$+H]$^+$.

Step 2: 1-tert-butyl 2-methyl 4-vinyl-1H-pyrrole-1,2-dicarboxylate

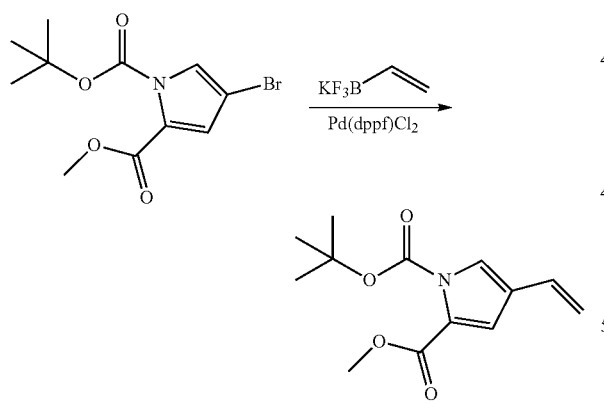

A mixture of 1-tert-butyl 2-methyl 4-bromo-1H-pyrrole-1,2-dicarboxylate (350 mg, 1.2 mmol), potassium trifluoro(vinyl)borate (308 mg, 2.3 mmol), [1,1'-Bis(diphenylphosphino)ferrocene]palladium(II) dichloride (168 mg, 0.23 mmol) and K$_2$CO$_3$ (477 mg, 3.5 mmol) in water (0.50 mL) and 1,4-Dioxane (5.0 mL) was degassed and backfilled with nitrogen (three times), and then heated to 80° C. for 4 h. The mixture was concentrated under reduced pressure, and the crude mixture was diluted with water, and extracted with EtOAc. The combined organic layer was washed with brine, dried over anhydrous Na$_2$SO$_4$, filtered and concentrated under reduced pressure. The residue was purified by silica gel column chromatography (EtOAc in hexanes) to give 1-tert-butyl 2-methyl 4-vinyl-H-pyrrole-1,2-dicarboxylate. LCMS (C$_9$H$_{10}$NO$_4$$^+$)(ES, m/z): 196 [M-C$_4$H$_8$+H]$^+$.

Step 3: 1-tert-butyl 2-methyl 4-(2-(4,4,5,5-tetramethyl-1,3,2-dioxaborolan-2-yl)ethyl)-1H-pyrrole-1,2-dicarboxylate

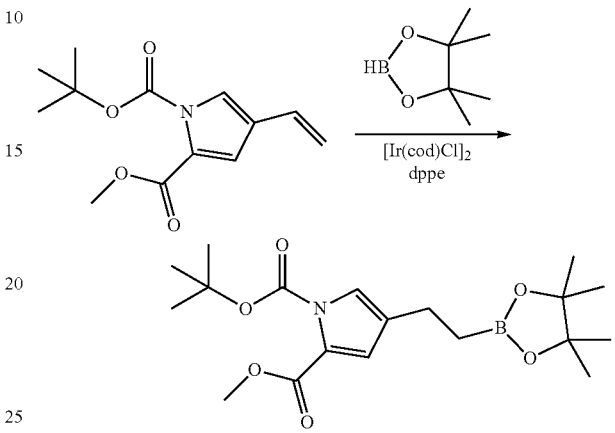

A solution of 4,4,5,5-tetramethyl-1,3,2-dioxaborolane (0.72 mL, 5.0 mmol), chloro(1,5-cyclooctadiene)iridium(I) dimer (33 mg, 0.050 mmol) and bis(diphenylphosphino)ethane (27 mg, 0.070 mmol) in anhydrous DCM (7.0 mL) was bubbled with a stream of nitrogen for 3 min, and then stirred at 15° C. for 20 min, followed by addition of 1-tert-butyl 2-methyl 4-vinyl-1H-pyrrole-1,2-dicarboxylate (250 mg, 1.0 mmol). The resulting mixture was stirred at 15° C. for 13 h under nitrogen, and the mixture was directly purified by silica gel preparative thin layer chromatography (EtOAc in hexanes) to give 1-tert-butyl 2-methyl 4-(2-(4,4,5,5-tetramethyl-1,3,2-dioxaborolan-2-yl)ethyl)-1H-pyrrole-1,2-dicarboxylate. LCMS (C$_{15}$H$_{23}$BNO$_6$$^+$)(ES, m/z): 324 [M-C$_4$H$_8$+H]$^+$.

Step 4: 1-tert-butyl 2-methyl 4-(2-(4,4,5,5-tetramethyl-1,3,2-dioxaborolan-2-yl)ethyl)pyrrolidine-1,2-dicarboxylate

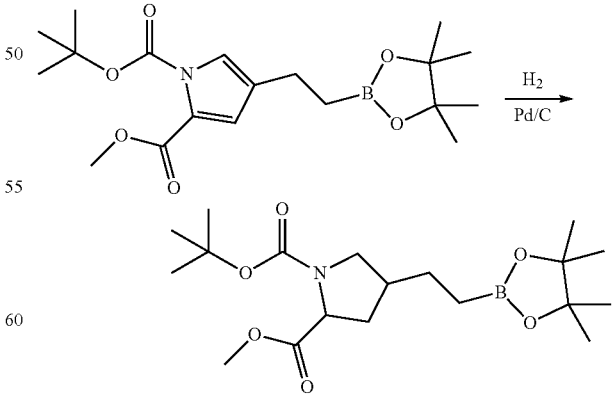

10% palladium on carbon (50 mg, 0.042 mmol) was added to a solution of 1-tert-butyl 2-methyl 4-(2-(4,4,5,5-tetramethyl-1,3,2-dioxaborolan-2-yl)ethyl)-1H-pyrrole-1,2- dicarboxylate (158 mg, 0.42 mmol) in MeOH (25 mL) under nitrogen atmosphere, and the mixture was degassed and backfilled with hydrogen (three times). The resulting mixture was stirred under hydrogen (45-50 psi) at 45° C. for 24 h, then filtered, and the filtrate was concentrated under reduced pressure. The residue was purified by silica gel column chromatography (EtOAc in hexanes) to give 1-tert-butyl 2-methyl 4-(2-(4,4,5,5-tetramethyl-1,3,2-dioxaborolan-2-yl)ethyl)pyrrolidine-1,2-dicarboxylate. HNMR showed that was rotamer. $^1$H NMR (400 MHz, CDCl$_3$) δ 4.26-4.14 (m, 1H), 3.76 (dd, J=7.5, 10.1 Hz, 1H), 3.73-3.69 (m, 3H), 2.98 (t, J=10.4 Hz, 1H), 2.38 (qd, J=6.4, 12.6 Hz, 1H), 2.15-2.05 (m, 1H), 1.55-1.47 (m, 3H), 1.44 (s, 3H), 1.39 (s, 6H), 1.23 (s, 12H), 0.81-0.73 (m, 2H).

Step 5: 4-[2-(dihydroxyboranyl)ethyl]proline

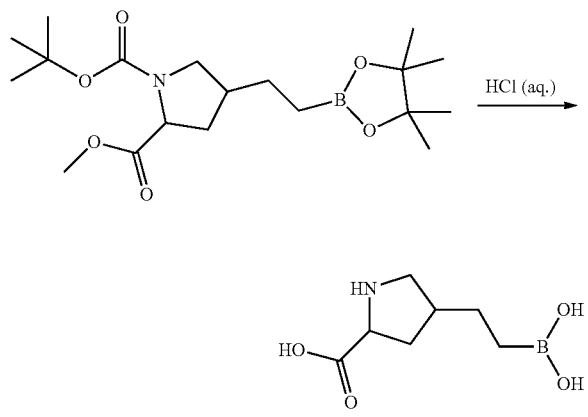

Example 18

A mixture of 1-tert-butyl 2-methyl 4-(2-(4,4,5,5-tetramethyl-1,3,2-dioxaborolan-2-yl)ethyl)pyrrolidine-1,2-dicarboxylate (50 mg, 0.13 mmol) and 12 N HCl in water (2.0 mL, 24 mmol) was stirred at 100° C. for 12 h, and the mixture was concentrated to give 4-[2-(dihydroxyboranyl)ethyl]proline as an HCl salt. LCMS (C$_7$H$_{15}$BNO$_4$$^+$)(ES, m/z): 188 [M+H]$^+$. $^1$H NMR (400 MHz, D$_2$O) δ 4.25 (t, J=8.9 Hz, 1H), 3.44 (dd, J=7.5, 11.5 Hz, 1H), 2.96-2.84 (m, 1H), 2.57-2.46 (m, 1H), 2.31-2.16 (m, 1H), 1.63 (td, J=9.9, 13.1 Hz, 1H), 1.51-1.33 (m, 2H), 0.74-0.63 (m, 2H).

Example 19: 4-[2-(dihydroxyboranyl)ethyl]-2-[2-(piperidin-1-yl)ethyl]proline

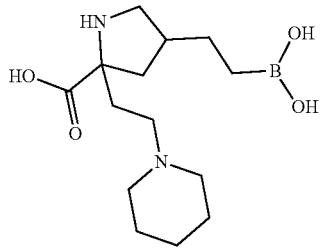 [SMILES: O=C(O)C1(CCN2CCCCC2)CC(CCB(O)O)CN1]

Step 1: 1-tert-butyl 2-methyl 2-allyl-4-(2-(4,4,5,5-tetramethyl-1,3,2-dioxaborolan-2-yl)ethyl)pyrrolidine-1,2-dicarboxylate

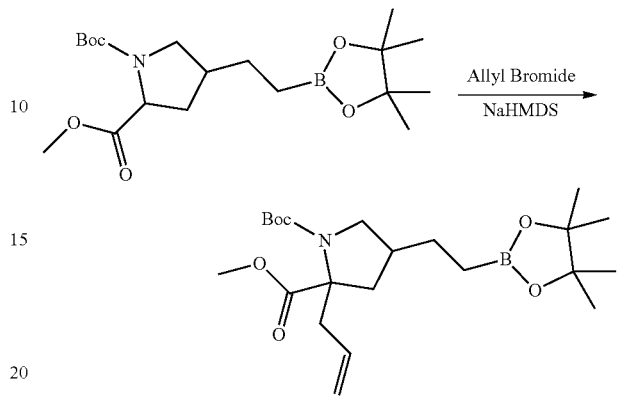

Sodium bis(trimethylsilyl)amide in THF (1.0 M in THF, 1.0 mL, 1.0 mmol) was added to a solution of 1-tert-butyl 2-methyl 4-(2-(4,4,5,5-tetramethyl-1,3,2-dioxaborolan-2-yl)ethyl)pyrrolidine-1,2-dicarboxylate (300 mg, 0.78 mmol) in THF (5.0 mL) at −30° C. under nitrogen, and the mixture was stirred at −30° C. for 0.5 h, followed by addition of 3-bromoprop-1-ene (0.27 mL, 3.1 mmol). The reaction mixture was stirred at −30° C. for 1 h, then warmed to 15° C. and stirred at 15° C. for 3 h. The mixture was poured into water and extracted with EtOAc, and the combined organic layer was washed with brine, dried over anhydrous Na$_2$SO$_4$, filtered and concentrated. The residue was purified by silica gel column chromatography (EtOAc in hexanes) to give 1-tert-butyl 2-methyl 2-allyl-4-(2-(4,4,5,5-tetramethyl-1,3, 2-dioxaborolan-2-yl)ethyl)pyrrolidine-1,2-dicarboxylate. $^1$H NMR (400 MHz, CDCl$_3$) δ 5.73-5.55 (m, 1H), 5.16-5.05 (m, 2H), 3.97-3.90 (m, 1H), 3.83-3.76 (m, 1H), 3.72-3.66 (m, 3H), 3.00-2.87 (m, 1H), 2.81-2.72 (m, 1H), 2.62 (br dd, J=8.3, 14.0 Hz, 1H), 2.58-2.47 (m, 1H), 2.28-2.10 (m, 1H), 2.08-1.97 (m, 1H), 1.80-1.70 (m, 1H), 1.43-1.39 (m, 9H), 1.23 (d, J=1.3 Hz, 12H), 0.78-0.70 (m, 2H).

Step 2: 1-tert-butyl 2-methyl 2-(2-oxoethyl)-4-(2-(4,4,5,5-tetramethyl-1,3,2-dioxaborolan-2-yl)ethyl)pyrrolidine-1,2-dicarboxylate

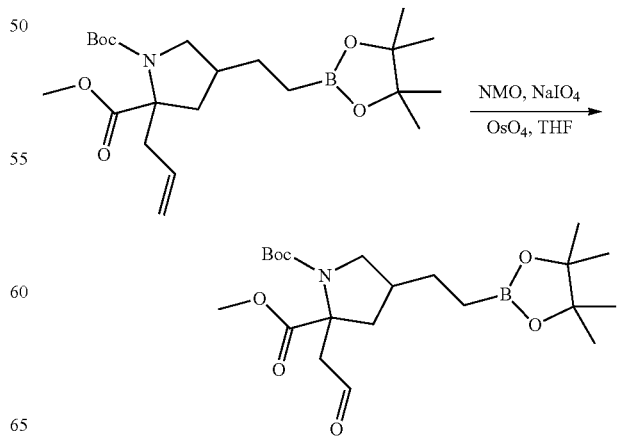

4-Methylmorpholine N-oxide (83 mg, 0.71 mmol) and osmium tetroxide (0.91 mL, 0.035 mmol, 500 mg in 50 mL of water) were added to a solution of 1-tert-butyl 2-methyl 2-allyl-4-(2-(4,4,5,5-tetramethyl-1,3,2-dioxaborolan-2-yl)ethyl)pyrrolidine-1,2-dicarboxylate (150 mg, 0.35 mmol) in THF (5.0 mL) and water (0.5 mL) were added, and the reaction mixture was stirred at 25° C. for 20 min. Then sodium periodate (152 mg, 0.71 mmol) was added, and the reaction mixture was stirred at 25° C. for 12 h. The mixture was diluted with water and extracted with EtOAc. The combined organic layer was washed with brine, dried over anhydrous Na$_2$SO$_4$, filtered, and concentrated under the reduced pressure to give crude 1-tert-butyl 2-methyl 2-(2-oxoethyl)-4-(2-(4,4,5,5-tetramethyl-1,3,2-dioxaborolan-2-yl)ethyl)pyrrolidine-1,2-dicarboxylate, which was used directly in next step. $^1$H NMR (400 MHz, CDCl$_3$) δ 9.92-9.66 (m, 1H), 3.75-3.71 (m, 3H), 3.70-3.61 (m, 1H), 3.20-2.77 (m, 3H), 2.45-2.20 (m, 2H), 1.98-1.83 (m, 1H), 1.56-1.45 (m, 2H), 1.43-1.39 (m, 9H), 1.23 (s, 12H), 0.84-0.72 (m, 2H).

Step 3: 1-tert-butyl 2-methyl 2-(2-(piperidin-1-yl)ethyl)-4-(2-(4,4,5,5-tetramethyl-1,3,2-dioxaborolan-2-yl)ethyl)pyrrolidine-1,2-dicarboxylate (2-(1-(tert-butoxycarbonyl)-5-(methoxycarbonyl)-5-(2-(piperidin-1-yl)ethyl)pyrrolidin-3-yl)ethyl)boronate

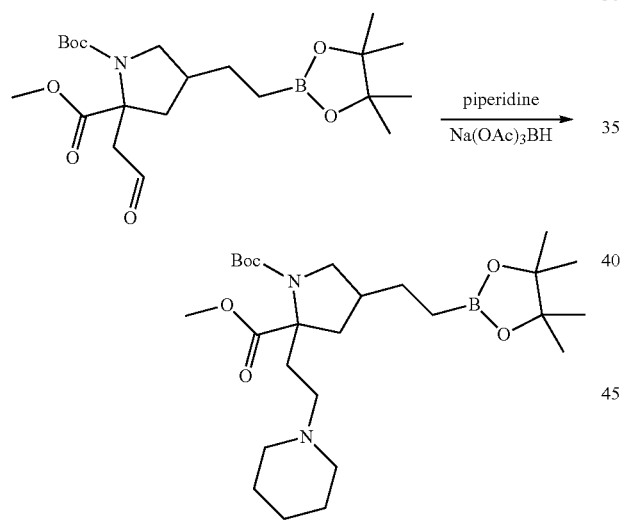

Sodium triacetoxyborohydride (199 mg, 0.94 mmol) was added to a solution of 1-tert-butyl 2-methyl 2-(2-oxoethyl)-4-(2-(4,4,5,5-tetramethyl-1,3,2-dioxaborolan-2-yl)ethyl)pyrrolidine-1,2-dicarboxylate (160 mg, 0.38 mmol) and piperidinyl (96 mg, 1.1 mmol) in 1,2-dichloroethane (5.0 mL), and the reaction mixture was stirred at 20° C. for 14 h under nitrogen. The mixture was quenched with water, and extracted with DCM. The combined organic layer was washed with brine, dried over anhydrous Na$_2$SO$_4$, filtered and concentrated. The residue was purified by RP-HPLC [C18 column, water (10 mM NH$_4$HCO$_3$)—CH$_3$CN] to give 1-tert-butyl 2-methyl 2-(2-(piperidin-1-yl)ethyl)-4-(2-(4,4,5,5-tetramethyl-1,3,2-dioxaborolan-2-yl)ethyl)pyrrolidine-1,2-dicarboxylate (2-(1-(tert-butoxycarbonyl)-5-(methoxycarbonyl)-5-(2-(piperidin-1-yl)ethyl)pyrrolidin-3-yl)ethyl)boronate. LCMS (C$_{26}$H$_4$BN$_2$O$_6^+$)(ES, m/z): 495 [M+H]$^+$.

Step 4: 4-[2-(dihydroxyboranyl)ethyl]-2-[2-(piperidin-1-yl)ethyl]proline

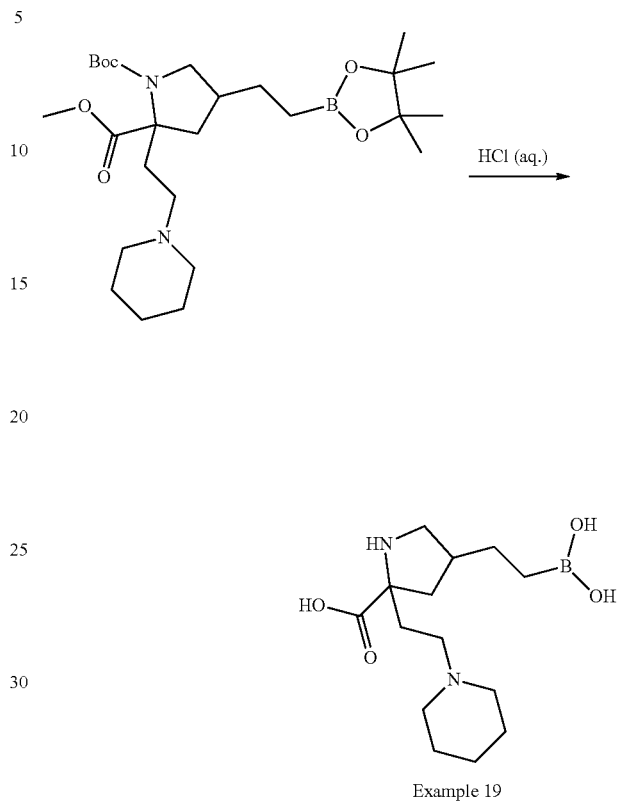

Example 19

A mixture of 1-tert-butyl 2-methyl 2-(2-(piperidin-1-yl)ethyl)-4-(2-(4,4,5,5-tetramethyl-1,3,2-dioxaborolan-2-yl)ethyl)pyrrolidine-1,2-dicarboxylate (2-(1-(tert-butoxycarbonyl)-5-(methoxycarbonyl)-5-(2-(piperidin-1-yl)ethyl)pyrrolidin-3-yl)ethyl)boronate (120 mg, 0.13 mmol) and 12 N HCl in water (3.0 mL, 36 mmol) was stirred at 100° C. for 12 h, and concentrated to give 4-[2-(dihydroxyboranyl)ethyl]-2-[2-(piperidin-1-yl)ethyl]proline as an HCl salt. LCMS (C$_{14}$H$_{28}$BN$_2$O$_4^+$)(ES, m/z): 299 [M+H]$^+$. $^1$H NMR (400 MHz, D$_2$O) δ 3.51-3.40 (m, 1H), 3.36 (br d, J=10.8 Hz, 2H), 3.16-3.03 (m, 1H), 3.17-3.03 (m, 1H), 2.99-2.88 (m, 1H), 2.87-2.71 (m, 3H), 2.48 (dd, J=6.6, 13.2 Hz, 1H), 2.31-2.20 (m, 2H), 2.05 (br d, J=6.6 Hz, 1H), 1.77 (br d, J=14.8 Hz, 2H), 1.68-1.45 (m, 4H), 1.43-1.22 (m, 3H), 0.66-0.55 (m, 2H).

Example 20A: (3R,4S)-3-[3-(dihydroxyboranyl)propyl]-4-hydroxy-L-proline

Step 1: 1-(tert-butyl) 2-methyl(2S)-3-allyl-4-hydroxypyrrolidine-1,2-dicarboxylate

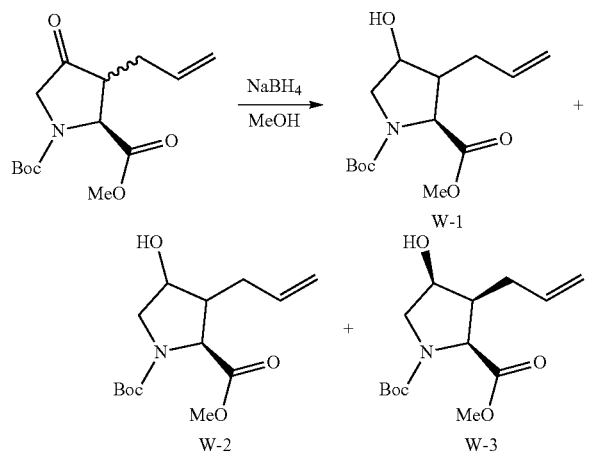

Sodium borohydride (109 mg, 2.9 mmol) was added to a mixture of (2S)-1-tert-butyl 2-methyl 3-allyl-4-oxopyrrolidine-1,2-dicarboxylate (680 mg, 2.4 mmol) in MeOH (15 mL) at 0° C., and the reaction mixture was stirred at 25° C. for 0.5 h. The mixture was quenched with acetone (50 mL), and concentrated under reduced pressure. The residue was purified by RP-HPLC [C18 column, water (0.1% TFA)-CH$_3$CN] to give the 1-(tert-butyl) 2-methyl (2S)-3-allyl-4-hydroxypyrrolidine-1,2-dicarboxylate (W-1) as the first eluted peak, 1-(tert-butyl) 2-methyl (2S)-3-allyl-4-hydroxypyrrolidine-1,2-dicarboxylate (W-2) as the second eluted peak, and 1-tert-butyl 2-methyl (2S,3S,4S)-4-hydroxy-3-(prop-2-en-1-yl)pyrrolidine-1,2-dicarboxylate (W-3) as the third eluted peak. Stereochemistry of W-3 was confirmed by 2D NMR. W-1 LCMS (C$_{14}$H$_{24}$NO$_5^+$)(ES, m/z): 286 [M+H]$^+$. $^1$H NMR (400 MHz, CD$_3$OD) δ 5.86 (tdd, J=6.7, 10.4, 17.1 Hz, 1H), 5.15 (s, 1H), 5.13-5.08 (m, 1H), 4.08-4.05 (m, 1H), 4.04-3.99 (m, 1H), 3.75-3.66 (m, 4H), 3.30-3.24 (m, 1H), 2.37-2.24 (m, 2H), 2.23-2.09 (m, 1H), 1.48-1.39 (m, 9H). W-2 LCMS (C$_{14}$H$_{24}$NO$_5^+$)(ES, m/z): 286 [M+H]$^+$. $^1$H NMR (400 MHz, CD$_3$OD) δ 5.95-5.71 (m, 1H), 5.07-5.12 (m, 2H), 4.04-3.98 (m, 1H), 3.77-3.63 (m, 4H), 3.29-3.22 (m, 2H), 2.35-2.23 (m, 2H), 2.22-2.09 (m, 1H), 1.47-1.37 (m, 9H). W-3 LCMS (C$_{14}$H$_{24}$NO$_5^+$)(ES, m/z): 286 [M+H]$^+$. $^1$H NMR (400 MHz, CD$_3$OD) δ 6.05-5.77 (m, 1H), 5.13 (dd, J=1.9, 17.1 Hz, 1H), 5.04 (td, J=1.0, 10.2 Hz, 1H), 4.32 (d, J=8.8 Hz, 1H), 4.19 (t, J=3.7 Hz, 1H), 3.77-3.71 (m, 3H), 3.61-3.44 (m, 2H), 2.57-2.36 (m, 1H), 2.29-2.16 (m, 2H), 1.48-1.36 (m, 9H).

Step 2: 1-(tert-butyl) 2-methyl (2S)-4-hydroxy-3-(3-(4,4,5,5-tetramethyl-1,3,2-dioxaborolan-2-yl)propyl) pyrrolidine-1,2-dicarboxylate

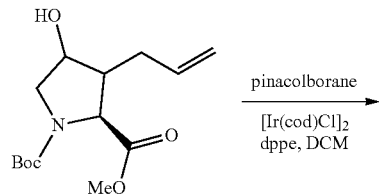

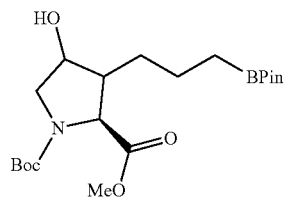

A mixture of (2S)-1-tert-butyl 2-methyl 3-allyl-4-hydroxypyrrolidine-1,2-dicarboxylate (W-1, 240 mg, 0.84 mmol), 4,4,5,5-tetramethyl-1,3,2-dioxaborolane (161 mg, 1.3 mmol) and 1,2-bis(diphenylphosphino)ethane (34 mg, 0.084 mmol) in anhydrous 1,2-dichloroethane (5.0 mL) was bubbled with a stream of nitrogen for 3 min, and stirred at 25° C. for 10 min, followed by addition of chloro(1,5-cyclooctadiene)iridium(I) dimer (28 mg, 0.042 mmol). The reaction mixture was stirred at 25° C. for 10 h under nitrogen, then filtered and concentrated in vacuum. The residue was purified by RP-HPLC [C18 column, water (0.1% TFA)-CH$_3$CN] to give (2S)-1-tert-butyl 2-methyl 4-hydroxy-3-(3-(4,4,5,5-tetramethyl-1,3,2-dioxaborolan-2-yl)propyl)pyrrolidine-1,2-dicarboxylate. LCMS (C$_{20}$H$_{37}$BNO$_7^+$)(ES, m/z): 414 [M+H]$^+$.

Step 3: (3R,4S-3-[3-(dihydroxyboranyl)propyl]-4-hydroxy-L-proline

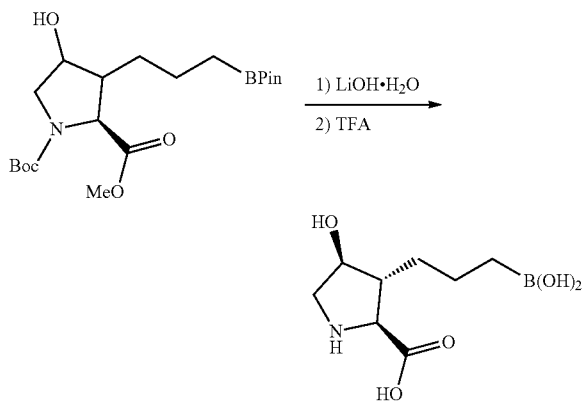

Example 20A

A mixture of (2S)-1-tert-butyl 2-methyl 4-hydroxy-3-(3-(4,4,5,5-tetramethyl-1,3,2-dioxaborolan-2-yl)propyl)pyrrolidine-1,2-dicarboxylate (35 mg, 0.085 mmol) and aqueous lithium hydroxide (1.0 M, 3.0 mL, 3.0 mmol) was stirred at 25° C. for 12 h, followed by addition of TFA (2.0 mL) and stirred at 25° C. for 3 h. The mixture was filtered and concentrated under reduced pressure, and the residue was purified by RP-HPLC [C18 column, water (0.1% TFA)-CH$_3$CN] to give (3R,4S)-3-[3-(dihydroxyboranyl)propyl]-4-hydroxy-L-proline as a TFA salt. The stereochemistry was confirmed by 2D NMR with 10% of a minor diastereomer. LCMS (C$_8$H$_{17}$BNO$_5^+$)(ES, m/z): 218 [M+H]$^+$. $^1$H NMR (400 MHz, D$_2$O) δ 4.32-4.23 (m, 1H), 4.11 (d, J=3.9 Hz, 1H), 3.51-3.20 (m, 2H), 2.50 (br s, 1H), 1.54-1.26 (m, 4H), 0.74 (br t, J=7.5 Hz, 2H).

Example 20B: (3S,4S) 3-[3-(dihydroxyboranyl)propyl]-4-hydroxy-L-proline

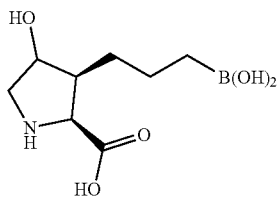 [SMILES: O=C(O)[C@H]1NCC(O)[C@H]1CCCB(O)O]

Example 20C was made from -tert-butyl 2-methyl (2S,3S,4S)-4-hydroxy-3-(prop-2-en-1-yl)pyrrolidine-1,2-dicarboxylate (W-3) as the third eluted peak using the same procedure as Example 20A. LCMS ($C_8H_{17}BNO_5^+$)(ES, m/z): 218 [M+H]; $^1$H NMR (400 MHz, $D_2O$) δ 4.44 (br s, 1H), 4.34 (d, J=9.7 Hz, 1H), 3.51-3.36 (m, 2H), 2.57-2.37 (m, 1H), 1.67-1.54 (m, 1H), 1.54-1.39 (m, 3H), 0.77 (br t, J=7.3 Hz, 2H).

Example 21A: 4-[3-(dihydroxyboranyl)propyl]pyrrolidine-3-carboxylic acid

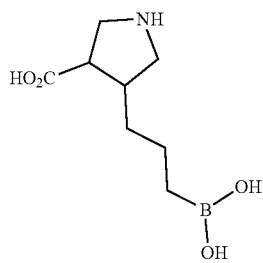

Step 1: 1-(tert-butyl) 3-methyl 4-bromo-H-pyrrole-1,3-dicarboxylate

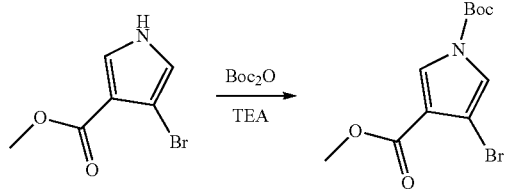

A mixture of methyl 4-bromo-1H-pyrrole-3-carboxylate (1.0 g, 4.9 mmol), TEA (1.4 mL, 9.8 mmol) and di-tert-butyl dicarbonate (2.1 g, 9.8 mmol) in DCM (50 mL) was stirred at 15° C. for 16 h. The mixture was concentrated under reduced pressure, and the residue was purified by silica gel column chromatography (EtOAc in hexanes) to give 1-tert-butyl 3-methyl 4-bromo-1H-pyrrole-1,3-dicarboxylate. LCMS ($C_{11}H_{15}BrNO_4^+$)(ES, m/z): 304 [M+H]$^+$.

Step 2: 1-(tert-butyl) 3-methyl 4-allyl-1H-pyrrole-1,3-dicarboxylate

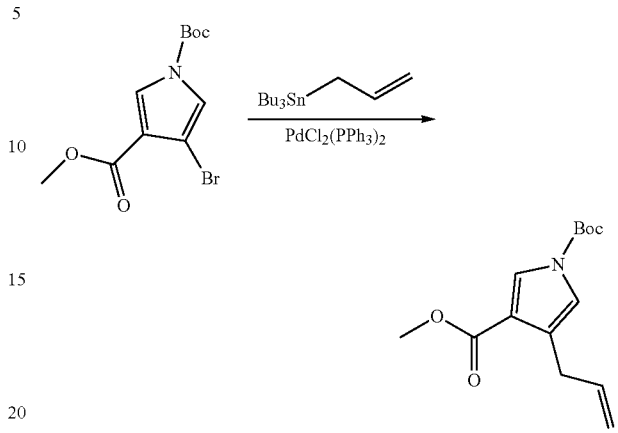

Allyltributylstannane (2.0 mL, 6.3 mmol) and dichlorobis(triphenylphosphine) palladium(II)(0.21 g, 0.30 mmol) were added to a stirred solution of 1-tert-butyl 3-methyl 4-bromo-1H-pyrrole-1,3-dicarboxylate (0.90 g, 3.0 mmol) in DMF (15 mL) under nitrogen, and the reaction mixture was degassed with nitrogen three times, and stirred at 120° C. for 2.5 h under nitrogen. The mixture was quenched with saturated aqueous potassium fluoride, then stirred 30 min at 15° C., and filtered through CELITE and concentrated in vacuo. The crude mixture was diluted with EtOAc and brine, and the separated organic phase was dried over $Na_2SO_4$, filtered and concentrated in vacuo. The residue was purified by RP-HPLC [C18 column, water (0.05% ammonia hydroxide)-$CH_3CN$] to give 1-tert-butyl 3-methyl 4-allyl-1H-pyrrole-1,3-dicarboxylate. LCMS ($C_{14}H_{20}NO_4^+$)(ES, m/z): 266 [M+H]$^+$.

Step 3: 1-(tert-butyl) 3-methyl 4-(3-(4,4,5,5-tetramethyl-1,3,2-dioxaborolan-2-yl)propyl)-H-pyrrole-1,3-dicarboxylate

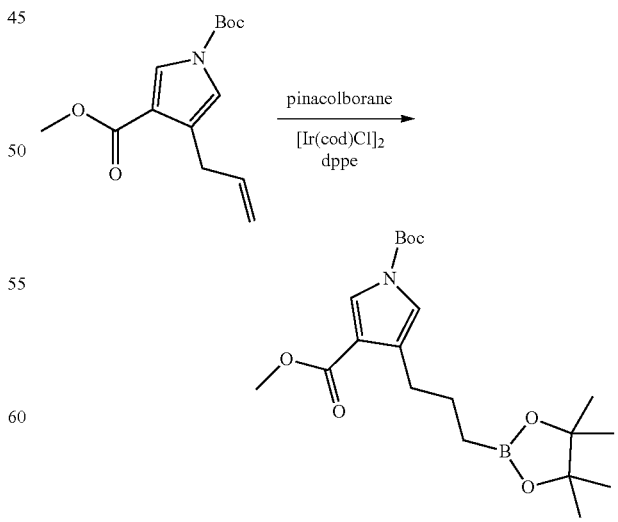

A mixture of 1,2-bis(diphenylphosphino)ethane (90 mg, 0.23 mmol) and chloro(1,5-cyclooctadiene)iridium(I) dimer (76 mg, 0.11 mmol) in DCM (5.0 mL) was degassed and backfilled with nitrogen (three times), followed by addition of 4,4,5,5-tetramethyl-1,3,2-dioxaborolane (579 mg, 4.5 mmol) and 1-tert-butyl 3-methyl 4-allyl-1H-pyrrole-1,3-dicarboxylate (600 mg, 2.3 mmol), and the reaction mixture was stirred at 15° C. for 16 h. The mixture was concentrated under reduced pressure, and the residue was purified by silica gel column chromatography (EtOAc in hexanes) to give 1-tert-butyl 3-methyl 4-(3-(4,4,5,5-tetramethyl-1,3,2-dioxaborolan-2-yl)propyl)-1H-pyrrole-1,3-dicarboxylate. LCMS ($C_{20}H_{33}BNO_6^+$)(ES, m/z): 394 [M+H]$^+$.

Step 4: 1-(tert-butyl) 3-methyl 4-(3-(4,4,5,5-tetramethyl-1,3,2-dioxaborolan-2-yl)propyl)pyrrolidine-1,3-dicarboxylate

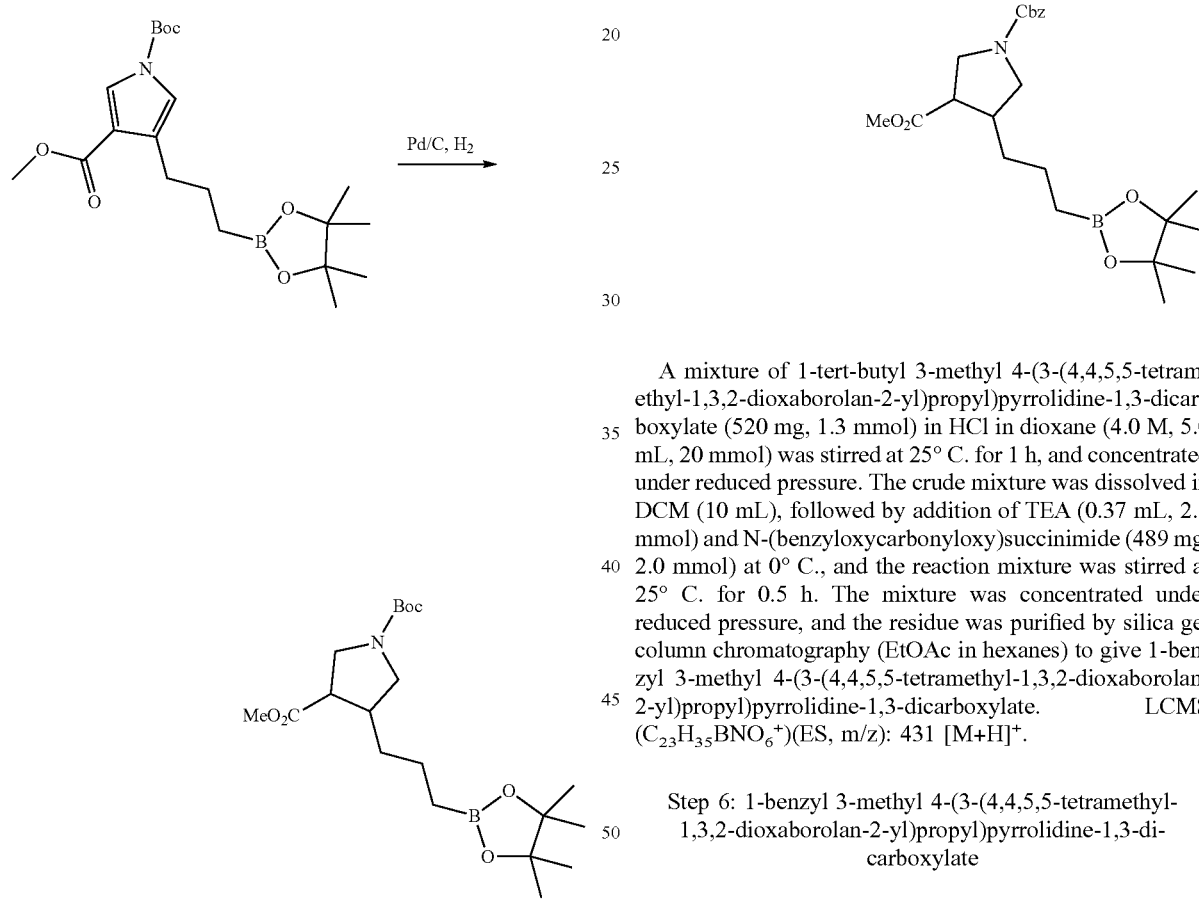

10% palladium on carbon (392 mg, 0.37 mmol) was added to a stirred solution of 1-tert-butyl 3-methyl 4-(3-(4,4,5,5-tetramethyl-1,3,2-dioxaborolan-2-yl)propyl)-1H-pyrrole-1,3-dicarboxylate (290 mg, 0.74 mmol) in MeOH (10 mL) under nitrogen atmosphere, and the reaction mixture was degassed and backfilled with hydrogen (three times), and stirred under hydrogen (Pressure: 50 psi) at 50° C. for 16 h. The mixture was filtered and the filtrate was concentrated under reduced pressure to give 1-tert-butyl 3-methyl 4-(3-(4,4,5,5-tetramethyl-1,3,2-dioxaborolan-2-yl)propyl) pyrrolidine-1,3-dicarboxylate, which was used in the next step without further purification. LCMS ($C_{15}H_{29}BNO_4^+$) (ES, m/z): 298 [M-CO$_2$C$_4$H$_8$+H]$^+$.

Step 5: 1-benzyl 3-methyl 4-(3-(4,4,5,5-tetramethyl-1,3,2-dioxaborolan-2-yl)propyl)pyrrolidine-1,3-dicarboxylate A mixture of 1-tert-butyl 3-methyl 4-(3-(4,4,5,5-tetramethyl-1,3,2-dioxaborolan-2-yl)propyl)pyrrolidine-1,3-dicarboxylate (520 mg, 1.3 mmol) in HCl in dioxane (4.0 M, 5.0 mL, 20 mmol) was stirred at 25° C. for 1 h, and concentrated under reduced pressure. The crude mixture was dissolved in DCM (10 mL), followed by addition of TEA (0.37 mL, 2.6 mmol) and N-(benzyloxycarbonyloxy)succinimide (489 mg, 2.0 mmol) at 0° C., and the reaction mixture was stirred at 25° C. for 0.5 h. The mixture was concentrated under reduced pressure, and the residue was purified by silica gel column chromatography (EtOAc in hexanes) to give 1-benzyl 3-methyl 4-(3-(4,4,5,5-tetramethyl-1,3,2-dioxaborolan-2-yl)propyl)pyrrolidine-1,3-dicarboxylate. LCMS ($C_{23}H_{35}BNO_6^+$)(ES, m/z): 431 [M+H]$^+$.

Step 6: 1-benzyl 3-methyl 4-(3-(4,4,5,5-tetramethyl-1,3,2-dioxaborolan-2-yl)propyl)pyrrolidine-1,3-dicarboxylate

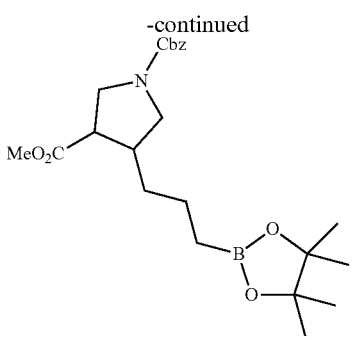

X-1

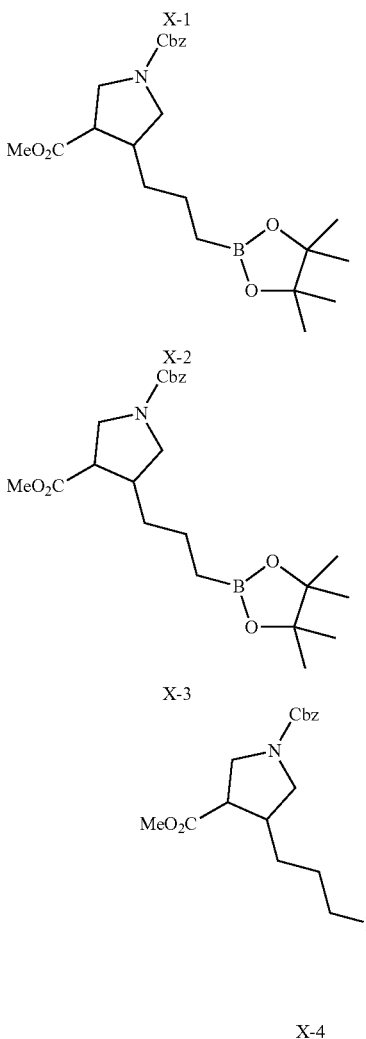

X-2

X-3

X-4

1-Benzyl 3-methyl 4-(3-(4,4,5,5-tetramethyl-1,3,2-dioxaborolan-2-yl)propyl)pyrrolidine-1,3-dicarboxylate (0.4 g) was resolved by chiral-SFC [Column: AD (250 mm*30 mm, 5 μm), Mobile phase: A: $CO_2$, B: MeOH (0.1% $NH_3.H_2O$), Gradient: 15% of B in 7.7 min and hold 15% for 1 min, Flow Rate (mL/min) 50, Column temperature: 40° C.] to give the 1-benzyl 3-methyl 4-(3-(4,4,5,5-tetramethyl-1,3,2-dioxaborolan-2-yl)propyl)pyrrolidine-1,3-dicarboxylate (X-1, $t_r$=2.36 min) as the first eluting peak, 1-benzyl 3-methyl 4-(3-(4,4,5,5-tetramethyl-1,3,2-dioxaborolan-2-yl)propyl) pyrrolidine-1,3-dicarboxylate (X-2, $t_r$=2.48 min) as the second eluting peak, 1-benzyl 3-methyl 4-(3-(4,4,5,5-tetramethyl-1,3,2-dioxaborolan-2-yl)propyl)pyrrolidine-1,3-dicarboxylate (X-3, $t_r$=2.78 min) as the third eluting peak, and 1-benzyl 3-methyl 4-(3-(4,4,5,5-tetramethyl-1,3,2-dioxaborolan-2-yl)propyl)pyrrolidine-1,3-dicarboxylate (X-4, $t_r$=2.93 min) as the fourth eluting peak. X-1 LCMS $(C_{23}H_{34}BNO_6Na^+)$(ES, m/z): 431 [M+Na]$^+$. X-2 LCMS $(C_{23}H_{34}BNO_6Na^+)$(ES, m/z): 431 [M+Na]$^+$. X-3 LCMS $(C_{23}H_{34}BNO_6Na^+)$(ES, m/z): 431 [M+Na]$^+$. X-4 LCMS $(C_{23}H_{34}BNO_6Na^+)$(ES, m/z): 431 [M+Na]$^+$.

Step 7: 4-[3-(dihydroxyboranyl)propyl]pyrrolidine-3-carboxylic acid

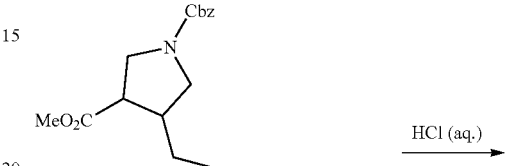

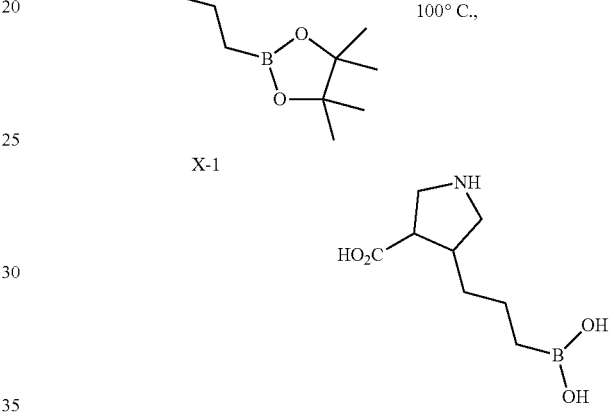

Example 21A

A mixture of 1-benzyl 3-methyl 4-(3-(4,4,5,5-tetramethyl-1,3,2-dioxaborolan-2-yl)propyl)pyrrolidine-1,3-dicarboxylate (X-1, 80 mg, 0.19 mmol) and 12N HCl in water (2.0 mL, 24 mmol) was stirred at 100° C. for 16 h, and the mixture was concentrated under reduced pressure to give 4-[3-(dihydroxyboranyl)propyl]pyrrolidine-3-carboxylic acid as an HCl salt. LCMS $(C_8H_{17}BNO_4^+)$(ES, m/z): 202 [M+H]$^+$. $^1$H NMR (400 MHz, $D_2O$) δ 3.58 (dd, J=2.6, 12.3 Hz, 1H), 3.54-3.43 (m, 1H), 3.36 (dd, J=6.6, 12.3 Hz, 1H), 3.23 (dt, J=2.9, 6.9 Hz, 1H), 3.03 (t, J=11.0 Hz, 1H), 2.66-2.51 (m, 1H), 1.47-1.26 (m, 4H), 0.73 (br t, J=7.2 Hz, 2H).

Example 21B: 4-[3-(dihydroxyboranyl)propyl]pyrrolidine-3-carboxylic acid

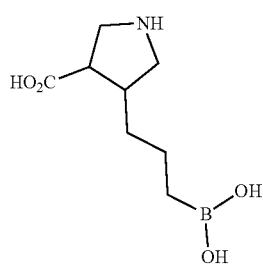 [SMILES: O=C(O)C1CNCC1CCCB(O)O]

Example 21B was made from 1-benzyl 3-methyl 4-(3-(4,4,5,5-tetramethyl-1,3,2-dioxaborolan-2-yl)propyl)pyrrolidine-1,3-dicarboxylate (X-2) as the second eluted peak using the same procedure as Example 21A. LCMS ($C_8H_{17}BNO_4^+$)(ES, m/z): 202 [M+H]$^+$. $^1$H NMR (400 MHz, D$_2$O) δ 3.58 (dd, J=2.6, 12.3 Hz, 1H), 3.54-3.43 (m, 1H), 3.36 (dd, J=6.6, 12.3 Hz, 1H), 3.23 (dt, J=2.9, 6.9 Hz, 1H), 3.03 (t, J=11.0 Hz, 1H), 2.66-2.51 (m, 1H), 1.47-1.26 (m, 4H), 0.73 (br t, J=7.2 Hz, 2H).

Example 21C: 4-[3-(dihydroxyboranyl)propyl]pyrrolidine-3-carboxylic acid

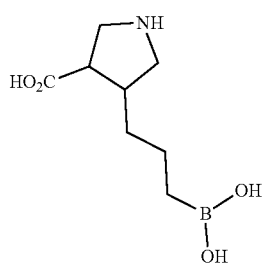

Example 21C was made from 1-benzyl 3-methyl 4-(3-(4,4,5,5-tetramethyl-1,3,2-dioxaborolan-2-yl)propyl)pyrrolidine-1,3-dicarboxylate (X-3) as the third eluted peak using the same procedure as Example 21A. LCMS ($C_8H_{17}BNO_4^+$) (ES, m/z): 202 [M+H]$^+$. $^1$H NMR (400 MHz, D$_2$O) δ 3.50-3.41 (m, 3H), 2.95-2.79 (m, 2H), 2.52-2.37 (m, 1H), 1.60-1.43 (m, 1H), 1.40-1.22 (m, 3H), 0.66 (br t, J=7.5 Hz, 2H).

Example 21D: 4-[3-(dihydroxyboranyl)propyl]pyrrolidine-3-carboxylic acid

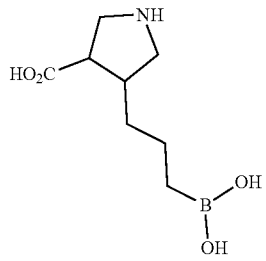

Example 21D was made from 1-benzyl 3-methyl 4-(3-(4,4,5,5-tetramethyl-1,3,2-dioxaborolan-2-yl)propyl)pyrrolidine-1,3-dicarboxylate (X-4) as the fourth eluted peak using the same procedure as Example 21A. LCMS ($C_8H_{15}BNO_3^+$) (ES, m/z): 184 [M−H$_2$O+H]$^+$. $^1$H NMR (400 MHz, D$_2$O) δ 3.48 (dd, J=2.4, 12.5 Hz, 1H), 3.37 (dd, J=7.7, 11.6 Hz, 1H), 3.30-3.21 (m, 1H), 3.18-3.08 (m, 1H), 2.93 (t, J=11.2 Hz, 1H), 2.48 (td, J=6.9, 10.4 Hz, 1H), 1.39-1.15 (m, 4H), 0.62 (br t, J=7.2 Hz, 2H).

Example 22: (2S,3R)-3-methyl-3-(3-((3aR,4R,6R,7aS)-3a,5,5-trimethylhexahydro-4,6-methanobenzo[d][1,3,2]dioxaborol-2-yl)propyl)pyrrolidine-2-carboxylic acid

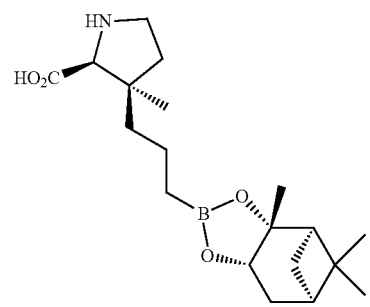 [SMILES: CC1(C)[C@H]2C[C@@H]3OB(CCC[C@]4(C)CCN[C@@H]4C(=O)O)O[C@]3(C)[C@@H]1C2]

Step 1: (2S,3R)-3-methyl-3-(3-((3aR,4R,6R,7aS)-3a,5,5-trimethylhexahydro-4,6-methanobenzo[d][1,3,2]dioxaborol-2-yl)propyl)pyrrolidine-2-carboxylic acid

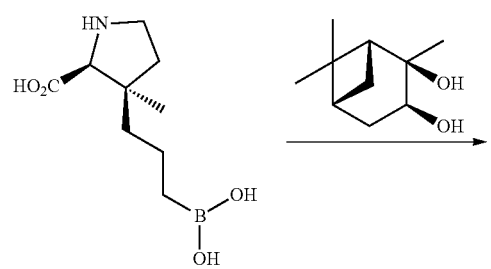

Example 14-free base

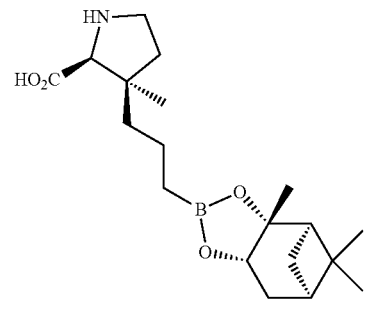

Example 22

(1R,2R,3S,5R)-(−)-2,3-pinanediol (165 mg, 0.97 mmol) was added to the stirred suspension of (3R)-3-[3-(dihydroxyboranyl)propyl]-3-methyl-L-proline (free base, 105 mg, 0.49 mmol) in CH$_3$CN (4.9 mL) in one portion at room temperature. The reaction mixture was heated to 85° C. with stirring for 4 h, and then cooled to room temperature. The mixture was concentrated under reduced pressure, and the residue was triturated three times with Et$_2$O to afford (2S,3R)-3-methyl-3-(3-((3aR,4R,6R,7aS)-3a,5,5-trimethylhexahydro-4,6-methanobenzo[d][1,3,2]dioxaborol-2-yl)propyl)pyrrolidine-2-carboxylic acid as a free base. LCMS ($C_{19}H_{33}BNO_4$)(ES, m/z): 350 [M+H]$^+$. $^1$H NMR (500 MHz, DMSO-d6) δ 4.28 (dd, J=8.5, 1.3 Hz, 1H), 3.19 (s, 1H), 3.15-3.09 (m, 1H), 3.06-3.01 (m, 1H), 2.30-2.26 (m, 1H), 2.20-2.15 (m, 1H), 1.95 (t, J=5.5 Hz, 1H), 1.88-1.83 (br, 2H), 1.72-1.68 (m, 1H), 1.52 (dt, J=12.5, 9.5 Hz, 1H), 1.38-1.31 (m, 1H), 1.31 (s, 3H), 1.25 (s, 3H), 1.24-1.18 (m, 3H), 1.12 (s, 3H), 1.00 (d, J=11 Hz, 1H), 0.81 (s, 3H), 0.72-0.61 (m, 2H).

Example 23: (2,3R,4R)-4-amino-3-(3-boronopropyl)pyrrolidine-2-carboxylic acid

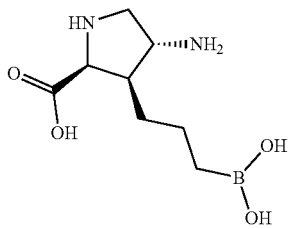 [SMILES: N[C@H]1CN[C@H](C(=O)O)[C@@H]1CCCB(O)O]

Step 1: 1-(tert-butyl) 2-methyl (2S,3S,4S)-3-allyl-4-hydroxypyrrolidine-1,2-dicarboxylate

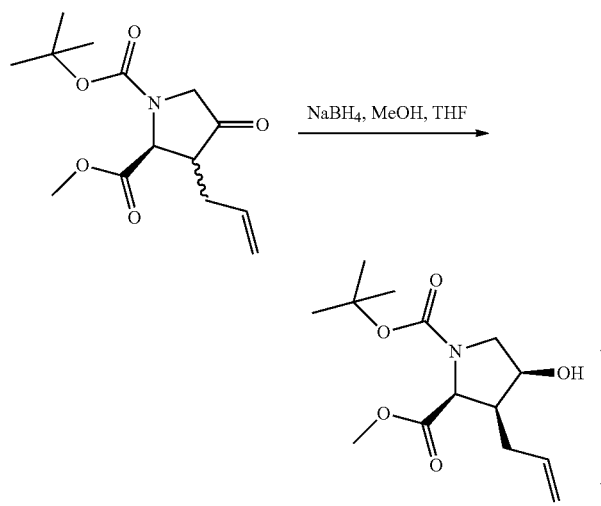

Sodium borohydride (20 mg, 5.3 mmol) was added to a solution of 1-(tert-butyl) 2-methyl (2S)-3-allyl-4-oxopyrrolidine-1,2-dicarboxylate (1.0 g, 3.5 mmol) in MeOH (6.0 mL) and THF (6.0 mL) at −78° C. The reaction mixture was held at −78° C. for 20 minutes then warmed to −5° C. for 30 minutes. The reaction was quenched with saturated aqueous NH$_4$Cl, and diluted with EtOAc. The organic layer was separated, washed with brine, dried over Na$_2$SO$_4$, filtered and concentrated. The residue was purified by silica gel chromatography (EtOAc in hexanes) to afford a mixture of stereoisomers, which was purified again by silica gel chromatography (EtOAc in DCM) to afford 1-(tert-butyl) 2-methyl (2S,3S,4S)-3-allyl-4-hydroxypyrrolidine-1,2-dicarboxylate as a single isomer (present as 1.5:1 mixture of rotamers by NMR). LCMS (C$_9$H$_{16}$NO$_3$$^+$)(ES, m/z): 186 [M-CO$_2$C$_4$H$_8$+H]$^+$. $^1$H NMR (499 MHz, methanol-d$_4$) δ 5.99-5.83 (m, 1H), 5.21-5.11 (m, 1H), 5.10-5.02 (m, 1H), 4.84 (s, 1H), 4.34 (d, J=9.0 Hz, 1H), 4.25-4.18 (m, 1H), 3.76 (s, 1.8H), 3.75 (s, 1.2H), 3.63-3.49 (m, 2H), 2.58-2.41 (m, 1H), 2.32-2.18 (m, 2H), 1.48 (s, 3.6H), 1.43 (s, 5.4H).

Step 2: 1-(tert-butyl) 2-methyl (2S,3S,4S)-3-allyl-4-((methylsulfonyl)oxy)pyrrolidine-1,2-dicarboxylate

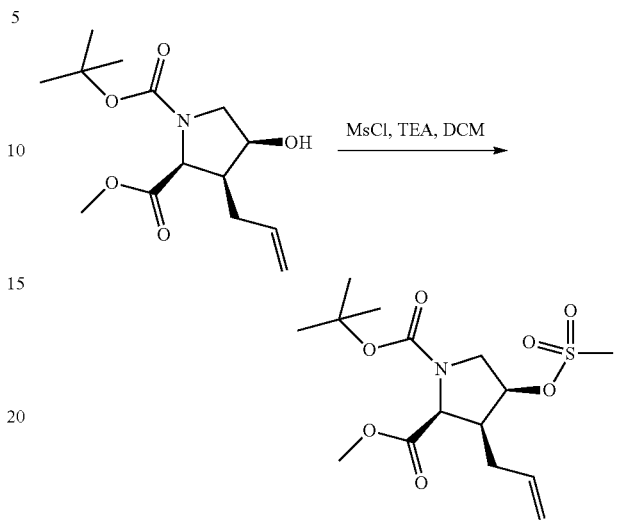

Triethylamine (0.16 mL, 1.2 mmol) followed by methanesulfonyl chloride (73 µL, 0.93 mmol) were added to a solution of 1-(tert-butyl) 2-methyl (2S,3S,4S)-3-allyl-4-hydroxypyrrolidine-1,2-dicarboxylate (0.14 g, 0.49 mmol) in DCM (1.5 mL) at 0° C. The resulting mixture was stirred at 0° C. for 1 h, then warmed to room temperature and stirred for 3 h. The reaction mixture was diluted with water and EtOAc. The organic layer was separated then washed with 1 N citric acid in water, saturated aqueous NaHCO$_3$ and brine. The resulting organic layer was dried over Na$_2$SO$_4$, filtered and concentrated to afford 1-(tert-butyl) 2-methyl (2S,3S,4S)-3-allyl-4-((methylsulfonyl)oxy)pyrrolidine-1,2-dicarboxylate. LCMS (C$_{10}$H$_{18}$NO$_5$S$^+$)(ES, m/z): 264 [M-CO$_2$C$_4$H$_8$+H]$^+$.

Step 3: 1-(tert-butyl) 2-methyl (2S,3S,4R)-3-allyl-4-azidopyrrolidine-1,2-dicarboxylate

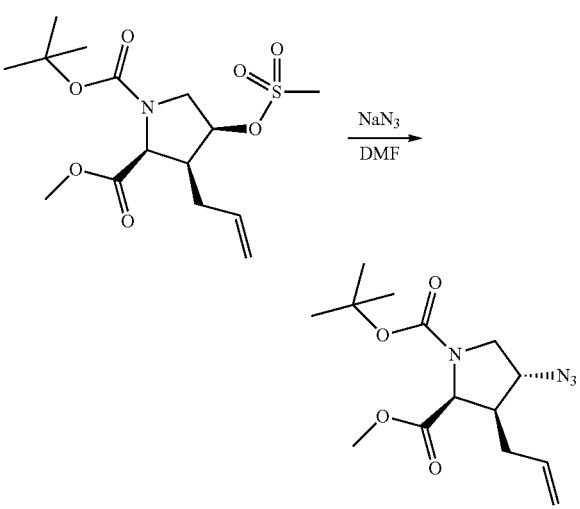

Sodium azide (0.12 g, 1.9 mmol) was added to a solution of 1-(tert-butyl) 2-methyl (2S,3S,4S)-3-allyl-4-((methylsulfonyl)oxy)pyrrolidine-1,2-dicarboxylate (0.17 g, 0.47 mmol) in DMF (2.2 mL). The reaction mixture was stirred at 80° C. for 22 h. After cooling to room temperature, the reaction was diluted with saturated aqueous NaHCO₃ and EtOAc. The organic layer was separated, washed with brine, dried over Na₂SO₄, filtered and concentrated. The residue was purified by silica gel chromatography (EtOAc in hexanes) to afford 1-(tert-butyl) 2-methyl (2S,3S,4R)-3-allyl-4-azidopyrrolidine-1,2-dicarboxylate. LCMS $(C_9H_{15}N_4O_2^+)$(ES, m/z): 211 $[M-CO_2C_4H_8+H]^+$.

Step 4: 1-(tert-butyl) 2-methyl (2S,3S,4R)-4-azido-3-(3-(4,4,5,5-tetramethyl-1,3,2-dioxaborolan-2-yl)propyl)pyrrolidine-1,2-dicarboxylate

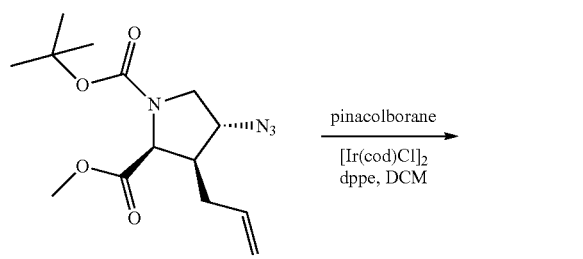

4,4,5,5-tetramethyl-1,3,2-dioxaborolane (84 µL, 0.58 mmol), chloro(1,5-cyclooctadiene)Iridium(I) dimer (7.8 mg, 0.012 mmol) and 1,2-bis(diphenylphosphino)ethane (9.2 mg, 0.023 mmol) in anhydrous DCM (3 mL) was placed under an atmosphere of argon and the resulting mixture was stirred at ambient temperature for 20 minutes, followed by addition of a solution of 1-(tert-butyl) 2-methyl (2S,3S,4R)-3-allyl-4-azidopyrrolidine-1,2-dicarboxylate (72 mg, 0.23 mmol) in DCM (1.5 mL). The reaction mixture was stirred at ambient temperature for 21 hours under argon. Reaction was quenched by slow addition of methanol then diluted with water and DCM. The organic layer was separated, washed with brine, dried over Na₂SO₄, filtered and concentrated under reduced pressure. The resulting residue was purified by silica gel chromatography (EtOAc in hexanes) to afford 1-(tert-butyl) 2-methyl (2S,3S,4R)-4-azido-3-(3-(4,4,5,5-tetramethyl-1,3,2-dioxaborolan-2-yl)propyl)pyrrolidine-1,2-dicarboxylate. LCMS $(C_{15}H_{28}BN_4O_4^+)$(ES, m/z): 339 $[M-CO_2C_4H_8+H]^+$.

Step 5: 1-(tert-butyl) 2-methyl (2S,3R,4R)-4-amino-3-(3-(4,4,5,5-tetramethyl-1,3,2-dioxaborolan-2-yl)propyl)pyrrolidine-1,2-dicarboxylate

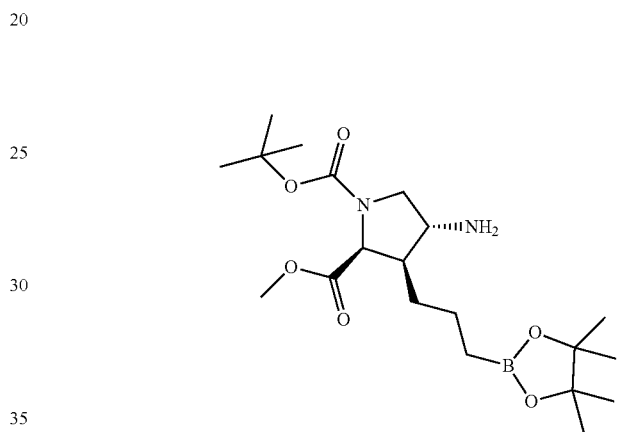

10% Pd/C (6.8 mg, 0.0064 mmol) was added to a solution of 1-(tert-butyl) 2-methyl (2S,3S,4R)-4-azido-3-(3-(4,4,5,5-tetramethyl-1,3,2-dioxaborolan-2-yl)propyl)pyrrolidine-1,2-dicarboxylate (28 mg, 0.064 mmol) in EtOAc (3.0 mL). The reaction mixture was degassed and backfilled with H₂ three times then stirred under H₂ for 16 h. The mixture was filtered and concentrated to give 1-(tert-butyl) 2-methyl (2S,3R,4R)-4-amino-3-(3-(4,4,5,5-tetramethyl-1,3,2-dioxaborolan-2-yl)propyl)pyrrolidine-1,2-dicarboxylate. LCMS $(C_{15}H_{30}BN_2O_4^+)$(ES, m/z): 313 $[M-CO_2C_4H_8+H]^+$.

Step 6: (2S,3R,4R)-4-amino-3-(3-boronopropyl)pyrrolidine-2-carboxylic acid

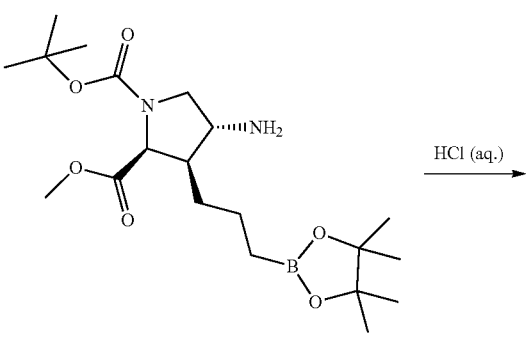

-continued

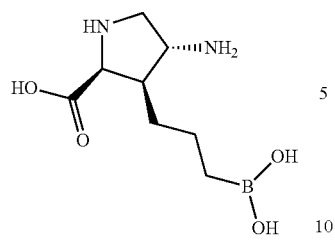

Example 23

A mixture of 1-(tert-butyl) 2-methyl (2S,3R,4R)-4-amino-3-(3-(4,4,5,5-tetramethyl-1,3,2-dioxaborolan-2-yl)propyl)pyrrolidine-1,2-dicarboxylate (26 mg, 0.064 mmol) and 6 N HCl in water (1.5 mL, 9.0 mmol) was heated in a microwave reactor with stirring at 120° C. for 1 h. The reaction mixture was concentrated to give (2S,3R,4R)-4-amino-3-(3-boronopropyl)pyrrolidine-2-carboxylic acid as an HCl salt. LCMS ($C_8H_{16}BN_2O_3^+$)(ES, m/z): 199 [M−H$_2$+H]$^+$. $^1$H NMR (499 MHz, D$_2$O) δ 4.52 (d, J=7.2 Hz, 1H), 4.02-3.88 (m, 2H), 3.44 (dd, J=13.0, 4.3 Hz, 1H), 2.74-2.61 (m, 1H), 1.54-1.31 (m, 4H), 0.81-0.66 (m, 2H).

Example 24: (2S,3S,4R)-3-(3-boronopropyl)-4-(dimethylamino)pyrrolidine-2-carboxylic acid

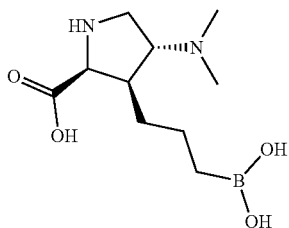 [SMILES: CN(C)[C@H]1CN[C@H](C(=O)O)[C@@H]1CCCB(O)O]

Step 1: 1-(tert-butyl) 2-methyl (2S,3R,4R)-4-(dimethylamino)-3-(3-(4,4,5,5-tetramethyl-1,3,2-dioxaborolan-2-yl)propyl)pyrrolidine-1,2-dicarboxylate

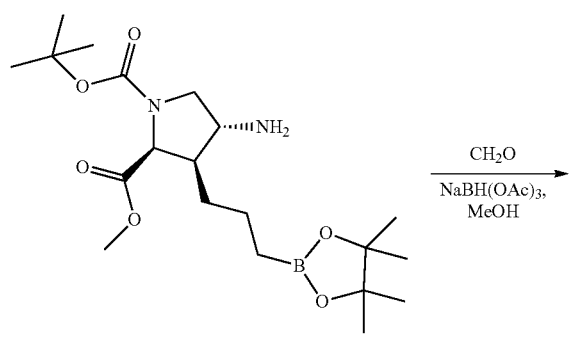

-continued

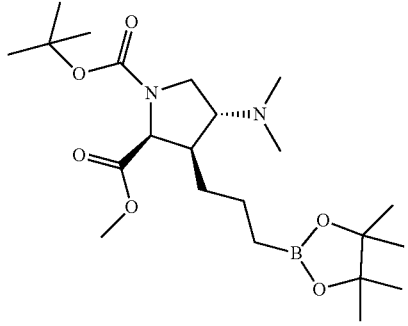

Formaldehyde (37 wt % in water, 36 μL, 0.49 mmol) and sodium triacetoxyborohydride (77 mg, 0.36 mmol), were added sequentially to a solution of 1-(tert-butyl) 2-methyl (2S,3R,4R)-4-amino-3-(3-(4,4,5,5-tetramethyl-1,3,2-dioxaborolan-2-yl)propyl)pyrrolidine-1,2-dicarboxylate (50 mg, 0.12 mmol) in MeOH (1.2 mL). The reaction mixture was stirred at room temperature for 1.5 h. Reaction was concentrated, and the residue was purified by silica gel chromatography (MeOH in DCM) to afford 1-(tert-butyl) 2-methyl (2S,3R,4R)-4-(dimethylamino)-3-(3-(4,4,5,5-tetramethyl-1,3,2-dioxaborolan-2-yl)propyl)pyrrolidine-1,2-dicarboxylate. LCMS ($C_{22}H_{42}BN_2O_6^+$)(ES, m/z): 441 [M+H]$^+$.

Step 2: (2S,3S 4R)-3-(3-boronopropyl)-4-(dimethylamino)pyrrolidine-2-carboxylic acid

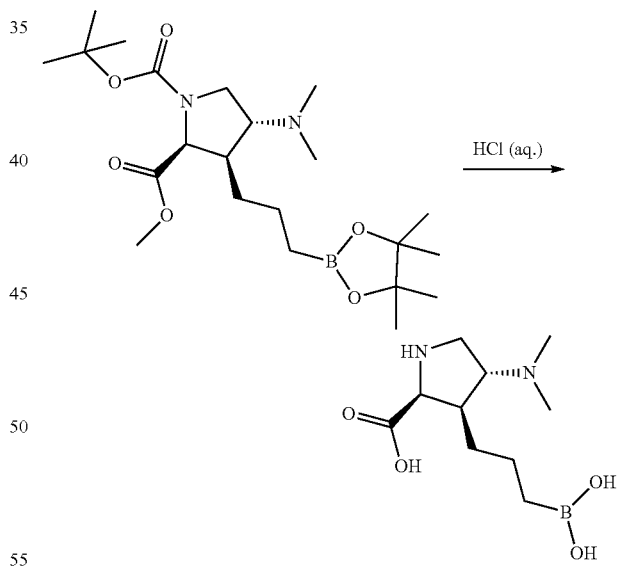

Example 24

A mixture of 1-(tert-butyl) 2-methyl (2S,3R,4R)-4-(dimethylamino)-3-(3-(4,4,5,5-tetramethyl-1,3,2-dioxaborolan-2-yl)propyl)pyrrolidine-1,2-dicarboxylate (28 mg, 0.063 mmol) and 6 N HCl in water (1.5 mL, 9.0 mmol) was heated in a microwave reactor with stirring at 120° C. for 2 hours. The reaction mixture was concentrated to give (2S,3S,4R)-3-(3-boronopropyl)-4-(dimethylamino)pyrrolidine-2-carboxylic acid as an HCl salt. LCMS ($C_{10}H_{20}BN_2O_3^+$)(ES, m/z): 227 [M−H$_2$+H]$^+$. $^1$H NMR (499 MHz, D$_2$O) δ 4.51 (d, J=7.3 Hz, 1H), 4.04-3.97 (m, 2H), 3.70-3.61 (m, 1H), 2.97-2.83 (m, 7H), 1.52-1.36 (m, 4H), 0.79-0.68 (m, 2H).

Example 25: (3'R,4'S,5'S)-4'-(3-boronopropyl)-[1,3'-bipyrrolidine]-5'-carboxylic acid

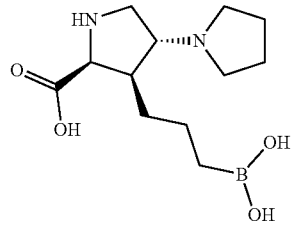 [SMILES: O=C(O)[C@H]1NC[C@H](N2CCCC2)[C@H]1CCCB(O)O]

Step 1: 1'-(tert-butyl) 5'-methyl 3'R,4'R,5'S)-4'-allyl-[1,3'-bipyrrolidine]-1'5'-dicarboxylate

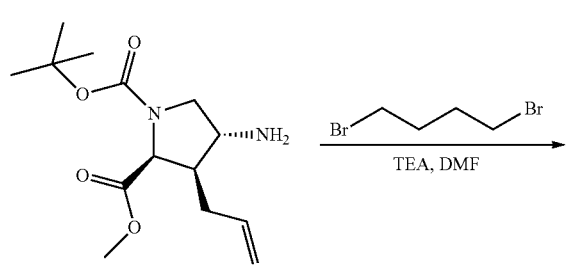

Triethylamine (0.20 mL, 1.4 mmol) and 1,4-dibromobutane (46 µL, 0.39 mmol) were added to a solution of 1-(tert-butyl) 2-methyl (2S,3R,4R)-3-allyl-4-aminopyrrolidine-1,2-dicarboxylate (0.10 g, 0.35 mmol) in DMF (1.5 mL). The resulting solution was stirred at 60° C. for 20 h. After cooling to room temperature, the reaction was diluted with saturated aqueous NaHCO₃ and EtOAc. The organic layer was separated, washed with brine, dried over Na₂SO₄, filtered and concentrated. The residue was purified by silica gel chromatography (MeOH in DCM) to afford 1'-(tert-butyl) 5'-methyl (3'R,4'R,5'S)-4'-allyl-[1,3'-bipyrrolidine]-1',5'-dicarboxylate. LCMS ($C_{18}H_{31}N_2O_4^+$)(ES, m/z): 339 [M+H]⁺.

Step 2: 1'-(tert-butyl) 5'-methyl (3'R,4'R,5'S)-4'-(3-((3aS,4S,6S,aR)-3a,5,5-trimethylhexahydro-4,6-methanobenzo[d][1,3,2]dioxaborol-2-yl)propyl)-[1,3'-bipyrrolidine]-1',5'-dicarboxylate

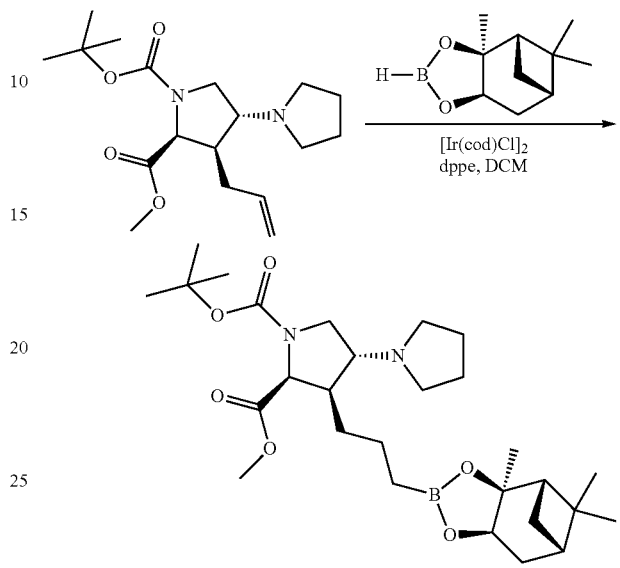

(3aS,4S,6S,7aR)-3a,5,5-trimethylhexahydro-4,6-methanobenzo[d][1,3,2]dioxaborole (65 mg, 0.36 mmol), chloro (1,5-cyclooctadiene)Iridium(I) dimer (4.9 mg, 0.0072 mmol) and 1,2-bis(diphenylphosphino)ethane (5.8 mg, 0.014 mmol) in anhydrous DCM (2.0 mL) was placed under argon and the resulting mixture was stirred at room temperature for 15 minutes, followed by addition of a solution of 1'-(tert-butyl) 5'-methyl (3'R,4'R,5'S)-4'-allyl-[1,3'-bipyrrolidine]-1',5'-dicarboxylate (49 mg, 0.15 mmol) in DCM (1.0 mL). The reaction mixture was stirred at room temperature for 19 h under argon. Reaction was quenched by slow addition of methanol then diluted with water and EtOAc. The organic layer was separated, washed with brine, dried over Na₂SO₄, filtered and concentrated. The residue was purified by RP-HPLC [C18 column, water (0.1% TFA)-CH₃CN] to afford 1'-(tert-butyl) 5'-methyl (3'R,4'R,5'S)-4'-(3-((3aS,4S,6S,7aR)-3a,5,5-trimethylhexahydro-4,6-methanobenzo[d][1,3,2]dioxaborol-2-yl)propyl)-[1,3'-bipyrrolidine]-1',5'-dicarboxylate as the TFA salt. LCMS ($C_{28}H_{48}BN_2O_6^+$)(ES, m/z): 519 [M+H]⁺.

Step 3: (3'R,4'S,5'S)-4'-(3-boronopropyl)-[1,3'-bipyrrolidine]-5'-carboxylic acid

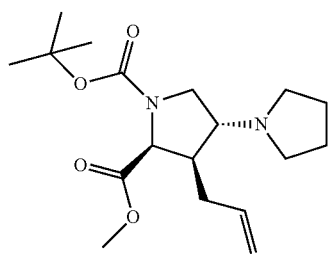

-continued

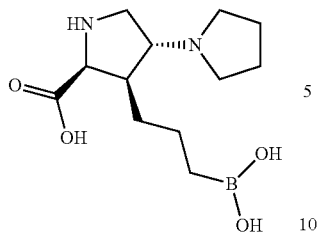

Example 25

A mixture of 1'-(tert-butyl) 5'-methyl (3'R,4'R,5'S)-4'-(3-((3aS,4S,6S,7aR)-3a,5,5-trimethylhexahydro-4,6-methanobenzo[d][1,3,2]dioxaborol-2-yl)propyl)-[1,3'-bipyrrolidine]-1',5'-dicarboxylate (48 mg, 0.076 mmol) and 6 N HCl in water (1.0 mL, 6.0 mmol) was heated in a microwave reactor with stirring at 120° C. for 1 h. The reaction mixture was concentrated and the residue was taken up in water then washed with DCM. The organic layer was removed and the aqueous layer was concentrated to afford (3'R,4'S,5'S)-4'-(3-boronopropyl)-[1,3'-bipyrrolidine]-5'-carboxylic acid as an HCl salt. LCMS ($C_{12}H_{24}BN_2O_4^+$)(ES, m/z): 271 [M+H]$^+$. $^1$H NMR (499 MHz, D$_2$O) δ 4.46 (d, J=6.9 Hz, 1H), 4.10-3.94 (m, 2H), 3.93-3.51 (m, 3H), 3.35-2.95 (m, 2H), 2.92-2.78 (m, 1H), 2.24-1.83 (m, 4H), 1.59-1.24 (m, 4H), 0.83-0.64 (m, 2H).

Example 26: (2S,3R,4R)-3-(3-boronopropyl)-4-((2,2,2-trifluoroethyl)amino)pyrrolidine-2-carboxylic acid

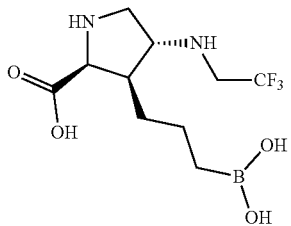 [SMILES: O=C(O)[C@H]1NC[C@H](NCC(F)(F)F)[C@H]1CCCB(O)O]

Step 1: 1-(tert-butyl) 2-methyl (2S,3R,4R)-3-allyl-4-((2,2,2-trifluoroethyl)amino)pyrrolidine-1,2-dicarboxylate

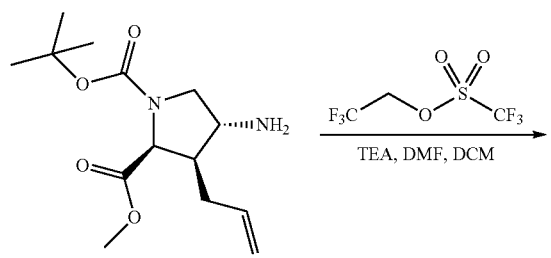

-continued

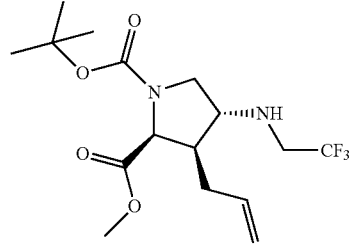

Triethylamine (98 µL, 0.70 mmol) followed by 2,2,2-trifluoroethyl trifluoromethanesulfonate (63 µL, 0.44 mmol) was added to a solution of 1-(tert-butyl) 2-methyl (2S,3R,4R)-3-allyl-4-aminopyrrolidine-1,2-dicarboxylate (50 mg, 0.18 mmol) in DMF (0.60 mL) and DCM (0.60 mL). Reaction was stirred at 50° C. for 2 h then at room temperature for 18 h. The reaction mixture was diluted with water and EtOAc. The organic layer was separated, washed with brine, dried over Na$_2$SO$_4$, filtered and concentrated. The residue was purified by silica gel chromatography (EtOAc in hexanes) to afford 1-(tert-butyl) 2-methyl (2S,3R,4R)-3-allyl-4-((2,2,2-trifluoroethyl)amino)pyrrolidine-1,2-dicarboxylate. LCMS ($C_{11}H_{18}F_3N_2O_2^+$)(ES, m/z): 267 [M-CO$_2$C$_4$H$_8$+H]$^+$.

Step 2: 1-(tert-butyl) 2-methyl (2S,3R,4R)-3-(3-(4,4,5,5-tetramethyl-1,3,2-dioxaborolan-2-yl)propyl)-4-((2,2,2-trifluoroethyl)amino)pyrrolidine-1,2-dicarboxylate

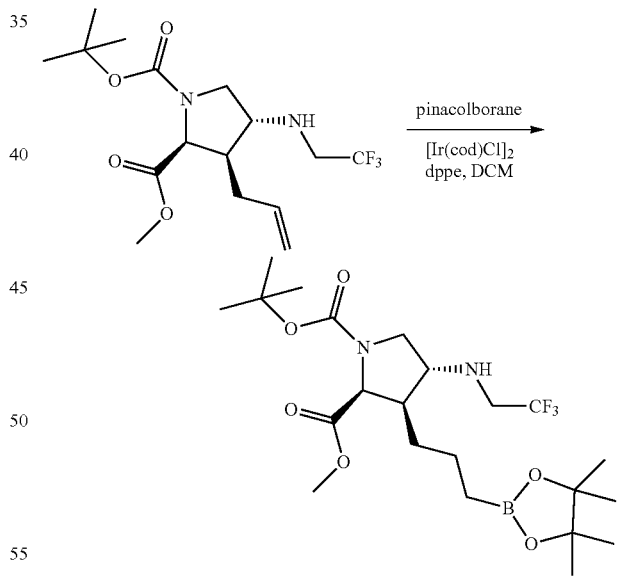

4,4,5,5-tetramethyl-1,3,2-dioxaborolane (1 M in THF, 0.28 mL, 0.28 mmol) was added to a solution of chloro(1,5-cyclooctadiene)iridium(I) dimer (3.8 mg, 0.0056 mmol) and 1,2-bis(diphenylphosphino)ethane (4.5 mg, 0.011 mmol) in anhydrous DCM (1.5 mL). The resulting solution was placed under argon and stirred at room temperature for 20 min, followed by addition of a solution of 1-(tert-butyl) 2-methyl (2S,3R,4R)-3-allyl-4-((2,2,2-trifluoroethyl)amino) pyrrolidine-1,2-dicarboxylate (41 mg, 0.11 mmol) in DCM (0.75 mL). The reaction mixture was stirred at room temperature for 1.5 h under argon. Reaction was quenched by slow addition of methanol then diluted with water and EtOAc. The organic layer was separated, dried over Na$_2$SO$_4$, filtered and concentrated. The residue was purified by silica gel chromatography (EtOAc in hexanes) to afford 1-(tert-butyl) 2-methyl (2S,3R,4R)-3-(3-(4,4,5,5-tetramethyl-1,3,2-dioxaborolan-2-yl)propyl)-4-((2,2,2-trifluoroethyl)amino)pyrrolidine-1,2-dicarboxylate. LCMS (C$_{17}$H$_{31}$BF$_3$N$_2$O$_4$$^+$)(ES, m/z): 395 [M-CO$_2$C$_4$H$_8$+H]$^+$.

Step 3: (2S,3R,4R)-3-(3-boronopropyl)-4-((2,2,2-trifluoroethyl)amino)pyrrolidine-2-carboxylic acid

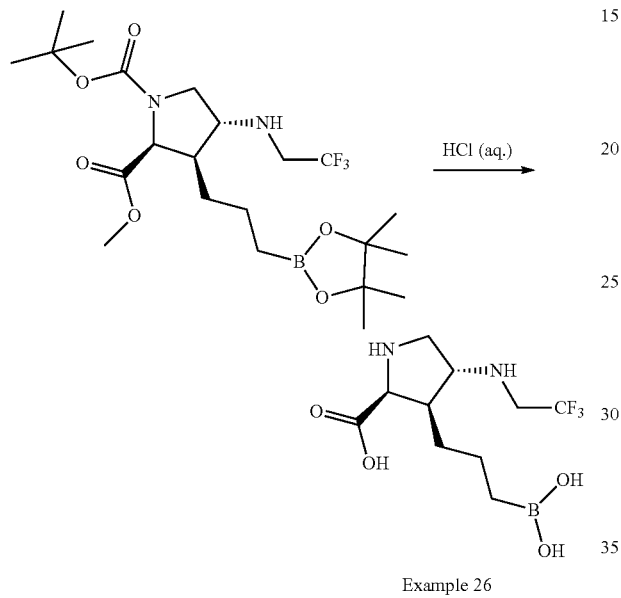

Example 26

A mixture of 1-(tert-butyl) 2-methyl (2S,3R,4R)-3-(3-(4,4,5,5-tetramethyl-1,3,2-dioxaborolan-2-yl)propyl)-4-((2,2,2-trifluoroethyl)amino)pyrrolidine-1,2-dicarboxylate (40 mg, 0.081 mmol) and 6 N HCl in water (1.5 mL, 9.0 mmol) was heated in a microwave reactor with stirring at 120° C. for 1 h. The reaction mixture was concentrated to afford (2S,3R,4R)-3-(3-boronopropyl)-4-((2,2,2-trifluoroethyl) amino)pyrrolidine-2-carboxylic acid as an HCl salt. LCMS (C$_{10}$H$_{19}$BF$_3$N$_2$O$_4$$^+$)(ES, m/z): 299 [M+H]$^+$. $^1$H NMR (499 MHz, D$_2$O) δ 4.61-4.51 (m, 1H), 3.89-3.79 (m, 1H), 3.79-3.71 (m, 1H), 3.71-3.54 (m, 2H), 3.42-3.31 (m, 1H), 2.73-2.57 (m, 1H), 1.53-1.21 (m, 4H), 0.81-0.66 (m, 2H).

Example 27: (2S,3R,4R)-3-(3-boronopropyl)-4-((2,2-difluoroethyl)amino)pyrrolidine-2-carboxylic acid 7

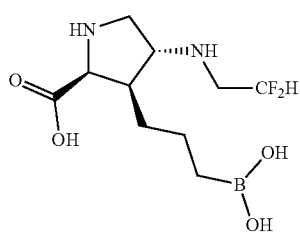 [SMILES: O=C(O)[C@H]1NC[C@H](NCC(F)F)[C@H]1CCCB(O)O]

Example 27 was made from 1-(tert-butyl) 2-methyl (2S,3R,4R)-3-allyl-4-aminopyrrolidine-1,2-dicarboxylate (1) and using the same procedure as Example 26:

LCMS (C$_{10}$H$_{20}$BF$_2$N$_2$O$_4$$^+$)(ES, m/z): 281 [M+H]$^+$. $^1$H NMR (499 MHz, D$_2$O) δ 6.25 (tt, J=53.0, 2.6 Hz, 1H), 4.51 (d, J=7.0 Hz, 1H), 4.03-3.93 (m, 2H), 3.71-3.50 (m, 3H), 2.87-2.71 (m, 1H), 1.52-1.23 (m, 4H), 0.80-0.60 (m, 2H).

Example 28: (2S,3 S,4R)-3-(3-boronopropyl)-4-(diethylamino)pyrrolidine-2-carboxylic acid Step 1: 1-(tert-butyl) 2-methyl (2S,3R,4R)-3-allyl-4-(diethylamino)pyrrolidine-1,2-dicarboxylate

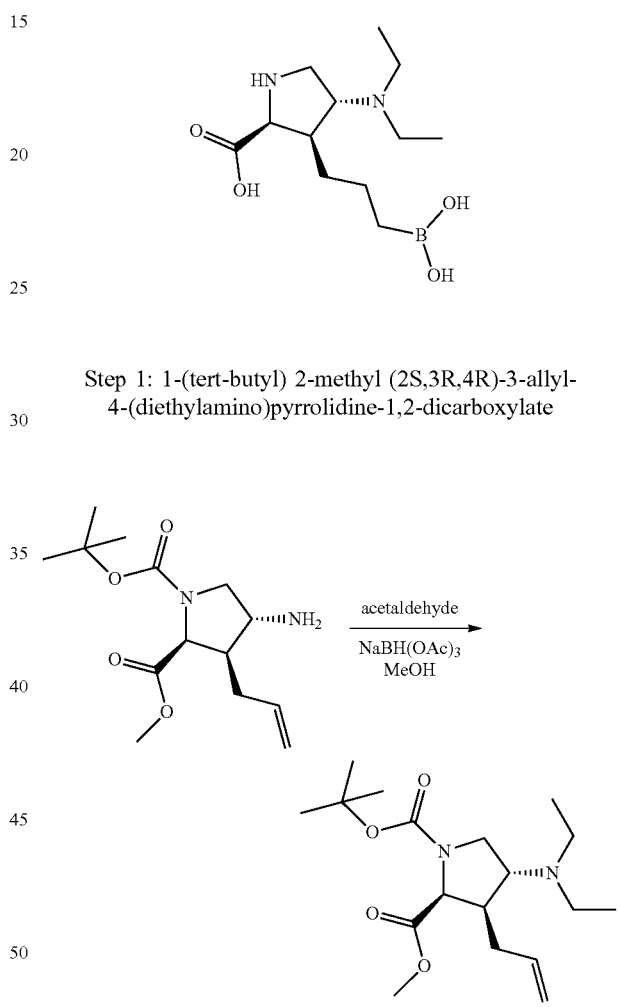

Acetaldehyde (37 wt % in water, 9.4 µL, 0.17 mmol) followed by sodium triacetoxyborohydride (56 mg, 0.26 mmol) were added to a solution of 1-(tert-butyl) 2-methyl (2S,3R,4R)-3-allyl-4-aminopyrrolidine-1,2-dicarboxylate (50 mg, 0.18 mmol) in MeOH (1.7 mL). The reaction mixture was stirred at room temperature for 1.5 h. Reaction was diluted with water and EtOAc. The organic layer was separated, washed with brine, dried over Na$_2$SO$_4$, filtered and concentrated. The residue was purified by silica gel chromatography (EtOAc in hexanes) to afford 1-(tert-butyl) 2-methyl (2S,3R,4R)-3-allyl-4-(diethylamino)pyrrolidine-1,2-dicarboxylate. LCMS (C$_1$H$_{33}$N$_2$O$_4$$^+$)(ES, m/z): 341 [M+H]$^+$.

Step 2: 1-(tert-butyl) 2-methyl (2S,3R,4R)-4-(diethylamino)-3-(3-(4,4,5,5-tetramethyl-1,3,2-dioxaborolan-2-yl)propyl)pyrrolidine-1,2-dicarboxylate

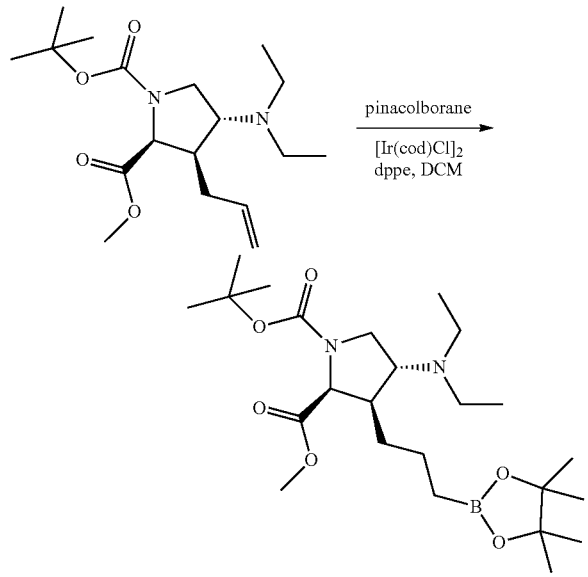

A solution of 4,4,5,5-tetramethyl-1,3,2-dioxaborolane (1M in THF, 0.20 mL, 0.20 mmol), chloro(1,5-cyclooctadiene)Iridium(I) dimer (2.7 mg, 0.0040 mmol) and 1,2-bis(diphenylphosphino)ethane (3.2 mg, 0.0079 mmol) in anhydrous DCM (1.0 mL) was placed under argon, and the resulting mixture was stirred at room temperature for 20 minutes, followed by addition of a solution of 1-(tert-butyl) 2-methyl (2S,3R,4R)-3-allyl-4-(diethylamino)pyrrolidine-1,2-dicarboxylate (27 mg, 0.079 mmol) in DCM (0.50 mL). The reaction mixture was stirred at room temperature for 1.5 hours under argon. Reaction was quenched by slow addition of methanol then diluted with water and EtOAc. The organic layer was separated, washed with brine, dried over Na$_2$SO$_4$, filtered and concentrated. The residue was purified by silica gel chromatography (EtOAc in hexanes) to afford 1-(tert-butyl) 2-methyl (2S,3R,4R)-4-(diethylamino)-3-(3-(4,4,5,5-tetramethyl-1,3,2-dioxaborolan-2-yl)propyl)pyrrolidine-1,2-dicarboxylate. LCMS (C$_{24}$H$_{46}$BN$_2$O$_6^+$)(ES, m/z): 469 [M+H]$^+$.

Step 2: (2S,3S,4R)-3-(3-boronopropyl)-4-(diethylamino)pyrrolidine-2-carboxylic acid

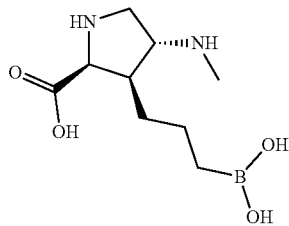 [SMILES: CN[C@H]1CN[C@H](C(=O)O)[C@@H]1CCCB(O)O]

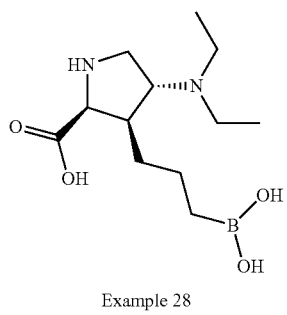

Example 28

A mixture of 1-(tert-butyl) 2-methyl (2S,3R,4R)-4-(diethylamino)-3-(3-(4,4,5,5-tetramethyl-1,3,2-dioxaborolan-2-yl)propyl)pyrrolidine-1,2-dicarboxylate (23 mg, 0.049 mmol) and 6 N HCl in water (1.0 mL, 6.0 mmol) was heated in a microwave reactor with stirring at 120° C. for 1 h. The reaction mixture was concentrated to give (2S,3S,4R)-3-(3-boronopropyl)-4-(diethylamino)pyrrolidine-2-carboxylic acid as an HCl salt. LCMS (C$_{12}$H$_{26}$BN$_2$O$_4^+$)(ES, m/z): 273 [M+H]$^+$. $^1$H NMR (499 MHz, D$_2$O) δ 4.44 (d, J=7.2 Hz, 1H), 4.09-3.95 (m, 2H), 3.62 (dd, J=13.6, 5.0 Hz, 1H), 3.38-3.18 (m, 4H), 2.96-2.85 (m, 1H), 1.53-1.37 (m, 4H), 1.29 (t, J=7.2 Hz, 6H), 0.80-0.68 (m, 2H).

Example 29: (2S,3R,4R)-3-(3-boronopropyl)-4-(methylamino)pyrrolidine-2-carboxylic acid Step 1: 1-(tert-butyl) 2-methyl (2S,3R,4R)-3-allyl-4-(benzylamino)pyrrolidine-1,2-dicarboxylate

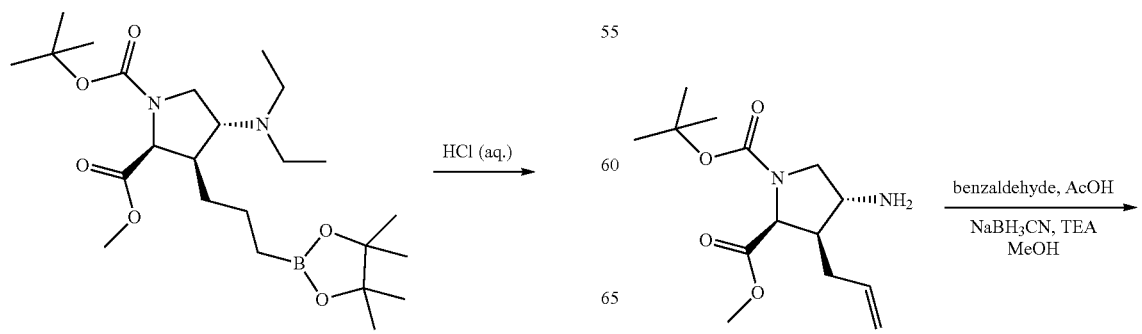

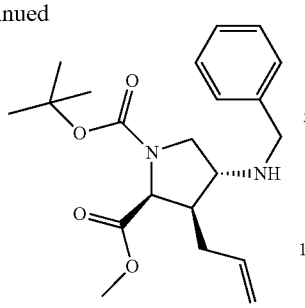

Benzaldehyde (33 µL, 0.32 mmol) and acetic acid (17 µL, 0.29 mmol) were added to a solution of 1-(tert-butyl) 2-methyl (2S,3R,4R)-3-allyl-4-aminopyrrolidine-1,2-dicarboxylate (83 mg, 0.29 mmol) in MeOH (2.0 mL). The resulting solution was stirred at room temperature for 1 h then brought to 0° C. Sodium cyanoborohydride (22 mg, 0.35 mmol) was added to the cooled solution which was allowed to warm to room temperature with stirring for 18 h. Triethylamine (81 µL, 0.58 mmol) was added to the reaction mixture which was then concentrated. The residue was purified by silica gel chromatography (EtOAc in hexanes) to afford 1-(tert-butyl) 2-methyl (2S,3R,4R)-3-allyl-4-(benzylamino)pyrrolidine-1,2-dicarboxylate. LCMS ($C_{21}H_{31}N_2O_4$)(ES, m/z): 375 [M+H]$^+$.

Step 2: 1-(tert-butyl) 2-methyl (2S,3R,4R)-3-allyl-4-(benzyl(methyl)amino)pyrrolidine-1,2-dicarboxylate

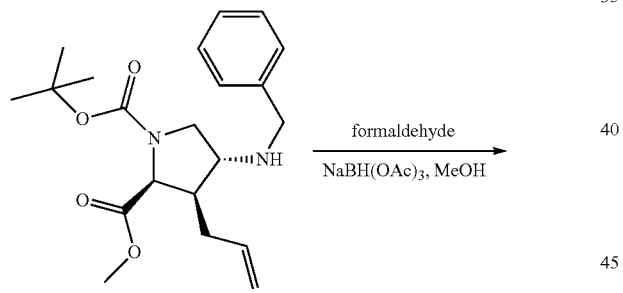

Formaldehyde (37 wt % in water)(38 µL, 0.51 mmol) followed by sodium triacetoxyborohydride (81 mg, 0.38 mmol) were added to a solution of 1-(tert-butyl) 2-methyl (2S,3R,4R)-3-allyl-4-(benzylamino)pyrrolidine-1,2-dicarboxylate (95 mg, 0.25 mmol) in MeOH (2.5 mL). The reaction mixture was stirred at ambient temperature for 17 hours. Reaction was concentrated under reduced pressure and purified directly by silica gel chromatography (EtOAc in hexanes) to afford 1-(tert-butyl) 2-methyl (2S,3R,4R)-3-allyl-4-(benzyl(methyl)amino)pyrrolidine-1,2-dicarboxylate as a colorless oil. LCMS ($C_{22}H_{33}N_2O_4^+$)(ES, m/z): 389 [M+H]$^+$.

Step 3: 1-(tert-butyl) 2-methyl (2S,3R,4R)-4-(benzyl(methyl)amino)-3-(3-(4,4,5,5-tetramethyl-1,3,2-dioxaborolan-2-yl)propyl)pyrrolidine-1,2-dicarboxylate

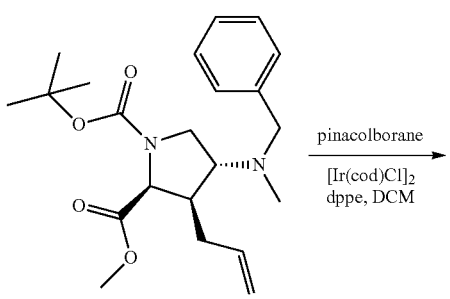

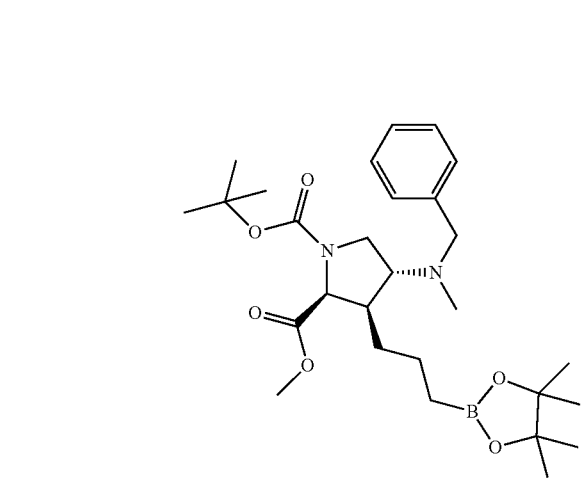

4,4,5,5-tetramethyl-1,3,2-dioxaborolane (68 µL, 0.47 mmol), chloro(1,5-cyclooctadiene)Iridium(I) dimer (6.3 mg, 0.0094 mmol) and 1,2-bis(diphenylphosphino)ethane (7.5 mg, 0.019 mmol) in anhydrous DCM (2.5 mL) was placed under argon and the resulting mixture was stirred at room temperature for 20 minutes, followed by addition of a solution of 1-(tert-butyl) 2-methyl (2S,3R,4R)-3-allyl-4-(benzyl(methyl)amino)pyrrolidine-1,2-dicarboxylate (73 mg, 0.19 mmol) in DCM (1.3 mL). The reaction mixture was stirred at room temperature for 1.5 h under argon. Reaction was quenched by slow addition of methanol then diluted with water and EtOAc. The organic layer was separated, washed with brine, dried over $Na_2SO_4$, filtered and concentrated. The residue was purified by silica gel chromatography (EtOAc in hexanes) to afford 1-(tert-butyl) 2-methyl (2S,3R,4R)-4-(benzyl(methyl)amino)-3-(3-(4,4,5,5-tetramethyl-1,3,2-dioxaborolan-2-yl)propyl)pyrrolidine-1,2-dicarboxylate. LCMS ($C_{28}H_{46}BN_2O_6^+$)(ES, m/z): 517 [M+H]$^+$.

Step 4: 1-(tert-butyl) 2-methyl (2S,3R,4R)-4-(methylamino)-3-(3-(4,4,5,5-tetramethyl-1,3,2-dioxaborolan-2-yl)propyl)pyrrolidine-1,2-dicarboxylate

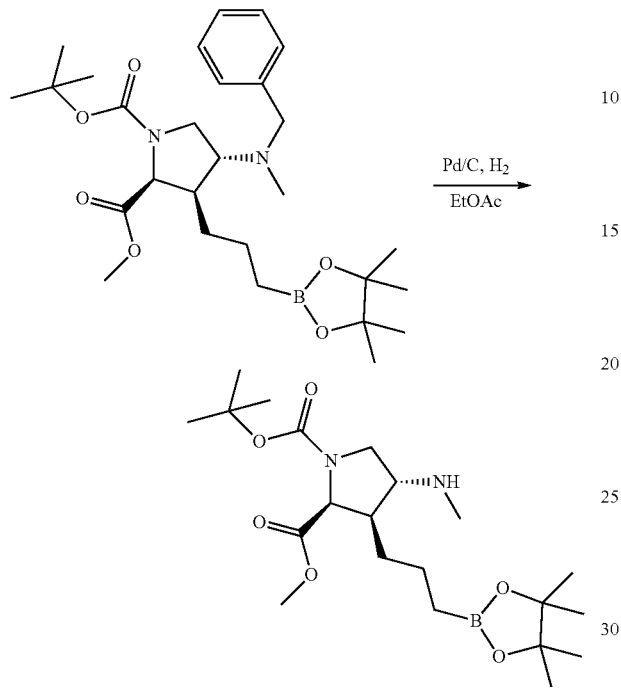

10% Pd/C (15 mg, 0.014 mmol) was added to a solution of 1-(tert-butyl) 2-methyl (2S,3R,4R)-4-(benzyl(methyl)amino)-3-(3-(4,4,5,5-tetramethyl-1,3,2-dioxaborolan-2-yl)propyl)pyrrolidine-1,2-dicarboxylate (72 mg, 0.14 mmol) in EtOAc (5.0 mL). The reaction mixture was degassed and backfilled with $H_2$ three times then stirred under $H_2$ for 19 h. The mixture was filtered and concentrated. The residue was purified by silica gel chromatography (MeOH in DCM) to afford 1-(tert-butyl) 2-methyl (2S,3R,4R)-4-(methylamino)-3-(3-(4,4,5,5-tetramethyl-1,3,2-dioxaborolan-2-yl)propyl)pyrrolidine-1,2-dicarboxylate, which was used in the next step without purification. LCMS ($C_{21}H_{40}BN_2O_6^+$)(ES, m/z): 427 [M+H]$^+$.

Step 5: (2S,3R,4R)-3-(3-boronopropyl)-4-(methylamino)pyrrolidine-2-carboxylic acid

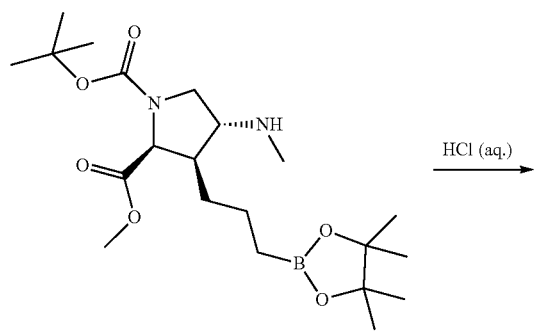

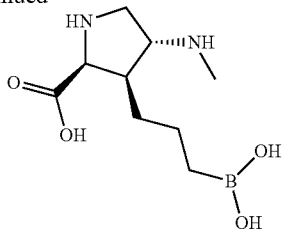

Example 29

A mixture of 1-(tert-butyl) 2-methyl (2S,3R,4R)-4-(methylamino)-3-(3-(4,4,5,5-tetramethyl-1,3,2-dioxaborolan-2-yl)propyl)pyrrolidine-1,2-dicarboxylate (41 mg, 0.095 mmol) and 6 N HCl in water (2.0 mL, 12 mmol) was heated in a microwave reactor with stirring at 120° C. for 2 h. The reaction mixture was concentrated to give (2S,3R,4R)-3-(3-boronopropyl)-4-(methylamino)pyrrolidine-2-carboxylic acid as an HCl salt. LCMS ($C_9H_{18}BN_2O_3^+$)(ES, m/z): 213 [M–H$_2$+H]$^+$. $^1$H NMR (499 MHz, D$_2$O) δ 4.52-4.43 (m, 1H), 3.98 (dd, J=14.0, 7.9 Hz, 1H), 3.90-3.79 (m, 1H), 3.61-3.48 (m, 1H), 2.82-2.69 (m, 4H), 1.55-1.28 (m, 4H), 0.82-0.65 (m, 2H).

Example 30: (2S,3R,4R)-3-(3-boronopropyl)-4-(ethylamino)pyrrolidine-2-carboxylic acid

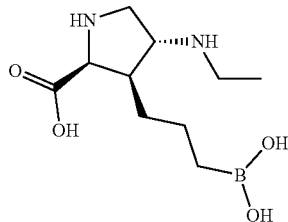 [SMILES: CCN[C@H]1CN[C@H](C(=O)O)[C@@H]1CCCB(O)O]

Example 30 was made from 1-(tert-butyl) 2-methyl (2S,3R,4R)-3-allyl-4-(benzylamino)pyrrolidine-1,2-dicarboxylate and acetaldehyde, and using the same procedure as Example 29:

LCMS ($C_{10}H_{22}BN_2O_4^+$)(ES, m/z): 245 [M+H]$^+$. $^1$H NMR (499 MHz, D$_2$O) δ 4.53-4.43 (m, 1H), 4.02-3.93 (m, 1H), 3.92-3.84 (m, 1H), 3.59-3.49 (m, 1H), 3.18-3.02 (m, 2H), 2.80-2.69 (m, 1H), 1.57-1.19 (m, 7H), 0.82-0.66 (m, 2H).

Example 31: (2S,3R,4R)-4-((2-aminoethyl)amino)-3-(3-boronopropyl)pyrrolidine-2-carboxylic acid

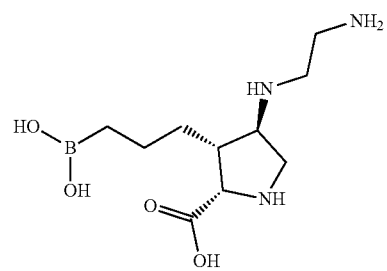 [SMILES: NCCN[C@H]1CN[C@H](C(=O)O)[C@@H]1CCCB(O)O]

Step 1: 1-(tert-butyl) 2-methyl (2S,3R,4R)-3-allyl-4-((2-((tert-butoxycarbonyl)amino)ethyl)amino)pyrrolidine-1,2-dicarboxylate

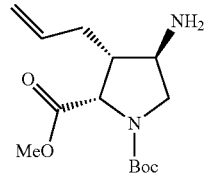
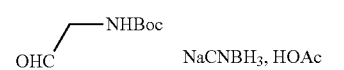

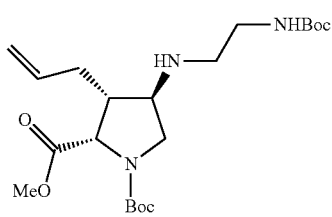

Tert-butyl (2-oxoethyl)carbamate (0.36 g, 2.3 mmol) and acetic acid (0.13 ml, 2.3 mmol) were added to the stirred solution of 1-(tert-butyl) 2-methyl (2S,3R,4R)-3-allyl-4-aminopyrrolidine-1,2-dicarboxylate (0.64 g, 2.3 mmol) in MeOH (12 mL), and the reaction mixture was stirred at room temperature for 1 h. The reaction was cooled to 0° C. and sodium cyanoborohydride (0.17 g, 2.7 mmol) was added in one portion. The reaction was allowed to warm to room temperature and stirred overnight. TEA (0.63 mL, 4.5 mmol) was added, and the reaction mixture was concentrated. The residue was purified by silica gel chromatography (EtOAc in hexanes) to afford 1-(tert-butyl) 2-methyl (2S,3R,4R)-3-allyl-4-((2-((tert-butoxycarbonyl)amino)ethyl)amino)pyrrolidine-1,2-dicarboxylate. LCMS ($C_{21}H_{38}N_3O_6^+$)(ES, m/z): 428 [M+H]$^+$.

Step 2: 1-(tert-butyl) 2-methyl (2S,3R,4R)-4-((2-((tert-butoxycarbonyl)amino)ethyl)amino)-3-(3-((3aS,4S,6S,7aR)-3a,5,5-trimethylhexahydro-4,6-methanobenzo[d][1,3,2]dioxaborol-2-yl)propyl)pyrrolidine-1,2-dicarboxylate

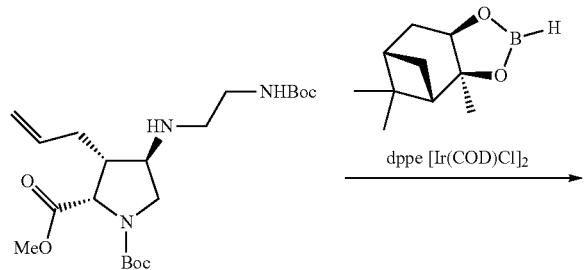

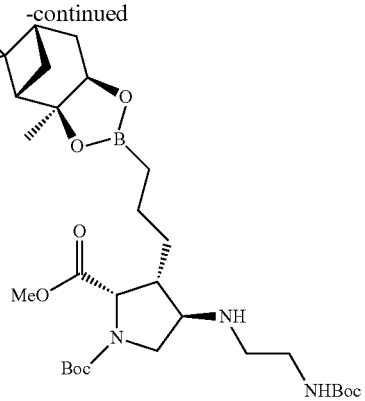

(3aS,4S,6S,7aR)-3a,5,5-trimethylhexahydro-4,6-methanobenzo[d][1,3,2]dioxaborole (1.4 g, 8.1 mmol) was added to the stirred solution of chloro(1,5-cyclooctadiene)iridium (I) dimer (42 mg, 0.080 mmol), DPPE (45 mg, 0.11 mmol) in DCM (25 mL) under $N_2$. The mixture was degassed and backfilled with $N_2$ (three times) and stirred at room temperature for 20 min, followed by addition of 1-(tert-butyl) 2-methyl (2S,3R,4R)-3-allyl-4-((2-((tert-butoxycarbonyl)amino)ethyl)amino) pyrrolidine-1,2-dicarboxylate (0.69 g, 1.6 mmol) in DCM (5.0 mL) under $N_2$. The mixture was stirred at room temperature for 12 h. The solvent was removed, and the residue was purified by silica gel chromatography (EtOAc in hexanes) to give 1-(tert-butyl) 2-methyl (2S,3R,4R)-4-((2-((tert-butoxycarbonyl)amino)ethyl)amino)-3-(3-((3aS,4S,6S,7aR)-3a,5,5-trimethylhexahydro-4,6-methanobenzo[d][1,3,2]dioxaborol-2-yl)propyl)pyrrolidine-1,2-dicarboxylate. LCMS ($C_{31}H_{55}BN_3O_8^+$)(ES, m/z): 608 [M+H]$^+$.

Step 3: (2S,3R,4R)-4-((2-aminoethyl)amino)-3-(3-boronopropyl)pyrrolidine-2-carboxylic acid

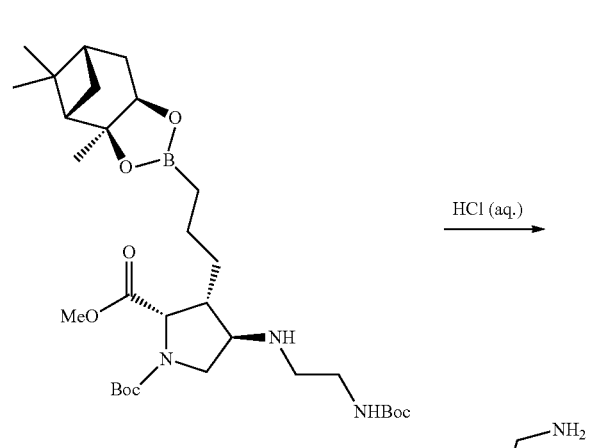

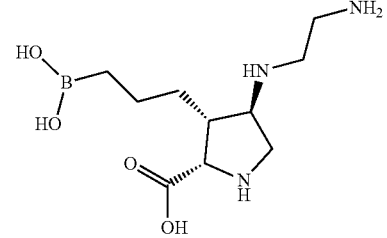

Example 31

12 N HCl in water (1.0 mL, 12 mmol) and acetic acid (0.50 mL, 8.7 mmol) were added sequentially to 1-(tert-butyl) 2-methyl (2S,3R,4R)-4-((2-((tert-butoxycarbonyl)amino)ethyl)amino)-3-(3-((3aS,4S,6S,7aR)-3a,5,5-trimethylhexahydro-4,6-methanobenzo[d][1,3,2]dioxaborol-2-yl)propyl)pyrrolidine-1,2-dicarboxylate (50 mg, 0.082 mmol), and the mixture was heated in a microwave reactor with stirring at 120° C. for 30 min. The reaction mixture was cooled to room temperature, diluted with water, extracted with DCM and concentrated. The residue was purified by RP-HPLC [C18 column, water (0.2 mM heptafluorobutyric acid/0.1% TFA)-CH$_3$CN] to give (2S,3R,4R)-4-((2-aminoethyl)amino)-3-(3-boronopropyl)pyrrolidine-2-carboxylic acid as a HFBA salt. LCMS ($C_{10}H_{21}BN_3O_3^+$)(ES, m/z): 242 [M–H$_2$+H]$^+$. $^1$H NMR (499 MHz, D$_2$O) 84.50 (d, J=6.9 Hz, 1H), 4.06-3.90 (m, 2H), 3.57 (dd, J=13.6, 3.6 Hz, 1H), 3.46-3.37 (m, 2H), 3.35 (d, J=6.9 Hz, 2H), 2.77 (d, J=4.2 Hz, 1H), 2.63 (s, 2H), 1.53-1.41 (m, 2H), 1.40-1.34 (m, 2H), 0.79-0.67 (m, 2H).

Example 32: (2S,3S,4R)-3-(3-boronopropyl)-4-hydroxypyrrolidine-2-carboxylic acid

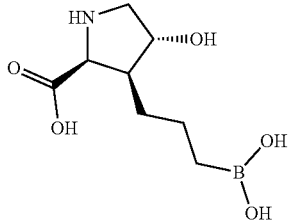 [SMILES: O=C(O)[C@H]1NC[C@H](O)[C@H]1CCCB(O)O]

Step 1: 1-(tert-butyl) 2-methyl (2S,3S,4S)-3-allyl-4-(((chloromethyl)sulfonyl)oxy)pyrrolidine-1,2-dicarboxylate

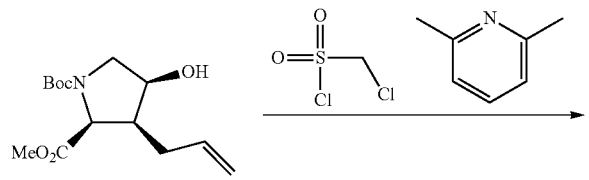

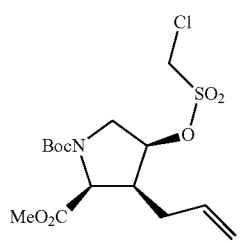

2,6-Lutidine (21 mL, 0.18 mol) followed by chloromethanesulfonyl chloride (90 wt %, 6.9 mL, 69 mmol) were added to a solution of 1-(tert-butyl) 2-methyl (2S,3S,4S)-3-allyl-4-hydroxypyrrolidine-1,2-dicarboxylate (8.5 g, 30 mmol) in DCM (99 mL) at 0° C. The resulting mixture was allowed to warm to room temperature and stirred overnight. The reaction mixture was quenched by water, then diluted with DCM. The organic layer was separated then washed with 1 N HCl twice, saturated aqueous NaHCO$_3$ and brine. The resulting organic layer was dried over Na$_2$SO$_4$, filtered and concentrated to afford crude 1-(tert-butyl) 2-methyl (2S,3S,4S)-3-allyl-4-(((chloromethyl)sulfonyl)oxy)pyrrolidine-1,2-dicarboxylate, which was used directly in the next step without further purification. LCMS ($C_{10}H_{17}ClNO_5S^+$) (ES, m/z): 298 [M-CO$_2$C$_4$H$_8$+H]$^+$.

Step 2: 1-(tert-butyl) 2-methyl (2S,3S,4R)-4-acetoxy-3-allylpyrrolidine-1,2-dicarboxylate (4) and 1-(tert-butyl) 2-methyl (S)-3-allyl-2,5-dihydro-1H-pyrrole-1,2-dicarboxylate (4A)

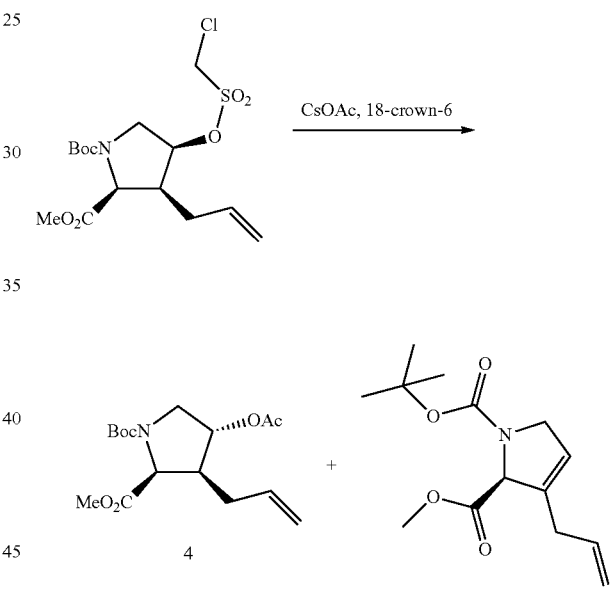

Cesium acetate (17 g, 89 mmol) was added to a solution of 1-(tert-butyl) 2-methyl (2S,3S,4S)-3-allyl-4-(((chloromethyl)sulfonyl)oxy)pyrrolidine-1,2-dicarboxylate (12 g, crude) in toluene (0.20 L), followed by addition of 18-crown-6 (3.9 g, 15 mmol) in one portion under N$_2$ at room temperature The resulting mixture was sonicated for 5 min, and then stirred at 80° C. for 4 h. After cooling to room temperature the reaction mixture was diluted with saturated aqueous NaHCO$_3$ and EtOAc. The organic layer was separated, washed with brine, dried over Na$_2$SO$_4$, filtered and concentrated. The residue was purified by silica gel chromatography (EtOAc in hexanes) to afford 1-(tert-butyl) 2-methyl (2S,3S,4R)-4-acetoxy-3-allylpyrrolidine-1,2-dicarboxylate (4) and 1-(tert-butyl) 2-methyl (S)-3-allyl-2,5-dihydro-1H-pyrrole-1,2-dicarboxylate (4A). 4: LCMS ($C_{11}H_{18}NO_4^+$) (ES, m/z): 228 [M-CO$_2$C$_4$H$_8$+H]$^+$; 4A: LCMS ($C_{14}H_{21}NNaO_4^+$)(ES, m/z): 290 [M+Na]$^+$;

Step 3: 1-(tert-butyl) 2-methyl (2S,3S,4R)-4-acetoxy-3-(3-(4,4,5,5-tetramethyl-1,3,2-dioxaborolan-2-yl)propyl)pyrrolidine-1,2-dicarboxylate

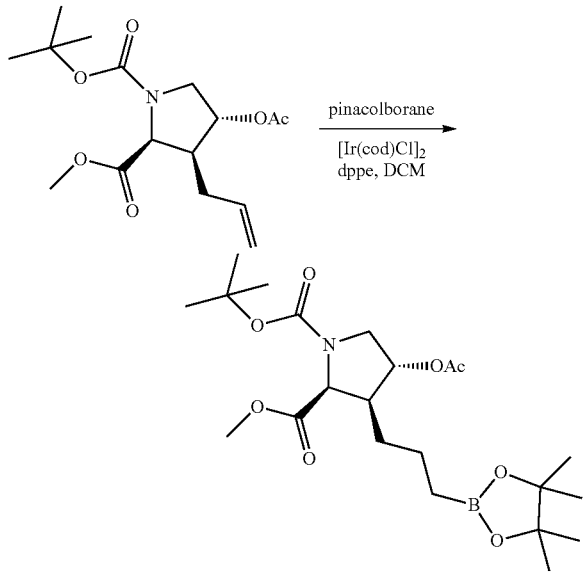

4,4,5,5-tetramethyl-1,3,2-dioxaborolane (5.9 mL, 41 mmol), chloro(1,5-cyclooctadiene)Iridium(I) dimer (0.46 g, 0.68 mmol) and 1,2-bis(diphenylphosphino)ethane (0.53 g, 1.4 mmol) in anhydrous DCM (36 mL) was placed under $N_2$ and the resulting mixture was stirred at room temperature for 20 minutes, followed by addition of a solution of 1-(tert-butyl) 2-methyl (2S,3S,4R)-4-acetoxy-3-allylpyrrolidine-1,2-dicarboxylate (4.5 g, 14 mmol) in DCM (18 mL). The reaction mixture was stirred at room temperature overnight under $N_2$. The reaction mixture was quenched with saturated aqueous $NH_4Cl$ and extracted with EtOAc. The combined organic phase was washed with brine, dried over $Na_2SO_4$, filtered and concentrated. The residue was purified by silica gel chromatography (EtOAc in hexanes) to afford 1-(tert-butyl) 2-methyl (2S,3S,4R)-4-acetoxy-3-(3-(4,4,5,5-tetramethyl-1,3,2-dioxaborolan-2-yl)propyl)pyrrolidine-1,2-dicarboxylate. LCMS $(C_{17}H_{31}BNO_6^+)$(ES, m/z): 356 $[M-CO_2C_4H_8+H]^+$.

Step 4: (2S,3S,4R)-3-(3-boronopropyl)-4-hydroxypyrrolidine-2-carboxylic acid

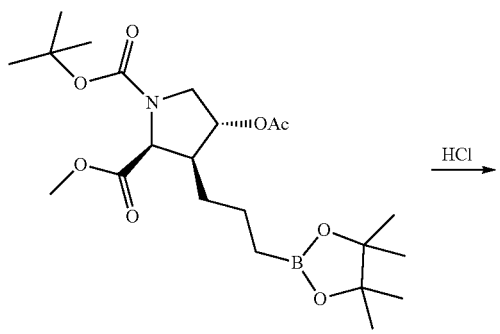

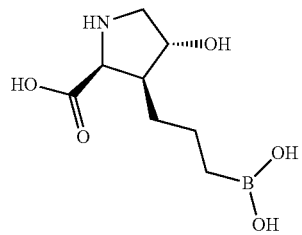

Example 32

12N HCl (40 mL, 0.48 mol) was added to the stirred suspension of 1-(tert-butyl) 2-methyl (2S,3S,4R)-4-acetoxy-3-(3-(4,4,5,5-tetramethyl-1,3,2-dioxaborolan-2-yl)propyl)pyrrolidine-1,2-dicarboxylate (5.5 g, 12 mmol) in water (40 mL) at room temperature, and the reaction mixture was heated to 95° C. with stirring for 24 h, then cooled to room temperature. The mixture was diluted with water, filtered through a 0.25 μm filter and lyophilized to give (2S,3S,4R)-3-(3-boronopropyl)-4-hydroxypyrrolidine-2-carboxylic acid as an HCl salt. LCMS $(C_8H_{15}BNO_4^+)$(ES, m/z): 200 $[M-H_2O+H]^+$. $^1H$ NMR (500 MHz, $D_2O$) δ 4.66 (d, J=6.8 Hz, 1H), 4.50-4.82 (m, 1H), 3.69 (dd, J=13.1, 4.5 Hz, 1H), 3.31 (d, J=13.1 Hz, 1H), 2.61-2.56 (m, 1H), 1.59-1.40 (m, 2H), 1.36-1.27 (m, 1H), 1.21-1.14 (m, 1H), 0.85-0.73 (m, 2H).

Step 5: (S,3S,4R)-3-(3-boronopropyl)-4-hydroxypyrrolidine-2-carboxylic acid (Free Base)

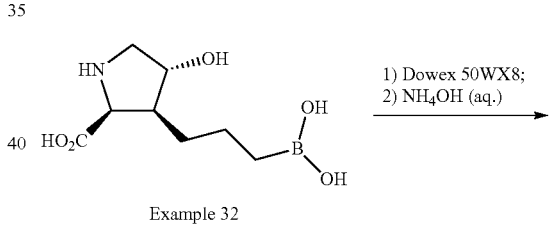

Example 32

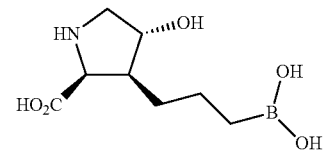

Example 32-free base (2S,3S,4R)-3-(3-boronopropyl)-4-hydroxypyrrolidine-2-carboxylic acid (HCl salt, 41 mg, 0.14 mmol) was purified on 2.6 g of Dowex 50WX8 acidic resin (washed with water until pH neutral, then eluted with 2N aqueous ammonium hydroxide) to afford (2S,3S,4R)-3-(3-boronopropyl)-4-hydroxypyrrolidine-2-carboxylic acid as a free base. LCMS $(C_8H_{15}BNO_4^+)$(ES, m/z): 200 $[M-H_2O+H]^+$. $^1H$ NMR (500 MHz, $D_2O$) δ 4.45 (br, 1H), 4.34 (d, J=5.9 Hz, 1H), 3.65 (dd, J=13.0, 4.6 Hz, 1H), 3.21 (d, J=12.7 Hz, 1H), 2.45 (br, 1H), 1.59-1.26 (m, 3H), 1.16-1.08 (m, 1H), 0.84-0.70 (m, 2H).

Example 33A: (2S)-4-amino-3-(3-boronopropyl)pyrrolidine-2-carboxylic acid

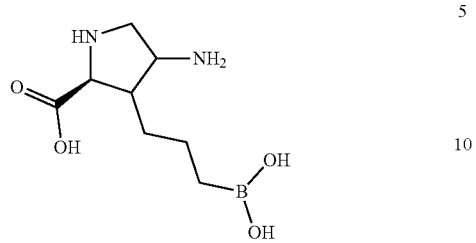

Step 1: 1-(tert-butyl)₂-methyl 3-allyl-4-(benzylamino)pyrrolidine-1,2-dicarboxylate

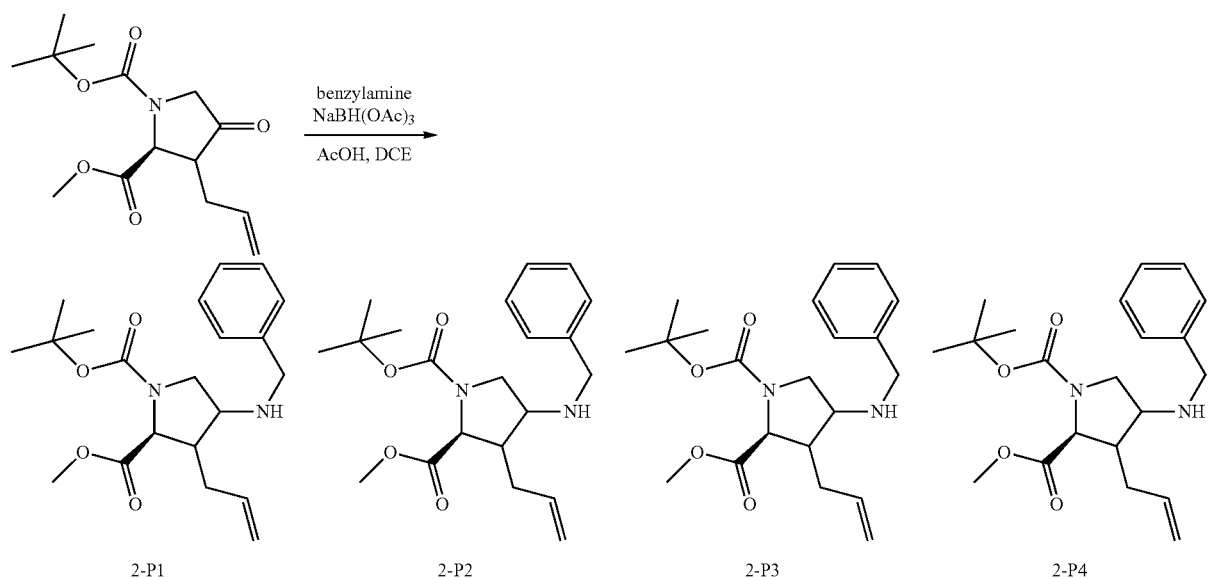

Benzylamine (240 μL, 2.2 mmol) and acetic acid (10 μL, 0.18 mmol) were added to a solution of 1-(tert-butyl) 2-methyl (2S)-3-allyl-4-oxopyrrolidine-1,2-dicarboxylate (500 mg, 1.8 mmol) in DCE (8.8 mL). The reaction mixture was brought to 50° C. for 1 h. NaBH(OAc)₃ (560 mg, 2.6 mmol) was added in one portion, and the reaction mixture was stirred at 50° C. for 23 h. The reaction was diluted with saturated aqueous NH₄Cl and EtOAc. The organic layer was separated, dried over Na₂SO₄, filtered and concentrated. The residue was purified by silica gel chromatography (EtOAc in hexanes) to afford 1-(tert-butyl) 2-methyl (2S)-3-allyl-4-(benzylamino)pyrrolidine-1,2-dicarboxylate (mixture of diastereomers) as a mixture of 4 stereoisomers, which was further purified by chiral SFC (Diacel IC column, 5%/95% methanol+0.1% NH₄₀H/CO₂). Retention times for peak collection were as follows: first eluting peak, 5.8 min.; second eluting peak, 6.6 min.; third eluting peak, 7.3 min. First eluting peak (2-P1) was a single diastereomer LCMS $(C_{21}H_{31}N_2O_4^+)$(ES, m/z): 375 [M+H]⁺. Second eluting peak (2-P2) was a single diastereomer LCMS $(C_{21}H_{31}N_2O_4^+)$ (ES, m/z): 375 [M+H]⁺. Third eluting peak was a mixture of two diastereomers and was resubjected to purification by chiral SFC (Diacel OD-H column, 5%/95% methanol+0.1% NH₄OH/CO₂). Retention times for peak collection were as follows: first eluting peak, 5.4 min, second eluting peak, 8.4 min. First eluting peak (2-P3) was a single diastereomer LCMS $(C_{21}H_{31}N_2O_4^+)$(ES, m/z): 375 [M+H]⁺. Second eluting peak (2-P4) was a single diastereomer LCMS $(C_{21}H_{31}N_2O_4^+)$(ES, m/z): 375 [M+H]⁺.

Step 2: 1-(tert-butyl) 2-methyl (2S)-4-(benzylamino)-3-(3-(4,4,5,5-tetramethyl-1,3,2-dioxaborolan-2-yl)propyl)pyrrolidine-1,2-dicarboxylate

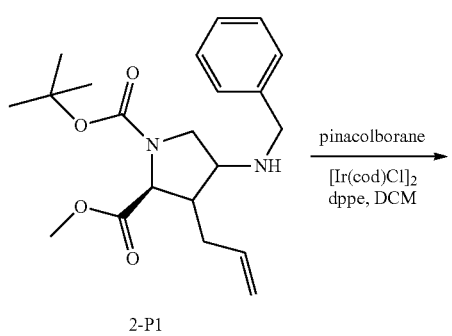

-continued

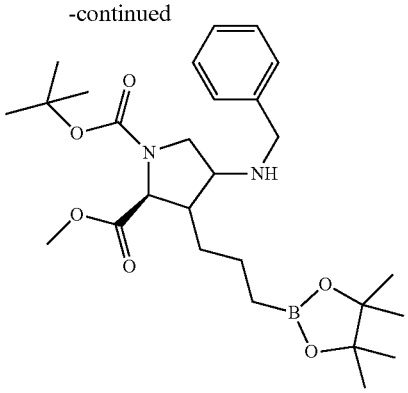

4,4,5,5-tetramethyl-1,3,2-dioxaborolane (65 mg, 0.51 mmol), chloro(1,5-cyclooctadiene)Iridium(I) dimer (9.8 mg, 0.010 mmol) and 1,2-bis(diphenylphosphino)ethane (8.1 mg, 0.020 mmol) in anhydrous DCM (2.7 mL) was placed under an atmosphere of argon, and the resulting mixture was stirred at ambient temperature for 15 min, followed by addition of a solution of 1-(tert-butyl) 2-methyl 3-allyl-4-(benzylamino)pyrrolidine-1,2-dicarboxylate (2-P1, 76 mg, 0.20 mmol) in DCM (1.4 mL). The reaction mixture was stirred at room temperature for 1.5 h under argon. Reaction was quenched by MeOH and then diluted with water and DCM. The organic layer was separated, dried over $Na_2SO_4$, filtered and concentrated. The residue was purified by silica gel chromatography (EtOAc in DCM) to afford 1-(tert-butyl) 2-methyl (2S)-4-(benzylamino)-3-(3-(4,4,5,5-tetramethyl-1,3,2-dioxaborolan-2-yl)propyl)pyrrolidine-1,2-dicarboxylate. LCMS ($C_{27}H_{44}BN_2O_6^+$)(ES, m/z): 503 [M+H]$^+$.

Step 3: 1-(tert-butyl) 2-methyl (2S)-4-amino-3-(3-(4,4,5,5-tetramethyl-1,3,2-dioxaborolan-2-yl)propyl)pyrrolidine-1,2-dicarboxylate

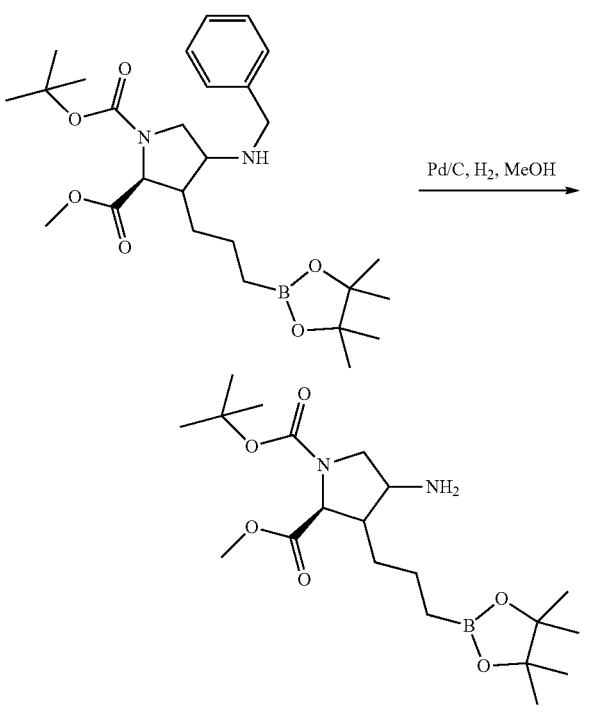

10% Pd/C (4.2 mg, 0.0039 mmol) was added to a solution of 1-(tert-butyl) 2-methyl (2S)-4-(benzylamino)-3-(3-(4,4,5,5-tetramethyl-1,3,2-dioxaborolan-2-yl)propyl)pyrrolidine-1,2-dicarboxylate (20 mg, 0.039 mmol) in MeOH (1.5 mL). The reaction mixture was degassed and backfilled with $H_2$ three times then stirred under $H_2$ for 1.5 h. The mixture was filtered and concentrated to give crude 1-(tert-butyl) 2-methyl (2S)-4-amino-3-(3-(4,4,5,5-tetramethyl-1,3,2-dioxaborolan-2-yl)propyl)pyrrolidine-1,2-dicarboxylate, which was used in the next step without purification. LCMS ($C_{20}H_{38}BN_2O_6^+$)(ES, m/z): 413 [M+H]$^+$.

Step 4: (2S)-4-amino-3-(3-boronopropyl)pyrrolidine-2-carboxylic acid

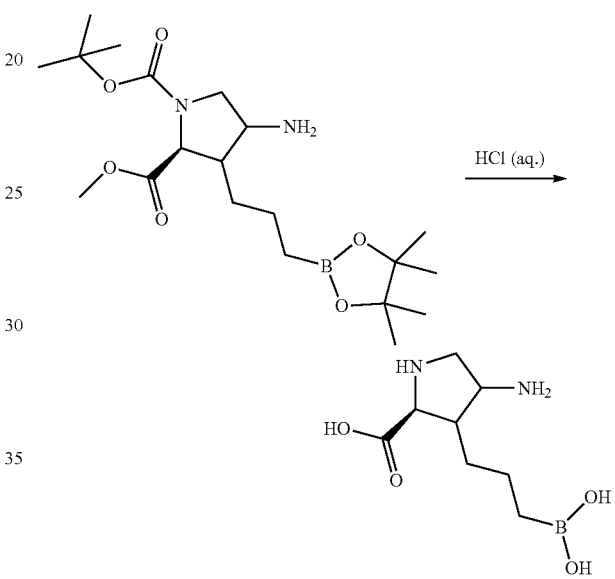

A mixture of 1-(tert-butyl) 2-methyl (2S)-4-amino-3-(3-(4,4,5,5-tetramethyl-1,3,2-dioxaborolan-2-yl)propyl)pyrrolidine-1,2-dicarboxylate (16 mg, 0.039 mmol) and 6 N HCl in water (0.60 mL, 3.6 mmol) was heated in a microwave reactor with stirring at 120° C. for 2 h. The reaction mixture was concentrated to give (2S)-4-amino-3-(3-boronopropyl)pyrrolidine-2-carboxylic acid as an HCl salt. LCMS ($C_8H_{16}BN_2O_3^+$)(ES, m/z): 199 [M−H$_2$O+H]$^+$.

Step 5: (2S)-4-amino-3-(3-((3aR,4R,6R,7aS)-3a,5,5-trimethylhexahydro-4,6-methanobenzo[d][1,3,2]dioxaborol-2-yl)propyl)pyrrolidine-2-carboxylic acid

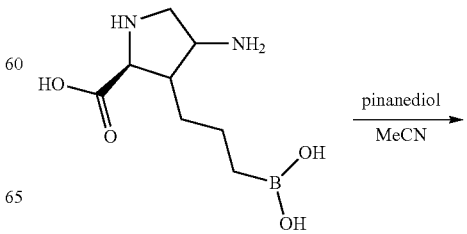

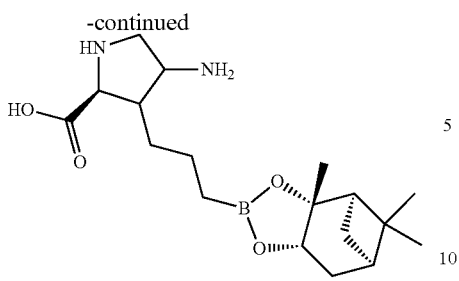

(1R,2R,3S,5R)-2,6,6-trimethylbicyclo[3.1.1]heptane-2,3-diol (12 mg, 0.069 mmol) was added to a solution of (2S)-4-amino-3-(3-boronopropyl)pyrrolidine-2-carboxylic acid (10 mg, 0.035 mmol) in acetonitrile (1.0 mL). The resulting slurry was stirred at 85° C. for 24 h. The crude reaction mixture was directly purified by RP-HPLC [C18 column, water (0.1% TFA)-CH$_3$CN] to afford (2S)-4-amino-3-(3-((3aR,4R,6R,7aS)-3a,5,5-trimethylhexahydro-4,6-methanobenzo[d][1,3,2]dioxaborol-2-yl)propyl)pyrrolidine-2-carboxylic acid as the TFA salt. LCMS (C$_{18}$H$_{32}$BN$_2$O$_4$$^+$) (ES, m/z): 351 [M+H]$^+$.

Step 6: (2S)-4-amino-3-(3-boronopropyl)pyrrolidine-2-carboxylic acid

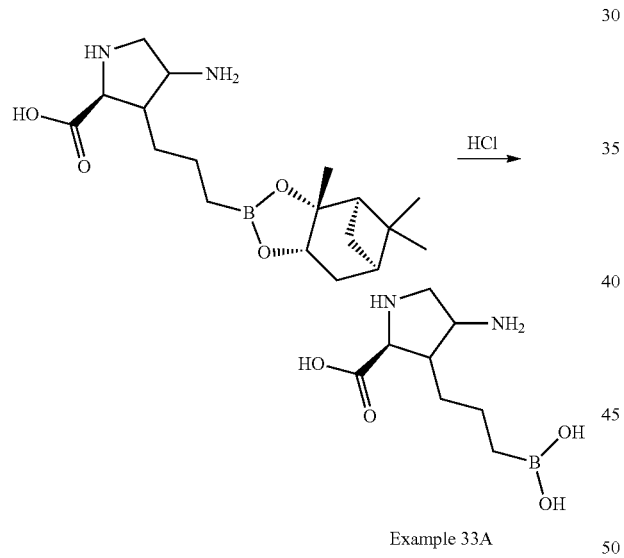

Example 33A

A mixture of (2S)-4-amino-3-(3-((3aR,4R,6R,7aS)-3a,5,5-trimethylhexahydro-4,6-methanobenzo[d][1,3,2]dioxaborol-2-yl)propyl)pyrrolidine-2-carboxylic acid (6.5 mg, 0.014 mmol) and 6 N HCl in water (0.50 mL, 3.0 mmol) was heated in a microwave reactor with stirring at 120° C. for 2 h. The reaction mixture was washed with DCM and the resulting aqueous layer was concentrated to give (2S)-4-amino-3-(3-boronopropyl)pyrrolidine-2-carboxylic acid as an HCl salt. LCMS (C$_8$H$_{16}$BN$_2$O$_3$$^+$)(ES, m/z): 199 [M–H$_2$O+H]$^+$. $^1$H NMR (499 MHz, D$_2$O) δ 4.45 (t, J=8.2 Hz, 1H), 4.18-4.12 (m, 1H), 4.12-4.05 (m, 1H), 2.68-2.60 (m, 1H), 2.58-2.50 (m, 1H), 1.79-1.66 (m, 2H), 1.62-1.41 (m, 2H), 0.87-0.75 (m, 2H).

Example 33B: (2S)-4-amino-3-(3-boronopropyl)pyrrolidine-2-carboxylic acid

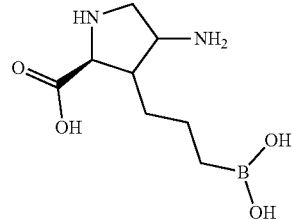 [SMILES: NC1CN[C@H](C(=O)O)C1CCCB(O)O]

Example 33B was made from 1-(tert-butyl) 2-methyl 3-allyl-4-(benzylamino)pyrrolidine-1,2-dicarboxylate (2-P2), using the same procedure as Example 33A:
LCMS (C$_8$H$_{18}$BN$_2$O$_4$$^+$)(ES, m/z): 217 [M+H]$^+$. $^1$H NMR (499 MHz, D$_2$O) δ 4.20-4.09 (m, 2H), 3.87 (dd, J=13.4, 7.1 Hz, 1H), 3.50 (dd, J=13.4, 5.1 Hz, 1H), 2.77-2.66 (m, 1H), 1.68-1.56 (m, 1H), 1.54-1.38 (m, 3H), 0.78 (t, J=7.4 Hz, 2H).

Example 34: (2S)-4-(aminomethyl)-3-(3-boronopropyl)pyrrolidine-2-carboxylic acid

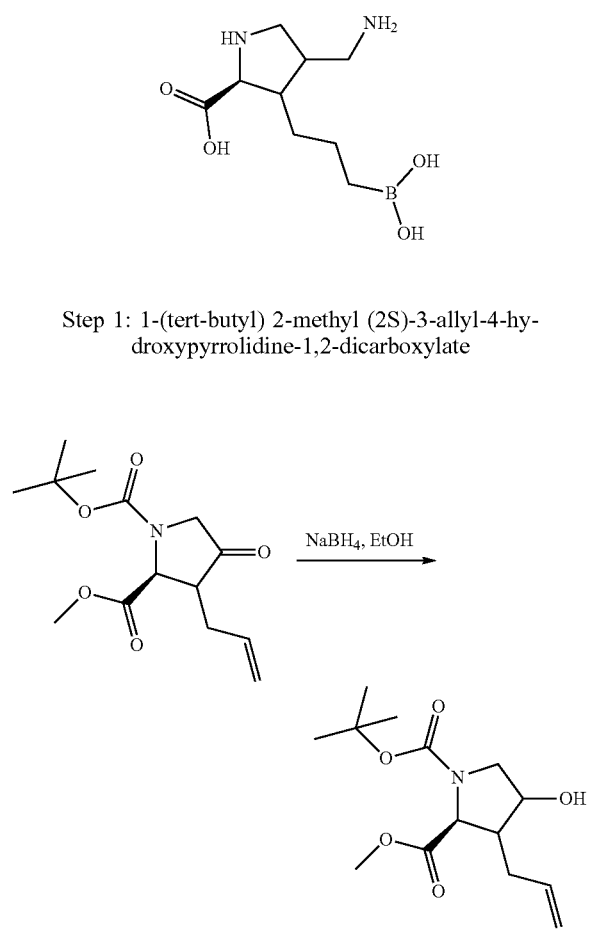

Step 1: 1-(tert-butyl) 2-methyl (2S)-3-allyl-4-hydroxypyrrolidine-1,2-dicarboxylate Sodium borohydride (270 mg, 7.1 mmol) was added to a solution of 1-(tert-butyl) 2-methyl (2S)-3-allyl-4-oxopyrrolidine-1,2-dicarboxylate (1.0 g, 3.5 mmol) in EtOH (35 mL) at 0° C. The reaction mixture was warmed to room temperature and stirred for 40 minutes. Reaction was quenched with saturated aqueous NH$_4$Cl then diluted with EtOAc. The organic layer was separated, washed with brine, dried over Na$_2$SO$_4$, filtered and concentrated. The residue was purified by silica gel chromatography (EtOAc in DCM) to afford 1-(tert-butyl) 2-methyl (2S)-3-allyl-4-hydroxypyrrolidine-1,2-dicarboxylate. LCMS (C$_9$H$_{16}$NO$_3$$^+$)(ES, m/z): 186 [M-CO$_2$C$_4$H$_8$+H]$^+$.

Step 2: 1-(tert-butyl) 2-methyl (2S)-3-allyl-4-((methylsulfonyl)oxy)pyrrolidine-1,2-dicarboxylate

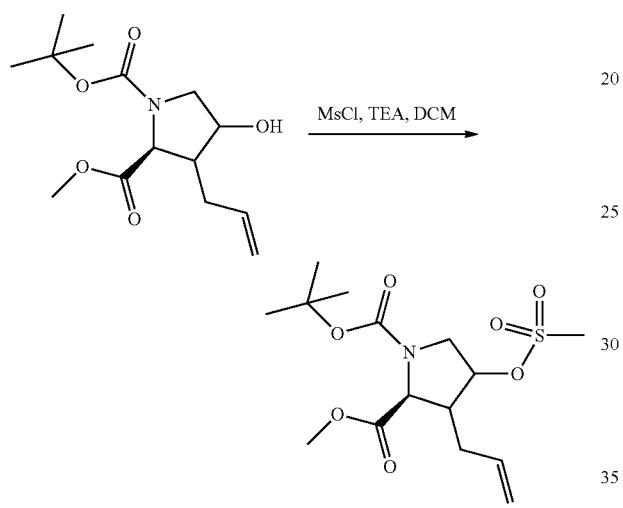

Triethylamine (0.34 mL, 2.4 mmol) was added to a solution of 1-(tert-butyl) 2-methyl (2S)-3-allyl-4-hydroxypyrrolidine-1,2-dicarboxylate (0.44 g, 1.5 mmol) in DCM (5.0 mL), and the resulting solution was brought to −78° C. Methanesulfonyl chloride (0.19 mL, 2.4 mmol) was added dropwise, and the reaction was stirred at −78° C. for 2.5 h. Reaction mixture was diluted with water and EtOAc. The organic layer was separated, washed with brine, dried over Na$_2$SO$_4$, filtered and concentrated to afford 1-(tert-butyl) 2-methyl (2S)-3-allyl-4-((methylsulfonyl)oxy)pyrrolidine-1,2-dicarboxylate. LCMS (C$_{10}$H$_{18}$NO$_5$S$^+$)(ES, m/z): 264 [M-CO$_2$C$_4$H$_8$+H]$^+$.

Step 3: 1-(tert-butyl) 2-methyl (2S)-3-allyl-4-cyanopyrrolidine-1,2-dicarboxylate

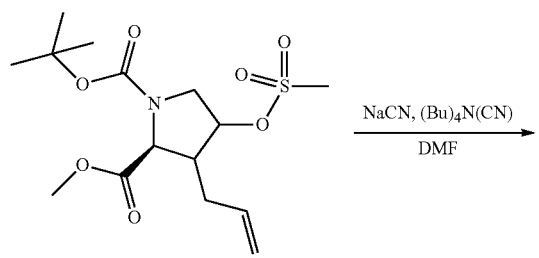

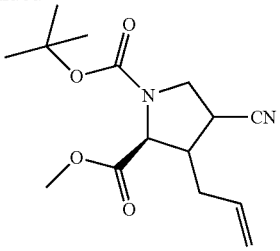

Sodium cyanide (0.15 mg, 3.0 mmol) and tetrabutylammonium cyanide (0.41 mg, 1.5 mmol) were added to a solution of 1-(tert-butyl) 2-methyl (2S)-3-allyl-4-((methylsulfonyl)oxy)pyrrolidine-1,2-dicarboxylate (0.55 mg, 1.5 mmol)) in DMF (10 mL). The reaction mixture was stirred at 80° C. for 18 hours. After cooling to room temperature the reaction was diluted with saturated aqueous NaHCO$_3$ and EtOAc. The organic layer was separated, washed with brine, dried over Na$_2$SO$_4$, filtered and concentrated. The residue was purified by silica gel chromatography (EtOAc in hexanes) to afford 1-(tert-butyl) 2-methyl (2S)-3-allyl-4-cyanopyrrolidine-1,2-dicarboxylate. LCMS (C$_{10}$H$_{15}$N$_2$O$_2$$^+$) (ES, m/z): 195 [M-CO$_2$C$_4$H$_8$+H]$^+$.

Step 4: 1-(tert-butyl) 2-methyl (2S)-4-cyano-3-(3-(4,4,5,5-tetramethyl-1,3,2-dioxaborolan-2-yl)propyl)pyrrolidine-1,2-dicarboxylate

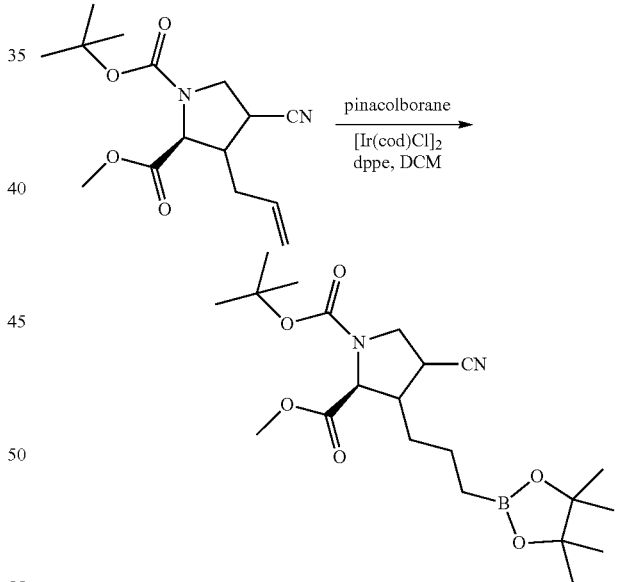

4,4,5,5-tetramethyl-1,3,2-dioxaborolane (0.10 g, 0.78 mmol), chloro(1,5-cyclooctadiene)Iridium(I) dimer (10 mg, 0.016 mmol) and 1,2-bis(diphenylphosphino)ethane (12 mg, 0.030 mmol) in anhydrous DCM (4.0 mL) was placed under an atmosphere of argon, and the resulting mixture was stirred at room temperature for 20 minutes, followed by addition of a solution of 1-(tert-butyl) 2-methyl (2S)-3-allyl-4-cyanopyrrolidine-1,2-dicarboxylate (92 mg, 0.31 mmol) in DCM (2.0 mL). The reaction mixture was stirred at room temperature for 2 h under argon. Reaction was quenched by slow addition of methanol then diluted with water and DCM.

The organic layer was separated, washed with brine, dried over Na$_2$SO$_4$, filtered and concentrated. The residue was purified by silica gel chromatography (EtOAc in hexanes) to afford 1-(tert-butyl) 2-methyl (2S)-4-cyano-3-(3-(4,4,5,5-tetramethyl-1,3,2-dioxaborolan-2-yl)propyl)pyrrolidine-1,2-dicarboxylate. LCMS (C$_{16}$H$_{28}$BN$_2$O$_4{}^+$)(ES, m/z): 323 [M-CO$_2$C$_4$H$_8$+H]$^+$.

Step 5: 1-(tert-butyl) 2-methyl (2S)-4-(aminomethyl)-3-(3-(4,4,5,5-tetramethyl-1,3,2-dioxaborolan-2-yl)propyl)pyrrolidine-1,2-dicarboxylate

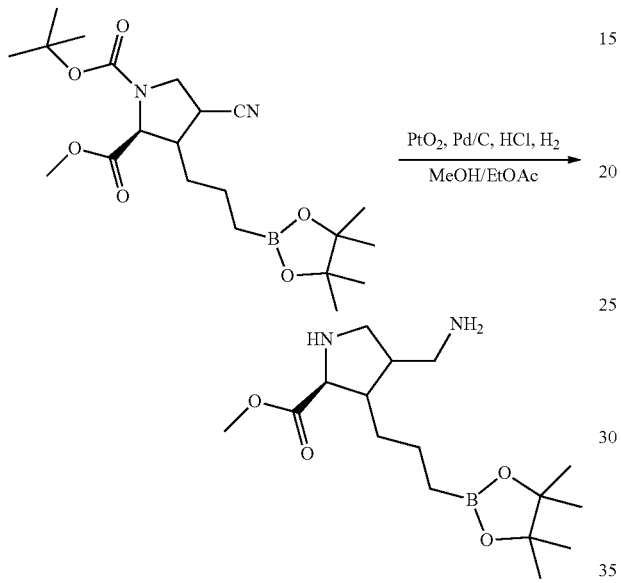

4 N HCl in dioxane (0.74 mL, 3.0 mmol) followed by PtO$_2$ (20 mg, 0.089 mmol) and 10% Pd/C (32 mg, 0.015 mmol) were added to a solution of 1-(tert-butyl) 2-methyl (2S)-4-cyano-3-(3-(4,4,5,5-tetramethyl-1,3,2-dioxaborolan-2-yl)propyl)pyrrolidine-1,2-dicarboxylate (0.13 g, 3.0 mmol) in a mixture of methanol (4.5 mL) and EtOAc (4.5 mL). The reaction mixture was degassed and backfilled with H$_2$ three times then stirred under H$_2$ for 3.5 h. The mixture was filtered and concentrated to give crude 1-(tert-butyl) 2-methyl (2S)-4-(aminomethyl)-3-(3-(4,4,5,5-tetramethyl-1,3,2-dioxaborolan-2-yl)propyl)pyrrolidine-1,2-dicarboxylate as an HCl salt. LCMS (C$_{16}$H$_{32}$BN$_2$O$_4{}^+$)(ES, m/z): 327 [M+H]$^+$.

Step 6: 1-(tert-butyl) 2-methyl (2S)-4-(((tert-butoxycarbonyl)amino)methyl)-3-(3-(4,4,5,5-tetramethyl-1,3,2-dioxaborolan-2-yl)propyl)pyrrolidine-1,2-dicarboxylate

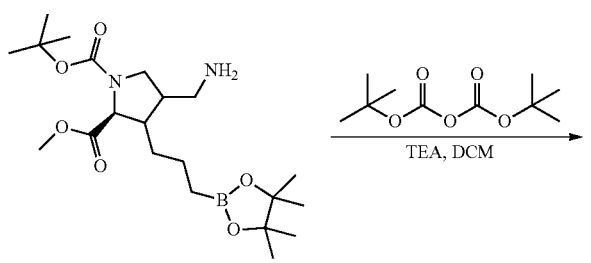

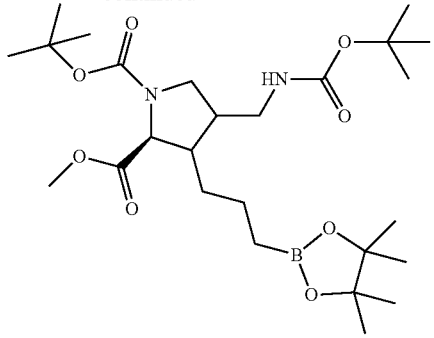

Triethylamine (0.18 mL, 1.3 mmol) followed by di-tert-buyl dicarbonate (0.12 g, 0.56 mmol) was added to a solution of 1-(tert-butyl) 2-methyl (2S)-4-(aminomethyl)-3-(3-(4,4,5,5-tetramethyl-1,3,2-dioxaborolan-2-yl)propyl)pyrrolidine-1,2-dicarboxylate (0.10 g, 0.25 mmol) in DCM (6.0 mL). Reaction mixture was stirred at room temperature for 3 h then diluted with water and DCM. The organic layer was separated, washed with brine, dried over Na$_2$SO$_4$, filtered and concentrated. The residue was purified by silica gel chromatography (MeOH in DCM) to afford 1-(tert-butyl) 2-methyl (2S)-4-(((tert-butoxycarbonyl)amino)methyl)-3-(3-(4,4,5,5-tetramethyl-1,3,2-dioxaborolan-2-yl)propyl)pyrrolidine-1,2-dicarboxylate. LCMS (C$_{17}$H$_{32}$BN$_2$O$_6{}^+$)(ES, m/z): 371 [M-CO$_2$C$_4$Hg-C$_4$H$_8$+H]$^+$.

Step 7: (2S)-4-(aminomethyl)-3-(3-boronopropyl)pyrrolidine-2-carboxylic acid (0098)

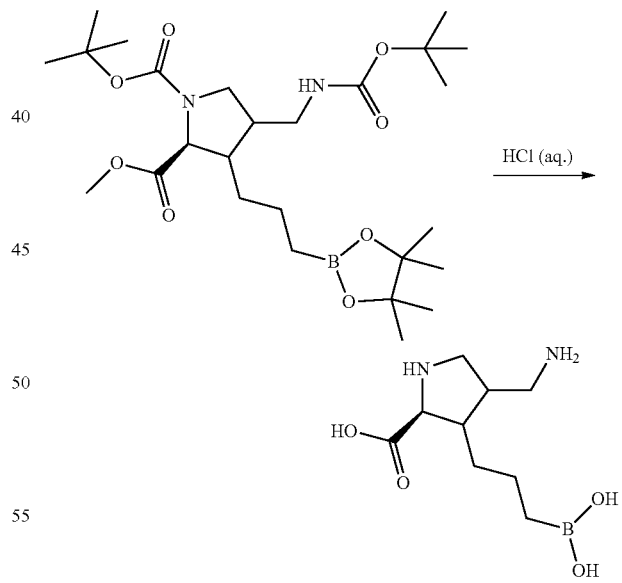

Example 34

A mixture of 1-(tert-butyl) 2-methyl (2S)-4-(((tert-butoxycarbonyl)amino)methyl)-3-(3-(4,4,5,5-tetramethyl-1,3,2-dioxaborolan-2-yl)propyl)pyrrolidine-1,2-dicarboxylate (51 mg, 0.097 mmol) and 6 N HCl in water (1.5 mL, 9.0 mmol) was heated in a microwave reactor with stirring at 120° C. for 3 h. The reaction mixture was concentrated then purified by RP-HPLC [C18 column, water (0.2 mM heptafluorobutyric acid/0.1% TFA)-CH₃CN] to afford (2S)-4-(aminomethyl)-3-(3-boronopropyl)pyrrolidine-2-carboxylic acid as an HFBA salt. LCMS (C₉H₂BN₂O₄⁺)(ES, m/z): 231 [M+H]⁺. ¹H NMR (499 MHz, D₂O) δ 4.08 (d, J=13.4 Hz, 1H), 3.65 (dd, J=12.0, 7.4 Hz, 1H), 3.28-3.13 (m, 2H), 3.02 (dd, J=13.2, 8.0 Hz, 1H), 2.68-2.56 (m, 2H), 1.59-1.46 (m, 1H), 1.46-1.33 (m, 2H), 1.32-1.20 (m, 1H), 0.87-0.68 (m, 2H).

Example 35: (2S,3R,4S)-3-(3-boronopropyl)-3,4-dihydroxypyrrolidine-2-carboxylic acid

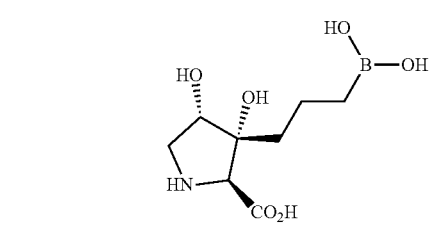 [SMILES: O=C(O)[C@H]1NC[C@H](O)[C@@]1(O)CCCB(O)O]

Step 1: 1-(tert-butyl) 2-methyl (S)-3-(3-(4,4,5,5-tetramethyl-1,3,2-dioxaborolan-2-yl)propyl)-2,5-dihydro-1H-pyrrole-1,2-dicarboxylate

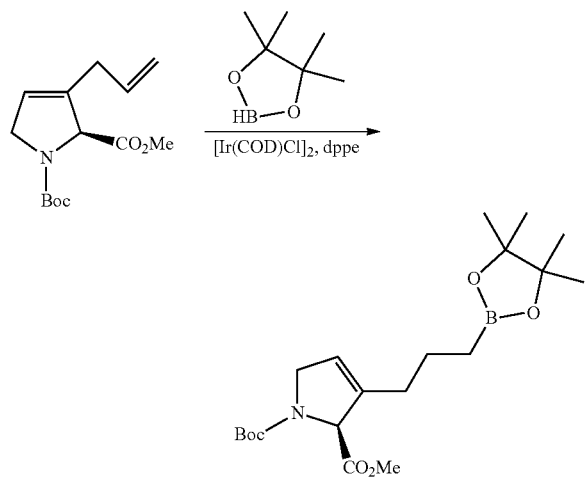

4,4,5,5-Tetramethyl-1,3,2-dioxaborolane (0.27 mL, 1.9 mmol) was added to a solution of chloro(1,5-cyclooctadiene)iridium(I)dimer (25 mg, 0.037 mmol) and DPPE (30 mg, 0.075 mmol) in DCM (0.50 mL) at room temperature under N₂. The resulting mixture was added to the solution of (S)-1-tert-butyl 2-methyl 3-allyl-1H-pyrrole-1,2(2H,5H)-dicarboxylate (0.10 g, 0.37 mmol) in DCM (1.0 mL) at room temperature under N₂, and stirred at room temperature overnight. The reaction mixture was quenched with saturated aqueous NH₄Cl solution and extracted with EtOAc, the combined organic phase was washed with brine, dried over anhydrous Na₂SO₄ and concentrated. The residue was purified by silica gel chromatography (EtOAc in hexanes) to give 1-(tert-butyl) 2-methyl (S)-3-(3-(4,4,5,5-tetramethyl-1,3,2-dioxaborolan-2-yl)propyl)-2,5-dihydro-1H-pyrrole-1,2-dicarboxylate. LCMS (C₁₆H₂₇BNO₆⁺)(ES, m/z): 340 [M-C₄H₈+H]⁺.

Step 2: 1-(tert-butyl) 2-methyl (2S,3R,4S)-3,4-dihydroxy-3-(3-(4,4,5,5-tetramethyl-1,3,2-dioxaborolan-2-yl)propyl)pyrrolidine-1,2-dicarboxylate

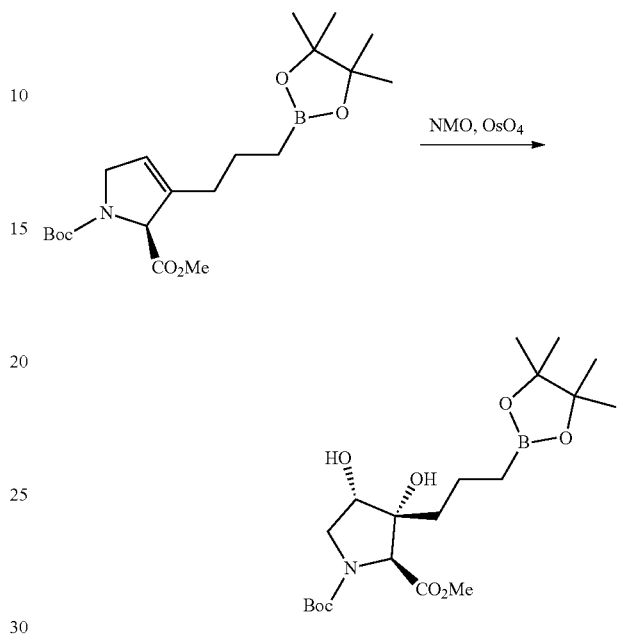

NMO (N-Methylmorpholine-N-Oxide)(53 mg, 0.46 mmol) and osmium tetroxide (2 wt % in water, 0.57 mL, 0.046 mmol) were sequentially added to the stirred solution of 1-(tert-butyl) 2-methyl (S)-3-(3-(4,4,5,5-tetramethyl-1,3,2-dioxaborolan-2-yl)propyl)-2,5-dihydro-1H-pyrrole-1,2-dicarboxylate (90 mg, 0.23 mmol) in THF (1.0 mL) and water (0.10 mL) at 0° C. The resulting mixture was allowed to warm to room temperature and stirred for 1 h. The reaction mixture was quenched with saturated aqueous NH₄Cl and extracted with 25% IPA in chloroform. The combined organic phase was washed with brine, dried over anhydrous Na₂SO₄ and concentrated. The residue was purified by silica gel chromatography (EtOAc in hexanes) to afford 1-(tert-butyl) 2-methyl (2S,3R,4S)-3,4-dihydroxy-3-(3-(4,4,5,5-tetramethyl-1,3,2-dioxaborolan-2-yl)propyl)pyrrolidine-1,2-dicarboxylate. LCMS (C₁₅H₂₈BNNaO₆⁺)(ES, m/z): 352 [M-CO₂C₄H₈+Na]⁺.

Step 3: (2S,3R,4S)-3-(3-boronopropyl)-3,4-dihydroxypyrrolidine-2-carboxylic acid

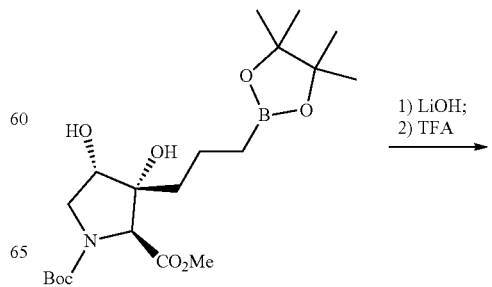

-continued

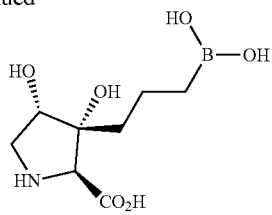

Example 35

Lithium hydroxide monohydrate (7.9 mg, 0.19 mmol) was added to a solution 1-(tert-butyl) 2-methyl (2S,3R,4S)-3,4-dihydroxy-3-(3-(4,4,5,5-tetramethyl-1,3,2-dioxaborolan-2-yl)propyl)pyrrolidine-1,2-dicarboxylate (10 mg, 0.023 mmol) in THF (0.20 mL) and water (0.50 mL), followed by 2 drops of MeOH at room temperature. The resulting mixture was stirred at room temperature overnight, then concentrated. The crude residue was taken up in TFA (0.018 mL, 0.23 mmol) and the reaction mixture was stirred at room temperature for 3 h. The resulting mixture was concentrated and the residue was purified by RP-HPLC [C18 column, water (0.1% TFA)-CH$_3$CN] to afford ((2S,3R,4S)-3-(3-boronopropyl)-3,4-dihydroxypyrrolidine-2-carboxylic acid as a TFA salt. LCMS (C$_8$H$_{15}$BNO$_6{}^+$)(ES, m/z): 216 [M−H$_2$O+H]$^+$. $^1$H NMR (500 MHz, D$_2$O) δ 4.23 (t, J=6.5 Hz, 1H), 4.17 (s, 1H), 3.69 (dd, J=11.7, 7.2 Hz, 1H), 3.20 (dd, J=12.0, 6.6 Hz, 1H), 1.64 (s, 4H), 0.82 (s, 2H).

Example 36: (2S,3S,4R)-3-(3-boronopropyl)-4-methoxypyrrolidine-2-carboxylic acid

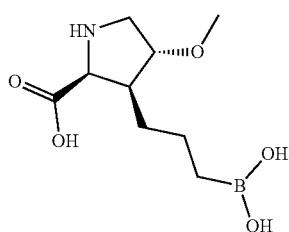 [SMILES: CO[C@H]1CN[C@H](C(=O)O)[C@@H]1CCCB(O)O]

Step 1: 1-(tert-butyl) 2-methyl (2S,3S,4R)-3-allyl-4-hydroxypyrrolidine-1,2-dicarboxylate

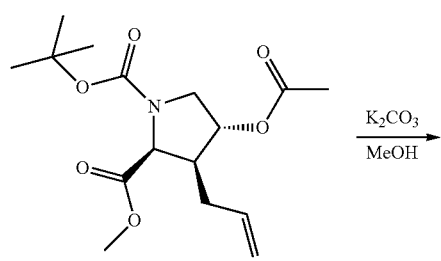

-continued

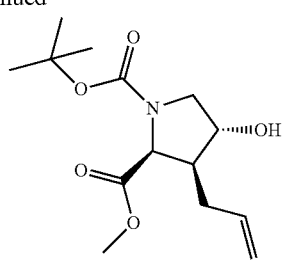

Potassium carbonate (0.22 mg, 1.6 mmol) was added to a solution of 1-(tert-butyl) 2-methyl (2S,3S,4R)-4-acetoxy-3-allylpyrrolidine-1,2-dicarboxylate (0.49 mg, 1.5 mmol) in MeOH (6.2 mL). The resulting mixture was stirred at room temperature for 1.5 h then filtered. The filtrate was concentrated and the residue was purified by silica gel chromatography (EtOAc in hexanes) to afford 1-(tert-butyl) 2-methyl (2S,3 S,4R)-3-allyl-4-hydroxypyrrolidine-1,2-dicarboxylate. LCMS (C$_9$H$_{16}$NO$_3{}^+$)(ES, m/z): 186 [M−CO$_2$C$_4$H$_8$+H]$^+$.

Step 2: 1-(tert-butyl) 2-methyl (2S,3S,4R)-3-allyl-4-methoxypyrrolidine-1,2-dicarboxylate

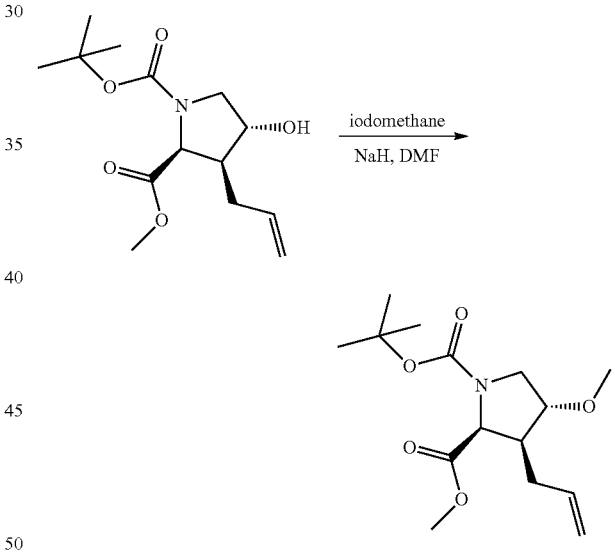

Sodium hydride (60 wt % in mineral oil, 22 mg, 0.55 mmol) was added to a solution of 1-(tert-butyl) 2-methyl (2S,3S,4R)-3-allyl-4-hydroxypyrrolidine-1,2-dicarboxylate (78 mg, 0.27 mmol) in DMF (2.5 mL). The resulting solution was stirred for 15 minutes at room temperature followed by addition of iodimethane (68 µL, 1.1 mmol). The reaction mixture was stirred at room temperature for 1 h then quenched by addition of saturated aqueous NH$_4$Cl and diluted with EtOAc. The organic layer was separated, washed with brine, dried over Na$_2$SO$_4$, filtered and concentrated. The residue was purified by silica gel chromatography (EtOAc in hexanes) to afford 1-(tert-butyl) 2-methyl (2S,3S,4R)-3-allyl-4-methoxypyrrolidine-1,2-dicarboxylate. LCMS (C$_{10}$H$_{18}$NO$_3{}^+$)(ES, m/z): 200 [M−CO$_2$C$_4$H$_8$+H]$^+$.

Step 3: 1-(tert-butyl) 2-methyl (2S,3S,4R)-4-methoxy-3-(3-((3aS,4S,6S,7aR)-3a,5,5-trimethyl-hexahydro-4,6-methanobenzo[d][1,3,2]dioxaborol-2-yl)propyl)pyrrolidine-1,2-dicarboxylate

Step 4: (2S,3S,4R)-1-(tert-butoxycarbonyl)-4-methoxy-3-(3-((3aS,4S,6S,7aR)-3a,5,5-trimethyl-hexahydro-4,6-methanobenzo[d][1,3,2]dioxaborol-2-yl)propyl)pyrrolidine-2-carboxylic acid

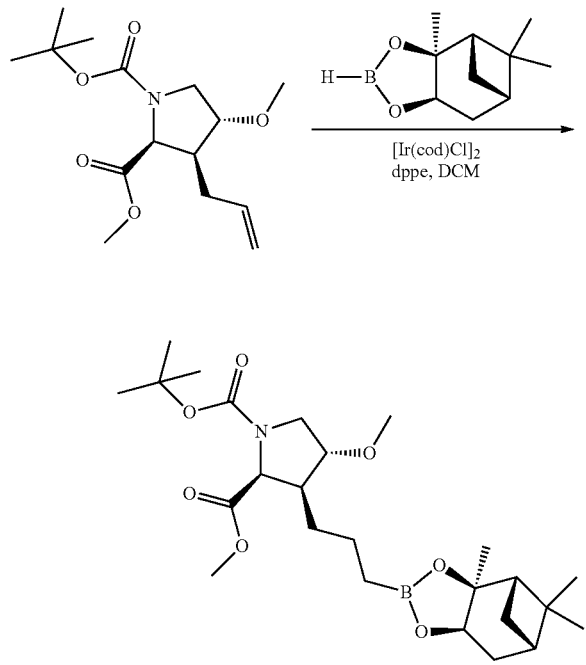

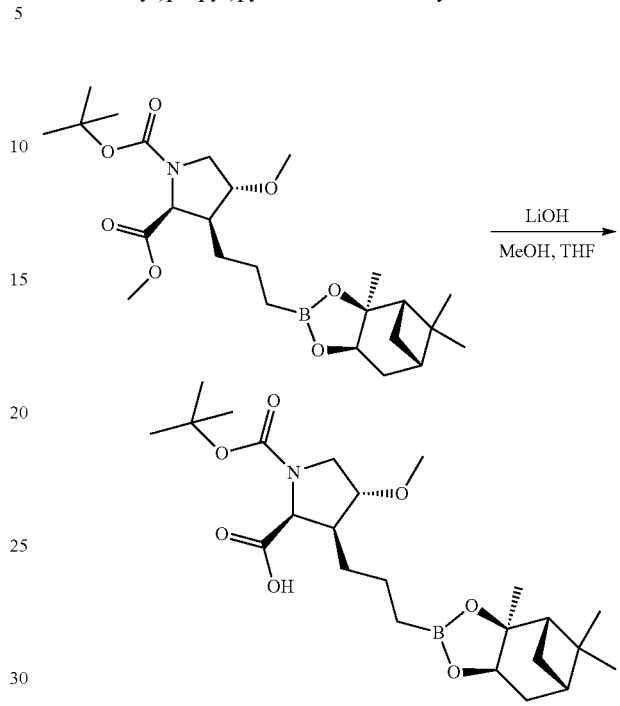

(3aS,4S,6S,7aR)-3a,5,5-trimethylhexahydro-4,6-methanobenzo[d][1,3,2]dioxaborole (68 mg, 0.38 mmol), chloro(1,5-cyclooctadiene)Iridium(I) dimer (5.0 mg, 0.0075 mmol) and 1,2-bis(diphenylphosphino)ethane (6.0 mg, 0.015 mmol) in anhydrous DCM (2.0 mL) was placed under argon and the resulting mixture was stirred at room temperature for 20 minutes, followed by addition of a solution of 1-(tert-butyl) 2-methyl (2S,3S,4R)-3-allyl-4-methoxypyrrolidine-1,2-dicarboxylate (45 mg, 0.15 mmol) in DCM (1.0 mL). The reaction mixture was stirred at room temperature for 19 h under argon. Reaction was quenched by slow addition of methanol then diluted with water and EtOAc. The organic layer was separated, washed with brine, dried over $Na_2SO_4$, filtered and concentrated. The residue was purified by silica gel chromatography (EtOAc in hexanes) to afford 1-(tert-butyl) 2-methyl (2S,3S,4R)-4-methoxy-3-(3-((3aS,4S,6S,7aR)-3a,5,5-trimethylhexahydro-4,6-methanobenzo[d][1,3,2]dioxaborol-2-yl)propyl)pyrrolidine-1,2-dicarboxylate. LCMS ($C_{20}H_{35}BNO_5$)(ES, m/z): 380 [M-$CO_2$ $C_4H_8$+H]$^+$.

Lithium hydroxide (61 mg, 1.5 mmol) was added to a solution of 1-(tert-butyl) 2-methyl (2S,3S,4R)-4-methoxy-3-(3-((3aS,4S,6S,7aR)-3a,5,5-trimethylhexahydro-4,6-methanobenzo[d][1,3,2]dioxaborol-2-yl)propyl)pyrrolidine-1,2-dicarboxylate (70 mg, 0.15 mmol) in a mixture of THF (3.5 mL) and MeOH (0.5 mL). The reaction mixture was stirred at room temperature for 89 h. Reaction mixture was acidified to pH ~4 by addition of 1 N HCl then diluted with EtOAc. The organic layer was separated, washed with brine, dried over $Na_2SO_4$, filtered and concentrated. The resulting residue was purified by silica gel chromatography (EtOAc in hexanes) to afford (2S,3S,4R)-1-(tert-butoxycarbonyl)-4-methoxy-3-(3-((3aS,4S,6S,7aR)-3a,5,5-trimethylhexahydro-4,6-methanobenzo[d][1,3,2]dioxaborol-2-yl)propyl)pyrrolidine-2-carboxylic acid. LCMS ($C_{19}H_{33}BNO_5^+$)(ES, m/z): 366 [M-$CO_2C_4H_8$+H]$^+$.

Step 5: (2S,3S,4R)-3-(3-boronopropyl)-4-methoxy-pyrrolidine-2-carboxylic acid

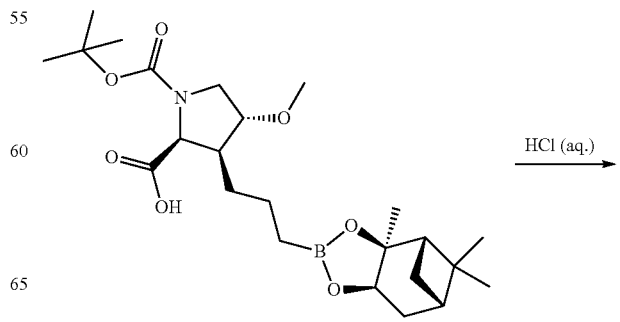

-continued

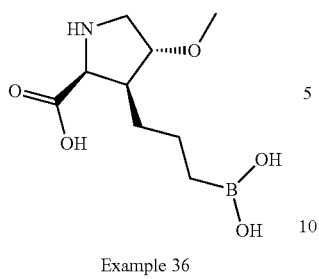

Example 36

A mixture of (2S,3S,4R)-1-(tert-butoxycarbonyl)-4-methoxy-3-(3-((3aS,4S,6S,7aR)-3a,5,5-trimethylhexahydro-4,6-methanobenzo[d][1,3,2]dioxaborol-2-yl)propyl)pyrrolidine-2-carboxylic acid (18 mg, 0.038 mmol) and 6 N HCl in water (0.80 mL, 4.8 mmol) was heated to 35° C. with stirring for 18 h. The reaction mixture was concentrated to give (2S,3S,4R)-3-(3-boronopropyl)-4-methoxypyrrolidine-2-carboxylic acid as an HCl salt. LCMS ($C_9H_{19}BNO_5^+$)(ES, m/z): 232 [M+H]$^+$. $^1$H NMR (499 MHz, D$_2$O) δ 4.44 (d, J=6.7 Hz, 1H), 4.05 (d, J=4.1 Hz, 1H), 3.58 (dd, J=13.4, 4.4 Hz, 1H), 3.38 (d, J=13.5 Hz, 1H), 3.30 (s, 3H), 2.72-2.62 (m, 1H), 1.55-1.43 (m, 1H), 1.42-1.31 (m, 1H), 1.31-1.21 (m, 1H), 1.13-1.03 (m, 1H), 0.79-0.65 (m, 2H).

Example 37: (2S,3R,4R)-4-((S)-2-amino-3-methylbutanamido)-3-(3-boronopropyl)pyrrolidine-2-carboxylic acid

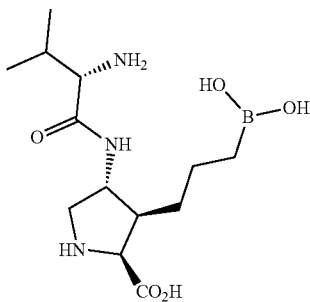 [SMILES: CC(C)[C@H](N)C(=O)N[C@H]1CN[C@H](C(=O)O)[C@@H]1CCCB(O)O]

Step 1: 1-(tert-butyl) 2-methyl (2S,3R,4R)-3-allyl-4-((S)-2-((tert-butoxycarbonyl)amino)-3-methylbutanamido)pyrrolidine-1,2-dicarboxylate

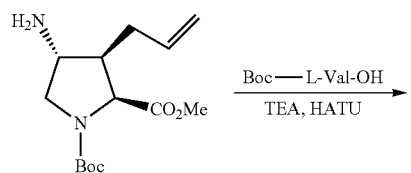

-continued

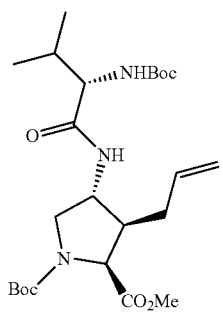

(Tert-butoxycarbonyl)-L-valine (Boc-L-Val-OH, 20 g, 92 mmol), triethylamine (33 mL, 0.23 mol) and HATU (33 g, 86 mmol) were added sequentially to the stirred solution of 1-(tert-butyl) 2-methyl (2S,3R,4R)-3-allyl-4-aminopyrrolidine-1,2-dicarboxylate (22 g, 78 mmol) in DMF (0.26 L) at room temperature. The reaction mixture was stirred at room temperature for 1 h, then diluted with saturated aqueous NaHCO$_3$ solution, and extracted with ether. The combined organic phase was washed with brine, dried over MgSO$_4$, and concentrated. The residue was purified by silica gel column chromatography (EtOAc in hexanes) to afford 1-(tert-butyl) 2-methyl (2S,3R,4R)-3-allyl-4-((S)-2-((tert-butoxycarbonyl)amino)-3-methylbutanamido)pyrrolidine-1,2-dicarboxylate. LCMS ($C_{24}H_{41}N_3NaO_7^+$)(ES, m/z): 506 [M+Na]$^+$.

Step 2: 1-(tert-butyl) 2-methyl (2S,3R,4R)-4-((S)-2-((tert-butoxycarbonyl)amino)-3-methylbutanamido)-3-(3-(4,4,5,5-tetramethyl-1,3,2-dioxaborolan-2-yl)propyl)pyrrolidine-1,2-dicarboxylate

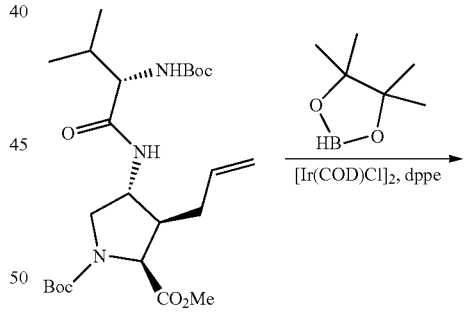

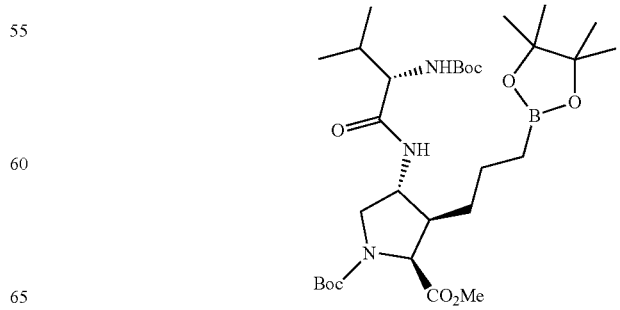

4,4,5,5-Tetramethyl-1,3,2-dioxaborolane (7.5 mL, 51 mmol) was added to a solution of chloro(1,5-cyclooctadiene)iridium(I)dimer (1.7 g, 2.6 mmol) and DPPE (2.1 g, 5.1 mmol) in DCM (69 mL) at room temperature under $N_2$. The resulting solution was stirred at room temperature for 10 min, then added to the solution of 1-(tert-butyl) 2-methyl (2S,3R,4R)-3-allyl-4-((S)-2-((tert-butoxycarbonyl)amino)-3-methylbutanamido)pyrrolidine-1,2-dicarboxylate (12 g, 26 mmol) in DCM (34 mL) at room temperature under $N_2$. The reaction mixture was stirred at room temperature overnight, then quenched with saturated aqueous $NH_4Cl$ solution and extracted with EtOAc. The combined organic phase was washed with brine, dried over $MgSO_4$, and concentrated. The residue was purified by silica gel column chromatography (EtOAc in hexanes) to afford 1-(tert-butyl) 2-methyl (2S,3R,4R)-4-((S)-2-((tert-butoxycarbonyl)amino)-3-methylbutanamido)-3-(3-(4,4,5,5-tetramethyl-1,3,2-dioxaborolan-2-yl)propyl)pyrrolidine-1,2-dicarboxylate. LCMS ($C_{30}H_{54}BN_3NaO_9^+$)(ES, m/z): 634 [M+Na]$^+$.

Step 3: (2S,3R,4R)-4-((S)-2-amino-3-methylbutanamido)-3-(3-boronopropyl)pyrrolidine-2-carboxylic acid

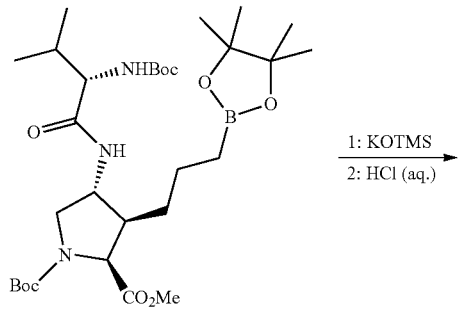

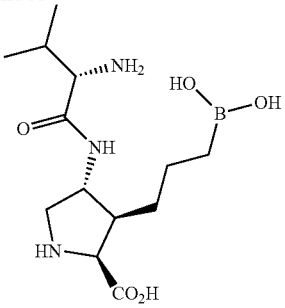

Example 37

Potassium trimethylsilanolate (2.7 g, 21 mmol) was added to the stirred solution of 1-(tert-butyl) 2-methyl (2S,3R,4R)-4-((S)-2-((tert-butoxycarbonyl)amino)-3-methylbutanamido)-3-(3-(4,4,5,5-tetramethyl-1,3,2-dioxaborolan-2-yl)propyl)pyrrolidine-1,2-dicarboxylate (4.3 g, 7.0 mmol) in THF (47 mL) at room temperature. The reaction mixture was stirred at room temperature overnight, then diluted with water and extracted with ether. The aqueous layer was acidified with 2N HCl in water to pH ~3 and then extracted with EtOAc. The combined organic phase was washed with brine, dried over anhydrous $Na_2SO_4$, and concentrated. The residue was purified by silica gel column chromatography (EtOAc in hexanes) to afford (2S,3R,4R)-1-(tert-butoxycarbonyl)-4-((S)-2-((tert-butoxycarbonyl)amino)-3-methylbutanamido)-3-(3-(4,4,5,5-tetramethyl-1,3,2-dioxaborolan-2-yl)propyl)pyrrolidine-2-carboxylic acid, which was treated with 6 N HCl in water (20 mL, 0.12 mol) and stirred at 60° C. for 1.5 h, then cooled to room temperature, diluted with water and washed with DCM. The aqueous layer was concentrated to afford (2S,3R,4R)-4-((S)-2-amino-3-methylbutanamido)-3-(3-boronopropyl)pyrrolidine-2-carboxylic acid as an HCl salt. LCMS ($C_3H_{25}BN_3O_4^+$)(ES, m/z): 298 [M–$H_2O$+H]$^+$. $^1$H NMR (500 MHz, $D_2O$) δ 4.44 (d, J=7.8 Hz, 1H), 4.39 (q, J=6.9 Hz, 1H), 3.92 (dd, J=12.7, 7.8 Hz, 1H), 3.80 (d, J=5.7 Hz, 1H), 3.25 (dd, J=12.7, 6.1 Hz, 1H), 2.59-2.53 (m, 1H), 2.27-2.21 (m, 1H), 1.56-1.38 (n, 4H), 1.05 (dd, J=8.5, 7.1 Hz, 6H), 0.88-0.75 (m, 2H).

Examples 38-41 were prepared using the method described in Example 37 and appropriate starting materials.

| Ex. # | Structure | Chemical Name | Mass [M – $H_2O$ + H]+ |
|---|---|---|---|
| 38 | 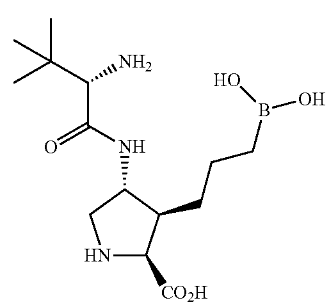 [SMILES: CC(C)(C)[C@H](N)C(=O)N[C@H]1CN[C@H](C(=O)O)[C@@H]1CCCB(O)O] | (2S,3R,4R)-4-((S)-2-amino-3,3-dimethylbutanamido)-3-(3-boronopropyl)pyrrolidine-2-carboxylic acid | 312 |

| Ex. # | Structure | Chemical Name | Mass [M − H₂O + H]+ |
|---|---|---|---|
| 39 | 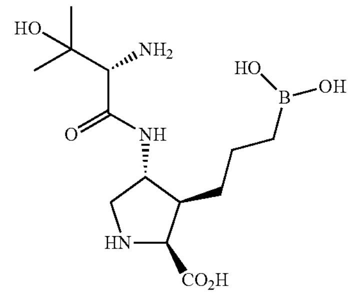 [SMILES: CC(C)(O)[C@H](N)C(=O)N[C@H]1CN[C@H](C(=O)O)[C@@H]1CCCB(O)O] | (2S,3R,4R)-4-((S)-2-amino-3-hydroxy-3-methylbutanamido)-3-(3-boronopropyl)pyrrolidine-2-carboxylic acid | 314 |
| 40 | 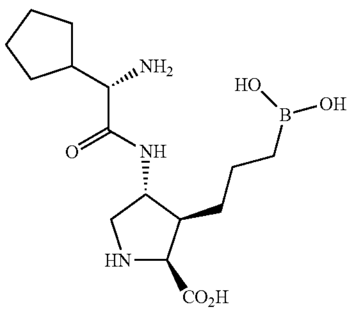 [SMILES: N[C@H](C(=O)N[C@H]1CN[C@H](C(=O)O)[C@@H]1CCCB(O)O)C1CCCC1] | (2S,3R,4R)-4-((S)-2-amino-2-cyclopentylacetamido)-3-(3-boronopropyl)pyrrolidine-2-carboxylic acid | 324 |
| 41 | 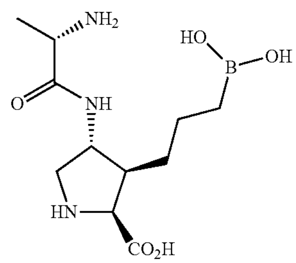 [SMILES: C[C@H](N)C(=O)N[C@H]1CN[C@H](C(=O)O)[C@@H]1CCCB(O)O] | (2S,3R,4R)-4-((S)-2-aminopropanamido)-3-(3-boronopropyl)pyrrolidine-2-carboxylic acid | 270 |

Step 4: (2S,3R,4R)-4-((S)-2-amino-3-methylbutanamido)-3-(3-boronopropyl)pyrrolidine-2-carboxylic acid (free base)

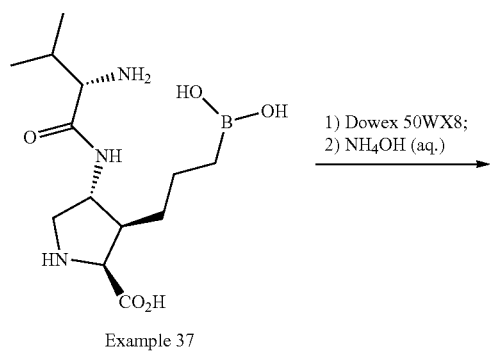

Example 37

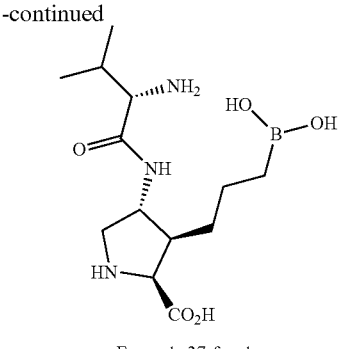

Example 37-free base (2S,3R,4R)-4-((S)-2-amino-3-methylbutanamido)-3-(3-boronopropyl)pyrrolidine-2-carboxylic acid (HCl salt, 3.7 g, 11 mmol) was purified on 70 g of Dowex 50WX8 acidic resin (washed with water until pH neutral, then eluted with 2 N aqueous ammonium hydroxide) to afford (2S,3R,4R)-

4-((S)-2-amino-3-methylbutanamido)-3-(3-boronopropyl) pyrrolidine-2-carboxylic acid as a white solid. LCMS ($C_{13}H_{25}BN_3O_4^+$)(ES, m/z): 298 [M–$H_2O$+H]$^+$. $^1$H NMR (500 MHz, $D_2O$) δ 4.22 (q, J=5.7 Hz, 1H), 4.15 (d, J=7.8 Hz, 1H), 3.73 (dd, J=12.5, 7.4 Hz, 1H), 3.18 (d, J=6.3 Hz, 1H), 3.04 (dd, J=12.5, 5.7 Hz, 1H), 2.44-2.34 (m, 1H), 1.93-1.83 (m, 1H), 1.48-1.20 (m, 4H), 0.87 (dd, J=6.8, 2.9 Hz, 6H), 0.72 (ddt, J=24.7, 16.0, 7.4 Hz, 2H).

Example 42: (2S,3R,4R)-4-((S)-2-amino-4-methylpentanamido)-3-(3-boronopropyl)pyrrolidine-2-carboxylic acid

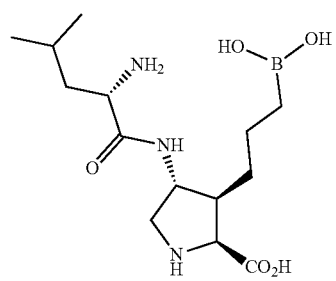 [SMILES: CC(C)C[C@H](N)C(=O)N[C@H]1CN[C@H](C(=O)O)[C@@H]1CCCB(O)O]

Step 1: 1-(tert-butyl) 2-methyl (2S,3R,4R)-4-amino-3-(3-((3aS,4S,6S,7aR)-3a,5,5-trimethylhexahydro-4,6-methanobenzo[d][1,3,2]dioxaborol-2-yl)propyl) pyrrolidine-1,2-dicarboxylate

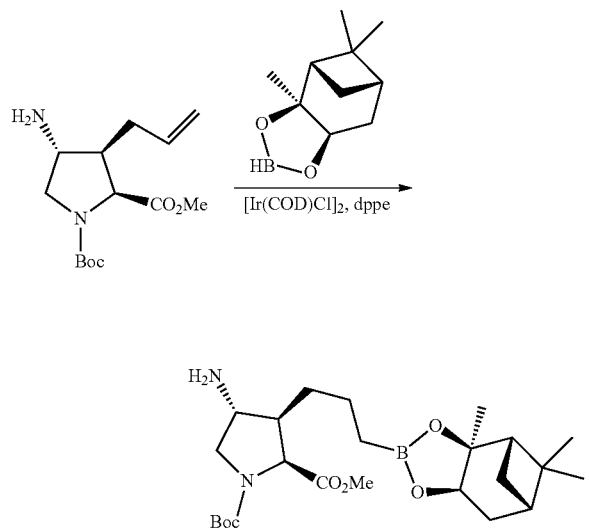

(3aR,4R,6R,7aS)-3a,5,5-trimethylhexahydro-4,6-methanobenzo[d][1,3,2]dioxaborole (1.0 g, 5.7 mmol) was added to the stirred solution of chloro(1,5-cyclooctadiene)iridium (I)dimer (0.13 g, 0.19 mmol) and DPPE (0.15 g, 0.38 mmol) in DCM (5.1 mL) at room temperature under $N_2$. The resulting mixture was stirred at room temperature for 5 min, then added dropwise to the stirred solution of 1-(tert-butyl) 2-methyl (2S,3R,4R)-3-allyl-4-aminopyrrolidine-1,2-dicarboxylate (0.54 mg, 1.9 mmol) in DCM (2.5 mL) under $N_2$. The reaction mixture was stirred at room temperature overnight, then diluted with saturated aqueous $NaHCO_3$ and extracted with EtOAc. The combined organic phase was washed with brine, dried over $NaSO_4$, and concentrated to yield crude 1-(tert-butyl) 2-methyl (2S,3R,4R)-4-amino-3-(3-((3aS,4S,6S,7aR)-3a,5,5-trimethylhexahydro-4,6-methanobenzo[d][1,3,2]dioxaborol-2-yl)propyl)pyrrolidine-1,2-dicarboxylate, which was used in the next step without further purification. LCMS ($C_{24}H_{42}BN_2O_6^+$)(ES, m/z): 465 [M+H]$^+$.

Step 2: 1-(tert-butyl) 2-methyl (2S,3R,4R)-4-((S)-2-((tert-butoxycarbonyl)amino)-4-methylpentanamido)-3-(3-((3aR,4R,6R)-3a,5,5-trimethylhexahydro-4,6-methanobenzo[d][1,3,2]dioxaborol-2-yl) propyl)pyrrolidine-1,2-dicarboxylate

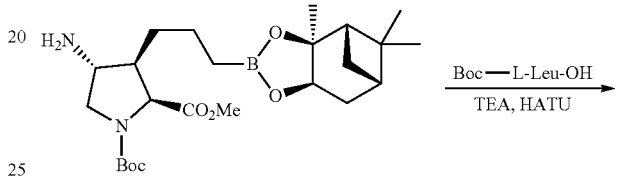

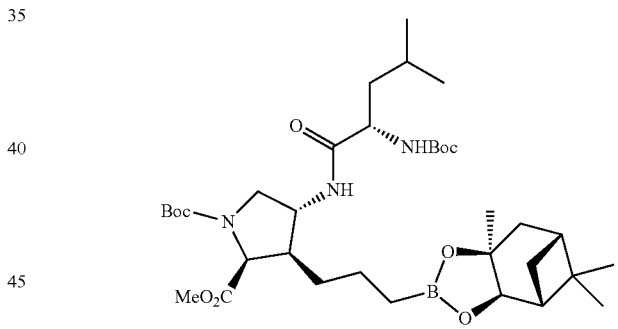

(Tert-butoxycarbonyl)-L-leucine (0.25 g, 1.1 mmol), triethylamine (0.31 mL, 2.2 mmol) and HATU (0.33 g, 0.88 mmol) were added sequentially to the stirred solution of 1-(tert-butyl) 2-methyl (2S,3R,4R)-4-amino-3-(3-((3aR,4R,6R)-3a,5,5-trimethylhexahydro-4,6-methanobenzo[d][1,3,2]dioxaborol-2-yl)propyl)pyrrolidine-1,2-dicarboxylate (0.34 mg, 0.73 mmol) in DMF (2.4 mL) at room temperature. The reaction mixture was stirred at room temperature for 1 h, then diluted with saturated aqueous $NaHCO_3$ solution, and extracted with ether. The combined organic phase was washed with brine, dried over $MgSO_4$, and concentrated. The residue was purified by silica gel column chromatography (EtOAc in hexanes) to afford 1-(tert-butyl) 2-methyl (2S,3R,4R)-4-((S)-2-((tert-butoxycarbonyl)amino)-4-methylpentanamido)-3-(3-((3aR,4R,6R)-3a,5,5-trimethylhexahydro-4,6-methanobenzo[d][1,3,2]dioxaborol-2-yl)propyl)pyrrolidine-1,2-dicarboxylate. LCMS ($C_{35}H_{60}BN_3NaO_9^+$)(ES, m/z): 700 [M+Na].

Step 3: (2S,3R,4R)-4-((S)-2-amino-4-methylpentanamido)-3-(3-boronopropyl)pyrrolidine-2-carboxylic acid

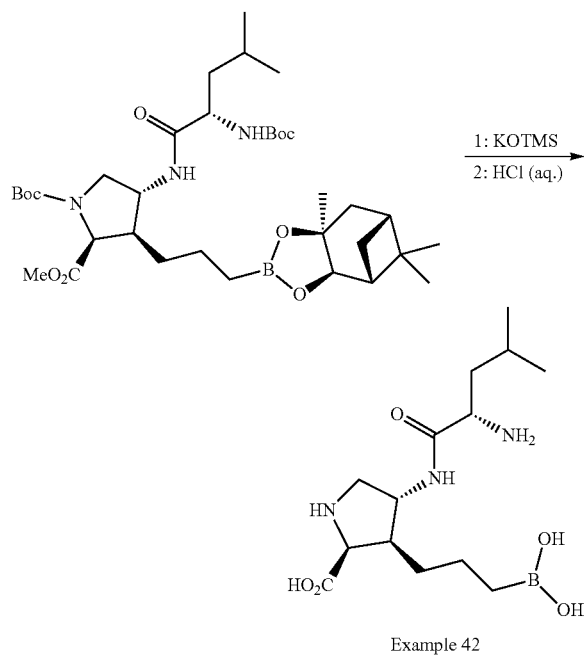

Example 42

Potassium trimethylsilanolate (0.15 g, 1.2 mmol) was added to a solution of 1-(tert-butyl) 2-methyl (2S,3R,4R)-4-((S)-2-((tert-butoxycarbonyl)amino)-4-methylpentanamido)-3-(3-((3aR,4R,6R)-3a,5,5-trimethylhexahydro-4,6-methanobenzo[d][1,3,2]dioxaborol-2-yl)propyl)pyrrolidine-1,2-dicarboxylate (0.26 g, 0.38 mmol) in THF (2.6 mL) at room temperature The reaction mixture was stirred at room temperature overnight, then diluted with water and extracted with ether. The aqueous layer was acidified with 2 N HCl in water to pH ~3 and extracted with EtOAc. The combined organic phase was washed with brine, dried over anhydrous $Na_2SO_4$, and concentrated. The residue was purified by RP-HPLC [C18 column, water (0.1% TFA)-$CH_3CN$] to give (2S,3R,4R)-1-(tert-butoxycarbonyl)-4-((S)-2-((tert-butoxycarbonyl)amino)-4-methylpentanamido)-3-(3-((3aS,4S,6S,7aR)-3a,5,5-trimethylhexahydro-4,6-methanobenzo[d][1,3,2]dioxaborol-2-yl)propyl)pyrrolidine-2-carboxylic acid, which was treated with 6 N HCl (3.0 mL, 18 mmol) and stirred at 60° C. for 3 h, then cooled to room temperature, diluted with water and washed with DCM. The aqueous layer was concentrated to afford (2S,3R,4R)-4-((S)-2-amino-4-methylpentanamido)-3-(3-boronopropyl)pyrrolidine-2-carboxylic acid as an HCl salt. LCMS ($C_{14}H_{27}BN_3O_4^+$)(ES, m/z): 312 [M–$H_2O$+H]$^+$. $^1$H NMR (500 MHz, $D_2O$) δ 4.40 (d, J=8.0 Hz, 1H), 4.30 (q, J=6.9 Hz, 1H), 3.91 (t, J=7.4 Hz, 1H), 3.88-3.78 (m, 1H), 3.17 (dd, J=12.6, 6.4 Hz, 1H), 2.55-2.43 (m, 1H), 1.66 (t, J=7.3 Hz, 2H), 1.58 (dq, J=13.6, 6.6 Hz, 1H), 1.49-1.35 (m, 3H), 1.34-1.21 (m, 1H), 0.89 (t, J=6.5 Hz, 6H), 0.78-0.63 (m, 2H).

Examples 43-49 were prepared using the methods described in Example 42 and appropriate starting materials.

| Ex. # | Structure | Chemical Name | Mass [M – $H_2O$ + H]+ |
|---|---|---|---|
| 43 | 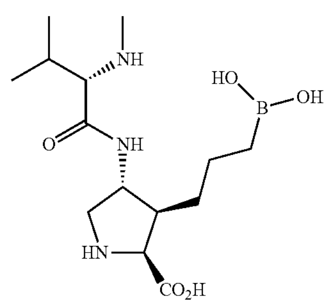 [SMILES: CN[C@H](C(=O)N[C@H]1CN[C@H](C(=O)O)[C@@H]1CCCB(O)O)C(C)C] | (2S,3R,4R)-3-(3-boronopropyl)-4-((S)-3-methyl-2-(methylamino)butanamido)pyrrolidine-2-carboxylic acid | 312 |
| 44 | 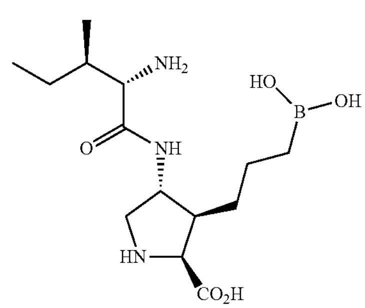 [SMILES: CC[C@@H](C)[C@H](N)C(=O)N[C@H]1CN[C@H](C(=O)O)[C@@H]1CCCB(O)O] | (2S,3R,4R)-4-((2S,3R)-2-amino-3-methylpentanamido)-3-(3-boronopropyl)pyrrolidine-2-carboxylic acid | 312 |

-continued

| Ex. # | Structure | Chemical Name | Mass [M − H₂O + H]+ |
|---|---|---|---|
| 45 | 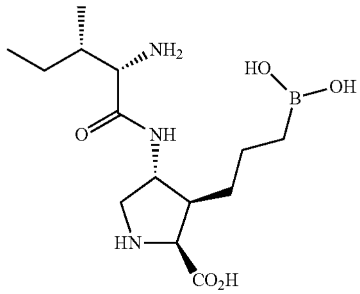 [SMILES: CC[C@H](C)[C@H](N)C(=O)N[C@H]1CN[C@H](C(=O)O)[C@@H]1CCCB(O)O] | (2S,3R,4R)-4-((2S,3S)-2-amino-3-methylpentanamido)-3-(3-boronopropyl)pyrrolidine-2-carboxylic acid | 312 |
| 46 | 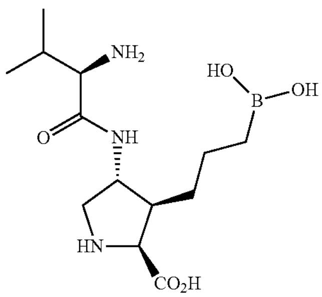 [SMILES: CC(C)[C@@H](N)C(=O)N[C@H]1CN[C@H](C(=O)O)[C@@H]1CCCB(O)O] | (2S,3R,4R)-4-((R)-2-amino-3-methylbutanamido)-3-(3-boronopropyl)pyrrolidine-2-carboxylic acid | 298 |
| 47 | 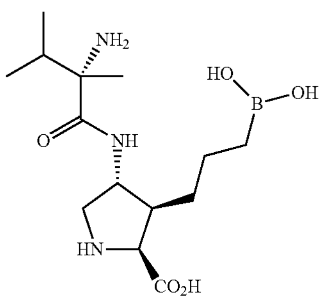 [SMILES: CC(C)[C@](C)(N)C(=O)N[C@H]1CN[C@H](C(=O)O)[C@@H]1CCCB(O)O] | (2S,3R,4R)-4-((S)-2-amino-2,3-dimethylbutanamido)-3-(3-boronopropyl)pyrrolidine-2-carboxylic acid | 312 |
| 48 | 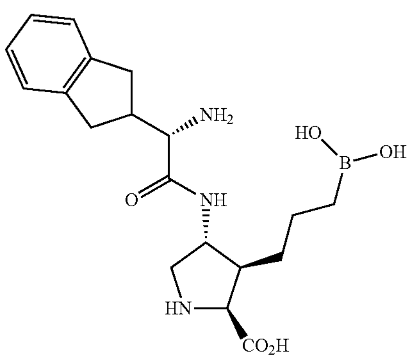 [SMILES: N[C@H](C(=O)N[C@H]1CN[C@H](C(=O)O)[C@@H]1CCCB(O)O)C1Cc2ccccc2C1] | (2S,3R,4R)-4-((S)-2-amino-2-(2,3-dihydro-1H-inden-2-yl)acetamido)-3-(3-boronopropyl)pyrrolidine-2-carboxylic acid | 372 |
| 49 | 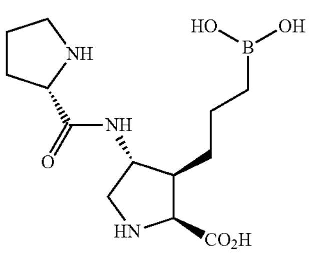 [SMILES: O=C(N[C@H]1CN[C@H](C(=O)O)[C@@H]1CCCB(O)O)[C@@H]1CCCN1] | (2S,3R,4R)-3-(3-boronopropyl)-4-((S)-pyrrolidine-2-carboxamido)pyrrolidine-2-carboxylic acid | 296 |

Example 50: (2S,3R,4R)-4-acetamido-3-(3-boronopropyl)pyrrolidine-2-carboxylic acid

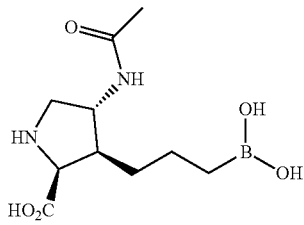 [SMILES: CC(=O)N[C@H]1CN[C@H](C(=O)O)[C@@H]1CCCB(O)O]

Step 1: 1-(tert-butyl) 2-methyl (2S,3R,4R)-4-acetamido-3-allylpyrrolidine-1,2-dicarboxylate

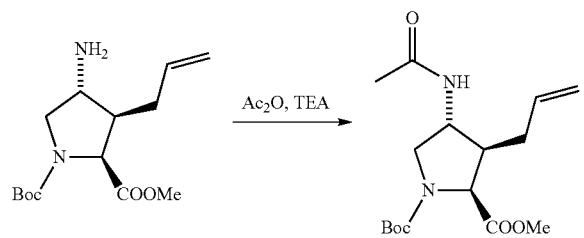 [SMILES: C=CC[C@H]1[C@@H](C(=O)OC)N(C(=O)OC(C)(C)C)C[C@@H]1N ; "Ac2O, TEA" ; C=CC[C@@H]1[C@@H](NC(C)=O)CN(C(=O)OC(C)(C)C)[C@@H]1C(=O)OC]

Triethylamine (0.22 mL, 1.5 mmol) was added to a solution of 1-(tert-butyl) 2-methyl (2S,3R,4R)-3-allyl-4-aminopyrrolidine-1,2-dicarboxylate (0.22 mg, 0.77 mmol) in DCM (3.9 mL), followed by addition of acetic anhydride (80 µL, 0.85 mmol) dropwise at room temperature The resulting mixture was stirred at room temperature for 1 h, then quenched with saturated aqueous NaHCO$_3$ solution, and extracted with EtOAc. The combined organic phase was washed with brine, dried over Na$_2$SO$_4$, filtered and concentrated. The residue was purified by silica gel column chromatography (EtOAc in hexanes) to afford 1-(tert-butyl) 2-methyl (2S,3R,4R)-4-acetamido-3-allylpyrrolidine-1,2-dicarboxylate. LCMS (C$_{16}$H$_{26}$N$_2$NaO$_5$)(ES, m/z): 349 [M+Na]$^+$.

Step 2: 1-(tert-butyl) 2-methyl (2S,3R,4R)-4-acetamido-3-(3-(4,4,5,5-tetramethyl-1,3,2-dioxaborolan-2-yl)propyl)pyrrolidine-1,2-dicarboxylate

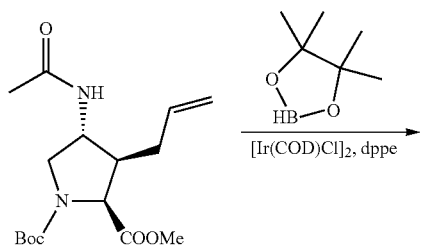

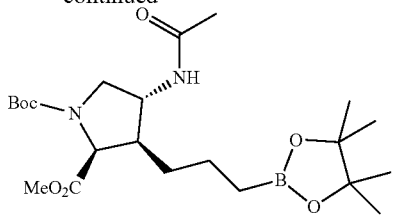

4,4,5,5-Tetramethyl-1,3,2-dioxaborolane (0.36 mL, 2.5 mmol) was added to the stirred solution of chloro (1,5-cyclooctadiene) iridium (I) dimer (41 mg, 0.061 mmol) and DPPE (49 mg, 0.12 mmol) in DCM (0.50 mL) at room temperature under N2. The resulting solution was added to the stirred solution of 1-(tert-butyl) 2-methyl (2S,3R,4R)-4-acetamido-3-allylpyrrolidine-1,2-dicarboxylate (0.20 g, 0.61 mmol) in DCM (2.0 mL) at room temperature under N2, and the reaction mixture was stirred for 2 h, then concentrated, and the residue was purified by silica gel column chromatography (EtOAc in hexanes) to afford 1-(tert-butyl) 2-methyl (2S,3R,4R)-4-acetamido-3-(3-(4,4,5,5-tetramethyl-1,3,2-dioxaborolan-2-yl) propyl) pyrrolidine-1,2-dicarboxylate. LCMS (C$_{22}$H$_{39}$BN$_2$NaO$_7^+$)(ES, m/z): 477 [M+Na]$^+$.

Step 3: (2S,3R,4R)-4-acetamido-3-(3-boronopropyl)pyrrolidine-2-carboxylic acid

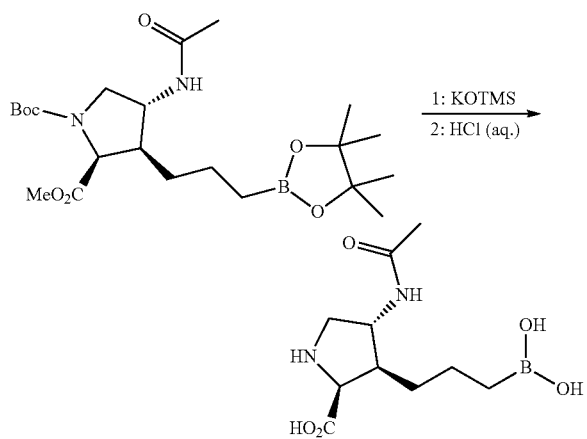

Potassium trimethylsilanolate (0.11 g, 0.86 mmol) was added to the stirred solution of 1-(tert-butyl) 2-methyl (2S,3R,4R)-4-acetamido-3-(3-(4,4,5,5-tetramethyl-1,3,2-dioxaborolan-2-yl) propyl) pyrrolidine-1,2-dicarboxylate (0.20 g, 0.43 mmol) in THF (4.3 mL) at room temperature The resulting mixture was stirred at room temperature overnight, and concentrated. The crude residue was treated with 6 N HCl in water (2.0 mL, 12 mmol) and stirred at 60° C. for 60 min. The reaction mixture was cooled to room temperature, diluted with water and washed with DCM. The aqueous layer was concentrated, and the residue was purified by RP-HPLC [C$_{18}$ column, water (0.2 mM heptafluorobutyric acid/0.1% TFA)-CH$_3$CN] to afford (2S,3R,4R)-4-acetamido-3-(3-boronopropyl) pyrrolidine-2-carboxylic acid as a HFBA salt. LCMS (C$_{10}$H$_{18}$BN$_2$O$_4^+$)(ES, m/z): 241 [M−H$_2$O+H]$^+$. 1H NMR (500 MHZ, D$_2$O) δ 4.42 (d, J=7.7 Hz, 1H), 4.22 (q, J=5.8 Hz, 1H), 3.76 (dd, J=12.6, 7.4 Hz, 1H), 3.18 (dd, J=12.6, 5.4 Hz, 1H), 2.49 (p, J=7.5, 7.0 Hz, 1H), 1.93 (s, 3H), 1.51-1.38 (m, 2H), 1.33 (qt, J=13.6, 6.4 Hz, 2H), 0.78-0.65 (m, 2H).

Example 51: (2S,3S,4R)-4-((S)-2-amino-N-methylpropanamido)-3-(3-boronopropyl) pyrrolidine-2-carboxylic acid

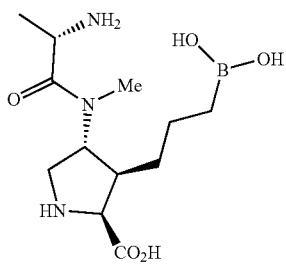 [SMILES: C[C@H](N)C(=O)N(C)[C@H]1CN[C@H](C(=O)O)[C@@H]1CCCB(O)O]

Step 1: 1-(tert-butyl) 2-methyl (2S,3R,4R)-4-((S)-2-((tert-butoxycarbonyl)amino)-N-methylpropanamido)-3-(3-(4,4,5,5-tetramethyl-1,3,2-dioxaborolan-2-yl)propyl)pyrrolidine-1,2-dicarboxylate

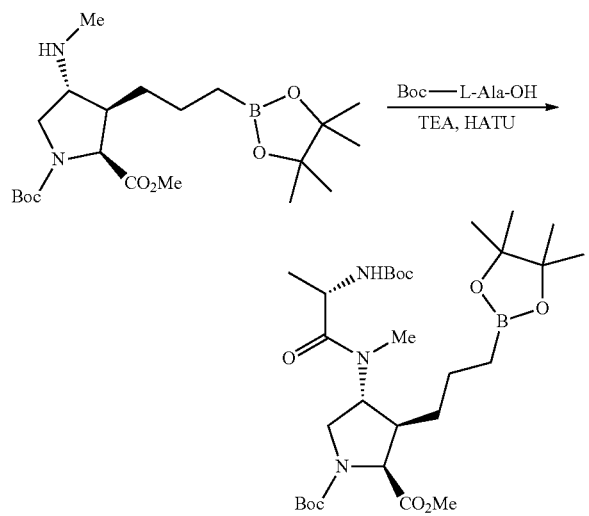

Boc-Ala-OH (0.13 g, 0.68 mmol), triethylamine (79 µL, 0.57 mmol) and HATU (0.28 g, 0.74 mmol) were added sequentially to the stirred solution of 1-(tert-butyl) 2-methyl (2S,3R,4R)-4-(methylamino)-3-(3-(4,4,5,5-tetramethyl-1,3,2-dioxaborolan-2-yl)propyl)pyrrolidine-1,2-dicarboxylate (0.24 g, 0.57 mmol) in DMF (1.9 mL) at room temperature The mixture was stirred at room temperature for 2 h. The reaction mixture was diluted with saturated aqueous NaHCO$_3$, and extracted with EtOAc. The organic layer was separated, washed with brine, dried over MgSO$_4$, and concentrated. The residue was purified by silica gel chromatography (EtOAc in hexanes) to give 1-(tert-butyl) 2-methyl (2S,3R,4R)-4-((S)-2-((tert-butoxycarbonyl)amino)-N-methylpropanamido)-3-(3-(4,4,5,5-tetramethyl-1,3,2-dioxaborolan-2-yl)propyl)pyrrolidine-1,2-dicarboxylate. LC-MS (C$_{29}$H$_{52}$BN$_3$NaO$_9{}^+$)(ES, m/z): 620 [M+Na]$^+$.

Step 2: (2S,3S,4R)-4-((S)-2-amino-N-methylpropanamido)-3-(3-boronopropyl)pyrrolidine-2-carboxylic acid

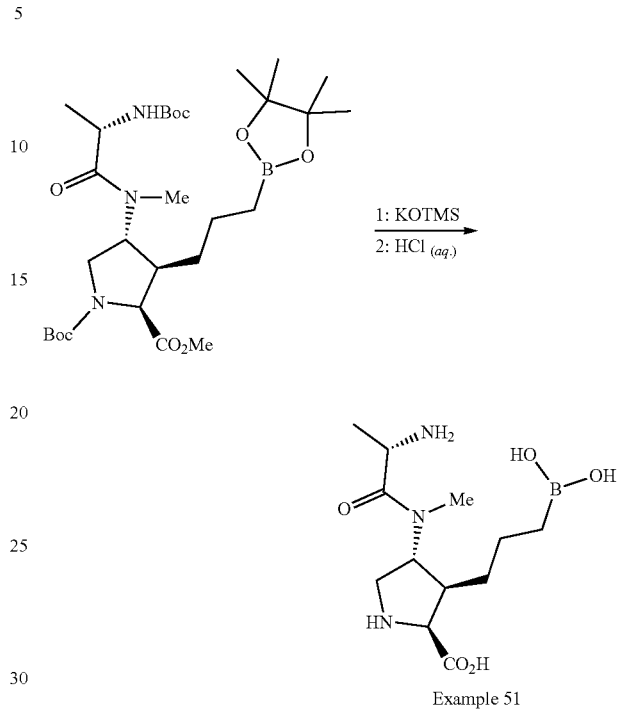

Example 51

KOTMS (0.12 g, 0.82 mmol) was added to the stirred solution of 1-(tert-butyl) 2-methyl (2S,3R,4R)-4-((S)-2-((tert-butoxycarbonyl)amino)-N-methylpropanamido)-3-(3-(4,4,5,5-tetramethyl-1,3,2-dioxaborolan-2-yl)propyl)pyrrolidine-1,2-dicarboxylate (0.24 g, 0.41 mmol) in THF (2.0 mL) at room temperature The mixture was stirred at room temperature for 14 h, then diluted with H$_2$O and extracted with Et$_2$O. The aqueous layer was separated and acidified with 1N HCl in water (1.0 mL, 1.0 mmol), then extracted with EtOAc. The combined organic layer was washed with brine, dried over MgSO$_4$, and concentrated. The crude residue was taken up in 6 N HCl in water (0.80 mL, 4.8 mmol), and the mixture was stirred at 60° C. for 1.5 h. The mixture was cooled to room temperature, diluted with H$_2$O, and extracted with DCM. The aqueous layer was separated, concentrated and purified by RP-HPLC [C18 column, water (0.2 mM heptafluorobutyric acid/0.1% TFA)-CH$_3$CN] to afford (2S,3S,4R)-4-((S)-2-amino-N-methylpropanamido)-3-(3-boronopropyl)pyrrolidine-2-carboxylic acid as a HFBA salt. LCMS 284 [M-18+H]$^+$. $^1$H NMR (500 MHz, D$_2$O) δ 4.62-4.74 (m, 1H), 4.48 (d, J=7.7 Hz, 1H), 4.36-4.44 (m, 1H), 3.66-3.73 (m, 1H), 3.28-3.34 (m, 1H), 3.02 (d, J=3.6 Hz, 3H), 2.66-2.74 (m, 1H), 1.24-1.50 (m, 7H), 0.78-0.65 (m, 2H).

Example 52: (2S,3S)-2-(3-boronopropyl)morpholine-3-carboxylic acid

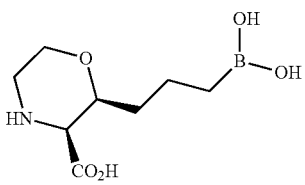 [SMILES: O=C(O)[C@H]1NCCO[C@H]1CCCB(O)O]

Step 1: (2S,3S)-methyl 3-(benzyloxy)-2-(4-methylphenylsulfonamido)hex-5-enoate

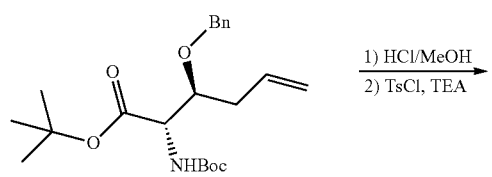

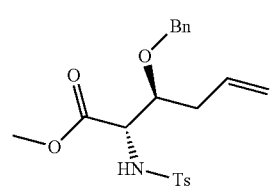

A mixture of (2S,3S)-tert-butyl 3-(benzyloxy)-2-((tert-butoxycarbonyl)amino)hex-5-enoate (1.0 g, 2.6 mmol) and 4 N HCl in MeOH (5.0 mL, 20 mmol) in DCM (10 mL) was stirred at 0° C. for 1 h, then allowed to warm to 29° C. and stirred for 14 h. SOCl$_2$ (1.0 mL, 14 mmol) was added, and the resulting mixture was stirred for 24 h. The reaction mixture was concentrated, and the crude residue was dissolved in DCM (10 mL) and then treated with Ts-Cl (4-Toluenesulfonyl chloride) (0.97 g, 5.1 mmol) and triethylamine (1.1 mL, 7.7 mmol) at 0° C. The mixture was allowed to warm to 29° C. and stirred for 73 h under N$_2$. The mixture was concentrated, and the residue was purified by silica gel column chromatography (EtOAc in hexanes) to give (2S,3S)-methyl 3-(benzyloxy)-2-(4-methylphenylsulfonamido)hex-5-enoate. LCMS (C$_{21}$H$_{26}$NO$_5$S$^+$)(ES, m/z): 404 [M+H]$^+$.

Step 2: (2S,3S)-methyl 3-(benzyloxy)-2-(4-methylphenylsulfonamido)-6-((3aS,4S,6S)-3a,5,5-trimethylhexahydro-4,6-methanobenzo[d][1,3,2]dioxaborol-2-yl)hexanoate

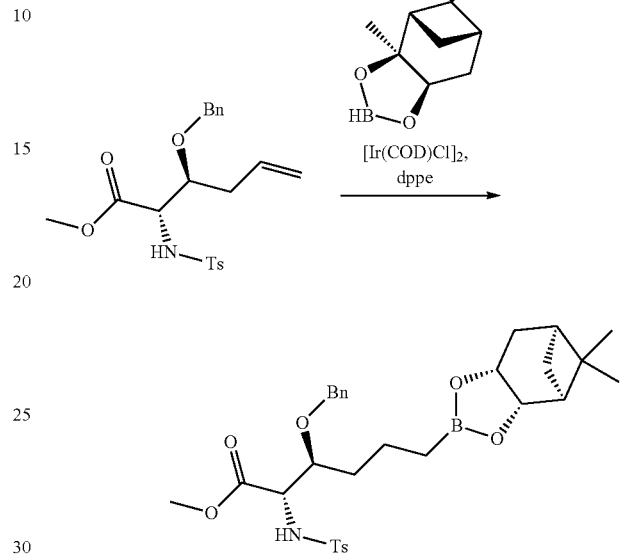

A solution of (3aS,4S,6S)-3a,5,5-trimethylhexahydro-4,6-methanobenzo[d][1,3,2]-dioxaborole (0.34 g, 1.9 mmol) and (2S,3S)-methyl 3-(benzyloxy)-2-(4-methylphenylsulfonamido)hex-5-enoate (0.30 g, 0.74 mmol) in DCM (2.0 mL) was added to the stirred solution of 1,2-bis(diphenylphosphino)ethane (50 mg, 0.13 mmol) and [Ir(cod)Cl]$_2$ (50 mg, 0.074 mmol) in DCM (5.0 mL) at 26° C. under N$_2$. The reaction mixture was stirred at 26° C. for 15 h, then quenched with water and extracted with DCM. The combined organic phase was washed with brine, dried over anhydrous Na$_2$SO$_4$, filtered and concentrated. The residue was purified by RP-HPLC [C18 column, water (0.1% TFA)-CH$_3$CN] to give (2S,3S)-methyl 3-(benzyloxy)-2-(4-methylphenylsulfonamido)-6-((3aS,4S,6S)-3a,5,5-trimethylhexahydro-4,6-methanobenzo[d][1,3,2]dioxaborol-2-yl)hexanoate. LCMS (C$_{31}$H$_{43}$BNO$_7$S$^+$)(ES, m/z): 584 [M+H]$^+$.

Step 3: (2S,3S)-methyl 4-tosyl-2-(3-((3aS,4S,6S,7aR)-3a,5,5-trimethylhexahydro-4,6-methanobenzo[d][1,3,2]dioxaborol-2-yl)propyl)morpholine-3-carboxylate -continued

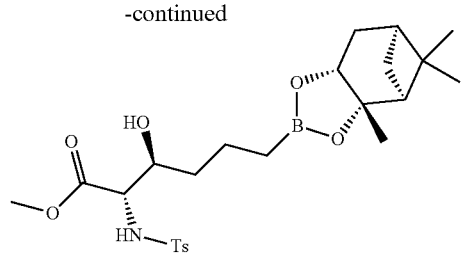

10% Pd—C (0.50 g, 0.47 mmol) was added to the stirred solution of (2S,3S)-methyl 3-(benzyloxy)-2-(4-methylphenylsulfonamido)-6-((3aS,4S,6S)-3a,5,5-trimethylhexahydro-4,6-methanobenzo[d][1,3,2]dioxaborol-2-yl)hexanoate (0.28 g, 0.48 mmol) in MeOH (15 mL) under Ar. The mixture was degassed and backfilled with $H_2$ (three times), and stirred under $H_2$ (Pressure: 15 psi) at 33° C. for 1 h. The reaction mixture was filtered and concentrated to give (2S,3S)-methyl 3-hydroxy-2-(4-methylphenylsulfonamido)-6-((3aS,4S,6S)-3a,5,5-trimethylhexahydro-4,6-methanobenzo[d][1,3,2]dioxaborol-2-yl)hexanoate, which was used in the next step directly without further purification. LCMS ($C_{24}H_{37}BNO_7S^+$)(ES, m/z): 494 $[M+H]^+$.

Step 4: (2S,3S)-methyl 4-tosyl-2-(3-((3aS,4S,6S,7aR)-3a,5,5-trimethylhexahydro-4,6-methanobenzo[d][1,3,2]dioxaborol-2-yl)propyl)morpholine-3-carboxylate

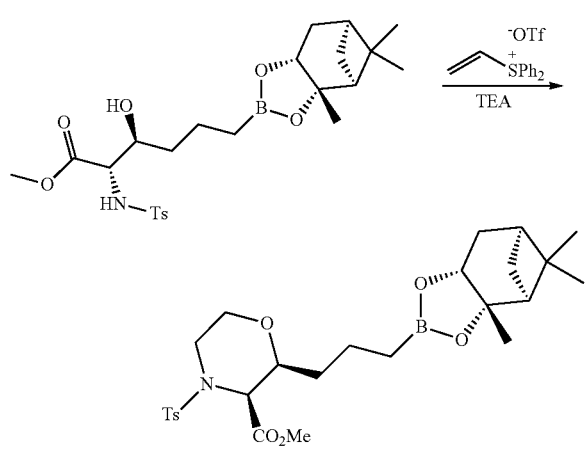

Triethylamine (0.13 mL, 0.93 mmol) was added to a solution of (2S,3S)-methyl 3-hydroxy-2-(4-methylphenylsulfonamido)-6-((3aS,4S,6S)-3a,5,5-trimethylhexahydro-4,6-methanobenzo[d][1,3,2]dioxaborol-2-yl)hexanoate (0.15 g, 0.30 mmol) in DCM (4.0 mL) at 0° C. After 10 min, diphenylvinylsulfonium triflate (0.13 g, 0.37 mmol) in DCM (1.0 mL) was added dropwise to the mixture at 0° C. and the resulting mixture was stirred for 12 h at 0° C. The reaction mixture was then quenched with saturated aqueous ammonium chloride solution, extracted with DCM, washed with brine, dried over $MgSO_4$, filtered and concentrated. The residue was purified by RP-HPLC [C18 column, water (0.1% TFA)-$CH_3CN$] to give (2S,3S)-methyl 4-tosyl-2-(3-((3aS,4S,6S,7aR)-3a,5,5-trimethylhexahydro-4,6-methanobenzo[d][1,3,2]dioxaborol-2-yl)propyl)morpholine-3-carboxylate. LCMS ($C_{26}H_{39}BNO_7S^+$)(ES, m/z): 520 $[M+H]^+$.

Step 5: (2S,3S)-2-(3-boronopropyl)morpholine-3-carboxylic acid

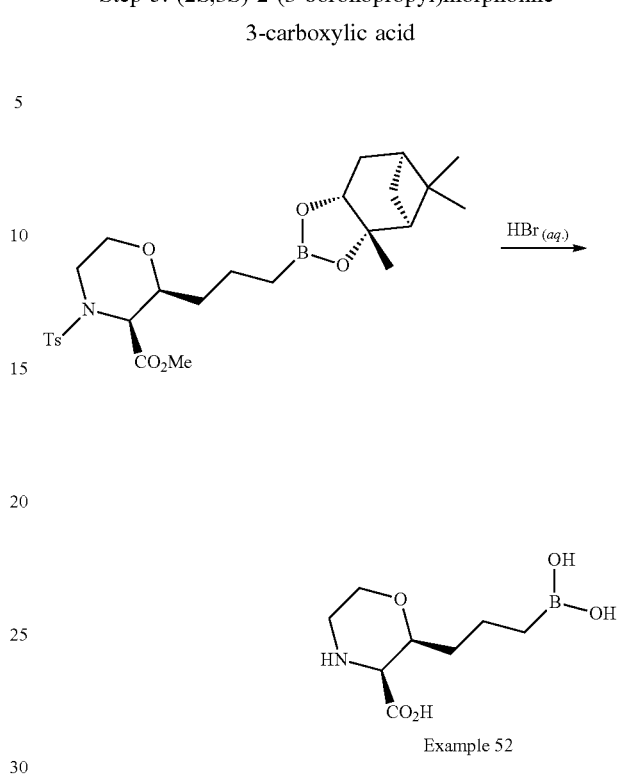

Example 52

A mixture of (2S,3S)-methyl 4-tosyl-2-(3-((3aS,4S,6S,7aR)-3a,5,5-trimethylhexahydro-4,6-methanobenzo[d][1,3,2]dioxaborol-2-yl)propyl)morpholine-3-carboxylate (0.10 g, 0.19 mmol) and 48% HBr in water (5.0 mL, 0.19 mmol) was stirred at 130° C. for 2 h, and concentrated. The residue was purified by RP-HPLC [C18 column, water (20 mM HFBA and 0.1% TFA)-$CH_3CN$] to give (2S,3S)-2-(3-boronopropyl)morpholine-3-carboxylic acid as a HFBA salt. LCMS ($C_8H_{15}BNO_4^+$) (ES, m/z): 200 $[M+H—H_2O]^+$. $^1H$ NMR (400 MHz, $D_2O$) δ 4.21-4.16 (m, 1H), 4.14-4.07 (m, 1H), 3.97-3.92 (m, 1H), 3.82-3.76 (m, 1H), 3.54-3.49 (m, 1H), 3.21-3.16 (m, 1H), 1.88-1.74 (m, 1H), 1.58-1.32 (m, 3H), 0.84-0.65 (m, 2H).

Example 53: (2S,3R)-3-(3-boronopropyl)-2-(2-hydroxyethyl)pyrrolidine-2-carboxylic acid

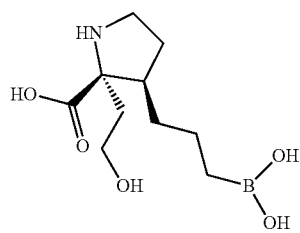 [SMILES: O=C(O)[C@@]1(CCO)NCC[C@H]1CCCB(O)O]

Step 1 2-(2-hydroxyethyl)-3-(3-(4,4,5,5-tetramethyl-1,3,2-dioxaborolan-2-yl)propyl)pyrrolidine-1,2-dicarboxylate

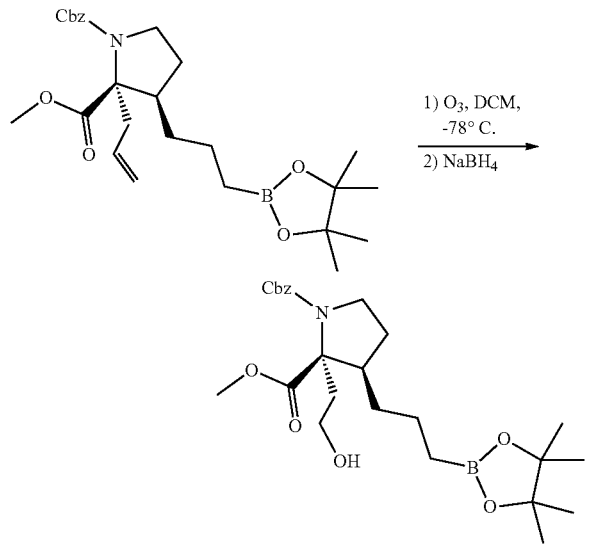

A solution of (2S,3R)-1-benzyl 2-methyl 2-allyl-3-(3-(4,4,5,5-tetramethyl-1,3,2-dioxaborolan-2-yl)propyl)pyrrolidine-1,2-dicarboxylate (0.30 g, 0.64 mmol) in DCM (20 mL) was bubbled with a stream of O₃ at −78° C. till the reaction mixture changed to a blue solution, then the solution was bubbled with a stream of O₂ for 5 min, followed by addition of MeOH (2.0 mL) and NaBH₄ (30 mg, 0.79 mmol) at 25° C. The reaction mixture was stirred at 25° C. for 3 h, followed by addition of a second portion of NaBH₄ (30 mg, 0.79 mmol) and the resulting mixture was stirred at 25° C. for 17 h. The reaction mixture was quenched with saturated aqueous NH₄Cl and extracted with DCM. The combined organic phase was washed with brine, dried over anhydrous Na₂SO₄, filtered and concentrated. The residue was purified by RP-HPLC [C18 column, water (0.1% TFA)-CH₃CN] to give (2S,3R)-1-benzyl 2-methyl 2-(2-hydroxyethyl)-3-(3-(4,4,5,5-tetramethyl-1,3,2-dioxaborolan-2-yl)propyl)pyrrolidine-1,2-dicarboxylate which contained minor corresponding boronic acid. LCMS (C₂₅H₃₉BNO₇⁺)(ES, m/z): 476 [M+H]⁺.

Step 2 (2S,3R)-3-(3-boronopropyl)-2-(2-hydroxyethyl)pyrrolidine-2-carboxylic acid

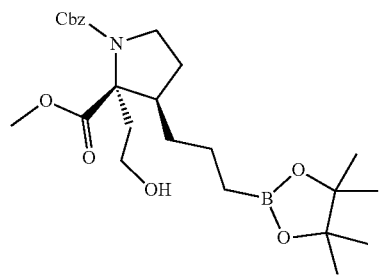

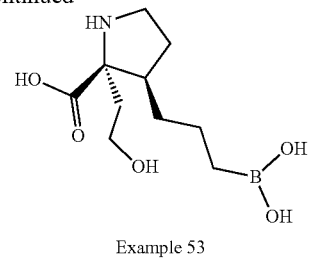

Example 53

Boron tribromide (0.12 mL, 1.3 mmol) was added to the stirred solution of (2S,3R)-1-benzyl 2-methyl 2-(2-hydroxyethyl)-3-(3-(4,4,5,5-tetramethyl-1,3,2-dioxaborolan-2-yl)propyl)pyrrolidine-1,2-dicarboxylate (30 mg, 0.063 mmol) in DCM (3.0 mL) at −78° C. under N₂, and the mixture was stirred at 25° C. for 18 h. The reaction mixture was quenched with water, filtered and washed with DCM. The aqueous phase was concentrated and the residue was purified by RP-HPLC [C18 column, water (0.2 mM HFBA+0.1% TFA)-CH₃CN] to give (2S,3R)-3-(3-boronopropyl)-2-(2-hydroxyethyl)pyrrolidine-2-carboxylic acid as a HFBA salt. LCMS (C₁₀H₁₉BNO₄⁺)(ES, m/z): 228 [M+H—H₂O]⁺. ¹H NMR (400 MHz, D₂O) δ 4.62-4.54 (m, 1H), 4.53-4.45 (m, 1H), 3.73-3.56 (m, 1H), 3.52-3.37 (m, 1H), 2.96-2.79 (m, 1H), 2.67-2.65 (m, 1H), 2.58-2.47 (m, 1H), 2.38-2.36 (m, 1H), 2.03-1.85 (m, 1H), 1.63-1.46 (m, 2H), 1.38 (br s, 1H), 1.31-1.14 (m, 1H), 0.92-0.65 (m, 2H).

Example 54: (2S,3R)-3-(3-boronopropyl)-2-(2-(dimethylamino)ethyl)pyrrolidine-2-carboxylic acid

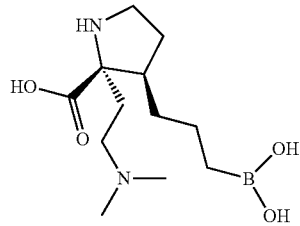 [SMILES: CN(C)CC[C@]1(C(=O)O)NCC[C@H]1CCCB(O)O]

Step 1: (2S,3R)-1-benzyl 2-methyl 2-(2-oxoethyl)-3-(3-(4,4,5,5-tetramethyl-1,3,2-dioxaborolan-2-yl)propyl)pyrrolidine-1,2-dicarboxylate

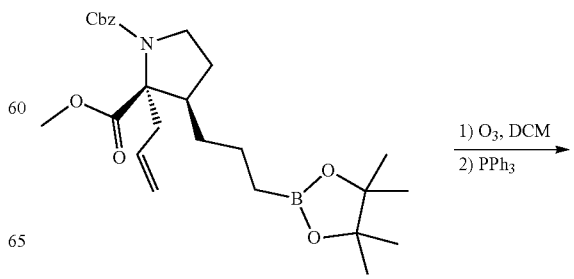

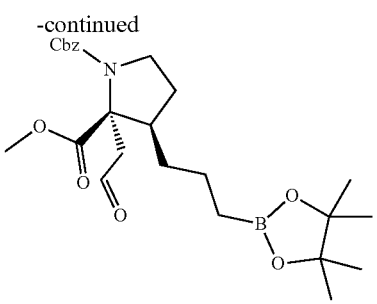

A mixture of (2S,3R)-1-benzyl 2-methyl 2-allyl-3-(3-(4,4,5,5-tetramethyl-1,3,2-dioxaborolan-2-yl)propyl)pyrrolidine-1,2-dicarboxylate (0.55 g, 1.2 mmol) in DCM (50 mL) was bubbled with a stream of $O_3$ at −78° C. for 15 min to give a blue solution and then bubbled with a stream of $O_2$ for 5 min to give a colorless solution. Triphenylphosphine (0.61 g, 2.3 mmol) was added at 25° C., and the resulting mixture was stirred for 3 h at 25° C. The reaction mixture was quenched with water and extracted with EtOAc. The combined organic phase was washed with brine, dried over anhydrous $Na_2SO_4$, filtered and concentrated. The residue was purified by silica gel column chromatography (EtOAc in hexanes) to give (2S,3R)-1-benzyl 2-methyl 2-(2-oxoethyl)-3-(3-(4,4,5,5-tetramethyl-1,3,2-dioxaborolan-2-yl)propyl)pyrrolidine-1,2-dicarboxylate. LCMS $(C_{25}H_{37}BNO_7^+)$(ES, m/z): 474 [M+H]$^+$.

Step 2: (2S,3R)-1-benzyl 2-methyl 2-(2-(dimethylamino)ethyl)-3-(3-(4,4,5,5-tetramethyl-1,3,2-dioxaborolan-2-yl)propyl)pyrrolidine-1,2-dicarboxylate

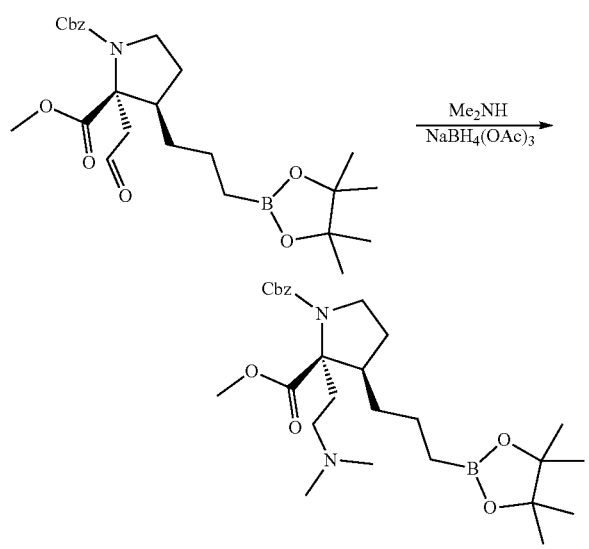

NaBH(OAc)$_3$ (134 mg, 0.634 mmol) was added to the stirred mixture of (2S,3R)-1-benzyl 2-methyl 2-(2-oxoethyl)-3-(3-(4,4,5,5-tetramethyl-1,3,2-dioxaborolan-2-yl)propyl)pyrrolidine-1,2-dicarboxylate (0.10 g, 0.21 mmol) and dimethylamine (40% in water, 0.48 g, 4.2 mmol) in THF (20 mL) at 25° C. under $N_2$. The resulting mixture was stirred for 10 h at 25° C., then quenched with saturated aqueous $Na_2CO_3$ and extracted with EtOAc. The combined organic phase was washed with brine, dried over anhydrous $Na_2SO_4$, filtered and concentrated. The residue was purified by RP-HPLC [C18 column, water (0.1% TFA)-$CH_3CN$] to give (2S,3R)-1-benzyl 2-methyl 2-(2-(dimethylamino)ethyl)-3-(3-(4,4,5,5-tetramethyl-1,3,2-dioxaborolan-2-yl)propyl)pyrrolidine-1,2-dicarboxylate, which contained minor corresponding boronic acid. LCMS $(C_{21}H_{34}BN_2O_6^+)$ (ES, m/z): 421 [M+H—$C_6H_{10}$]$^+$.

Step 3: (2S,3R)-3-(3-boronopropyl)-2-(2-(dimethylamino)ethyl)pyrrolidine-2-carboxylic acid

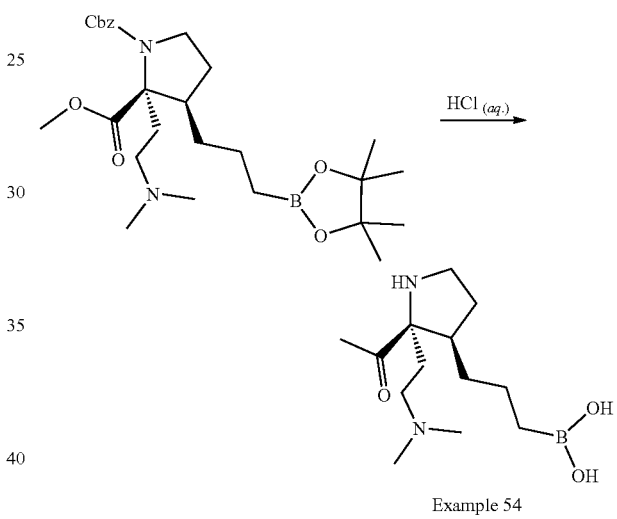

Example 54

A mixture of (2S,3R)-1-benzyl 2-methyl 2-(2-(dimethylamino)ethyl)-3-(3-(4,4,5,5-tetramethyl-1,3,2-dioxaborolan-2-yl)propyl)pyrrolidine-1,2-dicarboxylate (70 mg, 0.14 mmol) in 12 N HCl in water (6.0 mL, 72 mmol) was stirred at 120° C. for 96 h. The reaction mixture was filtered and concentrated. The residue was purified by RP-HPLC [C18 column, water (20 mM HFBA and 0.1% TFA)-$CH_3CN$] to give (2S,3R)-3-(3-boronopropyl)-2-(2-(dimethylamino)ethyl)pyrrolidine-2-carboxylic acid as a HFBA salt. LCMS $(C_2H_{24}BN_2O_3^+)$(ES, m/z): 255 [M+H—$H_2O$]$^+$. $^1$H NMR (400 MHz, $D_2O$) δ 3.63-3.50 (m, 1H), 3.42-3.09 (m, 3H), 2.85 (s, 6H), 2.63-2.51 (m, 1H), 2.36-2.12 (m, 3H), 1.75-1.62 (m, 1H), 1.60-1.38 (m, 2H), 1.37-1.24 (m, 1H), 1.22-1.07 (m, 1H), 0.82-0.63 (m, 2H).

Example 55 and Example 56 were made from (2S,3R)-1-benzyl 2-methyl 2-(2-oxoethyl)-3-(3-(4,4,5,5-tetramethyl-1,3,2-dioxaborolan-2-yl)propyl)pyrrolidine-1,2-dicarboxylate using the same procedure as Example 54.

| Ex. | Structure | MS, H NMR |
|---|---|---|
| 55 | 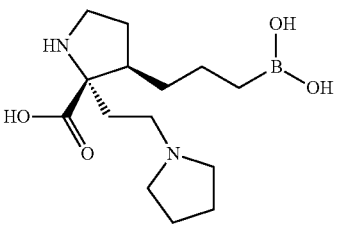 [SMILES: O=C(O)[C@@]1(CCN2CCCC2)NCC[C@H]1CCCB(O)O] | LCMS (C$_{14}$H$_{26}$BN$_2$O$_3$$^+$) (ES, m/z): 281 [M + H − H$_2$O]$^+$. $^1$H NMR (400 MHz, D$_2$O) δ 3.61-3.40 (m, 3H), 3.30-3.06 (m, 3H), 3.03-2.85 (m, 2H), 2.51-2.34 (m, 1H), 2.25-1.94 (m, 5H), 1.92-1.77 (m, 2H), 1.64-1.31 (m, 3H), 1.28-1.15 (m, 1H), 1.12-0.95 (m, 1H), 0.75-0.55 (m, 2H). |
| 56 | 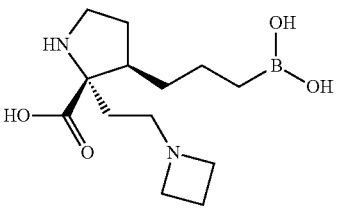 [SMILES: O=C(O)[C@@]1(CCN2CCC2)NCC[C@H]1CCCB(O)O] | LCMS (C$_{13}$H$_{24}$BN$_2$O$_3$$^+$) (ES, m/z): 267 [M + H − H$_2$O]$^+$. $^1$H NMR (400 MHz, D$_2$O) δ 4.29-4.07 (m, 2H), 4.03-3.85 (m, 2H), 3.54-3.40 (m, 1H), 3.34-3.10 (m, 3H), 2.54-2.39 (m, 1H), 2.35-2.16 (m, 3H), 2.14-1.97 (m, 1H), 1.96-1.83 (m, 1H), 1.64-1.52 (m, 1H), 1.51-1.31 (m, 2H), 1.28-1.18 (m, 1H), 1.16-1.00 (m, 1H), 0.74-0.56 (m, 2H). |

Example 57A: 2-(aminomethyl)-3-(3-boronopropyl)pyrrolidine-2-carboxylic acid

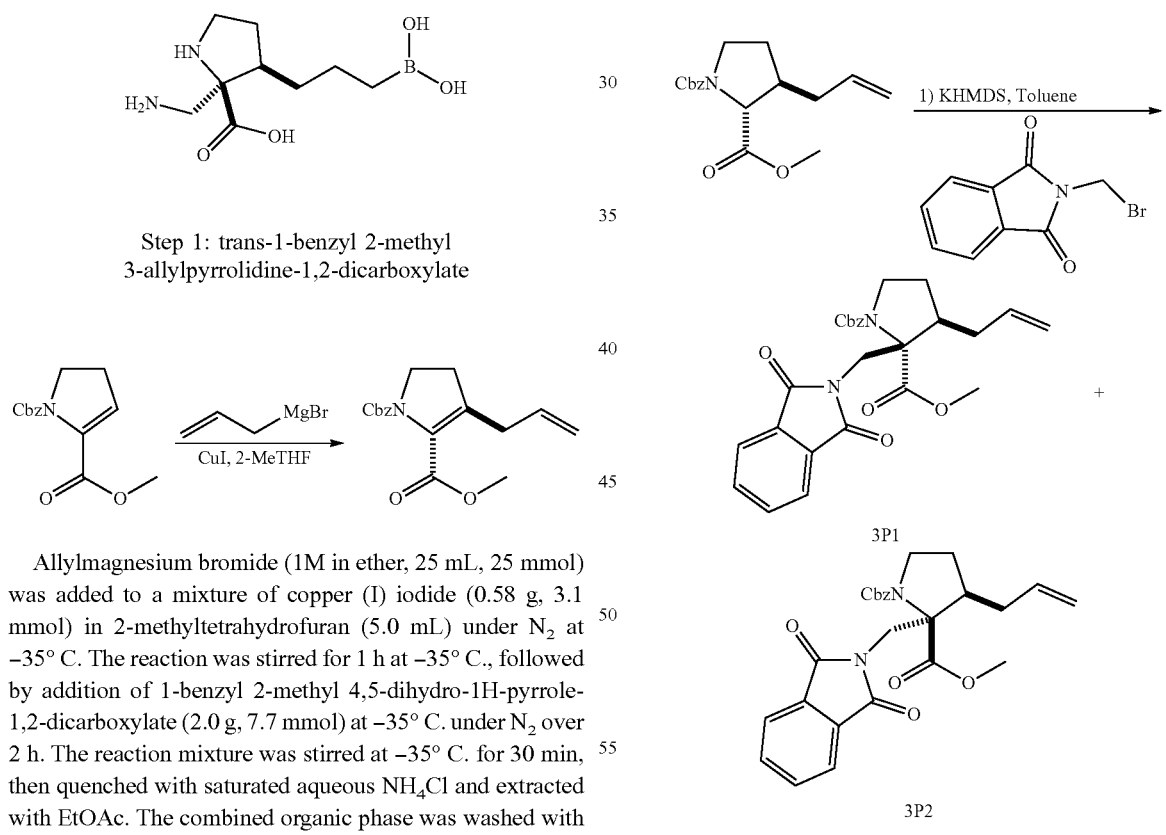

Step 1: trans-1-benzyl 2-methyl 3-allylpyrrolidine-1,2-dicarboxylate

Allylmagnesium bromide (1M in ether, 25 mL, 25 mmol) was added to a mixture of copper (I) iodide (0.58 g, 3.1 mmol) in 2-methyltetrahydrofuran (5.0 mL) under N$_2$ at −35° C. The reaction was stirred for 1 h at −35° C., followed by addition of 1-benzyl 2-methyl 4,5-dihydro-1H-pyrrole-1,2-dicarboxylate (2.0 g, 7.7 mmol) at −35° C. under N$_2$ over 2 h. The reaction mixture was stirred at −35° C. for 30 min, then quenched with saturated aqueous NH$_4$Cl and extracted with EtOAc. The combined organic phase was washed with brine, dried over anhydrous Na$_2$SO$_4$, filtered and concentrated. The residue was purified by silica gel column chromatography (EtOAc in hexanes) to give trans-1-benzyl 2-methyl 3-allylpyrrolidine-1,2-dicarboxylate. LCMS (C$_{17}$H$_{22}$NO$_4$$^+$)(ES, m/z): 304 [M+H]$^+$. $^1$H NMR (400 MHz, CDCl$_3$) δ 7.38-7.33 (m, 5H), 5.86-5.68 (m, 1H), 5.22-4.98 (m, 4H), 4.10-4.01 (m, 1H), 3.76-3.54 (m, 4H), 2.40-2.23 (m, 2H), 2.20-2.00 (m, 2H), 1.73-1.61 (m, 2H).

Step 2: ((2R,3R)-1-benzyl 2-methyl 3-allyl-2-((1,3-dioxoisoindolin-2-yl)methyl)pyrrolidine-1,2-dicarboxylate KHMDS (0.5 M in toluene, 15 mL, 7.4 mmol) was added to the stirred solution of trans-1-benzyl 2-methyl 3-allylpyrrolidine-1,2-dicarboxylate (1.5 g, 4.9 mmol) in toluene (20 mL) at −35° C. over 5 min under N$_2$. The reaction mixture was stirred for 40 min at −35° C., then allowed to warm to room temperature over 15 min. 2-(Bromomethyl)isoindoline-1,3-dione (1.5 g, 6.4 mmol) in THF (10 mL) was added at −35° C., and the resulting mixture was stirred for another 1 h at −35° C., then at 15° C. for 12 h. The reaction mixture was quenched with saturated aqueous NH$_4$Cl and extracted with EtOAc. The combined organic phase was washed with brine, dried over anhydrous Na$_2$SO$_4$, filtered and concentrated. The residue was purified by silica gel column chromatography (EtOAc in hexanes) to give crude product as a mixture of isomers, which was then purified by RP-HPLC [C18 column, water (0.1% TFA)-CH$_3$CN] to give trans-1-benzyl 2-methyl 3-allyl-2-((1,3-dioxoisoindolin-2-yl)methyl)pyrrolidine-1,2-dicarboxylate (3-P1) as the first eluted peak, and cis-1-benzyl 2-methyl 3-allyl-2-((1,3-dioxoisoindolin-2-yl)methyl)pyrrolidine-1,2-dicarboxylate (3-P2) as the second eluted peak. The stereochemistry was assigned by 2D NMR. 3-P1: LCMS (C$_{26}$H$_{27}$N$_2$O$_6^+$)(ES, m/z): 463 [M+H]$^+$. $^1$H NMR (400 MHz, chloroform-d) δ 7.83-7.79 (m, 1H), 7.76 (dd, J=3.0, 5.26 Hz, 1H), 7.73-7.70 (m, 1H), 7.67 (dd, J=3.0, 5.70 Hz, 1H), 7.33-7.18 (m, 5H), 5.82-5.61 (m, 1H), 5.22-4.98 (m, 2H), 4.94-4.45 (m, 2H), 4.37-4.19 (m, 1H) 4.02-3.83 (m, 1H), 3.77 (s, 1.5H), 3.62-3.44 (m, 2H), 3.35 (s, 1.5H), 2.60-2.38 (m, 2H), 2.13-2.07 (m, 2H), 1.92-1.55 (m, 1H). 3-P2: LCMS (C$_{26}$H$_{27}$N$_2$O$_6^+$)(ES, m/z): 463 [M+H]$^+$. $^1$H NMR (400 MHz, chloroform-d) δ 7.91-7.81 (m, 2H), 7.76-7.69 (m, 2H), 7.49-7.24 (m, 5H), 5.83-5.66 (m, 1H), 5.49-5.28 (m, 1H), 5.24-4.94 (m, 3H), 4.77-4.41 (m, 1H), 4.37-4.19 (m, 1H), 3.89-3.77 (m, 1H), 3.76-3.42 (m, 3H), 3.03-3.01 (m, 1H), 2.67-2.48 (m, 1H), 2.28-2.06 (m, 1H), 1.82-1.58 (m, 3H).

Step 3: 1-benzyl 2-methyl 3-allyl-2-((1,3-dioxoisoindolin-2-yl)methyl)pyrrolidine-1,2-dicarboxylate The cis isomer (3-P2) as a racemic mixture was resolved by SFC [Column: DAICEL CHIRALPAK AS (250 mm*50 mm, 10 μm), Mobile phase: A: CO$_2$, B: EtOH (0.1% NH$_3$.H$_2$O), Gradient: 25% of B in 4.5 min, and hold 25% of B for 1 min, Flow Rate (mL/min) 60, Column temperature: 40° C.] to give cis-1-benzyl 2-methyl 3-allyl-2-((1,3-dioxoisoindolin-2-yl)methyl)pyrrolidine-1,2-dicarboxylate (4-P1, t$_r$=2.433 min) as the first eluting peak, and cis-1-benzyl 2-methyl 3-allyl-2-((1,3-dioxoisoindolin-2-yl)methyl)pyrrolidine-1,2-dicarboxylate (4-P2, t$_r$=2.733 min) as the second eluting peak. 4-P1: LCMS (C$_{26}$H$_{27}$N$_2$O$_6^+$)(ES, m/z): 463 [M+H]$^+$; 4-P2: LCMS (C$_{26}$H$_{27}$N$_2$O$_6^+$)(ES, m/z): 463 [M+H]$^+$.

Step 4: 1-benzyl 2-methyl 2-((1,3-dioxoisoindolin-2-yl)methyl)-3-(3-(4,4,5,5-tetramethyl-1,3,2-dioxaborolan-2-yl)propyl)pyrrolidine-1,2-dicarboxylate

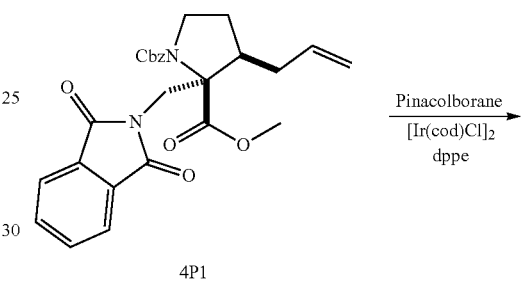

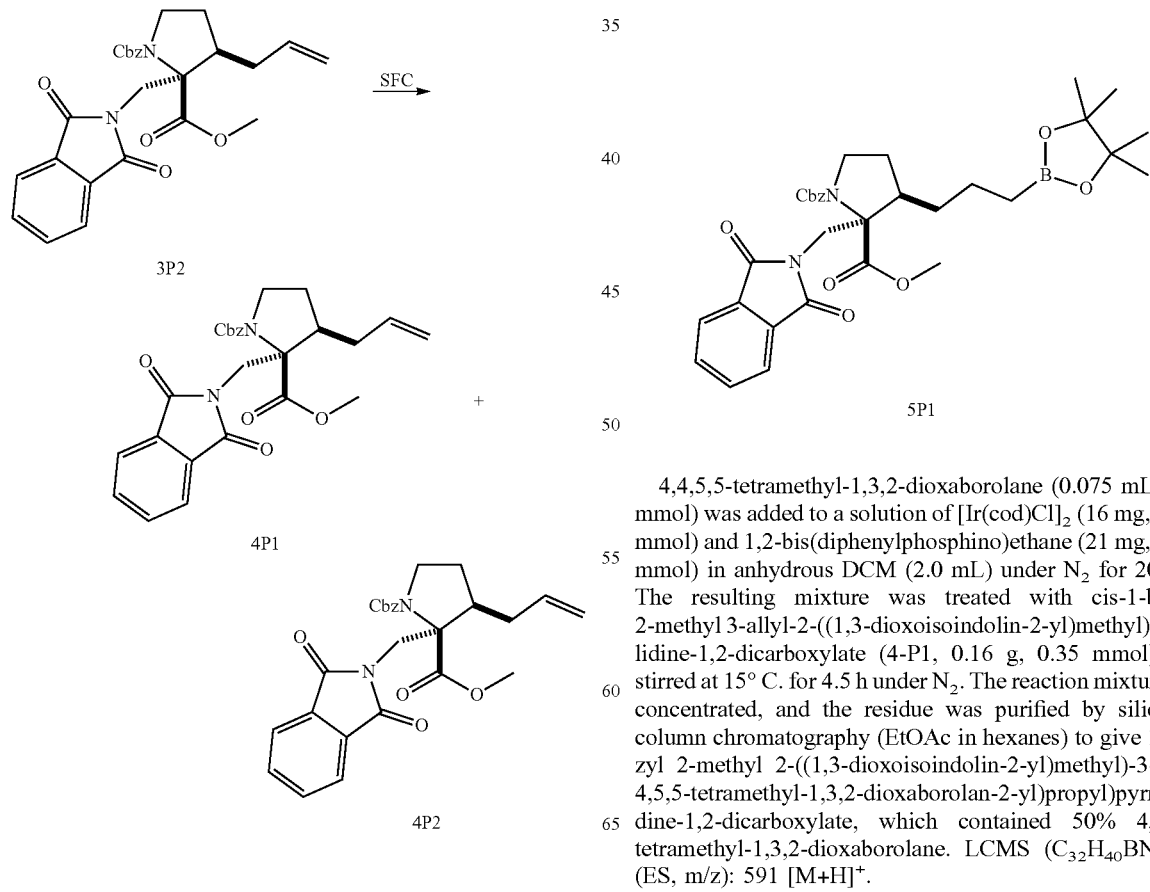

4,4,5,5-tetramethyl-1,3,2-dioxaborolane (0.075 mL, 0.52 mmol) was added to a solution of [Ir(cod)Cl]$_2$ (16 mg, 0.024 mmol) and 1,2-bis(diphenylphosphino)ethane (21 mg, 0.052 mmol) in anhydrous DCM (2.0 mL) under N$_2$ for 20 min. The resulting mixture was treated with cis-1-benzyl 2-methyl 3-allyl-2-((1,3-dioxoisoindolin-2-yl)methyl)pyrrolidine-1,2-dicarboxylate (4-P1, 0.16 g, 0.35 mmol), and stirred at 15° C. for 4.5 h under N$_2$. The reaction mixture was concentrated, and the residue was purified by silica gel column chromatography (EtOAc in hexanes) to give 1-benzyl 2-methyl 2-((1,3-dioxoisoindolin-2-yl)methyl)-3-(3-(4,4,5,5-tetramethyl-1,3,2-dioxaborolan-2-yl)propyl)pyrrolidine-1,2-dicarboxylate, which contained 50% 4,4,5,5-tetramethyl-1,3,2-dioxaborolane. LCMS (C$_{32}$H$_{40}$BN$_2$O$_8^+$)(ES, m/z): 591 [M+H]$^+$.

Step 5: 1-benzyl 2-methyl 2-(aminomethyl)-3-(3-(4,4,5,5-tetramethyl-1,3,2-dioxaborolan-2-yl)propyl)pyrrolidine-1,2-dicarboxylate

Step 7: 3-(3-boronopropyl)-2-(hydroxymethyl)pyrrolidine-2-carboxylic acid

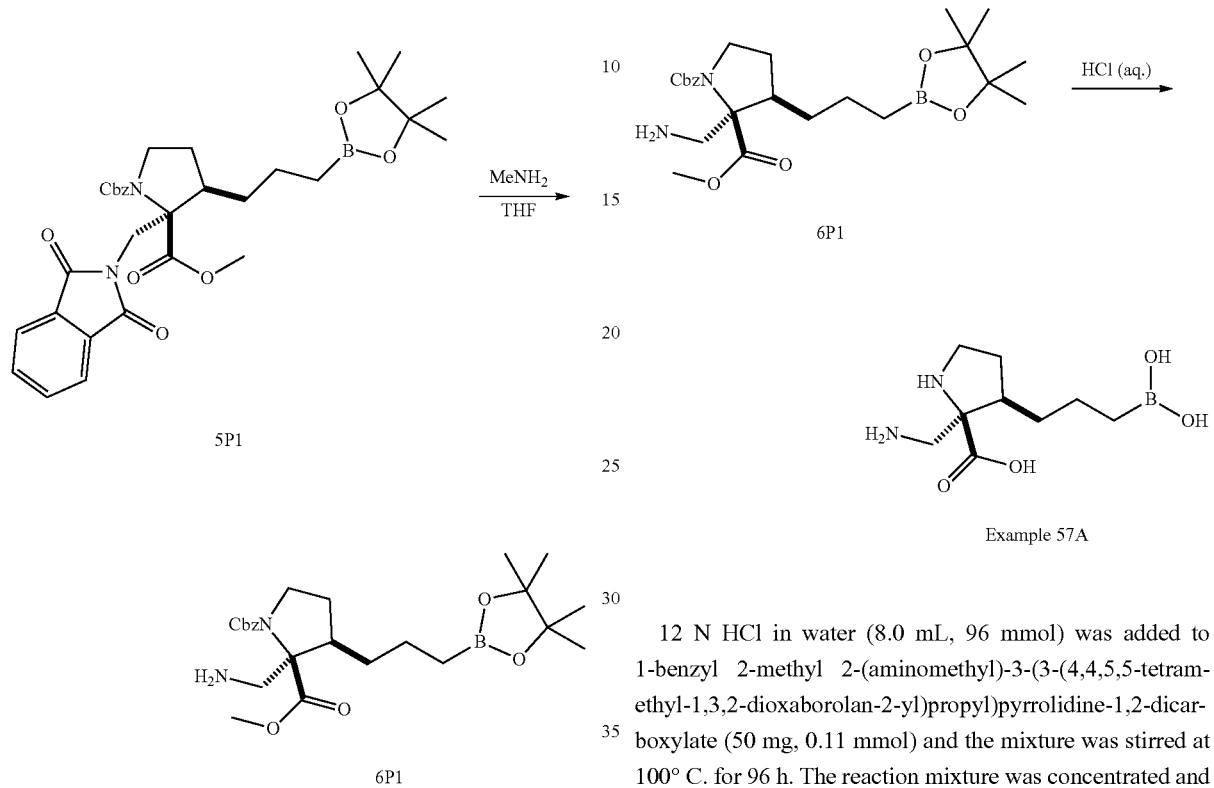

5P1

6P1

6P1

Example 57A

A mixture of 1-benzyl 2-methyl 2-((1,3-dioxoisoindolin-2-yl)methyl)-3-(3-(4,4,5,5-tetramethyl-1,3,2-dioxaborolan-2-yl)propyl)pyrrolidine-1,2-dicarboxylate (0.25 g, 0.42 mmol) and methylamine (2 M in THF, 0.64 mL, 1.3 mmol) was degassed and backfilled with $N_2$, and the mixture was stirred at 60° C. for 96 h. The reaction mixture was concentrated and the residue was purified by RP-HPLC [C18 column, water (0.1% TFA)-$CH_3CN$] to give benzyl 2-methyl 2-(aminomethyl)-3-(3-(4,4,5,5-tetramethyl-1,3,2-dioxaborolan-2-yl)propyl)pyrrolidine-1,2-dicarboxylate. LCMS ($C_{24}H_3BN_2O_6^+$)(ES, m/z): 461 [M+H]$^+$.

12 N HCl in water (8.0 mL, 96 mmol) was added to 1-benzyl 2-methyl 2-(aminomethyl)-3-(3-(4,4,5,5-tetramethyl-1,3,2-dioxaborolan-2-yl)propyl)pyrrolidine-1,2-dicarboxylate (50 mg, 0.11 mmol) and the mixture was stirred at 100° C. for 96 h. The reaction mixture was concentrated and the residue was purified by RP-HPLC [C18 column, water (20 mM HFBA and 0.1% TFA)-$CH_3CN$] to give 2-(aminomethyl)-3-(3-boronopropyl)pyrrolidine-2-carboxylic acid as a HFBA salt. LCMS ($C_9H_{18}BN_2O_3^+$)(ES, m/z): 213 [M+H—$H_2O$]$^+$; $^1H$ NMR (500 MHz, $D_2O$) δ 3.57-3.47 (m, 1H), 3.46-3.36 (m, 1H), 3.32-3.23 (m, 1H), 3.17 (dt, J=6.6, 11.3 Hz, 1H), 2.22-2.16 (m, 1H), 2.12-2.10 (m, 1H), 1.63-1.61 (m, 1H), 1.48-1.32 (m, 2H), 1.28-1.17 (m, 1H), 1.11-0.99 (m, 1H), 0.73-0.55 (m, 2H).

Example 57B was made from cis-1-benzyl 2-methyl 3-allyl-2-((1,3-dioxoisoindolin-2-yl)methyl)pyrrolidine-1,2-dicarboxylate (4-P2), using the same procedure as Example 57A.

| Ex. | Structure | MS and $^1$HNMR |
|---|---|---|
| 57B | (structure shown) | LCMS ($C_9H_{18}BN_2O_3^+$) (ES, m/z): 213 [M + H − $H_2O$]$^+$. |

Example 58: (2R,3R)-3-(3-boronopropyl)-2-((dimethylamino)methyl)pyrrolidine-2-carboxylic acid

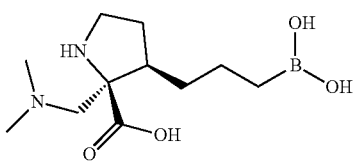 [SMILES: CN(C)C[C@]1(C(=O)O)NCC[C@H]1CCCB(O)O]

Step 1: (2R,3R)-1-benzyl 2-methyl 3-allyl-2-((1,3-dioxoisoindolin-2-yl)methyl)pyrrolidine-1,2-dicarboxylate

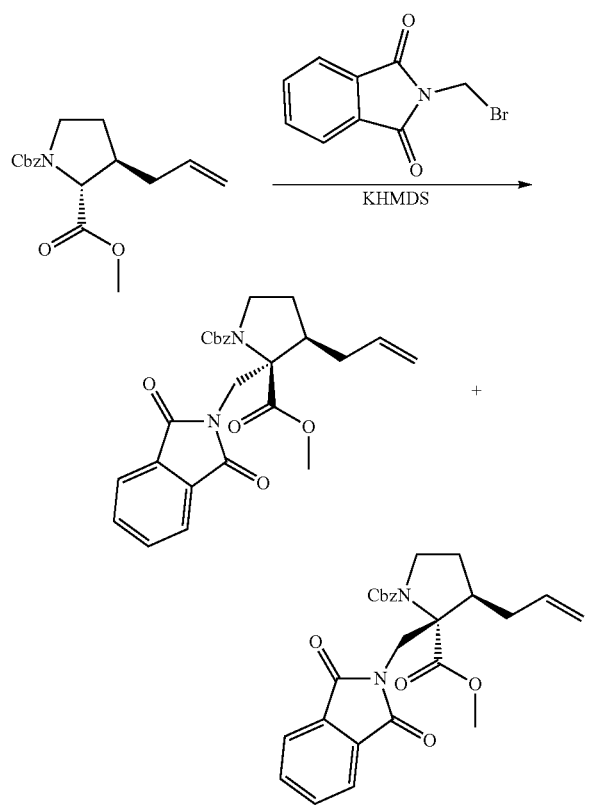

KHMDS (0.5 M in toluene, 13 mL, 6.7 mmol) was added to a solution of (2R,3R)-1-benzyl 2-methyl 3-allylpyrrolidine-1,2-dicarboxylate (1.4 g, 4.5 mmol) in toluene (20 mL) at −35° C. over 5 min. The resulting mixture was stirred for 40 min at −35° C., then allowed to warm to room temperature over 15 min. 2-(Bromomethyl)isoindoline-1,3-dione (1.4 g, 5.8 mmol) in THF (5.0 mL) was added to the mixture at −78° C., and the reaction mixture was stirred for 1 h at −35° C., then quenched with saturated aqueous NH$_4$Cl and extracted with EtOAc. The combined organic phase was washed with brine, dried over anhydrous Na$_2$SO$_4$, filtered and concentrated. The residue was purified by RP-HPLC [C18 column, water (0.1% TFA)-CH$_3$CN] to give (2S,3R)-1-benzyl 2-methyl 3-allyl-2-((1,3-dioxoisoindolin-2-yl)methyl)pyrrolidine-1,2-dicarboxylate and (2R,3R)-1-benzyl 2-methyl 3-allyl-2-((1,3-dioxoisoindolin-2-yl)methyl)pyrrolidine-1,2-dicarboxylate. The stereochemistry was assigned by 2D NMR. 2: LCMS (C$_{26}$H$_{27}$N$_2$O$_6$$^+$)(ES, m/z): 463 [M+H]$^+$. $^1$H NMR (400 MHz, CDCl$_3$) δ 7.91-7.81 (m, 2H), 7.76-7.69 (m, 2H), 7.49-7.24 (m, 5H), 5.83-5.66 (m, 1H), 5.49-5.28 (m, 1H), 5.24-5.18 (m, 1H), 5.14-5.01 (m, 1H), 5.10-4.94 (m, 1H), 4.77-4.41 (m, 1H), 4.37-4.19 (m, 1H), 3.89-3.77 (m, 1H), 3.73 (s, 1.3H), 3.37 (s, 1.7H), 2.93-2.90 (m, 1H), 2.67-2.48 (m, 1H), 2.28-2.06 (m, 1H), 1.82-1.79 (m, 1H), 1.70-1.58 (m, 2H).

Step 2: (2R,3R)-1-benzyl 2-methyl 3-allyl-2-(aminomethyl)pyrrolidine-1,2-dicarboxylate

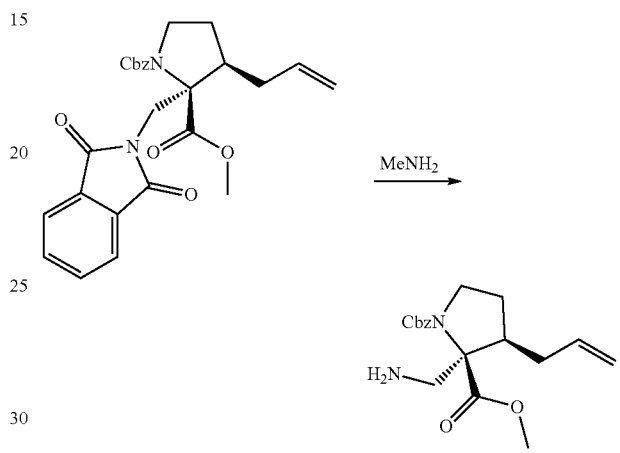

Methylamine (2 M in THF, 6.5 mL, 13 mmol) was added to (2R,3R)-1-benzyl 2-methyl 3-allyl-2-((1,3-dioxoisoindolin-2-yl)methyl)pyrrolidine-1,2-dicarboxylate (0.60 g, 1.3 mmol), and the resulting mixture was stirred at 40° C. for 72 h. The reaction mixture was concentrated to give crude (2R,3R)-1-benzyl 2-methyl 3-allyl-2-(aminomethyl)pyrrolidine-1,2-dicarboxylate, which was used in the next step without further purification. LCMS (C$_{18}$H$_{25}$N$_2$O$_4$$^+$)(ES, m/z): 333 [M+H]$^+$.

Step 3: (2R,3R)-1-benzyl 2-methyl 3-allyl-2-((dimethylamino)methyl)pyrrolidine-1,2-dicarboxylate

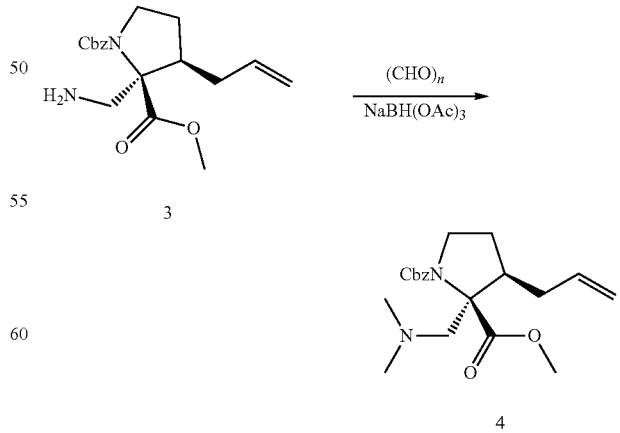

Paraformaldehyde (80 mg, 0.45 mmol) was added to the stirred mixture of (2R,3R)-1-benzyl 2-methyl 3-allyl-2-

(aminomethyl)pyrrolidine-1,2-dicarboxylate (0.15 mg, 0.45 mmol) and sodium triacetoxyborohydride (0.29 mg, 1.4 mmol) in DCE (10 mL) under $N_2$. The resulting mixture was bubbled with a stream of $N_2$ for 3 min and stirred at 80° C. for 12 h, then quenched with saturated aqueous $NaHCO_3$ and extracted with EtOAc. The combined organic phase was dried over anhydrous $Na_2SO_4$, filtered and concentrated. The residue was purified by RP-HPLC [C18 column, water (0.1% TFA)-$CH_3CN$] to give (2R,3R)-1-benzyl 2-methyl 3-allyl-2-((dimethylamino)methyl)pyrrolidine-1,2-dicarboxylate. LCMS ($C_{20}H_{29}N_2O_4^+$)(ES, m/z): 361 [M+H]$^+$.

Step 4: (2R,3R)-1-benzyl 2-methyl 2-((dimethylamino)methyl)-3-(3-(4,4,5,5-tetramethyl-1,3,2-dioxaborolan-2-yl)propyl)pyrrolidine-1,2-dicarboxylate

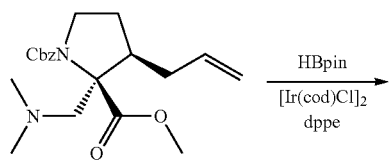

4,4,5,5-tetramethyl-1,3,2-dioxaborolane (0.048 mL, 0.33 mmol) was added to the stirred solution of [Ir(cod)Cl]$_2$ (7.8 mg, 0.012 mmol) and 1,2-bis(diphenylphosphino)ethane (10 mg, 0.025 mmol) in $CH_2Cl_2$ (2.0 mL) under $N_2$ and the mixture was stirred at 20° C. for 20 min. The reaction mixture was treated with (2R,3R)-1-benzyl 2-methyl 3-allyl-2-((dimethylamino)methyl)pyrrolidine-1,2-dicarboxylate (60 mg, 0.17 mmol) and stirred at 20° C. for 5 h under $N_2$, and concentrated. The residue was purified by RP-HPLC [C18 column, water (0.1% TFA)-$CH_3CN$] to afford (2R,3R)-1-benzyl 2-methyl 2-((dimethylamino)methyl)-3-(3-(4,4,5,5-tetramethyl-1,3,2-dioxaborolan-2-yl)propyl)pyrrolidine-1,2-dicarboxylate. LCMS ($C_{26}H_{42}BN_2O_6^+$)(ES, m/z): 489 [M+H]$^+$.

Step 5: (2R,3R)-3-(3-boronopropyl)-2-((dimethylamino)methyl)pyrrolidine-2-carboxylic acid

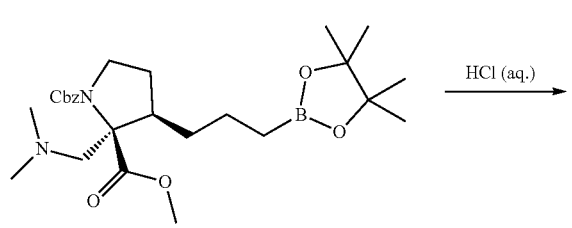

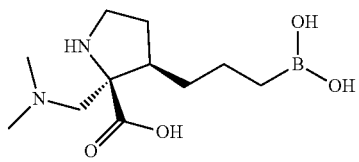

Example 58

A mixture of (2R,3R)-1-benzyl 2-methyl 2-((dimethylamino)methyl)-3-(3-(4,4,5,5-tetramethyl-1,3,2-dioxaborolan-2-yl)propyl)pyrrolidine-1,2-dicarboxylate (35 mg, 0.072 mmol) in 12 N HCl in water (3.0 mL, 36 mmol) was stirred at 110° C. for 108 h. The reaction mixture was concentrated, and the residue was purified by RP-HPLC [C18 column, water (20 mM HFBA and 0.1% TFA)-$CH_3CN$] to give (2R,3R)-3-(3-boronopropyl)-2-((dimethylamino)methyl)pyrrolidine-2-carboxylic acid. LCMS ($C_{11}H_{23}BN_2O_3^+$)(ES, m/z): 241 [M+H—H$_2$O]$^+$; $^1$H NMR (400 MHz, D$_2$O) δ 3.70 (d, J=14.9 Hz, 1H), 3.51 (br t, J=9.7 Hz, 1H), 3.37 (d, J=14.9 Hz, 1H), 3.24-3.22 (m, 1H), 2.79 (s, 6H), 2.21-1.97 (m, 2H), 1.58-1.55 (m, 1H), 1.46-1.26 (m, 2H), 1.19-1.18 (m, 1H), 1.08-0.94 (m, 1H), 0.69-0.50 (m, 2H).

Example 59A: (2R,3R)-3-(3-boronopropyl)-2-(hydroxymethyl)pyrrolidine-2-carboxylic acid

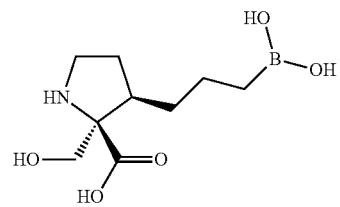 [SMILES: O=C(O)[C@@]1(CO)NCC[C@H]1CCCB(O)O]

Step 1: (2R,3R)-1-tert-butyl 2-methyl 3-allyl-2-((benzyloxy)methyl)pyrrolidine-1,2-dicarboxylate and (2S,3R)-1-tert-butyl 2-methyl 3-allyl-2-((benzyloxy)methyl)pyrrolidine-1,2-dicarboxylate

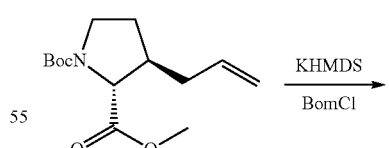

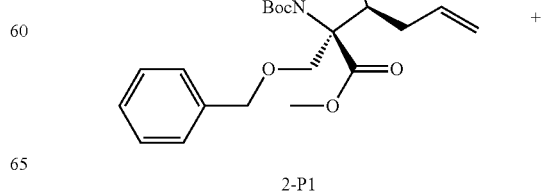

2-P1

229
-continued

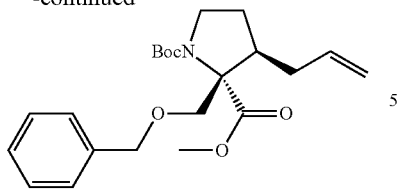

2-P2

KHMDS (0.5 M in toluene, 4.5 mL, 2.2 mmol) was added to the stirred solution of (2R,3R)-1-tert-butyl 2-methyl 3-allylpyrrolidine-1,2-dicarboxylate (0.40 g, 1.5 mmol) in Toluene (10 mL) at −35° C. over 5 min. The reaction mixture was stirred for 0.5 h at −35° C., then allowed to warm to room temperature over 15 min, followed by addition of ((chloromethoxy)methyl)benzene (0.27 mL, 1.9 mmol) at −35° C. The resulting mixture was stirred for another 0.5 h at −35° C., then quenched with saturated aqueous NH$_4$Cl and extracted with EtOAc. The combined organic phase was washed with brine, dried over anhydrous Na$_2$SO$_4$, filtered and concentrated. The residue was purified by RP-HPLC [C18 column, water (0.1% TFA)-CH$_3$CN] to give (2R,3R)-1-tert-butyl 2-methyl 3-allyl-2-((benzyloxy)methyl)pyrrolidine-1,2-dicarboxylate (2-P1) as the first eluting peak, and (2S,3R)-1-tert-butyl 2-methyl 3-allyl-2-((benzyloxy)methyl)pyrrolidine-1,2-dicarboxylate (2-P2) as the second eluting peak. The stereochemistry was assigned by 2D NMR. 2-P1: LCMS (C$_{22}$H$_{32}$NO$_5^+$)(ES, m/z): 390 [M+H]$^+$; H NMR (400 MHz, CDCl$_3$) δ 7.40-7.24 (m, 5H), 5.78-5.58 (m, 1H), 5.09-4.92 (m, 2H), 4.65-4.43 (m, 2H), 4.34-3.94 (m, 1H), 3.90-3.71 (m, 2H), 3.67 (s, 3H), 3.27 (tt, J=5.2, 10.8 Hz, 1H), 2.69 (dq, J=6.1, 11.3 Hz, 1H), 2.33-2.14 (m, 1H), 1.90 (qd, J=6.4, 12.3 Hz, 1H), 1.75-1.53 (m, 2H), 1.47-1.32 (m, 9H); 2-P2: LCMS (C$_{22}$H$_{32}$NO$_5^+$)(ES, m/z): 390 [M+H]; $^1$H NMR (400 MHz, CDCl$_3$) δ 7.38-7.27 (m, 5H), 5.80-5.63 (m, 1H), 5.11-4.93 (m, 2H), 4.58-4.40 (m, 2H), 4.19-3.93 (m, 2H), 3.91-3.83 (m, 1H), 3.69 (s, 3H), 3.54-3.37 (m, 1H), 2.46-2.26 (m, 2H), 2.25-2.14 (m, 1H), 2.01-1.86 (m, 2H), 1.40-1.33 (m, 9H).

Step 2: (2R,3R)-3-allyl-2-((benzyloxy)methyl)-1-(tert-butoxycarbonyl)pyrrolidine-2-carboxylic acid

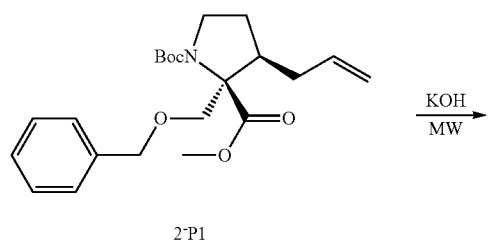

2-P1

230
-continued

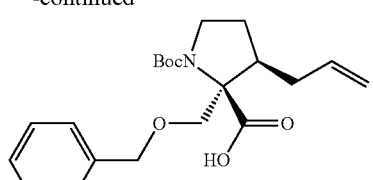

3-P1

A mixture of (2R,3R)-1-tert-butyl 2-methyl 3-allyl-2-((benzyloxy)methyl)pyrrolidine-1,2-dicarboxylate (80 mg, 0.21 mmol) and KOH (115 mg, 2.1 mmol) in ethanediol (2.0 mL) was heated in a microwave reactor with stirring at 140° C. for 1.5 h. The mixture was purified by RP-HPLC [C18 column, water (0.1% TFA)-CH$_3$CN] to give (2R,3R)-3-allyl-2-((benzyloxy)methyl)-1-(tert-butoxycarbonyl)pyrrolidine-2-carboxylic acid. LCMS (C$_{21}$H$_{30}$NO$_5^+$)(ES, m/z): 376 [M+H]$^+$.

Step 3: (2R,3R)-2-((benzyloxy)methyl)-1-(tert-butoxycarbonyl)-3-(3-(4,4,5,5-tetramethyl-1,3,2-dioxaborolan-2-yl)propyl)pyrrolidine-2-carboxylic acid

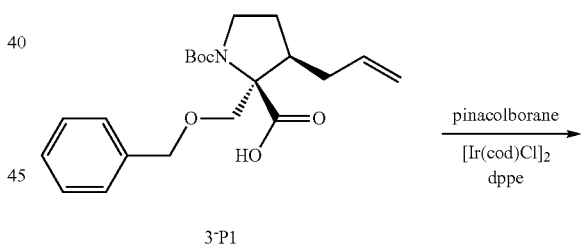

3-P1

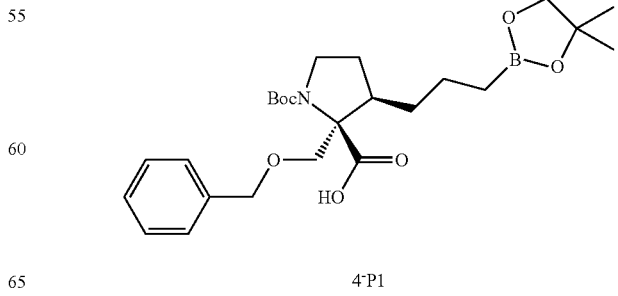

4-P1

4,4,5,5-tetramethyl-1,3,2-dioxaborolane (0.035 mL, 0.24 mmol) was added to the stirred solution of [Ir(cod)Cl]$_2$ (7.5 mg, 0.011 mmol) and 1,2-bis(diphenylphosphino)ethane (9.6 mg, 0.024 mmol) in CH$_2$Cl$_2$ (2.0 mL) under N$_2$ for 20 min. The resulting mixture was treated with (2R,3R)-3-allyl-2-((benzyloxy)methyl)-1-(tert-butoxycarbonyl)pyrrolidine-2-carboxylic acid (60 mg, 0.16 mmol), then stirred at 30° C. for 12 h. The reaction mixture was concentrated and the residue was purified by RP-HPLC [C18 column, water (0.1% TFA)-CH$_3$CN] to give (2R,3R)-2-((benzyloxy)methyl)-1-(tert-butoxycarbonyl)-3-(3-(4,4,5,5-tetramethyl-1,3,2-dioxaborolan-2-yl)propyl)pyrrolidine-2-carboxylic acid. LCMS (C$_{27}$H$_{43}$BNO$_7^+$)(ES, m/z): 504 [M+H]$^+$.

Step 4: (2R,3R)-3-(3-boronopropyl)-2-(hydroxymethyl)pyrrolidine-2-carboxylic acid

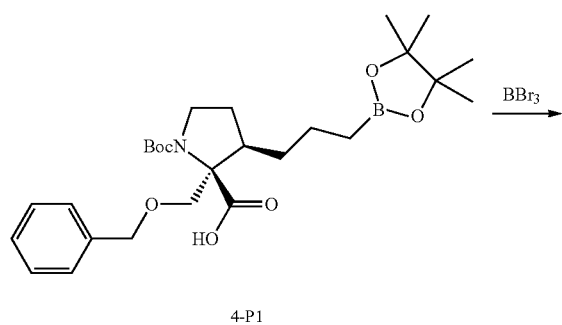

4-P1

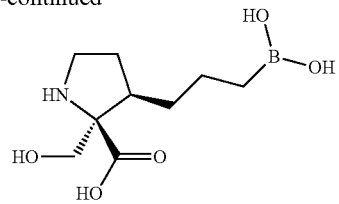

Example 59A

Boron tribromide (0.10 mL, 1.0 mmol) was added to a mixture of (2R,3R)-2-((benzyloxy)methyl)-1-(tert-butoxycarbonyl)-3-(3-(4,4,5,5-tetramethyl-1,3,2-dioxaborolan-2-yl)propyl)pyrrolidine-2-carboxylic acid (20 mg, 0.040 mmol) in DCM (2.0 mL) at −78° C. under N$_2$.

The mixture was then stirred at 15° C. for 1 h, then bubbled with N$_2$ and concentrated. The residue was diluted with water and purified by RP-HPLC [C18 column, water (20 mM HFBA and 0.1% TFA)-CH$_3$CN] to (2R,3R)-3-(3-boronopropyl)-2-(hydroxymethyl)pyrrolidine-2-carboxylic acid as a HFBA salt. LCMS (C$_9$H$_{17}$BNO$_4^+$)(ES, m/z): 214 [M+H—H$_2$O]$^+$; $^1$H NMR (400 MHz, D$_2$O) δ 3.96 (d, J=11.8 Hz, 1H), 3.58 (d, J=12.3 Hz, 1H), 3.42-3.41 (m, 1H), 3.18-3.04 (m, 1H), 2.19-2.09 (m, 1H), 2.08-1.99 (m, 1H), 1.68-1.52 (m, 1H), 1.47-1.28 (m, 2H), 1.26-1.14 (m, 1H), 1.11-0.98 (m, 1H), 0.71-0.55 (m, 2H).

Example 59B was made from the intermediate (2S,3R)-1-tert-butyl 2-methyl 3-allyl-2-((benzyloxy)methyl)pyrrolidine-1,2-dicarboxylate (2-P2) using a similar procedure as Example 59A:

| Ex. | Structure | MS and $^1$HNMR |
|---|---|---|
| 59B | 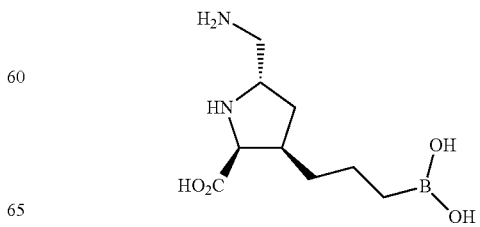 | LCMS (C$_9$H$_{19}$BNO$_5^+$) (ES, m/z): 232 [M + H]$^+$. $^1$H NMR (400 MHz, D$_2$O) δ 4.06-3.92 (m, 1H), 3.64 (d, J = 12.0 Hz, 1H), 3.37-3.27 (m, 1H), 3.25-3.16 (m, 1H), 2.34-2.21 (m, 1H), 2.18-2.07 (m, 1H), 1.72-1.57 (m, 1H), 1.56-1.45 (m, 1H), 1.43-1.29 (m, 1H), 1.27-1.06 (m, 2H), 0.75-0.52 (m, 2H). |

Example 60A: (2S,3R,5S)-5-(aminomethyl)-3-(3-boronopropyl)pyrrolidine-2-carboxylic acid Step 1: 1-benzyl 2-methyl (2S,3R)-5-(((benzyloxy)imino)methyl)-3-(3-(4,4,5,5-tetramethyl-1,3,2-dioxaborolan-2-yl)propyl)pyrrolidine-1,2-dicarboxylate

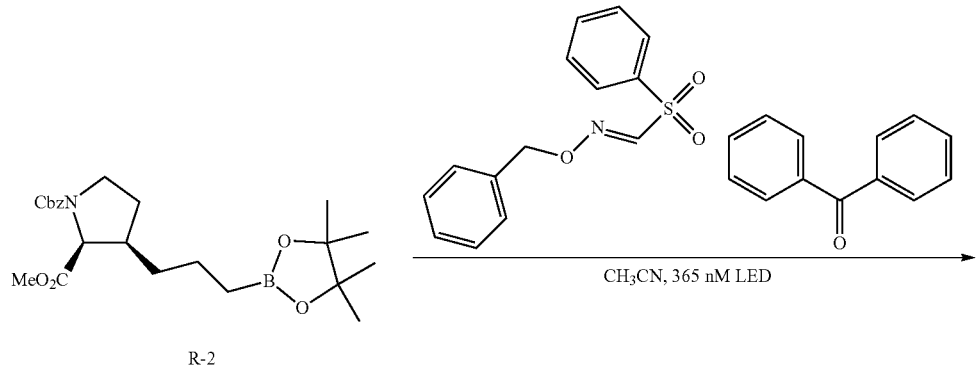

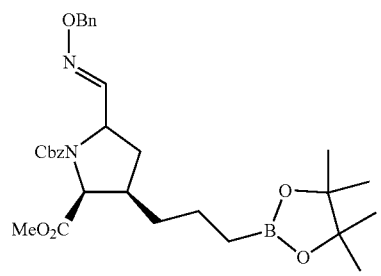

(Phenylsulfonyl)methanal O-benzyl oxime (1.6 g, 5.8 mmol) and benzophenone (0.71 g, 3.9 mmol) were added to a scintillation vial containing 1-benzyl 2-methyl 3-(3-(4,4,5,5-tetramethyl-1,3,2-dioxaborolan-2-yl)propyl)pyrrolidine-1,2-dicarboxylate (1.7 g, 3.9 mmol) under $N_2$, followed by addition of acetonitrile (40 mL). The reaction mixture was stirred under $N_2$ for 5 min, then irradiated at 365 nm for 24 h at 1000 rpm. The resulting mixture was filtered and concentrated, and the residue was purified by silica gel chromatography (EtOAc in hexanes) to afford 1-benzyl 2-methyl (2S,3R)-5-(((benzyloxy)imino)methyl)-3-(3-(4,4,5,5-tetramethyl-1,3,2-dioxaborolan-2-yl)propyl)pyrrolidine-1,2-dicarboxylate. LC-MS $(C_{31}H_{42}BN_2O_7^+)$(ES, m/z): 565 [M+H]$^+$.

Step 2: 1-benzyl 2-methyl (2S,3R)-5-(((benzyloxy)amino)methyl)-3-(3-(4,4,5,5-tetramethyl-1,3,2-dioxaborolan-2-yl)propyl)pyrrolidine-1,2-dicarboxylate

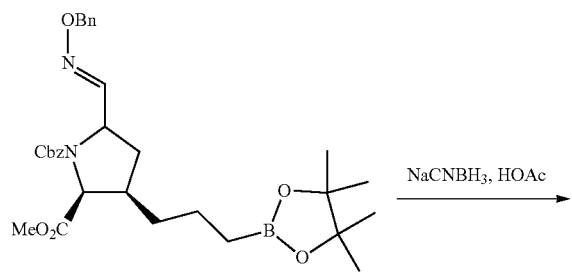

-continued

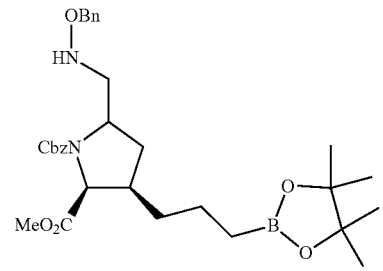

Sodium cyanoborohydride (0.25 g, 4.0 mmol) was added in one portion to the stirred solution of 1-benzyl 2-methyl (2S,3R)-5-(((benzyloxy)imino)methyl)-3-(3-(4,4,5,5-tetramethyl-1,3,2-dioxaborolan-2-yl)propyl)pyrrolidine-1,2-dicarboxylate (0.80 g, 1.0 mmol) in acetic acid (3.5 mL) at room temperature, and the reaction mixture was stirred overnight. The resulting mixture was diluted with EtOAc, quenched with saturated aqueous $Na_2CO_3$ to pH ~7, and extracted with EtOAc. The combined organic phase was dried over $Na_2SO_4$, filtered and concentrated. The residue was purified by silica gel chromatography (EtOAc in hexanes) to afford 1-benzyl 2-methyl (2S,3R)-5-(((benzyloxy)amino)methyl)-3-(3-(4,4,5,5-tetramethyl-1,3,2-dioxaborolan-2-yl)propyl)pyrrolidine-1,2-dicarboxylate. LC-MS $(C_{31}H_{44}BN_2O_7^+)$(ES, m/z): 567 [M+H]$^+$.

Step 3: 1-benzyl 2-methyl (2S,3R)-5-(aminomethyl)-3-(3-(4,4,5,5-tetramethyl-1,3,2-dioxaborolan-2-yl)propyl)pyrrolidine-1,2-dicarboxylate

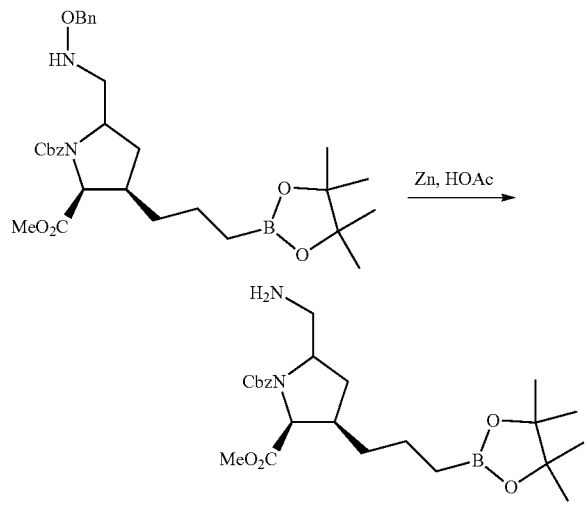

Zinc powder (0.34 g, 5.3 mmol) was added in one portion to the stirred solution of 1-benzyl 2-methyl (2S,3R)-5-(((benzyloxy)amino)methyl)-3-(3-(4,4,5,5-tetramethyl-1,3,2-dioxaborolan-2-yl)propyl)pyrrolidine-1,2-dicarboxylate (0.15 g, 0.26 mmol) in acetic acid (2.6 mL). The resulting slurry was sonicated for 30 s and then stirred at room temperature for 5 h. The reaction mixture was diluted with MeOH, filtered, and the filter cake was rinsed with EtOAc. The combined filtrate was concentrated to yield crude 1-benzyl 2-methyl (2S,3R)-5-(aminomethyl)-3-(3-(4,4,5,5-tetramethyl-1,3,2-dioxaborolan-2-yl)propyl)pyrrolidine-1,2-dicarboxylate, which was used without further purification in the next step. LC-MS ($C_{24}H_{38}BN_2O_6^+$)(ES, m/z): 461 [M+H]$^+$.

Step 4: 1-benzyl 2-methyl (2S,3R)-5-(((tert-butoxycarbonyl)amino)methyl)-3-(3-(4,4,5,5-tetramethyl-1,3,2-dioxaborolan-2-yl)propyl)pyrrolidine-1,2-dicarboxylate

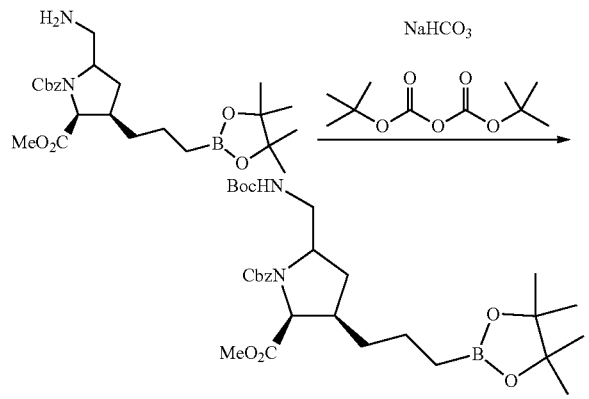

Saturated aqueous NaHCO$_3$ (1.2 mL) was added to the stirred solution of 1-benzyl 2-methyl (2S,3R)-5-(aminomethyl)-3-(3-(4,4,5,5-tetramethyl-1,3,2-dioxaborolan-2-yl)propyl)pyrrolidine-1,2-dicarboxylate (0.12 g, 0.26 mmol) in THF (3.7 mL), followed by di-tert-butyl dicarbonate (0.31 g, 1.4 mmol) in one portion at room temperature The reaction mixture was stirred at room temperature overnight, then concentrated, and extracted with EtOAc. The combined organic phase was dried over Na$_2$SO$_4$. Pinacol (150 mg, 1.3 mmol) was added. The resulting mixture was aged for 30 min at room temperature, filtered and concentrated. The residue was purified by silica gel chromatography (EtOAc in hexanes) to afford 1-benzyl 2-methyl (2S,3R)-5-(((tert-butoxycarbonyl)amino)methyl)-3-(3-(4,4,5,5-tetramethyl-1,3,2-dioxaborolan-2-yl)propyl)pyrrolidine-1,2-dicarboxylate. LC-MS ($C_{29}H_{45}BN_2NaO_8^+$)(ES, m/z): 583 [M+Na]$^+$.

Step 5: (2S,3R,5S)-5-(aminomethyl)-3-(3-boronopropyl)pyrrolidine-2-carboxylic acid

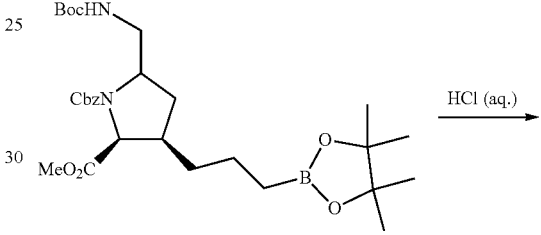

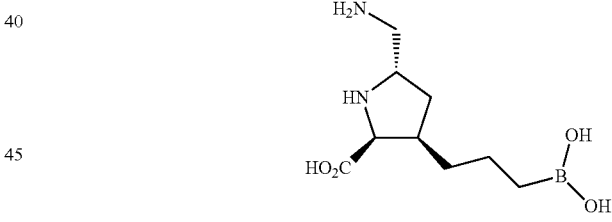

Example 60A

12N HCl (4.0 mL, 48 mmol) was added to the stirred suspension of 1-benzyl 2-methyl (2S,3R)-5-(((tert-butoxycarbonyl)amino)methyl)-3-(3-(4,4,5,5-tetramethyl-1,3,2-dioxaborolan-2-yl)propyl)pyrrolidine-1,2-dicarboxylate (156 mg, 0.26 mmol) in water (4.0 mL) at room temperature, and the reaction mixture was heated to 90° C. with stirring overnight, then cooled to room temperature. The mixture was diluted with water, filtered through a 0.25 m filter and lyophilized to afford (2S,3R,5S)-5-(aminomethyl)-3-(3-boronopropyl)pyrrolidine-2-carboxylic acid as a HCl salt. LCMS ($C_9H_{18}BN_2O_3^+$)(ES, m/z): 213 [M−H$_2$O+H]$^+$. $^1$H NMR (500 MHz, D$_2$O) δ 4.47 (d, J=7.2 Hz, 1H), 4.24 (quintet, J=7.4 Hz, 1H), 3.49 (dd, J=13.7, 7.0 Hz, 1H), 3.38 (dd, J=13.7, 7.0 Hz, 1H), 2.79-2.72 (m, 1H), 2.27 (ddd, J=13.3, 7.5, 5.0 Hz, 1H), 2.09 (dt, J=13.8, 7.2 Hz, 1H), 1.56-1.38 (m, 3H), 1.32-1.23 (m, 1H), 0.87-0.74 (m, 2H).

Step 7: (2S,3R,5S)-5-(aminomethyl)-3-(3-borono-propyl)pyrrolidine-2-carboxylic acid (Free Base)

Example 61: (2S,3R,5S)-3-(3-boronopropyl)-5-((dimethylamino)methyl)pyrrolidine-2-carboxylic acid

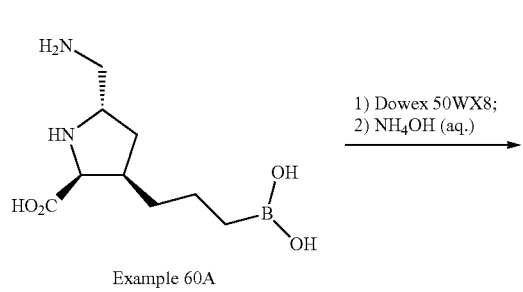

Example 60A

1) Dowex 50WX8;
2) NH₄OH (aq.)

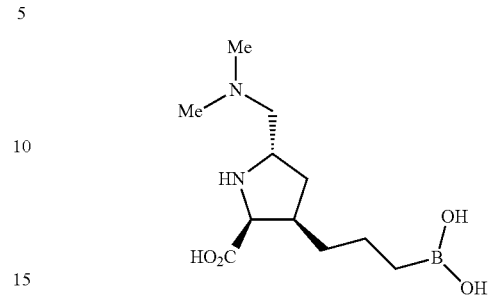

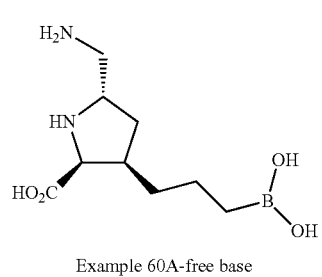

Example 60A-free base (2S,3R,5S)-5-(aminomethyl)-3-(3-boronopropyl)pyrrolidine-2-carboxylic acid (HCl salt, 41 mg, 0.14 mmol) was purified on 2.6 g of Dowex 50WX8 acidic resin (washed with water until pH neutral, then eluted with 2N aqueous ammonium hydroxide) to afford (2S,3R,5S)-5-(aminomethyl)-3-(3-boronopropyl)pyrrolidine-2-carboxylic acid as a free base. LCMS ($C_9H_{18}BN_2O_3^+$)(ES, m/z): 213 [M−H₂+H]⁺. ¹H NMR (500 MHz, D₂O) δ 3.93 (d, J=6.8 Hz, 1H), 3.84 (quintet, J=7.4 Hz, 1H), 3.03 (dd, J=13.3, 6.0 Hz, 1H), 2.98 (dd, J=13.4, 7.8 Hz, 1H), 2.53-2.47 (m, 1H), 2.04 (ddd, J=13.2, 7.3, 4.2 Hz, 1H), 1.80 (dt, J=13.4, 7.3 Hz, 1H), 1.55-1.46 (m, 1H), 1.43-1.32 (m, 2H), 1.22-1.14 (m, 1H), 0.86-0.73 (m, 2H).

Example 60B: (2R,3S,5R)-5-(aminomethyl)-3-(3-boronopropyl)pyrrolidine-2-carboxylic acid

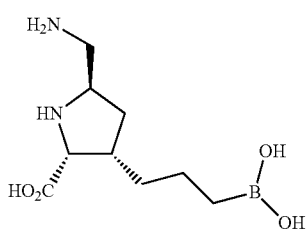

Example 60B was made from 1-benzyl 2-methyl 3-(3-(4,4,5,5-tetramethyl-1,3,2-dioxaborolan-2-yl)propyl)pyrrolidine-1,2-dicarboxylate R-1 using the same procedure as Example 60A. 213 [M−H₂O+H]⁺

Step 1: 1-benzyl 2-methyl (2S,3R)-5-((dimethylamino)methyl)-3-(3-(4,4,5,5-tetramethyl-1,3,2-dioxaborolan-2-yl)propyl)pyrrolidine-1,2-dicarboxylate

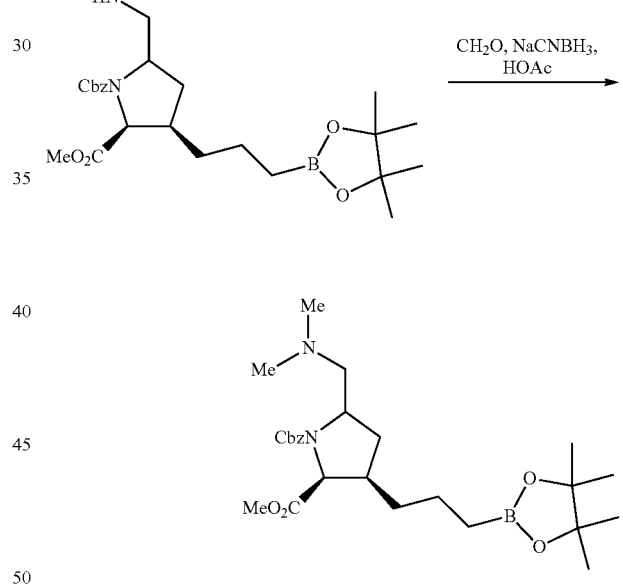

Formaldehyde solution (37 wt % in water, 2.0 mL, 27 mmol) was added in one portion to the stirred solution of 1-benzyl 2-methyl (2S,3R)-5-((methylamino)methyl)-3-(3-(4,4,5,5-tetramethyl-1,3,2-dioxaborolan-2-yl)pyrrolidine-1,2-dicarboxylate (0.13 g, 0.28 mmol) in MeOH (6.0 mL) and acetic acid (1.9 mL, 33 mmol) at room temperature, followed by addition of sodium cyanoborohydride (0.18 g, 2.8 mmol) in one portion at 0° C. The resulting mixture was allowed to warm to room temperature and stirred at 45° C. for 72 h. The reaction mixture was concentrated, and the residue was purified by RP-HPLC [C18 column, water (0.1% TFA)-CH₃CN] to yield 1-benzyl 2-methyl (2S,3R)-5-((dimethylamino)methyl)-3-(3-(4,4,5,5-tetramethyl-1,3,2-dioxaborolan-2-yl)propyl)pyrrolidine-1,2-dicarboxylate as a TFA salt. LC-MS ($C_{26}H_{42}BN_2O_6^+$)(ES, m/z): 489 [M+H]⁺.

Step 2: (2S,3R,5S)-3-(3-boronopropyl)-5-((dimethylamino)methyl)pyrrolidine-2-carboxylic acid

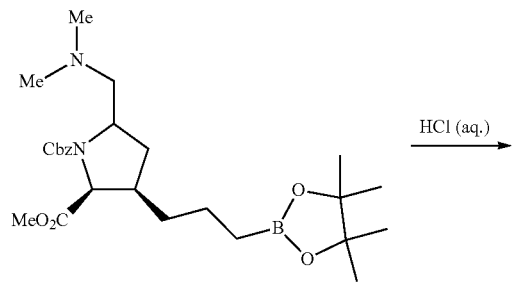

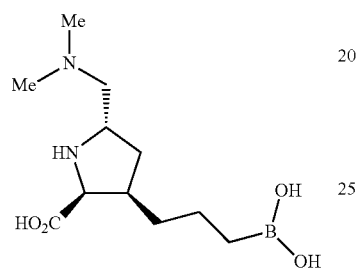

Example 61

12N HCl (1.0 mL, 12 mmol) was added to the stirred suspension of 1-benzyl 2-methyl (2S,3R)-5-((dimethylamino)methyl)-3-(3-(4,4,5,5-tetramethyl-1,3,2-dioxaborolan-2-yl)propyl)pyrrolidine-1,2-dicarboxylate (TFA salt, 14 mg, 0.023 mmol) in water (1.0 mL) at room temperature, and the reaction mixture was heated to 90° C. with stirring overnight, then cooled to room temperature. The mixture was diluted with water, filtered through a 0.25 m filter and lyophilized to afford (2S,3R,5S)-3-(3-boronopropyl)-5-((dimethylamino)methyl)pyrrolidine-2-carboxylic acid as a HCl salt. LCMS ($C_{11}H_{22}BN_2O_3^+$)(ES, m/z): 241 [M−H$_2$O+H]$^+$. $^1$H NMR (500 MHz, D$_2$O) δ 4.42 (d, J=7.0 Hz, 1H), 4.24 (quintet, J=7.2 Hz, 1H), 3.67 (dd, J=14.1, 7.4 Hz, 1H), 3.58 (dd, J=14.1, 5.7 Hz, 1H), 3.02 (s, 6H), 2.76-2.69 (m, 1H), 2.32 (ddd, J=13.4, 7.5, 4.4 Hz, 1H), 2.09 (ddd, J=13.6, 8.4, 7.0 Hz, 1H), 1.58-1.37 (m, 3H), 1.31-1.23 (m, 1H), 0.87-0.74 (m, 2H).

Example 62: (2S,3R,5S)-3-(3-boronopropyl)-5-((methylamino)methyl)pyrrolidine-2-carboxylic acid

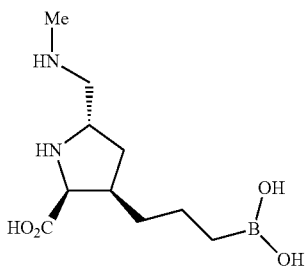 [SMILES: CNC[C@@H]1C[C@@H](CCCB(O)O)[C@@H](C(=O)O)N1]

Step 1: 1-benzyl 2-methyl (2S,3R)-5-(((benzyloxy)amino)methyl)-3-(3-(4,4,5,5-tetramethyl-1,3,2-dioxaborolan-2-yl)propy)pyrrolidine-1,2-dicarboxylate

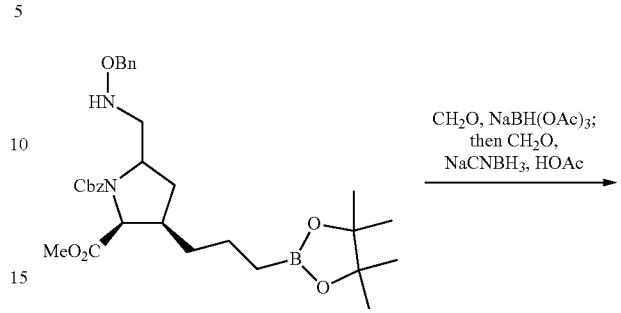

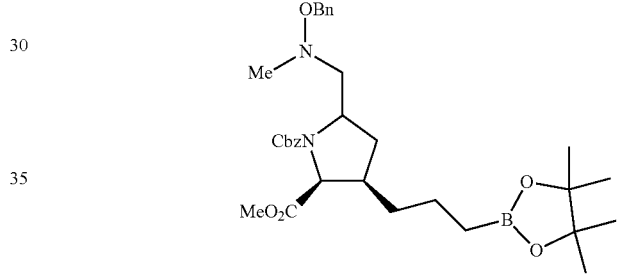

Formaldehyde solution (37 wt % in water, 0.54 mL, 7.3 mmol) was added in one portion to the stirred solution of 1-benzyl 2-methyl (2S,3R)-5-(((benzyloxy)amino)methyl)-3-(3-(4,4,5,5-tetramethyl-1,3,2-dioxaborolan-2-yl)propyl)pyrrolidine-1,2-dicarboxylate (1.0 g, 1.8 mmol) in MeOH (6.3 mL) at room temperature, followed by addition of sodium triacetoxyborohydride (1.2 g, 5.5 mmol) in one portion at 0° C. The resulting mixture was allowed to warm to room temperature and stirred for 2.5 h, then formaldehyde solution (37 wt % in water, 1.1 mL, 15 mmol), sodium cyanoborohydride (0.11 g, 1.8 mmol) and acetic acid (0.54 mL, 9.5 mmol) were added sequentially at room temperature, and the reaction mixture was stirred at 45° C. for 5 h. The reaction mixture was diluted with toluene and concentrated, and the residue was suspended in CH$_3$CN (7.5 mL), followed by addition of pinacol (0.65 g, 5.5 mmol). The resulting mixture was sonicated for 5 min and aged overnight at room temperature, then quenched with saturated aqueous NaHCO$_3$ to pH ~7, and extracted with EtOAc. The combined organic phase was washed with brine, dried over Na$_2$SO$_4$, filtered and concentrated. The residue was purified by silica gel chromatography (EtOAc in hexanes) to afford 1-benzyl 2-methyl (2S,3R)-5-(((benzyloxy)(methyl)amino)methyl)-3-(3-(4,4,5,5-tetramethyl-1,3,2-dioxaborolan-2-yl)propyl)pyrrolidine-1,2-dicarboxylate. LC-MS ($C_{32}H_{46}BN_2O_7^+$) (ES, m/z): 581 [M+H]$^+$.

Step 2: 1-benzyl 2-methyl (2S,3R)-5-(aminomethyl)-3-(3-(4,4,5,5-tetramethyl-1,3,2-dioxaborolan-2-yl)propyl)pyrrolidine-1,2-dicarboxylate

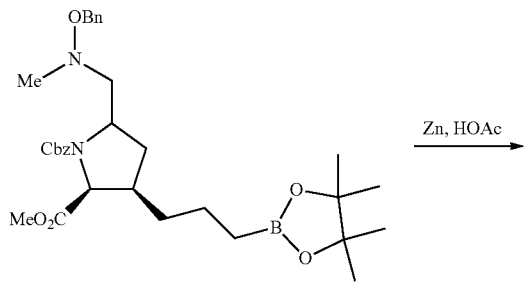

Zinc powder (2.2 g, 33.6 mmol) was added in one portion to the stirred solution of 1-benzyl 2-methyl (2S,3R)-5-(((benzyloxy)amino)methyl)-3-(3-(4,4,5,5-tetramethyl-1,3,2-dioxaborolan-2-yl)propyl)pyrrolidine-1,2-dicarboxylate (0.73 g, 1.3 mmol) in acetic acid (10 mL), the resulting slurry was sonicated for 30 s and then stirred at room temperature for 5 h. The reaction mixture was diluted with acetonitrile, filtered and the filter cake was rinsed with acetonitrile. The combined filtrate was concentrated, and the residue was purified by RP-HPLC [C18 column, water (0.1% TFA)-CH₃CN] to yield 1-benzyl 2-methyl (2S,3R)-5-(aminomethyl)-3-(3-(4,4,5,5-tetramethyl-1,3,2-dioxaborolan-2-yl)propyl)pyrrolidine-1,2-dicarboxylate as a TFA salt. LC-MS ($C_{25}H_{40}BN_2O_6$) (ES, m/z): 475 [M+H]$^+$.

Step 3: (2S,3R,5S)-3-(3-boronopropyl)-5-((methylamino)methyl)pyrrolidine-2-carboxylic acid

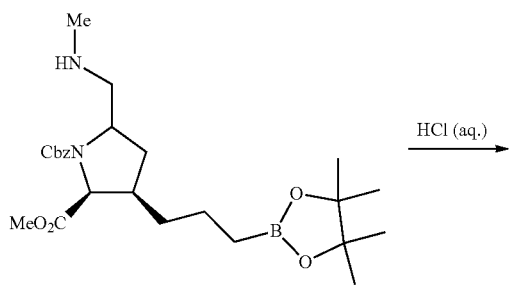

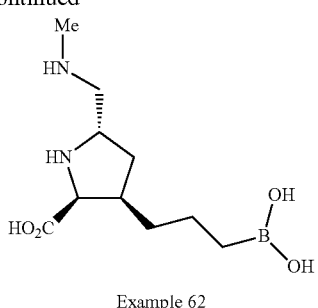

Example 62

12N HCl (1.0 mL, 12 mmol) was added to the stirred suspension of 1-benzyl 2-methyl (2S,3R)-5-(aminomethyl)-3-(3-(4,4,5,5-tetramethyl-1,3,2-dioxaborolan-2-yl)propyl)pyrrolidine-1,2-dicarboxylate (TFA salt, 24 mg, 0.040 mmol) in water (1.0 mL) at room temperature, and the reaction mixture was heated to 90° C. with stirring overnight, then cooled to room temperature. The mixture was diluted with water, filtered through a 0.25 μm filter and lyophilized to afford (2S,3R,5S)-3-(3-boronopropyl)-5-((methylamino)methyl)pyrrolidine-2-carboxylic acid as a HCl salt. LCMS ($C_{10}H_2BN_2O_3^+$)(ES, m/z): 227 [M−H₂+H]$^+$. ¹H NMR (500 MHz, D₂O) δ 4.43 (d, J=7.2 Hz, 1H), 4.27 (pentet, J=7.4 Hz, 1H), 3.53 (dd, J=13.6, 7.0 Hz, 1H), 3.45 (dd, J=13.6, 7.0 Hz, 1H), 2.83 (s, 3H), 2.77-2.70 (m, 1H), 2.27 (ddd, J=13.3, 7.5, 5.0 Hz, 1H), 2.09 (dt, J=13.8, 7.2 Hz, 1H), 1.58-1.37 (m, 3H), 1.30-1.22 (m, 1H), 0.87-0.74 (m, 2H).

Example 63: (2S,3R,5S)-3-(3-boronopropyl)-5-(hydroxymethyl)pyrrolidine-2-carboxylic acid

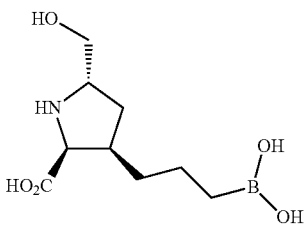 [SMILES: O=C(O)[C@H]1N[C@H](CO)C[C@H]1CCCB(O)O]

Step 1: 1-benzyl 2-methyl (2S,3R)-5-formyl-3-(3-(4,4,5,5-tetramethyl-1,3,2-dioxaborolan-2-yl)propyl)pyrrolidine-1,2-dicarboxylate

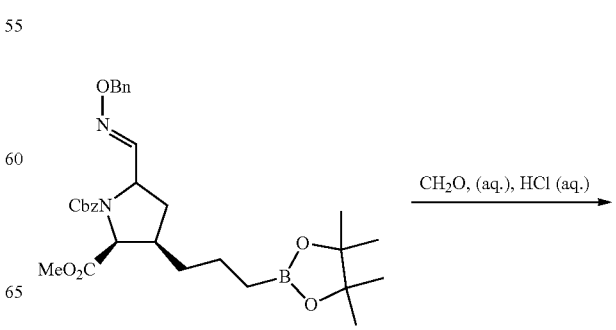

-continued

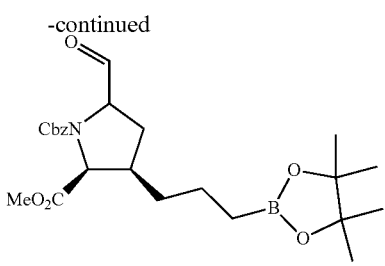

Formaldehyde solution (37 wt % in water, 11 mL, 142 mmol) was added in one portion to the stirred solution of 1-benzyl 2-methyl (2S,3R)-5-(((benzyloxy)imino)methyl)-3-(3-(4,4,5,5-tetramethyl-1,3,2-dioxaborolan-2-yl)propyl) pyrrolidine-1,2-dicarboxylate (50 wt %, 2.9 g, 2.5 mmol) in THF (42 mL) at room temperature, followed by addition of 1N HCl in water (11 mL, 11 mmol), and the reaction mixture was stirred overnight. The resulting mixture was quenched with saturated aqueous $Na_2CO_3$ to pH ~7, and extracted with EtOAc. The combined organic phase was dried over $Na_2SO_4$, filtered and concentrated to afford crude 1-benzyl 2-methyl (2S,3R)-5-formyl-3-(3-(4,4,5,5-tetramethyl-1,3,2-dioxaborolan-2-yl)propyl)pyrrolidine-1,2-dicarboxylate, which was used in the next step without further purification. LC-MS ($C_{24}H_{34}BNNaO_7^+$)(ES, m/z): 482 [M+Na]$^+$.

Step 2: 1-benzyl 2-methyl (2S,3R)-5-(hydroxymethyl)-3-(3-(4,4,5,5-tetramethyl-1,3,2-dioxaborolan-2-yl)propyl)pyrrolidine-1,2-dicarboxylate

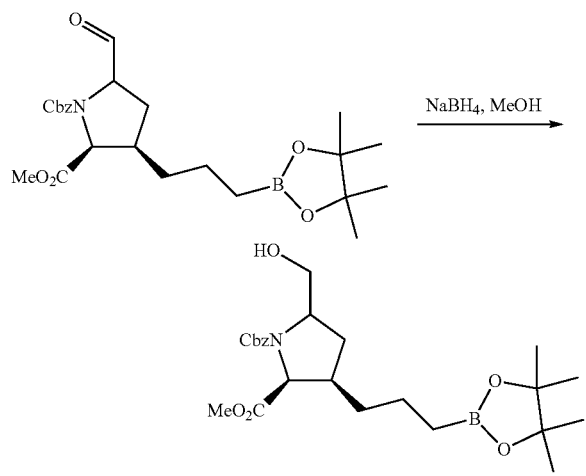

NaBH$_4$ (0.53 g, 14 mmol) was added in one portion to the stirred solution of crude 1-benzyl 2-methyl (2S,3R)-5-formyl-3-(3-(4,4,5,5-tetramethyl-1,3,2-dioxaborolan-2-yl) propyl)pyrrolidine-1,2-dicarboxylate (1.2 g, 2.5 mmol) in MeOH (25 mL) at −15° C. The resulting slurry was allowed to warm to room temperature and then stirred at room temperature overnight. The reaction mixture was quenched with saturated aqueous NH$_4$Cl solution, and extracted with EtOAc. The combined organic phase was dried Na$_2$SO$_4$, filtered and concentrated. The residue was purified by silica gel chromatography (EtOAc in hexanes) to afford 1-benzyl 2-methyl (2S,3R)-5-(hydroxymethyl)-3-(3-(4,4,5,5-tetramethyl-1,3,2-dioxaborolan-2-yl)propyl)pyrrolidine-1,2-dicarboxylate. LC-MS ($C_{24}H_{39}BNO_7^+$)(ES, m/z): 462 [M+H]$^+$.

Step 3: (2S,3R,5S)-3-(3-boronopropyl)-5-(hydroxymethyl)pyrrolidine-2-carboxylic acid

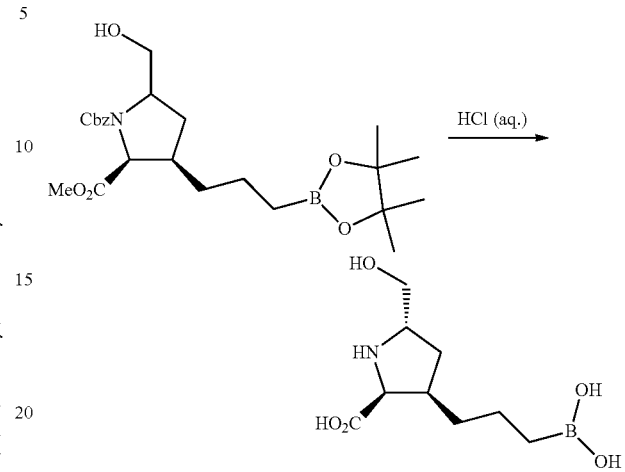

Example 63

12N HCl (89 mL, 1.1 mol) was added to the stirred suspension of 1-benzyl 2-methyl (2S,3R)-5-(((tert-butoxycarbonyl)amino)methyl)-3-(3-(4,4,5,5-tetramethyl-1,3,2-dioxaborolan-2-yl)propyl)pyrrolidine-1,2-dicarboxylate (1.9 g, 4.0 mmol) in water (89 mL) at room temperature, and the reaction mixture was heated to 90° C. with stirring for 24 h, then cooled to room temperature. The mixture was diluted with water, filtered through a 0.25 m filter and lyophilized to afford (2S,3R,5S)-3-(3-boronopropyl)-5-(hydroxymethyl) pyrrolidine-2-carboxylic acid as a HCl salt. LCMS ($C_9H_7BNO_4^+$)(ES, m/z): 214 [M−H$_2$+H]$^+$. $^1$H NMR (500 MHz, D$_2$O) δ 4.39 (d, J=7.0 Hz, 1H), 4.10-4.05 (m, 1H), 3.86 (dd, J=12.4, 3.9 Hz, 1H), 3.69 (dd, J=12.4, 7.2 Hz, 1H), 2.69 (septet, J=5.6, 1H), 2.08-1.97 (m, 2H), 1.58-1.37 (m, 3H), 1.31-1.22 (m, 1H), 0.86-0.74 (m, 2H).

Step 7: (2S,3R,5S)-3-(3-boronopropyl)-5-(hydroxymethyl)pyrrolidine-2-carboxylic acid (Free Base)

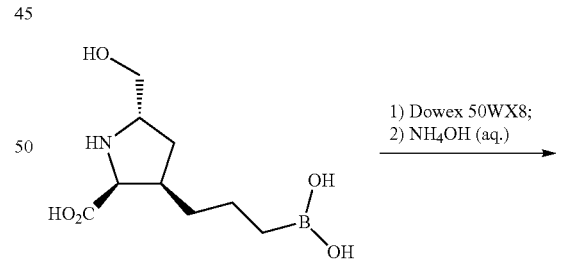

Example 63

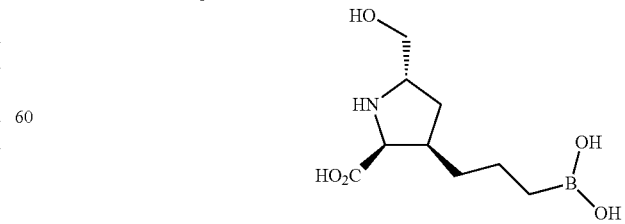

Example 63-free base (2S,3R,5S)-3-(3-boronopropyl)-5-(hydroxymethyl)pyrrolidine-2-carboxylic acid (crude HCl salt, 1.1 g, 4.0 mmol) was purified on 105 g of Dowex 50WX8 acidic resin (washed with water until pH neutral, then eluted with 2N aqueous ammonium hydroxide) to afford (2S,3R,5S)-3-(3-boronopropyl)-5-(hydroxymethyl)pyrrolidine-2-carboxylic acid as a free base. LCMS ($C_9H_{17}BNO_4^+$)(ES, m/z): 214 [M–$H_2$+H]$^+$. $^1$HNMR (500 MHz, $D_2O$) δ 4.16 (d, J=7.0 Hz, 1H), 4.06-4.01 (m, 1H), 3.85 (dd, J=12.4, 3.9 Hz, 1H), 3.69 (dd, J=12.4, 7.2 Hz, 1H), 2.64-2.58 (m, 1H), 2.06-1.93 (m, 2H), 1.57-1.35 (m, 3H), 1.27-1.18 (m, 1H), 0.87-0.74 (m, 2H).

Example 64: (2S,3R,5R)-3-(3-boronopropyl)-5-methylpyrrolidine-2-carboxylic acid

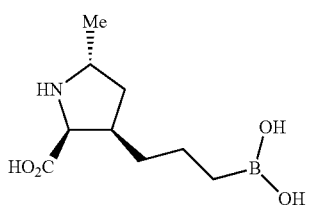 [SMILES: C[C@@H]1C[C@@H](CCCB(O)O)[C@@H](C(=O)O)N1]

Step 1: 1-benzyl 2-methyl (2S,3R)-5-(bromomethyl)-3-(3-(4,4,5,5-tetramethyl-1,3,2-dioxaborolan-2-yl)propyl)pyrrolidine-1,2-dicarboxylate

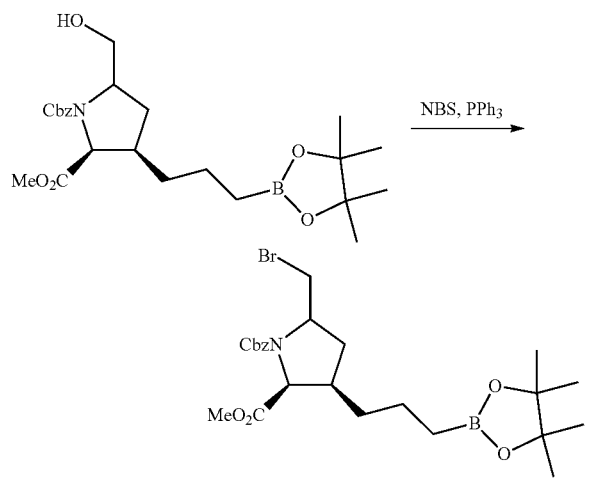

Triphenylphosphine (0.41 g, 1.6 mmol) was added in one portion to the stirred solution of 1-benzyl 2-methyl (2S,3R)-5-(hydroxymethyl)-3-(3-(4,4,5,5-tetramethyl-1,3,2-dioxaborolan-2-yl)propyl)pyrrolidine-1,2-dicarboxylate (0.14 g, 0.31 mmol) in THF (3.1 mL), followed by addition of N-bromosuccinimide (0.27 g, 1.5 mmol) in one portion at 0° C. The reaction mixture was allowed to warm to room temperature and diluted with dichloromethane (3.1 mL) and then stirred at room temperature overnight. The resulting mixture was concentrated, and the residue was purified by silica gel chromatography (EtOAc in hexanes) to yield crude 1-benzyl 2-methyl (2S,3R)-5-(bromomethyl)-3-(3-(4,4,5,5-tetramethyl-1,3,2-dioxaborolan-2-yl)propyl)pyrrolidine-1,2-dicarboxylate. LC-MS ($C_{24}H_{36}BBrNO_6^+$)(ES, m/z): 524 [M+H]$^+$.

Step 2: 1-benzyl 2-methyl (2S,3R)-5-methyl-3-(3-(4,4,5,5-tetramethyl-1,3,2-dioxaborolan-2-yl)propyl)pyrrolidine-1,2-dicarboxylate

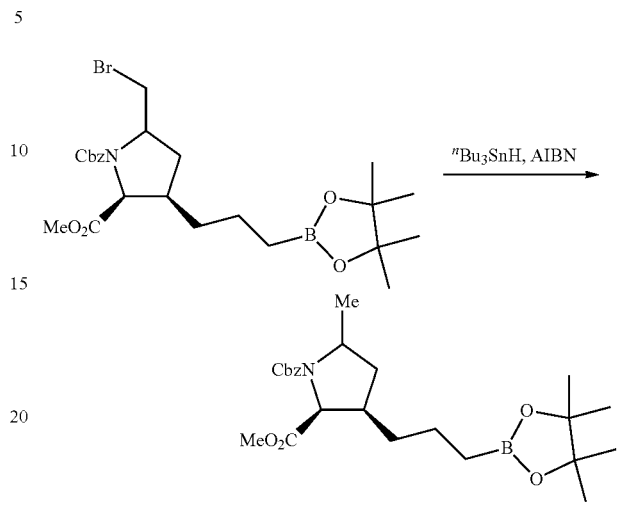

Tri-n-butyltin hydride (66 µL, 0.25 mmol) was added to the stirred solution of 1-benzyl 2-methyl (2S,3R)-5-(bromomethyl)-3-(3-(4,4,5,5-tetramethyl-1,3,2-dioxaborolan-2-yl)propyl)pyrrolidine-1,2-dicarboxylate (0.11 g, 0.20 mmol) in toluene (0.82 mL), followed by 2,2'-azobis(2-methylpropionitrile)(1.7 mg, 10 µmol) in one portion at room temperature The reaction mixture was stirred at 85° C. for 3 h, then diluted with dichloromethyl, and purified by silica gel chromatography (EtOAc in hexanes) to afford 1-benzyl 2-methyl (2S,3R)-5-methyl-3-(3-(4,4,5,5-tetramethyl-1,3,2-dioxaborolan-2-yl)propyl)pyrrolidine-1,2-dicarboxylate. LC-MS ($C_{24}H_{37}BNO_6^+$) (ES, m/z): 446 [M+H]$^+$.

Step 3: (23R,5R-3-(3-boronopropyl-5-methylpyrrolidine-2-carboxylic acid

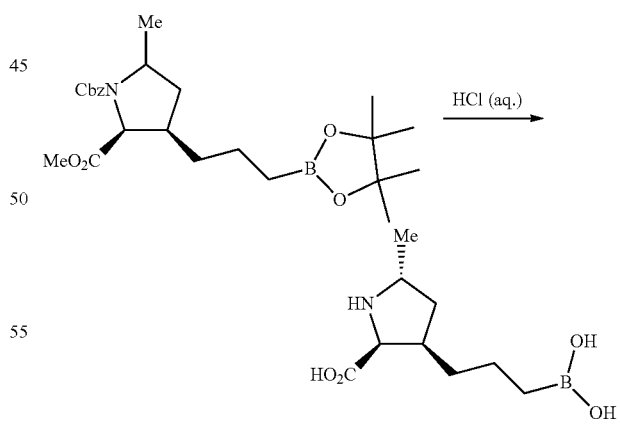

Example 64

12N HCl in water (3.0 mL, 36 mmol) was added to the stirred suspension of 1-benzyl 2-methyl (2S,3R)-5-methyl-3-(3-(4,4,5,5-tetramethyl-1,3,2-dioxaborolan-2-yl)propyl)pyrrolidine-1,2-dicarboxylate (81 mg, 0.16 mmol) in water (3.0 mL) at room temperature, and the reaction mixture was heated to 90° C. with stirring overnight, then cooled to room temperature. The mixture was diluted with water, filtered through a 0.25 μm filter and lyophilized to afford (2S,3R,5R)-3-(3-boronopropyl)-5-methylpyrrolidine-2-carboxylic acid as a HCl salt. LCMS ($C_9H_{17}BNO_3^+$)(ES, m/z): 198 [M–$H_2O$+H]$^+$. $^1$H NMR (500 MHz, $D_2O$) δ 4.37 (d, J=7.4 Hz, 1H), 4.04-4.00 (m, 1H), 2.74-2.68 (m, 1H), 2.13 (ddd, J=13.2, 7.0, 5.0 Hz, 1H), 1.90 (dt, J=13.2, 7.2 Hz, 1H), 1.54-1.34 (m, 3H), 1.40 (d, J=6.8 Hz, 3H), 1.28-1.20 (m, 1H), 0.86-0.74 (m, 2H).

Example 65: (2S,3S)-3-(3-boronopropyl)-3-(hydroxymethyl)azetidine-2-carboxylic acid

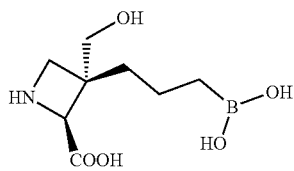 [SMILES: O=C(O)[C@H]1NC[C@@]1(CO)CCCB(O)O]

Step 1: (3S)-4-tert-butyl 1-methyl 2-allyl-2-((benzyloxy)methyl)-3-((9-phenyl-9H-fluoren-9-yl)amino)succinate

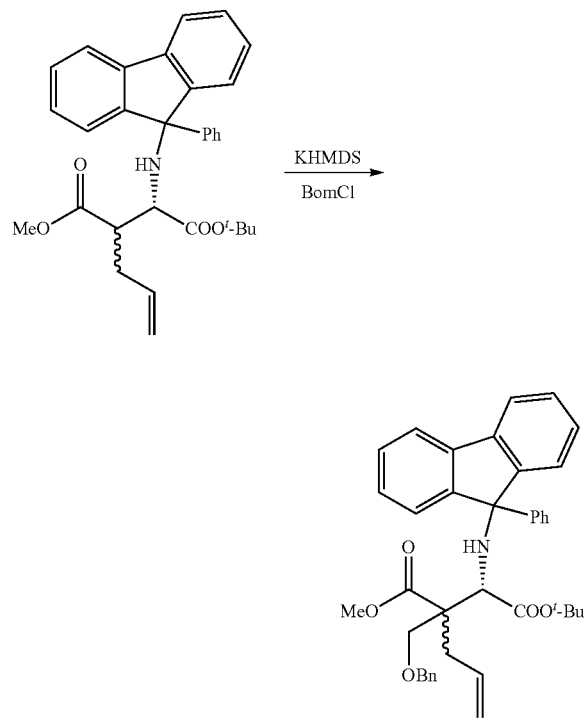

KHMDS (0.5 M in toluene, 0.12 L, 59 mmol) was dropwise added to a solution of (3S)-4-tert-butyl 1-methyl 2-allyl-3-((9-phenyl-9H-fluoren-9-yl)amino)succinate (13 g, 27 mmol) in dry THF (0.10 L) at –78° C. over 1 h under $N_2$, and the resulting mixture was stirred for 1 h at –78° C., then at 0° C. for another 1 h. ((Chloromethoxy)methyl)benzene (5.6 mL, 40 mmol) was added at –78° C., and the resulting mixture was stirred for 1 h at –78° C., then for 1 h at 0° C., and at 25° C. for 10 h. The reaction mixture was quenched with saturated aqueous $NH_4Cl$ and extracted with EtOAc. The combined organic phase was washed with brine, dried over anhydrous $Na_2SO_4$, filtered and concentrated. The residue was purified by silica gel column chromatography (EtOAc in hexanes), then further purified by RP-HPLC [C18 column, water (10 mM $NH_4HCO_3$)—$CH_3CN$] to give (3S)-4-tert-butyl 1-methyl 2-allyl-2-((benzyloxy)methyl)-3-((9-phenyl-9H-fluoren-9-yl)amino)succinate as a mixture of diastereomers. LCMS ($C_{39}H_{42}NO_5^+$)(ES, m/z): 604 [M+H]$^+$.

Step 2: (2S)-tert-butyl 3-((benzyloxy)methyl)-3-formyl-2-((9-phenyl-9H-fluoren-9-yl)amino)hex-5-enoate

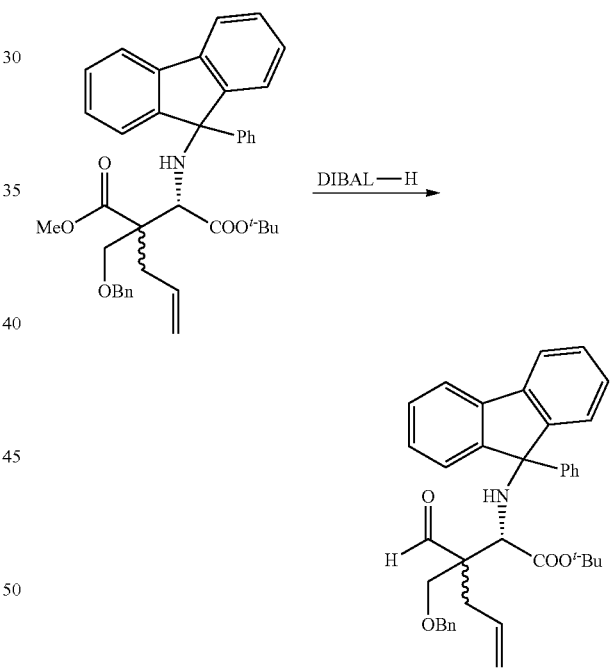

Diisobutylaluminum hydride (1 M in toluene, 0.11 L, 0.11 mol) was added dropwise to the stirred solution of (3S)-4-tert-butyl 1-methyl 2-allyl-2-((benzyloxy)methyl)-3-((9-phenyl-9H-fluoren-9-yl)amino)succinate (16 g, 27 mmol) in DCM (0.20 L) at –78° C. over 1 h under $N_2$, and the resulting mixture was stirred for 0.5 h at –78° C. The reaction mixture was quenched with brine at –78° C., and filtered. The organic phase was separated, and concentrated to give crude (2S)-tert-butyl 3-((benzyloxy)methyl)-3-formyl-2-((9-phenyl-9H-fluoren-9-yl)amino)hex-5-enoate, which was used in the next step directly without further purification. LCMS ($C_{38}H_{40}NO_4^+$)(ES, m/z): 574 [M+H]$^+$.

Step 3: (2S)-tert-butyl 3-((benzyloxy)methyl)-3-(hydroxymethyl)-2-((9-phenyl-9H-fluoren-9-yl)amino)hex-5-enoate

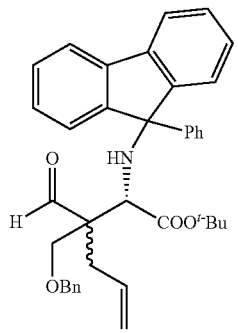

NaBH₄ (3.5 g, 92 mmol) was added to the stirred solution of (2S)-tert-butyl 3-((benzyloxy)methyl)-3-formyl-2-((9-phenyl-9H-fluoren-9-yl)amino)hex-5-enoate (18 g, 31 mmol) in MeOH (0.20 L) at 25° C. over 10 min, and the resulting mixture was stirred for 0.5 h at 25° C.

The reaction mixture was concentrated, quenched with brine and extracted with EtOAc. The combined organic phase was washed with brine, dried over anhydrous Na₂SO₄, filtered and concentrated. The residue was purified by silica gel column chromatography (EtOAc in hexanes) to give (2S)-tert-butyl 3-((benzyloxy)methyl)-3-(hydroxymethyl)-2-((9-phenyl-9H-fluoren-9-yl)amino)hex-5-enoate as a mixture of diastereomers. LCMS ($C_{38}H_{42}NO_4^+$)(ES, m/z): 576 [M+H]⁺.

Step 4: (2S)-tert-butyl 3-((benzyloxy)methyl)-3-(((methylsulfonyl)oxy)methyl)-2-((9-phenyl-9H-fluoren-9-yl)amino)hex-5-enoate

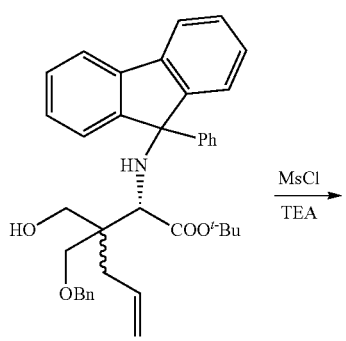

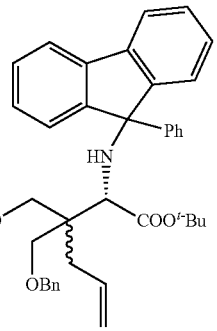

Methanesulfonyl chloride (12 g, 0.11 mol) was added to the stirred solution of (2S)-tert-butyl 3-((benzyloxy)methyl)-3-(hydroxymethyl)-2-((9-phenyl-9H-fluoren-9-yl)amino)hex-5-enoate (11 g, 19 mmol) in DCM (0.50 L) at 0° C., followed by addition of triethylamine (22 mL, 0.15 mol), and the mixture was stirred at 0° C. for 0.5 h, then at 25° C. for 2 h. The reaction mixture was quenched with water and extracted with DCM. The combined organic phase was washed with brine, and concentrated to afford crude (2S)-tert-butyl 3-((benzyloxy)methyl)-3-(((methylsulfonyl)oxy)methyl)-2-((9-phenyl-9H-fluoren-9-yl)amino)hex-5-enoate as a mixture of diastereomers, which was used in the next step directly without further purification. LCMS ($C_{39}H_{44}NO_6S^+$)(ES, m/z): 654 [M+H]⁺.

Step 5: (2S,3S)-tert-butyl 3-allyl-3-((benzyloxy)methyl)-1-(9-phenyl-9H-fluoren-9-yl)azetidine-2-carboxylate

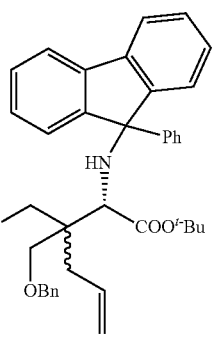

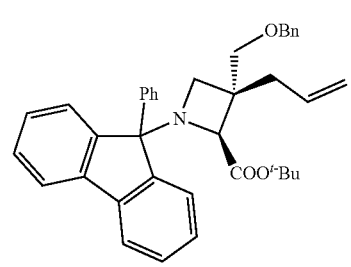

Triethylamine (8.8 mL, 63 mmol) was added to the stirred solution of (2S)-tert-butyl 3-((benzyloxy)methyl)-3-(((methylsulfonyl)oxy)methyl)-2-((9-phenyl-9H-fluoren-9-yl)amino)hex-5-enoate (14 g, 21 mmol) in DMF (0.10 L) at 25° C., and the mixture was stirred at 80° C. for 15 h. The reaction mixture was quenched with brine and extracted with EtOAc. The combined organic phase was washed with brine, dried over anhydrous Na₂SO₄, filtered and concentrated. The residue was purified by silica gel column chromatography (EtOAc in hexanes) to afford a mixture of diastereomers, which was resolved by chiral-SFC [Column: DAICEL CHIRALPAK IC (250 mm*50 mm, 10 μm), Mobile phase: A: CO₂, B: MeOH (0.1% NH₃.H₂O), Gradient: 15% of B in 3.5 min, and hold 15% of B for 1 min, Flow Rate (mL/min) 180, Column temperature: 40° C.] to give (2S,3S)-tert-butyl 3-allyl-3-((benzyloxy)methyl)-1-(9-phenyl-9H-fluoren-9-yl)azetidine-2-carboxylate ($t_r$=2.84 min) as the second eluting peak. LCMS ($C_{36}H_{40}NO_3^+$)(ES, m/z): 558 [M+H]; ¹H NMR (400 MHz, CDCl₃) δ 7.79-7.70 (m, 1H), 7.64-7.48 (m, 3H), 7.44-7.33 (m, 3H), 7.32-7.05 (m, 11H), 5.80-5.61 (m, 1H), 5.14-4.96 (m, 2H), 4.37-4.21 (m, 2H), 3.34-3.19 (m, 3H), 3.08-2.93 (m, 2H), 2.70-2.65 (m, 1H), 2.30-2.45 (m, 1H), 1.17 (s, 9H). Step 6: (2S,3S)-tert-butyl 3-((benzyloxy)methyl)-1-(9-phenyl-9H-fluoren-9-yl)-3-(3-(4,4,5,5-tetramethyl-1,3,2-dioxaborolan-2-yl)propyl)azetidine-2-carboxylate

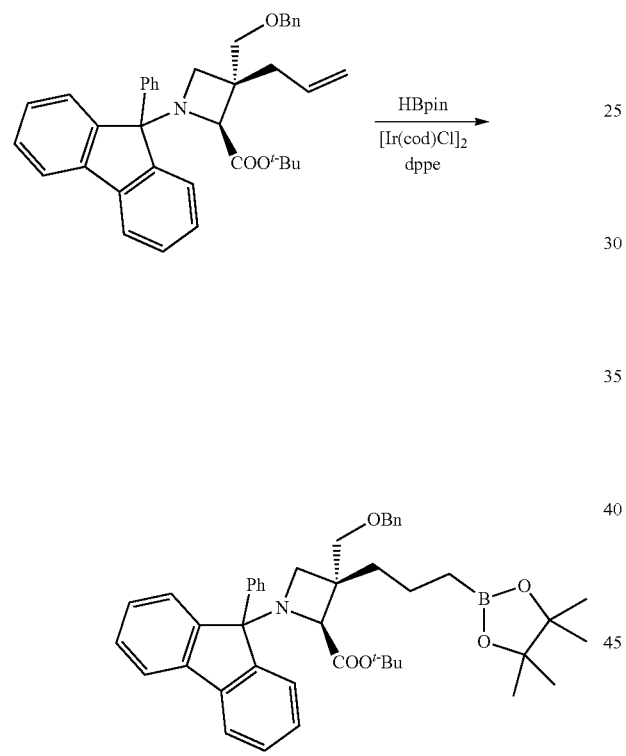

1,2-bis(diphenylphosphino)ethane (71 mg, 0.18 mmol) was added to the stirred solution of [Ir(cod)Cl]₂ (60 mg, 0.090 mmol) in DCM (30 mL), and the mixture was stirred at 25° C. under N₂ for 5 min. (2S,3S)-Tert-butyl 3-allyl-3-((benzyloxy)methyl)-1-(9-phenyl-9H-fluoren-9-yl)azetidine-2-carboxylate (0.50 g, 0.90 mmol) and 4,4,5,5-tetramethyl-1,3,2-dioxaborolane (0.46 g, 3.6 mmol) were added, and the resulting mixture was stirred at 25° C. for 4 h. The reaction mixture was quenched with water and extracted with DCM. The combined organic phase was concentrated, and the residue was purified by silica gel column chromatography (EtOAc in hexanes) to give (2S,3S)-tert-butyl 3-((benzyloxy)methyl)-1-(9-phenyl-9H-fluoren-9-yl)-3-(3-(4,4,5,5-tetramethyl-1,3,2-dioxaborolan-2-yl)propyl)azetidine-2-carboxylate. LCMS ($C_{44}H_{53}BNO_5^+$)(ES, m/z): 686 [M+H]⁺.

Step 7: (3-((2S,3S)-3-((benzyloxy)methyl)-2-(tert-butoxycarbonyl)-1-(9-phenyl-9H-fluoren-9-yl)azetidin-3-yl)propyl)boronic acid

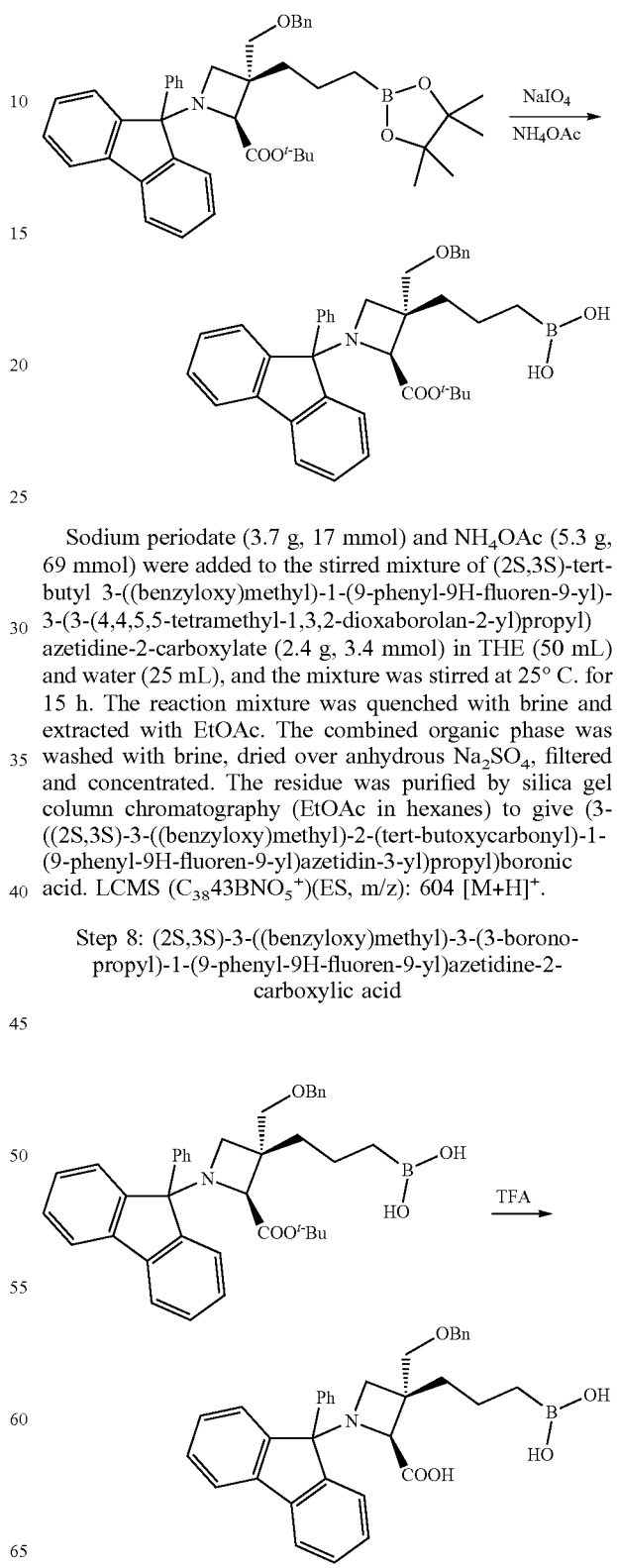

Sodium periodate (3.7 g, 17 mmol) and NH₄OAc (5.3 g, 69 mmol) were added to the stirred mixture of (2S,3S)-tert-butyl 3-((benzyloxy)methyl)-1-(9-phenyl-9H-fluoren-9-yl)-3-(3-(4,4,5,5-tetramethyl-1,3,2-dioxaborolan-2-yl)propyl)azetidine-2-carboxylate (2.4 g, 3.4 mmol) in THF (50 mL) and water (25 mL), and the mixture was stirred at 25° C. for 15 h. The reaction mixture was quenched with brine and extracted with EtOAc. The combined organic phase was washed with brine, dried over anhydrous Na₂SO₄, filtered and concentrated. The residue was purified by silica gel column chromatography (EtOAc in hexanes) to give (3-((2S,3S)-3-((benzyloxy)methyl)-2-(tert-butoxycarbonyl)-1-(9-phenyl-9H-fluoren-9-yl)azetidin-3-yl)propyl)boronic acid. LCMS ($C_{38}H_{43}BNO_5^+$)(ES, m/z): 604 [M+H]⁺.

Step 8: (2S,3S)-3-((benzyloxy)methyl)-3-(3-boronopropyl)-1-(9-phenyl-9H-fluoren-9-yl)azetidine-2-carboxylic acid (3-((2S,3S)-3-((benzyloxy)methyl)-2-(tert-butoxycarbonyl)-1-(9-phenyl-9H-fluoren-9-yl)azetidin-3-yl)propyl)boronic acid (1.2 g, 2.0 mmol) was added to TFA (30 mL, 0.39 mol) and the resulting mixture was stirred at 25° C. under N₂ for 6 h. The reaction mixture was concentrated to give crude (2S,3S)-3-((benzyloxy)methyl)-3-(3-boronopropyl)-1-(9-phenyl-9H-fluoren-9-yl)azetidine-2-carboxylic acid, which was used in the next step directly without further purification. LCMS ($C_{34}H_{33}BNO_4^+$)(ES, m/z): 530 [M–$H_2O$+H]⁺.

Step 9: (2S,3S)-3-(3-boronopropyl)-3-(hydroxymethyl)azetidine-2-carboxylic acid

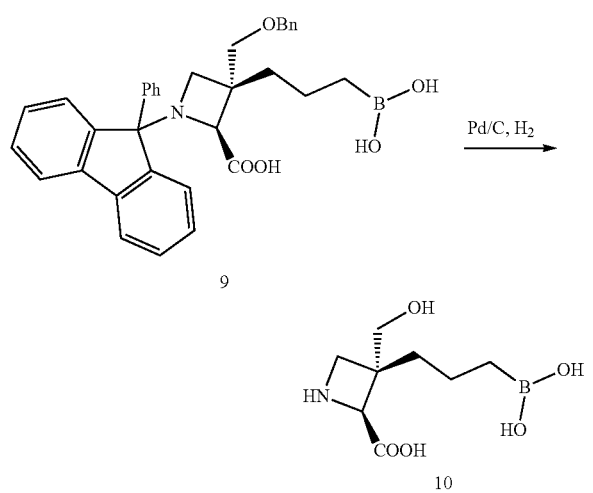

10% Pd/C (1.2 g, 1.1 mmol) was added to the stirred solution of (2S,3S)-3-((benzyloxy)methyl)-3-(3-boronopropyl)-1-(9-phenyl-9H-fluoren-9-yl)azetidine-2-carboxylic acid (1.2 g, 2.2 mmol) in MeOH (50 mL), and the mixture was degassed and backfilled with H₂ (three times), and stirred under H₂ (Pressure: 50 psi) at 25° C. for 18 h, then at 50° C. for another 72 h. The reaction mixture was filtered and concentrated, and the residue was diluted with DCM and water.

The aqueous layer was purified by RP-HPLC [C18 column, water (10 mM NH₄HCO₃)—CH₃CN] to give (2S,3S)-3-(3-boronopropyl)-3-(hydroxymethyl)azetidine-2-carboxylic acid as a free base. LCMS ($C_8H_{15}BNO_4^+$)(ES, m/z): 200 [M–$H_2$+H]⁺; ¹H NMR (400 MHz, D₂O) δ 4.51-4.39 (m, 1H), 3.85-3.70 (m, 1H), 3.65-3.40 (m, 3H), 1.56-1.35 (m, 2H), 1.30-0.98 (m, 2H), 0.71-0.45 (m, 2H).

Example 66: (2S,3S)-3-(3-boronopropyl)-3-(hydroxymethyl)-1-methylazetidine-2-carboxylic acid Step 1: (2S,3S)-3-(3-boronopropyl)-3-(hydroxymethyl)-1-methylazetidine-2-carboxylic acid

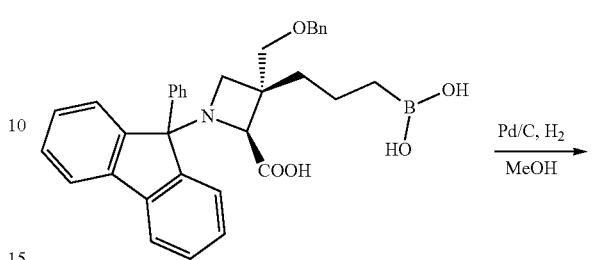

Example 66

10% Pd/C (5.0 g, 4.7 mmol) was added to the stirred solution of (2S,3S)-3-((benzyloxy)methyl)-3-(3-boronopropyl)-1-(9-phenyl-9H-fluoren-9-yl)azetidine-2-carboxylic acid (5.0 g, 9.1 mmol) in MeOH (0.50 L) under N₂ atmosphere, and the mixture was degassed and backfilled with H₂ (three times), and stirred under H₂ (Pressure: 50 psi) at 50° C. for 15 h. The reaction mixture was filtered and concentrated. The residue was dissolved in water and washed with DCM, and the aqueous layer was purified by RP-HPLC [C18 column, water (10 mM NH₄HCO₃)-acetonitrile] to give (2S,3S)-3-(3-boronopropyl)-3-(hydroxymethyl)-1-methylazetidine-2-carboxylic acid as a free base. LCMS ($C_9H_{17}BNO_4^+$)(ES, m/z): 214 [M–$H_2O$+H]; ¹H NMR (400 MHz, D₂O) δ 4.40-4.29 (m, 1H), 3.80-3.70 (m, 1H), 3.65-3.57 (m, 1H), 3.56-3.48 (m, 1H), 3.46-3.35 (m, 1H), 2.77-2.67 (m, 3H), 1.60-1.39 (m, 2H), 1.29-1.11 (m, 2H), 0.68-0.46 (m, 2H).

Example 67: (2S,3S)-3-(aminomethyl)-3-(3-boronopropyl)azetidine-2-carboxylic acid

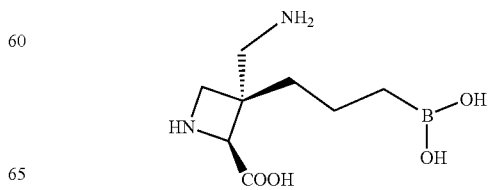

Step 1: (2S,3S)-tert-butyl 3-(hydroxymethyl)-3-(3-(4,4,5,5-tetramethyl-1,3,2-dioxaborolan-2-yl)propyl)azetidine-2-carboxylate

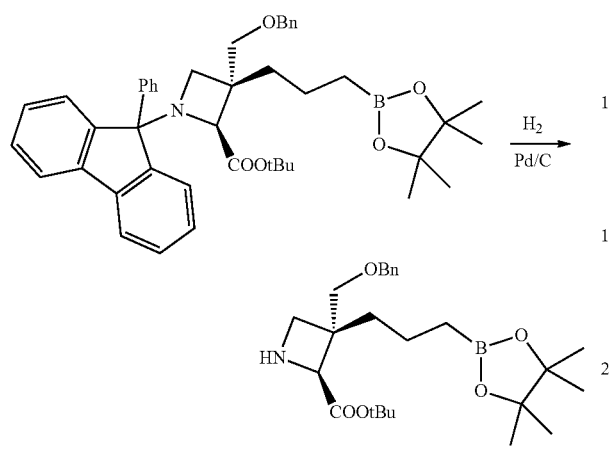

10% Pd/C (2.3 g, 2.2 mmol) was added to the stirred solution of (2S,3S)-tert-butyl 3-((benzyloxy)methyl)-1-(9-phenyl-9H-fluoren-9-yl)-3-(3-(4,4,5,5-tetramethyl-1,3,2-dioxaborolan-2-yl)propyl)azetidine-2-carboxylate (2.3 g, 3.4 mmol) in MeOH (20 mL) under $N_2$, and the mixture was degassed and backfilled with $H_2$ (three times), and stirred under $H_2$ (50 psi) at 50° C. for 65 h. The reaction mixture was filtered and concentrated to give crude (2S,3S)-tert-butyl 3-(hydroxymethyl)-3-(3-(4,4,5,5-tetramethyl-1,3,2-dioxaborolan-2-yl)propyl)azetidine-2-carboxylate, which was used in the next step directly without further purification. LCMS $(C_{25}H_{41}BNO_5^+)$(ES, m/z): 446 $[M+H]^+$.

Step 2: (2S,3S)-di-tert-butyl 3-((benzyloxy)methyl)-3-(3-(4,4,5,5-tetramethyl-1,3,2-dioxaborolan-2-yl)propyl)azetidine-1,2-dicarboxylate

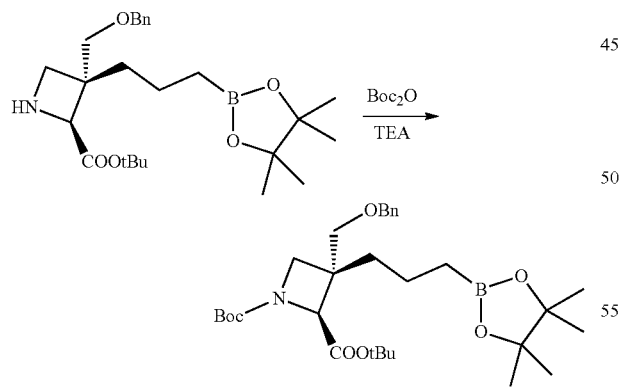

TEA (1.6 mL, 12 mmol) and Boc-anhydride (2.4 g, 10 mmol) were added to the stirred solution of (2S,3S)-tert-butyl 3-((benzyloxy)methyl)-3-(3-(4,4,5,5-tetramethyl-1,3,2-dioxaborolan-2-yl)propyl)azetidine-2-carboxylate (0.60 g, 1.3 mmol) at 0° C., and the mixture was stirred at 0° C. for 1 h then at 25° C. for 15 h. The reaction mixture was concentrated and the residue was purified by silica gel column chromatography (EtOAc in hexanes) to afford (2S, 3S)-di-tert-butyl 3-((benzyloxy)methyl)-3-(3-(4,4,5,5-tetramethyl-1,3,2-dioxaborolan-2-yl)propyl)azetidine-1,2-dicarboxylate. LCMS $(C_{30}H_{49}BNO_7^+)$(ES, m/z): 546 $[M+H]^+$.

Step 3: (2S,3S)-di-tert-butyl 3-(hydroxymethyl)-3-(3-(4,4,5,5-tetramethyl-1,3,2-dioxaborolan-2-yl)propyl)azetidine-1,2-dicarboxylate

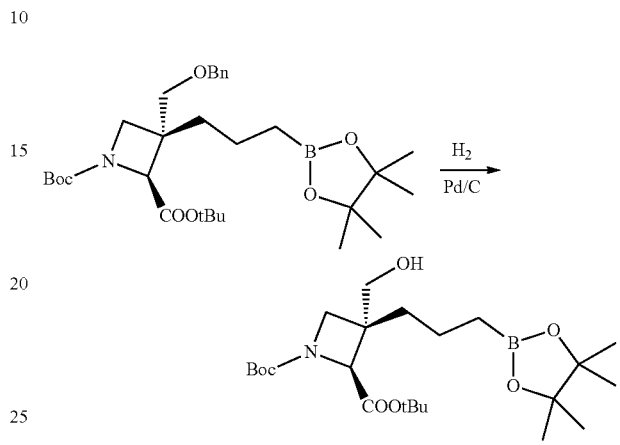

10% Pd/C (0.90 g, 0.85 mmol) was added to the stirred solution of (2S,3S)-di-tert-butyl 3-((benzyloxy)methyl)-3-(3-(4,4,5,5-tetramethyl-1,3,2-dioxaborolan-2-yl)propyl)azetidine-1,2-dicarboxylate (77% wt %, 0.95 g, 1.3 mmol) in MeOH (20 mL) under $N_2$, and the mixture was degassed and backfilled with $H_2$ (three times), then stirred under $H_2$ (50 psi) at 50° C. for 15 h. The reaction mixture was filtered and concentrated, and the residue was purified by silica gel column chromatography (EtOAc in hexanes) to afford (2S, 3S)-di-tert-butyl 3-(hydroxymethyl)-3-(3-(4,4,5,5-tetramethyl-1,3,2-dioxaborolan-2-yl)propyl)azetidine-1,2-dicarboxylate. LCMS $(C_{23}H_{43}BNO_7^+)$(ES, m/z): 456 $[M+H]^+$.

Step 4: (2S,3S)-di-tert-butyl 3-(((methylsulfonyl)oxy)methyl)-3-(3-(4,4,5,5-tetramethyl-1,3,2-dioxaborolan-2-yl)propyl)azetidine-1,2-dicarboxylate

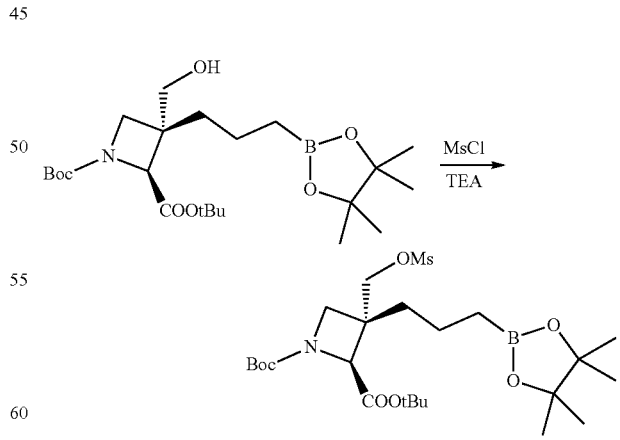

Ms-Cl (methanesulfonyl chloride)(0.11 mL, 1.4 mmol) and TEA (0.34 mL, 2.4 mmol) were added to the stirred solution of (2S,3S)-di-tert-butyl 3-(hydroxymethyl)-3-(3-(4,4,5,5-tetramethyl-1,3,2-dioxaborolan-2-yl)propyl)azetidine-1,2-dicarboxylate (0.22 g, 0.48 mmol) in DCM (20 mL) at 0° C., and the resulting mixture was stirred at 0° C. for 1 h then at 25° C. for 15 h. The reaction mixture was quenched with water and extracted with DCM. The combined organic phase was washed with brine, dried over anhydrous $Na_2SO_4$, filtered and concentrated to give crude (2S,3S)-di-tert-butyl 3-(((methylsulfonyl)oxy)methyl)-3-(3-(4,4,5,5-tetramethyl-1,3,2-dioxaborolan-2-yl)propyl)azetidine-1,2-dicarboxylate, which was used in the next step directly without further purification. LCMS $(C_{24}H_{44}BNO_9SNa^+)$(ES, m/z): 556 $[M+Na]^+$.

Step 5: (2S,3R)-di-tert-butyl 3-(azidomethyl)-3-(3-(4,4,5,5-tetramethyl-1,3,2-dioxaborolan-2-yl)propyl)azetidine-1,2-dicarboxylate

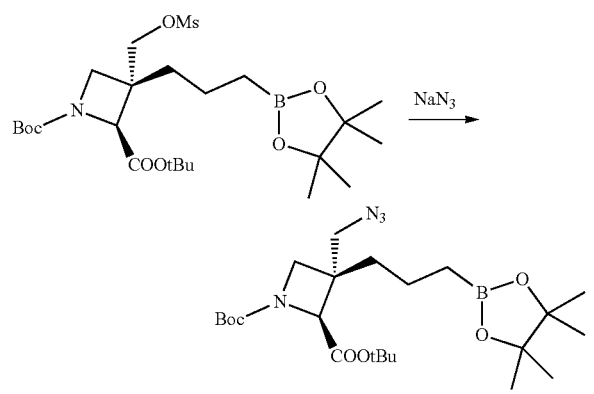

Sodium azide (0.32 g, 4.9 mmol) was added to a solution of (2S,3S)-di-tert-butyl 3-(((methylsulfonyl)oxy)methyl)-3-(3-(4,4,5,5-tetramethyl-1,3,2-dioxaborolan-2-yl)propyl)azetidine-1,2-dicarboxylate (0.26 g, 0.49 mmol) in DMF (20 mL), and the resulting mixture was stirred at 80° C. for 15 h. The reaction mixture was quenched with brine and extracted with EtOAc. The combined organic phase was washed with brine, dried over anhydrous $Na_2SO_4$, filtered and concentrated. The residue was purified by RP-HPLC [C18 column, water (0.1% TFA)-$CH_3CN$] to give (2S,3R)-di-tert-butyl 3-(azidomethyl)-3-(3-(4,4,5,5-tetramethyl-1,3,2-dioxaborolan-2-yl)propyl)azetidine-1,2-dicarboxylate. LCMS $(C_{23}H_{42}BN_4O_6^+)$(ES, m/z): 481 $[M+H]^+$.

Step 6: (3-((2S,3R)-3-(azidomethyl)-1,2-bis(tert-butoxycarbonyl)azetidin-3-yl)propyl)boronic acid

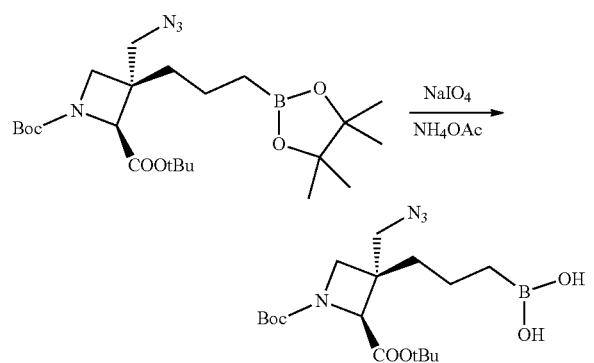

Sodium periodate (0.23 g, 1.1 mmol) and $NH_4OAc$ (0.31 g, 4.1 mmol) were added to the stirred mixture of (2S,3R)-di-tert-butyl 3-(azidomethyl)-3-(3-(4,4,5,5-tetramethyl-1,3,2-dioxaborolan-2-yl)propyl)azetidine-1,2-dicarboxylate (65 mg, 0.14 mmol) in THF (10 mL) and water (5.0 mL), and the resulting mixture was stirred for 15 h at 25° C. The reaction mixture was quenched with water and extracted with EtOAc. The combined organic phase was washed with brine, dried over anhydrous $Na_2SO_4$, filtered and concentrated to afford crude (3-((2S,3R)-3-(azidomethyl)-1,2-bis(tert-butoxycarbonyl)azetidin-3-yl)propyl)boronic acid, which was used in the next step directly without further purification. LCMS $(C_{17}H_{32}BN_4O_6^+)$(ES, m/z): 399 $[M+H]^+$.

Step 7: (3-((2S,3S)-3-(aminomethyl)-1,2-bis(tert-butoxycarbonyl)azetidin-3-yl)propyl)boronic acid

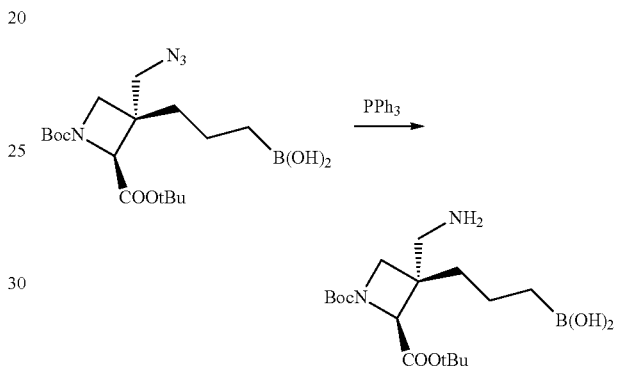

Triphenylphosphine (0.17 g, 0.63 mol) was added to the stirred mixture of (3-((2S,3R)-3-(azidomethyl)-1,2-bis(tert-butoxycarbonyl)azetidin-3-yl)propyl)boronic acid (50 mg, 0.13 mmol) in THF (10 mL) and water (1.0 mL), and the resulting mixture was stirred at 60° C. for 6 h under $N_2$.

The reaction mixture was concentrated and diluted with hexanes and HOAc. The aqueous layer was separated and purified by RP-HPLC [C18 column, water (0.1% TFA)-$CH_3CN$] to give (3-((2S,3S)-3-(aminomethyl)-1,2-bis(tert-butoxycarbonyl)azetidin-3-yl)propyl)boronic acid. LCMS $(C_{17}H_{34}BN_2O_6^+)$(ES, m/z): 373 $[M+H]^+$.

Step 8: (2S,3S)-3-(aminomethyl)-3-(3-boronopropyl)azetidine-2-carboxylic acid

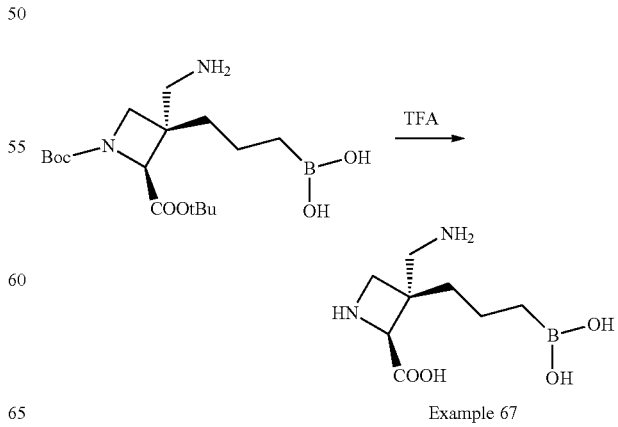

Example 67

TFA (2.0 mL, 26 mmol) was added to the stirred solution of (3-((2S,3S)-3-(aminomethyl)-1,2-bis(tert-butoxycarbonyl)azetidin-3-yl)propyl)boronic acid (10 mg, 0.027 mmol) in DCM (2.0 mL), and the mixture was stirred for 15 h at 20° C. The reaction mixture was concentrated and the residue was purified by RP-HPLC [C18 column, water (10 mM NH₄HCO₃)—CH₃CN] to give (2S,3S)-3-(aminomethyl)-3-(3-boronopropyl)azetidine-2-carboxylic acid as a free base. LCMS ($C_8H_{16}BN_2O_3^+$)(ES, m/z): 199 [M+H]; ¹H NMR (400 MHz, D₂O) δ 4.54-4.41 (m, 1H), 3.80-3.63 (m, 1H), 3.59-3.47 (m, 1H), 3.28-2.93 (m, 2H), 1.69-1.40 (m, 2H), 1.35-1.07 (m, 2H), 0.71-0.49 (m, 2H).

Example 68: (2S,3S)-3-(3-boronopropyl)-3-(2-hydroxypropan-2-yl)azetidine-2-carboxylic acid

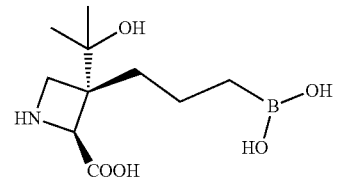 [SMILES: CC(C)(O)[C@@]1(CCCB(O)O)CN[C@@H]1C(=O)O]

Step 1: (2S,3S)-3-allyl-3-(hydroxymethyl)-1-(9-phenyl-9H-fluoren-9-yl)azetidine-2-carboxylic acid

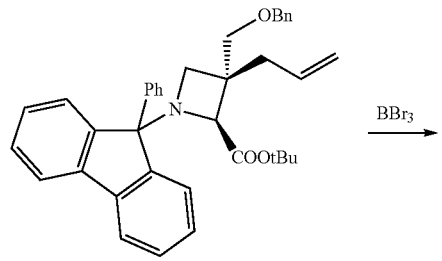

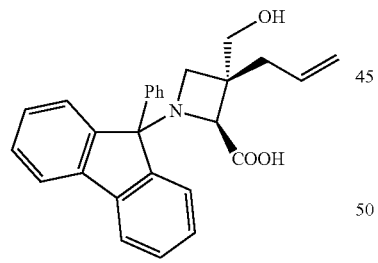

Boron tribromide (1.5 mL, 16 mmol) was added dropwise to the stirred solution of (2S,3S)-tert-butyl 3-allyl-3-((benzyloxy)methyl)-1-(9-phenyl-9H-fluoren-9-yl)azetidine-2-carboxylate (2.5 g, 4.5 mmol) in DCM (0.20 L) under N₂ at −78° C. over 10 min, and the mixture was stirred for 30 min at −78° C. under N₂. The reaction mixture was quenched with brine and extracted with DCM.

The combined organic phase was washed with brine, dried over anhydrous Na₂SO₄, filtered and concentrated. The residue was dissolved in EtOAc and diluted with hexanes, and the precipitate was filtered to give (2S,3S)-3-allyl-3-(hydroxymethyl)-1-(9-phenyl-9H-fluoren-9-yl)azetidine-2-carboxylic acid. LCMS ($C_{27}H_{26}NO_3^+$)(ES, m/z): 412 [M+H]⁺.

Step 2: (2S,3S)-3-allyl-3-formyl-1-(9-phenyl-9H-fluoren-9-yl)azetidine-2-carboxylic acid

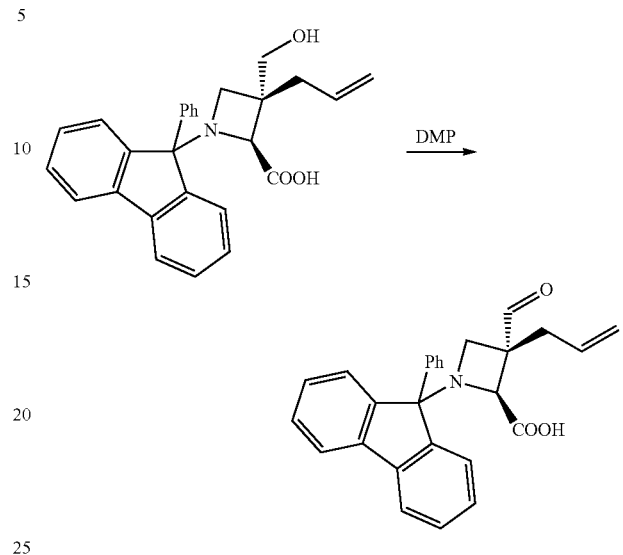

DMP (2.3 g, 5.5 mmol) was added to the stirred solution of (2S,3S)-3-allyl-3-(hydroxymethyl)-1-(9-phenyl-9H-fluoren-9-yl)azetidine-2-carboxylic acid (1.5 g, 3.7 mmol) in DCM (0.10 L), and the mixture was stirred for 2 h at 25° C. The reaction mixture was quenched with MeOH and water, and extracted with DCM. The combined organic phase was washed with brine, dried over anhydrous Na₂SO₄, filtered and concentrated. The residue was purified by silica gel column chromatography (MeOH in DCM) to give (2S,3S)-3-allyl-3-formyl-1-(9-phenyl-9H-fluoren-9-yl)azetidine-2-carboxylic acid. LCMS ($C_{27}H_{24}NO_3^+$)(ES, m/z): 410 [M+H]⁺.

Step 3: (2S,3S)-3-allyl-3-(I-hydroxyethyl)-1-(9-phenyl-9H-fluoren-9-yl)azetidine-2-carboxylic acid

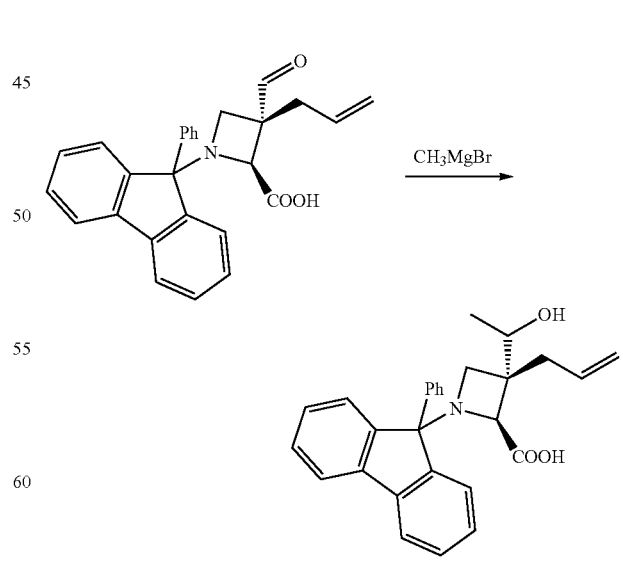

Methylmagnesium bromide (3 M in Me-THF, 4.9 mL, 14.7 mmol) was added to the stirred solution of (2S,3S)-3-allyl-3-formyl-1-(9-phenyl-9H-fluoren-9-yl)azetidine-2- carboxylic acid (0.60 g, 1.5 mmol) in THF (30 mL) under N₂, and the mixture was stirred for 1 h at −78° C. The reaction mixture was quenched with saturated aqueous NH₄Cl and extracted with EtOAc. The combined organic phase was washed with brine, dried over anhydrous Na₂SO₄, filtered and concentrated. The residue was purified by silica gel column chromatography (EtOAc in hexanes) to give (2S,3S)-3-allyl-3-(1-hydroxyethyl)-1-(9-phenyl-9H-fluoren-9-yl)azetidine-2-carboxylic acid. LCMS (C₂₈H₂₈NO₃⁺) (ES, m/z): 426 [M+H]⁺.

Step 4: (2S,3S)-3-acetyl-3-allyl-1-(9-phenyl-9H-fluoren-9-yl)azetidine-2-carboxylic acid

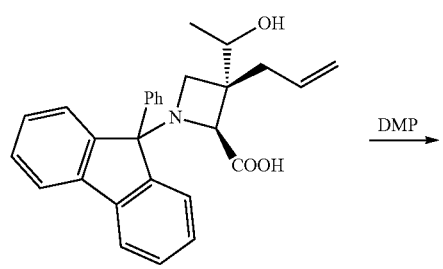

DMP (0.60 g, 1.4 mmol) was added to the stirred solution of (2S,3S)-3-allyl-3-(1-hydroxyethyl)-1-(9-phenyl-9H-fluoren-9-yl)azetidine-2-carboxylic acid (0.40 g, 0.94 mmol) in DCM (20 mL), and the mixture was stirred for 1 h at 20° C. The reaction mixture was quenched with MeOH and water, and extracted with DCM. The combined organic phase was washed with brine, dried over anhydrous Na₂SO₄, filtered and concentrated to give crude (2S,3S)-3-acetyl-3-allyl-1-(9-phenyl-9H-fluoren-9-yl)azetidine-2-carboxylic acid, which was used in the next step directly without further purification. LCMS (C₂₈H₂₆NO₃⁺)(ES, m/z): 424 [M+H]⁺.

Step 5: (2S,3S)-3-allyl-3-(2-hydroxypropan-2-yl)-1-(9-phenyl-9H-fluoren-9-yl)azetidine-2-carboxylic acid

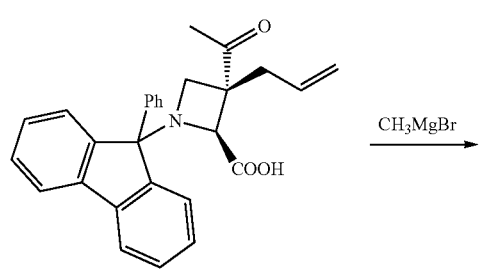

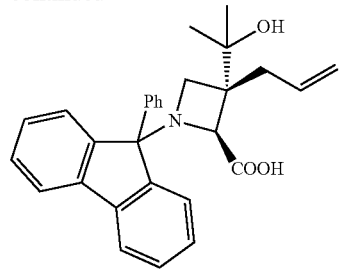

(2S,3S)-3-acetyl-3-allyl-1-(9-phenyl-9H-fluoren-9-yl)azetidine-2-carboxylic acid (0.35 g, 0.83 mmol) was added to the stirred solution of methylmagnesium bromide (3 M in Me-THF, 5.5 mL, 17 mmol) under N₂, and the mixture was stirred for 0.5 h at 20° C. The reaction mixture was quenched with saturated aqueous NH₄Cl and extracted with EtOAc. The combined organic phase was washed with brine, dried over anhydrous Na₂SO₄, filtered and concentrated. The residue was purified by silica gel column chromatography (EtOAc in hexanes) to give (2S,3S)-3-allyl-3-(2-hydroxypropan-2-yl)-1-(9-phenyl-9H-fluoren-9-yl)azetidine-2-carboxylic acid. LCMS (C₂₉H₃₀NO₃⁺)(ES, m/z): 440 [M+H]⁺.

Step 6: (2S,3S)-3-(2-hydroxypropan-2-yl)-1-(9-phenyl-9H-fluoren-9-yl)-3-(3-(4,4,5,5-tetramethyl-1,3,2-dioxaborolan-2-yl)propyl)azetidine-2-carboxylic acid

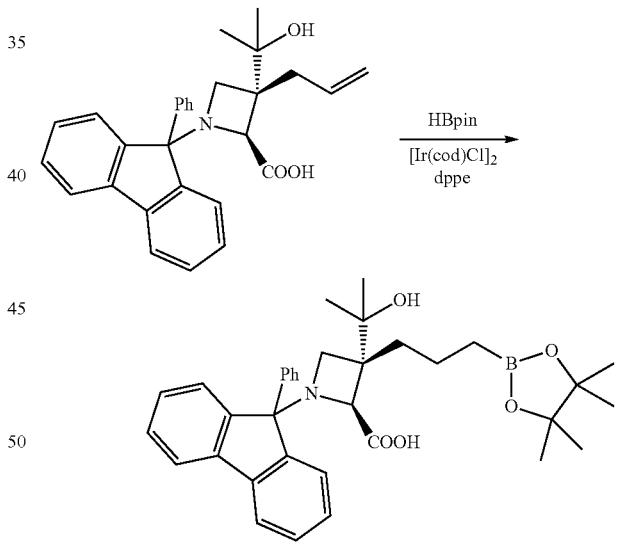

4,4,5,5-Tetramethyl-1,3,2-dioxaborolane (0.094 mL, 0.51 mmol) was added to the stirred solution of [Ir(cod)Cl]₂ (6.9 mg, 10 μmol) and 1,2-bis(diphenylphosphino)ethane (8.2 mg, 0.020 mmol) in DCM (20 mL) at 0° C. under N₂, followed by a solution of (2S,3S)-3-allyl-3-(2-hydroxypropan-2-yl)-1-(9-phenyl-9H-fluoren-9-yl)azetidine-2-carboxylic acid (45 mg, 0.10 mmol) in DCM (5.0 mL) at 0° C., and the mixture was stirred at 0° C. under N₂ for 1 h, then at 20° C. for 19 h. The reaction mixture was concentrated, and the residue was purified by RP-HPLC [C18 column, water (0.1% TFA)-CH₃CN] to give (2S,3S)-3-(2-hydroxypropan-2-yl)-1-(9-phenyl-9H-fluoren-9-yl)-3-(3-(4,4,5,5-tetram-

263 ethyl-1,3,2-dioxaborolan-2-yl)propyl)azetidine-2-carboxylic acid. LCMS (C$_{35}$H$_{43}$BNO$_5$$^+$)(ES, m/z): 568 [M+H]$^+$.

Step 7: (2S,3S)-3-(3-boronopropyl)-3-(2-hydroxypropan-2-yl)azetidine-2-carboxylic acid

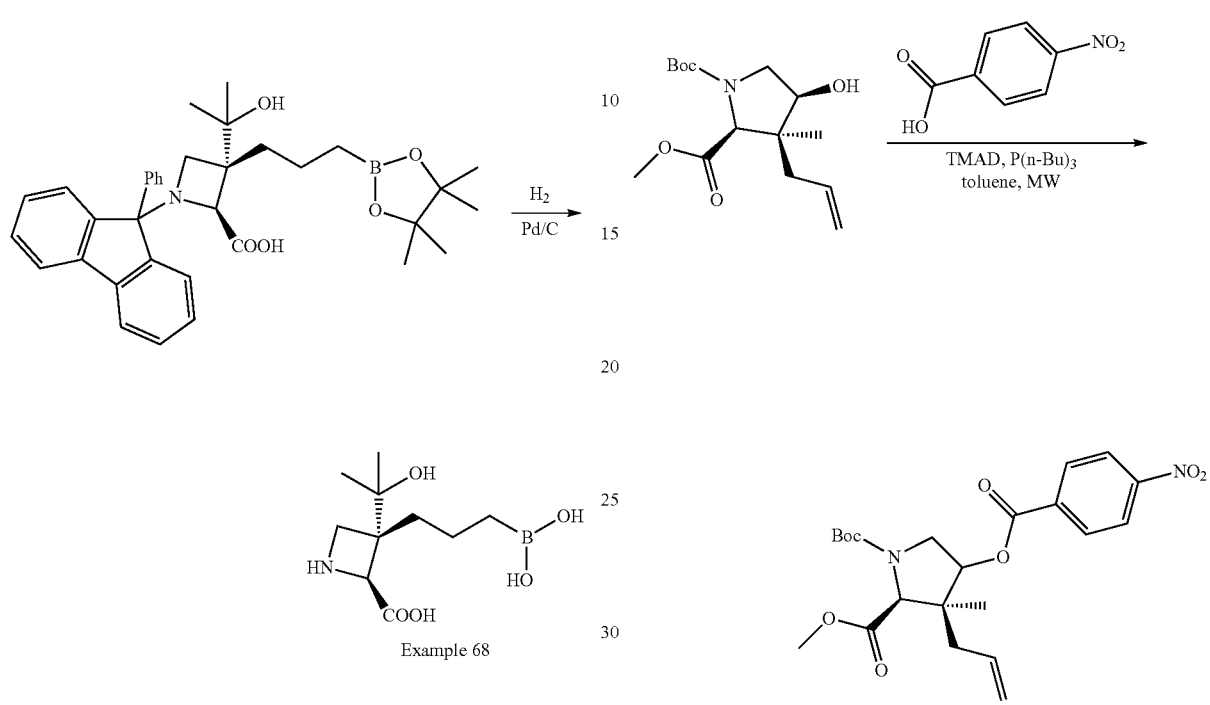

Example 68

10% Pd/C (60 mg, 0.056 mmol) was added to the stirred solution of (2S,3S)-3-(2-hydroxypropan-2-yl)-1-(9-phenyl-9H-fluoren-9-yl)-3-(3-(4,4,5,5-tetramethyl-1,3,2-dioxaborolan-2-yl)propyl)azetidine-2-carboxylic acid (40 mg, 0.070 mmol) in MeOH (10 mL) and acetic acid (0.20 mL) under N$_2$, and the mixture was degassed and backfilled with H$_2$ (three times), then stirred under H$_2$ (Pressure: 15 psi) at 20° C. for 0.5 h. The reaction mixture was filtered and concentrated, and the residue was purified by RP-HPLC [C18 column, water (10 mM NH$_4$HCO$_3$)-acetonitrile] to give (2S,3S)-3-(3-boronopropyl)-3-(2-hydroxypropan-2-yl)azetidine-2-carboxylic acid as a free base. LCMS (C$_{10}$H$_{19}$BNO$_4$$^+$)(ES, m/z): 228 [M+H—H$_2$O]$^+$. $^1$H NMR (500 MHz, D$_2$O) δ 4.65-4.63 (m, 1H), 3.94-3.83 (m, 1H), 3.78-3.68 (m, 1H), 1.59-1.32 (m, 4H), 1.16-1.12 (br s, 3H), 1.10-1.02 (br s, 3H), 0.75-0.59 (m, 2H).

Example 69: (2S,3S,4S)-3-(3-boronopropyl)-4-hydroxy-3-methylpyrrolidine-2-carboxylic acid

264

Step 1: 1-(tert-butyl) 2-methyl (2S,3S)-3-allyl-3-methyl-4-((4-nitrobenzoyl)oxy)pyrrolidine-1,2-dicarboxylate 4-Nitrobenzoic acid (0.34 g, 2.0 mmol) was added to the stirred solution of (2S,3S,4S)-1-tert-butyl 2-methyl 3-allyl-4-hydroxy-3-methylpyrrolidine-1,2-dicarboxylate (0.30 g, 1.0 mmol), tri-n-butylphosphine (0.61 g, 3.0 mmol), TMAD (Tetramethylazodicarboxamide)(0.52 g, 3.0 mmol) in toluene (4.0 mL) at 20° C., and the resulting mixture was heated in a microwave reactor with stirring at 120° C. for 1 h. The reaction mixture was filtered and concentrated, and the residue was purified by RP-HPLC [C18 column, water (0.1% TFA)-CH$_3$CN] to give (2S,3S)-1-tert-butyl 2-methyl 3-allyl-3-methyl-4-((4-nitrobenzoyl)oxy)pyrrolidine-1,2-dicarboxylate. LCMS (C$_{17}$H$_{21}$N$_2$O$_6$)(ES, m/z): 349 [M-CO$_2$C$_4$H$_8$+H]$^+$.

Step 2: 1-(tert-butyl) 2-methyl (2S,3S)-3-methyl-4-((4-nitrobenzoyl)oxy)-3-(3-(4,4,5,5-tetramethyl-1,3,2-dioxaborolan-2-yl)propyl)pyrrolidine-1,2-dicarboxylate

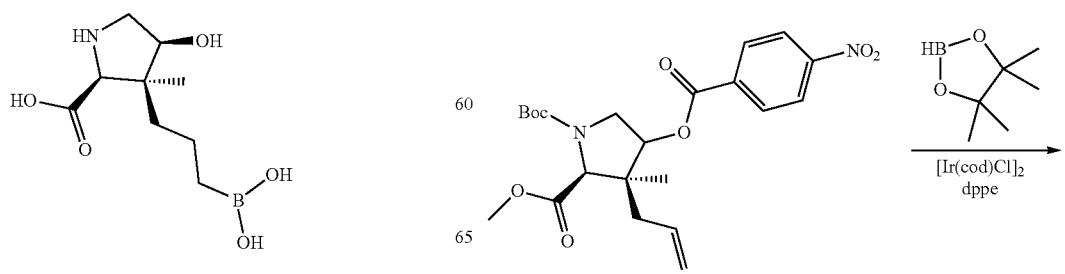

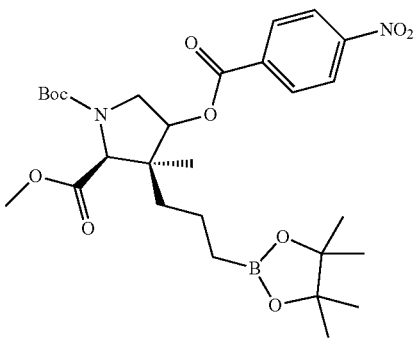

[Ir(cod)Cl]$_2$ (9.0 mg, 0.013 mmol) was added to the stirred solution of (2S,3S)-1-tert-butyl 2-methyl 3-allyl-3-methyl-4-((4-nitrobenzoyl)oxy)pyrrolidine-1,2-dicarboxylate (0.12 g, 0.27 mmol), 4,4,5,5-tetramethyl-1,3,2-dioxaborolane (0.10 g, 0.80 mmol) and 1,2-bis(diphenylphosphinyl) ethane (11 mg, 0.027 mmol) in DCM (3.0 mL) under N$_2$, and the resulting mixture was stirred at 25° C. for 10 h under N$_2$. The reaction mixture was filtered and concentrated, and the residue was purified by RP-HPLC [C18 column, water (0.1% TFA)-CH$_3$CN] to give (2S,3S)-1-tert-butyl 2-methyl 3-methyl-4-((4-nitrobenzoyl)oxy)-3-(3-(4,4,5,5-tetramethyl-1,3,2-dioxaborolan-2-yl)propyl)pyrrolidine-1,2-dicarboxylate which contained boronic acid. LCMS (C$_{23}$H$_{34}$BN$_2$O$_8$)(ES, m/z): 477 [M-CO$_2$C$_4$H$_8$+H]$^+$.

Step 3: (2S,3S)-3-(3-boronopropyl)-4-hydroxy-3-methylpyrrolidine-2-carboxylic acid

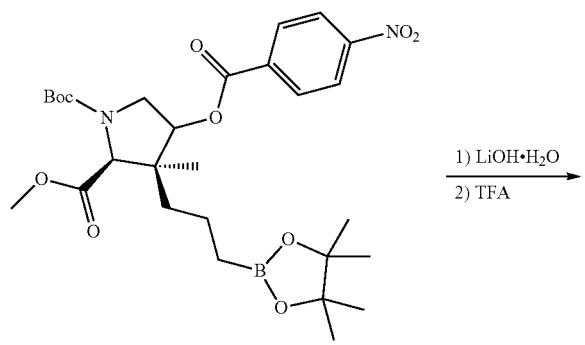

Example 69

A mixture of (2S,3S)-1-tert-butyl 2-methyl 3-methyl-4-((4-nitrobenzoyl)oxy)-3-(3-(4,4,5,5-tetramethyl-1,3,2-dioxaborolan-2-yl)propyl)pyrrolidine-1,2-dicarboxylate (60 mg, 0.10 mmol) and LiOH H$_2$O (25 mg, 1.0 mmol) in water (3.0 mL) was stirred at 20° C. for 12 h. The reaction mixture was acidified by TFA to pH ~4, then stirred for another 12 h, and concentrated. The residue was purified by RP-HPLC [C18 column, water (20 mM HFBA and 0.1% TFA)-acetonitrile] to give (2S,3S,4R)-3-(3-boronopropyl)-4-hydroxy-3-methylpyrrolidine-2-carboxylic acid as a HFBA salt. The stereochemistry was assigned by 2D NMR. LCMS (C$_9$H$_{17}$BNO$_4$$^+$)(ES, m/z): 214 [M−H$_2$O+H]; $^1$H NMR (500 MHz, D$_2$O) δ 4.09-3.95 (m, 1H), 3.81 (s, 1H), 3.52 (dd, J=5.5, 12.7 Hz, 1H), 3.24 (br d, J=12.1 Hz, 1H), 1.51-1.20 (m, 4H), 1.06-1.05 (m, 3H), 0.65 (br s, 2H).

Example 70: (2S,3R,4R)-4-((S)-2-amino-3-methylbutanamido)-3-(3-boronopropyl)-3-methylpyrrolidine-2-carboxylic acid

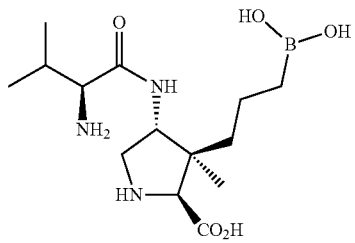 [SMILES: CC(C)[C@H](N)C(=O)N[C@H]1CN[C@H](C(=O)O)[C@]1(C)CCCB(O)O]

Step 1: 1-(tert-butyl) 2-methyl (2S,3S,4S)-3-allyl-4-(((chloromethyl)sulfonyl)oxy)-3-methylpyrrolidine-1,2-dicarboxylate

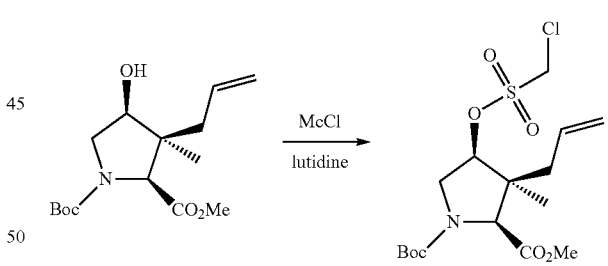

Chloromethanesulfonyl chloride (1.6 mL, 17 mmol) was added dropwise to the stirred solution of (2S,3S,4S)-1-tert-butyl 2-methyl 3-allyl-4-hydroxy-3-methylpyrrolidine-1,2-dicarboxylate (1.3 g, 4.3 mmol) and 2,6-lutidine (5.1 mL, 43 mmol) in DCM (25 mL) at 0° C., and the resulting mixture was stirred at 0° C. for 3 h and then at 20° C. for 13 h. The reaction mixture was diluted with DCM and 1 N HCl in water, and the organic phase was separated, washed with brine, and concentrated. The residue was purified by flash silica gel chromatography (EtOAc in hexanes) to give (2S,3S,4S)-1-tert-butyl 2-methyl 3-allyl-4-(((chloromethyl)sulfonyl)oxy)-3-methylpyrrolidine-1,2-dicarboxylate. LCMS (Cl$_{11}$H$_{19}$ClNO$_5$S$^+$)(ES, m/z): 312 [M+H−CO$_2$C$_4$H$_8$]$^+$.

Step 2: 1-(tert-butyl) 2-methyl (2S,3S,4R)-3-allyl-4-azido-3-methylpyrrolidine-1,2-dicarboxylate

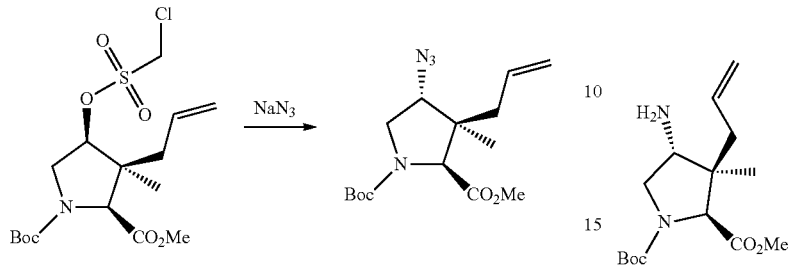

Sodium azide (2.8 g, 43 mmol) was added to a mixture of (2S,3S,4S)-1-tert-butyl 2-methyl 3-allyl-4-(((chloromethyl)sulfonyl)oxy)-3-methylpyrrolidine-1,2-dicarboxylate (1.6 g, 3.9 mmol) in DMF (25 mL), and the resulting mixture was stirred at 80° C. for 15 h. The reaction mixture was diluted with brine and extracted with EtOAc. The combined organic phase was washed with brine, dried over anhydrous $Na_2SO_4$, filtered and concentrated. The residue was purified by silica gel chromatography (EtOAc in hexanes) to give (2S,3S,4R)-1-tert-butyl 2-methyl 3-allyl-4-azido-3-methylpyrrolidine-1,2-dicarboxylate. LCMS ($C_{10}H_{17}N_{4O2}$)(ES, m/z): 325 [M+H—$CO_2C_4H_8$]$^+$.

Step 3: 1-(tert-butyl) 2-methyl (2S,3R,4R)-3-allyl-4-amino-3-methylpyrrolidine-1,2-dicarboxylate

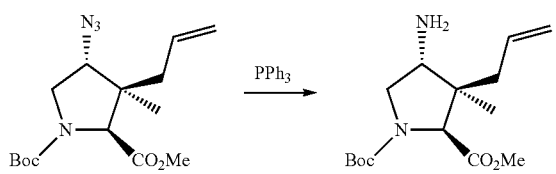 [SMILES: C=CC[C@]1(C)[C@@H](N=[N+]=[N-])CN(C(=O)OC(C)(C)C)[C@@H]1C(=O)OC ; C=CC[C@]1(C)[C@@H](N)CN(C(=O)OC(C)(C)C)[C@@H]1C(=O)OC ; "PPh3"]

Triphenylphosphine (0.12 g, 0.46 mmol) was added to the stirred solution of (2S,3S,4R)-1-tert-butyl 2-methyl 3-allyl-4-azido-3-methylpyrrolidine-1,2-dicarboxylate (0.10 g, 0.31 mmol) in THF (2.0 mL) and water (1.0 mL) at 0° C. under $N_2$, and the resulting mixture was stirred at 50° C. for 13 h. The reaction mixture was diluted with EtOAc and water, and the organic phase was dried over anhydrous $Na_2SO_4$, filtered and concentrated to give the crude (2S,3R,4R)-1-tert-butyl 2-methyl 3-allyl-4-amino-3-methylpyrrolidine-1,2-dicarboxylate, which was used in the next step directly without further purification. LCMS ($C_{10}H_{19}N_2O_2{}^+$)(ES, m/z): 199 [M+H—$CO_2C_4H_8$]$^+$.

Step 4: 1-(tert-butyl) 2-methyl (2S,3R,4R)-3-allyl-4-((S)-2-((tert-butoxycarbonyl)amino)-3-methylbutanamido)-3-methylpyrrolidine-1,2-dicarboxylate

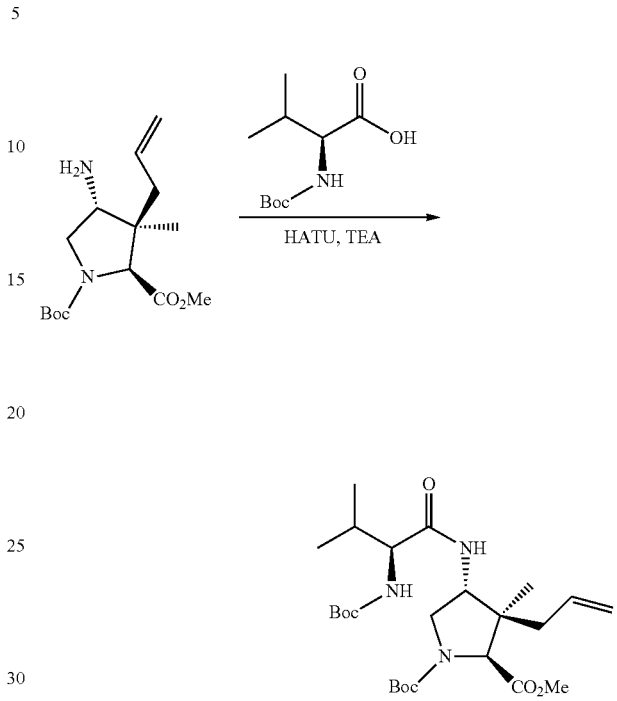

HATU (0.18 g, 0.46 mmol) was added to the stirred mixture of (2S,3R,4R)-1-tert-butyl 2-methyl 3-allyl-4-amino-3-methylpyrrolidine-1,2-dicarboxylate (92 mg, 0.31 mmol), (S)-2-((tert-butoxycarbonyl)amino)-3-methylbutanoic acid (87 mg, 0.40 mmol) and triethylamine (0.13 mL, 0.93 mmol) in DMF (2.0 mL) at 20° C., and the resulting mixture was stirred at 20° C. for 1 h. The reaction mixture was directly purified by RP-HPLC [C18 column, water (0.1% TFA)-$CH_3CN$] to give (2S,3R,4R)-1-tert-butyl 2-methyl 3-allyl-4-((S)-2-((tert-butoxycarbonyl)amino)-3-methylbutanamido)-3-methylpyrrolidine-1,2-dicarboxylate. LCMS ($C_{20}H_{36}N_3O_5{}^+$)(ES, m/z): 398 [M+H—$CO_2C_4H_8$]$^+$.

Step 5: 1-(tert-butyl) 2-methyl (2S,3R,4R)-4-((S)-2-((tert-butoxycarbonyl)amino)-3-methylbutanamido)-3-methyl-3-(3-(4,4,5,5-tetramethyl-1,3,2-dioxaborolan-2-yl)propyl)pyrrolidine-1,2-dicarboxylate

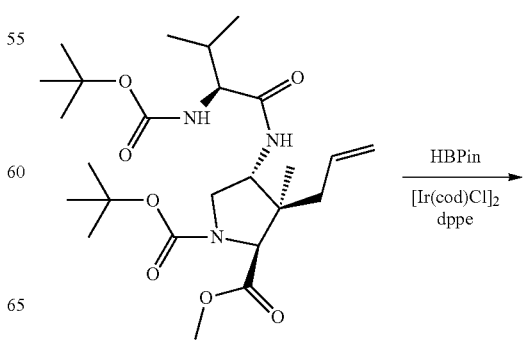

-continued

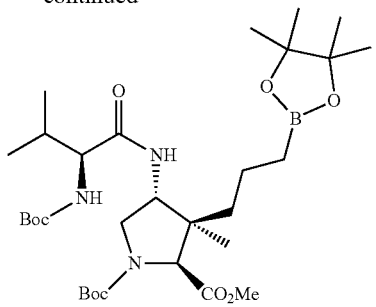

A solution of (2S,3R,4R)-1-tert-butyl 2-methyl 3-allyl-4-((S)-2-((tert-butoxycarbonyl)amino)-3-methylbutanamido)-3-methylpyrrolidine-1,2-dicarboxylate (80 mg, 0.16 mmol) in DCM (1.2 mL) was added to the stirred solution of 1,2-bis(diphenylphosphino)ethane (6.4 mg, 0.016 mmol), [Ir(cod)Cl]$_2$ (6.5 mg, 9.7 μmol) and 4,4,5,5-tetramethyl-1,3,2-dioxaborolane (0.12 mL, 0.80 mmol) in DCM (2.0 mL) under N$_2$ at 20° C., and the resulting mixture was stirred at 20° C. for 15 h under N$_2$. The reaction mixture was concentrated and the residue was purified by RP-HPLC [C18 column, water (0.1% TFA)-CH$_3$CN] to give (2S,3R,4R)-1-tert-butyl 2-methyl 4-((S)-2-((tert-butoxycarbonyl)amino)-3-methylbutanamido)-3-methyl-3-(3-(4,4,5,5-tetramethyl-1,3,2-dioxaborolan-2-yl)propyl)pyrrolidine-1,2-dicarboxylate. LCMS (C$_{31}$H$_{56}$BN$_3$O$_9$Na$^+$)(ES, m/z): 648 [M+Na]$^+$.

Step 6: (2S,3R,4R)-4-((S)-2-amino-3-methylbutanamido)-3-(3-boronopropyl)-3-methylpyrrolidine-2-carboxylic acid

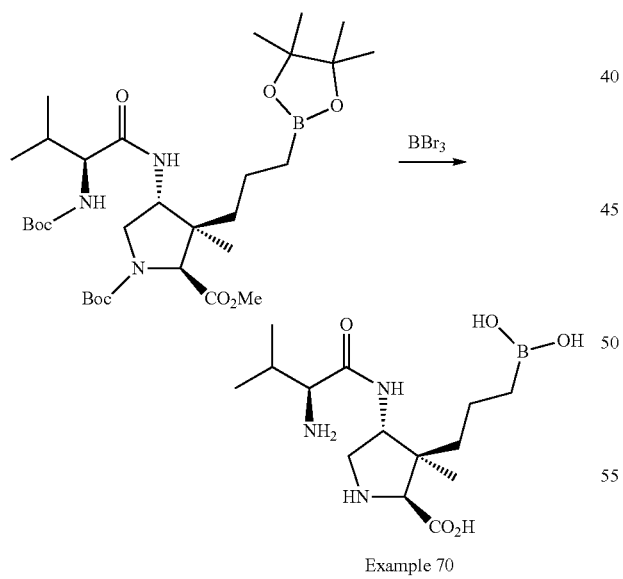

Example 70

Tribromoborane (10 mg, 0.040 mmol) was added to the stirred solution of (2S,3R,4R)-1-tert-butyl 2-methyl 4-((S)-2-((tert-butoxycarbonyl)amino)-3-methylbutanamido)-3-methyl-3-(3-(4,4,5,5-tetramethyl-1,3,2-dioxaborolan-2-yl)propyl)pyrrolidine-1,2-dicarboxylate (50 mg, 0.080 mmol) in DCM (1.0 mL) at 0° C., and the resulting mixture was stirred for 16 h. The reaction mixture was concentrated, and the residue was purified by RP-HPLC [C18 column, water (20 mM HFBA and 0.1% TFA)-CH$_3$CN] to give the (2S,3R,4R)-4-((S)-2-amino-3-methylbutanamido)-3-(3-boronopropyl)-1-(tert-butoxycarbonyl)-3-methylpyrrolidine-2-carboxylic acid as a HFBA salt. LCMS (C$_{14}$H$_{27}$BN$_3$O$_4$$^+$)(ES, m/z): 312 [M+H—H$_2$O]$^+$. $^1$H NMR (500 MHz, D$_2$O) δ 4.51-4.48 (m, 1H), 4.02 (s, 1H), 3.79-3.75 (m, 2H), 3.20-3.16 (m, 1H), 2.20-2.13 (m, 1H), 1.43-1.21 (m, 4H), 1.11 (s, 3H), 0.97 (d, J=7.0 Hz, 3H), 0.93 (d, J=6.9 Hz, 3H), 0.74-0.58 (m, 2H).

Example 71: (2S,3R,4R)-4-amino-3-(3-boronopropyl)-3-methylpyrrolidine-2-carboxylic acid

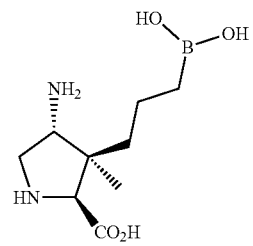

Step 1: (2S,3R,4R)-4-amino-3-(3-boronopropyl)-3-methylpyrrolidine-2-carboxylic acid

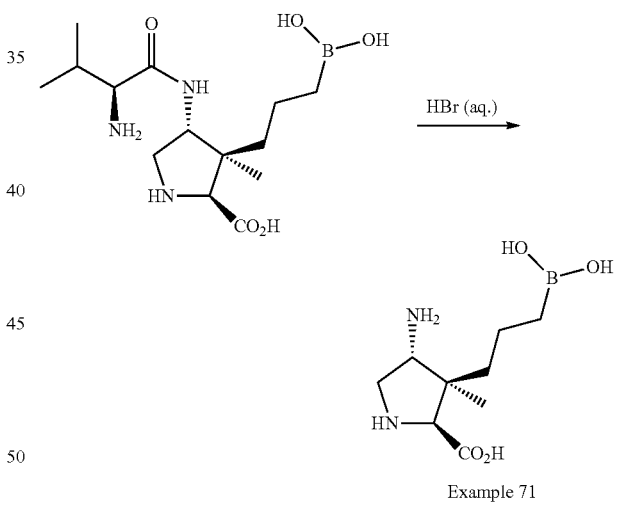

Example 71

A mixture of (2S,3R,4R)-4-((S)-2-amino-3-methylbutanamido)-3-(3-boronopropyl)-3-methylpyrrolidine-2-carboxylic acid (20 mg, 0.061 mmol) and 12 N HCl in water (1.0 mL, 12 mmol) was stirred at 100° C. for 24 h. The resulting mixture was concentrated, dissolved in 48% HBr in water (1.5 mL, 13 mmol) and stirred at 130° C. for 48 h. The reaction mixture was concentrated, and the residue was purified by RP-HPLC [C18 column, water (20 mM HFBA and 0.1% TFA)-CH$_3$CN] to give (2S,3R,4R)-4-amino-3-(3-boronopropyl)-3-methylpyrrolidine-2-carboxylic acid as a HFBA salt. LCMS (C$_9$H$_{18}$BN$_2$O$_3$$^+$)(ES, m/z): 213 [M+H—H$_2$O]$^+$; $^1$H NMR (400 MHz, D$_2$O) δ 4.26 (s, 1H), 4.03-3.95 (m, 2H), 3.92-3.89 (m, 1H), 1.50-1.28 (m, 4H), 1.01-0.95 (m, 3H), 0.78-0.68 (m, 2H).

Example 72: (2S,3R)-3-(3-boronopropyl)-2,3-dimethylpyrrolidine-2-carboxylic acid

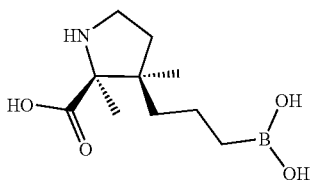 [SMILES: C[C@@]1(CCCB(O)O)CCN[C@]1(C)C(=O)O]

Step 1: (3R)-1-tert-butyl 2-methyl 3-allyl-2,3-dimethylpyrrolidine-1,2-dicarboxylate

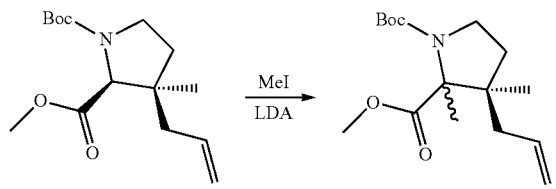 [SMILES: "MeI" ; C=CC[C@]1(C)CCN(C(=O)OC(C)(C)C)[C@@H]1C(=O)OC ; "LDA" ; C=CC[C@]1(C)CCN(C(=O)OC(C)(C)C)C1(C)C(=O)OC]

n-BuLi (2.5 M in hexanes, 2.0 mL, 5.0 mmol) was added to the stirred solution of diisopropylamine (0.70 mL, 4.8 mmol) in THF (2.0 mL) at −78° C. under $N_2$. After stirring for 30 min, (2S,3R)-1-tert-butyl 2-methyl 3-allyl-3-methylpyrrolidine-1,2-dicarboxylate (0.50 g, 1.8 mmol) in THF (2.0 mL) was added to the mixture dropwise at −78° C., and the resulting mixture was stirred for 30 min at −70° C., then allowed to warm to 15° C. over 30 min. MeI (6.0 mL, 96 mmol) was added at −78° C., and the mixture was allowed to warm to 15° C. and stirred for 18 h. The reaction mixture was quenched with saturated aqueous $NH_4Cl$ and extracted with EtOAc. The combined organic phase was washed with brine, dried over anhydrous $Na_2SO_4$, filtered and concentrated. The residue was purified by silica gel chromatography (EtOAc in hexanes) to give (3R)-1-tert-butyl 2-methyl 3-allyl-2,3-dimethylpyrrolidine-1,2-dicarboxylate as a mixture of diastereomers. LCMS ($C_{16}H_{28}NO_4^+$)(ES, m/z): 298 [M+H]$^+$.

Step 2: (3R)-methyl 3-allyl-2,3-dimethylpyrrolidine-2-carboxylate

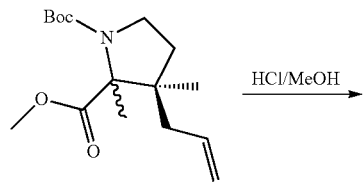

A mixture of (2S,3R)-1-tert-butyl 2-methyl 3-allyl-2,3-dimethylpyrrolidine-1,2-dicarboxylate (0.30 mg, 1.0 mmol) and 4 N HCl in MeOH (3.0 mL, 12 mmol) in DCM (3.0 mL) was stirred at 20° C. for 3 h, then concentrated to give crude (3R)-methyl 3-allyl-2,3-dimethylpyrrolidine-2-carboxylate, which was used in the next step directly without further purification. LCMS ($C_{11}H_{20}NO_2^+$)(ES, m/z): 198 [M+H]$^+$.

Step 3: (2S,3R)-1-benzyl 2-methyl 3-allyl-2,3-dimethylpyrrolidine-1,2-dicarboxylate

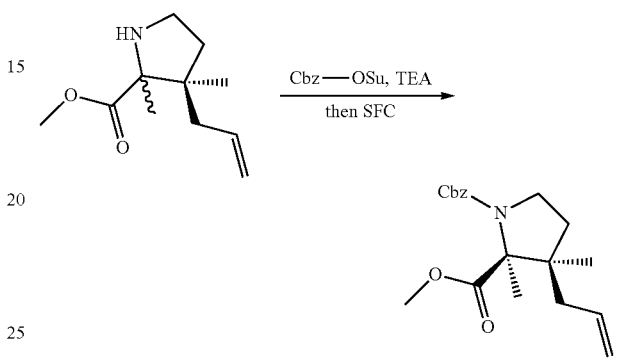

Triethylamine (0.50 mL, 3.6 mmol) was added to a solution of (2S,3R)-methyl 3-allyl-2,3-dimethylpyrrolidine-2-carboxylate (0.28 g, 1.4 mmol) in DCM (3.0 mL) at 20° C., followed by the addition of N-(benzyloxycarbonyloxy)succinimide (0.42 g, 1.7 mmol) under $N_2$. The resulting mixture was stirred at 20° C. for 18 h, then quenched with saturated aqueous $NaHCO_3$ and extracted with DCM. The combined organic phase was washed with brine, dried over anhydrous $Na_2SO_4$, filtered and concentrated. The residue was purified by RP-HPLC [C18 column, water (0.1% HCl)—$CH_3CN$] to give (3R)-1-benzyl 2-methyl 3-allyl-2,3-dimethylpyrrolidine-1,2-dicarboxylate as a mixture of diastereomers, which was resolved by Chiral-SFC [Column: AD-3 (250 mm*50 mm,10 μm), Mobile phase: A: $CO_2$, B: MeOH (0.1% $NH_3.H_2O$), Gradient: 15% of B in 3.5 min, and hold 15% of B for 1 min, Flow Rate (mL/min) 60, Column temperature: 40° C.] to give (2S,3R)-1-benzyl 2-methyl 3-allyl-2,3-dimethylpyrrolidine-1,2-dicarboxylate ($t_r$=2.844 min). The stereochemistry was assigned by 2D NMR. LCMS ($C_{19}H_{26}NO_4^+$)(ES, m/z): 332 [M+H]; $^1$H NMR (400 MHz, $CD_3OD$) δ 7.44-7.24 (m, 5H), 5.89-5.73 (m, 1H), 5.19-4.96 (m, 4H), 3.72-3.64 (m, 3H), 3.54-3.45 (m, 2H), 2.09-1.84 (m, 3H), 1.66-1.61 (m, 1H), 1.56-1.43 (m, 3H), 1.04 (s, 3H).

Step 4: (2S,3R)-1-benzyl 2-methyl 2,3-dimethyl-3-(3-(4,4,5,5-tetramethyl-1,3,2-dioxaborolan-2-yl)propyl)pyrrolidine-1,2-dicarboxylate

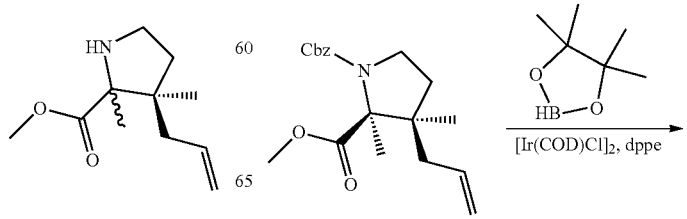

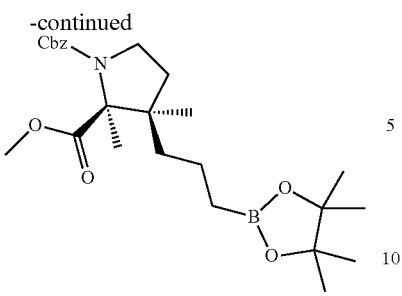

4,4,5,5-Tetramethyl-1,3,2-dioxaborolane (0.14 mL, 0.97 mmol) and (2S,3R)-1-benzyl 2-methyl 3-allyl-2,3-dimethylpyrrolidine-1,2-dicarboxylate (60 mg, 0.18 mmol) in DCM (2.0 mL) was added to the stirred solution of [Ir(cod)Cl]$_2$ (6.0 mg, 8.9 μmol) and 1,2-bis(diphenylphosphino)ethane (5.0 mg, 0.013 mmol) in DCM (2.0 mL) under N$_2$, and the resulting mixture was stirred for 15 h at 20° C. The reaction mixture was quenched with methanol, and concentrated. The residue was purified by RP-HPLC [C18 column, water (0.1% TFA)-CH$_3$CN] to give (2S,3R)-1-benzyl 2-methyl 2,3-dimethyl-3-(3-(4,4,5,5-tetramethyl-1,3,2-dioxaborolan-2-yl)propyl)pyrrolidine-1,2-dicarboxylate, which contained minor corresponding boronic acid. LCMS (C$_{25}$H$_{39}$BNO$_6^+$)(ES, m/z): 460 [M+H]$^+$.

Step 5: (2S,3R)-3-(3-boronopropyl)-2,3-dimethylpyrrolidine-2-carboxylic acid

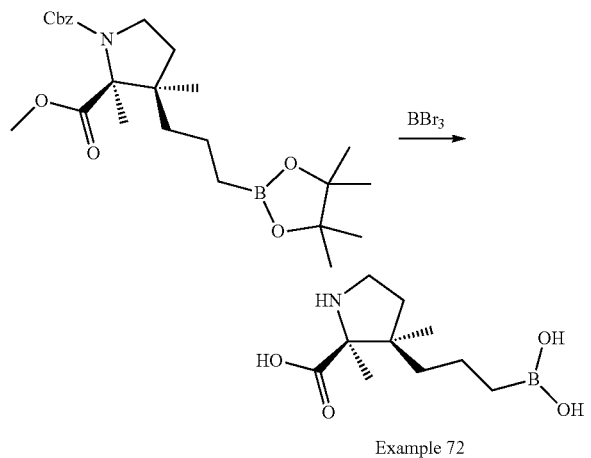

Example 72

Boron tribromide (0.40 mL, 4.2 mmol) in DCM (2.5 mL) was added dropwise to the stirred solution of (2S,3R)-1-benzyl 2-methyl 2,3-dimethyl-3-(3-(4,4,5,5-tetramethyl-1,3,2-dioxaborolan-2-yl)propyl)pyrrolidine-1,2-dicarboxylate (60 mg, 0.13 mmol) in DCM (2.5 mL) at 0° C. under N$_2$.

The resulting mixture was stirred at 25° C. for 14 h, then concentrated. The residue was purified by RP-HPLC [C18 column, water (20 mM HFBA and 0.1% TFA)-CH$_3$CN] to give (2S,3R)-3-(3-boronopropyl)-2,3-dimethylpyrrolidine-2-carboxylic acid as a HFBA salt. LCMS (C$_{10}$H$_{19}$BNO$_3$) (ES, m/z): 212 [M+H—H$_2$O]$^+$. $^1$H NMR (400 MHz, D$_2$O) δ 3.43-3.25 (m, 2H), 2.12-1.99 (m, 1H), 1.97-1.86 (m, 1H), 1.48 (s, 3H), 1.46-1.37 (m, 1H), 1.35-1.14 (m, 3H), 1.06 (s, 3H), 0.70 (br t, J=7.1 Hz, 2H).

Example 73: (2S,3S,4R)-3-(3-boronopropyl)-4-hydroxy-2,3-dimethylpyrrolidine-2-carboxylic acid

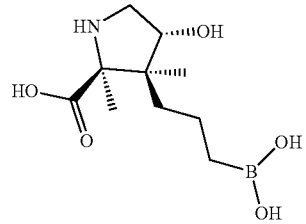 [SMILES: C[C@]1(C(=O)O)NC[C@H](O)[C@@]1(C)CCCB(O)O]

Step 1: (2S,3S)-3-allyl-1-(tert-butoxycarbonyl)-3-methyl-4-oxopyrrolidine-2-carboxylic acid

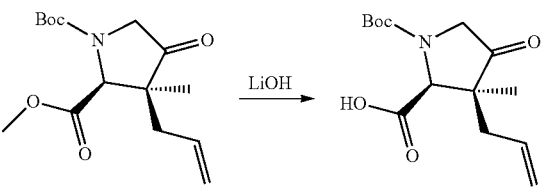

1 N LiOH in water (13 mL, 13 mmol) was added to the stirred solution of (2S,3S)-1-tert-butyl 2-methyl 3-allyl-3-methyl-4-oxopyrrolidine-1,2-dicarboxylate (2.0 g, 6.7 mmol) in THF (20 mL) at 20° C., and the mixture was stirred for 12 h. The reaction mixture was acidified by acetic acid to pH ~6, then diluted with water and extracted with EtOAc. The combined organic phase was washed with brine, dried over anhydrous Na$_2$SO$_4$, filtered and concentrated to give crude (2S,3S)-3-allyl-1-(tert-butoxycarbonyl)-3-methyl-4-oxopyrrolidine-2-carboxylic acid, which was used in the next step directly without further purification. LCMS (C$_9$H$_{14}$NO$_3^+$)(ES, m/z): 184 [M+H—CO$_2$C$_4$H$_8$]$^+$.

Step 2: (2S,3S,4R)-3-allyl-1-(tert-butoxycarbonyl)-4-hydroxy-3-methylpyrrolidine-2-carboxylic acid

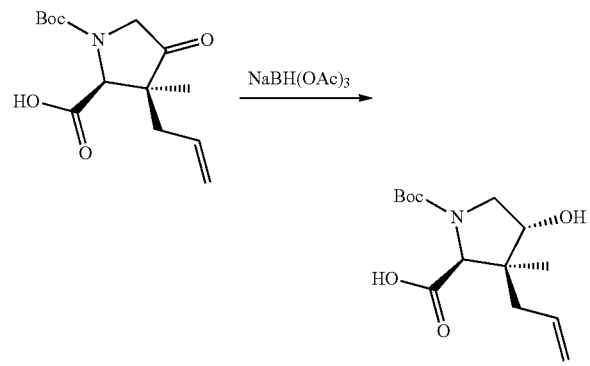

NaBH(OAc)$_3$ (2.2 g, 11 mmol) was added to the stirred solution of (2S,3S)-3-allyl-1-(tert-butoxycarbonyl)-3-methyl-4-oxopyrrolidine-2-carboxylic acid (2.0 g, 7.1 mmol) and acetic acid (0.40 mL, 7.1 mmol) in DCE (30 mL) at 0° C., and the mixture was allowed to warm to 25° C. and stirred for 15 h. The reaction mixture was quenched with water and extracted with DCM, and the combined organic phase was washed with brine, dried over anhydrous $Na_2SO_4$, filtered and concentrated. The residue was purified by RP-HPLC [C18 column, water (0.1% TFA)-$CH_3CN$] to give (2S,3S,4R)-3-allyl-1-(tert-butoxycarbonyl)-4-hydroxy-3-methylpyrrolidine-2-carboxylic acid.

The stereochemistry was assigned by 2D NMR. LCMS ($C_{10}H_{16}NO_3^+$)(ES, m/z): 186 [M+H—$CO_2C_4H_8$]$^+$; $^1$H NMR (500 MHz, $CD_3OD$) δ 5.99-5.86 (m, 1H), 5.10-5.03 (m, 2H), 4.14-4.03 (m, 1H), 4.00-3.95 (m, 1H), 3.76-3.68 (m, 1H), 3.28-3.22 (m, 1H), 2.24-2.16 (m, 1H), 2.11-2.01 (m, 1H), 1.50-1.37 (m, 9H), 1.14-1.05 (m, 3H).

Step 3: (2S,3S,4R)-1-tert-butyl 2-methyl 3-allyl-4-methoxy-3-methylpyrrolidine-1,2-dicarboxylate

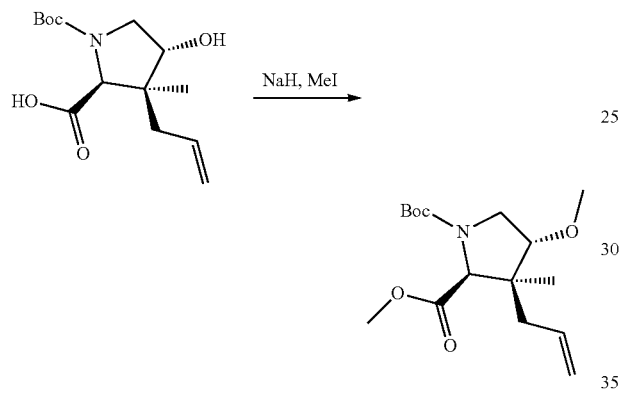

NaH (60% in mineral oil, 0.45 g, 11 mmol) was added to the stirred solution of (2S,3S,4R)-3-allyl-1-(tert-butoxycarbonyl)-4-hydroxy-3-methylpyrrolidine-2-carboxylic acid (0.50 g, 1.8 mmol) in DMF (5.0 mL), and the mixture was stirred at 0° C. for 0.5 h. Then MeI (2.1 mL, 34 mmol) was added, and the mixture was allowed to warm to 25° C. and stirred for 15 h. The reaction mixture was quenched by saturated aqueous $NH_4Cl$, and extracted with EtOAc. The combined organic phase was washed with 10% LiCl in water, dried over anhydrous $Na_2SO_4$, filtered and concentrated.

The residue was purified by silica gel chromatography (EtOAc in hexanes) to give (2S,3S,4R)-1-tert-butyl 2-methyl 3-allyl-4-methoxy-3-methylpyrrolidine-1,2-dicarboxylate. LCMS ($C_{16}H_{28}NO_5^+$) (ES, m/z): 314 [M+H]$^+$.

Step 4: (2S,3S,4R)-1-tert-butyl 2-methyl 3-allyl-4-methoxy-2,3-dimethylpyrrolidine-1,2-dicarboxylate

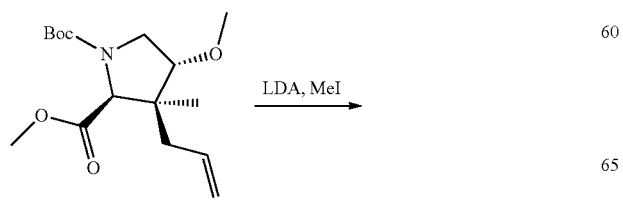

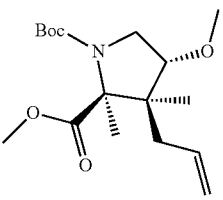

n-BuLi (2.5M in hexanes, 3.4 mL, 8.4 mmol) was added to the stirred solution of diisopropylamine (1.2 mL, 8.4 mmol) in THF (5.0 mL) at −78° C. under $N_2$, and the mixture was stirred for 0.5 h at −78° C. (2S,3S,4R)-1-tert-butyl 2-methyl 3-allyl-4-methoxy-3-methylpyrrolidine-1,2-dicarboxylate (0.75 g, 2.4 mmol) in THF (5.0 mL) was added at −78° C., and the resulting mixture was stirred for 30 min, followed by addition of iodomethane (8.0 mL, 0.13 mol) at −78° C.

The reaction mixture was allowed to warm to 25° C. and stirred for 12 h, then quenched with saturated aqueous $NH_4Cl$ and extracted with EtOAc. The combined organic phase was washed with brine, dried over anhydrous $Na_2SO_4$, filtered and concentrated. The residue was purified by RP-HPLC [C18 column, water (0.1% TFA)-$CH_3CN$] to give (2S,3S,4R)-1-tert-butyl 2-methyl 3-allyl-4-methoxy-2,3-dimethylpyrrolidine-1,2-dicarboxylate. The stereochemistry was assigned by 2D NMR. LCMS ($C_{17}H_{30}NO_5^+$)(ES, m/z): 328 [M+H]$^+$. $^1$H NMR (500 MHz, $CD_3OD$) δ 5.93-5.80 (m, 1H), 5.08-4.97 (m, 2H), 3.89-3.81 (m, 1H), 3.76-3.65 (m, 4H), 3.33-36.32 (m, 3H), 3.28-3.21 (m, 1H), 2.14-2.04 (m, 1H), 1.97-1.88 (m, 1H), 1.53 (s, 3H), 1.45-1.41 (m, 9H), 1.02-1.00 (dm, 3H).

Step 5: (2S,3S,4R)-1-tert-butyl 2-methyl 4-methoxy-2,3-dimethyl-3-(3-(4,4,5,5-tetramethyl-1,3,2-dioxaborolan-2-yl)propyl)pyrrolidine-1,2-dicarboxylate

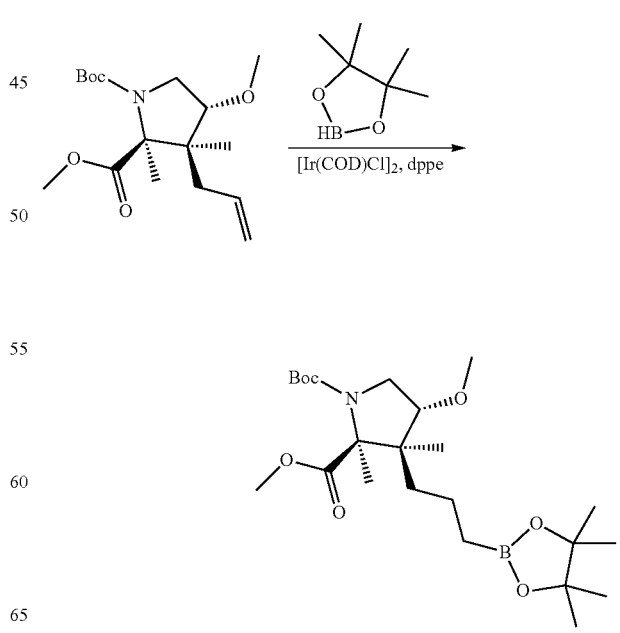

4,4,5,5-Tetramethyl-1,3,2-dioxaborolane (0.67 mL, 4.6 mmol) and (2S,3S,4R)-1-tert-butyl 2-methyl 3-allyl-4-methoxy-2,3-dimethylpyrrolidine-1,2-dicarboxylate (0.15 g, 0.46 mmol) in DCM (3.0 mL) was added to the stirred solution of [Ir(cod)Cl]$_2$ (0.12 g, 0.18 mmol) and 1,2-bis(diphenylphosphino)ethane (0.16 g, 0.41 mmol) in DCM (2.0 mL) under N$_2$. The mixture was stirred for 15 h at 26° C., then quenched with methanol and concentrated. The residue was purified by RP-HPLC [C18 column, water (0.1% TFA)-CH$_3$CN] to give (2S,3S,4R)-1-tert-butyl 2-methyl 4-methoxy-2,3-dimethyl-3-(3-(4,4,5,5-tetramethyl-1,3,2-dioxaborolan-2-yl)propyl)pyrrolidine-1,2-dicarboxylate. LCMS (C$_{23}$H$_{43}$BNO$_7$$^+$)(ES, m/z): 456 [M+H]$^+$.

Step 6: (2S,3S,4R)-3-(3-boronopropyl)-4-hydroxy-2,3-dimethylpyrrolidine-2-carboxylic acid

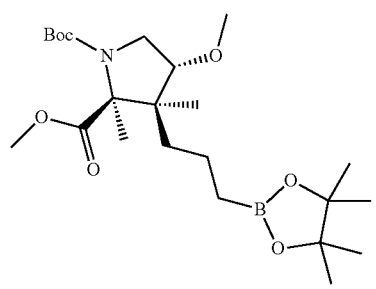

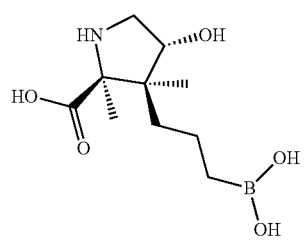

Example 73

Boron tribromide (0.60 mL, 6.4 mmol) was added to the stirred solution of (2S,3S,4R)-1-tert-butyl 2-methyl 4-methoxy-2,3-dimethyl-3-(3-(4,4,5,5-tetramethyl-1,3,2-dioxaborolan-2-yl)propyl)pyrrolidine-1,2-dicarboxylate (0.16 g, 0.35 mmol) in DCM (3.0 mL) at −78° C. over 2 min and the mixture was stirred for 45 h at 28° C. The reaction mixture was concentrated and the residue was purified by RP-HPLC [C18 column, water (20 mM HFBA and 0.1% TFA)-CH$_3$CN] to give (2S,3S,4R)-3-(3-boronopropyl)-4-hydroxy-2,3-dimethylpyrrolidine-2-carboxylic acid as a HFBA salt. LCMS (C$_{10}$H$_{19}$BNO$_4$$^+$)(ES, m/z): 228 [M+H—H$_2$O]$^+$. $^1$H NMR (500 MHz, D$_2$O) δ 4.31 (br s, 1H), 3.75-3.71 (m, 1H), 3.17-3.14 (m, 1H), 1.62 (s, 3H), 1.54-1.40 (m, 1H), 1.40-1.16 (m, 3H), 1.09 (br s, 3H), 0.70 (br s, 2H).

Example 74A: (2S,3S,4R,5R)-3-(3-boronopropyl)-4-hydroxy-3,5-dimethylpyrrolidine-2-carboxylic acid

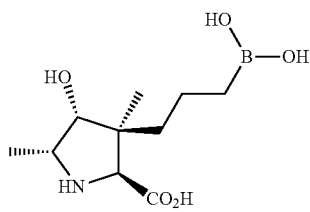 [SMILES: C[C@H]1N[C@H](C(=O)O)[C@](C)(CCCB(O)O)[C@H]1O]

Step 1: (2S,3S)-1-benzyl 2-methyl 3-allyl-3-methyl-4-oxopyrrolidine-1,2-dicarboxylate

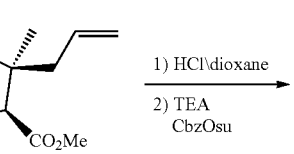

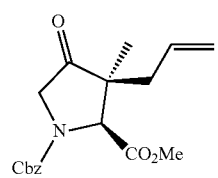

4 N HCl in dioxane (3.4 mL, 13 mmol) was added to the stirred solution of (2S,3S)-1-tert-butyl 2-methyl 3-allyl-3-methyl-4-oxopyrrolidine-1,2-dicarboxylate (2.0 g, 6.7 mmol) in DCM (30 mL), and the mixture was stirred at 20° C. for 12 h, then concentrated. The crude residue was dissolved in DCM (20 mL) and treated with Cbz-OSu (2.0 g, 8.1 mmol), triethylamine (2.8 mL, 20 mmol) and DMAP (0.082 g, 0.67 mmol) at 0° C. The resulting mixture was stirred at 20° C. for 12 h, then quenched with saturated aqueous NH$_4$Cl and extracted with EtOAc. The combined organic phase was dried over anhydrous Na$_2$SO$_4$, filtered and concentrated. The residue was purified by silica gel column chromatography (EtOAc in hexanes) to give (2S,3S)-1-benzyl 2-methyl 3-allyl-3-methyl-4-oxopyrrolidine-1,2-dicarboxylate. LCMS (C$_{18}$H$_{22}$NO$_5$$^+$)(ES, m/z): 332 [M+H]$^+$.

Step 2: (2S,3S)-1-benzyl 2-methyl 3-allyl-3,5-dimethyl-4-oxopyrrolidine-1,2-dicarboxylate and (2S,3S)-1-benzyl 2-methyl 3-allyl-3,5,5-trimethyl-4-oxopyrrolidine-1,2-dicarboxylate

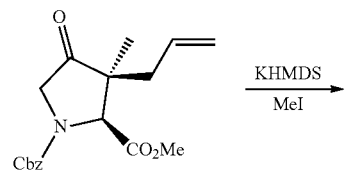

-continued

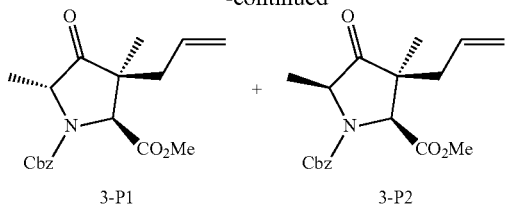

3-P1   3-P2

+

Step 3: (2S,3S,5R)-1-benzyl 2-methyl 3-allyl-4-hydroxy-3,5-dimethylpyrrolidine-1,2-dicarboxylate

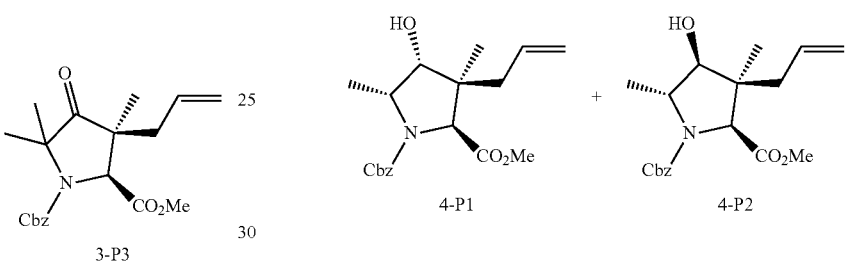

KHMDS (0.5M in toluene, 3.6 mL, 1.8 mmol) was added to the stirred solution of (2S,3S)-1-benzyl 2-methyl 3-allyl-3-methyl-4-oxopyrrolidine-1,2-dicarboxylate (0.50 g, 1.5 mmol) in toluene (15 mL) at −78° C. over 10 min, and the resulting mixture was stirred for 40 min at −78° C. Iodomethane (0.86 mL, 14 mmol) was added to the mixture at −78° C., and the reaction mixture was stirred for 0.5 h at −78° C., then for another 2 h at 25° C. The reaction mixture was quenched with saturated aqueous $NH_4Cl$ and extracted with EtOAc. The combined organic phase was dried over anhydrous $Na_2SO_4$, filtered and concentrated. The residue was purified RP-HPLC [C18 column, water (0.1% TFA)-$CH_3CN$] to give (2S,3S,5R)-1-benzyl 2-methyl 3-allyl-3,5-dimethyl-4-oxopyrrolidine-1,2-dicarboxylate (3-Pt), (2S,3S,5S)-1-benzyl 2-methyl 3-allyl-3,5-dimethyl-4-oxopyrrolidine-1,2-dicarboxylate (3-P2), and (2S,3S)-1-benzyl 2-methyl 3-allyl-3,5,5-trimethyl-4-oxopyrrolidine-1,2-dicarboxylate (3-P3). The stereochemistry was assigned by 2D NMR. 3-P1: LCMS ($C_{19}H_{24}NO_5^+$)(ES, m/z): 346 [M+H]; $^1$H NMR (500 MHz, $CDCl_3$) δ 7.42-7.27 (m, 5H), 5.91-5.72 (m, 1H), 5.28-4.97 (m, 4H), 4.49-4.39 (m, 1H), 4.18-4.06 (m, 1H), 3.72-3.44 (m, 3H), 2.47-2.35 (m, 1H), 2.09-1.97 (m, 1H), 1.61 (br s, 3H), 1.25 (br s, 3H); 3-P2: LCMS ($C_{19}H_{24}NO_5^+$)(ES, m/z): 346 [M+H]; $^1$H NMR (400 MHz, $CDCl_3$) δ 7.38-7.35 (m, 5H), 5.83-5.70 (m, 1H), 5.29-5.01 (m, 4H), 4.59-4.43 (m, 1H), 4.35-4.16 (m, 1H), 3.79-3.60 (m, 3H), 2.44-2.41 (m, 1H), 2.19-2.01 (m, 1H), 1.53 (br s, 3H), 1.22 (s, 3H); 3-P3: LCMS ($C_{20}H_{26}NO_5^+$) (ES, m/z): 360 [M+H]; $^1$H NMR (500 MHz, $CDCl_3$) δ 7.43-7.29 (m, 5H), 5.85-5.69 (m, 1H), 5.27-4.97 (m, 4H), 4.50-4.41 (m, 1H), 3.76-3.47 (m, 3H), 2.50-2.36 (m, 1H), 2.23-2.10 (m, 1H), 1.61 (s, 3H), 1.59 (s, 3H), 1.30 (d, J=5.3 Hz, 3H).

$NaBH_4$ (0.16 g, 4.3 mmol) was added to the stirred solution of (2S,3S,5R)-1-benzyl 2-methyl 3-allyl-3,5-dimethyl-4-oxopyrrolidine-1,2-dicarboxylate (0.30 g, 0.87 mmol) in MeOH (3.0 mL) at 0° C., and the mixture was stirred for 0.5 h at 20° C. The reaction mixture was quenched with water and extracted with EtOAc. The combined organic phase was dried over anhydrous $Na_2SO_4$, filtered and concentrated. The residue was purified by RP-HPLC [C18 column, water (0.1% TFA)-$CH_3CN$] to give (2S,3S,4R,5R)-1-benzyl 2-methyl 3-allyl-4-hydroxy-3,5-dimethylpyrrolidine-1,2-dicarboxylate (4-P1) as the first eluting peak, and (2S,3S,4S,5R)-1-benzyl 2-methyl 3-allyl-4-hydroxy-3,5-dimethylpyrrolidine-1,2-dicarboxylate (4-P2) as the second eluting peak. The stereochemistry was assigned by 2D NMR. 4-P1: LCMS ($C_{19}H_{26}NO_5^+$)(ES, m/z): 348 [M+H]; $^1$H NMR (400 MHz, $CDCl_3$) δ 7.41-7.23 (m, 5H), 6.05-5.80 (m, 1H), 5.21 (d, J=12.7 Hz, 1H), 5.16-5.06 (m, 2H), 4.94 (d, J=12.3 Hz, 1H), 4.31-4.11 (m, 3H), 3.75-3.38 (m, 3H), 2.24-1.94 (m, 2H), 1.39-1.26 (m, 3H), 1.20 (s, 3H); 4-P2: LCMS ($C_{19}H_{26}NO_5^+$)(ES, m/z): 348 [M+H]; $^1$H NMR (400 MHz, $CDCl_3$) δ 7.43-7.25 (m, 5H), 5.92-5.70 (m, 1H), 5.26-4.89 (m, 4H), 4.18-4.06 (m, 2H), 3.87-3.34 (m, 4H), 2.30-2.27 (m, 1H), 2.07-1.94 (m, 1H), 1.51-1.38 (m, 3H), 1.20 (s, 3H).

Step 4: (2S,3S,4R,5R)-1-benzyl 2-methyl 4-hydroxy-3,5-dimethyl-3-(3-(4,4,5,5-tetramethyl-1,3,2-dioxaborolan-2-yl)propyl)pyrrolidine-1,2-dicarboxylate Step 5: (2S,3S,4R,5R)-3-(3-boronopropyl)-4-hydroxy-3,5-dimethylpyrrolidine-2-carboxylic acid

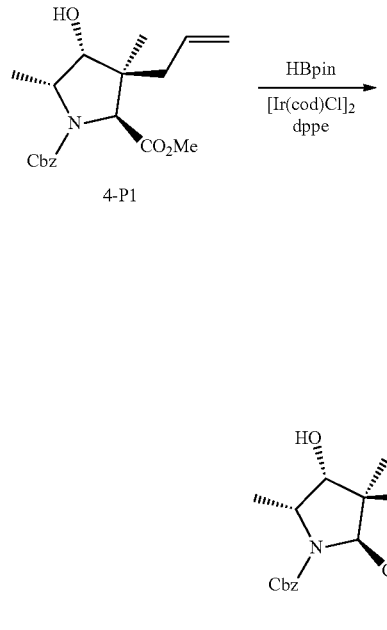

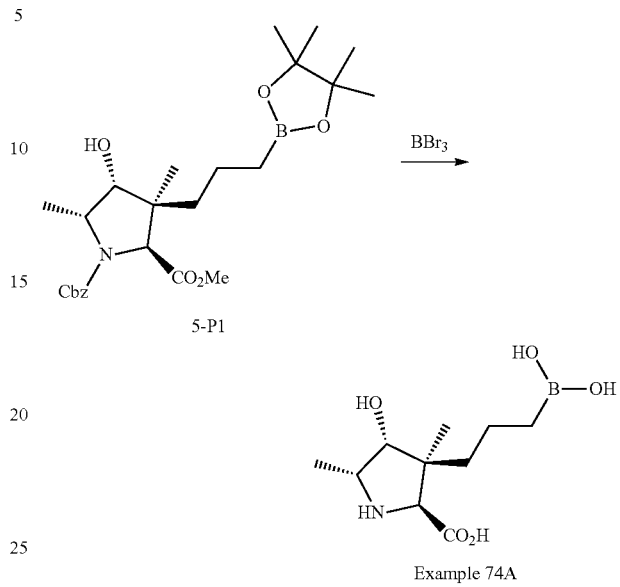

4,4,5,5-Tetramethyl-1,3,2-dioxaborolane (0.075 mL, 0.52 mmol) was added to a solution of [Ir(cod)Cl]$_2$ (8.1 mg, 0.012 mmol) and 1,2-bis(diphenylphosphino)ethane (10 mg, 0.026 mmol) in anhydrous CH$_2$C$_2$ (2.0 mL) under N$_2$ and the mixture was stirred at 26° C. for 20 min. (2S,3S,4R,5R)-1-benzyl 2-methyl 3-allyl-4-hydroxy-3,5-dimethylpyrrolidine-1,2-dicarboxylate (60 mg, 0.17 mmol) was added and the mixture was stirred at 26° C. for 3.5 h, then concentrated. The residue was purified by silica gel column chromatography (EtOAc in hexanes) to give (2S,3S, 4R,5R)-1-benzyl 2-methyl 4-hydroxy-3,5-dimethyl-3-(3-(4,4,5,5-tetramethyl-1,3,2-dioxaborolan-2-yl)propyl)pyrrolidine-1,2-dicarboxylate, which contained 4,5,5-tetramethyl-1,3,2-dioxaborolane. LCMS (C$_{25}$H$_{39}$BNO$_7^+$)(ES, m/z): 476 [M+H]$^+$.

Boron tribromide (0.20 mL, 2.1 mmol) was added to the stirred solution of (2S,3S,4R,5R)-1-((benzyloxy)carbonyl)-4-hydroxy-3,5-dimethyl-3-(3-(4,4,5,5-tetramethyl-1,3,2-dioxaborolan-2-yl)propyl)pyrrolidine-2-carboxylic acid (95 mg, 0.21 mmol) in DCM (1.0 mL) at −78° C., and the mixture was stirred for 12 h at 26° C. The reaction mixture was diluted with H$_2$O, and the aqueous phase was purified by RP-HPLC [C18 column, water (20 mM HFBA and 0.1% TFA)-CH$_3$CN] to give (2S,3S,4R,5R)-3-(3-boronopropyl)-4-hydroxy-3,5-dimethylpyrrolidine-2-carboxylic acid as a HFBA salt. LCMS (C$_{10}$H$_{19}$BNO$_4^+$)(ES, m/z): 228 [M+H—H$_2$O]$^+$; $^1$H NMR (400 MHz, D$_2$O) δ 3.96-3.95 (m, 1H), 3.93-3.82 (m, 2H), 1.35-1.25 (m, 1H), 1.20 (d, J=6.6 Hz, 4H), 1.17-1.08 (m, 5H), 0.66-0.52 (m, 2H).

Example 74B was made from (2S,3S,4S,5R)-1-benzyl 2-methyl 3-allyl-4-hydroxy-3,5-dimethylpyrrolidine-1,2-dicarboxylate (4-P2) using the same procedure as Example 74A.

Example 75 was made from (2S,3S)-1-benzyl 2-methyl 3-allyl-3,5,5-trimethyl-4-oxopyrrolidine-1,2-dicarboxylate (3-P3) using the similar procedure as example 74B.

| Ex. | Structure | MS and $^1$HNMR |
|---|---|---|
| 74B | 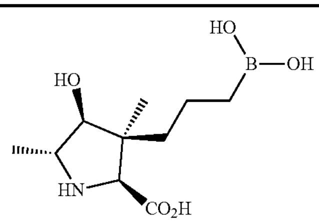 | LCMS (C$_{10}$H$_{19}$BNO$_4^+$) (ES, m/z): 228 [M + H − H$_2$O]$^+$. $^1$H NMR (400 MHz, D$_2$O) δ 3.80 (s, 1H), 3.59 (d, J = 9.2 Hz, 1H), 3.49-3.38 (m, 1H), 1.41-1.26 (m, 5H), 1.25-1.16 (m, 1H), 1.14-1.01 (m, 4H), 0.57 (t, J = 7.7 Hz, 2H). |
| 75 | 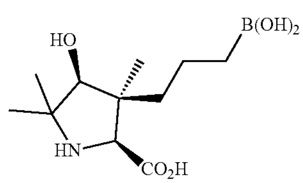 [SMILES: CC1(C)N[C@H](C(=O)O)[C@](C)(CCCB(O)O)[C@@H]1O] | LCMS (C$_{11}$H$_{21}$BNO$_4^+$) (ES, m/z): 242 [M + H − H$_2$O]$^+$. $^1$H NMR (500 MHz, D$_2$O) δ 3.83 (s, 1H), 3.72 (s, 1H), 1.55-1.43 (m, 1H), 1.34 (br d, J = 10.4 Hz, 7H), 1.30-1.24 (m, 1H), 1.24-1.15 (m, 4H), 0.64 (br t, J = 7.4 Hz, 2H). |

Example 76: (2S,3S,4R)-3-(3-boronopropyl)-4-hydroxy-3-methylpyrrolidine-2-carboxylic acid

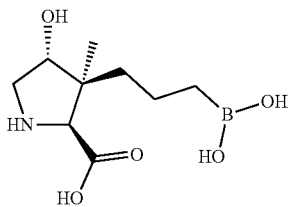 [SMILES: C[C@]1(CCCB(O)O)[C@@H](C(=O)O)NC[C@@H]1O]

Step 1: (2,3S)-3-allyl-1-((benzyloxy)carbonyl)-3-methyl-4-oxopyrrolidine-2-carboxylic acid

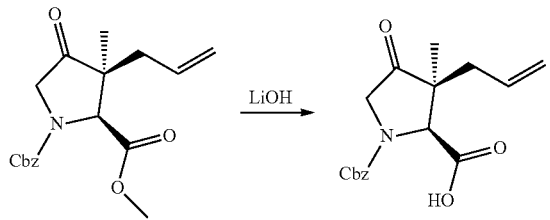

1 N LiOH in water (1.8 mL, 1.8 mmol) was added to the stirred solution of (2S,3S)-1-benzyl 2-methyl 3-allyl-3-methyl-4-oxopyrrolidine-1,2-dicarboxylate (0.30 mg, 0.91 mmol) in THF (3.0 mL) at 20° C., and the mixture was stirred for 15 h. The reaction mixture was acidified by acetic acid to pH ~6, then diluted with water and extracted with EtOAc. The combined organic phase was washed with brine, dried over anhydrous $Na_2SO_4$, filtered and concentrated to give crude (2S,3S)-3-allyl-1-((benzyloxy)carbonyl)-3-methyl-4-oxopyrrolidine-2-carboxylic acid, which was used in the next step directly without further purification. LCMS $(C_{17}H_{20}NO_5^+)$(ES, m/z): 318 [M+H]$^+$.

Step 2: (2S,3S,4R)-3-allyl-1-((benzyloxy)carbonyl)-4-hydroxy-3-methylpyrrolidine-2-carboxylic acid

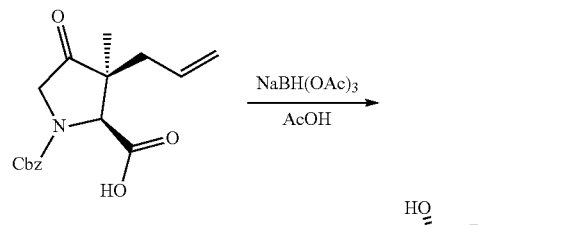

NaBH(OAc)$_3$ (0.19 g, 0.88 mmol) was added to the stirred solution of (2S,3S)-3-allyl-1-((benzyloxy)carbonyl)-3-methyl-4-oxopyrrolidine-2-carboxylic acid (0.28 g, 0.88 mmol) and acetic acid (0.050 mL, 0.88 mmol) in DCE (14 mL) at 0° C., and the resulting mixture was allowed to warm to 25° C., and stirred for 3 h. The reaction mixture was quenched with water, and extracted with EtOAc. The combined organic phase was washed with brine, dried over anhydrous $Na_2SO_4$, filtered and concentrated. The residue was purified by RP-HPLC [C18 column, water (0.1% TFA)-CH$_3$CN] to give (2S,3S,4R)-3-allyl-1-((benzyloxy)carbonyl)-4-hydroxy-3-methylpyrrolidine-2-carboxylic acid. The stereochemistry was assigned by 2D NMR. LCMS $(C_{17}H_{22}NO_5^+)$(ES, m/z): 320 [M+H]; $^1$H NMR (400 MHz, CDCl$_3$) δ 7.41-7.28 (m, 5H), 5.99-5.81 (m, 1H), 5.23-5.03 (m, 4H), 4.28-2.3 (m, 1H), 4.21-4.17 (m, 1H), 3.93-3.89 (m, 1H), 3.46-3.32 (m, 1H), 2.29-2.10 (m, 2H), 1.19 (s, 3H).

Step 3: (2S,3S,4R)-1-((benzyloxy)carbonyl)-4-hydroxy-3-methyl-3-(3-(4,4,5,5-tetramethyl-1,3,2-dioxaborolan-2-yl)propyl)pyrrolidine-2-carboxylic acid

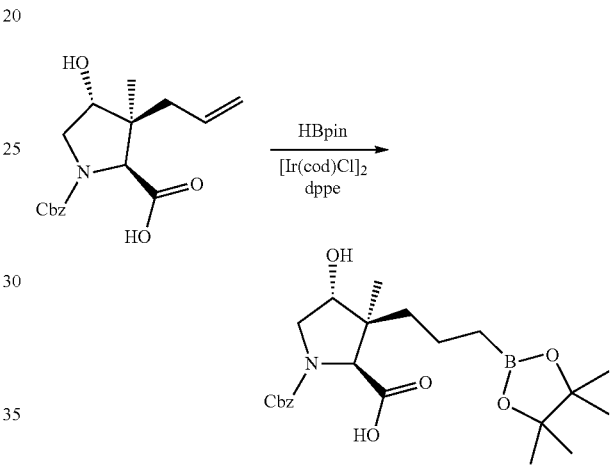

1,2-Bis(diphenylphosphino)ethane (25 mg, 0.063 mmol) and [Ir(cod)Cl]$_2$ (25 mg, 0.038 mmol) were added to the stirred solution of (2S,3S,4R)-3-allyl-1-((benzyloxy)carbonyl)-4-hydroxy-3-methylpyrrolidine-2-carboxylic acid (0.10 g, 0.31 mmol) and 4,4,5,5-tetramethyl-1,3,2-dioxaborolane (0.10 mL, 0.69 mmol) in DCM (8.0 mL) at 25° C. under N$_2$. The resulting mixture was stirred at 25° C. for 15 h, then concentrated. The residue was purified by RP-HPLC [C18 column, water (0.1% TFA)-CH$_3$CN] to give (2S,3S,4R)-1-((benzyloxy)carbonyl)-4-hydroxy-3-methyl-3-(3-(4,4,5,5-tetramethyl-1,3,2-dioxaborolan-2-yl)propyl)pyrrolidine-2-carboxylic acid, which contained minor corresponding boronic acid. LCMS $(C_{23}H_{35}BNO_7^+)$(ES, m/z): 448 [M+H]$^+$.

Step 4: (2S,3S,4R)-3-(3-boronopropyl)-4-hydroxy-3-methylpyrrolidine-2-carboxylic acid

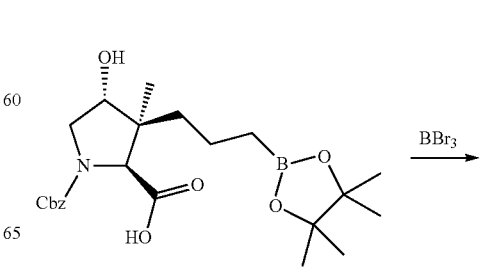

-continued

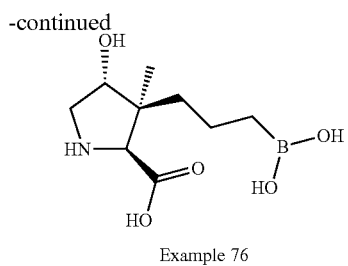

Example 76

Boron tribromide (0.15 mL, 1.6 mmol) was added to the stirred solution of (2S,3S,4R)-1-((benzyloxy)carbonyl)-4-hydroxy-3-methyl-3-(3-(4,4,5,5-tetramethyl-1,3,2-dioxaborolan-2-yl)propyl)pyrrolidine-2-carboxylic acid (20 mg, 0.045 mmol) in DCM (2.0 mL) at 0° C., and the mixture was stirred at 20° C. for 2 h. The reaction mixture was concentrated and the residue was purified by RP-HPLC [C18 column, water (20 mM HFBA and 0.1% TFA)-CH$_3$CN] to give (2S,3S,4R)-3-(3-boronopropyl)-4-hydroxy-3-methylpyrrolidine-2-carboxylic acid as a HFBA salt. LCMS (C$_9$H$_{17}$BNO$_4^+$)(ES, m/z): 214 [M+H—H$_2$O]$^+$. $^1$H NMR (400 MHz, D$_2$O) δ 4.16-4.15 (m, 1H), 3.95 (s, 1H), 3.58-3.53 (m, 1H), 3.10 (d, J=13.2 Hz, 1H), 1.37-1.15 (m, 2H), 1.10 (s, 3H), 1.08-0.92 (m, 2H), 0.58 (br t, J=7.6 Hz, 2H).

Example 77: (2S,3R,4S)-4-(aminomethyl)-3-(3-boronopropyl)-3-methylpyrrolidine-2-carboxylic acid

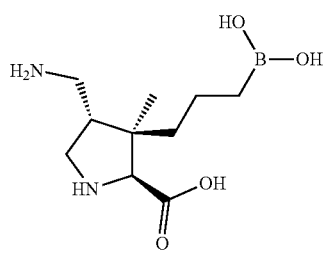 [SMILES: C[C@@]1(CCCB(O)O)[C@@H](CN)CN[C@@H]1C(=O)O]

Step 1: (2S,3R,Z)-1-benzyl 2-methyl 3-allyl-4-(methoxymethylene)-3-methylpyrrolidine-1,2-dicarboxylate

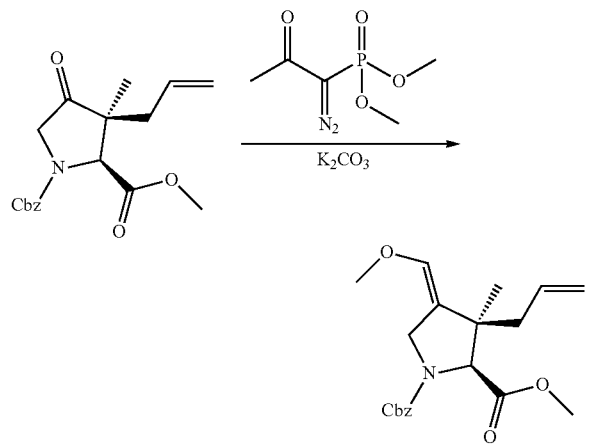

Potassium carbonate (1.1 g, 7.8 mmol) was added in one portion to the stirred solution of dimethyl (1-diazo-2-oxopropyl)phosphonate (0.80 mL, 5.3 mmol) and (2S,3S)-1-benzyl 2-methyl 3-allyl-3-methyl-4-oxopyrrolidine-1,2-dicarboxylate (1.9 g, 5.9 mmol) in MeOH (10 mL) at 0° C. The reaction mixture was allowed to warm to room temperature and stirred for 4 h, then diluted with saturated aqueous NH$_4$Cl and extracted with EtOAc. The combined organic phase was washed with brine, dried over anhydrous Na$_2$SO$_4$, filtered and concentrated. The residue was purified by silica gel column chromatography (EtOAc in hexanes) to give (2S,3R,Z)-1-benzyl 2-methyl 3-allyl-4-(methoxymethylene)-3-methylpyrrolidine-1,2-dicarboxylate. LCMS (C$_2$H$_{26}$NO$_5^+$)(ES, m/z): 360 [M+H]$^+$.

Step 2: (2S,3R,4R)-1-benzyl 2-methyl 3-allyl-4-formyl-3-methylpyrrolidine-1,2-dicarboxylate

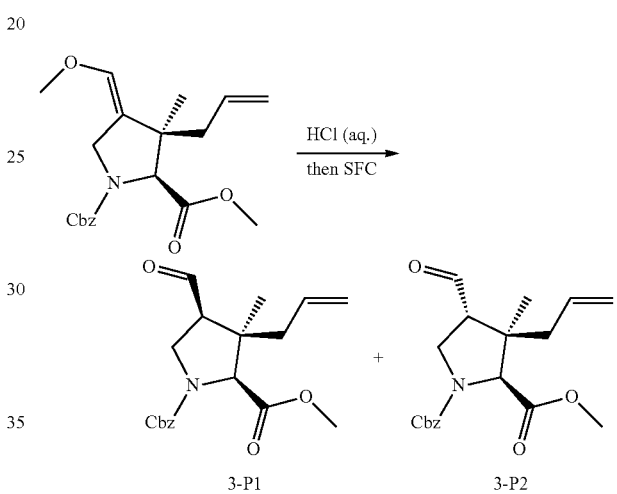

3 N HCl in water (0.60 mL, 1.8 mmol) was added to a solution of (2S,3R,Z)-1-benzyl 2-methyl 3-allyl-4-(methoxymethylene)-3-methylpyrrolidine-1,2-dicarboxylate (0.70 g, 1.9 mmol) in THF (10 mL) at 0° C. The resulting mixture was stirred at 25° C. for 0.5 h, then at 50° C. for 6 h. The reaction mixture was quenched with saturated aqueous NaHCO$_3$ and extracted with EtOAc. The combined organic phase was washed with brine, dried over anhydrous Na$_2$SO$_4$, filtered and concentrated. The residue was purified by silica gel column chromatography (EtOAc in hexanes) to give 1-benzyl 2-methyl (2S,3R)-3-allyl-4-formyl-3-methylpyrrolidine-1,2-dicarboxylate as a mixture of diastereomers, which was resolved by Chiral-SFC [Column: OD (250 mm*50 mm,10 μm), Mobile phase: A: CO$_2$, B: IPA, Gradient: 20% of B in 4.5 min, and hold 20% of B for 1 min, Flow Rate (mL/min) 50, Column temperature: 40° C.] to give (2S,3R,4S)-1-benzyl 2-methyl 3-allyl-4-formyl-3-methylpyrrolidine-1,2-dicarboxylate (3-P1, t$_r$=3.1 min) as the first eluting peak, and (2S,3R,4R)-1-benzyl 2-methyl 3-allyl-4-formyl-3-methylpyrrolidine-1,2-dicarboxylate (3-P2, t$_r$=3.4 min) as the second eluting peak. The stereochemistry was assigned by 2D NMR. 3-P1: LCMS (C$_{19}$H$_{24}$NO$_5^+$)(ES, m/z): 346 [M+H]$^+$. 3-P2: LCMS (C$_{19}$H$_{24}$NO$_5^+$)(ES, m/z): 346 [M+H]; $^1$H NMR (400 MHz, CDCl$_3$) δ 9.78-9.74 (m, 1H), 7.39-7.28 (m, 5H), 5.91-5.75 (m, 1H), 5.24-5.09 (m, 4H), 4.11-3.98 (m, 1H), 3.96-3.80 (m, 2H), 3.78-3.72 (m, 1.5H), 3.59 (s, 1.5H), 3.26-3.13 (m, 1H), 2.36-2.26 (m, 2H), 1.14-1.13 (m, 3H).

Step 3: (2S,3R,4S)-1-benzyl 2-methyl 3-allyl-4-((4-methoxybenzylamino)methyl)-3-methylpyrrolidine-1,2-dicarboxylate

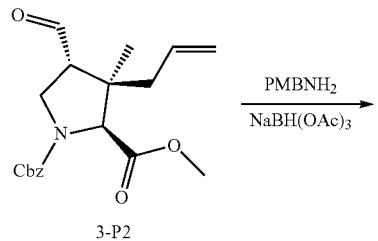

3-P2

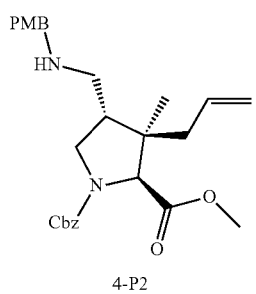

4-P2

Sodium triacetoxyborohydride (0.18 g, 0.87 mmol) was added to a mixture of (4-methoxyphenyl)methanamine (0.12 mL, 0.92 mmol) and (2S,3R,4R)-1-benzyl 2-methyl 3-allyl-4-formyl-3-methylpyrrolidine-1,2-dicarboxylate (0.10 g, 0.29 mmol) in DCE (2.0 mL) at 0° C. The resulting mixture was stirred at 28° C. for 14 h, then quenched with saturated aqueous NH$_4$Cl and extracted with DCM. The combined organic phase was washed with brine, dried over anhydrous Na$_2$SO$_4$, filtered and concentrated. The residue was purified by RP-HPLC [C18 column, water (0.1% TFA)-CH$_3$CN] to give (2S,3R,4S)-1-benzyl 2-methyl 3-allyl-4-(((4-methoxybenzyl)amino)methyl)-3-methylpyrrolidine-1,2-dicarboxylate. LCMS (C$_{27}$H$_{35}$N$_2$O$_5{}^+$)(ES, m/z): 467 [M+H]$^+$.

Step 4: (2S,3R,4S)-1-benzyl 2-methyl 4-(((4-methoxybenzyl)amino)methyl)-3-methyl-3-(3-(4,4,5,5-tetramethyl-1,3,2-dioxaborolan-2-yl)propyl)pyrrolidine-1,2-dicarboxylate

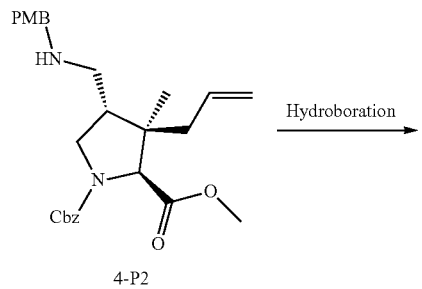

4-P2

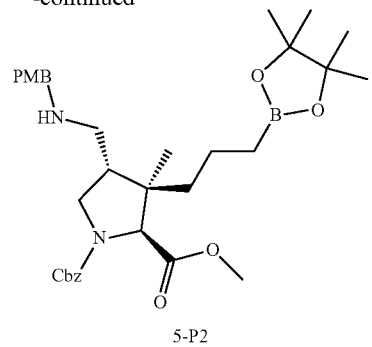

5-P2

A mixture of [Ir(cod)Cl]$_2$ (4.3 mg, 6.4 μmol) and 1,2-bis(diphenylphosphino)ethane (4.1 mg, 10 μmol) in DCM (1.0 mL) was degassed and backfilled with N$_2$, and the mixture was stirred for 10 min at 26° C. 4,4,5,5-Tetramethyl-1,3,2-dioxaborolane (0.10 mL, 0.69 mmol) and (2S,3R,4S)-1-benzyl 2-methyl 3-allyl-4-(((4-methoxybenzyl)amino)methyl)-3-methylpyrrolidine-1,2-dicarboxylate (60 mg, 0.13 mmol) in DCM (0.50 mL) was added, and the reaction mixture was stirred at 20° C. for 15 h. The reaction mixture was quenched with methanol, and concentrated. The residue was purified by RP-HPLC [C18 column, water (0.1% TFA)-CH$_3$CN] to give (2S,3R,4S)-1-benzyl 2-methyl 4-(((4-methoxybenzyl)amino)methyl)-3-methyl-3-(3-(4,4,5,5-tetramethyl-1,3,2-dioxaborolan-2-yl)propyl)pyrrolidine-1,2-dicarboxylate. LCMS (C$_{33}$H$_{48}$BN$_2$O$_7{}^+$)(ES, m/z): 595 [M+H]$^+$.

Step 5: (3-((2S,3R,4S)-4-(aminomethyl)-2-(methoxycarbonyl)-3-methylpyrrolidin-3-yl)propyl)boronic acid

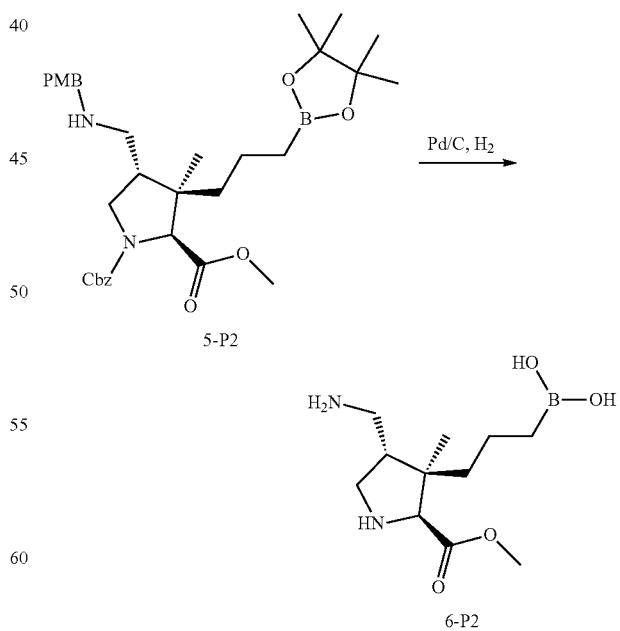

10% Pd—C (15 mg, 0.014 mmol) was added to the stirred solution of (3-((2S,3R,4S)-1-((benzyloxy)carbonyl)-4-(((4-methoxybenzyl)amino)methyl)-2-(methoxycarbonyl)-3- methylpyrrolidin-3-yl)propyl)boronic acid (60 mg, 0.12 mmol) in MeOH (5.0 mL) under N$_2$. The resulting mixture was degassed and backfilled with H$_2$, and stirred under H$_2$ (pressure: 50 psi) at 35° C. for 15 h. Additional 10% Pd—C (10 mg, 0.094 mmol) was added and the reaction mixture was degassed and backfilled with H$_2$, and stirred under H$_2$ (pressure: 50 psi) at 35° C. for 40 h. The reaction mixture was filtered and the filtrate was concentrated to give crude (3-((2S,3R,4S)-4-(aminomethyl)-2-(methoxycarbonyl)-3-methylpyrrolidin-3-yl)propyl)boronic acid, which was used in next step directly without further purification. LCMS (C$_1$H$_{24}$BN$_2$O$_4^+$)(ES, m/z): 259 [M+H]$^+$.

Step 6: (2S,3R,4S)-4-(aminomethyl)-3-(3-borono-propyl)-3-methylpyrrolidine-2-carboxylic acid

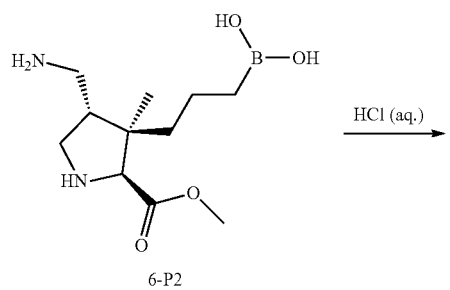

6-P2

HCl (aq.) →

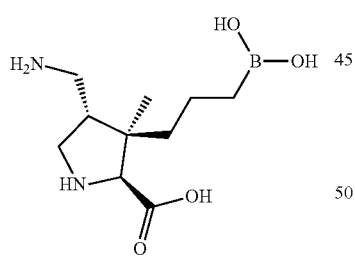

Example 77

A mixture of 12 N HCl in water (1.5 mL, 18 mmol) and (3-((2S,3R,4S)-4-(aminomethyl)-2-(methoxycarbonyl)-3-methylpyrrolidin-3-yl)propyl)boronic acid (50 mg, 0.19 mmol) was stirred at 110° C. for 15 h, and concentrated. The residue was purified by RP-HPLC [C18 column, water (20 mM HFBA and 0.1% TFA)-CH$_3$CN] to give (2S,3R,4S)-4-(aminomethyl)-3-(3-boronopropyl)-3-methylpyrrolidine-2-carboxylic acid as a HFBA salt. LCMS (C$_{10}$H$_{20}$BN$_2$O$_3^+$) (ES, m/z): 227 [M+H—H$_2$O]$^+$. $^1$H NMR (400 MHz, D$_2$O) δ 4.11 (s, 1H), 3.82-3.77 (m, 1H), 3.34-3.18 (m, 1H), 3.02-2.90 (m, 1H), 2.55-2.45 (m, 1H), 1.56-1.33 (m, 3H), 1.22-1.18 (m, 2H), 1.10 (s, 3H), 0.70 (br t, J=7.2 Hz, 2H).

Example 78: (2S,3R,4R)-3-(3-boronopropyl)-4-((dimethylamino)methyl)-3-methylpyrrolidine-2-carboxylic acid

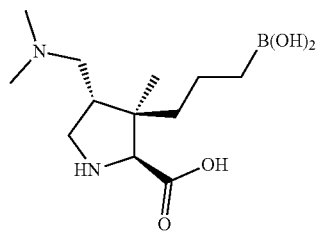 [SMILES: CN(C)C[C@H]1CN[C@H](C(=O)O)[C@]1(C)CCCB(O)O]

Step 1: (2S,3R,4S)-1-benzyl 2-methyl 3-allyl-4-((dimethylamino)methyl)-3-methylpyrrolidine-1,2-dicarboxylate

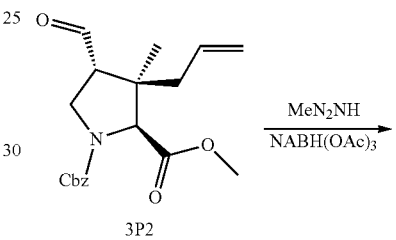

3P2

MeN$_2$NH / NABH(OAc)$_3$ →

Dimethylamine (40 wt % in water, 0.65 g, 5.8 mmol) was added to the stirred solution of (2S,3R,4R)-1-benzyl 2-methyl 3-allyl-4-formyl-3-methylpyrrolidine-1,2-dicarboxylate (0.10 g, 0.29 mmol) in THF (20 mL) at 25° C. under N$_2$, followed by addition of sodium triacetoxyborohydride (0.18 mg, 0.87 mmol) at 25° C. The resulting mixture was stirred for 2 h at 25° C., then quenched with saturated aqueous Na$_2$CO$_3$ and extracted with EtOAc. The combined organic phase was washed with brine, dried over anhydrous Na$_2$SO$_4$, filtered and concentrated. The residue was purified by RP-HPLC [C18 column, water (0.1% TFA)-CH$_3$CN] to give (2S,3R,4S)-1-benzyl 2-methyl 3-allyl-4-((dimethylamino)methyl)-3-methylpyrrolidine-1,2-dicarboxylate. LCMS (C$_{21}$H$_{31}$N$_2$O$_4$)(ES, m/z): 375 [M+H]$^+$.

Step 2: (2S,3R,4S)-1-benzyl 2-methyl 4-((dimethyl-amino)methyl)-3-methyl-3-(3-(4,4,5,5-tetramethyl-1,3,2-dioxaborolan-2-yl)propyl)pyrrolidine-1,2-dicarboxylate Step 3: (2S,3R,4R)-3-(3-boronopropyl)-4-((dimethylamino)methyl)-3-methylpyrrolidine-2-carboxylic acid

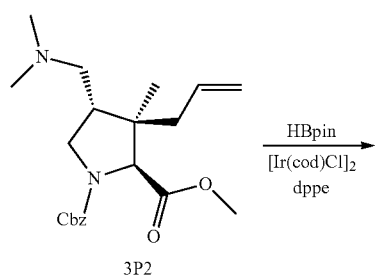

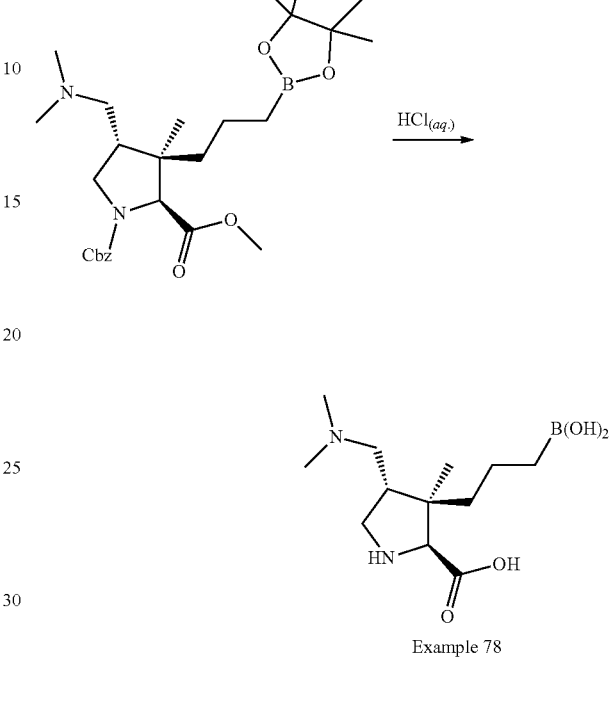

Example 78

4,4,5,5-Tetramethyl-1,3,2-dioxaborolane (0.23 mL, 1.6 mmol) and (2S,3R,4S)-1-benzyl2-methyl 3-allyl-4-((dimethylamino)methyl)-3-methylpyrrolidine-1,2-dicarboxylate (60 mg, 0.16 mmol) were added to the stirred solution of [Ir(cod)Cl]$_2$ (11 mg, 0.016 mmol) and 1,2-bis(diphenylphosphino)ethane (13 mg, 0.032 mmol) in DCM (10 mL) at 25° C. under N$_2$. The resulting mixture was stirred for 2 h at 25° C., then quenched with water and extracted with DCM.

The combined organic phase was washed with brine, dried over anhydrous Na$_2$SO$_4$, filtered and concentrated. The residue was purified by RP-HPLC [C18 column, water (0.1% TFA)-CH$_3$CN] to give (2S,3R,4S)-1-benzyl 2-methyl 4-((dimethylamino)methyl)-3-methyl-3-(3-(4,4,5,5-tetramethyl-1,3,2-dioxaborolan-2-yl)propyl)pyrrolidine-1,2-dicarboxylate. LCMS (C$_{27}$H$_{44}$BN$_2$O$_6{}^+$)(ES, m/z): 503 [M+H]$^+$.

A mixture of (2S,3R,4S)-1-benzyl 2-methyl 4-((dimethylamino)methyl)-3-methyl-3-(3-(4,4,5,5-tetramethyl-1,3,2-dioxaborolan-2-yl)propyl)pyrrolidine-1,2-dicarboxylate (40 mg, 0.080 mmol) and 12 N HCl in water (5.0 mL, 60 mmol) was stirred at 110° C. for 8 h. LCMS showed that the most of starting material was consumed and the desired target was formed. The mixture was filtered and the filtrate was concentrated under reduced pressure, the residue was purified by RP-HPLC [C18 column, water (20 mM HFBA and 0.1% TFA)-CH$_3$CN] to give (2S,3R,4R)-3-(3-boronopropyl)-4-((dimethylamino)methyl)-3-methylpyrrolidine-2-carboxylic acid as a HFBA salt. LCMS (C$_{12}$H$_{24}$BN$_2$O$_3{}^+$)(ES, m/z): 255 [M+H—H$_2$O]$^+$. $^1$H NMR (400 MHz, D$_2$O) δ 4.07 (s, 1H), 3.79-3.76 (m, 1H), 3.33-3.09 (m, 3H), 2.77 (s, 3H), 2.75 (s, 3H), 2.50-2.41 (m, 1H), 1.52-1.28 (m, 3H), 1.21-1.13 (m, 1H), 0.98 (s, 3H), 0.61 (t, J=7.5 Hz, 2H).

Example 79 was made from (2S,3R,4R)-1-benzyl 2-methyl 3-allyl-4-formyl-3-methylpyrrolidine-1,2-dicarboxylate (3-P2) and MeNH$_2$ using the same procedure as Example 78.

| Ex. | Structure | MS and $^1$HNMR |
|---|---|---|
| 79 | ![structure] | LCMS (C$_{11}$H$_{22}$BN$_2$O$_3{}^+$) (ES, m/z): 241 [M + H − H$_2$O]$^+$. $^1$H NMR (400 MHz, D$_2$O) δ 4.14 (s, 1H), 3.84-3.81 (m, 1H), 3.37-3.23 (m, 2H), 3.13-3.03 (m, 1H), 2.71 (s, 3H), 2.61-2.47 (m, 1H), 1.60-1.39 (m, 3H), 1.35-1.24 (m, 1H), 1.16-1.08 (m, 3H), 0.77-0.69 (m, 2H). |

Example 80: (2S,3R,4R)-3-(3-boronopropyl)-4-(hydroxymethyl)-3-methylpyrrolidine-2-carboxylic acid

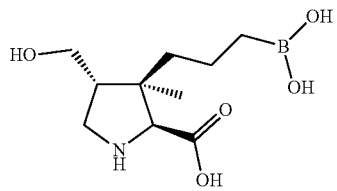 [SMILES: C[C@@]1(CCCB(O)O)[C@@H](CO)CN[C@@H]1C(=O)O]

Step 1: 1-benzyl 2-methyl (2S,3R)-3-allyl-4-formyl-3-methylpyrrolidine-1,2-dicarboxylate

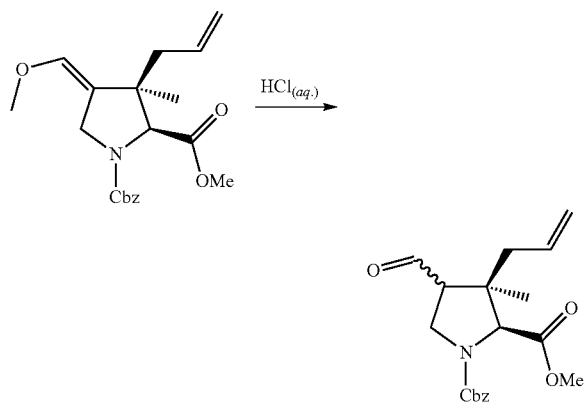

3 N HCl in water (0.67 mL, 2.0 mmol) was added to a solution of (2S,3S,Z)-1-benzyl 2-methyl 3-allyl-4-(methoxymethylene)-3-methylpyrrolidine-1,2-dicarboxylate (0.80 g, 2.3 mmol) in THF (25 mL) at 0° C. After stirring for 0.5 h at 26° C., the mixture was heated to 50° C. and stirred for 6 h, LCMS showed that the starting material was used up, and the target material was formed. The reaction mixture was diluted with water and extracted with EtOAc. The combined organic phases were washed with brine (20 mL), dried over anhydrous Na$_2$SO$_4$, filtered and concentrated under reduced pressure. The residue was purified by RP-HPLC [C18 column, water (0.1% TFA)-CH$_3$CN] to give (2S,3R)-1-benzyl 2-methyl 3-allyl-4-formyl-3-methylpyrrolidine-1,2-dicarboxylate as a mixture of diastereomers.

Step 2: (2S,3R,4R)-1-benzyl 2-methyl 3-allyl-4-(hydroxymethyl)-3-methylpyrrolidine-1,2-dicarboxylate

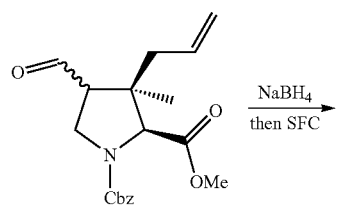

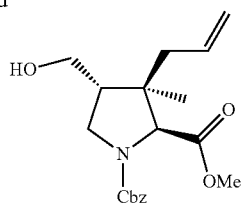

NaBH$_4$ (25 mg, 0.66 mmol) was added to the stirred solution of (2S,3R)-1-benzyl 2-methyl 3-allyl-4-formyl-3-methylpyrrolidine-1,2-dicarboxylate (0.20 mg, 0.58 mmol) in MeOH (3.0 mL) at 0° C. The reaction mixture was allowed to warm to 25° C., and stirred for 15 h, then quenched with saturated aqueous NaHCO$_3$ and extracted with EtOAc. The combined organic phase was washed with brine, dried over anhydrous Na$_2$SO$_4$, filtered and concentrated. The residue was resolved by Chiral-SFC [Column: IG (250 mm*50 mm,10 μm), Mobile phase: A: CO$_2$, B: MeOH (0.1% NH$_3$.H$_2$O), Gradient: 40% of B in 12 min, and hold 40% of B for 2 min, Flow Rate (mL/min) 60, Column temperature: 40° C.] to give (2S,3R,4R)-1-benzyl 2-methyl 3-allyl-4-(hydroxymethyl)-3-methylpyrrolidine-1,2-dicarboxylate, the stereochemistry was assigned by 2D NMR. LCMS (C$_{19}$H$_{26}$NO$_5^+$)(ES, m/z): 348 [M+H]$^+$. $^1$H NMR (400 MHz, CDCl$_3$) δ 7.40-7.24 (m, 5H), 5.94-5.75 (m, 1H), 5.24-4.95 (m, 4H), 4.16-4.04 (m, 1H), 3.96-3.87 (m, 1H), 3.82-3.75 (m, 1H), 3.73 (m, 1.5H), 3.59-3.51 (m, 2.5H), 3.41-3.30 (m, 1H), 2.59-2.42 (m, 1H), 2.34-2.20 (m, 2H), 2.13-1.98 (m, 1H), 1.03 (s, 3H).

Step 3: (2S,3R,4R)-1-benzyl 2-methyl 4-(hydroxymethyl)-3-methyl-3-(3-(4,4,5,5-tetramethyl-1,3,2-dioxaborolan-2-yl)propyl)pyrrolidine-1,2-dicarboxylate

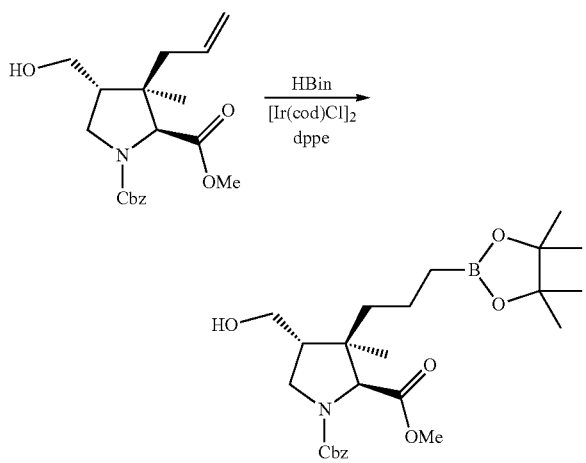

4,4,5,5-Tetramethyl-1,3,2-dioxaborolane (0.10 mL, 0.69 mmol) was added to a mixture of (2S,3R,4R)-1-benzyl 2-methyl 3-allyl-4-(hydroxymethyl)-3-methylpyrrolidine-1,2-dicarboxylate (90 mg, 0.26 mmol) in DCM (4.0 mL) at 25° C. The mixture was degassed and backfilled with N$_2$, then treated with 1,2-bis(diphenylphosphino)ethane (21 mg, 0.053 mmol) and [Ir(cod)Cl]$_2$ (21 mg, 0.031 mmol), and stirred at 25° C. for 15 h. The reaction mixture was concentrated and the residue was purified by RP-HPLC [C18 column, water (0.1% TFA)-CH$_3$CN] to give (2S,3R,4R)-1-benzyl 2-methyl 4-(hydroxymethyl)-3-methyl-3-(3-(4,4,5,5-tetramethyl-1,3,2-dioxaborolan-2-yl)propyl)pyrrolidine-1,2-dicarboxylate, which contained the corresponding boronic acid as a minor impurity. LCMS (C$_{25}$H$_{39}$BNO$_7^+$)(ES, m/z): 476 [M+H]$^+$.

Step 4: (2S,3R,4R)-3-(3-boronopropyl)-4-(hydroxymethyl)-3-methylpyrrolidine-2-carboxylic acid

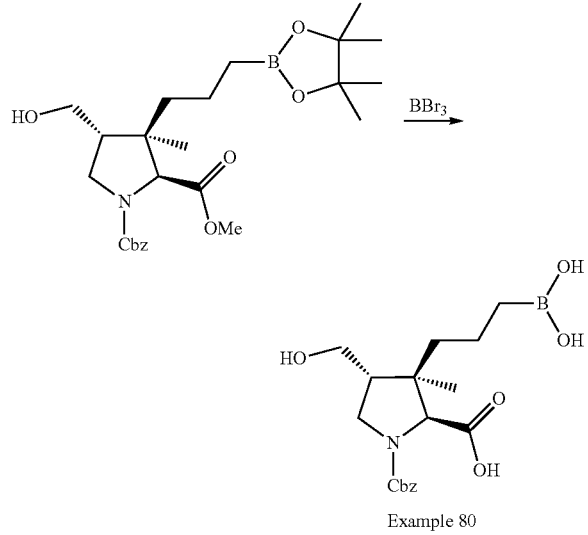

Example 80

Boron tribromide (0.30 mL, 3.2 mmol) was added to a mixture of (2S,3R,4R)-1-benzyl 2-methyl 4-(hydroxymethyl)-3-methyl-3-(3-(4,4,5,5-tetramethyl-1,3,2-dioxaborolan-2-yl)propyl)pyrrolidine-1,2-dicarboxylate (40 mg, 0.084 mmol) in DCM (2.0 mL) at 0° C. The resulting mixture was allowed to warm to 25° C. and stirred for 15 h. The reaction mixture was concentrated, and the residue was purified by RP-HPLC [C18 column, water (20 mM HFBA and 0.1% TFA)-CH$_3$CN] to give (2S,3R,4R)-3-(3-boronopropyl)-4-(hydroxymethyl)-3-methylpyrrolidine-2-carboxylic acid. LCMS (C$_{10}$H$_{19}$BNO$_4^+$)(ES, m/z): 228 [M+H—H$_2$O]$^+$. $^1$H NMR (400 MHz, D$_2$O) δ 4.01 (s, 1H), 3.77-3.67 (m, 1H), 3.66-3.51 (m, 2H), 3.31-3.21 (m, 1H), 2.44-2.33 (m, 1H), 1.48-1.29 (m, 3H), 1.23-1.11 (m, 4H), 0.70 (t, J=7.2 Hz, 2H).

Example 81: (2S,3R,4R)-3-(3-boronopropyl)-4-(difluoromethyl)-3-methylpyrrolidine-2-carboxylic acid

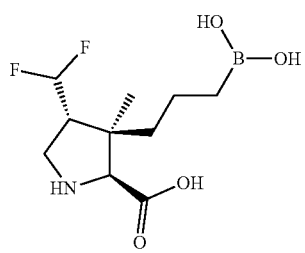 [SMILES: C[C@]1(CCCB(O)O)[C@@H](C(=O)O)NC[C@@H]1C(F)F]

Step 1: (2S,3R,4R)-1-benzyl 2-methyl 3-allyl-4-(difluoromethyl)-3-methylpyrrolidine-1,2-dicarboxylate

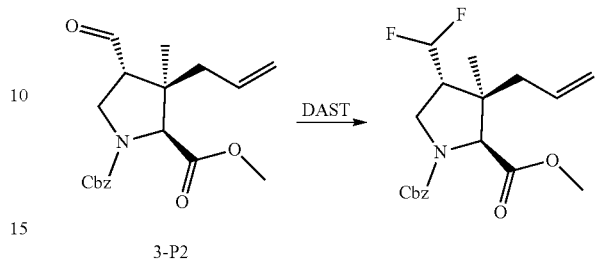

3-P2

A solution of DAST (0.30 mL, 2.3 mmol) in DCM (2.0 mL) was added dropwise to the stirred solution of (2S,3R,4R)-1-benzyl 2-methyl 3-allyl-4-formyl-3-methylpyrrolidine-1,2-dicarboxylate (0.25 mg, 0.72 mmol) in DCM (20 mL) at 0° C. The mixture was allowed to warm to 35° C. and stirred for 5 h, then diluted with DCM, quenched with saturated aqueous NaHCO$_3$, and extracted with DCM. The combined organic phase was washed with brine, dried over anhydrous Na$_2$SO$_4$, filtered and concentrated. The residue was purified by silica gel column chromatography (EtOAc in hexanes) to give (2S,3R,4R)-1-benzyl 2-methyl 3-allyl-4-(difluoromethyl)-3-methylpyrrolidine-1,2-dicarboxylate. LCMS (C$_{19}$H$_{24}$F$_2$NO$_4^+$)(ES, m/z): 368 [M+H]$^+$.

Step 2: 2S,3R,4R)-1-benzyl 2-methyl 4-(difluoromethyl)-3-methyl-3-(3-(4,4,5,5-tetramethyl-1,3,2-dioxaborolan-2-yl)propyl)pyrrolidine-1,2-dicarboxylate

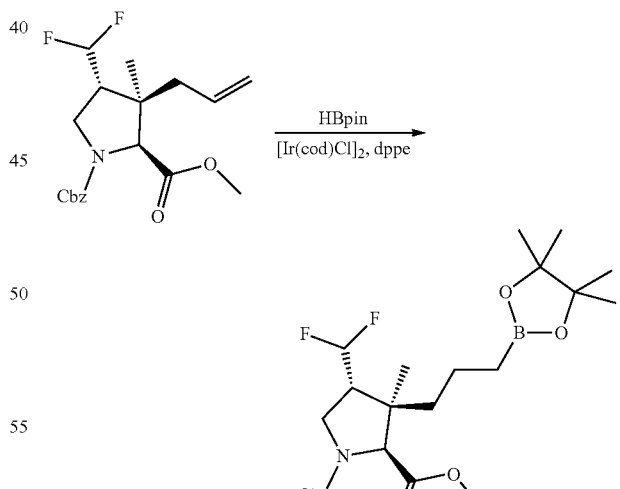

A solution of 4,4,5,5-tetramethyl-1,3,2-dioxaborolane (0.40 mL, 2.8 mmol) and (2S,3R,4R)-1-benzyl 2-methyl 3-allyl-4-(difluoromethyl)-3-methylpyrrolidine-1,2-dicarboxylate (0.15 g, 0.41 mmol) in DCM (3.0 mL) was added to the stirred solution of [Ir(cod)Cl]$_2$ (14 mg, 0.020 mmol) and 1,2-bis(diphenylphosphino)ethane (13 mg, 0.033 mmol) in DCM (1.0 mL) under N$_2$. The mixture was stirred at 34°

C. for 5 h, then quenched with methanol, and concentrated. The residue was purified by RP-HPLC [C18 column, water (0.1% TFA)-CH₃CN] to give (2S,3R,4R)-1-benzyl 2-methyl 4-(difluoromethyl)-3-methyl-3-(3-(4,4,5,5-tetramethyl-1,3,2-dioxaborolan-2-yl)propyl)pyrrolidine-1,2-dicarboxylate, which contained minor corresponding boronic acid. LCMS $(C_{25}H_{37}BF_2NO_6^+)$(ES, m/z): 496 $[M+H]^+$.

Step 3: (2S,3R,4R)-3-(3-boronopropyl)-4-(difluoromethyl)-3-methylpyrrolidine-2-carboxylic acid

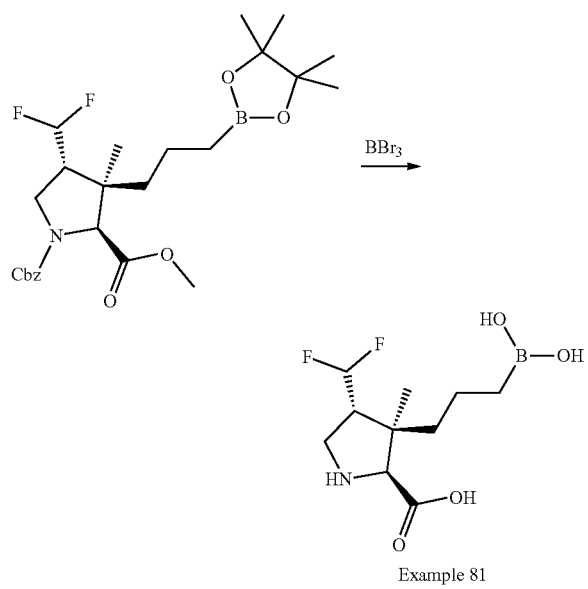

Example 81

Boron tribromide (0.60 mL, 6.4 mmol) was added dropwise to the stirred solution of (2S,3R,4R)-1-benzyl 2-methyl 4-(difluoromethyl)-3-methyl-3-(3-(4,4,5,5-tetramethyl-1,3,2-dioxaborolan-2-yl)propyl)pyrrolidine-1,2-dicarboxylate (0.13 g, 0.26 mmol) in DCM (5.0 mL) at −78° C., and the resulting mixture was allowed to warm to 30° C. and stirred for 48 h at 30° C. The reaction mixture was concentrated, and the residue was purified by RP-HPLC [C18 column, water (20 mM HFBA and 0.1% TFA)-CH₃CN] to give (2S,3R,4R)-3-(3-boronopropyl)-4-(difluoromethyl)-3-methylpyrrolidine-2-carboxylic acid as a HFBA salt. LCMS $(C_{10}H_{17}BF_2NO_3^+)$(ES, m/z): 248 $[M+H-H_2O]^+$. ¹H NMR (500 MHz, D₂O) δ 6.30-6.03 (m, 1H), 4.14-3.94 (m, 1H), 3.67-3.56 (m, 2H), 2.95-2.78 (m, 1H), 1.50-1.30 (m, 6H), 1.28-1.18 (m, 1H), 0.81-0.65 (m, 2H).

Example 82: (2S,3R,4R)-3-(3-boronopropyl)-4-hydroxypyrrolidine-2-carboxylic acid

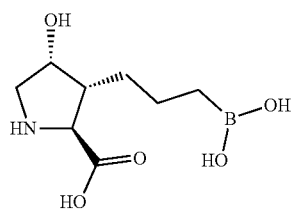 [SMILES: O=C(O)[C@H]1NC[C@H](O)[C@@H]1CCCB(O)O]

Step 1: (2S)-1-benzyl 2-methyl 3-allyl-4-oxopyrrolidine-1,2-dicarboxylate

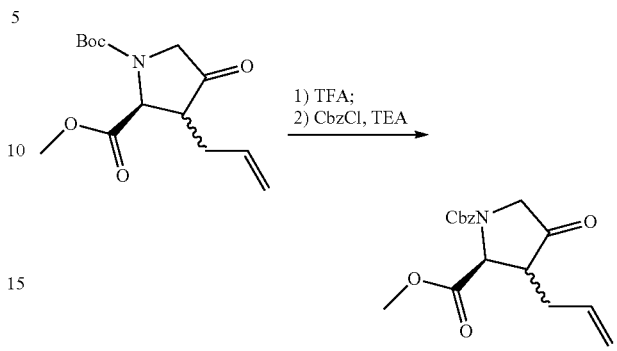

TFA (3.0 L) was added dropwise to the stirred solution of 1-tert-butyl 2-methyl (2S)-4-oxopyrrolidine-1,2-dicarboxylate (590 g, 2.4 mol) in DCM (3.0 L) at 0° C., and the mixture was stirred for 2 h at room temperature. The resulting mixture was concentrated, and the crude residue was dissolved in THF (2.0 L), followed by addition of CbzCl (298 g, 1.7 mol), H₂O (2.0 L), and dropwise addition of TEA (588 g, 5.8 mol) at 0° C. The reaction mixture was stirred for 16 h at room temperature, then extracted with EtOAc. The combined organic phase was concentrated, and the residue was purified by RP-HPLC[C18 column, water (0.1% TFA)-CH₃CN] to give 1-benzyl 2-methyl (2S)-4-oxo-3-(prop-2-en-1-yl)pyrrolidine-1,2-dicarboxylate as a mixture of diastereomers. LCMS $(C_{17}H_{20}NO_5^+)$(ES, m/z): 318 $[M+H]^+$;

Step 2: (2S,3R,4S)-1-benzyl 2-methyl 3-allyl-4-hydroxypyrrolidine-1,2-dicarboxylate

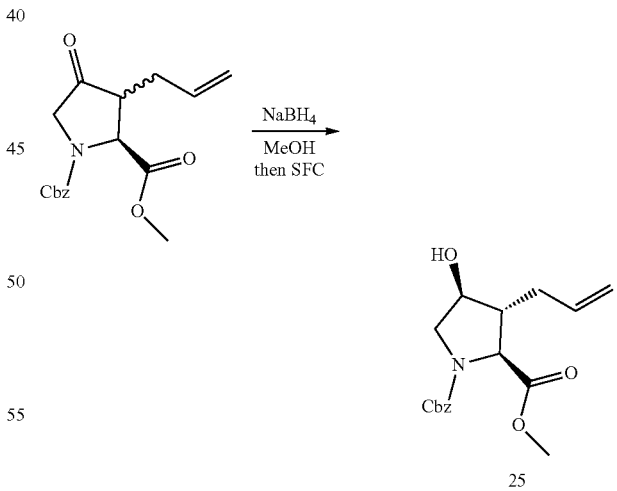

NaBH₄ (60 mg, 1.6 mmol) was added to the stirred solution of (2S)-1-benzyl 2-methyl 3-allyl-4-oxopyrrolidine-1,2-dicarboxylate (0.50 g, 1.6 mmol) in MeOH (6.0 mL) at 0° C., and the mixture was allowed to warm to 15° C. and stirred for 15 h. The reaction mixture was quenched with saturated aqueous NaHCO₃ and extracted with EtOAc. The combined organic phase was washed with brine, dried over anhydrous Na₂SO₄, filtered and concentrated. The residue was purified by RP-HPLC[C18 column, water (0.1% TFA)-CH$_3$CN] to give a mixture of isomers, which was resolved by Chiral-SFC [Column: DAICEL CHIRALCEL OJ-H (250 mm*30 mm, 5 μm), Mobile phase: A: CO$_2$, B: MeOH (0.1% NH$_3$.H$_2$O), Gradient: 10% of B in 7 min, and hold 10% of B for 1 min, Flow Rate (mL/min) 50, Column temperature: 40° C.] to give (2S,3R,4S)-1-benzyl 2-methyl 3-allyl-4-hydroxypyrrolidine-1,2-dicarboxylate. The stereochemistry was assigned by 2D NMR. LCMS (C$_{17}$H$_{22}$NO$_5^+$) (ES, m/z): 320 [M+H]; $^1$H NMR (400 MHz, CDCl$_3$) δ 7.42-7.28 (m, 5H), 5.85-5.72 (m, 1H), 5.26-5.00 (m, 4H), 4.19 (d, J=1.7 Hz, 0.5H), 4.13 (d, J=1.7 Hz, 0.5H), 4.10-4.05 (m, 1H), 3.81 (s, 1.5H), 3.78-3.64 (m, 2H), 3.62 (s, 1.5H), 3.18 (d, J=9.5 Hz, 0.5H), 3.01 (d, J=9.0 Hz, 0.5H), 2.42-2.36 (m, 1H), 2.27-2.03 (m, 2H).

Step 3: (2S,3R,4S)-1-benzyl 2-methyl 3-allyl-4-(((chloromethyl)sulfonyl)oxy)pyrrolidine-1,2-dicarboxylate

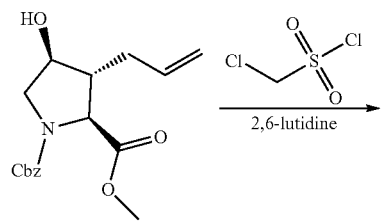

Chloromethanesulfonyl chloride (0.11 mL, 1.3 mmol) was added to the stirred solution of (2S,3R,4S)-1-benzyl 2-methyl 3-allyl-4-hydroxypyrrolidine-1,2-dicarboxylate (0.13 g, 0.41 mmol) and 2,6-dimethylpyridine (0.047 mL, 0.41 mmol) in DCM (2.0 mL) at 0° C., and the mixture was allowed to warm to 20° C. and stirred for 10 h. The reaction mixture was diluted with water, and extracted with DCM. The combined organic phase was washed with saturated aqueous NaHCO$_3$, 1 N HCl in water, brine, dried over anhydrous Na$_2$SO$_4$, filtered and concentrated. The residue was purified by silica gel chromatography (EtOAc in hexanes) to give (2S,3R,4S)-1-benzyl 2-methyl 3-allyl-4-(((chloromethyl)sulfonyl)oxy)pyrrolidine-1,2-dicarboxylate. LCMS (C$_{18}$H$_{23}$ClNO$_7$S$^+$)(ES, m/z): 432 [M+H]$^+$.

Step 4: (2S,3R,4R)-1-benzyl 2-methyl 4-acetoxy-3-allylpyrrolidine-1,2-dicarboxylate

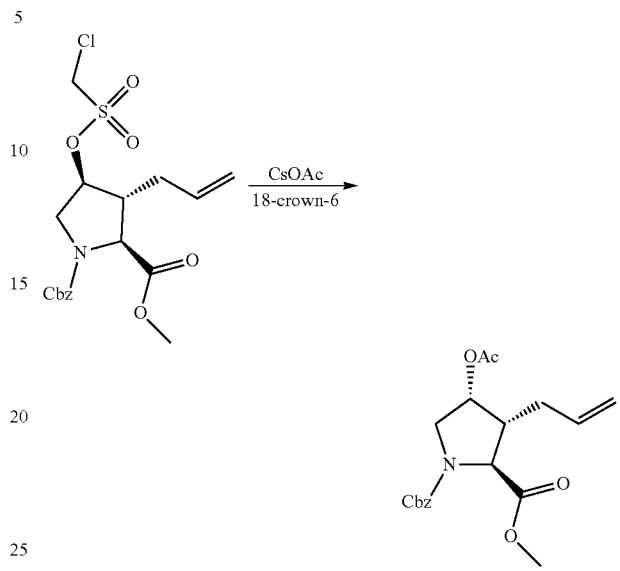

Cesium acetate (53 mg, 0.28 mmol) was added to the stirred solution of (2S,3R,4S)-1-benzyl 2-methyl 3-allyl-4-(((chloromethyl)sulfonyl)oxy)pyrrolidine-1,2-dicarboxylate (40 mg, 0.093 mmol) and 18-crown-6 (12 mg, 0.046 mmol) in toluene (1.0 mL) at 20° C., and the mixture was stirred at 80° C. for 3 h. The reaction was diluted with EtOAc and water, and extracted with EtOAc. The combined organic phase was washed with brine, dried over anhydrous Na$_2$SO$_4$, filtered and concentrated. The residue was purified by RP-HPLC [C18 column, water (0.1% HCl)—CH$_3$CN] to give (2S,3R,4R)-1-benzyl 2-methyl 4-acetoxy-3-allylpyrrolidine-1,2-dicarboxylate. The stereochemistry was assigned by 2D NMR. LCMS (C$_{19}$H$_{24}$NO$_6^+$)(ES, m/z): 362 [M+H]$^+$.

Step 5: (2S,3R,4R)-1-benzyl 2-methyl 4-acetoxy-3-(3-(4,4,5,5-tetramethyl-1,3,2-dioxaborolan-2-yl)propyl)pyrrolidine-1,2-dicarboxylate

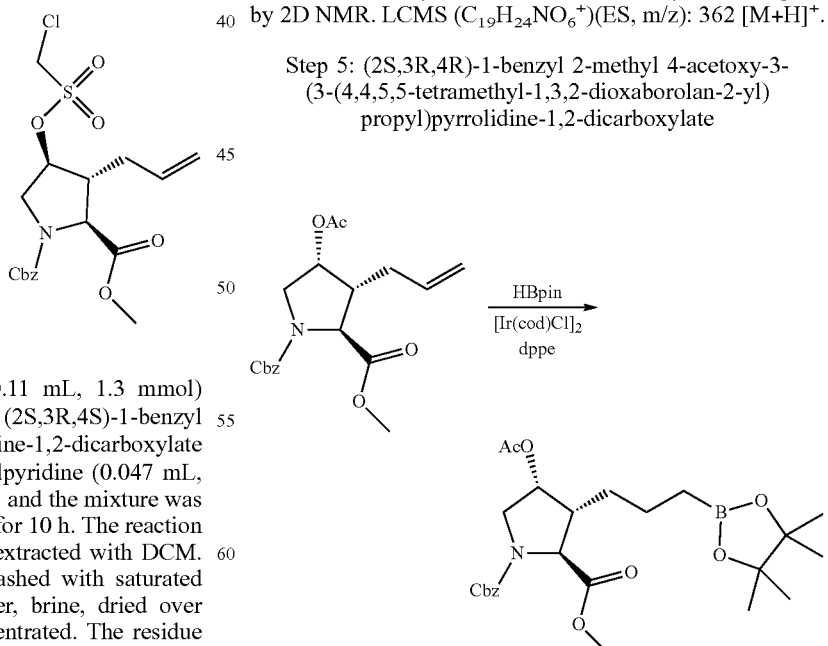

[Ir(cod)Cl]$_2$ (22 mg, 0.033 mmol) and 1,2-bis(diphenylphosphino)ethane (22 mg, 0.055 mmol) were added to the stirred solution of (2S,3R,4R)-1-benzyl 2-methyl 4-acetoxy-3-allylpyrrolidine-1,2-dicarboxylate (0.10 g, 0.28 mmol) and 4,4,5,5-tetramethyl-1,3,2-dioxaborolane (0.20 mL, 1.4 mmol) in DCM (2.0 mL) at 20° C. under $N_2$. The mixture was stirred at 20° C. for 15 h, then concentrated. The residue was purified by RP-HPLC [C18 column, water (0.1% TFA)-$CH_3CN$] to give (2S,3R,4R)-1-benzyl 2-methyl 4-acetoxy-3-(3-(4,4,5,5-tetramethyl-1,3,2-dioxaborolan-2-yl)propyl)pyrrolidine-1,2-dicarboxylate. LCMS ($C_{25}H_{37}BNO_8^+$)(ES, m/z): 490 [M+H]$^+$.

Step 6: (2S,3R,4R)-3-(3-boronopropyl)-4-hydroxypyrrolidine-2-carboxylic acid

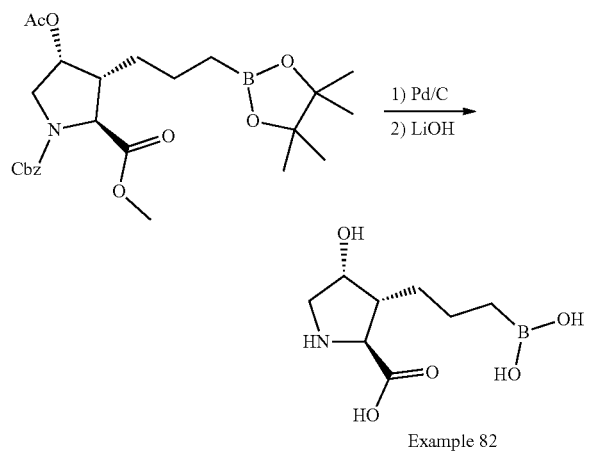

Example 82

10% Pd—C (13 mg, 0.012 mmol) was added to the stirred solution of (2S,3R,4R)-1-benzyl 2-methyl 4-acetoxy-3-(3-(4,4,5,5-tetramethyl-1,3,2-dioxaborolan-2-yl)propyl)pyrrolidine-1,2-dicarboxylate (60 mg, 0.12 mmol) in MeOH (2.0 mL) under $N_2$, and the mixture was degassed and backfilled with $H_2$ (three times). The resulting mixture was stirred under $H_2$ (15 psi) at 20° C. for 2 h, filtered and concentrated. The residue was dissolved in THF (2.0 mL) and then treated with 1 N LiOH in water (0.25 mL, 0.25 mmol). The resulting mixture was stirred at 20° C. for 18 h, then concentrated. The residue was purified by RP-HPLC [C18 column, water (20 mM HFBA and 0.1% TFA)-$CH_3CN$] to give (2S,3R,4R)-3-(3-boronopropyl)-4-hydroxypyrrolidine-2-carboxylic acid as a HFBA salt. LCMS ($C_8H_{17}BNO_5^+$)(ES, m/z): 218 [M+H]; $^1$H NMR (400 MHz, $D_2O$) δ 4.40 (br s, 1H), 3.78 (d, J=10.8 Hz, 1H), 3.36-3.18 (m, 2H), 2.23-2.09 (m, 1H), 1.63-1.17 (m, 4H), 0.76-0.53 (m, 2H).

Example 83: (2S,3S)-3-(3-boronopropyl)-3-(hydroxymethyl)pyrrolidine-2-carboxylic acid

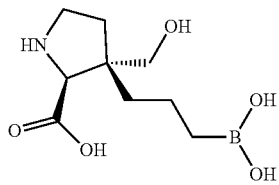 [SMILES: O=C(O)[C@H]1NCC[C@@]1(CO)CCCB(O)O]

Step 1: (2S,3S)-1-benzyl 2-methyl 3-allyl-3-(hydroxymethyl)-4-oxopyrrolidine-1,2-dicarboxylate

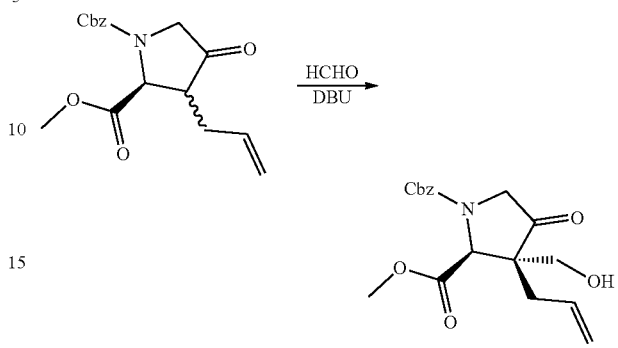

DBU (0.14 mL, 0.95 mmol) was added to the stirred solution of (2S)-1-benzyl 2-methyl 3-allyl-4-oxopyrrolidine-1,2-dicarboxylate (3.0 g, 9.5 mmol) and formaldehyde (37% in water, 0.70 mL, 9.5 mmol) in THF (45 mL) at 0° C., and the resulting mixture was stirred for 12 h at 0° C. The reaction mixture was concentrated, and the residue was purified by silica gel column chromatography (EtOAc in hexanes) to give (2S,3S)-1-benzyl 2-methyl 3-allyl-3-(hydroxymethyl)-4-oxopyrrolidine-1,2-dicarboxylate. The stereochemistry was assigned by 2D NMR. LCMS ($C_{18}H_{22}NO_6^+$)(ES, m/z): 348 [M+H]; $^1$H NMR (400 MHz, $CDCl_3$) δ 7.44-7.28 (m, 5H), 5.91-5.69 (m, 1H), 5.33-5.02 (m, 4H), 4.77 (br d, J=12.3 Hz, 1H), 4.06-3.98 (m, 2H), 3.75 (s, 3H), 3.70 (br s, 1H), 3.57 (s, 1H), 2.53-2.43 (m, 1H), 2.17-2.09 (m, 1H).

Step 2: (2S,3S)-1-benzyl 2-methyl 3-allyl-3-(((tert-butyldimethylsilyl)oxy)methyl)-4-oxopyrrolidine-1,2-dicarboxylate

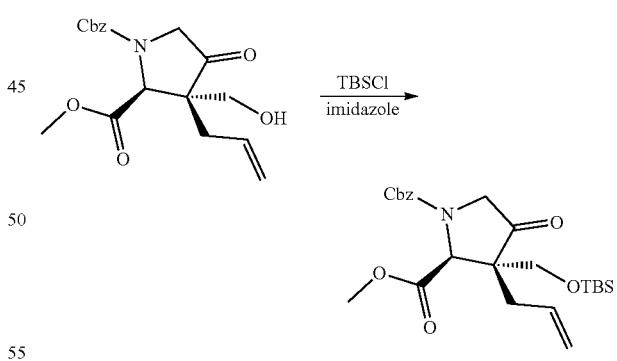

TBS-Cl (tert-Butyldimethylsilyl chloride)(3.5 g, 23 mmol) was added to the stirred solution of (2S,3S)-1-benzyl 2-methyl 3-allyl-3-(hydroxymethyl)-4-oxopyrrolidine-1,2-dicarboxylate (4.0 g, 12 mmol) and imidazole (2.4 g, 35 mmol) in DCM (50 mL) and the mixture was stirred at 20° C. for 5 h. The reaction mixture was quenched with saturated aqueous $NH_4Cl$ and extracted with EtOAc. The combined organic phase was washed with brine, dried over anhydrous $Na_2SO_4$, filtered and concentrated. The residue was purified by silica gel column chromatography (EtOAc in hexanes) to give (2S,3S)-1-benzyl 2-methyl 3-allyl-3-(((tert-butyldimethylsilyl)oxy)methyl)-4-oxopyrrolidine-1,2-dicarboxylate. LCMS ($C_{24}H_{36}NO_6Si^+$)(ES, m/z): 462 [M+H]$^+$.

Step 3: ((2S,3S,4S)-1-benzyl 2-methyl 3-allyl-3-(((tert-butyldimethylsilyl)oxy)methyl)-4-hydroxypyrrolidine-1,2-dicarboxylate as the first eluting peak (4-P1) and (2S,3S,4R)-1-benzyl 2-methyl 3-allyl-3-(((tert-butyldimethylsilyl)oxy)methyl)-4-hydroxypyrrolidine-1,2-dicarboxylate as the second eluting peak (4-P2)

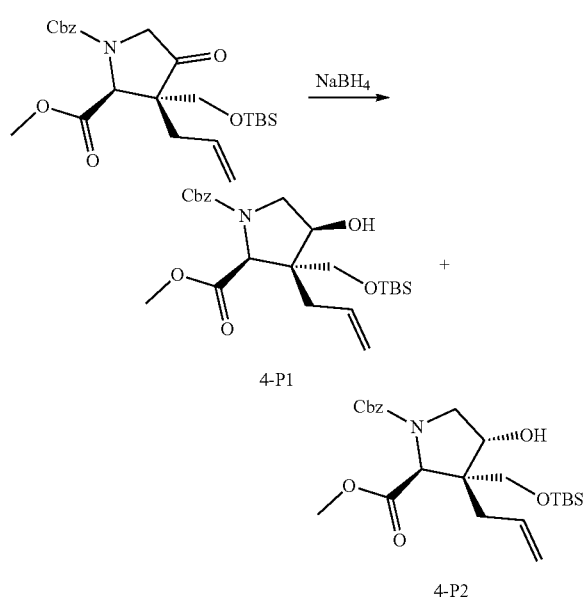

NaBH$_4$ (1.1 g, 29 mmol) was added to the stirred solution of (2S,3S)-1-benzyl 2-methyl 3-allyl-3-(((tert-butyldimethylsilyl)oxy)methyl)-4-oxopyrrolidine-1,2-dicarboxylate (4.5 g, 9.8 mmol) in MeOH (50 mL), and the mixture was stirred at 0° C. for 0.5 h. The reaction mixture was diluted with acetone and stirred for 10 min at 0° C., then concentrated. The residue was quenched with saturated aqueous NH$_4$Cl and extracted with EtOAc. The combined organic phase was washed with brine, dried over anhydrous Na$_2$SO$_4$, filtered and concentrated. The residue was purified by silica gel column chromatography (EtOAc in hexanes) to give (2S,3S,4S)-1-benzyl 2-methyl 3-allyl-3-(((tert-butyldimethylsilyl)oxy)methyl)-4-hydroxypyrrolidine-1,2-dicarboxylate as the first eluting peak (4-P1) and (2S,3S,4R)-1-benzyl 2-methyl 3-allyl-3-(((tert-butyldimethylsilyl)oxy)methyl)-4-hydroxypyrrolidine-1,2-dicarboxylate as the second eluting peak (4-P2). The stereochemistry was assigned by 2D NMR. 4-P1: LCMS ($C_{24}H_3NO_6Si^+$)(ES, m/z): 464 [M+H]$^+$; H NMR (400 MHz, CDCl$_3$) δ 7.42-7.26 (m, 5H), 5.89-5.71 (m, 1H), 5.24-4.99 (m, 4H), 4.30-4.29 (m, 1H), 4.00-3.84 (m, 1H), 3.82 (s, 1.5H), 3.79-3.75 (m, 2H), 3.62 (s, 1.5H), 3.51-3.42 (m, 1H), 3.35-3.23 (m, 1H), 2.34-2.23 (m, 2H), 0.94-0.82 (m, 9H), 0.05-0.03 (m, 6H). 4-P2: LCMS ($C_{24}H_3NO_6Si^+$) (ES, m/z): 464 [M+H]; $^1$H NMR (400 MHz, CDCl$_3$) δ 7.39-7.23 (m, 5H), 5.89-5.71 (m, 1H), 5.22-4.99 (m, 4H), 4.41-4.31 (m, 2H), 3.94-3.78 (m, 3H), 3.74 (s, 1.5H), 3.53 (s, 1.5H), 3.50-3.39 (m, 1H), 2.31-2.18 (m, 1H), 2.14-2.04 (m, 1H), 0.92-0.85 (m, 9H), 0.12-0.04 (m, 6H).

Step 4: 1-benzyl 2-methyl (2S,3S,4S)-3-allyl-3-(((tert-butyldimethylsilyl)oxy)methyl)-4-(((methylthio)carbonothioyl)oxy)pyrrolidine-1,2-dicarboxylate

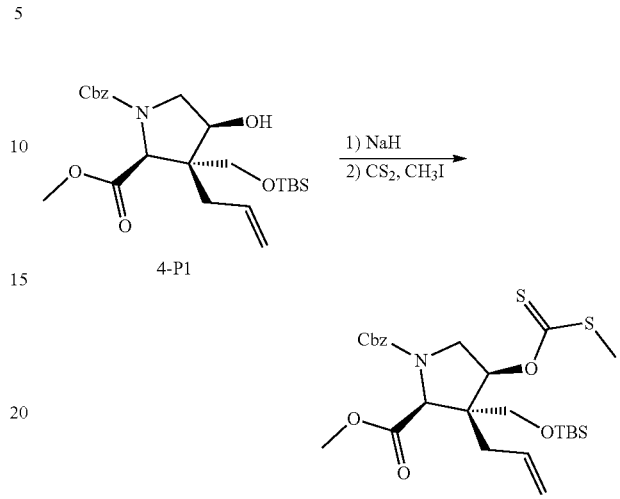

NaH (60% in mineral oil, 65 mg, 1.6 mmol) was added to the stirred solution of (2S,3S,4S)-1-benzyl 2-methyl 3-allyl-3-(((tert-butyldimethylsilyl)oxy)methyl)-4-hydroxypyrrolidine-1,2-dicarboxylate (0.50 g, 1.1 mmol) in THF (15 mL) under N$_2$ and the mixture was stirred at 0° C. for 30 min. Carbon disulfide (0.21 g, 2.7 mmol) and iodomethane (0.64 mL, 10 mmol) were added at 0° C., and the resulting mixture was stirred for another 30 min. The reaction mixture was quenched with saturated aqueous NH$_4$Cl and extracted with EtOAc. The combined organic phase was washed with brine, dried over anhydrous Na$_2$SO$_4$, filtered and concentrated. The residue was purified by silica gel column chromatography (EtOAc in hexanes) to give (2S,3S,4S)-1-benzyl 2-methyl 3-allyl-3-(((tert-butyldimethylsilyl)oxy)methyl)-4-(((methylthio)carbonothioyl)oxy)pyrrolidine-1,2-dicarboxylate. LCMS ($C_{26}H_{40}NO_6S_2Si^+$)(ES, m/z): 554 [M+H]$^+$.

Step 5: (2S,3S)-1-benzyl 2-methyl 3-allyl-3-(((tert-butyldimethylsilyl)oxy)methyl)pyrrolidine-1,2-dicarboxylate

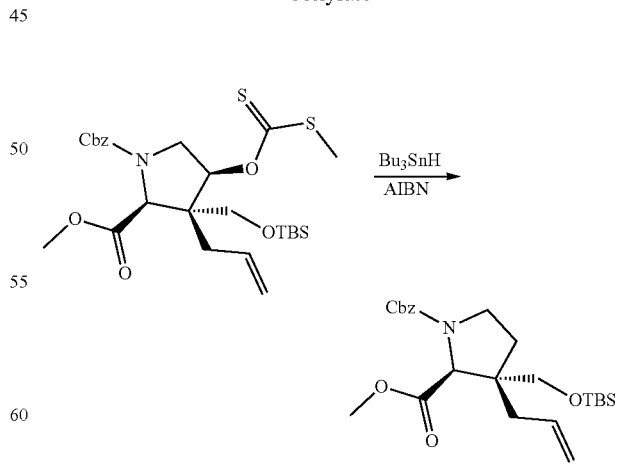

Tributylstannane (0.83 mL, 3.6 mmol) was added to the stirred solution of (2S,3S,4R)-1-benzyl 2-methyl 3-allyl-3-(((tert-butyldimethylsilyl)oxy)methyl)-4-(((methylthio)carbonothioyl)oxy)pyrrolidine-1,2-dicarboxylate (1.0 g, 1.8 mmol) and AIBN (0.030 g, 0.18 mmol) in toluene (10 mL) at 15° C. under N₂. The reaction mixture was stirred at 110° C. for 2 h, then cooled to room temperature and quenched with saturated aqueous KF, and extracted with EtOAc. The combined organic phase was dried over anhydrous Na₂SO₄, filtered and concentrated. The residue was purified by silica gel chromatography (EtOAc in hexanes) to give (2S,3S)-1-benzyl 2-methyl 3-allyl-3-(((tert-butyldimethylsilyl)oxy)methyl)pyrrolidine-1,2-dicarboxylate. LCMS (C₂₄H₃NO₅Si⁺)(ES, m/z): 448 [M+H]⁺.

Step 6: (2S,3S)-1-benzyl 2-methyl 3-(((tert-butyldimethylsilyl)oxy)methyl)-3-(3-(4,4,5,5-tetramethyl-1,3,2-dioxaborolan-2-yl)propyl)pyrrolidine-1,2-dicarboxylate

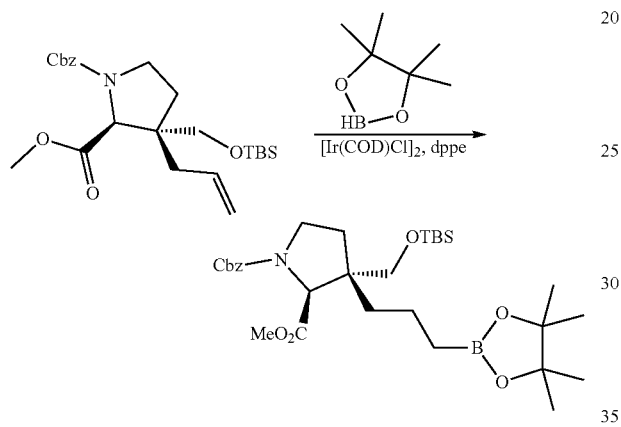

4,4,5,5-Tetramethyl-1,3,2-dioxaborolane (0.049 mL, 0.34 mmol) was added to the stirred solution of [Ir(cod)Cl]₂ (5.3 mg, 7.8 µmol) and 1,2-bis(diphenylphosphino)ethane (6.7 mg, 0.017 mmol) in CH₂Cl₂ (2.0 mL) under N₂, and the mixture was stirred for 20 min, followed by addition of (2S,3S)-1-benzyl 2-methyl 3-allyl-3-(((tert-butyldimethylsilyl)oxy)methyl)pyrrolidine-1,2-dicarboxylate (50 mg, 0.11 mmol). The resulting mixture was stirred at 26° C. for 12 h under N₂. The reaction mixture was concentrated, and the residue was purified by RP-HPLC [C18 column, water (0.1% TFA)-CH₃CN] to give (2S,3S)-1-benzyl 2-methyl 3-(((tert-butyldimethylsilyl)oxy)methyl)-3-(3-(4,4,5,5-tetramethyl-1,3,2-dioxaborolan-2-yl)propyl)pyrrolidine-1,2-dicarboxylate. LCMS (C₃₀H₅₁BNO₇Si⁺)(ES, m/z): 576 [M+H]⁺.

Step 7: (2S,3S)-3-(3-boronopropyl)-3-(hydroxymethyl)pyrrolidine-2-carboxylic acid

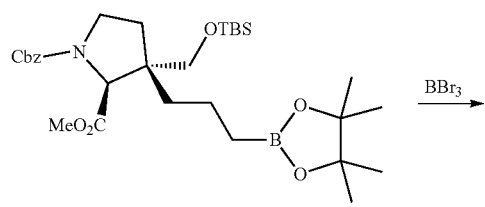

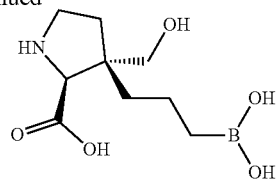

Example 83

Boron tribromide (0.20 mL, 2.1 mmol) was added to the stirred solution of (2S,3S)-1-benzyl 2-methyl 3-(((tert-butyldimethylsilyl)oxy)methyl)-3-(3-(4,4,5,5-tetramethyl-1,3,2-dioxaborolan-2-yl)propyl)pyrrolidine-1,2-dicarboxylate (50 mg, 0.087 mmol) in DCM (1.0 mL) at −78° C., and the resulting mixture was stirred for 12 h at 26° C. The reaction mixture was diluted with H₂O and the aqueous layer was purified by RP-HPLC [C18 column, water (20 mM HFBA and 0.1% TFA)-CH₃CN] to give ((2S,3S)-3-(3-boronopropyl)-3-(hydroxymethyl)pyrrolidine-2-carboxylic acid as a HFBA salt. LCMS (C₉H₁₇BNO₄⁺)(ES, m/z): 214 [M+H—H₂O]⁺. ¹H NMR (400 MHz, D₂O) δ 4.00 (s, 1H), 3.59-3.48 (m, 2H), 3.36-3.27 (m, 1H), 3.27-3.17 (m, 1H), 1.93-1.82 (m, 2H), 1.36-1.10 (m, 4H), 0.68-0.54 (m, 2H).

Example 84: (2S,3S)-3-(3-boronopropyl)-3-(difluoromethyl)pyrrolidine-2-carboxylic acid

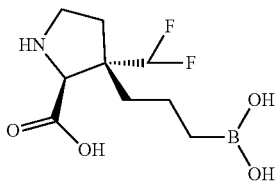 [SMILES: O=C(O)[C@H]1NCC[C@]1(CCCB(O)O)C(F)F]

Step 1: (2S,3S)-1-benzyl 2-methyl 3-allyl-3-(hydroxymethyl)pyrrolidine-1,2-dicarboxylate

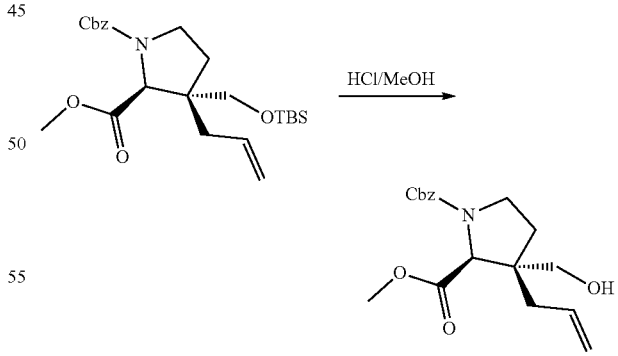

4 N HCl in MeOH (10 mL, 40.0 mmol) was added to the stirred mixture of (2S,3S)-1-benzyl 2-methyl 3-allyl-3-(((tert-butyldimethylsilyl)oxy)methyl)pyrrolidine-1,2-dicarboxylate (0.70 g, 1.6 mmol) in THF (2.0 mL) and H₂O (3.0 mL), and the mixture was stirred at 45° C. for 2 h. The reaction mixture was concentrated, quenched with saturated aqueous NaHCO₃, and extracted with EtOAc. The combined organic phase was washed with brine, dried over anhydrous Na$_2$SO$_4$, filtered and concentrated. The residue was purified by silica gel chromatography (EtOAc in hexanes) to give (2S,3S)-1-benzyl 2-methyl 3-allyl-3-(hydroxymethyl)pyrrolidine-1,2-dicarboxylate. LCMS (C$_{18}$H$_{24}$NO$_5^+$)(ES, m/z): 334 [M+H]$^+$.

Step 2: (2S,3S)-1-benzyl 2-methyl 3-allyl-3-formylpyrrolidine-1,2-dicarboxylate

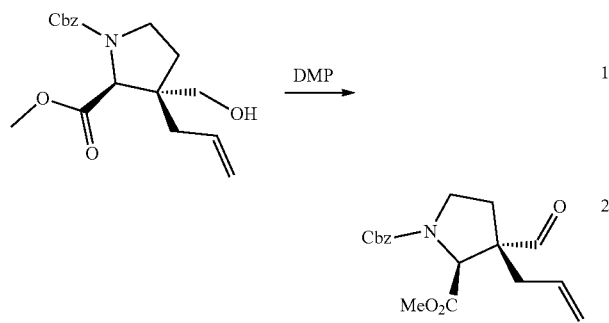

Dess-Martin Periodinane (0.97 g, 2.3 mmol) was added to a mixture of (2S,3S)-1-benzyl 2-methyl 3-allyl-3-(hydroxymethyl)pyrrolidine-1,2-dicarboxylate (0.38 g, 1.1 mmol) in CH$_2$Cl$_2$ (5.0 mL) and the mixture was stirred at 25° C. for 12 h. The reaction mixture was filtered and the filtrate was purified by silica gel chromatography (EtOAc in hexanes) to give (2S,3S)-1-benzyl 2-methyl 3-allyl-3-formylpyrrolidine-1,2-dicarboxylate. LCMS (C$_{18}$H$_{22}$NO$_5^+$)(ES, m/z): 332 [M+H]$^+$.

Step 3: (2S,3S)-1-benzyl 2-methyl 3-allyl-3-(difluoromethyl)pyrrolidine-1,2-dicarboxylate

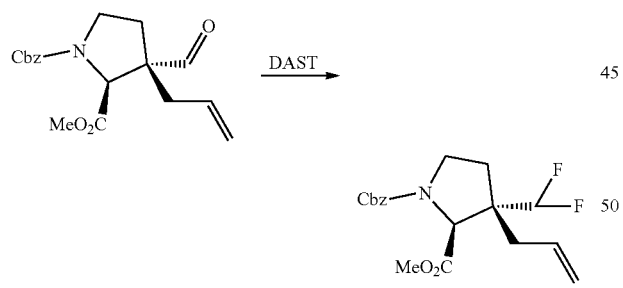

DAST (0.060 mL, 0.45 mmol) was added to a mixture of (2S,3S)-1-benzyl 2-methyl 3-allyl-3-formylpyrrolidine-1,2-dicarboxylate (0.10 g, 0.30 mmol) in DCM (4.0 mL) at 0° C. under N$_2$. The resulting mixture was allowed to warm to 25° C. and stirred at 25° C. for 13 h. The reaction mixture was quenched with saturated aqueous NaHCO$_3$ and extracted with DCM. The combined organic phase was washed with brine, dried over anhydrous Na$_2$SO$_4$, filtered and concentrated. The residue was purified by silica gel chromatography (EtOAc in hexanes) to give (2S,3S)-1-benzyl 2-methyl 3-allyl-3-(difluoromethyl)pyrrolidine-1,2-dicarboxylate. LCMS (C$_8$H$_{22}$F$_2$NO$_4^+$)(ES, m/z): 354 [M+H]$^+$.

Step 4: (2S,3S)-1-benzyl 2-methyl 3-(difluoromethyl)-3-(3-(4,4,5,5-tetramethyl-1,3,2-dioxaborolan-2-yl)propyl)pyrrolidine-1,2-dicarboxylate

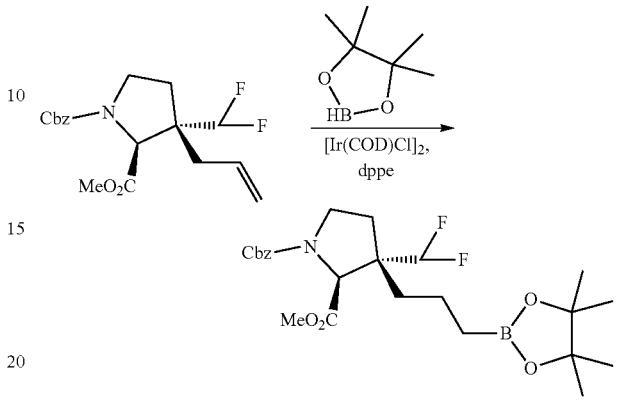

[Ir(cod)Cl]$_2$ (7.9 mg, 0.012 mmol) and 1,2-bis(diphenylphosphino)ethane (9.4 mg, 0.023 mmol) were added to the stirred solution of 4,4,5,5-tetramethyl-1,3,2-dioxaborolane (0.10 mL, 0.71 mmol) in CH$_2$Cl$_2$ (5.0 mL), and the mixture was stirred at 25° C. under N$_2$ for 20 min, followed by addition of (2S,3S)-1-benzyl 2-methyl 3-allyl-3-(difluoromethyl)pyrrolidine-1,2-dicarboxylate (83 mg, 0.24 mmol), and the resulting mixture was stirred at 25° C. for 12 h under N$_2$. The reaction mixture was concentrated, and the residue was purified by silica gel chromatography (EtOAc in hexanes) to give (2S,3S)-1-benzyl 2-methyl 3-(difluoromethyl)-3-(3-(4,4,5,5-tetramethyl-1,3,2-dioxaborolan-2-yl)propyl)pyrrolidine-1,2-dicarboxylate. LCMS (C$_{24}$H$_{35}$BF$_2$NO$_6^+$)(ES, m/z): 482 [M+H]$^+$.

Step 5: (2S,3S)-3-(3-boronopropyl)-3-(difluoromethyl)pyrrolidine-2-carboxylic acid

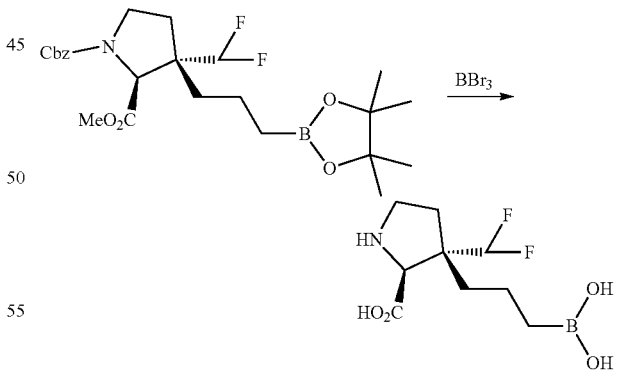

Example 84

Boron tribromide (0.20 mL, 2.1 mmol) was added to the stirred solution of (2S,3S)-1-benzyl 2-methyl 3-(difluoromethyl)-3-(3-(4,4,5,5-tetramethyl-1,3,2-dioxaborolan-2-yl)propyl)pyrrolidine-1,2-dicarboxylate (80 mg, 0.17 mmol) in DCM (2.0 mL) at −78° C. The resulting mixture was allowed to warm to 26° C. and stirred for 12 h at 26° C. The reaction mixture was diluted with H$_2$O, and the aqueous phase was purified by RP-HPLC [C18 column, water (20 mM HFBA and 0.1% TFA)-CH$_3$CN] to give ((2S,3S)-3-(3-boronopropyl)-3-(difluoromethyl)pyrrolidine-2-carboxylic acid as a HFBA salt. LCMS (C$_9$H$_{15}$BF$_2$NO$_3^+$)(ES, m/z): 234 [M+H—H$_2$O]$^+$; $^1$H NMR (400 MHz, D$_2$O) δ 6.28-5.90 (m, 1H), 4.34 (s, 1H), 3.54-3.43 (m, 1H), 3.39-3.25 (m, 1H), 2.36-2.24 (m, 1H), 2.13-1.99 (m, 1H), 1.78-1.61 (m, 1H), 1.54-1.26 (m, 3H), 0.78-0.63 (m, 2H).

Example 85: (2S,3R)-3-(aminomethyl)-3-(3-boronopropyl)pyrrolidine-2-carboxylic acid

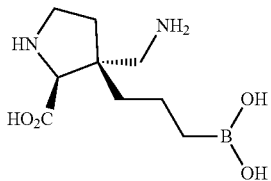 [SMILES: NC[C@@]1(CCCB(O)O)CCN[C@@H]1C(=O)O]

Step 1: (2S,3R)-1-benzyl 2-methyl 3-allyl-3-(((4-methoxybenzyl)amino)methyl)pyrrolidine-1,2-dicarboxylate

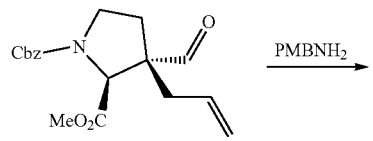

Titanium(IV) isopropoxide (0.43 g, 1.5 mmol) was added to the stirred solution of (2S,3S)-1-benzyl 2-methyl 3-allyl-3-formylpyrrolidine-1,2-dicarboxylate (0.10 g, 0.30 mmol) and (4-methoxyphenyl)methanamine (83 mg, 0.60 mmol) in THF (4.0 mL) at 25° C. under N$_2$, and the mixture was stirred at 25° C. for 4 h. The reaction mixture was diluted with MeOH, followed by addition of NaBH$_4$ (11 mg, 0.30 mmol) and the resulting mixture was stirred at 25° C. for 2 h. The reaction mixture was filtered and concentrated. The residue was purified by RP-HPLC [C18 column, water (0.1% TFA)-CH$_3$CN] to give (2S,3R)-1-benzyl 2-methyl 3-allyl-3-(((4-methoxybenzyl)amino)methyl)pyrrolidine-1,2-dicarboxylate. LCMS (C$_{26}$H$_{33}$N$_2$O$_5^+$)(ES, m/z): 453 [M+H]$^+$.

Step 2: (2S,3R)-1-benzyl 2-methyl 3-(((4-methoxybenzyl)amino)methyl)-3-(3-(4,4,5,5-tetramethyl-1,3,2-dioxaborolan-2-yl)propyl)pyrrolidine-1,2-dicarboxylate

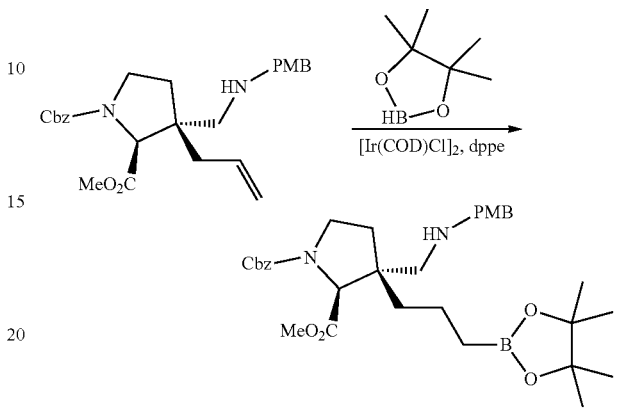

[Ir(cod)Cl]$_2$ (4.1 mg, 6.1 μmol) and 1,2-bis(diphenylphosphino)ethane (4.8 mg, 0.012 mmol) were added to the stirred solution of 4,4,5,5-tetramethyl-1,3,2-dioxaborolane (0.088 mL, 0.61 mmol) in CH$_2$Cl$_2$ (5.0 mL), and the mixture was stirred at 25° C. under N$_2$ for 20 min, followed by addition of (2S,3R)-1-benzyl 2-methyl 3-allyl-3-(((4-methoxybenzyl)amino)methyl)pyrrolidine-1,2-dicarboxylate (55 mg, 0.12 mmol). The resulting mixture was stirred at 25° C. for 12 h under N$_2$.

The reaction mixture was concentrated and the residue was purified by RP-HPLC [C18 column, water (0.1% TFA)-CH$_3$CN] to give (2S,3R)-1-benzyl 2-methyl 3-(((4-methoxybenzyl)amino)methyl)-3-(3-(4,4,5,5-tetramethyl-1,3,2-dioxaborolan-2-yl)propyl)pyrrolidine-1,2-dicarboxylate, which contained minor corresponding boronic acid. LCMS (C$_{32}$H$_{46}$BN$_2$O$_7^+$)(ES, m/z): 581 [M+H]$^+$.

Step 3: (3-((2S,3R)-3-(aminomethyl)-2-(methoxycarbonyl)pyrrolidin-3-yl)propyl)boronic acid

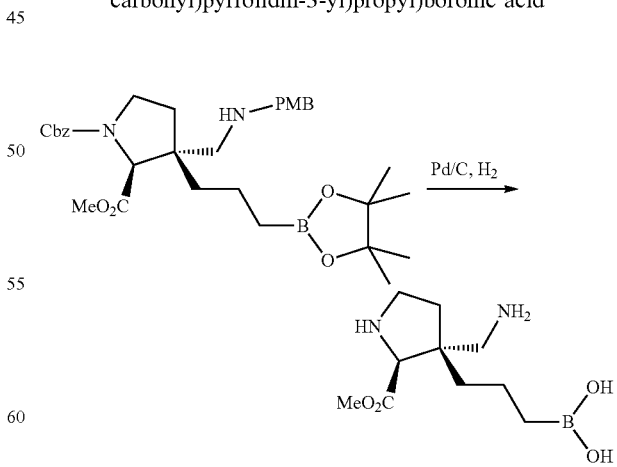

A mixture of 10% Pd—C and 20% Pd(OH)$_2$ (1:1, 37 mg, 0.034 mmol) was added to the stirred solution of (2S,3R)-1-benzyl 2-methyl 3-(((4-methoxybenzyl)amino)methyl)-3-(3-(4,4,5,5-tetramethyl-1,3,2-dioxaborolan-2-yl)propyl)pyrrolidine-1,2-dicarboxylate (20 mg, 0.034 mmol) in MeOH (8.0 mL) under $N_2$ atmosphere. The mixture was degassed and backfilled with $H_2$ (three times), and stirred under $H_2$ (15 psi) at 25° C. for 6 h. The reaction mixture was filtered and concentrated to give crude (3-((2S,3R)-3-(aminomethyl)-2-(methoxycarbonyl)pyrrolidin-3-yl)propyl)boronic acid, which was used in the next step directly without further purification. LCMS $(C_{10}H_{22}BN_2O_4^+)$(ES, m/z): 245 $[M+H]^+$.

Step 4: (2S,3R)-3-(aminomethyl)-3-(3-boronopropyl)pyrrolidine-2-carboxylic acid

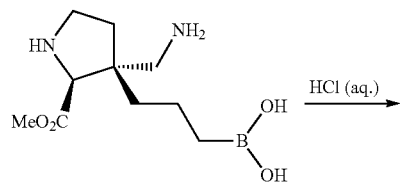

Example 85

A mixture of (3-((2S,3R)-3-(aminomethyl)-2-(methoxycarbonyl)pyrrolidin-3-yl)propyl)boronic acid (10 mg, 0.041 mmol) in 12 N HCl in water (10 mL, 0.12 mol) was stirred at 105° C. for 13 h. The reaction mixture was concentrated and the residue was purified by RP-HPLC [C18 column, water (20 mM HFBA and 0.1% TFA)-$CH_3CN$] to give (2S,3R)-3-(aminomethyl)-3-(3-boronopropyl)pyrrolidine-2-carboxylic acid as a HFBA salt. LCMS $(C_9H_{18}BN_2O_3^+)$(ES, m/z): 213 $[M+H-H_2O]^+$; $^1H$ NMR (500 MHz, $D_2O$) δ 4.12 (s, 1H), 3.49-3.39 (m, 3H), 3.11 (d, J=13.7 Hz, 1H), 2.29-2.26 (m, 1H), 1.93-1.82 (m, 1H), 1.48-1.32 (m, 4H), 0.82-0.80 (m, 2H).

Example 86: (2S,3R)-3-(3-boronopropyl)-3-((dimethylamino)methyl)pyrrolidine-2-carboxylic acid

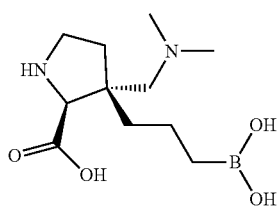 [SMILES: CN(C)C[C@@]1(CCCB(O)O)CCN[C@@H]1C(=O)O]

Step 1: 1-benzyl 2-methyl (2S,3S)-3-allyl-3-formylpyrrolidine-1,2-dicarboxylate

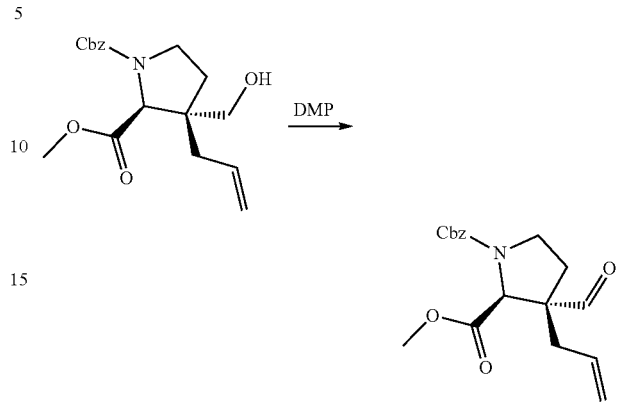

Dess-Martin Periodinane (0.95 g, 2.3 mmol) was added to the stirred solution of (2S,3S)-1-benzyl 2-methyl 3-allyl-3-(hydroxymethyl)pyrrolidine-1,2-dicarboxylate (0.50 g, 1.5 mmol) in DCM (20 mL) under Ar, and the mixture was stirred at 25° C. for 2 h. The reaction mixture was quenched with saturated aqueous $Na_2SO_3$, and extracted with DCM. The combined organic layer was dried over anhydrous $Na_2SO_4$, filtered and concentrated to give crude (2S,3S)-1-benzyl 2-methyl 3-allyl-3-formylpyrrolidine-1,2-dicarboxylate. LCMS $(C_{18}H_{22}NO_5^+)$(ES, m/z): 332 $[M+H]^+$.

Step 2: 1-benzyl 2-methyl (2S,3R)-3-allyl-3-((dimethylamino)methyl)pyrrolidine-1,2-dicarboxylate

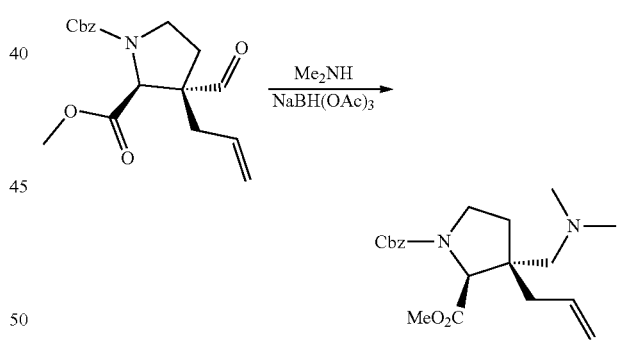

Sodium triacetoxyborohydride (0.38 g, 1.8 mmol) was added to the stirred mixture of (2S,3S)-1-benzyl 2-methyl 3-allyl-3-formylpyrrolidine-1,2-dicarboxylate (83 wt %, 0.20 g, 0.50 mmol) and dimethylamine (2 M in THF, 4.5 mL, 9.1 mmol) in DCE (2.0 mL) at 20° C., and the mixture was stirred at 20° C. for 2 h. The reaction was concentrated, and the residue was purified by RP-HPLC [C18 column, water (0.1% TFA)-$CH_3CN$] to give crude (2S,3R)-1-benzyl 2-methyl 3-allyl-3-((dimethylamino)methyl)pyrrolidine-1,2-dicarboxylate. LCMS $(C_{20}H_{29}N_2O_4^+)$(ES, m/z): 361 $[M+H]^+$. $^1H$ NMR (400 MHz, chloroform-d) δ 7.41-7.26 (m, 5H), 5.88-5.61 (m, 1H), 5.38-5.19 (m, 2H), 5.17-4.95 (m, 1H), 4.46-4.25 (m, 1H), 3.72 (s, 3H), 3.55 (s, 3H), 3.23-3.00 (m, 2H), 2.90-2.73 (m, 6H), 2.57-2.04 (m, 4H).

Step 3: 1-benzyl 2-methyl (2S,3R)-3-((dimethylamino)methyl)-3-(3-(4,4,5,5-tetramethyl-1,3,2-dioxaborolan-2-yl)propyl)pyrrolidine-1,2-dicarboxylate

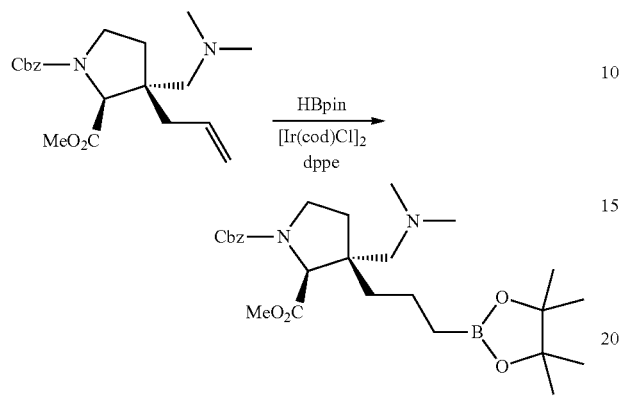

(2S,3R)-1-benzyl 2-methyl 3-allyl-3-((dimethylamino)methyl)pyrrolidine-1,2-dicarboxylate (150 mg, 0.416 mmol), 4,4,5,5-tetramethyl-1,3,2-dioxaborolane (160 mg, 1.248 mmol) and 1,2-bis(diphenylphosphino)ethane (16.58 mg, 0.042 mmol) in anhydrous DCM (3 mL) was bubbled with a stream of $N_2$ for 3 min. The reaction mixture was stirred at 25° C. for 10 min and then treated with [Ir(cod)Cl]$_2$ (13.98 mg, 0.021 mmol). The resulting mixture was stirred at 25° C. for 4 h under $N_2$. LCMS showed that the desired compound was formed. The reaction was filtered and concentrated in vacuum. The residue was purified by RP-HPLC [C18 column, water (0.1% TFA)-CH$_3$CN] to give (2S,3R)-1-benzyl 2-methyl 3-((dimethylamino)methyl)-3-(3-(4,4,5,5-tetramethyl-1,3,2-dioxaborolan-2-yl)propyl)pyrrolidine-1,2-dicarboxylate (110 mg, 54% yield) as yellow oil and contained boronic acid. LCMS (C$_{26}$H$_{42}$BN$_2$O$_6$$^+$)(ES, m/z): 489 [M+H]$^+$.

Step 4: (2,3R)-3-(3-boronopropyl)-3-((dimethylamino)methyl)pyrrolidine-2-carboxylic acid

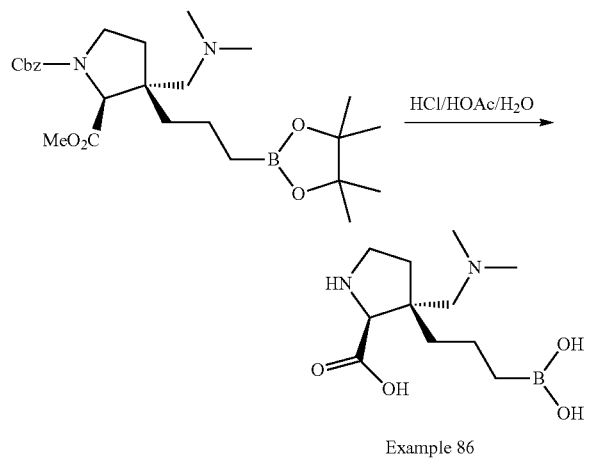

Example 86

A mixture of (2S,3R)-1-benzyl 2-methyl 3-((dimethylamino)methyl)-3-(3-(4,4,5,5-tetramethyl-1,3,2-dioxaborolan-2-yl)propyl)pyrrolidine-1,2-dicarboxylate (40 mg, 0.082 mmol) in 12 N HCl in water (2.0 mL, 24 mmol), acetic acid (1.0 mL) and water (1.0 mL) was heated in a microwave reactor with stirring at 120° C. for 0.5 h. The reaction mixture was concentrated, neutralized with saturated aqueous NaHCO$_3$, and washed with DCM. The aqueous layer was concentrated, acidified with 2 N HCl in water till pH ~6 and concentrated. The residue was purified by RP-HPLC [C18 column, water (20 mM HFBA and 0.1% TFA)-CH$_3$CN] to give (2S,3R)-3-(3-boronopropyl)-3-((dimethylamino)methyl)pyrrolidine-2-carboxylic acid as a HFBA salt. LCMS (C$_{11}$H$_{22}$BN$_2$O$_3$$^+$)(ES, m/z): 241 [M+H—H$_2$O]$^+$; $^1$H NMR (400 MHz, D$_2$O) δ 4.23 (s, 1H), 3.65-3.61 (m, 1H), 3.44-3.38 (m, 2H), 3.25-3.22 (m, 1H), 2.96 (s, 3H), 2.90 (s, 3H), 2.28-2.22 (m, 1H), 1.83-1.80 (m, 1H), 1.59-1.31 (m, 4H), 0.83-0.67 (m, 2H).

Example 87: (2S,3R)-3-(3-boronopropyl)-3-((methylamino)methyl)pyrrolidine-2-carboxylic acid

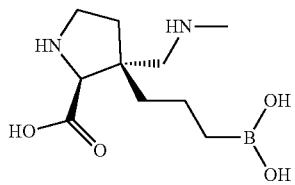 [SMILES: CNC[C@@]1(CCCB(O)O)CCN[C@@H]1C(=O)O]

Step 1: (3-((2S,3R)-3-(aminomethyl)-2-(methoxycarbonyl)pyrrolidin-3-yl)propyl)boronic acid

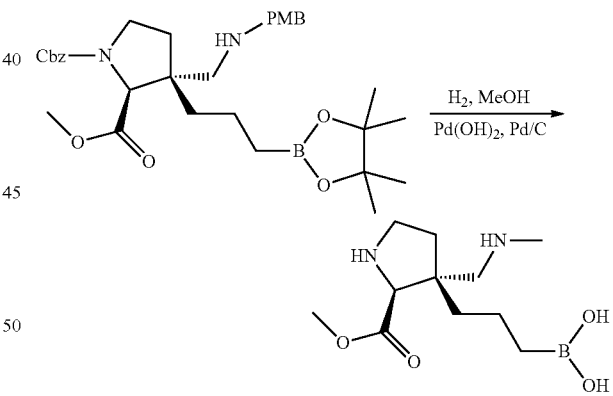

10% Pd—C and 10% Pd(OH)$_2$ (5:1, 30 mg, 0.028 mmol) was added to the stirred solution of (2S,3R)-1-benzyl 2-methyl 3-(((4-methoxybenzyl)amino)methyl)-3-(3-(4,4,5,5-tetramethyl-1,3,2-dioxaborolan-2-yl)propyl)pyrrolidine-1,2-dicarboxylate (0.23 g, 0.39 mmol) in MeOH (8.0 mL) and 30% NH$_3$.H$_2$O in water (0.50 mL) under N$_2$, and the mixture was degassed and backfilled with H$_2$ (three times), then stirred under H$_2$ (15 psi) at 25° C. for 4 h, and at 45° C. for 3 h. The reaction mixture was filtered and concentrated to give crude (3-((2S,3R)-3-(aminomethyl)-2-(methoxycarbonyl)pyrrolidin-3-yl)propyl)boronic acid, which was used in next step directly without further purification. LCMS (C$_{11}$H$_{24}$BN$_2$O$_4$$^+$)(ES, m/z): 259 [M+H]$^+$.

Step 2: (2S,3R)-3-(3-boronopropyl)-3-((methyl-amino)methyl)pyrrolidine-2-carboxylic acid Step 1: (2S,3S)-1-benzyl 2-methyl 3-allyl-3-cyanopyrrolidine-1,2-dicarboxylate

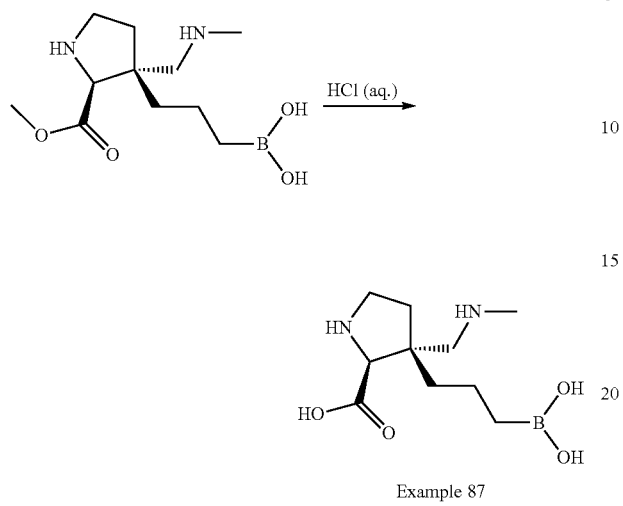

Example 87

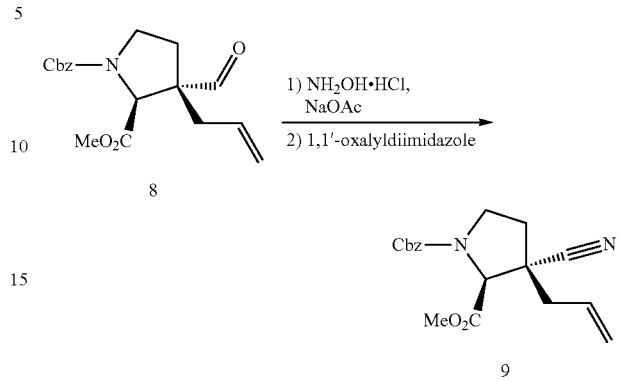

Hydroxylamine hydrochloride (0.10 g, 1.4 mmol) was added to the stirred solution of (2S,3S)-1-benzyl 2-methyl 3-allyl-3-formylpyrrolidine-1,2-dicarboxylate (80 mg, 0.24 mmol) and sodium acetate (59 mg, 0.72 mmol) in MeOH (1.0 mL), and the mixture was stirred at 26° C. for 12 h. The reaction mixture was concentrated, quenched by saturated aqueous NaHCO$_3$, and extracted with EtOAc. The combined organic phase was dried over anhydrous Na$_2$SO$_4$, filtered and concentrated. The crude residue was dissolved in toluene (1.0 mL) and treated with 1,2-di(1H-imidazol-1-yl)ethane-1,2-dione (41 mg, 0.22 mmol), and the mixture was stirred at 75° C. for 5 h. The reaction mixture was diluted with water and extracted with EtOAc. The combined organic phase was washed with brine, dried over anhydrous Na$_2$SO$_4$, filtered and concentrated. The residue was purified by silica gel column chromatography (EtOAc in hexanes) to give (2S,3S)-1-benzyl 2-methyl 3-allyl-3-cyanopyrrolidine-1,2-dicarboxylate. LCMS (C$_8$H$_{21}$N$_2$O$_4^+$)(ES, m/z): 329 [M+H]$^+$.

A mixture of (3-((2S,3R)-3-(aminomethyl)-2-(methoxycarbonyl)pyrrolidin-3-yl)propyl)boronic acid (80 mg, 0.16 mmol) and 12 N HCl in water (10 mL, 0.12 mol) was stirred at 105° C. for 13 h, then concentrated. The residue was purified by RP-HPLC [C18 column, water (20 mM HFBA and 0.1% TFA)-CH$_3$CN] to give (2S,3R)-3-(3-boronopropyl)-3-((methylamino)methyl)pyrrolidine-2-carboxylic acid as a HFBA salt. Structure was confirmed by 2D NMR. LCMS (C$_{10}$H$_{22}$BN$_2$O$_4^+$)(ES, m/z): 245 [M+H]; $^1$H NMR (500 MHz, D$_2$O) δ 4.15 (s, 1H), 3.54-3.46 (m, 1H), 3.42-3.35 (m, 2H), 3.08-3.01 (m, 1H), 2.73 (s, 3H), 2.26-2.17 (m, 1H), 1.90-1.79 (m, 1H), 1.45-1.30 (m, 4H), 0.83-0.68 (m, 2H).

Example 88: (2S,3S)-3-(3-boronopropyl)-3-cyano-pyrrolidine-2-carboxylic acid

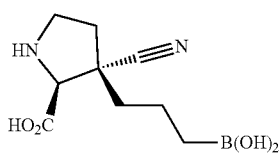

Example 89: (2S,3S)-3-(3-boronopropyl)-3-carbamoylpyrrolidine-2-carboxylic acid

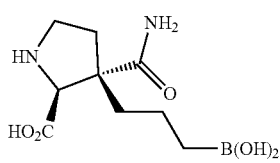 [SMILES: NC(=O)[C@@]1(CCCB(O)O)CCN[C@@H]1C(=O)O]

Step 4: (2S,3S)-1-benzyl 2-methyl 3-cyano-3-(3-(4,4,5,5-tetramethyl-1,3,2-dioxaborolan-2-yl)propyl)pyrrolidine-1,2-dicarboxylate

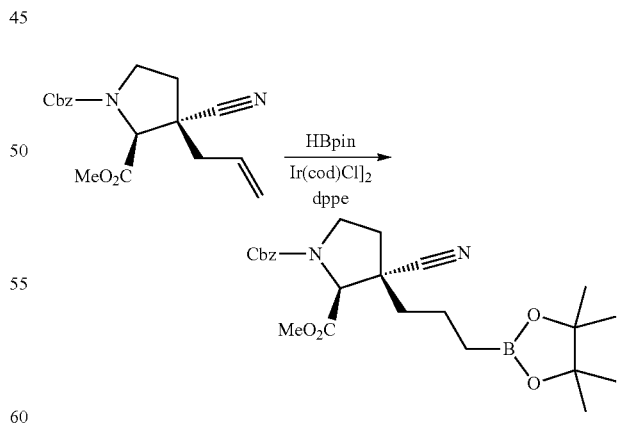

4,4,5,5-tetramethyl-1,3,2-dioxaborolane (0.086 mL, 0.59 mmol) was added to the stirred solution of [Ir(cod)Cl]$_2$ (9.3 mg, 0.014 mmol) and 1,2-bis(diphenylphosphino)ethane (12 mg, 0.030 mmol) in CH$_2$Cl$_2$ (2.0 mL) under N$_2$, and the mixture was stirred for 20 min, followed by addition of (2S,3S)-1-benzyl 2-methyl 3-allyl-3-cyanopyrrolidine-1,2- dicarboxylate (65 mg, 0.20 mmol), and the resulting mixture was stirred at 26° C. for 12 h. The reaction mixture was concentrated, and the residue was purified by silica gel column chromatography (EtOAc in hexanes) to give (2S,3S)-1-benzyl 2-methyl 3-cyano-3-(3-(4,4,5,5-tetramethyl-1,3,2-dioxaborolan-2-yl)propyl)pyrrolidine-1,2-dicarboxylate, which contained about 50% 4,4,5,5-tetramethyl-1,3,2-dioxaborolane. LCMS $(C_{24}H_{34}BN_2O_6^+)$(ES, m/z): 457 [M+H]$^+$.

Step 5: (2S,3S)-3-(3-boronopropyl)-3-cyanopyrrolidine-2-carboxylic acid an (2S,3S)-3-(3-boronopropyl)-3-carbamoylpyrrolidine-2-carboxylic acid

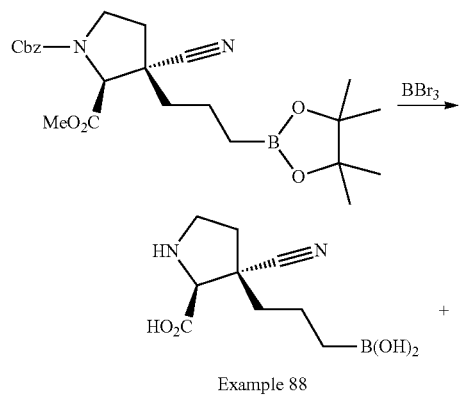

Example 88

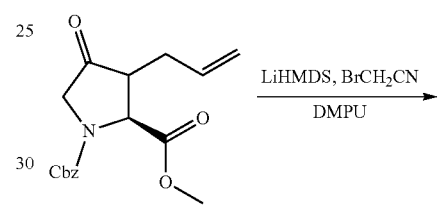

Example 89

Boron tribromide (10 μL, 0.11 mmol) was added to the stirred solution of (2S,3S)-1-benzyl 2-methyl 3-cyano-3-(3-(4,4,5,5-tetramethyl-1,3,2-dioxaborolan-2-yl)propyl)pyrrolidine-1,2-dicarboxylate (0.10 g, 0.11 mmol) in DCM (4.0 mL) at −78° C., and the resulting mixture was stirred at 26° C. for 18 h. The reaction mixture was diluted with water, and the aqueous phase was purified by RP-HPLC [C18 column, water (20 mM HFBA and 0.1% TFA)-CH$_3$CN] to give (2S,3S)-3-(3-boronopropyl)-3-cyanopyrrolidine-2-carboxylic acid (Example 88) as a HFBA salt, and (2S,3S)-3-(3-boronopropyl)-3-carbamoylpyrrolidine-2-carboxylic acid (Example 89) as a HFBA salt. Example 88: LCMS $(C_9H_{14}BN_2O_3^+)$(ES, m/z): 209 [M+H—H$_2$O]$^+$; $^1$H NMR (400 MHz, D$_2$O) δ 4.45 (s, 1H), 3.53-3.38 (m, 2H), 2.53-2.42 (m, 1H), 2.30-2.28 (m, 1H), 1.70-1.60 (m, 1H), 1.58-1.37 (m, 3H), 0.79-0.62 (m, 2H); Example 89: LCMS $(C_9H_{16}BN_2O_4^+)$(ES, m/z): 227 [M+H—H$_2$O]$^+$; $^1$H NMR (400 MHz, D$_2$O) δ 4.30 (s, 1H), 3.42-3.30 (m, 1H), 3.27-3.16 (m, 1H), 2.41-2.28 (m, 1H), 2.02-1.99 (m, 1H), 1.67-1.53 (m, 1H), 1.51-1.40 (m, 1H), 1.36-1.17 (m, 2H), 0.74-0.60 (m, 2H).

Example 90: (2S,3R,4S)-3-(3-boronopropyl)-3-(carboxymethyl)-4-hydroxypyrrolidine-2-carboxylic acid

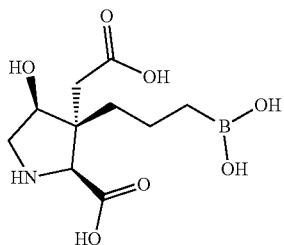 [SMILES: O=C(O)C[C@@]1(CCCB(O)O)[C@H](O)CN[C@@H]1C(=O)O]

Step 1: (2S,3R)-1-benzyl 2-methyl 3-allyl-3-(cyanomethyl)-4-oxopyrrolidine-1,2-dicarboxylate

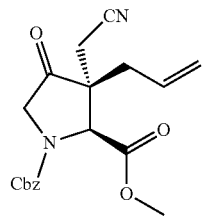

KHMDS (0.5 M in toluene, 21 mL, 10 mmol) was added to the stirred solution of (2S)-1-benzyl 2-methyl 3-allyl-4-oxopyrrolidine-1,2-dicarboxylate (3.0 g, 9.5 mmol) in THF (10 mL) and 1,3-dimethyltetrahydropyrimidin-2(1H)-one (1.5 mL, 12 mmol) at −78° C. under N$_2$, and the mixture was stirred at −78° C., for 1 h. 2-Bromoacetonitrile (1.2 mL, 17 mmol) was added in one portion at −78° C. and the reaction mixture was allowed to warm to 20° C. and stirred for 12 h. The reaction mixture was quenched with saturated aqueous NH$_4$Cl and extracted with EtOAc. The combined organic phase was washed with brine, dried over anhydrous Na$_2$SO$_4$, filtered and concentrated. The residue was purified by silica gel column chromatography (EtOAc in hexanes) to afford (2S,3R)-1-benzyl 2-methyl 3-allyl-3-(cyanomethyl)-4-oxopyrrolidine-1,2-dicarboxylate. LCMS $(C_{19}H_{21}N_2O_5^+)$(ES, m/z): 357 [M+H]$^+$.

Step 2: (2S,3R,4S)-1-benzyl 2-methyl 3-allyl-3-(cyanomethyl)-4-hydroxypyrrolidine-1,2-dicarboxylate

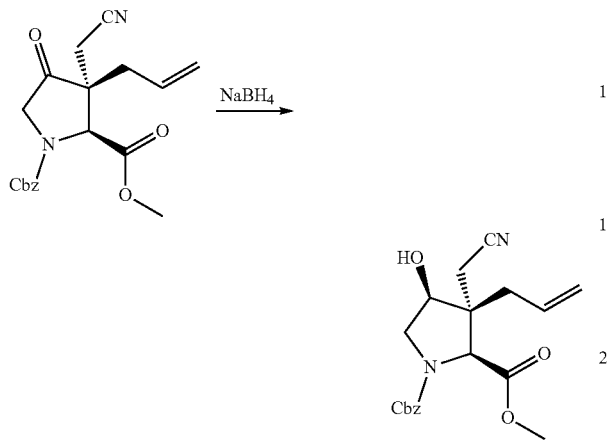

NaBH$_4$ (0.28 g, 7.3 mmol) was added to the stirred solution of (2S,3R)-1-benzyl 2-methyl 3-allyl-3-(cyanomethyl)-4-oxopyrrolidine-1,2-dicarboxylate (1.3 g, 3.7 mmol) in MeOH (15 mL) at −40° C., and the resulting mixture was stirred for 0.5 h at −40° C., then allowed to warm to 0° C. and stirred for another 2 h. The reaction mixture was quenched with water and concentrated. The residue was purified by RP-HPLC [C18 column, water (0.1% TFA)-CH$_3$CN] to give (2S,3R,4S)-1-benzyl 2-methyl 3-allyl-3-(cyanomethyl)-4-hydroxypyrrolidine-1,2-dicarboxylate. LCMS (C$_{19}$H$_{23}$N$_2$O$_5{}^+$)(ES, m/z): 359 [M+H]; $^1$H NMR (400 MHz, CDCl$_3$) δ 7.44-7.27 (m, 5H), 5.94-5.68 (m, 1H), 5.43-5.23 (m, 3H), 5.22-4.97 (m, 2H), 4.29 (d, J=16.7 Hz, 1H), 3.97-3.79 (m, 4H), 3.61 (s, 1H), 2.51-2.24 (m, 4H).

Step 3: (2S,3R,4S)-1-benzyl 2-methyl 3-(cyanomethyl)-4-hydroxy-3-(2-(4,4,5,5-tetramethyl-1,3,2-dioxaborolan-2-yl)ethyl)pyrrolidine-1,2-dicarboxylate

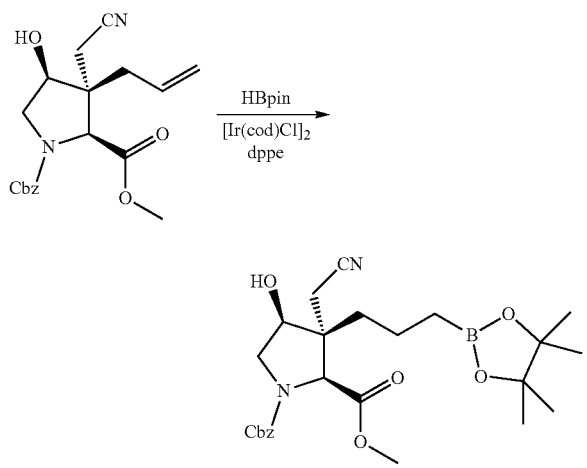

(2S,3R,4S)-1-benzyl 2-methyl 3-allyl-3-(cyanomethyl)-4-hydroxypyrrolidine-1,2-dicarboxylate (0.24 g, 0.67 mmol), 4,4,5,5-tetramethyl-1,3,2-dioxaborolane (0.26 g, 2.0 mmol) and 1,2-bis(diphenylphosphaneyl)ethane (27 mg, 0.067 mmol) in DCM (3.0 mL) was bubbled with a stream of N$_2$ for 3 min, and the mixture was stirred at 25° C. for 10 min, followed by addition of [Ir(cod)Cl]$_2$ (22 mg, 0.033 mmol). The resulting mixture was stirred at 25° C. for 5 h under N$_2$, then filtered and concentrated. The residue was purified by RP-HPLC [C18 column, water (0.1% TFA)-CH$_3$CN] to give (2S,3R,4S)-1-benzyl 2-methyl 3-(cyanomethyl)-4-hydroxy-3-(2-(4,4,5,5-tetramethyl-1,3,2-dioxaborolan-2-yl)ethyl)pyrrolidine-1,2-dicarboxylate which contained minor corresponding boronic acid. LCMS (C$_{24}$H$_{36}$BN$_2$O$_5{}^+$)(ES, m/z): 443 [M+H−CO$_2$]$^+$.

Step 4: (2S,3R,4S)-3-(3-boronopropyl)-3-(carboxymethyl)-4-hydroxypyrrolidine-2-carboxylic acid

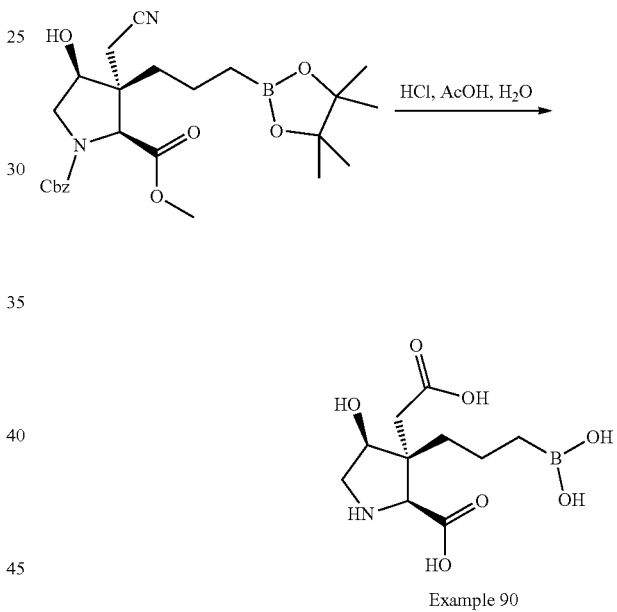

Example 90

(2S,3R, 4S)-1-benzyl 2-methyl 3-(cyanomethyl)-4-hydroxy-3-(3-(4,4,5,5-tetramethyl-1,3,2-dioxaborolan-2-yl)propyl)pyrrolidine-1,2-dicarboxylate (0.12 g, 0.25 mmol) was added to the stirred solution of 12 N HCl in water (1.0 mL, 12 mmol), acetic acid (0.5 mL) and water (0.5 mL), and the reaction mixture was heated in a microwave reactor with stirring at 120° C. for 0.5 h. The reaction mixture was concentrated, and neutralized with saturated aqueous NaHCO$_3$, then washed with DCM. The aqueous phase was concentrated, acidified with 2 N HCl in water to pH ~6 and concentrated. The residue was purified by RP-HPLC [C18 column, water (20 mM HFBA and 0.1% TFA)-CH$_3$CN] to give (2S,3R,4S)-3-(3-boronopropyl)-3-(carboxymethyl)-4-hydroxypyrrolidine-2-carboxylic acid as a HFBA salt. LCMS (C$_{10}$H$_{17}$BNO$_6{}^+$)(ES, m/z): 258 [M+H−H$_2$O]$^+$; $^1$H NMR (400 MHz, D$_2$O) δ 4.53 (s, 1H), 4.40-4.32 (m, 1H), 3.67-3.51 (m, 1H), 3.35-3.33 (m, 1H), 2.72-2.44 (m, 2H), 1.62-1.51 (m, 2H), 1.48-1.33 (m, 2H), 0.81-0.64 (m, 2H).

Example 91: (2S,3R)-3-(3-boronopropyl)-4-(hydroxymethyl)pyrrolidine-2-carboxylic acid

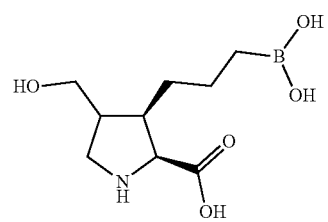 [SMILES: O=C(O)[C@H]1NCC(CO)[C@H]1CCCB(O)O]

Step 1: (2S,3R,Z)-1-benzyl 2-methyl 3-allyl-4-(methoxymethylene)pyrrolidine-1,2-dicarboxylate

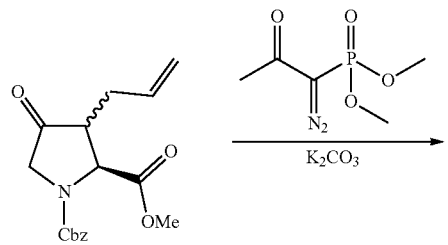

Dimethyl (1-diazo-2-oxopropyl)phosphonate (2.7 g, 14 mmol) and $K_2CO_3$ (3.9 g, 28 mmol) were added to the stirred mixture of (2S)-1-benzyl 2-methyl 3-allyl-4-oxopyrrolidine-1,2-dicarboxylate (3.0 g, 9.5 mmol) in MeOH (45 mL) at 0° C., and the resulting mixture was allowed to warm to 25° C. and stirred for 14 h. The reaction mixture was quenched with saturated aqueous $NH_4Cl$ and extracted with EtOAc. The combined organic phase was washed with brine, dried over anhydrous $Na_2SO_4$, filtered and concentrated. The residue was purified by silica gel chromatography (EtOAc in hexanes) to give a mixture of isomers, which was resolved by SFC [Column: DAICEL CHIRALPAK IC (250 mm*50 mm, 10 μm), Mobile phase: A: $CO_2$, B: MeOH (0.1% $NH_3.H_2O$), Gradient: 30% of B in 4.5 min, and hold 30% of B for 1 min, Flow Rate (mL/min) 200, Column temperature: 40° C.] to give (2S,3R,Z)-1-benzyl 2-methyl 3-allyl-4-(methoxymethylene)pyrrolidine-1,2-dicarboxylate. The stereochemistry was assigned by 2D NMR. LCMS $(C_{19}H_{24}NO_5^+)$(ES, m/z): 346, [M+H]; $^1$H NMR (500 MHz, $CDCl_3$) δ 7.29-7.16 (m, 5H), 5.83-5.69 (m, 2H), 5.12-4.90 (m, 4H), 4.50-4.36 (m, 1H), 4.25-4.15 (m, 1H), 4.03-3.94 (m, 1H), 3.65-3.43 (m, 6H), 3.04-2.89 (m, 1H), 2.17-1.93 (m, 2H).

Step 2: (2S,3R)-1-benzyl 2-methyl 3-allyl-4-formylpyrrolidine-1,2-dicarboxylate

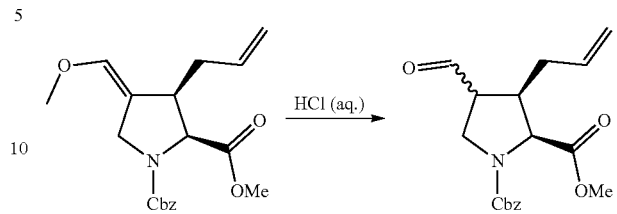

2 N HCl in water (1.0 mL, 2.0 mmol) was added to the stirred solution of (2S,3R,E)-1-benzyl 2-methyl 3-allyl-4-(methoxymethylene)pyrrolidine-1,2-dicarboxylate (0.21 g, 0.61 mmol) in THF (8.0 mL) at 25° C., and the mixture was stirred at 50° C. for 3 h. The reaction mixture was quenched with saturated aqueous $NH_4Cl$ and extracted with EtOAc. The combined organic phase was washed with brine, dried over anhydrous $Na_2SO_4$, filtered and concentrated to give crude (2S,3R)-1-benzyl 2-methyl 3-allyl-4-formylpyrrolidine-1,2-dicarboxylate, which was used in the next step directly without further purification. LCMS $(C_1H_{22}NO_5^+)$ (ES, m/z): 332, [M+H]$^+$.

Step 3: (2S,3R)-1-benzyl 2-methyl 3-allyl-4-(hydroxymethyl)pyrrolidine-1,2-dicarboxylate

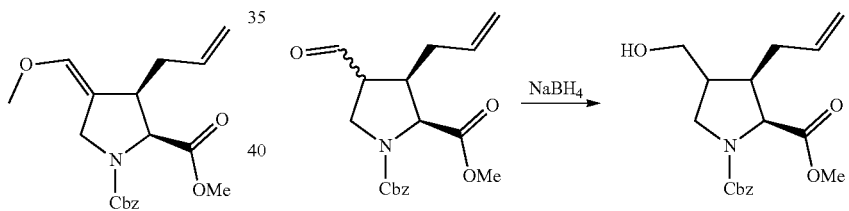

$NaBH_4$ (24 mg, 0.63 mmol) was added to the stirred mixture of (2S,3R)-1-benzyl 2-methyl 3-allyl-4-formylpyrrolidine-1,2-dicarboxylate (0.21 g, 0.63 mmol) in MeOH (2.0 mL), and the mixture was stirred at 0° C. for 1 h. Acetone (1.0 mL) was added and the resulting mixture was stirred for 10 min at 0° C., then concentrated, and the residue was purified by silica gel chromatography (EtOAc in hexanes) to give a mixture of diastereomers, which was resolved by SFC [Column: Phenomenex-Amylose-1 (250 mm*30 mm, 5 μm), Mobile phase: A: $CO_2$, B: MeOH (0.1% $NH_3.H_2O$), Gradient: 30% of B in 5.5 min, and hold 30% of B for 1 min, Flow Rate (mL/min) 60, Column temperature: 40° C.] to give (2S,3R)-1-benzyl 2-methyl 3-allyl-4-(hydroxymethyl)pyrrolidine-1,2-dicarboxylate. LCMS $(C_{18}H_{24}N_0^+)$(ES, m/z): 334, [M+H]; $^1$H NMR (500 MHz, Acetone-d6) δ 7.41-7.27 (m, 5H), 5.96-5.81 (m, 1H), 5.17-4.96 (m, 4H), 4.50-4.42 (m, 1H), 3.77-3.70 (m, 2H), 3.69-3.59 (m, 3H), 3.58-3.52 (m, 1H), 3.40-3.30 (m, 1H), 2.50-2.37 (m, 1H), 2.35-2.23 (m, 2H), 2.02-1.91 (m, 1H).

Step 4: (2S,3R)-1-benzyl 2-methyl 4-(hydroxymethyl)-3-(3-(4,4,5,5-tetramethyl-1,3,2-dioxaborolan-2-yl)propyl)pyrrolidine-1,2-dicarboxylate

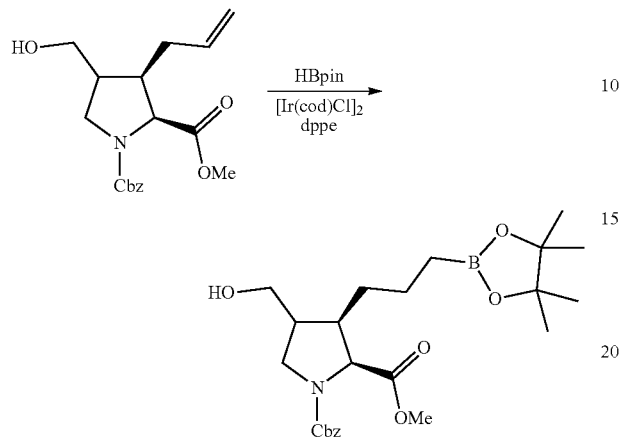

[Ir(cod)Cl]$_2$ (8.0 mg, 0.012 mmol) and dppe (7.0 mg, 0.018 mmol) were added to the stirred solution of 4,4,5,5-tetramethyl-1,3,2-dioxaborolane (0.078 mL, 0.54 mmol) in DCM (5.0 mL) and the mixture was stirred at 25° C. under N$_2$ for 20 min. (2S,3R)-1-benzyl 2-methyl 3-allyl-4-(hydroxymethyl)pyrrolidine-1,2-dicarboxylate (60 mg, 0.18 mmol) was added and the resulting mixture was stirred at 25° C. for 12 h under N$_2$, then concentrated. The residue was purified by silica gel chromatography (EtOAc in hexanes) to give (2S,3R)-1-benzyl 2-methyl 4-(hydroxymethyl)-3-(3-(4,4,5,5-tetramethyl-1,3,2-dioxaborolan-2-yl)propyl)pyrrolidine-1,2-dicarboxylate. LCMS (C$_{24}$H$_{37}$BNO$_7$$^+$)(ES, m/z): 462 [M+H]$^+$.

Step 5: (2S,3R)-3-(3-boronopropyl)-4-(hydroxymethyl)pyrrolidine-2-carboxylic acid

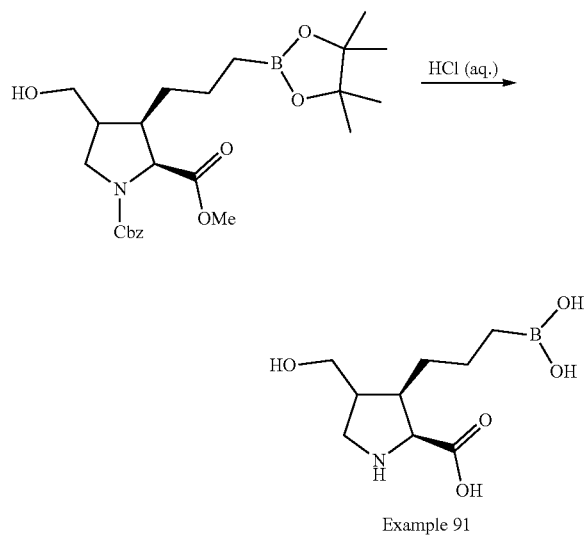

Example 91

A mixture of (2S,3R)-1-benzyl 2-methyl 4-(hydroxymethyl)-3-(3-(4,4,5,5-tetramethyl-1,3,2-dioxaborolan-2-yl)propyl)pyrrolidine-1,2-dicarboxylate (60 mg, 0.13 mmol) and 12 N HCl in water (5.0 mL, 60 mmol) was stirred at 105° C. for 13 h. The reaction mixture was washed with DCM, and the aqueous phase was concentrated. The residue was purified by RP-HPLC [C18 column, water (20 mM HFBA and 0.1% TFA)-CH$_3$CN] to give (2S,3R)-3-(3-boronopropyl)-4-(hydroxymethyl)pyrrolidine-2-carboxylic acid as a HFBA salt. LCMS (C$_9$H$_{17}$BNO$_4$$^+$)(ES, m/z): 214 [M+H—H$_2$O]$^+$; $^1$H NMR (500 MHz, D$_2$O) δ 4.34 (d, J=7.2 Hz, 1H), 3.69-3.58 (m, 2H), 3.58-3.49 (m, 1H), 3.18-3.08 (m, 1H), 2.43-2.33 (m, 2H), 1.52-1.37 (m, 2H), 1.37-1.28 (m, 2H), 0.81-0.66 (m, 2H).

Example 92A: (2R,3R,4R)-3-(3-boronopropyl-3-fluoro-4-hydroxypyrrolidine-2-carboxylic acid

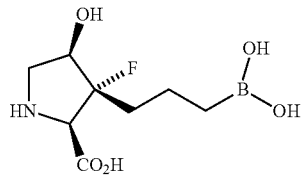 [SMILES: O=C(O)[C@H]1NC[C@@H](O)[C@@]1(F)CCCB(O)O]

Step 1: 1-(tert-butyl) 2-methyl (S)-3-allyl-4-((triethylsilyl)oxy)-2,5-dihydro-1H-pyrrole-1,2-dicarboxylate

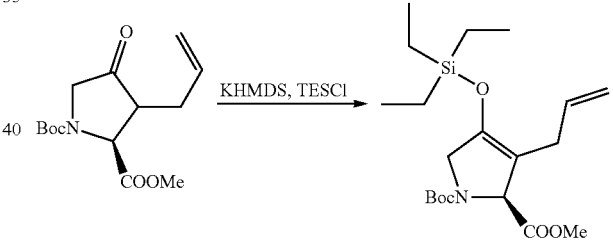

KHMDS (1.0 M in THF, 1.9 mL, 1.9 mmol) was added dropwise to the stirred solution of 1-(tert-butyl) 2-methyl (2S)-3-allyl-4-oxopyrrolidine-1,2-dicarboxylate (0.50 g, 1.8 mmol) in THF (6.6 mL) and 1,3-Dimethyl-3,4,5,6-tetrahydro-2(1H)-pyrimidinone (2.2 mL) at −78° C. over 1 h, followed by addition of a solution of chlorotriethylsilane (0.30 mL, 1.8 mmol) in THF (1.0 mL), and the reaction mixture was stirred at −78° C. for 0.5 h, then allowed to warm up to room temperature and stirred overnight. The reaction mixture was quenched with saturated aqueous NaHCO$_3$ and extracted with EtOAc. The combined organic phase was washed with brine, dried over anhydrous Na$_2$SO$_4$, and concentrated. The residue was purified by silica gel column chromatography (EtOAc in hexanes) to afford 1-(tert-butyl) 2-methyl (S)-3-allyl-4-((triethylsilyl)oxy)-2,5-dihydro-1H-pyrrole-1,2-dicarboxylate. LCMS (C$_{15}$H$_{28}$NO$_3$Si$^+$)(ES, m/z): 298 [M-CO$_2$C$_4$H$_8$+H]$^+$.

Step 2: 1-(tert-butyl) 2-methyl (2R)-3-allyl-3-fluoro-4-oxopyrrolidine-1,2-dicarboxylate

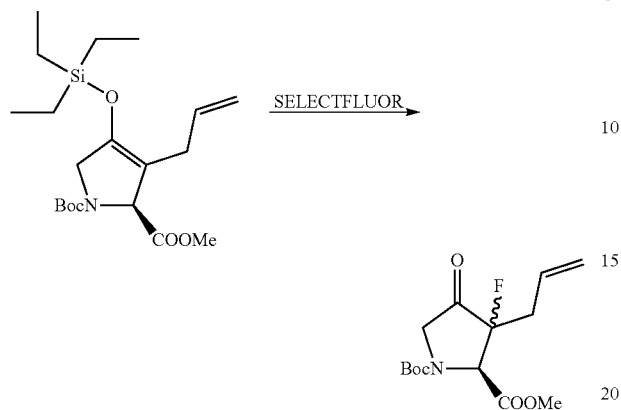

Selectfluor (0.62 g, 1.7 mmol) was added portion wise to the stirred solution of 1-(tert-butyl) 2-methyl (S)-3-allyl-4-((triethylsilyl)oxy)-2,5-dihydro-1H-pyrrole-1,2-dicarboxylate (0.66 g, 1.7 mmol) in acetonitrile (8.3 mL) at 0° C., and the resulting mixture was stirred at 0° C. for 1 h. The reaction mixture was concentrated, and the residue was purified by silica gel column chromatography (EtOAc in hexanes) to afford 1-(tert-butyl) 2-methyl (2R)-3-allyl-3-fluoro-4-oxopyrrolidine-1,2-dicarboxylate as a mixture of diastereomers. LCMS ($C_4H_{20}FNNaO_5^+$)(ES, m/z): 324 [M+Na]$^+$.

Step 3: 1-(tert-butyl) 2-methyl (2R,3R,4R)-3-allyl-3-fluoro-4-hydroxypyrrolidine-1,2-dicarboxylate & 1-(tert-butyl) 2-methyl (2R,3S,4R)-3-allyl-3-fluoro-4-hydroxypyrrolidine-1,2-dicarboxylate

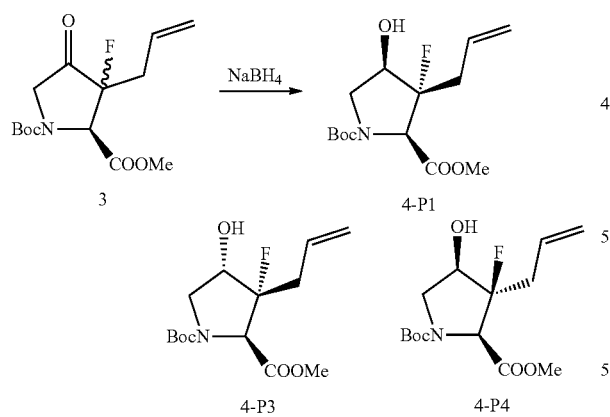

Sodium borohydride (19 mg, 0.51 mmol) was added to the stirred solution of 1-(tert-butyl) 2-methyl (2R)-3-allyl-3-fluoro-4-oxopyrrolidine-1,2-dicarboxylate (0.15 mg, 0.51 mmol) in MeOH (1.7 mL) at 0° C. The reaction mixture was allowed to warm to room temperature and stirred for 1 h, then concentrated, quenched with saturated aqueous NH$_4$Cl, and extracted with EtOAc. The combined organic phase was washed with brine, dried over Na$_2$SO$_4$, filtered, and concentrated. The residue was purified by silica gel column chromatography (EtOAc in hexanes) to afford 1-(tert-butyl) 2-methyl (2R,3R,4R)-3-allyl-3-fluoro-4-hydroxypyrrolidine-1,2-dicarboxylate (4-P1, the first eluting peak) as a single isomer, 1-(tert-butyl) 2-methyl (2R,3R,4S)-3-allyl-3-fluoro-4-hydroxypyrrolidine-1,2-dicarboxylate (4-P3, the third eluting peak) as a single isomer, and 1-(tert-butyl) 2-methyl (2R,3S,4R)-3-allyl-3-fluoro-4-hydroxypyrrolidine-1,2-dicarboxylate (4-P4, the fourth eluting peak) as a single isomer. 4-P1: LCMS ($C_{14}H_{22}FNNaO_5^+$)(ES, m/z): 326 [M+Na]$^+$; 4-P3: LCMS ($C_{14}H_{22}FNNaO_5^+$)(ES, m/z): 326 [M+Na]$^+$; 4-P4: LCMS ($C_{14}H_{22}FNNaO_5^+$)(ES, m/z): 326 [M+Na]$^+$.

Step 4: 1-(tert-butyl) 2-methyl (2R,3R,4R)-3-fluoro-4-hydroxy-3-(3-(4,4,5,5-tetramethyl-1,3,2-dioxaborolan-2-yl)propyl)pyrrolidine-1,2-dicarboxylate

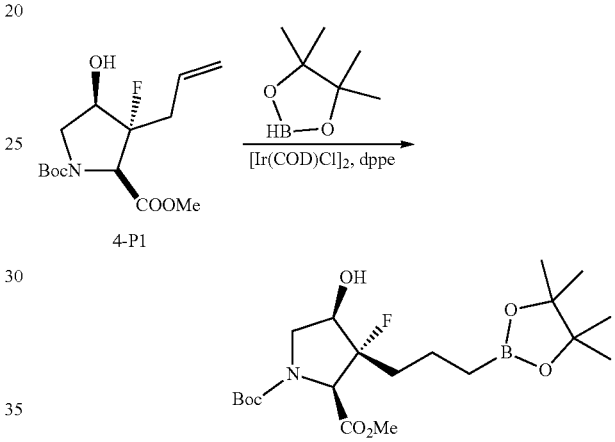

4,4,5,5-Tetramethyl-1,3,2-dioxaborolane (48 μL, 0.33 mmol) was added to the stirred solution of chloro(1,5-cyclooctadiene)iridium(I)dimer (5.5 mg, 8.2 μmol) and DPPE (6.6 mg, 0.016 mmol) in DCM (0.30 mL) at room temperature under N$_2$. The resulting mixture was added to the stirred solution of 1-(tert-butyl) 2-methyl (2R,3R,4R)-3-allyl-3-fluoro-4-hydroxypyrrolidine-1,2-dicarboxylate (4-P1, 25 mg, 0.082 mmol) in DCM (0.40 mL) at room temperature under N$_2$. The reaction mixture was stirred at room temperature for 1.5 h, then concentrated and the residue was purified by silica gel column chromatography (EtOAc in hexanes) to afford 1-(tert-butyl) 2-methyl (2R,3R,4R)-3-fluoro-4-hydroxy-3-(3-(4,4,5,5-tetramethyl-1,3,2-dioxaborolan-2-yl)propyl)pyrrolidine-1,2-dicarboxylate. LCMS ($C_{20}H_{35}BFNNaO_7^+$)(ES, m/z): 454 [M+Na]$^+$.

Step 5: (2R,3R,4R)-3-(3-boronopropyl)-3-fluoro-4-hydroxypyrrolidine-2-carboxylic acid hydrochloride

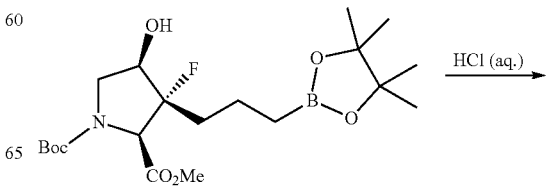

-continued

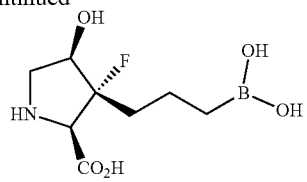

Example 92A 1-(tert-butyl) 2-methyl (2R,3R,4R)-3-fluoro-4-hydroxy-3-(3-(4,4,5,5-tetramethyl-1,3,2-dioxaborolan-2-yl)propyl)pyrrolidine-1,2-dicarboxylate (55 mg, 0.13 mmol) was treated with 6 N HCl in water (0.50 mL, 3.0 mmol) and the reaction mixture was stirred at 90° C. for 1 h. The reaction mixture was cooled to room temperature, diluted with water and washed with DCM, and the aqueous layer was lyophilized to afford (2R,3R,4R)-3-(3-boronopropyl)-3-fluoro-4-hydroxypyrrolidine-2-carboxylic acid hydrochloride as an HCl salt. LCMS ($CH_{14}BFNO_4^+$)(ES, m/z): 218 [M–$H_2$+H]$^+$. $^1$H NMR (500 MHz, $D_2O$) δ 4.50 (d, J=20.5 Hz, 1H), 4.42-4.37 (m, 1H), 3.68 (dt, J=12.9, 3.8 Hz, 1H), 3.49 (d, J=12.9 Hz, 1H), 2.12-1.98 (m, 1H), 1.97-1.81 (m, 1H), 1.69-1.50 (m, 2H), 0.79 (t, J=7.7 Hz, 2H).

Example 92B: (2R,3R,4S)-3-(3-boronopropyl)-3-fluoro-4-hydroxypyrrolidine-2-carboxylic acid

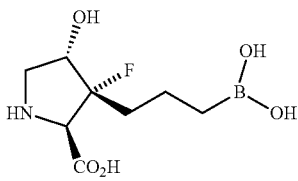

Example 92B was made from 1-(tert-butyl) 2-methyl (2R,3R,4S)-3-allyl-3-fluoro-4-hydroxypyrrolidine-1,2-dicarboxylate (4-P3) as the third eluted peak using the same procedure as Example 92A. LCMS ($C_8H_{14}BFNO_4^+$)(ES, m/z): 218 [M–$H_2O$+H]$^+$. $^1$H NMR (500 MHz, $D_2O$) δ 4.42 (d, J=18.4 Hz, 1H), 4.32 (dt, J=20.0, 7.7 Hz, 1H), 3.75 (dd, J=12.0, 7.8 Hz, 1H), 3.19 (dd, J=11.9, 8.1 Hz, 1H), 1.93-1.50 (m, 4H), 0.76 (t, J=7.7 Hz, 2H).

Example 92C: (2R,3S,4R)-3-(3-boronopropyl)-3-fluoro-4-hydroxypyrrolidine-2-carboxylic acid

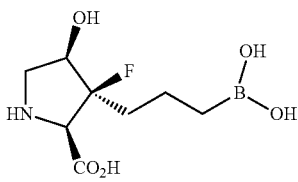 [SMILES: O=C(O)[C@H]1NC[C@@H](O)[C@]1(F)CCCB(O)O]

Example 92C was made from 1-(tert-butyl) 2-methyl (2R,3S,4R)-3-allyl-3-fluoro-4-hydroxypyrrolidine-1,2-dicarboxylate (4-P4) as the fourth eluted peak using the same procedure as Example 92A. LCMS ($C_8H_{16}BFNO_5^+$)(ES, m/z): 236 [M+H]$^+$. $^1$H NMR (500 MHz, $D_2O$) δ 4.45 (dt, J=22.1, 8.6 Hz, 1H), 4.32 (d, J=30.4 Hz, 1H), 3.64 (dd, J=11.8, 8.1 Hz, 1H), 3.29-3.21 (m, 1H), 2.16-1.89 (m, 2H), 1.56-1.42 (m, 2H), 0.81 (t, J=7.7 Hz, 2H).

Example 93: (2R,3R)-3-((2-boronoethyl)thio)pyrrolidine-2-carboxylic acid hydrochloride

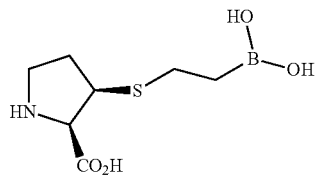 [SMILES: O=C(O)[C@H]1NCC[C@H]1SCCB(O)O]

Step 1: (2S,3S)-1-tert-butyl 2-methyl 3-hydroxypyrrolidine-1,2-dicarboxylate

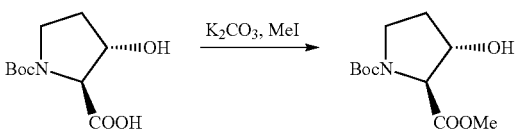

Potassium carbonate (1.1 g, 8.2 mmol) was added to the stirred solution of (2S,3S)-1-(tert-butoxycarbonyl)-3-hydroxypyrrolidine-2-carboxylic acid (0.95 g, 4.1 mmol) in DMF (5.9 mL) at 0° C., followed by MeI (0.31 mL, 4.9 mmol). The reaction mixture was allowed to warm to room temperature over 1 h and then stirred at 90° C. for 1 h. The reaction mixture was cooled to room temperature, diluted with brine, extracted with ether, and the combined organic phase was dried over anhydrous $Na_2SO_4$, filtered and concentrated to afford (2S,3S)-1-tert-butyl 2-methyl 3-hydroxypyrrolidine-1,2-dicarboxylate. LCMS ($C_{11}H_{19}NNaO_5^+$)(ES, m/z): 268 [M+Na]$^+$.

Step 2: 1-(tert-butyl) 2-methyl (2R,3R)-3-(acetylthio)pyrrolidine-1,2-dicarboxylate

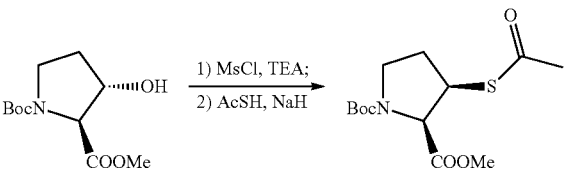

Triethylamine (0.23 mL, 1.6 mmol) was added to the stirred solution of (2S,3S)-1-tert-butyl 2-methyl 3-hydroxypyrrolidine-1,2-dicarboxylate (0.20 g, 0.81 mmol) in THF (1.6 mL) at 0° C., followed by dropwise addition of methanesulfonyl chloride (76 µL, 0.98 mmol). The resulting mixture was stirred at room temperature overnight, and then diluted with EtOAc and water. The organic layer was separated, washed with brine, dried over $Na_2SO_4$, filtered, and concentrated. The crude residue was taken up in DMF (1.0 mL), and a mixture of NaH (60 wt % in mineral oil, 59 mg, 1.5 mmol) and thioacetic acid (53 µL, 0.74 mmol) in DMF (1.0 mL) was added dropwise at room temperature The reaction mixture was stirred at 60° C. overnight. The mixture was quenched with saturated aqueous NH₄Cl solution, and extracted with EtOAc, and the combined organic phase was washed with brine, dried over anhydrous Na₂SO₄ and concentrated. The residue was purified by silica gel chromatography (EtOAc in hexanes) to afford 1-(tert-butyl) 2-methyl (2R,3R)-3-(acetylthio)pyrrolidine-1,2-dicarboxylate. LCMS (C₁₃H₂₁NNaO₅S⁺)(ES, m/z): 326 [M+Na]⁺.

Step 3: 1-(tert-butyl) 2-methyl (2R,3R)-3-mercapto-pyrrolidine-1,2-dicarboxylate

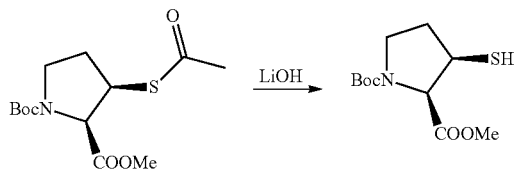

A solution of LiOH (53 mg, 2.2 mmol) in water (1.2 mL) was added to the stirred solution of 1-(tert-butyl) 2-methyl (2R,3R)-3-(acetylthio)pyrrolidine-1,2-dicarboxylate (0.22 g, 0.74 mmol) in THF (1.2 mL) at room temperature The reaction mixture was stirred at room temperature for 15 min. The resulting mixture was neutralized with 2 N HCl in water and extracted with EtOAc, and the combined organic phase was washed with brine, dried over anhydrous Na₂SO₄ and concentrated.

The residue was purified by silica gel chromatography (EtOAc in hexanes) to afford 1-(tert-butyl) 2-methyl (2R,3R)-3-mercaptopyrrolidine-1,2-dicarboxylate. LCMS (C₁₁H₁₉NNaO₄S⁺)(ES, m/z): 284 [M+Na]⁺.

Step 4: (2-(((2R,3R)-1-(tert-butoxycarbonyl)-2-(methoxycarbonyl)pyrrolidin-3-yl)thio)ethyl)boronic acid

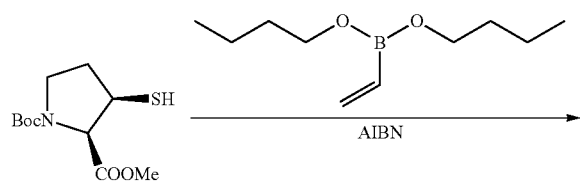

Vinylboronic acid dibutyl ester (0.11 mL, 0.51 mmol) and 1-(tert-butyl) 2-methyl (2R,3R)-3-mercaptopyrrolidine-1,2-dicarboxylate (0.13 g, 0.51 mmol) were mixed in MeOH (1.6 mL) and water (0.95 mL) under N₂, and AIBN (10 mg, 0.061 mmol) was added and the mixture was stirred at 80° C. for 6 h. The reaction mixture was concentrated and the residue was purified by silica gel chromatography (EtOAc in hexanes) to get (2-(((2R,3R)-1-(tert-butoxycarbonyl)-2-(methoxycarbonyl)pyrrolidin-3-yl)thio)ethyl)boronic acid. LCMS (C₁₃H₂₄BNNaO₆S⁺)(ES, m/z): 356 [M+Na]⁺.

Step 5: (2R,3R)-3-((2-boronoethyl)thio)pyrrolidine-2-carboxylic acid

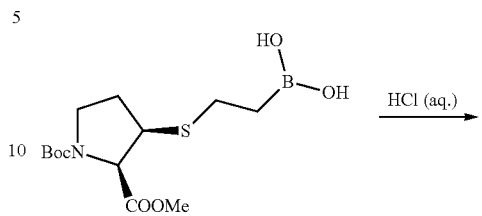

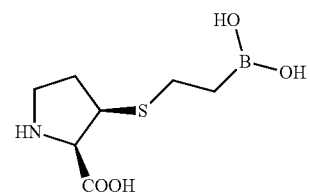

Example 93

(2-(((2R,3R)-1-(tert-butoxycarbonyl)-2-(methoxycarbonyl)pyrrolidin-3-yl)thio)ethyl)boronic acid (12 mg, 0.036 mmol) was treated with 6 N HCl in water (0.50 mL, 3.0 mmol) and stirred at 90° C. for 1 h. The reaction mixture was cooled to room temperature, diluted with water and washed with DCM, and the aqueous layer was lyophilized to get (2R,3R)-3-((2-boronoethyl)thio)pyrrolidine-2-carboxylic acid hydrochloride as an HCl salt. LCMS (C₇H₁₃BNO₃S⁺) (ES, m/z): 202 [M–H₂+H]⁺. ¹H NMR (500 MHz, D₂O) δ 4.48 (d, J=6.5 Hz, 1H), 3.85 (td, J=6.2, 3.8 Hz, 1H), 3.51 (dt, J=11.8, 8.2 Hz, 1H), 3.38 (ddd, J=12.0, 8.6, 4.5 Hz, 1H), 2.72 (tt, J=8.0, 3.8 Hz, 2H), 2.47-2.40 (m, 1H), 2.12 (ddt, J=13.8, 7.8, 4.1 Hz, 1H), 1.08 (t, J=7.9 Hz, 2H).

Example 94A: 3-amino-4-(3-boronopropyl)-4-(hydroxymethyl)pyrrolidine-3-carboxylic acid

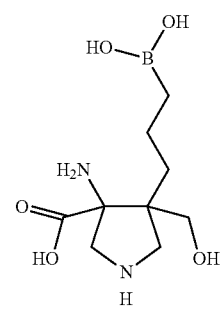

Step 1: 1-tert-butyl 3-ethyl 3-allyl-4-oxopyrrolidine-,3-dicarboxylate

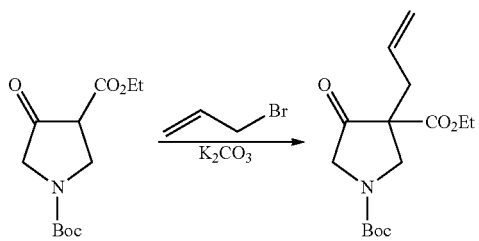

Potassium carbonate (23 g, 0.17 mol) was added to a mixture of 1-tert-butyl 3-ethyl 4-oxopyrrolidine-1,3-dicarboxylate (29 g, 0.11 mol) and 3-bromoprop-1-ene (15 mL, 0.17 mol) in acetone (0.30 L) at 15° C., and the mixture was stirred at 40° C. for 14 h. The reaction mixture was filtered and concentrated. The residue was purified by silica gel column chromatography (EtOAc in hexanes) to afford 1-tert-butyl 3-ethyl 3-allyl-4-oxopyrrolidine-1,3-dicarboxylate. LCMS ($C_{11}H_{16}NO_5^+$)(ES, m/z): 242 [M+H—$C_4H_8$]f.

Step 2: 1-(tert-butyl)3-ethyl 4-acetamido-3-allyl-4-(tert-butylcarbamoyl)pyrrolidine-1,3-dicarboxylate

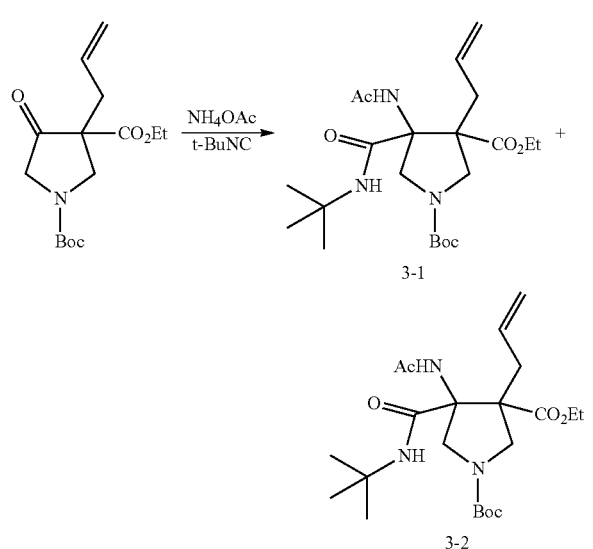

NH$_4$OAc (16 g, 0.20 mol) and 2-isocyano-2-methylpropane (17 mL, 0.15 mol) were added to the stirred solution of 1-tert-butyl 3-ethyl 3-allyl-4-oxopyrrolidine-1,3-dicarboxylate (30 g, 0.10 mol) in CF$_3$CH$_2$OH (0.10 L), and the mixture was stirred at 60° C. for 14 h. The reaction mixture was concentrated, and the residue was purified by silica gel column chromatography (EtOAc in hexanes) to afford 1-tert-butyl 3-ethyl 4-acetamido-3-allyl-4-(tert-butylcarbamoyl)pyrrolidine-1,3-dicarboxylate (3-1) as the first eluting peak; and 1-tert-butyl 3-ethyl 4-acetamido-3-allyl-4-(tert-butylcarbamoyl)pyrrolidine-1,3-dicarboxylate (3-2) as the second eluting peak. 3-1: LCMS ($C_{22}H_3N_3O_6^+$)(ES, m/z): 440 [M+H]; $^1$H NMR (500 MHz, CDCl$_3$) δ 6.37 (br s, 1H), 5.62-5.60 (m, 1H), 5.11-5.04 (m, 2H), 4.17-3.92 (m, 2H), 3.71-3.56 (m, 2H), 2.42-2.41 (m, 2H), 2.05 (s, 3H), 1.84-1.63 (m, 2H), 1.54 (s, 9H), 1.42 (s, 9H), 1.33-1.32 (m, 3H); 3-2: LCMS ($C_{22}H_{38}N_3O_6^+$)(ES, m/z): 440 [M+H]; $^1$H NMR (500 MHz, CDCl$_3$) δ 6.70 (br s, 1H), 6.04 (br s, 1H), 5.65-5.51 (m, 1H), 5.16-5.05 (m, 2H), 4.42-4.17 (m, 3H), 3.96-3.81 (m, 1H), 3.61-3.50 (m, 2H), 2.70-2.56 (m, 1H), 2.16-2.06 (m, 1H), 2.03-1.97 (s, 3H), 1.44 (s, 9H), 1.34 (s, 9H), 1.31-1.28 (m, 3H).

Step 3: 4-acetamido-3-allyl-1-(tert-butoxycarbonyl)-4-(tert-butylcarbamoyl)pyrrolidine-3-carboxylic acid

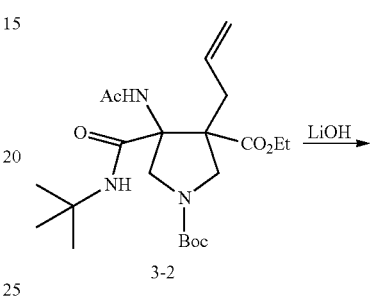

LiOH (1 M in water, 4.6 mL, 4.6 mmol) was added to the stirred solution of 1-tert-butyl 3-ethyl 4-acetamido-3-allyl-4-(tert-butylcarbamoyl)pyrrolidine-1,3-dicarboxylate (3-2, 1.0 g, 2.3 mmol) in THF (2.3 mL) at 20° C., and the mixture was stirred at 20° C. for 12 h. The reaction mixture was acidified with 1 N HCl in water to pH ~6, and extracted with EtOAc. The combined organic phase was concentrated to give crude 4-acetamido-3-allyl-1-(tert-butoxycarbonyl)-4-(tert-butylcarbamoyl)pyrrolidine-3-carboxylic acid, which was used in the next step directly without further purification. LCMS ($C_{20}H_{34}N_3O_6^+$)(ES, m/z): 412 [M+H]$^+$.

Step 4: tert-butyl 3-acetamido-4-allyl-3-(tert-butylcarbamoyl)-4-(hydroxymethyl)pyrrolidine-1-carboxylate

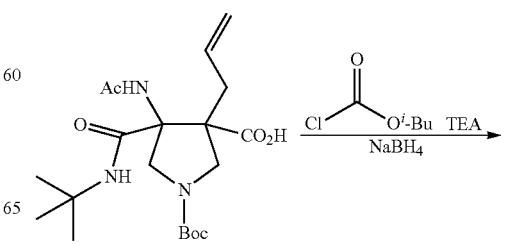

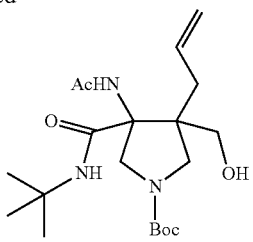

TEA (0.51 mL, 3.7 mmol) was added to the stirred mixture of isobutyl chloroformate (0.47 mL, 3.7 mmol) and 4-acetamido-3-allyl-1-(tert-butoxycarbonyl)-4-(tert-butylcarbamoyl)pyrrolidine-3-carboxylic acid (1.0 g, 2.4 mmol) in THF (10 mL) at 0° C., and the mixture was stirred at 20° C. for 1 h. The reaction mixture was diluted with diethyl ether, filtered and concentrated. The residue was dissolved in MeOH (5.0 mL), followed by addition of NaBH$_4$ (0.18 g, 4.9 mmol), and the resulting mixture was stirred at 20° C. for 1 h. The reaction mixture was quenched with saturated aqueous NH$_4$Cl and extracted with EtOAc. The combined organic phase was concentrated, and the residue was purified by RP-HPLC [C18 column, water (0.1% TFA)-CH$_3$CN] to give tert-butyl 3-acetamido-4-allyl-3-(tert-butylcarbamoyl)-4-(hydroxymethyl)pyrrolidine-1-carboxylate. LCMS (C$_{20}$H$_{36}$N$_3$O$_5^+$) (ES, m/z): 398 [M+H]$^+$.

Step 5: tert-butyl 3-acetamido-4-allyl-3-(tert-butylcarbamoyl)-4-(hydroxymethyl)pyrrolidine-1-carboxylate

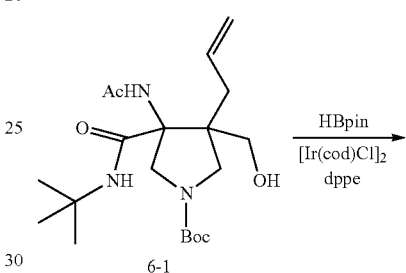

The tert-butyl 3-acetamido-4-allyl-3-(tert-butylcarbamoyl)-4-(hydroxymethyl)pyrrolidine-1-carboxylate (0.40 g, 1.0 mmol) was resolved by Chiral-SFC [Column: DAICEL CHIRALPAK AD-H (250 mm*50 mm,10 μm), Mobile phase: A: CO$_2$, B: EtOH (0.1% NH$_3$.H$_2$O), Gradient: 30% of B in 3.5 min, and hold 30% of B for 1 min, Flow Rate (mL/min) 180, Column Temperature: 40° C.] to give tert-butyl 3-acetamido-4-allyl-3-(tert-butylcarbamoyl)-4-(hydroxymethyl)pyrrolidine-1-carboxylate (6-1: t$_r$=2.13 min) as the first eluting peak, and tert-butyl 3-acetamido-4-allyl-3-(tert-butylcarbamoyl)-4-(hydroxymethyl)pyrrolidine-1-carboxylate (6-2: t$_r$=2.29 min) as the second eluting peak.

6-1: LCMS (C$_{20}$H$_{36}$N$_3$O$_5^+$)(ES, m/z): 398 [M+H]; $^1$H NMR (500 MHz, CDCl$_3$) δ 6.07-5.89 (m, 1H), 5.83-5.58 (m, 1H), 5.23-5.08 (m, 2H), 4.38-4.21 (m, 1H), 3.84-3.76 (m, 2H), 3.72-3.71 (m, 2H), 3.58 (br d, J=11.9 Hz, 1H), 3.47-3.34 (m, 2H), 2.43-2.23 (m, 1H), 2.16-2.05 (m, 1H), 2.01 (s, 3H), 1.50-1.40 (s, 9H), 1.34 (s, 9H); 6-2: LCMS (C$_{20}$H$_{36}$N$_3$O$_5^+$) (ES, m/z): 398 [M+H]; $^1$H NMR (500 MHz, CDCl$_3$) δ 6.11-5.91 (m, 1H), 5.81-5.57 (m, 1H), 5.23-5.02 (m, 2H), 4.42-4.21 (m, 1H), 3.86-3.72 (m, 3H), 3.65-3.53 (m, 1H), 3.46-3.33 (m, 2H), 2.43-2.21 (m, 1H), 2.14-2.10 (m, 2H), 2.00 (s, 3H), 1.43 (s, 9H), 1.34 (s, 9H).

Step 6: tert-butyl 3-acetamido-3-(tert-butylcarbamoyl)-4-(hydroxymethyl)-4-(3-(4,4,5,5-tetramethyl-1,3,2-dioxaborolan-2-yl)propyl)pyrrolidine-1-carboxylate

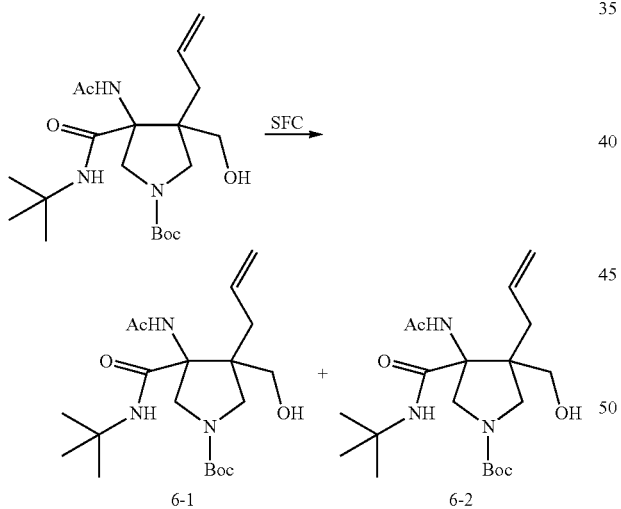

[Ir(cod)Cl]$_2$ (10 mg, 0.015 mmol) was added to the stirred solution of tert-butyl 3-acetamido-4-allyl-3-(tert-butylcarbamoyl)-4-(hydroxymethyl)pyrrolidine-1-carboxylate (0.12 g, 0.30 mmol), 4,4,5,5-tetramethyl-1,3,2-dioxaborolane (0.12 g, 0.91 mmol) and 1,2-bis(diphenylphosphino)ethane (12 mg, 0.030 mmol) in DCM (3.0 mL) at 25° C. under N$_2$, and the resulting mixture was stirred at 25° C. for 5 h under N$_2$. The reaction mixture was filtered and concentrated. The residue was purified by RP-HPLC [C18 column, water (0.1% TFA)-CH$_3$CN] to give tert-butyl 3-acetamido-3-(tert-butylcarbamoyl)-4-(hydroxymethyl)-4-(3-(4,4,5,5-tetramethyl-1,3,2-dioxaborolan-2-yl)propyl)pyrrolidine-1-carboxylate, which contained minor corresponding boronic acid. LCMS (C$_{21}$H$_{41}$BN$_3$O$_6^+$)(ES, m/z): 426 [M+H—CO$_2$C$_4$H$_8$]$^+$.

Step 7: 3-amino-4-(3-boronopropyl)-4-(hydroxymethyl)pyrrolidine-3-carboxylic acid

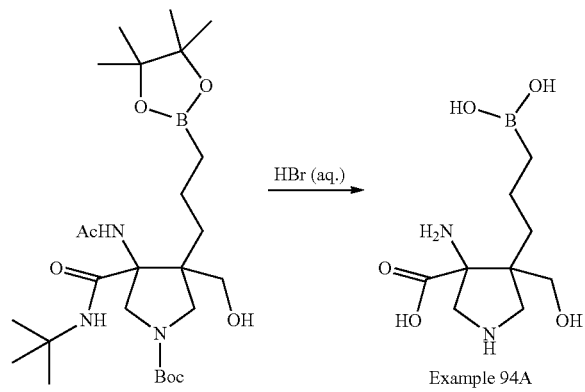 [SMILES: CC(=O)NC1(C(=O)NC(C)(C)C)CN(C(=O)OC(C)(C)C)CC1(CO)CCCB1OC(C)(C)C(C)(C)O1 ; NC1(C(=O)O)CNCC1(CO)CCCB(O)O]

Example 94A

A mixture of tert-butyl 3-acetamido-3-(tert-butylcarbamoyl)-4-(hydroxymethyl)-4-(3-(4,4,5,5-tetramethyl-1,3,2-dioxaborolan-2-yl)propyl)pyrrolidine-1-carboxylate (90 mg, 0.17 mmol) and 48% HBr in water (10 mL) was stirred at 120° C. for 12 h, then at 130° C. for 48 h. The reaction mixture was concentrated, then neutralized with saturated aqueous $NaHCO_3$, and washed with DCM. The aqueous layer was concentrated, acidified with 2 N HCl in water to pH ~6 and concentrated. The residue was purified by RP-HPLC [C18 column, water (20 mM HFBA and 0.1% TFA)-$CH_3CN$] to give 3-amino-4-(3-boronopropyl)-4-(hydroxymethyl)pyrrolidine-3-carboxylic acid as a HFBA salt. LCMS $(C_9H_{18}BN_2O_4^+)$(ES, m/z): 229 $[M+H—H_2O]^+$. $^1H$ NMR (500 MHz, $D_2O$) δ 3.93-3.88 (m, 2H), 3.79-3.66 (m, 2H), 3.64-3.50 (m, 2H), 1.69-1.64 (m, 1H), 1.48-1.26 (m, 2H), 1.20 (br s, 1H), 0.73-0.70 (m, 2H).

Example 94B was made from tert-butyl 3-acetamido-4-allyl-3-(tert-butylcarbamoyl)-4-(hydroxymethyl)pyrrolidine-1-carboxylate (6-2), Examples 94C and 94D were made from 1-tert-butyl 3-ethyl 4-acetamido-3-allyl-4-(tert-butylcarbamoyl)pyrrolidine-1,3-dicarboxylate (3-1) using the same procedure as Example 94A.

| Ex. | Structure | MS and $^1$HNMR |
|---|---|---|
| 94B | 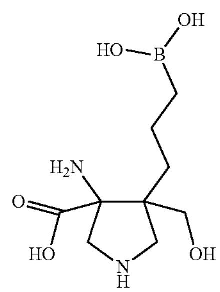 [SMILES: NC1(C(=O)O)CNCC1(CO)CCCB(O)O] | LCMS $(C_9H_{18}BN_2O_4^+)$ (ES, m/z): 229 $[M + H - H_2O]^+$. $^1H$ NMR (500 MHz, $D_2O$) δ 3.94-3.91 (m, 2H), 3.78-3.67 (m, 2H), 3.66-3.49 (m, 2H), 1.69-1.66 (m, 1H), 1.51-1.26 (m, 2H), 1.20 (br s, 1H), 0.74-0.70 (m, 2H). |
| 94C | 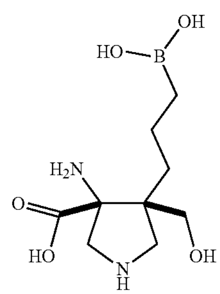 | LCMS $(C_9H_{18}BN_2O_4^+)$ (ES, m/z): 229 $[M + H - H_2O]^+$. $^1H$ NMR (500 MHz, $D_2O$) δ 4.61-4.59 (m, 1H), 4.37-4.35 (m, 1H), 3.92-3.84 (m, 1H), 3.87-3.64 (m, 2H), 3.59-3.43 (m, 1H), 1.79-1.77 (m, 1H), 1.69-1.50 (m, 2H), 1.31-1.30 (m, 1H), 0.75-0.72 (m, 2H). |
| 94D | 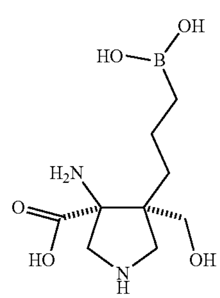 | LCMS $(C_9H_{18}BN_2O_4^+)$ (ES, m/z): 229 $[M + H - H_2O]^+$. $^1H$ NMR (500 MHz, $D_2O$) δ 4.64-4.61 (m, 1H), 4.42-4.40 (m, 1H), 3.95-3.92 (m, 1H), 3.88-3.82 (m, 1H), 3.78-3.71 (m, 1H), 3.53-3.51 (m, 1H), 1.92-1.75 (m, 1H), 1.73-1.53 (m, 2H), 1.38-1.26 (m, 1H), 0.84-0.59 (m, 2H). |

Example 95: 1-(aminomethyl)-3-(2-boronoethyl)cyclopentane-1-carboxylic acid

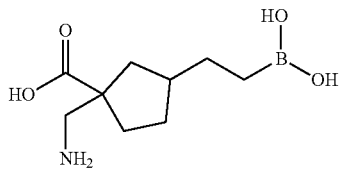 [SMILES: NCC1(C(=O)O)CCC(CCB(O)O)C1]

Step 1: diethyl 2-allyl-2-(2-bromoethyl)malonate

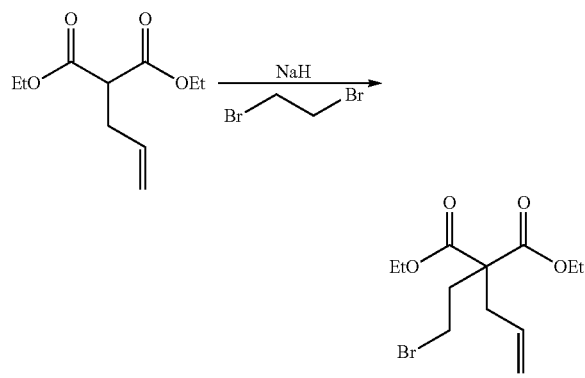

Diethyl 2-allylmalonate (5.0 g, 25 mmol) was added to the suspension of sodium hydride (60 wt % in mineral oil, 1.2 g, 30 mmol) in DMF (0.10 L) at 0° C. under N, and the mixture was stirred for 1 h at room temperature, followed by dropwise addition of 1,2-dibromoethane (5.6 g, 30 mmol) at room temperature, and the resulting mixture was stirred overnight. The reaction mixture was quenched with $H_2O$ and extracted with $Et_2O$. The combined organic phase was dried over $Na_2SO_4$, filtered and concentrated. The residue was purified by silica gel chromatography (tBuOMe in hexanes) to give diethyl 2-allyl-2-(2-bromoethyl)malonate. $^1$H NMR (500 MHz, CDCl$_3$) δ 5.81-5.47 (m, 1H), 5.30-5.00 (m, 2H), 4.19 (q, J=7.1 Hz, 4H), 3.48-3.21 (m, 2H), 2.65 (d, J=7.2 Hz, 2H), 2.54-2.29 (m, 2H), 1.25 (t, J=7.1 Hz, 6H).

Step 2: diethyl 3-((4,4,5,5-tetramethyl-1,3,2-dioxaborolan-2-yl)methyl)cyclopentane-1,1-dicarboxylate

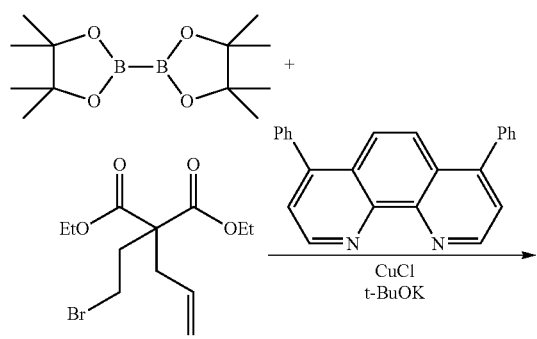

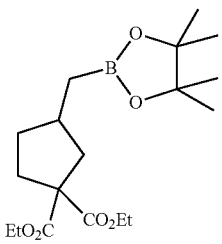

Potassium 2-methylpropan-2-olate (1 M in THF, 6.0 mL, 6.0 mmol) was added to the stirred mixture of Copper(I) chloride (0.049 g, 0.50 mmol) and 4,4,4',4',5,5,5',5'-octamethyl-2,2'-bi(1,3,2-dioxaborolane)(1.5 g, 6.0 mmol), and 4,7-diphenyl-1,10-phenanthroline (0.17 g, 0.50 mmol) in THF (39 mL), and the mixture was stirred for 30 min at 0° C., followed by addition of diethyl 2-allyl-2-(2-bromoethyl)malonate (1.5 g, 5.0 mmol) at 0° C. The reaction mixture was stirred overnight at room temperature, filtered through a short plug of silica gel eluting with $Et_2O$, and concentrated. The residue was purified by silica gel column chromatography (MeOtBu in hexanes) to give diethyl 3-((4,4,5,5-tetramethyl-1,3,2-dioxaborolan-2-yl)methyl)cyclopentane-1,1-dicarboxylate. LCMS ($C_{18}H_{32}BO_6$)(ES, m/z): 355 [M+H]$^+$.

Step 3: diethyl 3-(2-(4,4,5,5-tetramethyl-1,3,2-dioxaborolan-2-yl)ethyl)cyclopentane-1,1-dicarboxylate

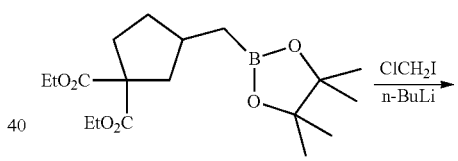

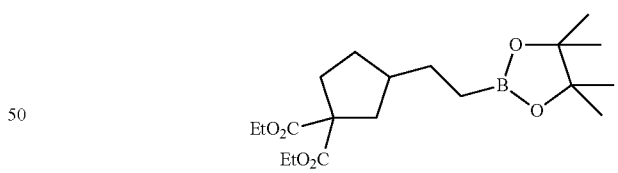

n-Butyllithium (2.5 M in hexanes, 0.85 mL, 2.1 mmol) was added dropwise to the stirred solution of diethyl 3-((4,4,5,5-tetramethyl-1,3,2-dioxaborolan-2-yl)methyl)cyclopentane-1,1-dicarboxylate (0.50 g, 1.4 mmol) and chloroiodomethane (0.16 mL, 2.3 mmol) in THF (4.0 mL) at −78° C., and the mixture was stirred for 30 min at −78° C., then stirred at 75° C. for 4 h. The reaction mixture was quenched by a few drops of saturated aqueous NH$_4$Cl, dried over anhydrous Na$_2$SO$_4$, then filtered and concentrated. The residue was purified by silica gel column chromatography (EtOAc in tBuOMe) to give diethyl 3-(2-(4,4,5,5-tetramethyl-1,3,2-dioxaborolan-2-yl)ethyl)cyclopentane-1,1-dicarboxylate. LCMS ($C_{19}H_{33}BO_6^+$)(ES, m/z): 370 [M+H]$^+$.

Step 4: ethyl 1-(hydroxymethyl)-3-(2-(4,4,5,5-tetramethyl-1,3,2-dioxaborolan-2-yl)ethyl)cyclopentane-1-carboxylate

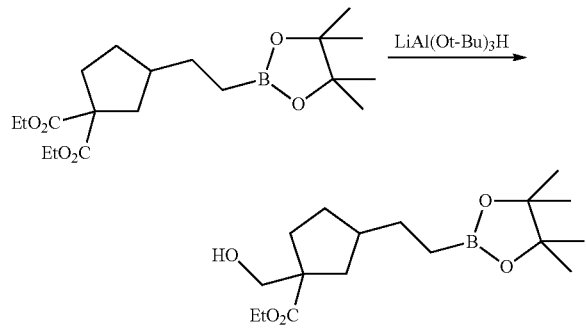

A solution of LiAl(Ot-Bu)₃H (1 M in THF, 2.2 mL, 2.2 mmol) was added dropwise to the stirred solution of diethyl 3-(2-(4,4,5,5-tetramethyl-1,3,2-dioxaborolan-2-yl)ethyl)cyclopentane-1,1-dicarboxylate (0.40 g, 1.1 mmol) in THF (6.0 mL) at −78° C. The resulting mixture was allowed to warm to room temperature and stirred for 12 h, then quenched by 2 N HCl in water and extracted with EtOAc. The combined organic layer was washed with brine, dried over anhydrous Na₂SO₄, filtered and concentrated. The residue was purified by silica gel chromatography (EtOAc in hexanes) to give ethyl 1-(hydroxymethyl)-3-(2-(4,4,5,5-tetramethyl-1,3,2-dioxaborolan-2-yl)ethyl)cyclopentane-1-carboxylate as a mixture of diastereomers. LCMS ($C_{17}H_{31}BO_5^+$) (ES, m/z): 327 [M+H]⁺.

Step 5: ethyl 3-(2-(4,4,5,5-tetramethyl-1,3,2-dioxaborolan-2-yl)ethyl)-1-((tosyloxy)methyl)cyclopentane-1-carboxylate

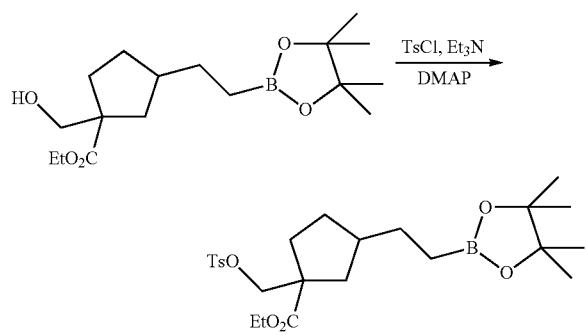

4-Methylbenzenesulfonyl chloride (92 mg, 0.48 mmol), N,N-dimethylpyridin-4-amine (3.9 mg, 0.032 mmol), and triethylamine (0.11 mL, 0.81 mmol) were added sequentially to the stirred solution of ethyl 1-(hydroxymethyl)-3-(2-(4,4,5,5-tetramethyl-1,3,2-dioxaborolan-2-yl)ethyl)cyclopentane-1-carboxylate (0.11 g, 0.32 mmol) in DCM (0.64 mL) at room temperature, and the mixture was stirred at room temperature overnight. The reaction mixture was diluted with water and extracted with DCM. The combined organic phase was dried over Na₂SO₄, filtered, and concentrated. The residue was purified by silica gel chromatography (tBuOMe in hexanes) to give ethyl 3-(2-(4,4,5,5-tetramethyl-1,3,2-dioxaborolan-2-yl)ethyl)-1-((tosyloxy)methyl)cyclopentane-1-carboxylate. LCMS ($C_{24}H_{37}BO_7S^+$)(ES, m/z): 481 [M+H]⁺.

Step 6: ethyl 1-(azidomethyl)-3-(2-(4,4,5,5-tetramethyl-1,3,2-dioxaborolan-2-yl)ethyl)cyclopentane-1-carboxylate

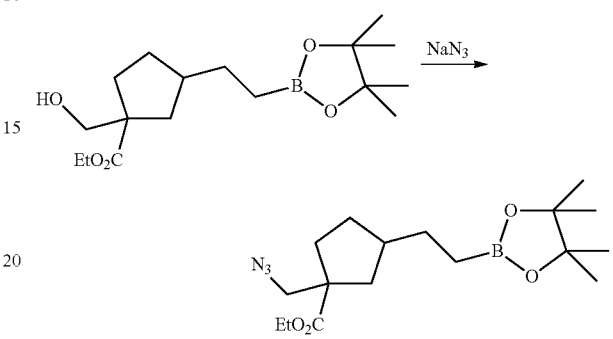

Sodium azide (47 mg, 0.73 mmol) was added to the stirred solution of ethyl 3-(2-(4,4,5,5-tetramethyl-1,3,2-dioxaborolan-2-yl)ethyl)-1-((tosyloxy)methyl)cyclopentane-1-carboxylate (70 mg, 0.15 mmol) in DMF (0.29 mL) at room temperature, and the mixture was stirred at 100° C. overnight. The reaction mixture was diluted with water, and extracted with diethyl-ether. The combined organic phase was washed with brine, dried over anhydrous Na₂SO₄, filtered and concentrated to give the crude ethyl 1-(azidomethyl)-3-(2-(4,4,5,5-tetramethyl-1,3,2-dioxaborolan-2-yl)ethyl)cyclopentane-1-carboxylate, which was used for the next step directly without further purification. LCMS ($C_7H_{30}BN_3O_4^+$)(ES, m/z): 352 [M+H]⁺.

Step 7: ethyl 1-(((tert-butoxycarbonyl)amino)methyl)-3-(2-(4,4,5,5-tetramethyl-1,3,2-dioxaborolan-2-yl)ethyl)cyclopentane-1-carboxylate

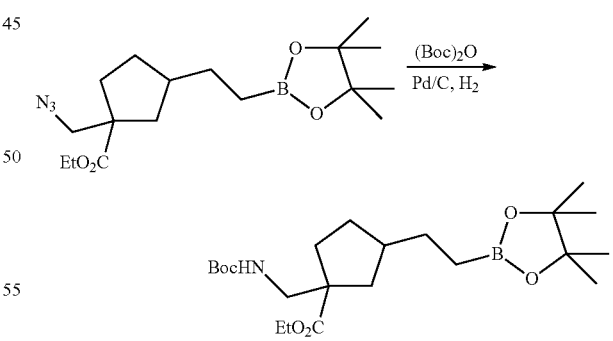

A solution of ethyl 1-(azidomethyl)-3-(2-(4,4,5,5-tetramethyl-1,3,2-dioxaborolan-2-yl)ethyl)cyclopentane-1-carboxylate (51 mg, 0.15 mmol), di-tert-butyl dicarbonate (35 mg, 0.16 mmol) and 10% Pd/C (16 mg, 0.015 mmol) in THF (0.29 mL) was bubbled with H₂, and the mixture was stirred under H₂ at room temperature for 3 h. The reaction mixture was filtered and concentrated. The residue was purified by silica gel chromatography (tBuOMe in hexanes) to give ethyl 1-(((tert-butoxycarbonyl)amino)methyl)-3-(2-(4,4,5,5- tetramethyl-1,3,2-diox aborolan-2-yl)ethyl)cyclopentane-1-carboxylate. LCMS ($C_{22}H_{40}BNO_6^+$)(ES, m/z): 426 [M+H]$^+$.

Step 8: 1-(aminomethyl)-3-(2-boronoethyl)cyclopentane-1-carboxylic acid

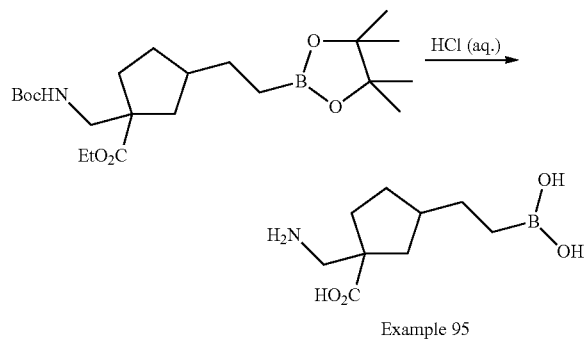

Example 95

A mixture of ethyl 1-(((tert-butoxycarbonyl)amino)methyl)-3-(2-(4,4,5,5-tetramethyl-1,3,2-dioxaborolan-2-yl)ethyl)cyclopentane-1-carboxylate (38 mg, 0.089 mmol) in 6 N HCl in water (0.27 mL, 1.6 mmol) was stirred at 90° C. overnight. The reaction mixture was concentrated and the residue was purified by RP-HPLC [C18 column, water (0.1% TFA)-CH$_3$CN] to give 1-(aminomethyl)-3-(2-boronoethyl)cyclopentane-1-carboxylic acid as a TFA salt, which is a mixture of 4 isomers. LCMS ($C_9H_{18}BNO_4$)(ES, m/z): 216 [M+H]; $^1$H NMR (500 MHz, CD$_3$OD) δ 3.17-3.04 (m, 2H), 2.33 (dd, J=13.0, 7.3 Hz, 0.5H), 2.26-2.11 (m, 1.5H), 2.07-1.87 (m, 2.5H), 1.84-1.72 (m, 1H), 1.63 (ddd, J=13.2, 9.5, 7.1 Hz, 0.75H), 1.56-1.41 (m, 2.5H), 1.40-1.26 (m, 0.75H), 1.18 (dd, J=13.1, 10.2 Hz, 0.5H), 0.82 (t, J=8.0 Hz, 2H).

Assay

Arginase Thioornithine Generating Assay (TOGA)

Compounds were serially diluted in ten 3-fold steps in DMSO starting from 10 mM DMSO stocks. Compound dilutions or DMSO alone were then dispensed from the dilution plate into a Greiner black 384-well assay plate (catalog #781086) using an Echo 555 acoustic liquid handler (Labcyte).

Arginase protein was recombinantly expressed in *Escherichia coli*. Purified protein was then diluted in assay buffer (50 mM Tris pH 7.5, 50 mM NaCl, 1 mM manganese chloride, 0.05% bovine serum albumin to obtain a final Arginase concentration of 1.88 nM. Arginase solution (20 µL) or buffer alone (20 µL) were dispensed to wells of the assay plate using a BioRAPTR liquid dispenser (Beckman Coulter). Assay plates containing compound and ARG1 enzyme were incubated at room temperature for 30 minutes. Afterwards, 5 µL of 2.5 mM thioarginine (Cayman Chemicals) in assay buffer were added to each well of the assay plate using a BioRAPTR liquid dispenser. Plates were incubated at room temperature for 60 minutes and reactions were quenched by addition of 15 µL of 200 µm 7-Diethylamine-3-(4-maleimidophenyl)-4-methylcoumarin (Sigma Chemical) in 70% ethanol. Plates were briefly shaken to mix and the fluorescence was measured in an Spectramax plate reader (Molecular Devices) with a 410 nm excitation wavelength and an 490 nm emission wavelength.

The fluorescence intensity of each well was corrected for the background observed in wells that did not receive arginase and was expressed as a fraction of the intensity observed in wells that received arginase enzyme and DMSO only. Potencies were calculated by linear least squares fit to the four parameter logistic IC50 equation.

| Structure | Example No. | TOGA IC50 (nM) | % inhibition @ top dose |
|---|---|---|---|
| 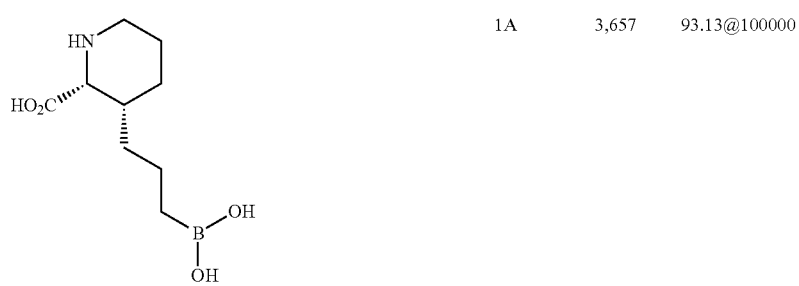 | 1 | 660 | 99.28@100000 |
| 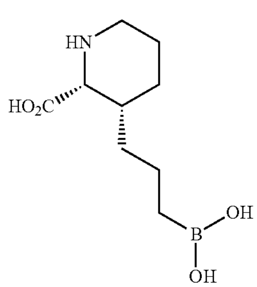 [SMILES: O=C(O)[C@@H]1NCCC[C@@H]1CCCB(O)O] | 1A | 3,657 | 93.13@100000 |

-continued

| Structure | Example No. | TOGA IC50 (nM) | % inhibition @ top dose |
|---|---|---|---|
| (piperidine with HO2C and propyl-B(OH)2 substituent) | 1B | 377 | 99.91@100000 |
| (piperidine with HO2C and propyl-B(OH)2 substituent, different stereo) | 1C | 83,250 | 56.08@100000 |
| (piperidine with HO2C and propyl-B(OH)2 substituent, different stereo) | 1D | 22,830 | 85.52@100000 |
| (piperidine with piperidinyl-ethyl, carboxylic acid and propyl-B(OH)2 substituents) | 2 | 396 | 99.18@100000 |
| (piperidine with carboxylic acid and O-ethyl-B(OH)2 substituent) | 3 | >10,000 | 21.31@10000 |
| (piperidine with ethyl-B(OH)2 and carboxylic acid substituents) | 4 | 19,840 | 75.95@100000 |

-continued
| Structure | Example No. | TOGA IC50 (nM) | % inhibition @ top dose |
|---|---|---|---|
| 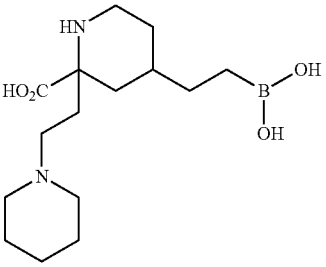 [SMILES: O=C(O)C1(CCN2CCCCC2)CC(CCB(O)O)CCN1] | 5 | 1,327 | 97.71@100000 |
| 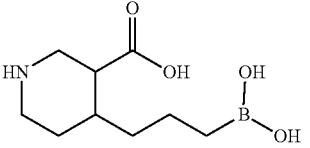 [SMILES: O=C(O)C1CNCCC1CCCB(O)O] | 6 | 57,510 | 60.93@100000 |
| 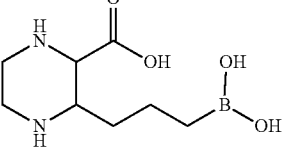 | 7 | 98,980 | 39.73@100000 |
| 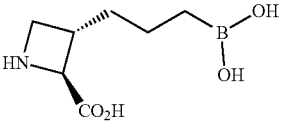 | 8A | 340 | 98.99@10000 |
| 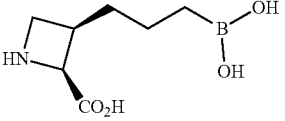 [SMILES: O=C(O)[C@H]1NC[C@H]1CCCB(O)O] | 8B | 447 | 92@10000 |
| 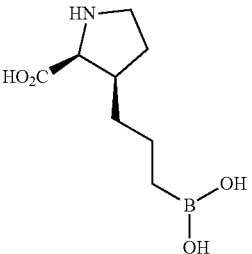 [SMILES: O=C(O)[C@H]1NCC[C@H]1CCCB(O)O] | 9A | 18 | 99.48@10000 |
| 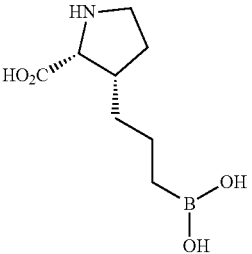 | 9B | 8,037 | 79.65@100000 |

-continued
| Structure | Example No. | TOGA IC50 (nM) | % inhibition @ top dose |
|---|---|---|---|
| 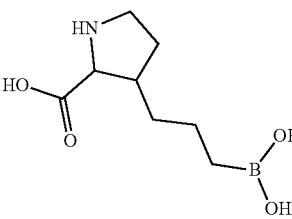 | 9 | 113 | 100.7@100000 |
| 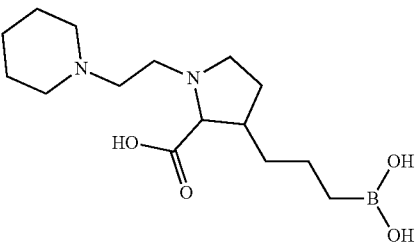 [SMILES: O=C(O)C1C(CCCB(O)O)CCN1CCN1CCCCC1] | 10 | 12,900 | 87.17@100000 |
| 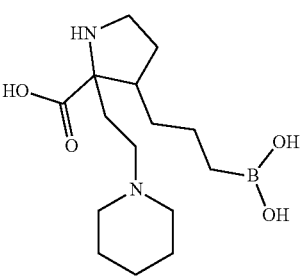 [SMILES: O=C(O)C1(CCN2CCCCC2)NCCC1CCCB(O)O] | 11 | 84 | 103.7@100000 |
| 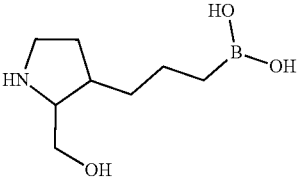 [SMILES: OCC1NCCC1CCCB(O)O] | 12 | 3,814 | 49.18@10000 |
| 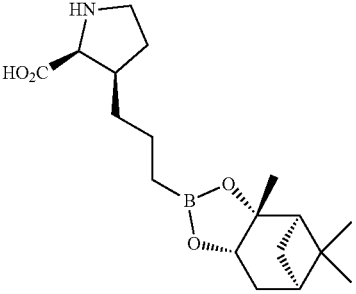 [SMILES: CC1(C)[C@H]2C[C@@H]3OB(CCC[C@@H]4CCN[C@@H]4C(=O)O)O[C@]3(C)[C@@H]1C2] | 13 | 30 | 97.08@10000 |
| 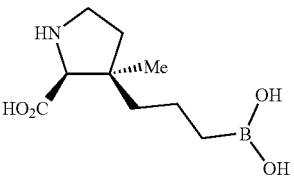 | 14 | 16 | 97.77@10000 |

-continued
| Structure | Example No. | TOGA IC50 (nM) | % inhibition @ top dose |
|---|---|---|---|
| 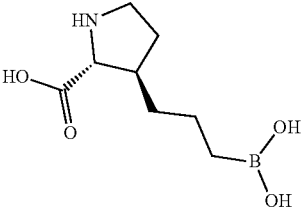 [SMILES: O=C(O)[C@@H]1NCC[C@H]1CCCB(O)O] | 15A | >10,000 | 22.08@10000 |
| 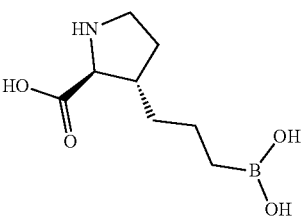 [SMILES: O=C(O)[C@H]1NCC[C@@H]1CCCB(O)O] | 15B | 413 | 90.31@10000 |
| 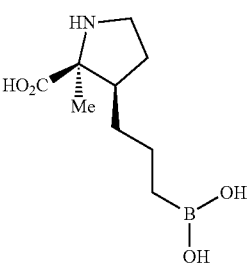 | 16A | 70 | 96.48@10000 |
| 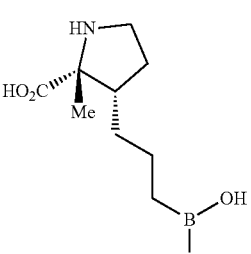 | 16B | 2,257 | 44.51@10000 |
| 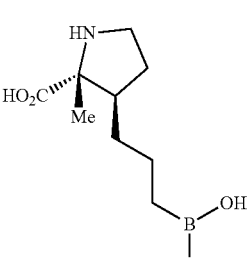 | 16C | 1,453 | 73.28@10000 |
| 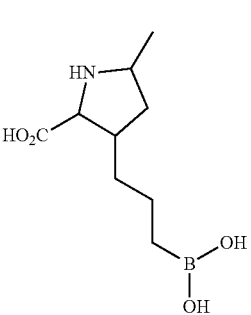 | 17 | >10,000 | 21.3@10000 |

-continued
| Structure | Example No. | TOGA IC50 (nM) | % inhibition @ top dose |
|---|---|---|---|
| 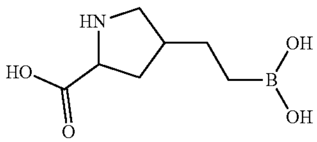 [SMILES: O=C(O)C1CC(CCB(O)O)CN1] | 18 | 8,733 | 96.56@160000 |
| 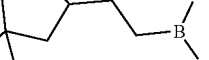 | 19 | 5,371 | 95.14@100000 |
| 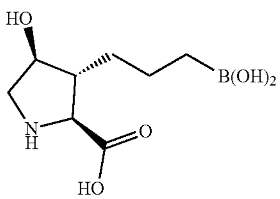 [SMILES: O=C(O)[C@H]1NC[C@@H](O)[C@@H]1CCCB(O)O] | 20A | 475 | 88.53@10000 |
| 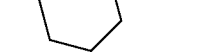 | 20B | >10,000 | 18.38@10000 |
| 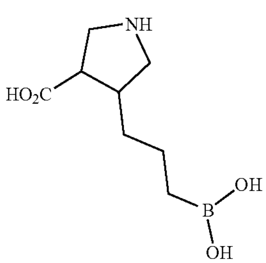 | 21A | >10,000 | .9355@10000 |
| 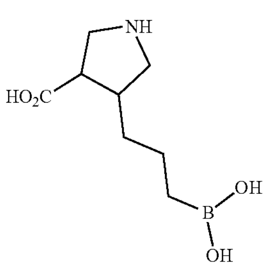 [SMILES: O=C(O)C1CNCC1CCCB(O)O] | 21B | 602.1 | 85.55@10000 |
| 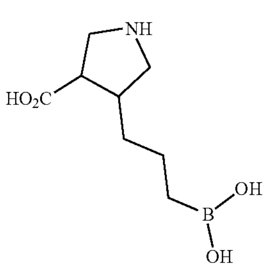 | 21C | >10,000 | 21.31@10000 |

-continued

| Structure | Example No. | TOGA IC50 (nM) | % inhibition @ top dose |
|---|---|---|---|
| (structure) | 21D | 1523 | 62.58@10000 |
| (structure) | 22 | 151.2 | 97.44@10000 |
| (structure) | 23 | 3.228 | 93.46@10000 |
| (structure) | 24 | 66.16 | 99.37@10000 |
| (structure) | 25 | 522.4 | 91.95@10000 |
| (structure) | 26 | 119.5 | 94.11@10000 |

-continued
| Structure | Example No. | TOGA IC50 (nM) | % inhibition @ top dose |
|---|---|---|---|
| 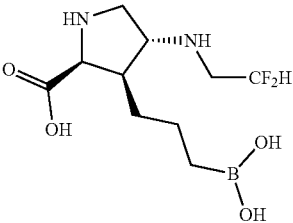 [SMILES: O=C(O)[C@H]1NC[C@H](NCC(F)F)[C@H]1CCCB(O)O] | 27 | 128.3 | 94.28@10000 |
| 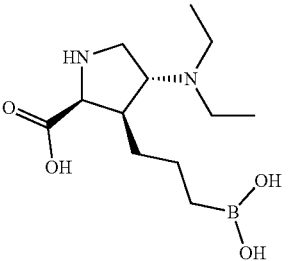 [SMILES: CCN(CC)[C@H]1CN[C@H](C(=O)O)[C@@H]1CCCB(O)O] | 28 | 3291 | 70.67@10000 |
| 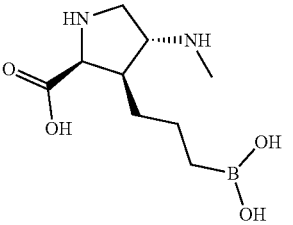 [SMILES: CN[C@H]1CN[C@H](C(=O)O)[C@@H]1CCCB(O)O] | 29 | 20.1 | 99.91@10000 |
| 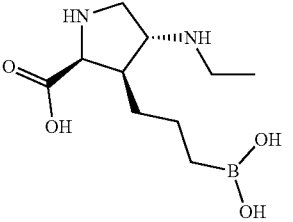 [SMILES: CCN[C@H]1CN[C@H](C(=O)O)[C@@H]1CCCB(O)O] | 30 | 84.45 | 98.27@10000 |
| 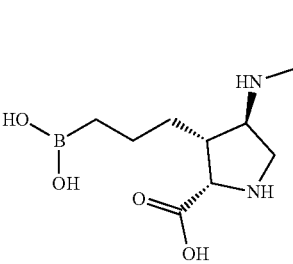 | 31 | 6.69 | 100.4@10000 |
| 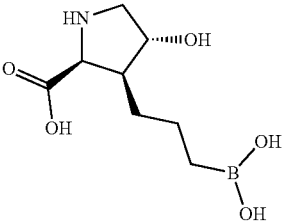 [SMILES: O=C(O)[C@H]1NC[C@H](O)[C@H]1CCCB(O)O] | 32 | 6.022 | 93.55@10000 |

-continued
| Structure | Example No. | TOGA IC50 (nM) | % inhibition @ top dose |
|---|---|---|---|
| 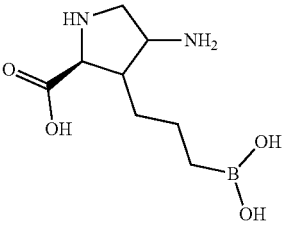 [SMILES: NC1CN[C@H](C(=O)O)C1CCCB(O)O] | 33A | >10,000 | 39.26@10000 |
| 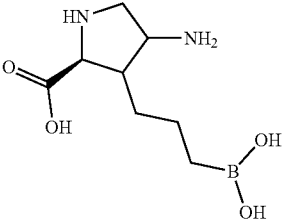 [SMILES: NC1CN[C@H](C(=O)O)C1CCCB(O)O] | 33B | >10,000 | 9.625@10000 |
| 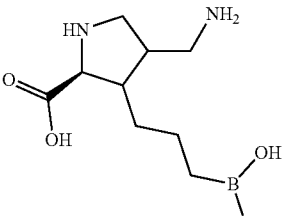 | 34 | 3448 | 71.81@10000 |
| 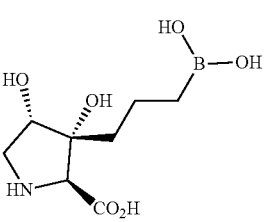 | 35 | 8301 | 92.17@10000 |
| 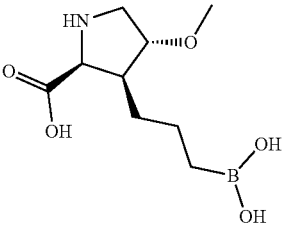 [SMILES: CO[C@H]1CN[C@H](C(=O)O)[C@@H]1CCCB(O)O] | 36 | 46.06 | 96.8@10000 |
| 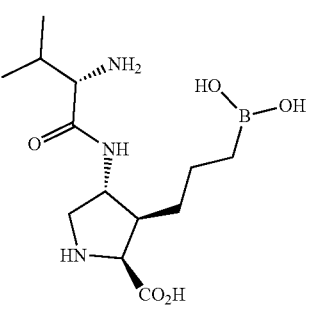 [SMILES: CC(C)[C@H](N)C(=O)N[C@H]1CN[C@H](C(=O)O)[C@@H]1CCCB(O)O] | 37 | 2.091 | 99.07@10000 |

-continued

| Structure | Example No. | TOGA IC50 (nM) | % inhibition @ top dose |
|---|---|---|---|
| (structure) | 38 | 0.8182 | 101.1@10000 |
| (structure) | 39 | 10.17 | 98.5@10000 |
| (structure) | 40 | 0.7777 | 101.8@10000 |
| (structure) | 41 | 13.64 | 98.63@10000 |
| (structure) | 42 | 1.579 | 99.17@10000 |

-continued

| Structure | Example No. | TOGA IC50 (nM) | % inhibition @ top dose |
|---|---|---|---|
| 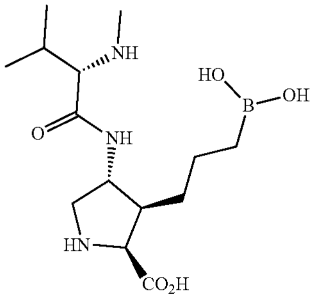 [SMILES: CN[C@H](C(=O)N[C@H]1CN[C@H](C(=O)O)[C@@H]1CCCB(O)O)C(C)C] | 43 | 2.977 | 97.24@10000 |
| 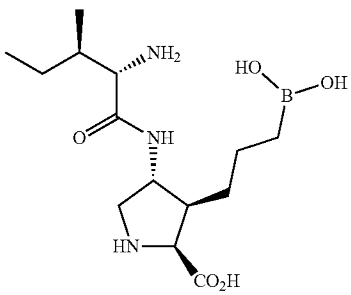 [SMILES: CC[C@@H](C)[C@H](N)C(=O)N[C@H]1CN[C@H](C(=O)O)[C@@H]1CCCB(O)O] | 44 | 2 | 98@10000 |
| 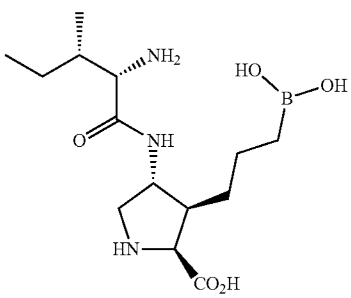 [SMILES: CC[C@H](C)[C@H](N)C(=O)N[C@H]1CN[C@H](C(=O)O)[C@@H]1CCCB(O)O] | 45 | 2 | 98@10000 |
| 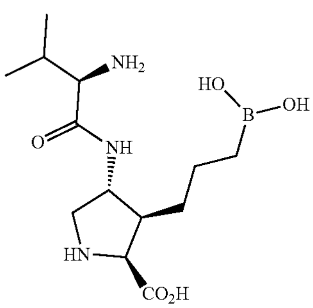 [SMILES: CC(C)[C@@H](N)C(=O)N[C@H]1CN[C@H](C(=O)O)[C@@H]1CCCB(O)O] | 46 | 35.41 | 98.48@10000 |
| 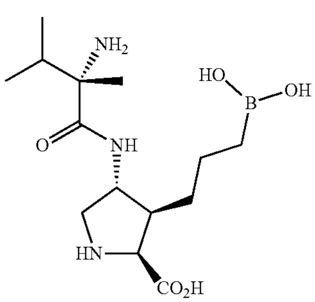 [SMILES: CC(C)[C@](C)(N)C(=O)N[C@H]1CN[C@H](C(=O)O)[C@@H]1CCCB(O)O] | 47 | 29 | 100@10000 |

-continued

| Structure | Example No. | TOGA IC50 (nM) | % inhibition @ top dose |
|---|---|---|---|
| (indane-glycinamide pyrrolidine boronic acid structure) | 48 | 2 | 99@10000 |
| (prolinamide pyrrolidine boronic acid structure) | 49 | 13 | 100@10000 |
| (acetamido pyrrolidine boronic acid structure) | 50 | 246.6 | 94.33@10000 |
| (N-methyl alaninamide pyrrolidine boronic acid structure) | 51 | 985 | 87.99@10000 |
| (morpholine carboxylic acid boronic acid structure) | 52 | 210.6 | 92.12@10000 |
| (pyrrolidine dicarboxylic acid boronic acid structure) | 53 | 1479 | 77.21@10000 |

-continued
| Structure | Example No. | TOGA IC50 (nM) | % inhibition @ top dose |
|---|---|---|---|
| 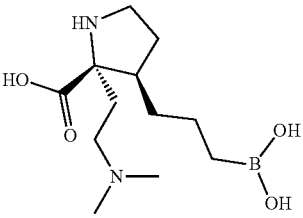 [SMILES: CN(C)CC[C@]1(C(=O)O)NCC[C@H]1CCCB(O)O] | 54 | 31.47 | 97.94@10000 |
| 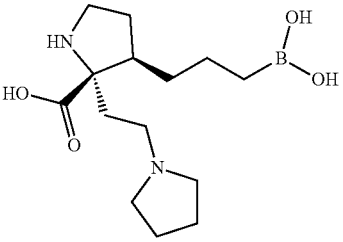 [SMILES: O=C(O)[C@@]1(CCN2CCCC2)NCC[C@H]1CCCB(O)O] | 55 | 15.85 | 98.27@10000 |
| 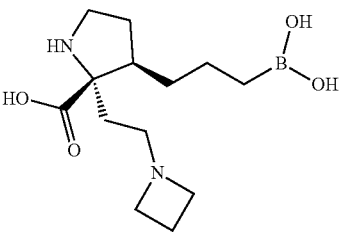 [SMILES: O=C(O)[C@@]1(CCN2CCC2)NCC[C@H]1CCCB(O)O] | 56 | 20.8 | 97.74@10000 |
| 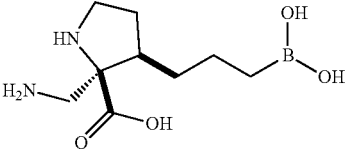 [SMILES: NC[C@]1(C(=O)O)NCC[C@H]1CCCB(O)O] | 57A | 111.8 | 93.59@10000 |
| 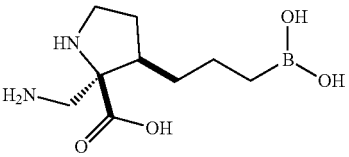 [SMILES: NC[C@]1(C(=O)O)NCC[C@H]1CCCB(O)O] | 57B | 5711 | 59.98@10000 |
| 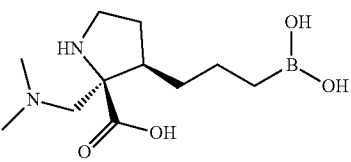 [SMILES: CN(C)C[C@]1(C(=O)O)NCC[C@H]1CCCB(O)O] | 58 | >10,000 | 7.821@@10000 |
| 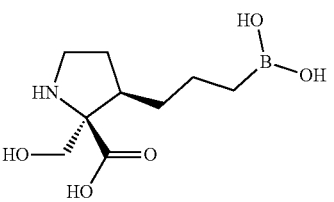 [SMILES: O=C(O)[C@@]1(CO)NCC[C@H]1CCCB(O)O] | 59A | 310.5 | 85.02@10000 |

-continued

| Structure | Example No. | TOGA IC50 (nM) | % inhibition @ top dose |
|---|---|---|---|
| (structure) | 59B | 133 | 87.45@10000 |
| (structure) | 60A | 29.53 | 95.78@10000 |
| (structure) | 60B | 1778 | 81.81@10000 |
| (structure) | 61 | 438.6 | 101.5@10000 |
| (structure) | 62 | 34.9 | 98.3@10000 |
| (structure) | 63 | 7.707 | 100.1@10000 |

-continued

| Structure | Example No. | TOGA IC50 (nM) | % inhibition @ top dose |
|---|---|---|---|
| 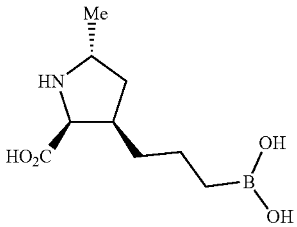 [SMILES: C[C@@H]1C[C@@H](CCCB(O)O)[C@@H](C(=O)O)N1] | 64 | 6.622 | 99.25@10000 |
| 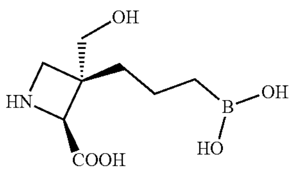 [SMILES: O=C(O)[C@H]1NC[C@@]1(CO)CCCB(O)O] | 65 | 12.95 | 98.81@10000 |
| 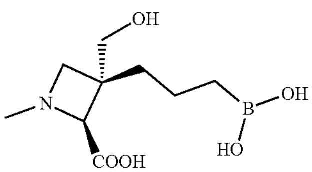 [SMILES: CN1C[C@@](CO)(CCCB(O)O)[C@H]1C(=O)O] | 66 | 268.8 | 96.98@10000 |
| 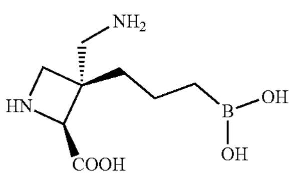 [SMILES: NC[C@@]1(CCCB(O)O)CN[C@@H]1C(=O)O] | 67 | 8 | 100@10000 |
| 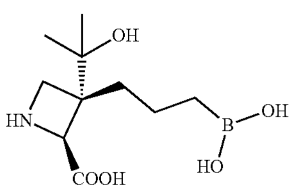 [SMILES: CC(C)(O)[C@@]1(CCCB(O)O)CN[C@@H]1C(=O)O] | 68 | 343 | 96@10000 |
| 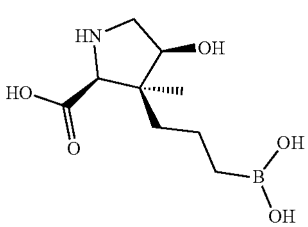 [SMILES: C[C@@]1(CCCB(O)O)[C@H](O)CN[C@@H]1C(=O)O] | 69 | >10,000 | 22.61@10000 |
| 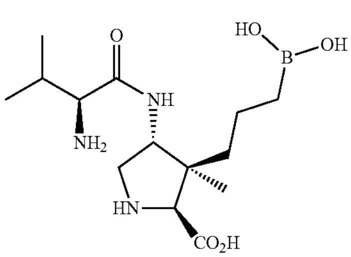 [SMILES: CC(C)[C@H](N)C(=O)N[C@H]1CN[C@H](C(=O)O)[C@]1(C)CCCB(O)O] | 70 | 83 | 100@10000 |

-continued
| Structure | Example No. | TOGA IC50 (nM) | % inhibition @ top dose |
|---|---|---|---|
| 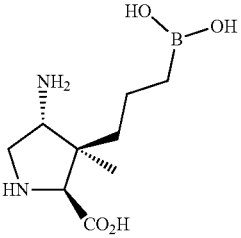 [SMILES: C[C@]1(CCCB(O)O)[C@@H](C(=O)O)NC[C@@H]1N] | 71 | 17 | 100@10000 |
| 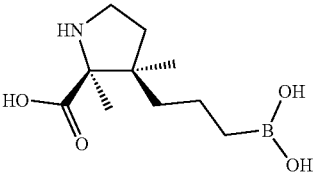 [SMILES: C[C@@]1(CCCB(O)O)CCN[C@]1(C)C(=O)O] | 72 | 118.9 | 96.66@10000 |
| 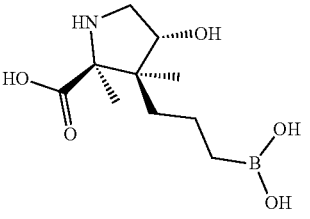 [SMILES: C[C@]1(C(=O)O)NC[C@H](O)[C@@]1(C)CCCB(O)O] | 73 | 99.43 | 99.43@10000 |
| 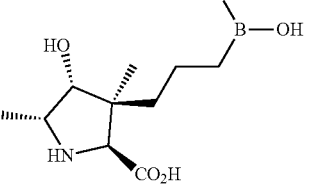 | 74A | 48.58 | 99.29@10000 |
| 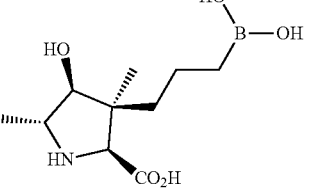 | 74B | >10,000 | 20.47@10000 |
| 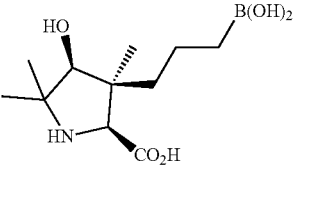 [SMILES: CC1(C)N[C@H](C(=O)O)[C@](C)(CCCB(O)O)[C@@H]1O] | 75 | >10,000 | 4.535@10000 |
| 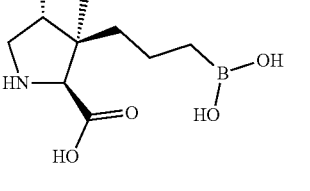 | 76 | 17.67 | 99@10000 |

-continued
| Structure | Example No. | TOGA IC50 (nM) | % inhibition @ top dose |
|---|---|---|---|
| 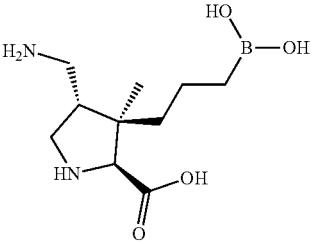 [SMILES: C[C@@]1(CCCB(O)O)[C@@H](CN)CN[C@@H]1C(=O)O] | 77 | 84.99 | 97.96@10000 |
| 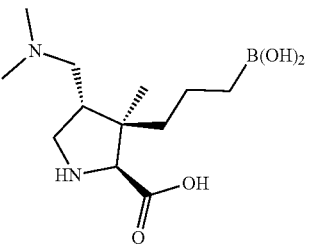 [SMILES: CN(C)C[C@H]1CN[C@H](C(=O)O)[C@]1(C)CCCB(O)O] | 78 | >10,000 | 21.99@10000 |
| 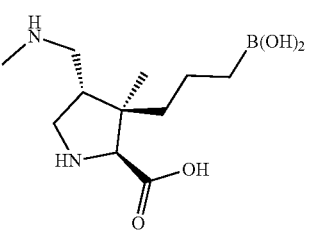 [SMILES: CNC[C@H]1CN[C@H](C(=O)O)[C@]1(C)CCCB(O)O] | 79 | 66.26 | 97.48@10000 |
| 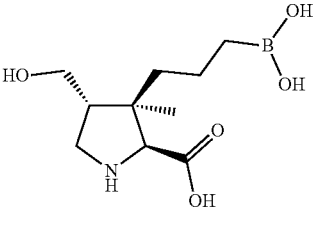 [SMILES: C[C@@]1(CCCB(O)O)[C@@H](CO)CN[C@@H]1C(=O)O] | 80 | 27.25 | 96.71@10000 |
| 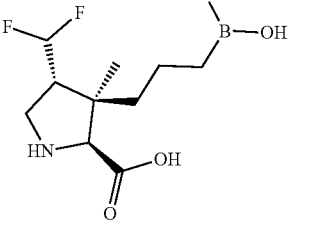 | 81 | 138.6 | 95.31@10000 |
| 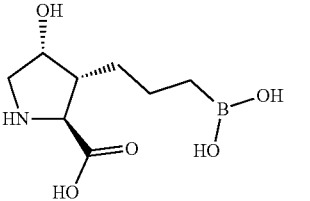 [SMILES: O=C(O)[C@H]1NC[C@H](O)[C@@H]1CCCB(O)O] | 82 | >10,000 | 28.35@10000 |

-continued

| Structure | Example No. | TOGA IC50 (nM) | % inhibition @ top dose |
|---|---|---|---|
| (pyrrolidine with CH2OH, propyl-B(OH)2, CO2H) | 83 | 19.34 | 99.59@10000 |
| (pyrrolidine with CHF2, propyl-B(OH)2, CO2H) | 84 | 28.95 | 99.41@10000 |
| (pyrrolidine with CH2NH2, propyl-B(OH)2, HO2C) | 85 | 7.178 | 100.5@10000 |
| (pyrrolidine with CH2N(CH3)2, propyl-B(OH)2, CO2H) | 86 | 119 | 100@10000 |
| (pyrrolidine with CH2NHCH3, propyl-B(OH)2, HO2C) | 87 | 7 | 100@10000 |
| (pyrrolidine with CN, propyl-B(OH)2, HO2C) | 88 | 13.38 | 101@10000 |
| (pyrrolidine with C(O)NH2, propyl-B(OH)2, HO2C) | 89 | 288.7 | 92.09@10000 |
| (4-hydroxy pyrrolidine with CH2CO2H, propyl-B(OH)2, CO2H) | 90 | 2910 | 80.09@10000 |

-continued

| Structure | Example No. | TOGA IC50 (nM) | % inhibition @ top dose |
|---|---|---|---|
| (structure) | 91 | 20 | 98@10000 |
| (structure) | 92A | >10,000 | 29.17@10000 |
| (structure) | 92B | 123.7 | 96.22@10000 |
| (structure) | 92C | >10,000 | 22.45@10000 |
| (structure) | 93 | 92.15 | 90.06@10000 |
| (structure) | 94A | 3081 | 82@10000 |
| (structure) | 94B | 940 | 93@10000 |

-continued

| Structure | Example No. | TOGA IC50 (nM) | % inhibition @ top dose |
|---|---|---|---|
| 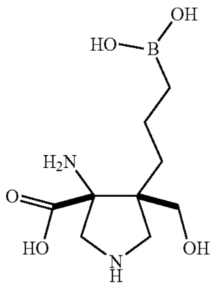 | 94C | >10,000 | 38@10000 |
| 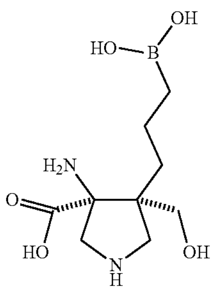 | 94D | >10,000 | 27@10000 |
| 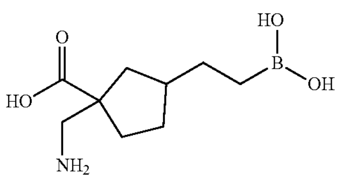 [SMILES: NCC1(C(=O)O)CCC(CCB(O)O)C1] | 95 | >10,000 | 30@10000 |

What is claimed is:

1. A compound of Formula I:

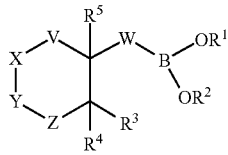

I or a pharmaceutically acceptable salt thereof, wherein:

W is selected from the group consisting of straight or branched ($C_2$-$C_5$) alkylene, wherein one or more —$CH_2$— groups in W are optionally and independently replaced with a moiety selected from the group consisting of —O—, —S— or —NH—;

V is selected from the group consisting of a bond, O, S, $CR^6R^7$ or $NR^8$;

X is selected from the group consisting of a bond, O, S, $CR^9R^{10}$ or $NR^{11}$;

Y is selected from the group consisting of a bond, O, S, $CR^{12}R^{13}$ or $NR^{14}$, is selected from the group consisting of a bond, O, S, $CR^{15}R^{16}$ or $NR^{17}$, $R^1$ is selected from the group consisting of hydrogen, —$C_3$-$C_6$cycloalkyl or —$C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, —$C_1$-$C_6$alkyl or —OH;

$R^2$ is selected from the group consisting of hydrogen, —$C_3$-$C_6$cycloalkyl or —$C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, —$C_1$-$C_6$alkyl or —OH;

$R^3$ is —COOH;

$R^4$ is hydrogen, halogen, —$C_3$-$C_6$cycloalkyl, —$C_1$-$C_6$alkyl, —$C_1$-$C_6$alkylOH, —COOH, —$C_1$-$C_6$alkylN($R^{18}$)($R^{19}$), —$C_1$-$C_6$alkylheteroaryl, heteroaryl, —$C_1$-$C_6$alkoxy or —COO$C_1$-$C_6$alkyl;

$R^5$ is selected from the group consisting of hydrogen, halogen, —CN, —OH, —$C_1$-$C_6$alkylCOOH, —COOH, —$C_3$-$C_6$cycloalkyl, —$C_1$-$C_6$alkyl, -halo$C_1$-$C_6$alkyl, —$C_1$-$C_6$alkylOH, —$C_1$-$C_6$alkylheteroaryl, —CON($R^{18}$)($R^{19}$), —N($R^{18}$)($R^{19}$) or —$C_1$-$C_6$alkylN($R^{18}$)($R^{19}$);

$R^6$ is selected from the group consisting of hydrogen, halogen, —OH, $C_1$-$C_6$alkylOH, —$C_3$-$C_6$cycloalkyl, —$C_1$-$C_6$alkyl, -halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^7$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^8$ is selected from the group consisting of hydrogen, —$C_3$-$C_6$cycloalkyl, —$C_1$-$C_6$alkyl, —$C_1$-$C_6$alkylheteroaryl, or —$C_1$-$C_6$alkylN($R^{18}$)($R^{19}$);

$R^9$ is selected from the group consisting of hydrogen, halogen, —OH, —$C_1$-$C_6$alkylOH, —$C_3$-$C_6$cycloalkyl, —$C_1$-$C_6$alkyl, -halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{10}$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{11}$ is selected from the group consisting of hydrogen, —$C_3$-$C_6$cycloalkyl, —$C_1$-$C_6$alkyl, —$C_1$-$C_6$alkylheteroaryl, or —$C_1$-$C_6$alkylN($R^{18}$)($R^{19}$);

$R^{12}$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{13}$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{14}$ is selected from the group consisting of hydrogen, —$C_3$-$C_6$cycloalkyl, —$C_1$-$C_6$alkyl, —$C_1$-$C_6$alkylheteroaryl, or —$C_1$-$C_6$alkylN($R^{18}$)($R^{19}$);

$R^{15}$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{16}$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{17}$ is selected from the group consisting of hydrogen, —$C_3$-$C_6$cycloalkyl, —$C_1$-$C_6$alkyl, —$C_1$-$C_6$alkylheteroaryl, and —$C_1$-$C_6$alkylN($R^{18}$)($R^{19}$);

$R^{18}$ is independently selected from the group consisting of hydrogen, —$C_3$-$C_6$cycloalkyl, —halo$C_1$-$C_6$alkyl, —$C_1$-$C_6$alkyl, —$C_1$-$C_6$alkylNH$_2$, —COheterocycle, and —COC$_1$-$C_6$alkyl, wherein the —COC$_1$-$C_6$alkyl can be optionally substituted with one or two substituents selected from the group consisting of —N($R^{19}$)($R^{19}$), —OH, cycloalkyl, or a 3-7 membered nitrogen containing ring or $R^{18}$ taken with $R^{19}$ forms a 3-7 membered nitrogen containing ring; and $R^{19}$ is independently selected from the group consisting of hydrogen, —$C_3$-$C_6$cycloalkyl, —halo$C_1$-$C_6$alkyl and —$C_1$-$C_6$alkyl, or $R^{19}$ taken with $R^{18}$ forms a 3-7 membered nitrogen containing ring;

wherein $R^6$ and $R^7$, $R^9$ and $R^{10}$, $R^{12}$ and $R^{13}$, and $R^{15}$ and $R^{16}$ cannot be: —COOH and —N ($R^{18}$)($R^{19}$), or —N($R^{18}$)($R^{19}$) and —COOH.

2. The compound of claim 1, or a pharmaceutically salt thereof, wherein $R^1$ and $R^2$ are both hydrogen.

3. The compound of claim 1, or a pharmaceutically acceptable salt thereof, wherein W is propylenyl.

4. The compound of claim 1, or a pharmaceutically acceptable salt thereof, wherein $R^4$ and $R^5$ are independently hydrogen or methyl.

5. The compound of claim 1 having Formula II:

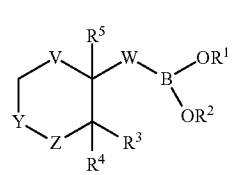

II or a pharmaceutically acceptable salt thereof, wherein:

W is selected from the group consisting of straight or branched ($C_2$-$C_5$) alkylene, wherein one or more —CH$_2$— groups in W are optionally and independently replaced with a moiety selected from the group consisting of —O—, —S— or —NH—;

V is selected from the group consisting of a bond, O, S, CR$^6$R$^7$ or NR$^8$;

Y is selected from the group consisting of a bond, O, S, CR$^{12}$R$^{13}$ or NR$^{14}$, Z is selected from the group consisting of a bond, O, S, CR$^{15}$R$^{16}$ or NR$^{17}$, $R^1$ is selected from the group consisting of hydrogen, —$C_3$-$C_6$cycloalkyl or —$C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, —$C_1$-$C_6$alkyl or —OH;

$R^2$ is selected from the group consisting of hydrogen, —$C_3$-$C_6$cycloalkyl or —$C_1$-$C_6$alkyl or, taken with $R^1$ forms a $C_3$-$C_8$cycloalkyl, wherein the $C_3$-$C_6$cycloalkyl is optionally substituted with one to four substituents selected from the group consisting of halogen, —$C_1$-$C_6$alkyl or —OH;

$R^3$ is —COOH;

$R^4$ is hydrogen, halogen, —$C_3$-$C_6$cycloalkyl, —$C_1$-$C_6$alkyl, —halo$C_1$-$C_6$alkyl, $C_1$-$C_6$alkylOH, —COOH, —$C_1$-$C_6$alkylN($R^{18}$)($R^{19}$), —$C_1$-$C_6$alkylheteroaryl, heteroaryl, —$C_1$-$C_6$alkoxy and —COO$C_1$-$C_6$alkyl;

$R^5$ is selected from the group consisting of hydrogen, halogen —CN, —OH, —$C_1$-$C_6$alkylCOOH, —COOH, —$C_3$-$C_6$cycloalkyl, —$C_1$-$C_6$alkyl, —halo$C_1$-$C_6$alkyl, —$C_1$-$C_6$alkylOH, —$C_1$-$C_6$alkylheteroaryl, —CON($R^{18}$)($R^{19}$), —N($R^{18}$)($R^{19}$) or —$C_1$-$C_6$alkylN($R^{18}$)($R^{19}$);

$R^6$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^7$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^8$ is selected from the group consisting of hydrogen, —$C_3$-$C_6$cycloalkyl, —$C_1$-$C_6$alkyl, —$C_1$-$C_6$alkylheteroaryl, or —$C_1$-$C_6$alkylN($R^{18}$)($R^{19}$);

$R^{12}$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{13}$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{14}$ is selected from the group consisting of hydrogen, —$C_3$-$C_6$cycloalkyl, —$C_1$-$C_6$alkyl, —$C_1$-$C_6$alkylheteroaryl, or —$C_1$-$C_6$alkylN($R^{18}$)($R^{19}$);

$R^{15}$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{16}$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{17}$ is selected from the group consisting of hydrogen, —$C_3$-$C_6$cycloalkyl, —$C_1$-$C_6$alkyl, —$C_1$-$C_6$alkylheteroaryl, and —$C_1$-$C_6$alkylN($R^{18}$)($R^{19}$);

$R^{18}$ is selected from the group consisting of hydrogen, —$C_3$-$C_6$cycloalkyl, —halo$C_1$-$C_6$alkyl, —$C_1$-$C_6$alkyl, —$C_1$-$C_6$alkylNH$_2$, —COheterocycle and —CO$C_1$-$C_6$alkyl, wherein the —CO$C_1$-$C_6$alkyl can be optionally substituted with one or two substituents selected from the group consisting of —N($R^{19}$)($R^{19}$), —OH, cycloalkyl, or a 3-7 membered nitrogen containing ring or $R^{18}$ taken with $R^{19}$ forms a 3-7 membered nitrogen containing ring; and $R^{19}$ is selected from the group consisting of hydrogen, —$C_3$-$C_6$cycloalkyl, —halo$C_1$-$C_6$alkyl and —$C_1$-$C_6$alkyl, or $R^{19}$ taken with $R^{18}$ forms a 3-7 membered nitrogen containing ring;

wherein $R^6$ and $R^7$, $R^{12}$ and $R^{13}$, and $R^{15}$ and $R^{16}$ cannot be —COOH and —N($R^{18}$)($R^{19}$) or —N($R^{18}$)($R^{19}$) and —COOH.

6. The compound of claim 5, or a pharmaceutically salt thereof, wherein $R^1$ and $R^2$ are both hydrogen.

7. The compound of claim 5, or a pharmaceutically acceptable salt thereof, wherein W is propylenyl.

8. The compound of claim 1, having Formula III

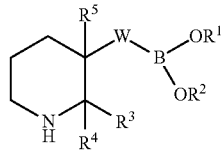

III or a pharmaceutically acceptable salt thereof, wherein:

W is selected from the group consisting of straight or branched ($C_2$-$C_5$) alkylene, wherein one or more —CH$_2$— groups in W are optionally and independently replaced with a moiety selected from the group consisting of —O—, —S— or —NH—;

$R^1$ is selected from the group consisting of hydrogen, —$C_3$-$C_6$cycloalkyl or —$C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, —$C_1$-$C_6$alkyl or —OH;

$R^2$ is selected from the group consisting of hydrogen, —$C_3$-$C_6$cycloalkyl or —$C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, —$C_1$-$C_6$alkyl or —OH;

$R^3$ is —COOH;

$R^4$ is hydrogen, halogen, —$C_3$-$C_6$cycloalkyl, —$C_1$-$C_6$alkyl, —halo$C_1$-$C_6$alkyl, —$C_1$-$C_6$alkylOH, —COOH, —$C_1$-$C_6$alkylN($R^{18}$)($R^{19}$), —$C_1$-$C_6$alkylheteroaryl, heteroaryl, —$C_1$-$C_6$alkoxy and —COO$C_1$-$C_6$alkyl;

$R^5$ is selected from the group consisting of hydrogen, halogen, —CN, —OH, —$C_1$-$C_6$alkylCOOH, —COOH, —$C_3$-$C_6$cycloalkyl, —$C_1$-$C_6$alkyl, —halo$C_1$-$C_6$alkyl, —$C_1$-$C_6$alkylOH, —$C_1$-$C_6$alkylheteroaryl, CON($R^{18}$)($R^{19}$), —N($R^{18}$)($R^{19}$) or —$C_1$-$C_6$alkylN($R^{18}$)($R^{19}$);

$R^{18}$ is selected from the group consisting of hydrogen, —$C_3$-$C_6$cycloalkyl, —halo$C_1$-$C_6$alkyl, —$C_1$-$C_6$alkyl, —$C_1$-$C_6$alkylNH$_2$, and —CO$C_1$-$C_6$alkyl, wherein the —CO$C_1$-$C_6$alkyl can be optionally substituted with one or two substituents selected from the group consisting of —N($R^{19}$)($R^{19}$), —OH, cycloalkyl, or a 3-7 membered nitrogen containing ring or $R^{18}$ taken with $R^{19}$ forms a 3-7 membered nitrogen containing ring; and $R^{19}$ is selected from the group consisting of hydrogen, —$C_3$-$C_6$cycloalkyl, —halo$C_1$-$C_6$alkyl and —$C_1$-$C_6$alkyl, or $R^{19}$ taken with $R^{18}$ forms a 3-7 membered nitrogen containing ring.

9. The compound of claim 8, or a pharmaceutically salt thereof, wherein $R^1$ and $R^2$ are both hydrogen.

10. The compound of claim 8, or a pharmaceutically acceptable salt thereof, wherein W is propylenyl.

11. The compound of claim 1, having Formula IV:

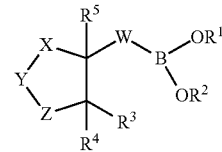

IV or a pharmaceutically acceptable salt thereof, wherein:

W is selected from the group consisting of straight or branched ($C_2$-$C_5$) alkylene, wherein one or more —CH$_2$— groups in W are optionally and independently replaced with a moiety selected from the group consisting of —O—, —S— or —NH—;

Y is selected from the group consisting of a bond, O, S, $CR^{12}R^{13}$ or $NR^{14}$, X is selected from the group consisting of a bond, O, S, $CR^9R^{10}$ or $NR^{11}$, Z is selected from the group consisting of a bond, O, S, $CR^{15}R^{16}$ or $NR^{17}$;

$R^1$ is selected from the group consisting of hydrogen, —$C_3$-$C_6$cycloalkyl or —$C_1$-$C_6$alkyl or, taken with $R^2$ forms a $C_3$-$C_8$cycloalkyl, wherein the $C_3$-$C_6$cycloalkyl is optionally substituted with one to four substituents selected from the group consisting of halogen, —$C_1$-$C_6$alkyl or —OH;

$R^2$ is selected from the group consisting of hydrogen, —$C_3$-$C_6$cycloalkyl or —$C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, —$C_1$-$C_6$alkyl or —OH;

$R^3$ is —COOH;

$R^4$ is hydrogen, halogen, —$C_3$-$C_6$cycloalkyl, —$C_1$-$C_6$alkyl, —$C_1$-$C_6$alkylOH, —COOH, —$C_1$-$C_6$alkylN($R^{18}$)($R^{19}$), —$C_1$-$C_6$alkylheteroaryl, heteroaryl, —$C_1$-$C_6$alkoxy or —COO$C_1$-$C_6$alkyl;

$R^5$ is selected from the group consisting of hydrogen, halogen, —CN, —OH, —$C_1$-$C_6$alkylCOOH, —COOH, —$C_3$-$C_6$cycloalkyl, —$C_1$-$C_6$alkyl, —halo$C_1$-$C_6$alkyl, —$C_1$-$C_6$alkylOH, —$C_1$-$C_6$alkylheteroaryl, —CON($R^{18}$)($R^{19}$), —N($R^{18}$)($R^{19}$) or —$C_1$-$C_6$alkylN($R^{18}$)($R^{19}$);

$R^9$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{10}$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{11}$ is selected from the group consisting of hydrogen, —$C_3$-$C_6$cycloalkyl, —$C_1$-$C_6$alkyl, —$C_1$-$C_6$alkylheteroaryl, or —$C_1$-$C_6$alkylN($R^{18}$)($R^{19}$);

$R^{12}$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{13}$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{14}$ is selected from the group consisting of hydrogen, —$C_3$-$C_6$cycloalkyl, —$C_1$-$C_6$alkyl, —$C_1$-$C_6$alkylheteroaryl, or —$C_1$-$C_6$alkylN($R^{18}$)($R^{19}$);

$R^{15}$ is selected from the group consisting of hydrogen, halogen, —OH, —$C_1$-$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{16}$ is selected from the group consisting of hydrogen, halogen, —OH, —$C_6$alkylOH, —$C_3$-$C_6$cycloalkyl, —$C_1$-$C_6$alkyl, —halo$C_1$-$C_6$alkyl, —COOH, —N($R^{18}$)($R^{19}$), —$C_1$-$C_6$alkylheteroaryl, —$C_1$-$C_6$alkylN($R^{18}$)($R^{19}$), —$C_1$-$C_6$alkoxy or —COO$C_1$-$C_6$alkyl;

$R^{17}$ is selected from the group consisting of hydrogen, —$C_3$-$C_6$cycloalkyl, —$C_1$-$C_6$alkyl, —$C_1$-$C_6$alkylheteroaryl, and —$C_1$-$C_6$alkylN($R^{18}$)($R^{19}$);

$R^{18}$ is selected from the group consisting of hydrogen, —$C_3$-$C_6$cycloalkyl, —halo$C_1$-$C_6$alkyl, —$C_1$-$C_6$alkyl, —$C_1$-$C_6$alkyl$NH_2$, —COheterocycle and —CO$C_1$-$C_6$alkyl, wherein the CO$C_1$-$C_6$alkyl can be optionally substituted with one or two substituents selected from the group consisting of —N($R^{19}$)($R^{19}$), —OH, cycloalkyl, or a 3-7 membered nitrogen containing ring or $R^{18}$ taken with $R^{19}$ forms a 3-7 membered nitrogen containing ring; and $R^{19}$ is selected from the group consisting of hydrogen, —$C_3$-$C_6$cycloalkyl, —halo$C_1$-$C_6$alkyl and —$C_1$-$C_6$alkyl, or $R^{19}$ taken with $R^{18}$ forms a 3-7 membered nitrogen containing ring;

wherein $R^9$ and $R^{10}$, $R^{12}$ and $R^{13}$ and $R^{15}$ and $R^{16}$ cannot be —COOH and —N($R^{18}$)($R^{19}$) or —N($R^{18}$)($R^{19}$) and —COOH.

12. The compound of claim 1, having Formula V:

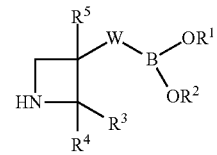

V or a pharmaceutically acceptable salt thereof, wherein:
W is selected from the group consisting of straight or branched ($C_2$-$C_5$) alkylene, wherein one or more —$CH_2$— groups in W are optionally and independently replaced with a moiety selected from the group consisting of —O—, —S— or —NH—;

$R^1$ is selected from the group consisting of hydrogen, —$C_3$-$C_6$cycloalkyl or —$C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, $C_1$-$C_6$alkyl-$C_1$-$C_6$alkyl or —OH;

$R^2$ is selected from the group consisting of hydrogen, —$C_3$-$C_6$cycloalkyl or —$C_1$-$C_6$alkyl or, taken with $R^1$ forms a $C_3$-$C_8$cycloalkyl, wherein the $C_3$-$C_6$cycloalkyl is optionally substituted with one to four substituents selected from the group consisting of halogen, —$C_1$-$C_6$alkyl or —OH;

$R^3$ is —COOH;

$R^4$ is hydrogen, halogen, —$C_3$-$C_6$cycloalkyl, —$C_1$-$C_6$alkyl, —$C_1$-$C_6$alkylOH, —COOH, —$C_1$-$C_6$alkylN($R^{18}$)($R^{19}$), —$C_1$-$C_6$alkylheteroaryl, heteroaryl, —$C_1$-$C_6$alkoxy and —COO$C_1$-$C_6$alkyl;

$R^5$ is selected from the group consisting of hydrogen, halogen, —CN, —OH, —$C_1$-$C_6$alkylCOOH, COOH, —$C_3$-$C_6$cycloalkyl, —$C_1$-$C_6$alkyl, —halo$C_1$-$C_6$alkyl, —$C_1$-$C_6$alkylOH, —$C_1$-$C_6$alkylheteroaryl, —CON($R^{18}$)($R^{19}$), —N($R^{18}$)($R^{19}$) or —$C_1$-$C_6$alkylN($R^{18}$)($R^{19}$);

$R^{18}$ is selected from the group consisting of hydrogen, —$C_3$-$C_6$cycloalkyl, —halo$C_1$-$C_6$alkyl, —$C_1$-$C_6$alkyl, —$C_1$-$C_6$alkyl$NH_2$, —COheterocycle and —CO$C_1$-$C_6$alkyl, wherein the —CO$C_1$-$C_6$alkyl can be optionally substituted with one or two substituents selected from the group consisting of —N($R^{19}$)($R^{19}$), —OH, cycloalkyl, or a 3-7 membered nitrogen containing ring or $R^{18}$ taken with $R^{19}$ forms a 3-7 membered nitrogen containing ring; and $R^{19}$ is selected from the group consisting of hydrogen, —$C_3$-$C_6$cycloalkyl, —halo$C_1$-$C_6$alkyl and —$C_1$-$C_6$alkyl, or $R^{19}$ taken with $R^{18}$ forms a 3-7 membered nitrogen containing ring.

13. The compound of claim 1, having Formula VI:

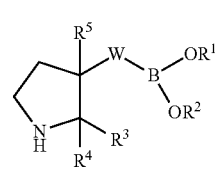

VI or a pharmaceutically acceptable salt thereof, wherein:
W is selected from the group consisting of straight or branched ($C_2$-$C_5$) alkylene, wherein one or more —$CH_2$— groups in W are optionally and independently replaced with a moiety selected from the group consisting of —O—, —S— or —NH—;

$R^1$ is selected from the group consisting of hydrogen, —$C_3$-$C_6$cycloalkyl or —$C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, or —OH;

$R^2$ is selected from the group consisting of hydrogen, —$C_3$-$C_6$cycloalkyl or —$C_1$-$C_6$alkyl or, taken with $R^1$ forms a $C_3$-$C_8$cycloalkyl, wherein the $C_3$-$C_6$cycloalkyl is optionally substituted with one to four substituents selected from the group consisting of halogen, —$C_1$-$C_6$alkyl or —OH;

$R^3$ is —COOH;

$R^4$ is hydrogen, halogen, —$C_3$-$C_6$cycloalkyl, —$C_1$-$C_6$alkyl, —$C_1$-$C_6$alkylOH, —COOH, —$C_1$-$C_6$alkylN($R^{18}$)($R^{19}$), —$C_1$-$C_6$alkylheteroaryl, heteroaryl, —$C_1$-$C_6$alkoxy or —COO$C_1$-$C_6$alkyl;

$R^5$ is selected from the group consisting of hydrogen, halogen, —CN, —OH, —$C_1$-$C_6$alkylCOOH, —COOH, —$C_3$-$C_6$cycloalkyl, —$C_1$-$C_6$alkyl, —halo$C_1$-$C_6$alkyl, —$C_1$-$C_6$alkylOH, —$C_1$-$C_6$alkylheteroaryl, CON($R^{18}$)($R^{19}$),>—N($R^{18}$)($R^{19}$) or —$C_1$-$C_6$alkylN($R^{18}$)($R^{19}$);

$R^{18}$ is selected from the group consisting of hydrogen, —$C_3$-$C_6$cycloalkyl, —halo$C_1$-$C_6$alkyl, —$C_1$-$C_6$alkyl, —$C_1$-$C_6$alkylNH$_2$, —COheterocycle and —COC$_1$-$C_6$alkyl, wherein the —COC$_1$-$C_6$alkyl can be optionally substituted with one or two substituents selected from the group consisting of —N($R^{19}$)($R^{19}$), —OH, cycloalkyl, or a 3-7 membered nitrogen containing ring or $R^{18}$ taken with $R^{19}$ forms a 3-7 membered nitrogen containing ring; and $R^{19}$ is selected from the group consisting of hydrogen, —$C_3$-$C_6$cycloalkyl, —halo$C_1$-$C_6$alkyl and —$C_1$-$C_6$alkyl, or $R^{19}$ taken with $R^{18}$ forms a 3-7 membered nitrogen containing ring.

14. The compound of claim 1, having Formula VII:

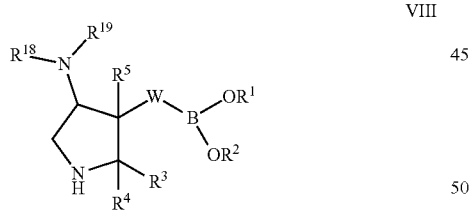

VIII or a pharmaceutically acceptable salt thereof, wherein:

W is selected from the group consisting of straight or branched ($C_2$-$C_5$) alkylene, wherein one or more —$CH_2$— groups in W are optionally and independently replaced with a moiety selected from the group consisting of —O—, —S— or —NH—;

$R^1$ is selected from the group consisting of hydrogen, —$C_3$-$C_6$cycloalkyl or —$C_1$-$C_6$alkyl or, taken with $R^2$ forms a $C_3$-$C_8$cycloalkyl, wherein the $C_3$-$C_8$cycloalkyl is optionally substituted with one to four substituents selected from the group consisting of halogen, —$C_1$-$C_6$alkyl or —OH;

$R^2$ is selected from the group consisting of hydrogen, —$C_3$-$C_6$cycloalkyl or —$C_1$-$C_6$alkyl or, taken with $R^1$ forms a $C_3$-$C_8$cycloalkyl, wherein the $C_3$-$C_8$cycloalkyl is optionally substituted with one to four substituents selected from the group consisting of halogen, —$C_1$-$C_6$alkyl or —OH;

$R^3$ is —COOH;

$R^4$ is hydrogen, halogen, —$C_3$-$C_6$cycloalkyl, —$C_1$-$C_6$alkyl, —$C_1$-$C_6$alkylOH, —COOH, N ($R^{18}$)($R^{19}$), —$C_1$-$C_6$alkylN($R^{18}$)($R^{19}$), —$C_1$-$C_6$alkylheteroaryl, heteroaryl, —$C_1$-$C_6$alkoxy or —COO$C_1$-$C_6$alkyl;

$R^5$ is selected from the group consisting of hydrogen, halogen, —CN, —OH, —$C_1$-$C_6$alkylCOOH, —COOH, —$C_3$-$C_6$cycloalkyl, —$C_1$-$C_6$alkyl, —halo$C_1$-$C_6$alkyl, —$C_1$-$C_6$alkylOH, —$C_1$-$C_6$alkylheteroaryl, —CON($R^{18}$)($R^{19}$), —N($R^{18}$)($R^{19}$) or —$C_1$-$C_6$alkylN($R^{18}$)($R^{19}$);

$R^{18}$ is selected from the group consisting of hydrogen, —halo$C_1$-$C_6$alkyl, —$C_1$-$C_6$alkyl, —$C_1$-$C_6$alkylNH$_2$, —COheterocycle and —COC$_1$-$C_6$alkyl, wherein the —COC$_1$-$C_6$alkyl can be optionally substituted with one or two substituents selected from the group consisting of —N($R^{19}$)($R^{19}$), —OH, cycloalkyl, or a 3-7 membered nitrogen containing ring or $R^{18}$ taken with $R^{19}$ forms a 3-7 membered nitrogen containing ring; and $R^{19}$ is selected from the group consisting of hydrogen, —$C_3$-$C_6$cycloalkyl, —halo$C_1$-$C_6$alkyl and —$C_1$-$C_6$alkyl, or $R^{19}$ taken with $R^{18}$ forms a 3-7 membered nitrogen containing ring.

15. A compound which is:

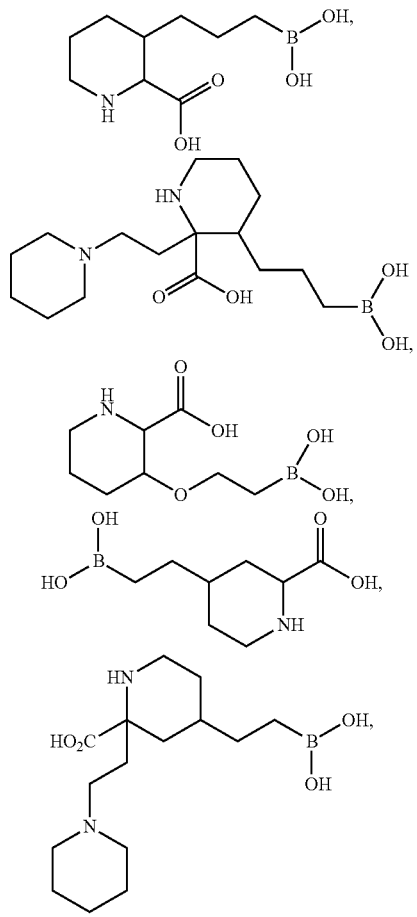

-continued
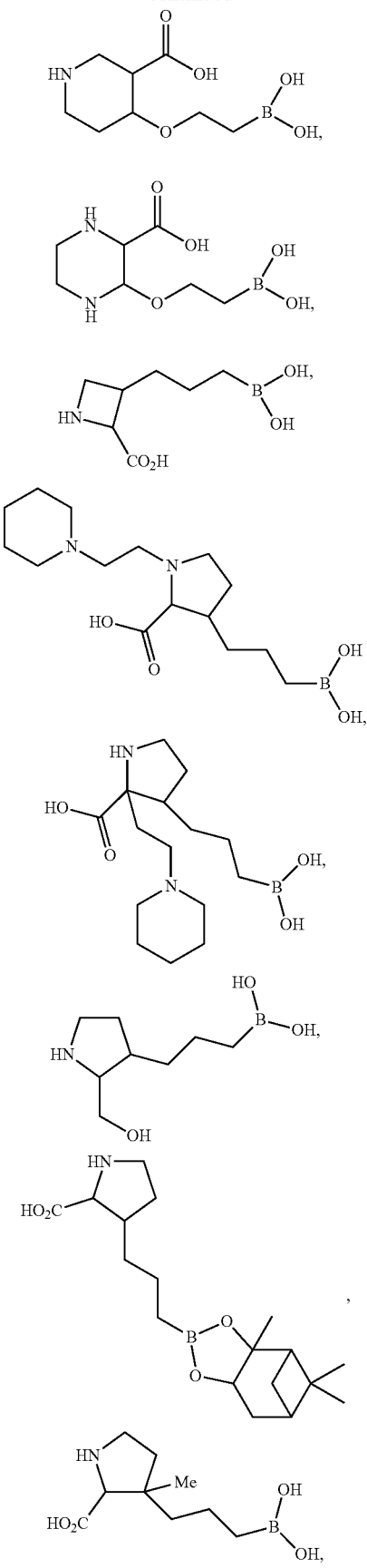
-continued
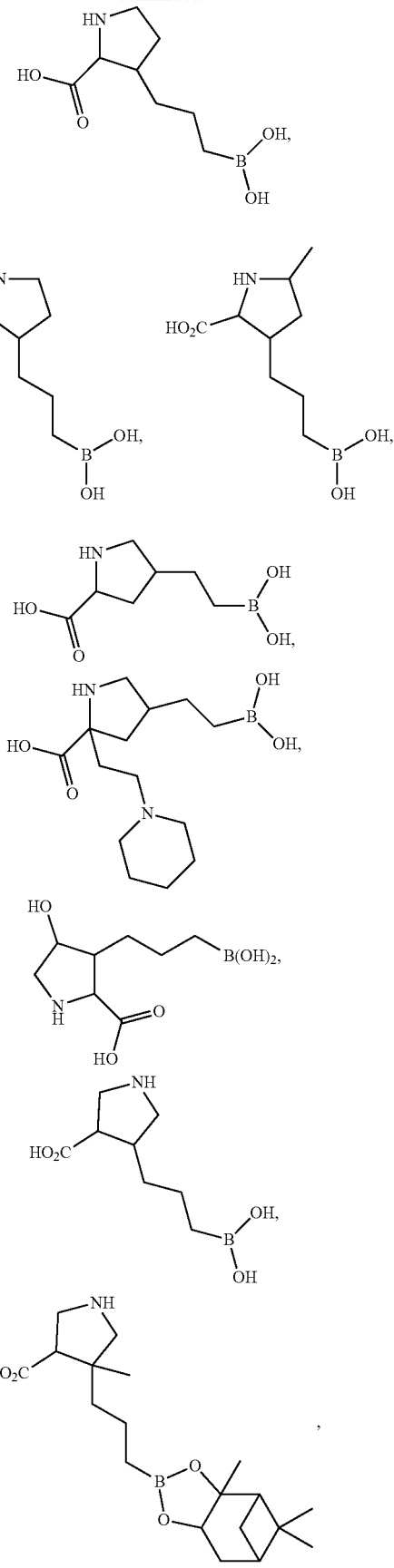

-continued
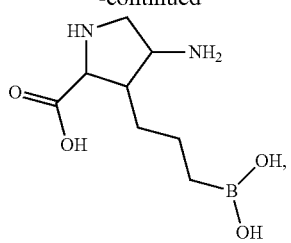
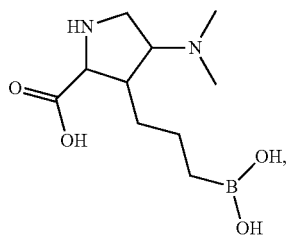
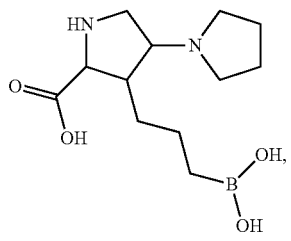
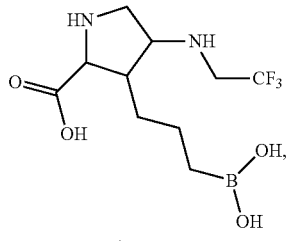
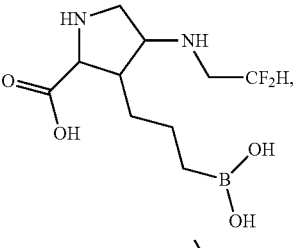
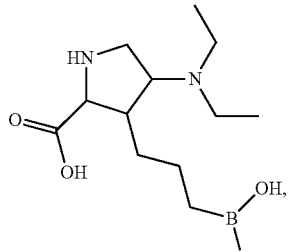
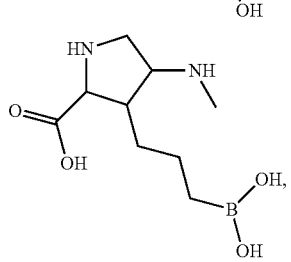
-continued
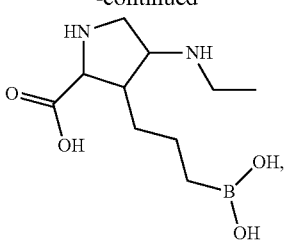
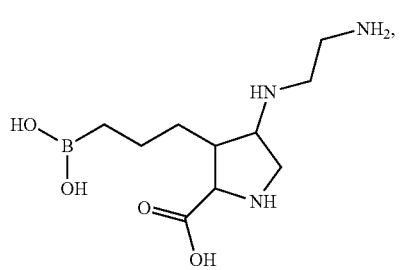
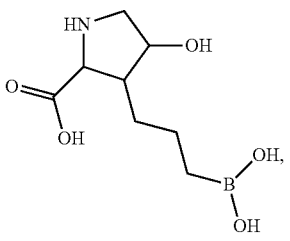
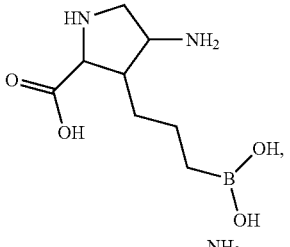
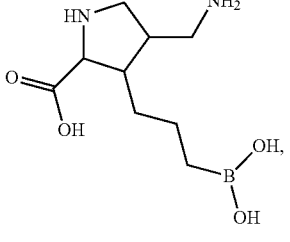
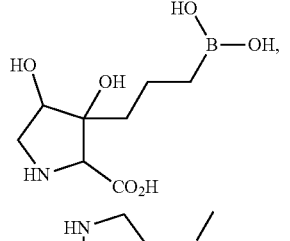
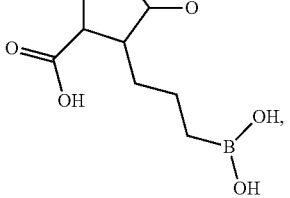

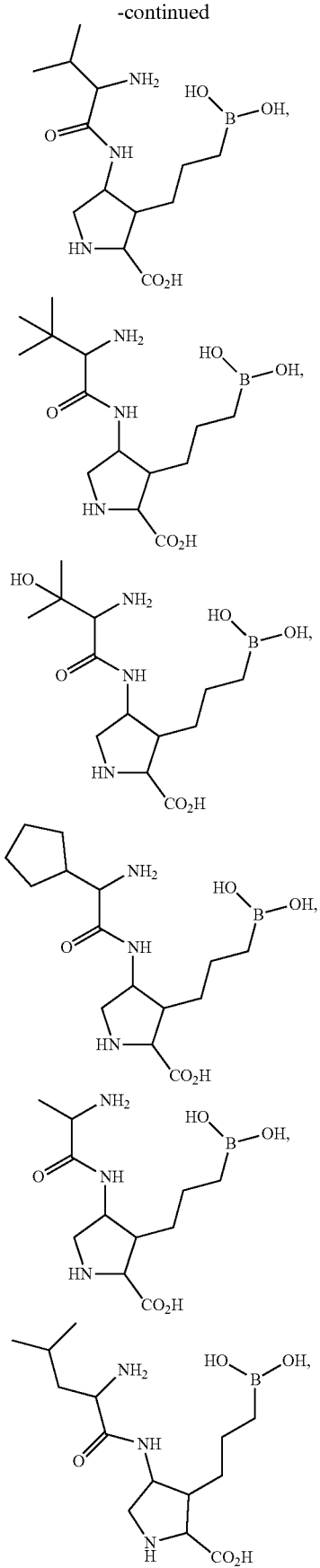
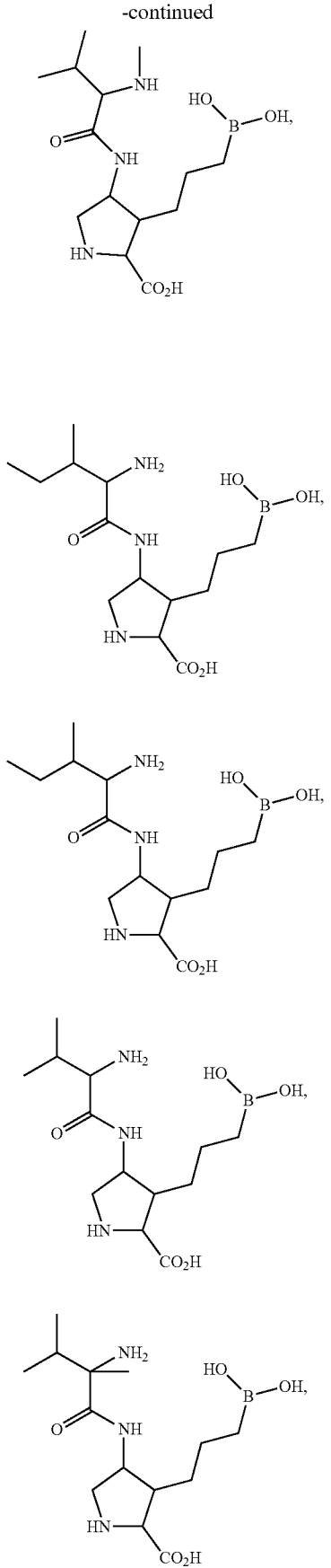

395
-continued
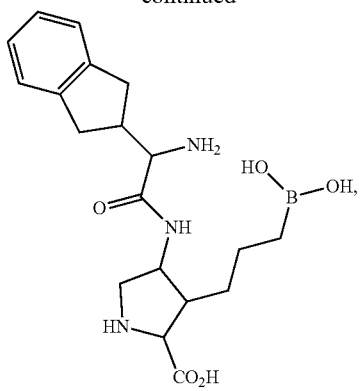
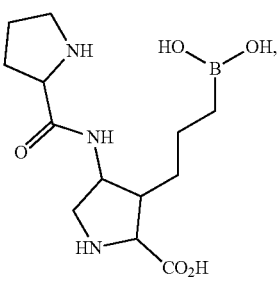
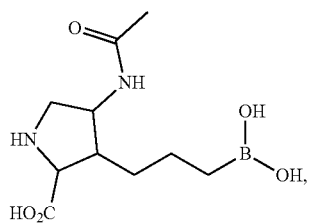
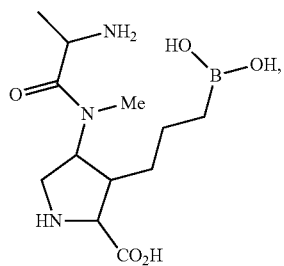
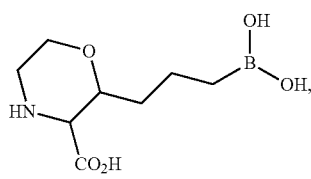
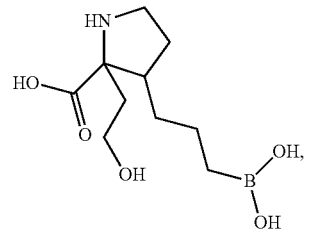
396
-continued
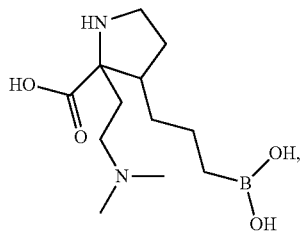
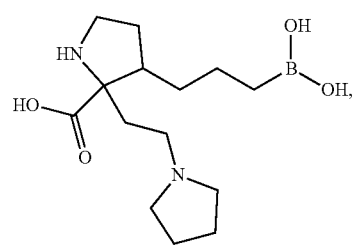
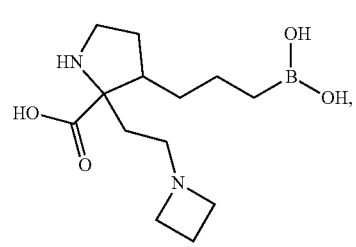
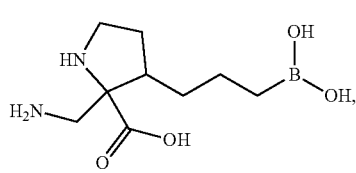
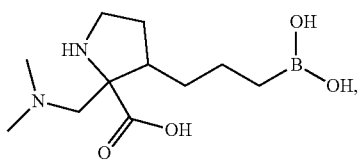
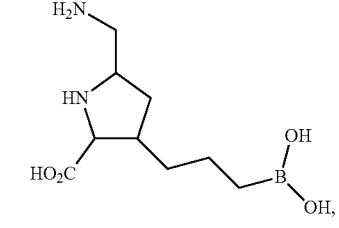
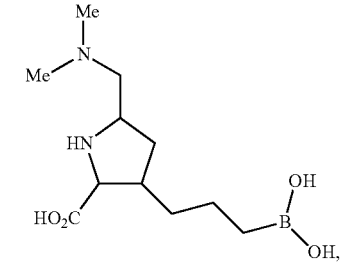

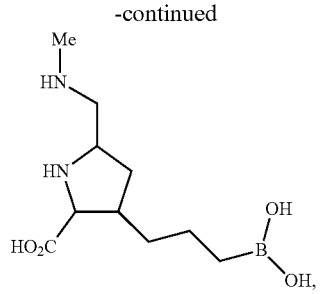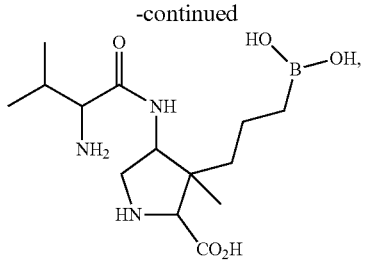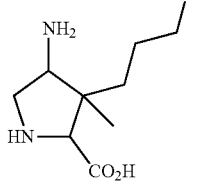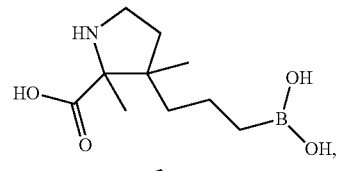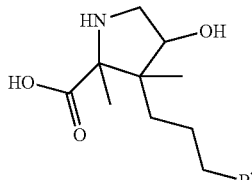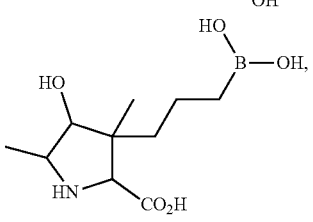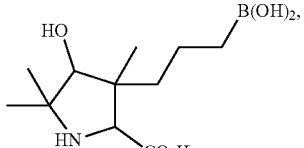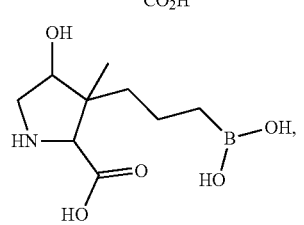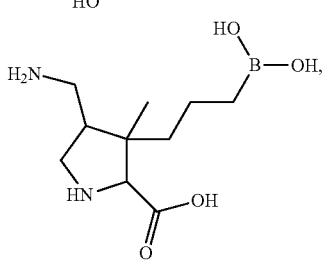

-continued or a pharmaceutically acceptable salt thereof.

16. A compound which is:
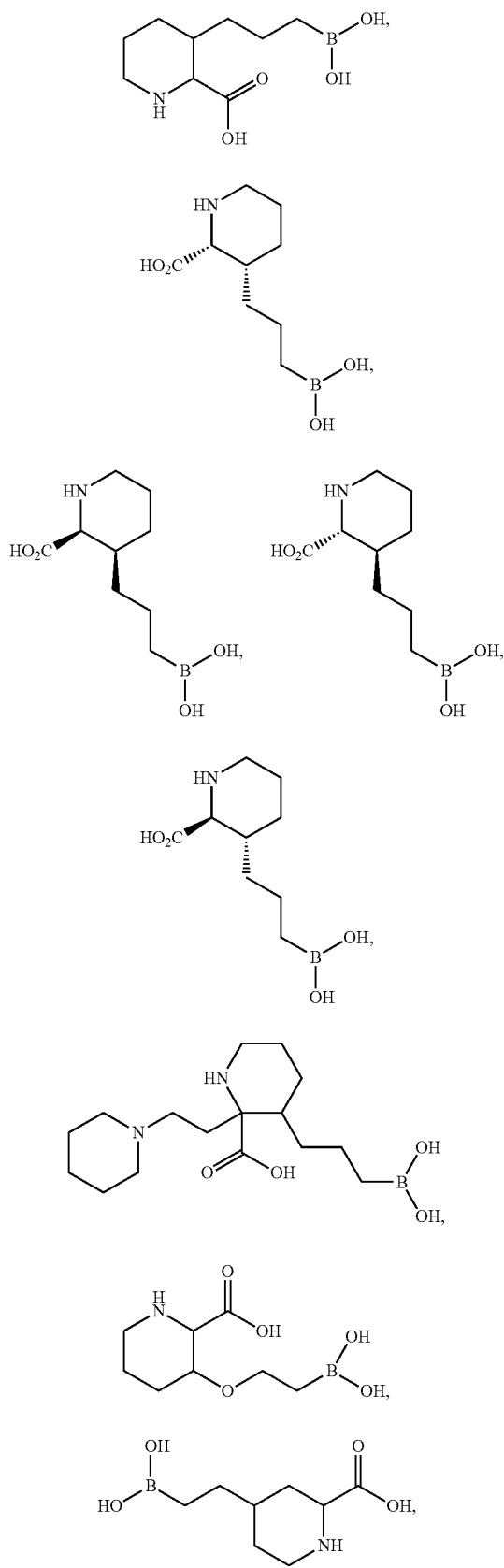
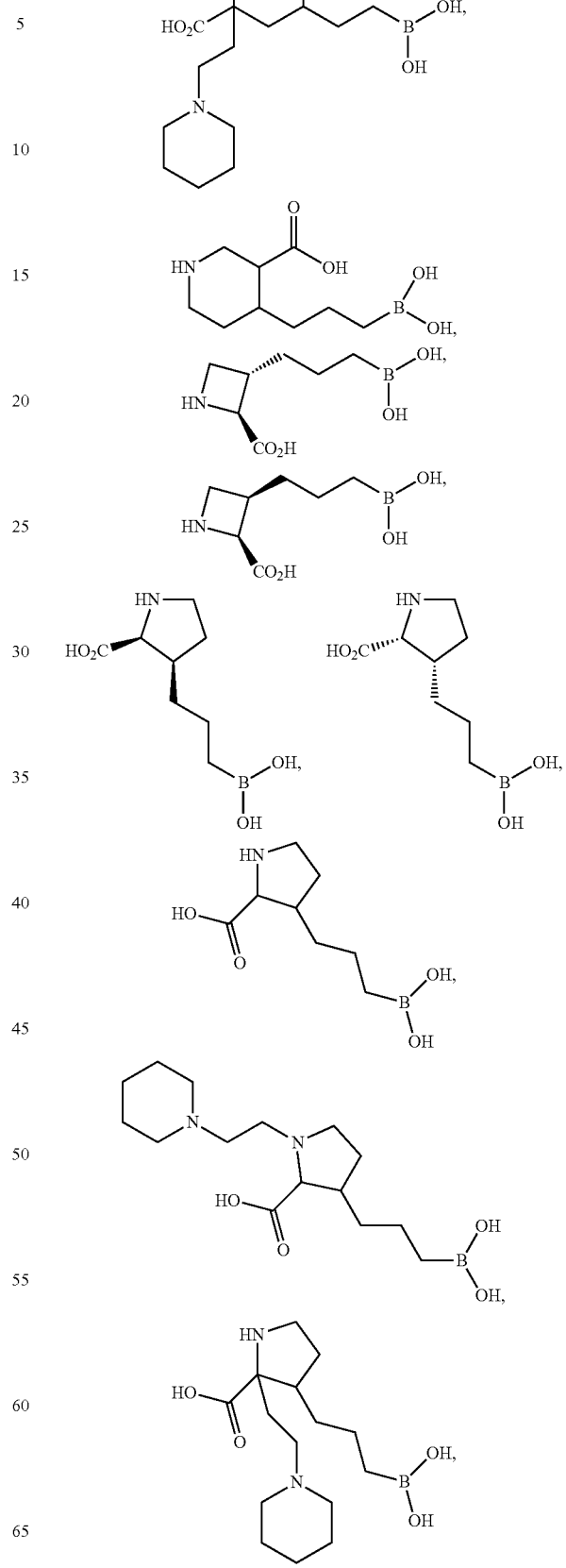

403

-continued

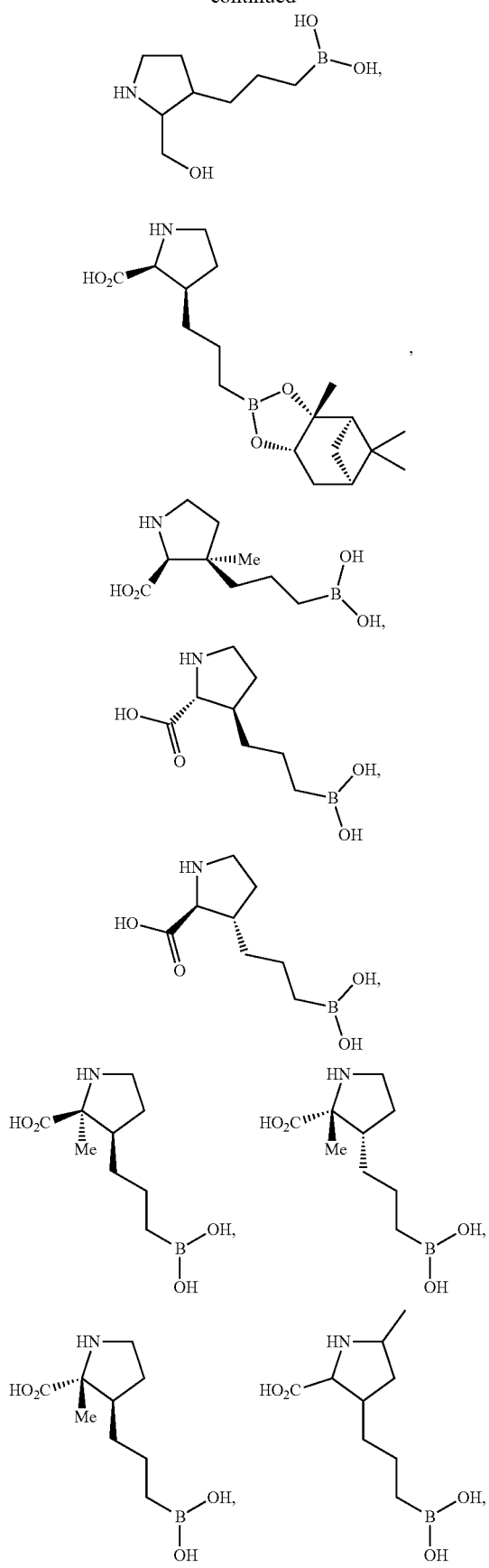

404

-continued

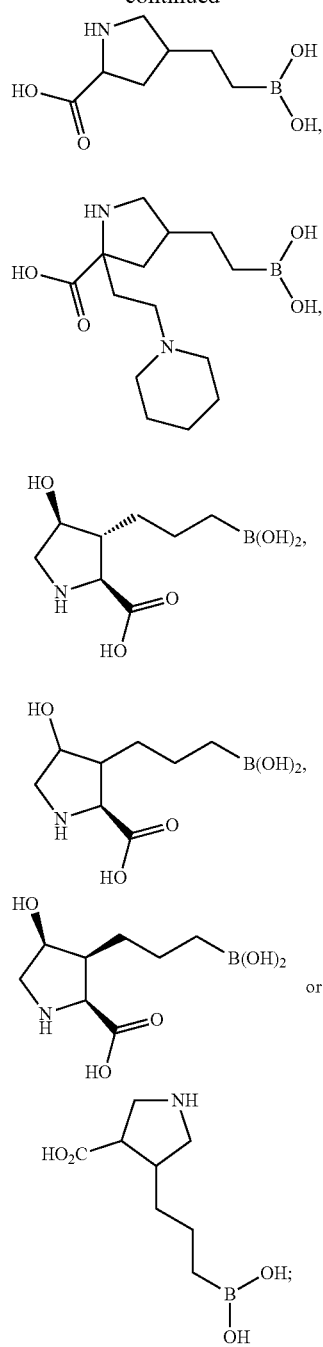

or a pharmaceutically acceptable salt thereof.

17. A method of treating cancer comprising administering to a patient in need thereof a compound, or pharmaceutically acceptable salt thereof, of claim 1.

18. A pharmaceutical composition comprising a compound, or a pharmaceutically acceptable salt thereof, of claim 1 and a pharmaceutically acceptable carrier.

19. A pharmaceutical composition comprising a compound of claim 1 and a pharmaceutically acceptable carrier.

20. A method of treating cancer comprising administering to a patient in need thereof a compound, or pharmaceutically acceptable salt thereof, of claim 1 and pembrolizumab.

21. The compound of claim 15 which is:

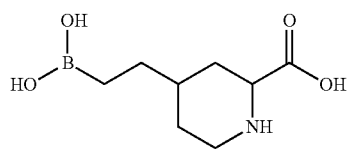 [SMILES: O=C(O)C1CC(CCB(O)O)CCN1]

or a pharmaceutically acceptable salt thereof.

22. The compound of claim 15 which is:

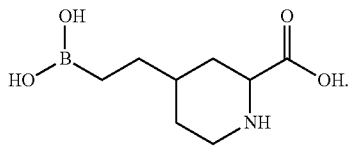 [SMILES: O=C(O)C1CC(CCB(O)O)CCN1]

23. The compound of claim 15 which is:

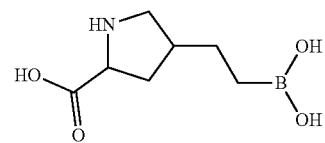 [SMILES: O=C(O)C1CC(CCB(O)O)CN1]

or a pharmaceutically acceptable salt thereof.

24. The compound of claim 15 which is:

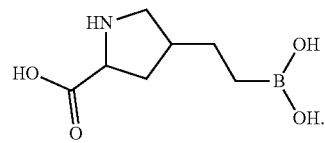

25. The compound of claim 15 which is:

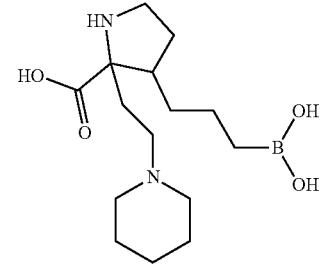 [SMILES: O=C(O)C1(CCN2CCCCC2)NCCC1CCCB(O)O]

or a pharmaceutically acceptable salt thereof.

26. The compound of claim 15 which is:

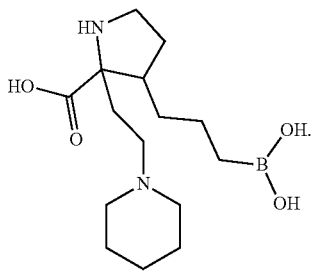 [SMILES: O=C(O)C1(CCN2CCCCC2)NCCC1CCCB(O)O]

27. The compound of claim 15 which is:

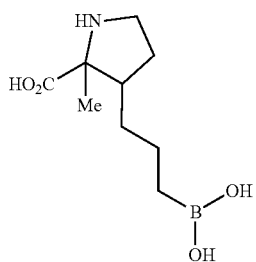 [SMILES: CC1(C(=O)O)NCCC1CCCB(O)O]

or a pharmaceutically acceptable salt thereof.

28. The compound of claim 15 which is:

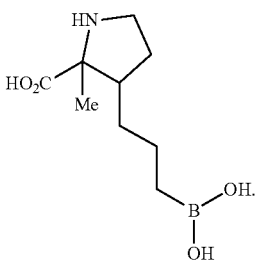 [SMILES: CC1(C(=O)O)NCCC1CCCB(O)O]

29. The compound of claim 15 which is:

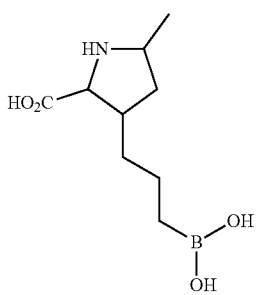

or a pharmaceutically acceptable salt thereof.

30. The compound of claim 15 which is:

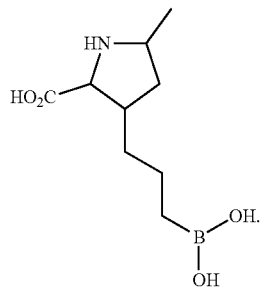

31. The compound of claim 16 which is:

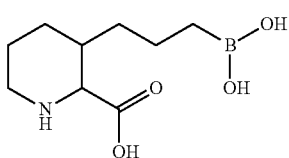 [SMILES: O=C(O)C1NCCCC1CCCB(O)O]

or a pharmaceutically acceptable salt thereof.

32. The compound of claim 16 which is:

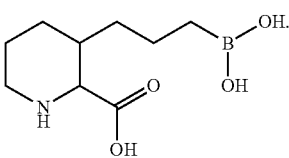 [SMILES: O=C(O)C1NCCCC1CCCB(O)O]

33. The compound of claim 16 which is:

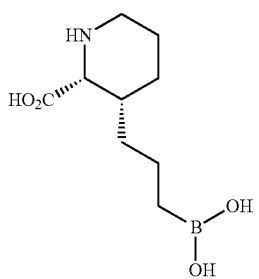

or a pharmaceutically acceptable salt thereof.

34. The compound of claim 16 which is:

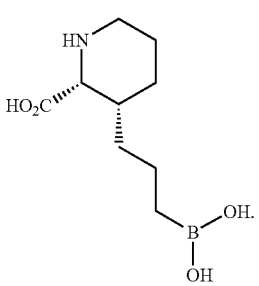 [SMILES: O=C(O)[C@@H]1NCCC[C@@H]1CCCB(O)O]

35. The compound of claim 16 which is:

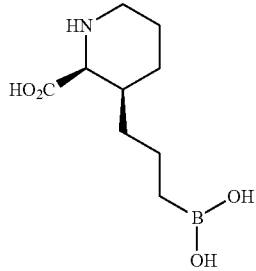 [SMILES: O=C(O)[C@H]1NCCC[C@H]1CCCB(O)O]

or a pharmaceutically acceptable salt thereof.

36. The compound of claim 16 which is:

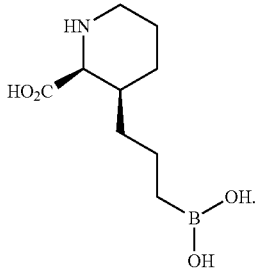 [SMILES: O=C(O)[C@H]1NCCC[C@H]1CCCB(O)O]

37. The compound of claim 16 which is:

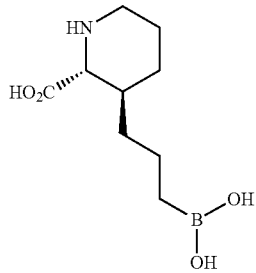 [SMILES: O=C(O)[C@@H]1NCCC[C@H]1CCCB(O)O]

or a pharmaceutically acceptable salt thereof.

38. The compound of claim 16 which is:

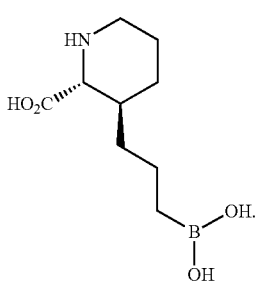 [SMILES: O=C(O)[C@@H]1NCCC[C@H]1CCCB(O)O]

39. The compound of claim 19 which is:

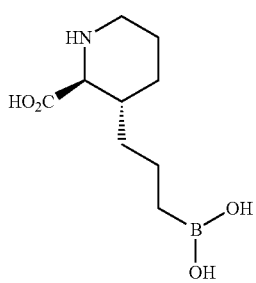

or a pharmaceutically acceptable salt thereof.

40. The compound of claim 16 which is:

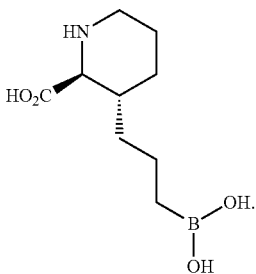 [SMILES: O=C(O)[C@H]1NCCC[C@@H]1CCCB(O)O]

41. The compound of claim 16 which is:

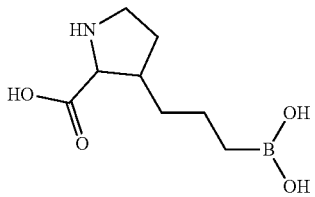 [SMILES: O=C(O)C1NCCC1CCCB(O)O]

or a pharmaceutically acceptable salt thereof.

42. The compound of claim 16 which is:

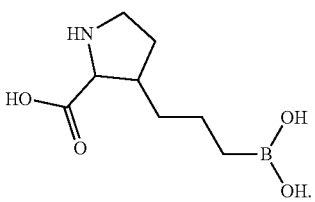

43. A method of treating cancer comprising administering to a patient in need thereof a compound, or pharmaceutically acceptable salt thereof, of claim 16.

44. A pharmaceutical composition comprising a compound, or a pharmaceutically acceptable salt thereof, of claim 16 and a pharmaceutically acceptable carrier.

45. A pharmaceutical composition comprising a compound of claim 19 and a pharmaceutically acceptable carrier.

46. A method of treating cancer comprising administering to a patient in need thereof a compound, or pharmaceutically acceptable salt thereof, of claim 16 and pembrolizumab.

* * * * *

UNITED STATES PATENT AND TRADEMARK OFFICE
CERTIFICATE OF CORRECTION

| | | |
|---|---|---|
| PATENT NO. | : 12,215,116 B2 | Page 1 of 1 |
| APPLICATION NO. | : 16/977253 | |
| DATED | : February 4, 2025 | |
| INVENTOR(S) | : Abdelghani Abe Achab et al. | |

It is certified that error appears in the above-identified patent and that said Letters Patent is hereby corrected as shown below:

In the Claims

Column 382, Line 36, delete "—haloC1-C6alkyl,".

Column 382, Line 38, delete "and" and insert --or--.

Column 384, Line 3, delete "—haloC1-C6alkyl,".

Column 384, Line 5, delete "and" and insert --or--.

Column 386, Line 33, delete "and" and insert --or--.

Signed and Sealed this
Twenty-second Day of April, 2025

Coke Morgan Stewart
*Acting Director of the United States Patent and Trademark Office*